(12) United States Patent
Ogura et al.

(10) Patent No.: US 12,378,260 B2
(45) Date of Patent: Aug. 5, 2025

(54) BENZOTRIAZOLE COMPOUND

(71) Applicants: DAIICHI SANKYO COMPANY, LIMITED, Tokyo (JP); KYOTO PHARMACEUTICAL INDUSTRIES, LTD., Kyoto (JP)

(72) Inventors: Yoshihiro Ogura, Tokyo (JP); Rieko Takano, Tokyo (JP); Junya Kawai, Tokyo (JP); Teppei Fujimoto, Tokyo (JP); Masaharu Inui, Tokyo (JP); Masafumi Ofuku, Tokyo (JP); Masaki Miyazaki, Tokyo (JP); Masaya Fujii, Tokyo (JP); Ken Ishii, Tokyo (JP); Wakana Yokozeki, Tokyo (JP); Kazuya Otake, Kyoto (JP); Shunsuke Takashima, Kyoto (JP); Masafumi Ando, Kyoto (JP)

(73) Assignees: DAIICHI SANKYO COMPANY, LIMITED, Tokyo (JP); KYOTO PHARMACEUTICAL INDUSTRIES, LTD., Kyoto (JP)

( * ) Notice: Subject to any disclaimer, the term of this patent is extended or adjusted under 35 U.S.C. 154(b) by 0 days.

(21) Appl. No.: 18/927,756

(22) Filed: Oct. 25, 2024

(65) Prior Publication Data
US 2025/0092064 A1 Mar. 20, 2025

Related U.S. Application Data

(63) Continuation of application No. PCT/JP2023/016629, filed on Apr. 27, 2023.

(30) Foreign Application Priority Data

Apr. 28, 2022 (JP) .................. 2022-075223

(51) Int. Cl.
| | |
|---|---|
| *C07D 409/06* | (2006.01) |
| *A61K 31/4192* | (2006.01) |
| *A61K 31/4353* | (2006.01) |
| *A61K 31/553* | (2006.01) |
| *A61K 31/554* | (2006.01) |
| *C07D 417/10* | (2006.01) |
| *C07D 419/10* | (2006.01) |

(Continued)

(52) U.S. Cl.
CPC .......... *C07D 515/04* (2013.01); *A61K 31/554* (2013.01); *C07D 417/10* (2013.01); *C07D 419/10* (2013.01); *C07D 419/14* (2013.01); *C07D 513/04* (2013.01); *C07D 515/20* (2013.01); *C07D 519/00* (2013.01)

(58) Field of Classification Search
CPC .. C07D 409/06; C07D 417/10; C07D 491/10; C07D 491/14; C07D 498/04; C07D 513/04; A61K 31/4192; A61K 31/4353; A61K 31/553
See application file for complete search history.

(56) References Cited

U.S. PATENT DOCUMENTS

| | | |
|---|---|---|
| 2016/0318917 A1 | 11/2016 | Boehm et al. |
| 2018/0179187 A1 | 6/2018 | Kerns et al. |

(Continued)

FOREIGN PATENT DOCUMENTS

| | | |
|---|---|---|
| JP | 2017-503786 A | 2/2017 |
| JP | 2018-517731 A | 7/2018 |

(Continued)

OTHER PUBLICATIONS

International Search Report mailed Jul. 25, 2023, issued in corresponding International Patent Application No. PCT/JP2023/016629, filed Apr. 27, 2023, 9 pages.

(Continued)

*Primary Examiner* — Bruck Kifle
(74) *Attorney, Agent, or Firm* — Christensen O'Connor Johnson Kindness PLLC

(57) ABSTRACT

The present invention aims to provide a medicament capable of treating and/or preventing diseases associated with oxidative stress by inhibiting the protein-protein interaction between Keap1 and Nrf2 and activating Nrf2. The present invention relates to a compound represented by the following formula (1):

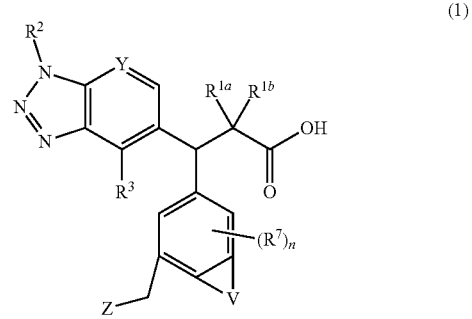

wherein each symbol is as described in the DESCRIPTION, or a pharmaceutically acceptable salt thereof. In addition, the present invention also relates to a medicament containing the aforementioned compound, for the prophylaxis and/or treatment of diseases involving oxidative stress selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa and glaucoma.

8 Claims, No Drawings

(51) Int. Cl.
*C07D 419/14* (2006.01)
*C07D 491/10* (2006.01)
*C07D 491/14* (2006.01)
*C07D 498/04* (2006.01)
*C07D 513/04* (2006.01)
*C07D 515/04* (2006.01)
*C07D 515/20* (2006.01)
*C07D 519/00* (2006.01)

(56) References Cited

U.S. PATENT DOCUMENTS

| | | | |
|---|---|---|---|
| 2020/0055874 | A1 | 2/2020 | Barbay et al. |
| 2020/0062781 | A1 | 2/2020 | Callahan et al. |
| 2022/0204526 | A1 | 6/2022 | Elban et al. |

FOREIGN PATENT DOCUMENTS

| | | | |
|---|---|---|---|
| JP | 2020-502123 | A | 1/2020 |
| JP | 2021-535118 | A | 12/2021 |
| JP | 2022-520442 | A | 3/2022 |
| WO | 2015/092713 | A1 | 6/2015 |
| WO | 2016/202253 | A1 | 12/2016 |
| WO | 2016/203400 | A1 | 12/2016 |
| WO | 2016/203401 | A1 | 12/2016 |
| WO | 2018/109647 | A1 | 6/2018 |
| WO | 2018/109648 | A1 | 6/2018 |
| WO | 2018109643 | A1 | 6/2018 |
| WO | 2018/181345 | A1 | 10/2018 |
| WO | 2019/224667 | A1 | 11/2019 |
| WO | 2020/018788 | A1 | 1/2020 |
| WO | 2020/210229 | A1 | 10/2020 |
| WO | 2020/241853 | A1 | 12/2020 |
| WO | 2021/002473 | A1 | 1/2021 |

OTHER PUBLICATIONS

Written Opinion mailed Jul. 25, 2023, issued in corresponding International Patent Application No. PCTJP2023/016629, filed Apr. 27, 2023, 10 pages.

Mou, Y., et al., "Recent progress in Keap1-Nrf2 protein-protein interaction inhibitors," European Journal of Medicinal Chemistry 202 (2020) 112532, 12 pages.

Cuadrado, A., et al., "Therapeutic targeting of the NRF2 and KEAP1 partnership in chronic diseases," Nature Reviews, Apr. 2019, vol. 18, pp. 295-317.

Chapple, S.J., et al., "Crosstalk between Nrf2 and the proteasome: Therapeutic potential of Nrf2 inducers in vascular disease and aging," The International Journal of Biochemistry & Cell Biology 44 (2012):1315-1320.

BENZOTRIAZOLE COMPOUND

This application is a continuation of PCT/JP2023/016629, filed on Apr. 27, 2023, which claims priority to Japanese Application No. 2022-075223, filed on Apr. 28, 2022, each expressly incorporated herein by reference in its entirety.

TECHNICAL FIELD

The present invention relates to a benzotriazole compound or a pharmaceutically acceptable salt thereof, which is useful for the treatment and/or prophylaxis of diseases involving oxidative stress, particularly, a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma, by inhibiting Kelch-like ECH-associated protein 1 (Keap1) and activating NF-E2-related factor2 (Nrf2).

BACKGROUND ART

When reactive oxygen species generated during the energy metabolism are detected, the body's defense system, including antioxidant enzymes and detoxification metabolic enzymes, is activated. Nrf2 controls the activation of this defense system.

It is known that activation of Nrf2 induces its target genes, such as NAD(P)H quinone oxidoreductase-1 (NQO1), heme oxygenase-1 (HO-1), gamma-glutamate cysteine ligase catalytic subunit (GCLC) and the like (Non Patent Literature 1). NQO1 is a phase II enzyme of the xenobiotic metabolic system, and is important for detoxification. HO-1 and GCLC are known as typical antioxidant enzymes. When the amount of these enzymes increases or these enzymes are activated, cells become resistant to toxins, oxidative stress, inflammation, and the like, and therefore, compounds that activate Nrf2 are considered to be therapeutic agents for various diseases (Non Patent Literature 2).

Since Nrf2 is ubiquitinated by Keap1 and degraded in the proteasome system in the steady state, compounds that inhibit Keap1 activate Nrf2. Compounds that activate Nrf2 by modifying the cysteine residues of Keap1 have been known; however, low specificity thereof due to its activation mechanism is of concern. On the other hand, compounds that inhibit the protein-protein interaction (PPI) between Keap1 and Nrf2 are expected to more specifically activate Nrf2, and have been attracting increasing attention in recent years as prophylactic and/or therapeutic drugs for various diseases caused by oxidative stress (Non Patent Literature 3).

To date, compounds that inhibit Keap1 and activate Nrf2, for example, compounds described in Patent Literatures 1 to 11, have been reported but all of them are structurally different from the compound of the present invention.

CITATION LIST

Patent Literature

Patent Literature 1

WO 2015/092713

Patent Literature 2

WO 2016/202253

Patent Literature 3

WO 2016/203400

Patent Literature 4

WO 2016/203401

Patent Literature 5

WO 2018/109643

Patent Literature 6

WO 2018/109647

Patent Literature 7

WO 2018/109648

Patent Literature 8

WO 2019/224667

Patent Literature 9

WO 2020/165776

Patent Literature 10

WO 2018/181345

Patent Literature 11

WO 2020/241853

Non Patent Literature

Non Patent Literature 1

Int. J. Biochem. Cell. Biol., 2012, 44, 1315-1320

Non Patent Literature 2

Nat. Rev. Drug. Discov., 2019, 18, 295-317

Non Patent Literature 3

Eur. J. Med. Chem., 2020, 202, 112532

SUMMARY OF INVENTION

Technical Problem

The present invention aims to provide a medicament capable of treating and/or preventing diseases involving oxidative stress, particularly, a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma, by inhibiting protein-protein interactions between Keap1 and Nrf2 and activating Nrf2.

Solution to Problem

The present inventors have conducted intensive studies in an attempt to solve the above-mentioned problems and found that a compound represented by the following formula (1):

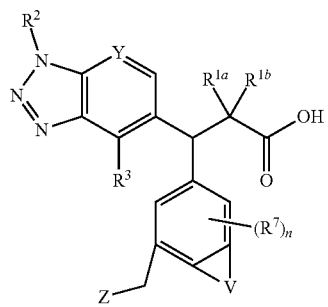

wherein
$R^{1a}$ and $R^{1b}$ are each independently a hydrogen atom or a $C_{1-6}$ alkyl group,
$R^2$ is a $C_{1-6}$ alkyl group optionally substituted by 1 to 3 substituents selected from substituent group a,
$R^3$ is a hydrogen atom, a halogen atom or a $C_{1-6}$ alkyl group,
Y is —CH—, —CR$^4$— or a nitrogen atom,
$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
—V— is a group represented by any of the following formulas:

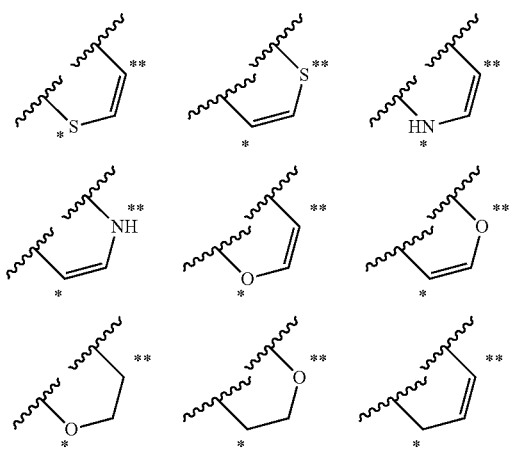

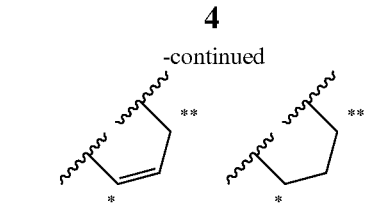

wherein * and ** show a bonding position to a benzene ring,
$R^7$ in the number of n are each independently a halogen atom, a cyano group, a $C_{1-6}$ alkyl group or a $C_{1-6}$ alkoxy group,
n is an integer of 0 to 2, and
Z is a group represented by the following formula (A1), (A2) or (A3):

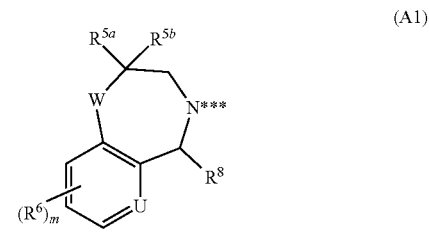

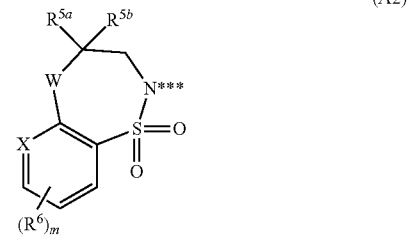

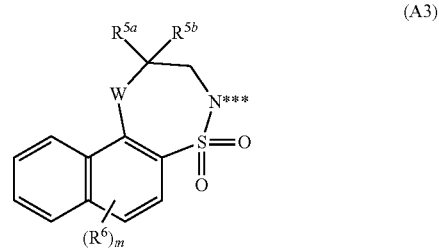

wherein
*** is the bonding position to the carbon atom to which Z is bonded,
$R^8$ is a $C_{1-6}$ alkyl group optionally substituted by 1 to 3 substituents selected from substituent group a,
$R^{5a}$ and $R^{5b}$ are each independently a hydrogen atom, a $C_{1-6}$ alkyl group optionally substituted by 1 to 3 substituents selected from substituent group a, or a $C_{3-6}$ cycloalkyl group,
or $R^{5a}$ and $R^{5b}$ are bonded together to form, together with the carbon atom to which $R^{5a}$ and $R^{5b}$ are bonded, a $C_{3-8}$ cycloalkane which is optionally substituted by 1 to 3 substituents selected from substituent group b, or a 3- to 8-membered saturated oxygen-containing heterocycle,
$R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3,
W is —CH$_2$—, —CHR$^9$— or an oxygen atom,
R$^9$ is a halogen atom, a cyano group, a C$_{1-6}$ alkyl group, a C$_{1-6}$ alkoxy group, a C$_{3-6}$ cycloalkyl group, a C$_{1-6}$ haloalkyl group or a C$_{1-6}$ haloalkoxy group,
X is —CH—, —CR$^{10}$— or a nitrogen atom,
R$^{10}$ is a halogen atom, a cyano group, a C$_{1-6}$ alkyl group, a C$_{1-6}$ alkoxy group, a C$_{3-6}$ cycloalkyl group, a C$_{1-6}$ haloalkyl group or a C$_{1-6}$ haloalkoxy group,
U is —CH—, —CR$^{11}$— or a nitrogen atom, and
R$^{11}$ is a halogen atom, a cyano group, a C$_{1-6}$ alkyl group, a C$_{1-6}$ alkoxy group, a C$_{3-6}$ cycloalkyl group, a C$_{1-6}$ haloalkyl group or a C$_{1-6}$ haloalkoxy group substituent group a:
a hydroxy group,
a halogen atom,
a cyano group,
a C$_{1-6}$ alkyl group optionally substituted by 1 to 3 substituents selected from substituent group b,
a C$_{1-6}$ alkoxy group optionally substituted by 1 to 3 substituents selected from substituent group b,
a C$_{1-6}$ alkylsulfonyl group optionally substituted by 1 to 3 substituents selected from substituent group b,
an amino group optionally substituted by 1 or 2 C$_{1-6}$ alkyl groups substituent group b:
a halogen atom,
a cyano group,
a C$_{1-6}$ alkyl group,
a C$_{1-6}$ alkoxy group
(hereinafter sometimes abbreviated as "compound (1)") or a pharmaceutically acceptable salt thereof has a superior Nrf2 activation action by inhibiting Keap1, and completed the present invention.

That is, the present invention provides the following.
[1] A compound represented by the following formula (1):

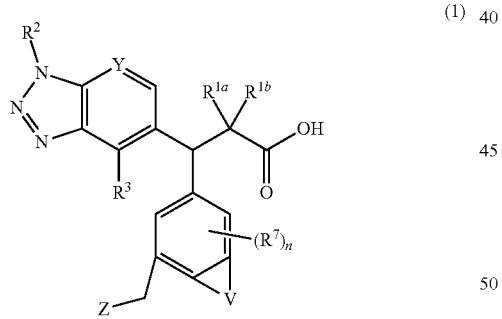

wherein
R$^{1a}$ and R$^{1b}$ are each independently a hydrogen atom or a C$_{1-6}$ alkyl group,
R$^2$ is a C$_{1-6}$ alkyl group optionally substituted by 1 to 3 substituents selected from substituent group a,
R$^3$ is a hydrogen atom, a halogen atom or a C$_{1-6}$ alkyl group,
Y is —CH—, —CR$^4$— or a nitrogen atom,
R$^4$ is a hydroxy group, a halogen atom, a cyano group, a C$_{1-6}$ alkyl group, a C$_{1-6}$ alkoxy group, a C$_{3-6}$ cycloalkyl group, a C$_{1-6}$ haloalkyl group or a C$_{1-6}$ haloalkoxy group,
—V— is a group represented by any of the following formulas:

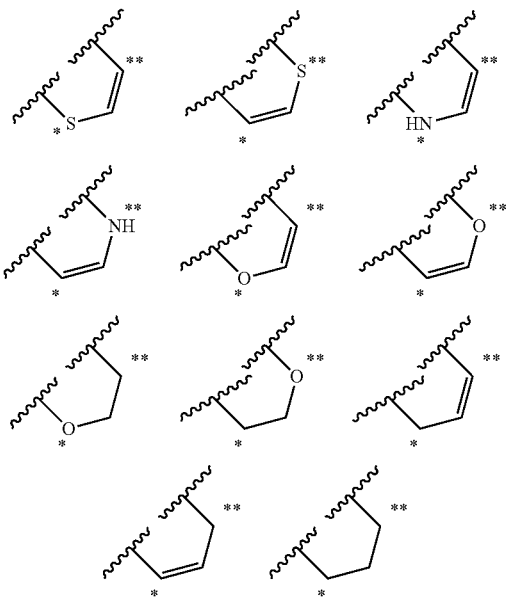

wherein * is a bonding position to a benzene ring,
R$^7$ in the number of n are each independently a halogen atom, a cyano group, a C$_{1-6}$ alkyl group or a C$_{1-6}$ alkoxy group,
n is an integer of 0 to 2, and
Z is a group represented by the following formula (A1), (A2) or (A3):

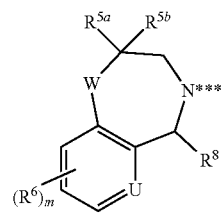

(A1)

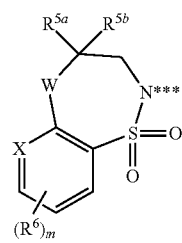

(A2)

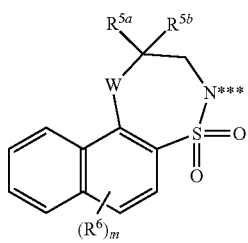

(A3)

wherein
*** is the bonding position to the carbon atom to which Z is bonded, $R^8$ is a $C_{1-6}$ alkyl group optionally substituted by 1 to 3 substituents selected from substituent group a, $R^{5a}$ and $R^{5b}$ are each independently a hydrogen atom, a $C_{1-6}$ alkyl group optionally substituted by 1 to 3 substituents selected from substituent group a, or a $C_{3-6}$ cycloalkyl group, or $R^{5a}$ and $R^{5b}$ are bonded together to form, together with the carbon atom to which $R^{5a}$ and $R^{5b}$ are bonded, a $C_{3-8}$ cycloalkane which is optionally substituted by 1 to 3 substituents selected from substituent group b, or a 3- to 8-membered saturated oxygen-containing heterocycle, $R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3, W is —$CH_2$—, —$CHR^9$— or an oxygen atom, $R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —$CR^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —$CR^{11}$— or a nitrogen atom, and $R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, substituent group a:

a hydroxy group, a halogen atom, a cyano group, a $C_{1-6}$ alkyl group optionally substituted by 1 to 3 substituents selected from substituent group b, a $C_{1-6}$ alkoxy group optionally substituted by 1 to 3 substituents selected from substituent group b, a $C_{1-6}$ alkylsulfonyl group optionally substituted by 1 to 3 substituents selected from substituent group b, an amino group optionally substituted by 1 or 2 $C_{1-6}$ alkyl groups substituent group b:

a halogen atom, a cyano group, a $C_{1-6}$ alkyl group, a $C_{1-6}$ alkoxy group, or a pharmaceutically acceptable salt thereof.

[2] The compound of the above-mentioned [1], wherein $R^{1a}$ and $R^{1b}$ are each independently a hydrogen atom or a methyl group, or a pharmaceutically acceptable salt thereof.

[3] The compound of the above-mentioned [1] or [2], wherein $R^2$ is a $C_{1-6}$ alkyl group, a 2-dimethylaminoethyl group, a 2,2,2-trifluoroethyl group, a 2-hydroxy-2-methylpropyl group or a 3-(methylsulfonyl)propyl group, or a pharmaceutically acceptable salt thereof.

[4] The compound of any of the above-mentioned [1] to [3], wherein $R^3$ is a halogen atom or a $C_{1-6}$ alkyl group, or a pharmaceutically acceptable salt thereof.

[5] The compound of any of the above-mentioned [1] to [4], wherein $R^4$ is a hydroxy group, a chlorine atom, a cyano group, a methyl group, a methoxy group, a cyclopropyl group, a trifluoromethyl group, a difluoromethoxy group or a trifluoromethoxy group, or a pharmaceutically acceptable salt thereof.

[6] The compound of any of the above-mentioned [1] to [5], wherein —V— is a group represented by any of the following formulas:

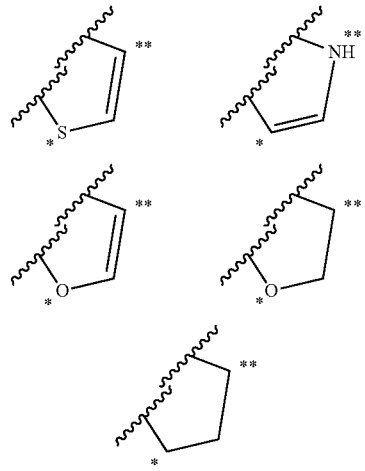

wherein * and ** are as defined above, or a pharmaceutically acceptable salt thereof.

[7] The compound of any of the above-mentioned [1] to [6], wherein n is 1 and $R^7$ is a $C_{1-6}$ alkyl group, or a pharmaceutically acceptable salt thereof.

[8] The compound of any of the above-mentioned [1] to [6], wherein n is 0, or a pharmaceutically acceptable salt thereof.

[9] The compound of any of the above-mentioned [1] to [8], wherein Z is a group represented by the following formula (A1) or (A2):

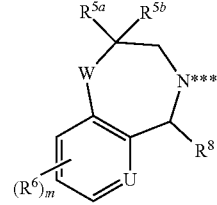

(A1)

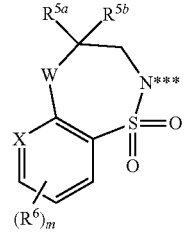

(A2)

wherein each symbol is as defined above, or a pharmaceutically acceptable salt thereof.

[10] The compound of the above-mentioned [9], wherein $R^8$ is a methyl group or an ethyl group, or a pharmaceutically acceptable salt thereof.

[11] The compound of the above-mentioned [9] or [10], wherein $R^{5a}$ and $R^{5b}$ are each independently a hydrogen atom, a methyl group, an ethyl group or a cyclopropyl group, or R⁵ᵃ and R⁵ᵇ are bonded together to form cyclopropane, cyclobutane, oxetane or tetrahydropyran, or a pharmaceutically acceptable salt thereof.

[12] The compound of any of the above-mentioned [9] to [11], wherein R⁶ in the number of m are each independently a hydroxy group, a fluorine atom, a chlorine atom, a methyl group, an ethoxy group or a trifluoromethyl group, and m is an integer of 0 to 2, or a pharmaceutically acceptable salt thereof.

[13] The compound of any of the above-mentioned [9] to [12], wherein W is —CH₂— or an oxygen atom, or a pharmaceutically acceptable salt thereof.

[14] A compound represented by the following formula (1'):

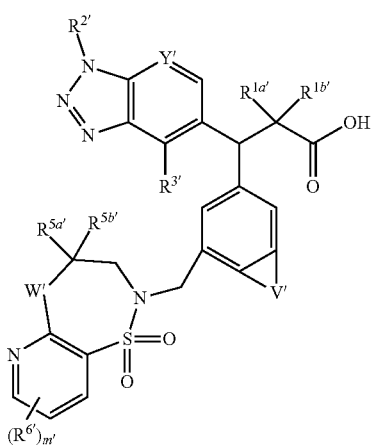

(1')

wherein
R¹ᵃ' and R¹ᵇ' are each independently a hydrogen atom or a methyl group,
R²' is a methyl group,
R³' is a chlorine atom or a methyl group,
Y' is —CH—, —CR⁴'— or a nitrogen atom,
R⁴' is a chlorine atom, a methyl group, a cyclopropyl group, a difluoromethoxy group or a trifluoromethoxy group,
—V'— is a group represented by any of the following formulas:

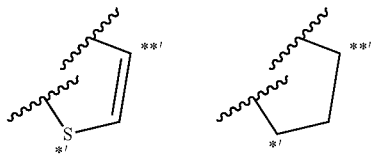 [SMILES: */C=C\S* ; *CCC*]

wherein *' and **' are each a bonding position to a benzene ring, R⁵ᵃ' and R⁵ᵇ' are each independently a hydrogen atom or an ethyl group, or R⁵ᵃ' and R⁵ᵇ' are bonded together to form cyclopropane, R⁶' in the number of m' are each independently a fluorine atom or a chlorine atom,
m' is an integer of 0 to 2, and
W' is an oxygen atom
(hereinafter sometimes abbreviated as "compound (1')") or a pharmaceutically acceptable salt thereof.

[15] Any compound selected from the following group or a pharmaceutically acceptable salt thereof:

(3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)-2,2-dimethylpropanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoic acid, and (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoic acid.

[16] Any compound selected from the following group or a pharmaceutically acceptable salt thereof:

(3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid, and (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid.

[17] (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid or a pharmaceutically acceptable salt thereof.

[18] (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid or a pharmaceutically acceptable salt thereof.

[19] (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid or a pharmaceutically acceptable salt thereof.

[20] (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid or a pharmaceutically acceptable salt thereof.

[21] A compound represented by the following formula (1"):

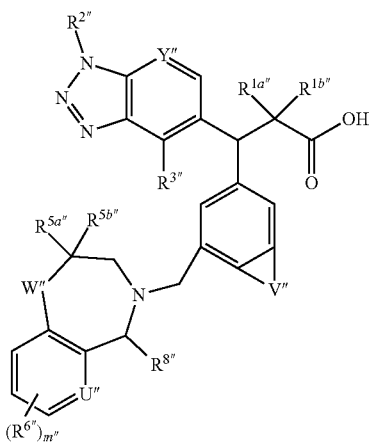

wherein
$R^{a1''}$ and $R^{1b''}$ are each independently a hydrogen atom or a methyl group,
$R^{2''}$ is a methyl group,
$R^{3''}$ is a chlorine atom or a methyl group,
Y" is —CH—, —$CR^{4''}$— or a nitrogen atom,
$R^{4''}$ is a chlorine atom, a methyl group, a cyclopropyl group, a difluoromethoxy group or a trifluoromethoxy group, —V"— is a group represented by any of the following formulas:

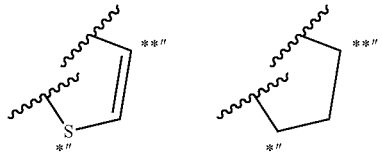

wherein *" and **" are each a bonding position to a benzene ring,
$R^{5a''}$ and $R^{5b''}$ are each independently a hydrogen atom or an ethyl group, or
$R^{5a''}$ and $R^{5b''}$ are bonded together to form cyclopropane,
$R^{8''}$ is a methyl group or an ethyl group,
$R^{6''}$ in the number of m" are each independently a chlorine atom or a hydroxy group,
m" is 0 or 1,
U" is a nitrogen atom, and
W" is an oxygen atom
(hereinafter sometimes abbreviated as "compound (1")") or a pharmaceutically acceptable salt thereof.

[22] Any compound selected from the following group or a pharmaceutically acceptable salt thereof:

(3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, (3S)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, (3R)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, (3R)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid, (3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid, (3R)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoic acid, (3S)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoic acid, (3S)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)-3-(1,4,7-trimethyl-1H-benzotriazol-5-yl)propanoic acid, (3R)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid, (3S)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid, (3S)-3-(4-chloro-1-methyl-1H-benzotriazol-5-yl)-3-((7-{[(2R,5S)-2-ethyl-5-methyl-2,3-dihydropyrido[2,3-f][1,4]oxazepin-4(5H)-yl]methyl}-1-benzothiophen-5-yl)propanoic acid, (3R)-3-(4-chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, and (3S)-3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid.

[23] A medicament comprising the compound of any of the above-mentioned [1] to [22] or a pharmaceutically acceptable salt thereof as an active ingredient (hereinafter sometimes abbreviated as "the medicament of the present invention").

[24] The medicament of the above-mentioned [23], for activating Nrf2.

[25] The medicament of the above-mentioned [23], for inhibiting a protein-protein interaction between Keap1 and Nrf2.

[26] The medicament of the above-mentioned [23], for the prophylaxis and/or treatment of an oxidative stress-related disease.

[27] The medicament of the above-mentioned [26], wherein the oxidative stress-related disease is selected from the group consisting of renal diseases, liver diseases, respiratory diseases, dermatic diseases, cardiovascular diseases, central nervous system diseases, autoimmune diseases and ophthalmic diseases.

[28] The medicament of the above-mentioned [23], for the prophylaxis and/or treatment of a disease selected from the group consisting of a renal disease selected from the group consisting of chronic kidney disease, acute nephritis, chronic nephritis, acute renal failure, chronic renal failure, nephrotic syndrome, IgA nephropathy, diabetic nephropathy, gouty kidney, nephrosclerosis, hydronephrosis and tubulointerstitial nephritis; a liver disease selected from the group consisting of alcoholic fatty liver, non-alcoholic steatohepatitis, hepatic fibrosis and cirrhosis; a respiratory disease selected from the group consisting of bronchitis, pneumonia, pleurisy, chronic obstructive pulmonary diseases, acute lung disorder, diffuse panbronchiolitis, interstitial pneumonia and asthma; a dermatic disease selected from the group consisting of UV and radiation skin disorder, radiation mucosal disorder, epidermolysis blister syndrome, psoriasis, atopic dermatitis and scleroderma; a cardiovascular disease selected from the group consisting of cardiac failure, myocardial infarction, arteriosclerosis and pulmonary arterial hypertension; a central nervous system disease selected from the group consisting of Alzheimer's disease, Parkinson's disease, Huntington's disease, amyotrophic lateral sclerosis, cerebral infarction, polyglutamine disease and autism; a mitochondrial disease selected from the group consisting of Friedreich's ataxia and mitochondrial myopathy; an autoimmune disease selected from the group consisting of multiple sclerosis, rheumatoid arthritis, systemic lupus erythematosus, Sjogren syndrome, type 1 diabetes, ulcerative colitis and Crohn's disease; and an ophthalmic disease selected from the group consisting of allergic conjunctival diseases, viral conjunctivitis, pterygium, cornea infectious disease, dry eye, corneal disorders, uveitis, Behcet's disease, diabetic retinopathy, retinal detachment, retinal vein occlusion, central serous chorioretinopathy, age-related macular degeneration, diabetic macular edema, macular disease, retinitis pigmentosa, glaucoma and cataract.

[29] The medicament of the above-mentioned [23], for the prophylaxis and/or treatment of a disease selected from the group consisting of chronic kidney disease, non-alcoholic steatohepatitis, chronic obstructive pulmonary disease, radiation so skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma.

[30] The medicament of the above-mentioned [23], for the prophylaxis and/or treatment of a disease selected from the group consisting of glaucoma, age-related macular degeneration and retinitis pigmentosa.

[31] The medicament of the above-mentioned [23], for the prophylaxis and/or treatment of a radiation skin disorder or a radiation mucosal disorder.

[32] The medicament of the above-mentioned [23], for the prophylaxis and/or treatment of a chronic obstructive pulmonary disease.

[33] Use of the compound of any of the above-mentioned [1] to [22] or a pharmaceutically acceptable salt thereof in producing a prophylactic and/or therapeutic agent for a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma.

[34] A method for the prophylaxis and/or treatment of a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma in a mammal, comprising administering a pharmaceutically effective amount of the compound of any of the above-mentioned [1] to [22] or a pharmaceutically acceptable salt thereof to the mammal.

[35] A method for activating Nrf2 in a mammal, comprising administering a pharmaceutically effective amount of the compound of any of the above-mentioned [1] to [22] or a pharmaceutically acceptable salt thereof to the mammal.

[36] A method for inhibiting protein-protein interaction between Keap1 and Nrf2 in a mammal, comprising administering a pharmaceutically effective amount of the compound of any of the above-mentioned [1] to [22] or a pharmaceutically acceptable salt thereof to the mammal.

[37] An Nrf2 activator comprising the compound of any of the above-mentioned [1] to [22] or a pharmaceutically acceptable salt thereof as an active ingredient.

[38] An inhibitor of protein-protein interaction between Keap1 and Nrf2, comprising the compound of any of the above-mentioned [1] to [22] or a pharmaceutically acceptable salt thereof as an active ingredient.

[39] The compound of any of the above-mentioned [1] to [22] or a salt thereof, for use in the prophylaxis and/or treatment of a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma.

[40] The medicament of the above-mentioned [23], for use in the prophylaxis and/or treatment of a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma.

[41] The medicament of any of the above-mentioned [23] to [32] and [40], which is administered in combination with other medicament.

[42] The medicament of the above-mentioned [41], wherein said other medicament is a prophylactic agent and/or a therapeutic agent for a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma.

[43] The medicament of the above-mentioned [41] or [42], wherein the medicament of any of the above-mentioned [23] to [32] and [40] and other medicament are separately contained as active ingredients of different preparations, and administered simultaneously or at different times.

[44] The medicament of the above-mentioned [41] or [42], wherein the compound of any of the above-mentioned [1] to [22] or a pharmaceutically acceptable salt thereof and other medicament are contained in a single preparation.

[45] A pharmaceutical composition comprising the compound of any of the above-mentioned [1] to [22] or a pharmaceutically acceptable salt thereof, and a pharmaceutically acceptable carrier (hereinafter sometimes abbreviated as "the pharmaceutical composition of the present invention").

[46] A method for producing the compound of any of the above-mentioned [1] to [22] or a salt thereof.

[47] A prodrug of the compound of any of the above-mentioned [1] to [22] or a salt thereof.

Advantageous Effects of Invention

The compound (1) of the present invention or a pharmaceutically acceptable salt thereof shows an action to effectively activate Nrf2 by inhibiting the protein-protein interaction between Keap1 and Nrf2. That is, a medicament containing the compound (1) of the present invention or a pharmaceutically acceptable salt thereof as an active ingredient can be used for the prophylaxis and/or treatment of diseases whose symptoms are improved by activating Nrf2 when administered to mammals. Examples of the diseases whose symptoms are improved by activation of Nrf2 include oxidative stress-related diseases, specifically, for example, a disease selected from the group consisting of a renal disease selected from the group consisting of chronic kidney disease, acute nephritis, chronic nephritis, acute renal failure, chronic renal failure, nephrotic syndrome, IgA nephropathy, diabetic nephropathy, gouty kidney, nephrosclerosis, hydronephrosis and tubulointerstitial nephritis; a liver disease selected from the group consisting of alcoholic fatty liver, non-alcoholic steatohepatitis, hepatic fibrosis and cirrhosis; a respiratory disease selected from the group consisting of bronchitis, pneumonia, pleurisy, chronic obstructive pulmonary diseases, acute lung disorder, diffuse panbronchiolitis, interstitial pneumonia and asthma; a dermatic disease selected from the group consisting of UV and radiation skin disorder, radiation mucosal disorder, epidermolysis blister syndrome, psoriasis, atopic dermatitis and scleroderma; a cardiovascular disease selected from the group consisting of cardiac failure, myocardial infarction, arteriosclerosis and pulmonary arterial hypertension; a central nervous system disease selected from the group consisting of Alzheimer's disease, Parkinson's disease, Huntington's disease, amyotrophic lateral sclerosis, cerebral infarction, polyglutamine disease and autism; a mitochondrial disease selected from the group consisting of Friedreich's ataxia and mitochondrial myopathy; an autoimmune disease selected from the group consisting of multiple sclerosis, rheumatoid arthritis, systemic lupus erythematosus, Sjogren syndrome, type 1 diabetes, ulcerative colitis and Crohn's disease; and an ophthalmic disease selected from the group consisting of allergic conjunctival diseases, viral conjunctivitis, pterygium, cornea infectious disease, dry eye, corneal disorders, uveitis, Behcet's disease, diabetic retinopathy, retinal detachment, retinal vein occlusion, central serous chorioretinopathy, age-related macular degeneration, diabetic macular edema, macular disease, retinitis pigmentosa, glaucoma and cataract, and the like. Among these, a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa, and glaucoma can be preferably mentioned.

DESCRIPTION OF EMBODIMENTS

The definitions of the terms and symbols used in the present specification are explained below. Unless otherwise defined, all technical and scientific terms used herein have the same meaning as generally understood by those skilled in the art to which the present invention belongs.

In the present specification, the "halogen atom" means a fluorine atom, a chlorine atom, a bromine atom or an iodine atom.

In the present specification, the "$C_{1-6}$ alkyl group" means a linear or branched alkyl group having 1 to 6 carbon atoms. Examples of the $C_{1-6}$ alkyl group include methyl group, ethyl group, n-propyl group, isopropyl group, n-butyl group, sec-butyl group, tert-butyl group, n-pentyl group, isopentyl group, 2-methylbutyl group, neopentyl group, 1-ethylpropyl group, n-hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 2-ethylbutyl group and the like.

In the present specification, the "$C_{1-6}$ haloalkyl group" means a group in which one or more hydrogen atoms in the aforementioned "$C_{1-6}$ alkyl group" are substituted by a halogen. Examples of the $C_{1-6}$ haloalkyl group include fluoromethyl, difluoromethyl, trifluoromethyl, 2-chloroethyl, 2-bromoethyl, 2-iodoethyl, 2-fluoroethyl, 2,2-difluoroethyl, 2,2,2-trifluoroethyl, pentafluoroethyl, 2,2,3,3-tetrafluoropropyl, 3,3,3-trifluoropropyl, 4,4,4-trifluorobutyl, 5,5,5-trifluoropentyl, 6,6,6-trifluorohexyl and the like.

In the present specification, the "$C_{1-6}$ alkoxy group" means a group in which the aforementioned "$C_{1-6}$ alkyl group" is bonded to an oxygen atom. Examples of the $C_{1-6}$ alkoxy group include methoxy group, ethoxy group, n-propoxy group, isopropoxy group, n-butoxy group, sec-butoxy group, tert-butoxy group, n-pentoxy group, isopentoxy group, 2-methylbutoxy group, n-hexyloxy group and the like.

In the present specification, the "$C_{1-6}$ haloalkoxy group" means a group in which one or more hydrogen atoms in the aforementioned "$C_{1-6}$ alkoxy group" are substituted by a halogen. Examples of the $C_{1-6}$ haloalkoxy group include fluoromethoxy, difluoromethoxy, trifluoromethoxy, 2-chloroethoxy, 2-bromoethoxy, 2-iodoethoxy, 2-fluoroethoxy, 2,2-difluoroethoxy, 2,2,2-trifluoroethoxy, pentafluoroethoxy, 2,2,3,3-tetrafluoropropoxy, 3,3,3-trifluoropropoxy, 4,4,4-trifluorobutoxy, 5,5,5-trifluoropentyloxy, 6,6,6-trifluorohexyloxy and the like.

In the present specification, the "$C_{3-6}$ cycloalkyl group" means a 3- to 6-membered monocyclic saturated hydrocarbocyclic group and, for example, cyclopropyl group, cyclobutyl group, cyclopentyl group, and cyclohexyl group can be mentioned.

In the present specification, the "$C_{1-6}$ alkylsulfonyl group" means a group in which the aforementioned "$C_{1-6}$ alkyl group" is bonded to the sulfur atom of the sulfonyl group. Examples of the $C_{1-6}$ alkylsulfonyl group include methylsulfonyl group, ethylsulfonyl group, n-propylsulfonyl group, isopropylsulfonyl group, n-butylsulfonyl group, sec-butylsulfonyl group, tert-butylsulfonyl group, n-pentylsulfonyl group and the like.

In the present specification, the "amino group optionally substituted by 1 or 2 $C_{1-6}$ alkyl groups" means an unsubstituted amino group, or a group in which one or two hydrogen atoms of an amino group are each independently substituted by the aforementioned "$C_{1-6}$ alkyl group". As an amino group optionally substituted by 1 or 2 $C_{1-6}$ alkyl groups, amino group, methylamino group, dimethylamino group, ethylamino group, diethylamino group, ethyl(methyl)amino group, n-propylamino group, di(n-propyl)amino group, isopropylamino group, n-butylamino group, di(n-butyl)amino group, sec-butylamino group, tert-butylamino group, n-pentylamino group, n-hexylamino group and the like can be mentioned.

In the present specification, the "$C_{3-8}$ cycloalkane" means a 3- to 8-membered monocyclic saturated hydrocarbocycle and, for example, cyclopropane, cyclobutane, cyclopentane, cyclohexane, cycloheptane and cyclooctane can be mentioned. The "$C_{3-8}$ cycloalkane" is preferably cyclopropane or cyclobutane.

In the present specification, the "3- to 8-membered saturated oxygen-containing heterocycle" means a 3- to 8-membered monocyclic saturated oxygen-containing heterocycle and, for example, oxirane, oxetane, tetrahydrofuran, tetrahydropyran, oxepane, oxocane and the like can be mentioned. The "3- to 8-membered saturated oxygen-containing heterocycle" is preferably oxetane or tetrahydropyran.

In the present specification, the "optionally substituted" means that it is unsubstituted or substituted by a specific number of specific substituents at any substitutable position (any hydrogen atom is replaced with a substituent). The "substituent" may be a substituent selected from the group consisting of "substituent group a" and "substituent group b" below. When multiple substituents are present, each substituent may be the same or different.

Substituent Group a:
  a hydroxy group,
  a halogen atom,
  a cyano group,
  a $C_{1-6}$ alkyl group optionally substituted by 1 to 3 substituents selected from substituent group b,
  a $C_{1-6}$ alkoxy group optionally substituted by 1 to 3 substituents selected from substituent group b,
  a $C_{1-6}$ alkylsulfonyl group optionally substituted by 1 to 3 substituents selected from substituent group b, an amino group optionally substituted by 1 or 2 $C_{1-6}$ alkyl groups.

Substituent Group b:
  a halogen atom,
  a cyano group,
  a $C_{1-6}$ alkyl group,
  a $C_{1-6}$ alkoxy group However, when an optional substituent of the "optionally substituted $C_{1-6}$ alkyl group" or the "optionally substituted $C_{1-6}$ alkoxy group" is selected from the aforementioned substituent group a or substituent group b, the list of the aforementioned substituent group a or substituent group b does not include the "$C_{1-6}$ alkyl group".

In the present specification, the "pharmaceutically acceptable salt" means a salt that can be used as a medicament, and includes both pharmaceutically acceptable acid addition salts and pharmaceutically acceptable base addition salts.

In the present specification, the "pharmaceutically acceptable carrier" means a pharmaceutically acceptable material (e.g., excipient, diluent, additive, solvent, etc.) involved in transporting compound (1) (or compound (1') or compound (1")) of the present invention or a composition containing the same from one organ to another organ.

In the present specification, "treatment" and its derivatives mean, in a patient who has developed a disease, illness, disorder, etc. (hereinafter referred to as "disease, and the like."), the remission, alleviation, or delayed aggravation of the clinical symptoms of said disease, and the like.

In the present specification, "prophylaxis" and its derivatives mean to inhibit, deter, control, slow down, or stop the onset of clinical symptoms of a disease, and the like in mammals that are likely to develop the disease, and the like but have not yet done so, or are concerned about the recurrence of the disease, and the like after treatment of the disease, and the like.

In the present specification, the "oxidative stress" means a state in which the production of reactive oxygen species is excessive due to external factors (e.g., ultraviolet rays, radiation, air pollution, tobacco, drugs, intake of oxidized substances, etc.) and the balance of antioxidant defense mechanisms is upset. In addition, "oxidative stress-related diseases" means diseases in which such oxidative stress is involved in the onset or worsening of symptoms. Such "oxidative stress-related diseases" include, for example, a disease selected from the group consisting of a renal disease selected from the group consisting of chronic kidney disease, acute nephritis, chronic nephritis, acute renal failure, chronic renal failure, nephrotic syndrome, IgA nephropathy, diabetic nephropathy, gouty kidney, nephrosclerosis, hydronephrosis and tubulointerstitial nephritis; a liver disease selected from the group consisting of alcoholic fatty liver, non-alcoholic steatohepatitis, hepatic fibrosis and cirrhosis; a respiratory disease selected from the group consisting of bronchitis, pneumonia, pleurisy, chronic obstructive pulmonary diseases, acute lung disorder, diffuse panbronchiolitis, interstitial pneumonia and asthma; a dermatic disease selected from the group consisting of UV and radiation skin disorder, radiation mucosal disorder, epidermolysis blister syndrome, psoriasis, atopic dermatitis and scleroderma; a cardiovascular disease selected from the group consisting of cardiac failure, myocardial infarction, arteriosclerosis and pulmonary arterial hypertension; a central nervous system disease selected from the group consisting of Alzheimer's disease, Parkinson's disease, Huntington's disease, amyotrophic lateral sclerosis, cerebral infarction, polyglutamine disease and autism; a mitochondrial disease selected from the group consisting of Friedreich's ataxia and mitochondrial myopathy; an autoimmune disease selected from the group consisting of multiple sclerosis, rheumatoid arthritis, systemic lupus erythematosus, Sjogren syndrome, type 1 diabetes, ulcerative colitis and Crohn's disease; and an ophthalmic disease selected from the group consisting of allergic conjunctival diseases, viral conjunctivitis, pterygium, cornea infectious disease, dry eye, corneal disorders, uveitis, Behcet's disease, diabetic retinopathy, retinal detachment, retinal vein occlusion, central serous chorioretinopathy, age-related macular degeneration, diabetic macular edema, macular disease, retinitis pigmentosa, glaucoma and cataract and the like. The "oxidative stress-related disease" in the present invention is, in particular, a disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa and glaucoma.

Generally, Keap1 and Nrf2 form a complex and the function of Nrf2 is inhibited by ubiquitination by E3 ubiquitin ligase. In the present specification, the "inhibitor of protein-protein interaction between Keap1 and Nrf2" means a substance that inhibits the formation of the complex and releases Nrf2.

In the present specification, the "activating Nrf2" or "Nrf2 activator" means a substance that inhibits the protein-protein interaction between Keap1 and Nrf2, thereby preventing the formation of a complex between Keap1 and Nrf2, and allows the liberated Nrf2 to transfer into the nucleus and promote the expression of antioxidant genes, or that induces high expression of antioxidant genes.

In the present specification, the "pharmaceutically effective amount" means the dose of the compound (1) (or compound (1') or compound (1")) of the present invention or a pharmaceutically acceptable salt thereof to be orally or parenterally (topically, rectally, intravenously, intramuscularly, subcutaneously, etc.) administered to a mammal.

In the present specification, the "mammal" is not particularly limited, and human and mammals other than human (e.g., mouse, rat, hamster, guinea pig, rabbit, cat, dog, swine, bovine, horse, sheep, monkey, etc.) can be mentioned.

(Compound of the Present Invention (Compound (1)))

Each group in the aforementioned formula (1) of compound (1) explained in the following.

$R^{1a}$ and $R^{1b}$ are each independently a hydrogen atom or a $C_{1-6}$ alkyl group.

Preferably, $R^{1a}$ and $R^{1b}$ are each independently a hydrogen atom or a methyl group.

$R^2$ is a $C_{1-6}$ alkyl group optionally substituted by 1 to 3 substituents selected from the aforementioned substituent group a.

$R^2$ is preferably a $C_{1-6}$ alkyl group, a 2-dimethylaminoethyl group, a 2,2,2-trifluoroethyl group, a 2-hydroxy-2-methylpropyl group or a 3-(methylsulfonyl)propyl group, more preferably a methyl group.

$R^3$ is a hydrogen atom, a halogen atom or a $C_{1-6}$ alkyl group.

$R^3$ is preferably a halogen atom or a $C_{1-6}$ alkyl group, more preferably a chlorine atom or a methyl group.

Y is —CH—, —$CR^4$— wherein $R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a nitrogen atom.

Y is preferably —CH—, —$CR^4$— wherein $R^4$ is a hydroxy group, a chlorine atom, a cyano group, a methyl group, a methoxy group, a cyclopropyl group, a trifluoromethyl group, a difluoromethoxy group or a trifluoromethoxy group, or a nitrogen atom, more preferably —CH—, —$CR^4$— wherein $R^4$ is a chlorine atom, a methyl group, a cyclopropyl group, a difluoromethoxy group or a trifluoromethoxy group, or a nitrogen atom.

—V— is a group represented by any of the following formulas:

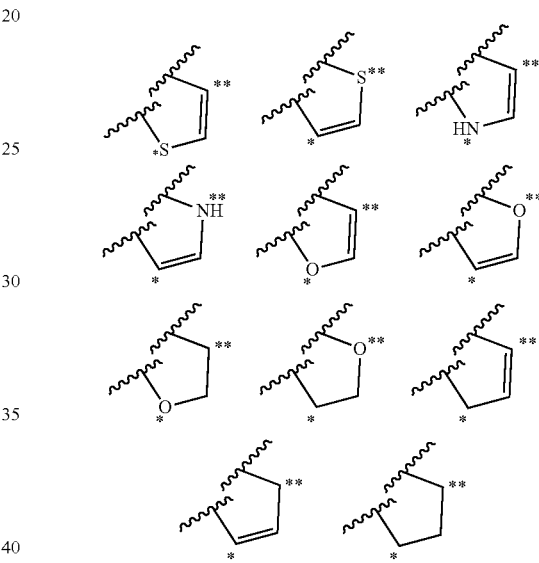

wherein * show a bonding position to a benzene ring.

—V— is preferably a group represented by any of the following formulas:

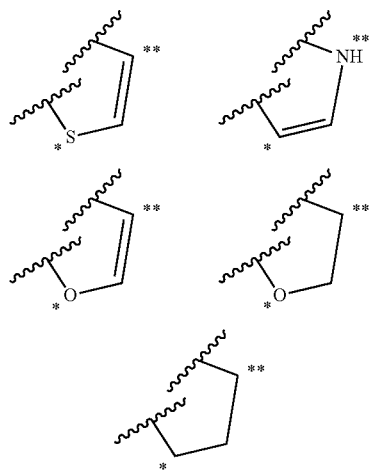

wherein * and ** are as defined above, more preferably a group represented by any of the following formulas:

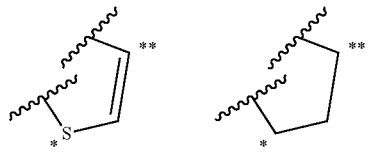 [SMILES: */C=C\S* ; *CCC*]

wherein * and ** are as defined above.

$R^7$ in the number of n are each independently a halogen atom, a cyano group, a $C_{1-6}$ alkyl group or a $C_{1-6}$ alkoxy group.

$R^7$ in the number of n is preferably a $C_{1-6}$ alkyl group.

n is an integer of 0 to 2.

n is preferably 0 or 1, more preferably 0.

Z is a group represented by the following formula (A1), (A2) or (A3):

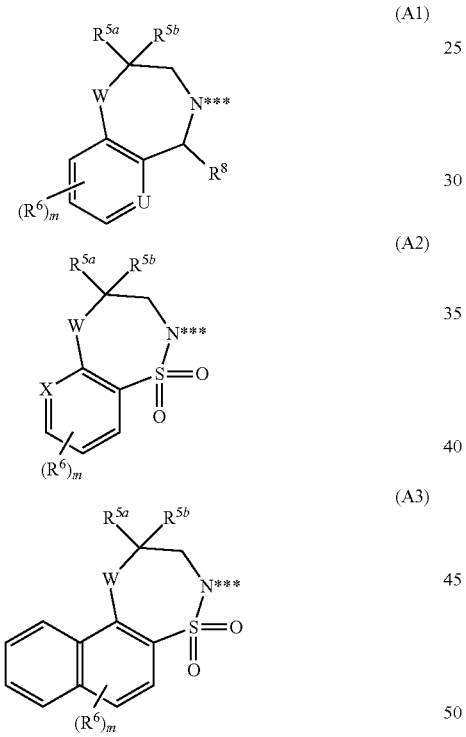

wherein
*** is the bonding position to the carbon atom to which Z is bonded,
$R^8$ is a $C_{1-6}$ alkyl group optionally substituted by 1 to 3 substituents selected from substituent group a,
$R^{5a}$ and $R^{5b}$ are each independently a hydrogen atom, a $C_{1-6}$ alkyl group optionally substituted by 1 to 3 substituents selected from substituent group a, or a $C_{3-6}$ cycloalkyl group, or
$R^{5a}$ and $R^{5b}$ are bonded together to form, together with the carbon atom to which $R^{5a}$ and $R^{5b}$ are bonded, a $C_{3-8}$ cycloalkane which is optionally substituted by 1 to 3 substituents selected from substituent group b, or a 3- to 8-membered saturated oxygen-containing heterocycle, $R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups,
m is an integer of 0 to 3,
W is —$CH_2$—, —$CHR^9$— or an oxygen atom,
$R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
X is —CH—, —$CR^{10}$— or a nitrogen atom,
$R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
U is —CH—, —$CR^{11}$— or a nitrogen atom, and
$R^{11}$— is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group.

Z is preferably a group represented by the following formula (A1) or (A2):

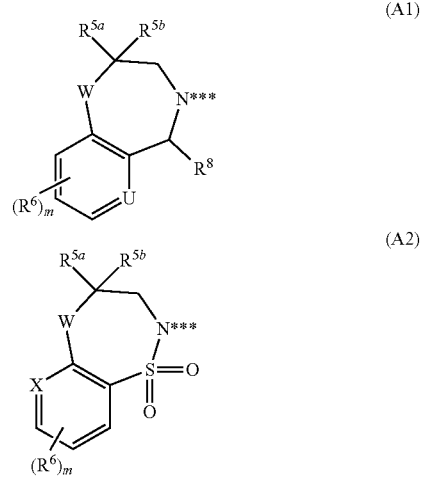

wherein each symbol is as defined above,
more preferably a group represented by the following formula:

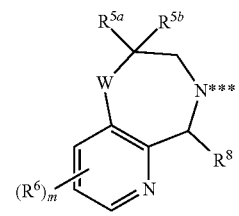

wherein $R^8$ is a methyl group or an ethyl group,
$R^{5a}$ and $R^{5b}$ are each independently a hydrogen atom, a methyl group, an ethyl group or a cyclopropyl group, or
$R^{5a}$ and $R^{5b}$ are bonded together to form cyclopropane, cyclobutane, oxetane or tetrahydropyran,
$R^6$ in the number of m are each independently a hydroxy group, a fluorine atom, a chlorine atom, a methyl group, an ethoxy group or a trifluoromethyl group,
m is an integer of 0 to 2, and
W is —$CH_2$— or an oxygen atom, or a group represented by the following formula:

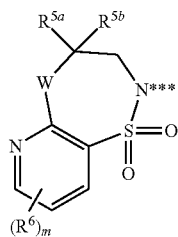

wherein $R^{5a}$ and $R^{5b}$ are each independently a hydrogen atom, a methyl group, an ethyl group or a cyclopropyl group, or $R^{5a}$ and $R^{5b}$ are bonded together to form cyclopropane, cyclobutane, oxetane or tetrahydropyran, $R^6$ in the number of m are each independently a hydroxy group, a fluorine atom, a chlorine atom, a methyl group, an ethoxy group or a trifluoromethyl group, m is an integer of 0 to 2, and W is —CH$_2$— or an oxygen atom, further preferably a group represented by the following formula:

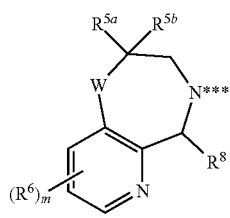

wherein $R^8$ is a methyl group or an ethyl group, $R^{5a}$ and $R^{5b}$ are each independently a hydrogen atom or an ethyl group, or $R^{5a}$ and $R^{5b}$ are bonded together to form cyclopropane, $R^6$ in the number of m are each independently a chlorine atom or a hydroxy group, m is 0 or 1, and W is an oxygen atom, or a group represented by the following formula:

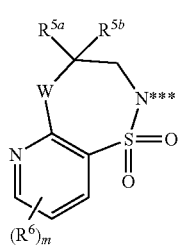

wherein $R^{5a}$ and $R^{5b}$ are each independently a hydrogen atom, a methyl group, an ethyl group or a cyclopropyl group, or $R^{5a}$ and $R^{5b}$ are bonded together to form cyclopropane, cyclobutane, oxetane or tetrahydropyran, $R^6$ in the number of m are each independently a hydroxy group, a fluorine atom, a chlorine atom, a methyl group, an ethoxy group or a trifluoromethyl group, m is an integer of 0 to 2, and W is an oxygen atom.

As compound (1), the following compounds are preferred.

[Compound (1A)]

Compound (1) wherein $R^{1a}$ and $R^{1b}$ are each independently a hydrogen atom or a methyl group;

$R^2$ is a $C_{1-6}$ alkyl group optionally substituted by 1 to 3 substituents selected from the aforementioned substituent group a;

$R^3$ is a hydrogen atom, a halogen atom or a $C_{1-6}$ alkyl group;

Y is —CH—, —CR$^4$— or a nitrogen atom;

$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group;

—V— is a group represented by any of the following formulas:

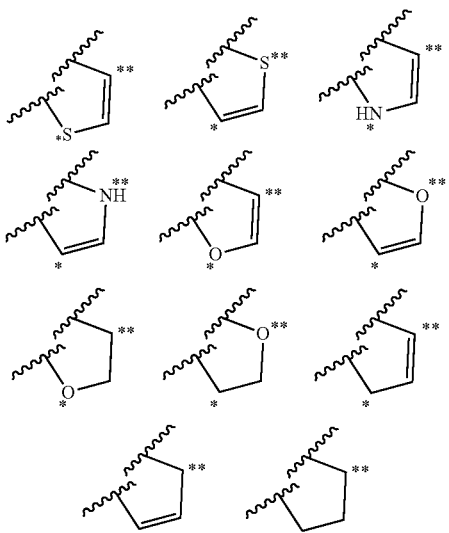

wherein symbols are as defined above;

$R^7$ in the number of n are each independently a halogen atom, a cyano group, a $C_{1-6}$ alkyl group or a $C_{1-6}$ alkoxy group;

n is an integer of 0 to 2; and

Z is a group represented by the following formula (A1), (A2) or (A3):

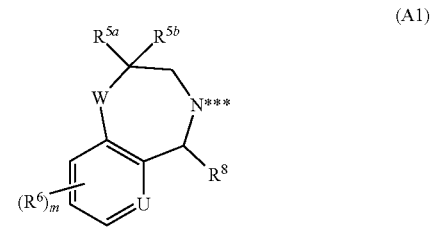

(A1)

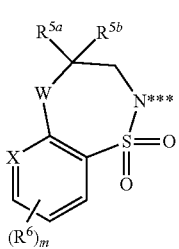

(A2)

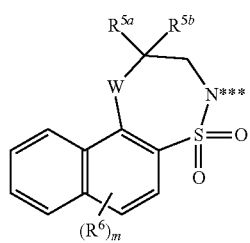

(A3)

wherein

*** is the bonding position to the carbon atom to which Z is bonded, $R^8$ is a $C_{1-6}$ alkyl group optionally substituted by 1 to 3 substituents selected from the aforementioned substituent group a, $R^{5a}$ and $R^{5b}$ are each independently a hydrogen atom, a $C_{1-6}$ alkyl group optionally substituted by 1 to 3 substituents selected from the aforementioned substituent group a, or a $C_{3-6}$ cycloalkyl group, or $R^{5a}$ and $R^{5b}$ are bonded together to form, together with the carbon atom to which $R^{5a}$ and $R^{5b}$ are bonded, a $C_{3-8}$ cycloalkane which is optionally substituted by 1 to 3 substituents selected from substituent group b, or a 3- to 8-membered saturated oxygen-containing heterocycle, $R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3, W is —$CH_2$—, —$CHR^9$— or an oxygen atom, $R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —$CR^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —$CR^{11}$— or a nitrogen atom, and $R^{11}$— is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1B)]

Compound (1) wherein $R^{1a}$ and $R^{1b}$ are each independently a hydrogen atom or a $C_{1-6}$ alkyl group (preferably each independently a hydrogen atom or a methyl group);

$R^2$ is a $C_{1-6}$ alkyl group, a 2-dimethylaminoethyl group, a 2,2,2-trifluoroethyl group, a 2-hydroxy-2-methylpropyl group or a 3-(methylsulfonyl)propyl group;

$R^3$ is a hydrogen atom, a halogen atom or a $C_{1-6}$ alkyl group;

Y is —CH—, —$CR^4$— or a nitrogen atom;

$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group;

—V— is a group represented by any of the following formulas:

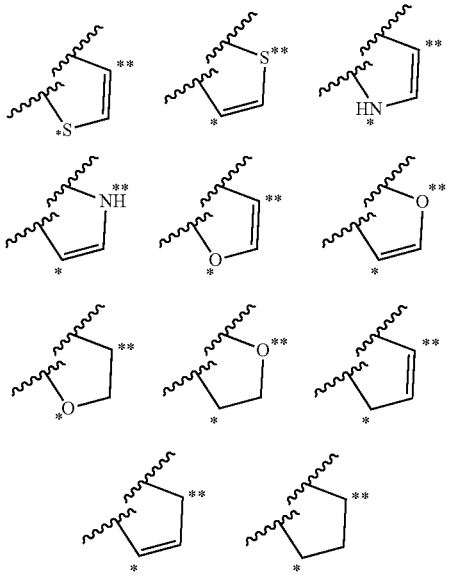

wherein symbols are as defined above, $R^7$ in the number of n are each independently a halogen atom, a cyano group, a $C_{1-6}$ alkyl group or a $C_{1-6}$ alkoxy group;

n is an integer of 0 to 2; and

Z is a group represented by the following formula (A1), (A2) or (A3):

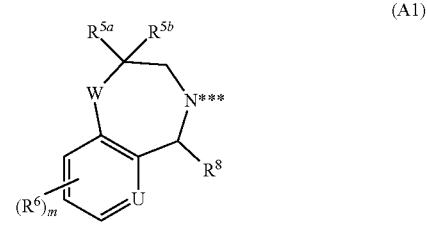

(A1)

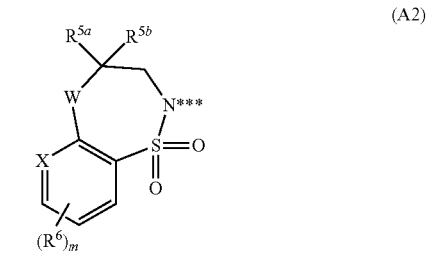

(A2)

(A3)

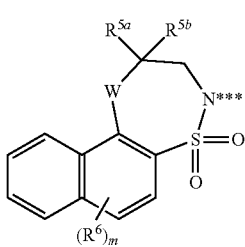

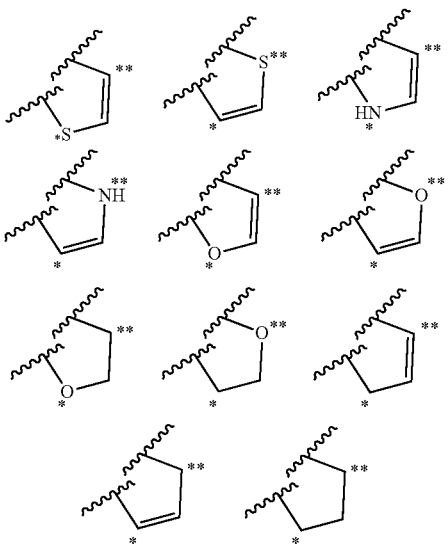

wherein
\*\*\* is the bonding position to the carbon atom to which Z is bonded, $R^8$ is a $C_{1-6}$ alkyl group optionally substituted by 1 to 3 substituents selected from the aforementioned substituent group a, $R^{5a}$ and $R^{5b}$ are each a hydrogen atom, a $C_{1-6}$ alkyl group optionally substituted by 1 to 3 substituents selected from the aforementioned substituent group a, or a $C_{3-6}$ cycloalkyl group, or $R^{5a}$ and $R^{5b}$ are bonded together to form, together with the carbon atom to which $R^{5a}$ and $R^{5b}$ are bonded, a $C_{3-8}$ cycloalkane which is optionally substituted by 1 to 3 substituents selected from substituent group b, or a 3- to 8-membered saturated oxygen-containing heterocycle, $R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3, W is —$CH_2$—, —$CHR^9$— or an oxygen atom, $R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —$CR^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —$CR^{11}$— or a nitrogen atom, and $R^{11}$— is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1C)]

Compound (1) wherein $R^{1a}$ and $R^{1b}$ are each independently a hydrogen atom or a $C_{1-6}$ alkyl group (preferably, each independently a hydrogen atom or a methyl group);

$R^2$ is a $C_{1-6}$ alkyl group optionally substituted by 1 to 3 substituents selected from the aforementioned substituent group a (preferably, a $C_{1-6}$ alkyl group, a 2-dimethylaminoethyl group, a 2,2,2-trifluoroethyl group, a 2-hydroxy-2-methylpropyl group or a 3-(methylsulfonyl)propyl group);

$R^3$ is a halogen atom or a $C_{1-6}$ alkyl group;

Y is —CH—, —$CR^4$— or a nitrogen atom;

$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group;

—V— is a group represented by any of the following formulas:

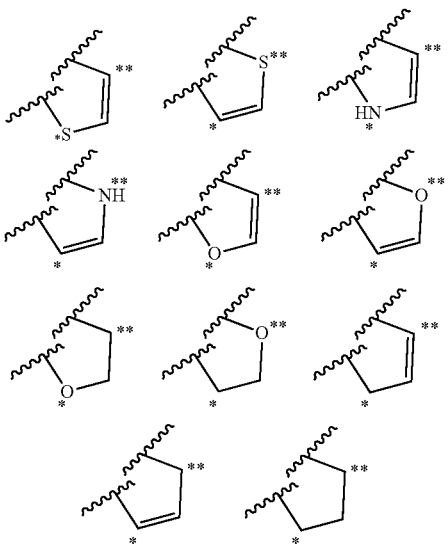

wherein symbols are as defined above;

$R^7$ in the number of n are each independently a halogen atom, a cyano group, a $C_{1-6}$ alkyl group or a $C_{1-6}$ alkoxy group;

n is an integer of 0 to 2; and

Z is a group represented by the following formula (A1), (A2) or (A3):

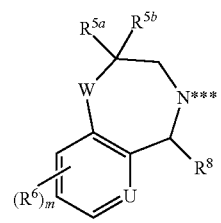

(A1)

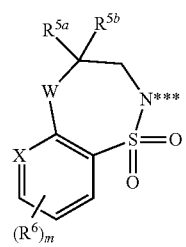

(A2)

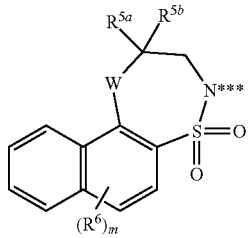

(A3)

wherein
\*\*\* is the bonding position to the carbon atom to which Z is bonded, $R^8$ is a $C_{1-6}$ alkyl group optionally substituted by 1 to 3 substituents selected from the aforementioned substituent group a, $R^{5a}$ and $R^{5b}$ are each a hydrogen atom, a $C_{1-6}$ alkyl group optionally substituted by 1 to 3 substituents selected from the aforementioned substituent group a, or a $C_{3-6}$ cycloalkyl group, or $R^{5a}$ and $R^{5b}$ are bonded together to form, together with the carbon atom to which $R^{5a}$ and $R^{5b}$ are bonded, a $C_{3-8}$ cycloalkane which is optionally substituted by 1 to 3 substituents selected from the aforementioned substituent group b, or a 3- to 8-membered saturated oxygen-containing heterocycle $R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3, W is —CH$_2$—, —CHR$^9$— or an oxygen atom, $R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —CR$^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —CR$^{11}$— or a nitrogen atom, and $R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1D)]

Compound (1) wherein $R^{1a}$ and $R^{1b}$ are each independently a hydrogen atom or a $C_{1-6}$ alkyl group (preferably, each independently a hydrogen atom or a methyl group);

$R^2$ is a $C_{1-6}$ alkyl group optionally substituted by 1 to 3 substituents selected from the aforementioned substituent group a (preferably, a $C_{1-6}$ alkyl group, a 2-dimethylaminoethyl group, a 2,2,2-trifluoroethyl group, a 2-hydroxy-2-methylpropyl group or a 3-(methylsulfonyl)propyl group);

$R^3$ is a hydrogen atom, a halogen atom or a $C_{1-6}$ alkyl group (preferably, a halogen atom or a $C_{1-6}$ alkyl group);

Y is —CH—, —CR$^4$— or a nitrogen atom;

$R^4$ is a hydroxy group, a chlorine atom, a cyano group, a methyl group, a methoxy group, a cyclopropyl group, a trifluoromethyl group, a difluoromethoxy group or a trifluoromethoxy group;

—V— is a group represented by any of the following formulas:

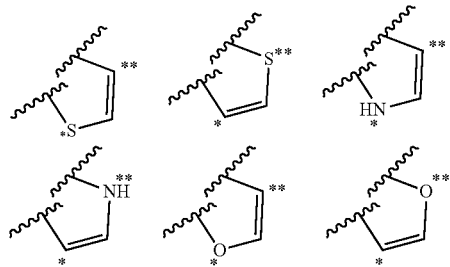

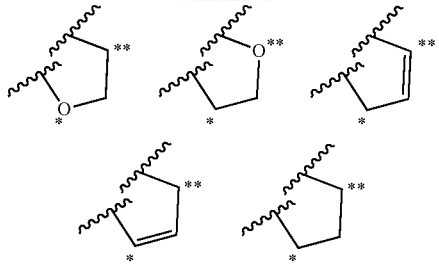

wherein symbols are as defined above;

$R^7$ in the number of n are each independently a halogen atom, a cyano group, a $C_{1-6}$ alkyl group or a $C_{1-6}$ alkoxy group;

n is an integer of 0 to 2; and

Z is a group represented by the following formula (A1), (A2) or (A3):

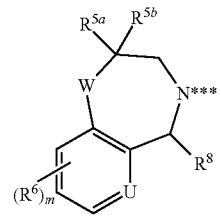

(A1)

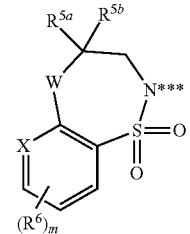

(A2)

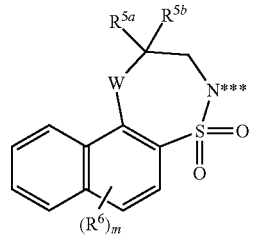

(A3)

wherein

*** is the bonding position to the carbon atom to which Z is bonded, $R^8$ is a $C_{1-6}$ alkyl group optionally substituted by 1 to 3 substituents selected from the aforementioned substituent group a, $R^{5a}$ and $R^{5b}$ is a hydrogen atom, a $C_{1-6}$ alkyl group optionally substituted by 1 to 3 substituents selected from the aforementioned substituent group a, or a $C_{3-6}$ cycloalkyl group, or $R^{5a}$ and $R^{5b}$ are bonded together to form, together with the carbon atom to which $R^{5a}$ and $R^{5b}$ are bonded, a $C_{3-6}$ cycloalkane which is optionally substituted by 1 to 3 substituents selected from substituent group b, or a 3- to 8-membered saturated oxygen-containing heterocycle, R⁶ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3, W is —$CH_2$—, —$CHR^9$— or an oxygen atom, $R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —$CR^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —$CR^{11}$— or a nitrogen atom, and $R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1E)]

Compound (1) wherein $R^{1a}$ and $R^{1b}$ are each independently a hydrogen atom or a $C_{1-6}$ alkyl group (preferably, each independently a hydrogen atom or a methyl group);

$R^2$ is a $C_{1-6}$ alkyl group optionally substituted by 1 to 3 substituents selected from the aforementioned substituent group a (preferably, a $C_{1-6}$ alkyl group, a 2-dimethylaminoethyl group, a 2,2,2-trifluoroethyl group, a 2-hydroxy-2-methylpropyl group or a 3-(methylsulfonyl)propyl group);

$R^3$ is a hydrogen atom, a halogen atom or a $C_{1-6}$ alkyl group (preferably, a halogen atom or a $C_{1-6}$ alkyl group);

Y is —CH—, —$CR^4$— or a nitrogen atom;

$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group (preferably, a hydroxy group, a chlorine atom, a cyano group, a methyl group, a methoxy group, a cyclopropyl group, a trifluoromethyl group, a difluoromethoxy group or a trifluoromethoxy group);

—V— is a group represented by any of the following formulas:

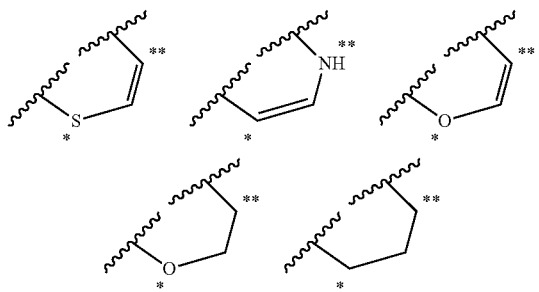

wherein * and ** are as defined above;

$R^7$ in the number of n are each independently a halogen atom, a cyano group, a $C_{1-6}$ alkyl group or a $C_{1-6}$ alkoxy group (preferably, each independently a $C_{1-6}$ alkyl group);

n is an integer of 0 to 2 (preferably, 0 or 1); and

Z is a group represented by the following formula (A1), (A2) or (A3) group

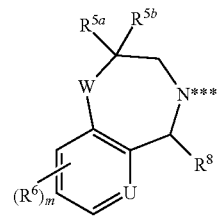

(A1)

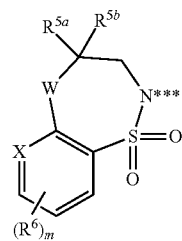

(A2)

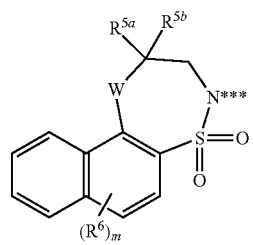

(A3)

wherein

*** is the bonding position to the carbon atom to which Z is bonded, $R^8$ is a $C_{1-6}$ alkyl group optionally substituted by 1 to 3 substituents selected from the aforementioned substituent group a, $R^{5a}$ and $R^{5b}$ is a hydrogen atom, a $C_{1-6}$ alkyl group optionally substituted by 1 to 3 substituents selected from the aforementioned substituent group a, or a $C_{3-6}$ cycloalkyl group, or $R^{5a}$ and $R^{5b}$ are bonded together to form, together with the carbon atom to which $R^{5a}$ and $R^{5b}$ are bonded, a $C_{3-6}$ cycloalkane which is optionally substituted by 1 to 3 substituents selected from substituent group b, or a 3- to 8-membered saturated oxygen-containing heterocycle, $R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3, W is —$CH_2$—, —$CHR^9$— or an oxygen atom, $R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —$CR^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —$CR^{11}$— or a nitrogen atom, and $R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1F)]

Compound (1) wherein $R^{1a}$ and $R^{1b}$ are each independently a hydrogen atom or a $C_{1-6}$ alkyl group (preferably, each independently a hydrogen atom or a methyl group);

$R^2$ is a $C_{1-6}$ alkyl group optionally substituted by 1 to 3 substituents selected from the aforementioned substituent group a (preferably, a $C_{1-6}$ alkyl group, a 2-dimethylaminoethyl group, a 2,2,2-trifluoroethyl group, a 2-hydroxy-2-methylpropyl group or a 3-(methylsulfonyl)propyl group);

$R^3$ is a hydrogen atom, a halogen atom or a $C_{1-6}$ alkyl group (preferably, a halogen atom or a $C_{1-6}$ alkyl group);

Y is —CH—, —$CR^4$— or a nitrogen atom;

$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group (preferably, a hydroxy group, a chlorine atom, a cyano group, a methyl group, a methoxy group, a cyclopropyl group, a trifluoromethyl group, a difluoromethoxy group or a trifluoromethoxy group);

—V— is a group represented by any of the following formulas:

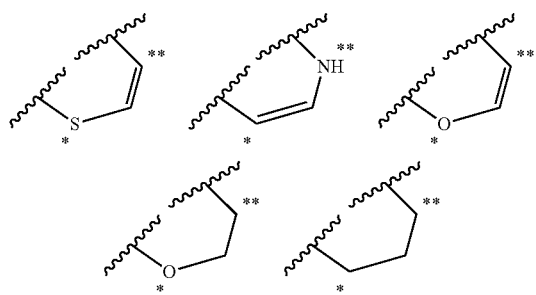

wherein * and ** are as defined above;

$R^7$ in the number of n are each independently a halogen atom, a cyano group, a $C_{1-6}$ alkyl group or a $C_{1-6}$ alkoxy group (preferably, each independently a $C_{1-6}$ alkyl group);

n is an integer of 0 to 2 (preferably, 0 or 1); and

Z is a group represented by the following formula (A1) or (A2):

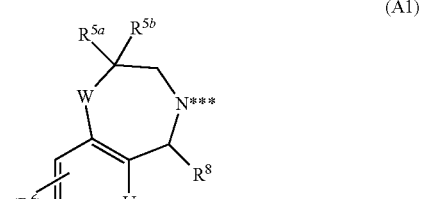
(A1)

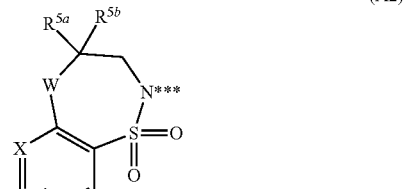
(A2)

wherein

*** is the bonding position to the carbon atom to which Z is bonded, $R^8$ is a $C_{1-6}$ alkyl group optionally substituted by 1 to 3 substituents selected from the aforementioned substituent group a, $R^{5a}$ and $R^{5b}$ is a hydrogen atom, a $C_{1-6}$ alkyl group optionally substituted by 1 to 3 substituents selected from the aforementioned substituent group a, or a $C_{3-6}$ cycloalkyl group, or $R^{5a}$ and $R^{5b}$ are bonded together to form, together with the carbon atom to which $R^{5a}$ and $R^{5b}$ are bonded, a $C_{3-8}$ cycloalkane which is optionally substituted by 1 to 3 substituents selected from substituent group b, or a 3- to 8-membered saturated oxygen-containing heterocycle, $R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3, W is —$CH_2$—, —$CHR^9$— or an oxygen atom, $R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —$CR^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —$CR^{11}$— or a nitrogen atom, and $R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1G)]

Compound (1) wherein $R^{1a}$ and $R^{1b}$ are each independently a hydrogen atom or a $C_{1-6}$ alkyl group (preferably, each independently a hydrogen atom or a methyl group);

$R^2$ is a $C_{1-6}$ alkyl group optionally substituted by 1 to 3 substituents selected from the aforementioned substituent group a (preferably, a $C_{1-6}$ alkyl group, a 2-dimethylaminoethyl group, a 2,2,2-trifluoroethyl group, a 2-hydroxy-2-methylpropyl group or a 3-(methylsulfonyl)propyl group);

$R^3$ is a hydrogen atom, a halogen atom or a $C_{1-6}$ alkyl group (preferably, a halogen atom or a $C_{1-6}$ alkyl group);

Y is —CH—, —$CR^4$— or a nitrogen atom;

$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group (preferably, a hydroxy group, a chlorine atom, a cyano group, a methyl group, a methoxy group, a cyclopropyl group, a trifluoromethyl group, a difluoromethoxy group or a trifluoromethoxy group);

—V— is a group represented by any of the following formulas:

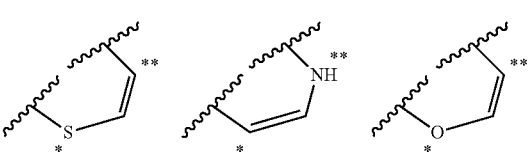

-continued

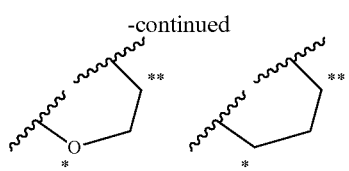

wherein * and ** are as defined above;
$R^7$ in the number of n are each independently a halogen atom, a cyano group, a $C_{1-6}$ alkyl group or a $C_{1-6}$ alkoxy group (preferably, each independently a $C_{1-6}$ alkyl group);
n is an integer of 0 to 2 (preferably, 0 or 1); and
Z is a group represented by the following formula (A1) or (A2):

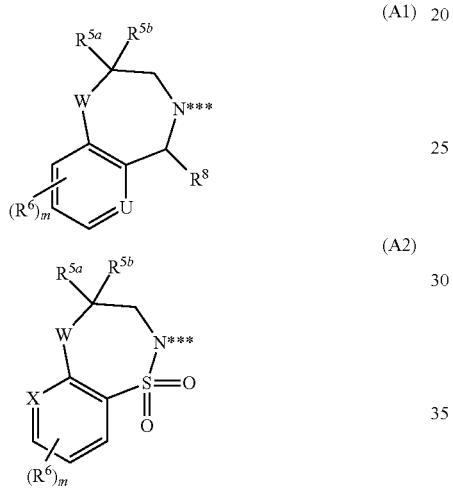

wherein
*** is the bonding position to the carbon atom to which Z is bonded,
$R^8$ is a methyl group or an ethyl group,
$R^{5a}$ and $R^{5b}$ are each a hydrogen atom, a $C_{1-6}$ alkyl group optionally substituted by 1 to 3 substituents selected from the aforementioned substituent group a, or a $C_{3-6}$ cycloalkyl group, or
$R^{5a}$ and $R^{5b}$ are bonded together to form, together with the carbon atom to which $R^{5a}$ and $R^{5b}$ are bonded, a $C_{3-6}$ cycloalkane which is optionally substituted by 1 to 3 substituents selected from substituent group b, or a 3- to 8-membered saturated oxygen-containing heterocycle,
$R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups,
m is an integer of 0 to 3,
W is —$CH_2$—, —$CHR^9$— or an oxygen atom,
$R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
X is —CH—, —$CR^{10}$— or a nitrogen atom,
$R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
U is —CH—, —$CR^{11}$— or a nitrogen atom, and
$R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
or a pharmaceutically acceptable salt thereof.

[Compound (1H)]
Compound (1) wherein $R^{1a}$ and $R^{1b}$ are each independently a hydrogen atom or a $C_{1-6}$ alkyl group (preferably, each independently a hydrogen atom or a methyl group);
$R^2$ is a $C_{1-6}$ alkyl group optionally substituted by 1 to 3 substituents selected from the aforementioned substituent group a (preferably, a $C_{1-6}$ alkyl group, a 2-dimethylaminoethyl group, a 2,2,2-trifluoroethyl group, a 2-hydroxy-2-methylpropyl group or a 3-(methylsulfonyl)propyl group);
$R^3$ is a hydrogen atom, a halogen atom or a $C_{1-6}$ alkyl group (preferably, a halogen atom or a $C_{1-6}$ alkyl group);
Y is —CH—, —$CR^4$— or a nitrogen atom;
$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group (preferably, a hydroxy group, a chlorine atom, a cyano group, a methyl group, a methoxy group, a cyclopropyl group, a trifluoromethyl group, a difluoromethoxy group or a trifluoromethoxy group);
—V— is a group represented by any of the following formulas:

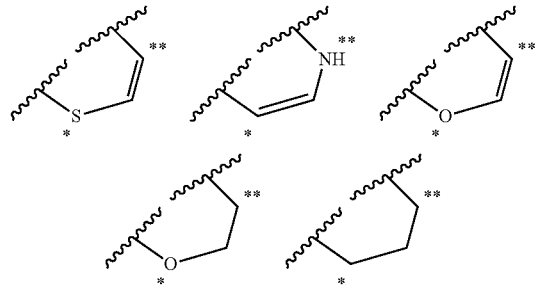

wherein * and ** are as defined above;
$R^7$ in the number of n are each independently a halogen atom, a cyano group, a $C_{1-6}$ alkyl group or a $C_{1-6}$ alkoxy group (preferably, each independently a $C_{1-6}$ alkyl group);
n is an integer of 0 to 2 (preferably, 0 or 1); and
Z is a group represented by the following formula (A1) or (A2):

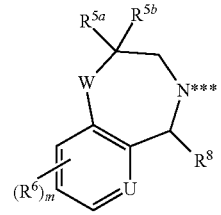

-continued

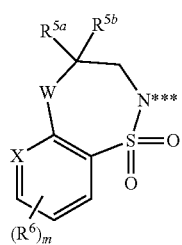

(A2)

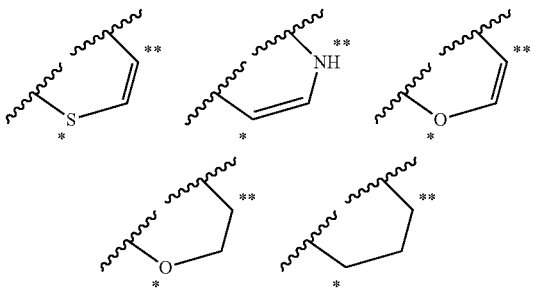

wherein * and ** are as defined above;
R⁷ in the number of n are each independently a halogen atom, a cyano group, a $C_{1-6}$ alkyl group or a $C_{1-6}$ alkoxy group (preferably, each independently a $C_{1-6}$ alkyl group);
n is an integer of 0 to 2 (preferably, 0 or 1); and
Z is a group represented by the following formula (A1) or (A2):

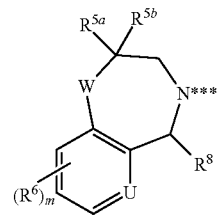

(A1)

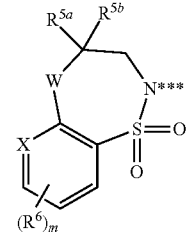

(A2)

wherein

*** is the bonding position to the carbon atom to which Z is bonded,

R⁸ is a methyl group or an ethyl group, $R^{5a}$ and $R^{5b}$ are each independently a hydrogen atom, a methyl group, an ethyl group or a cyclopropyl group, or $R^{5a}$ and $R^{5b}$ are bonded together to form cyclopropane, cyclobutane, oxetane or tetrahydropyran, R⁶ in the number of m are each independently a hydroxy group, a fluorine atom, a chlorine atom, a methyl group, an ethoxy group or a trifluoromethyl group, and m is an integer of 0 to 2, W is —CH₂—, —CHR⁹— or an oxygen atom, R⁹ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —CR¹⁰— or a nitrogen atom, R¹⁰ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —CR¹¹— or a nitrogen atom, and R¹¹ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1J)]

Compound (1) wherein $R^{1a}$ and $R^{1b}$ are each independently a hydrogen atom or a $C_{1-6}$ alkyl group (preferably, each independently a hydrogen atom or a methyl group);

R² is a $C_{1-6}$ alkyl group optionally substituted by 1 to 3 substituents selected from the aforementioned substituent group a (preferably, a $C_{1-6}$ alkyl group, a 2-dimethylaminoethyl group, a 2,2,2-trifluoroethyl group, a 2-hydroxy-2-methylpropyl group or a 3-(methylsulfonyl) propyl group);

R³ is a hydrogen atom, a halogen atom or a $C_{1-6}$ alkyl group (preferably, a halogen atom or a $C_{1-6}$ alkyl group);

Y is —CH—, —CR⁴— or a nitrogen atom;

R⁴ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group (preferably, a hydroxy group, a chlorine atom, a cyano group, a methyl group, a methoxy group, a cyclopropyl group, a trifluoromethyl group, a difluoromethoxy group or a trifluoromethoxy group);

—V— is a group represented by any of the following formulas:

wherein

*** is the bonding position to the carbon atom to which Z is bonded,

R⁸ is a methyl group or an ethyl group, $R^{5a}$ and $R^{5b}$ are each independently a hydrogen atom, a methyl group, an ethyl group or a cyclopropyl group, or $R^{5a}$ and $R^{5b}$ are bonded together to form cyclopropane, cyclobutane, oxetane or tetrahydropyran, R⁶ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups, m is an integer of 0 to 3, W is —CH₂—, —CHR⁹— or an oxygen atom, R⁹ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, X is —CH—, —CR¹⁰— or a nitrogen atom, R¹⁰ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —CR¹¹— or a nitrogen atom, and R¹¹ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1K)]

Compound (1) wherein $R^{1a}$ and $R^{1b}$ are each independently a hydrogen atom or a $C_{1-6}$ alkyl group (preferably, each independently a hydrogen atom or a methyl group);

$R^2$ is a $C_{1-6}$ alkyl group optionally substituted by 1 to 3 substituents selected from the aforementioned substituent group a (preferably, a $C_{1-6}$ alkyl group, a 2-dimethylaminoethyl group, a 2,2,2-trifluoroethyl group, a 2-hydroxy-2-methylpropyl group or a 3-(methylsulfonyl)propyl group);

$R^3$ is a hydrogen atom, a halogen atom or a $C_{1-6}$ alkyl group (preferably, a halogen atom or a $C_{1-6}$ alkyl group);

Y is —CH—, —$CR^4$— or a nitrogen atom;

$R^4$ is a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group (preferably, a hydroxy group, a chlorine atom, a cyano group, a methyl group, a methoxy group, a cyclopropyl group, a trifluoromethyl group, a difluoromethoxy group or a trifluoromethoxy group);

—V— is a group represented by any of the following formulas:

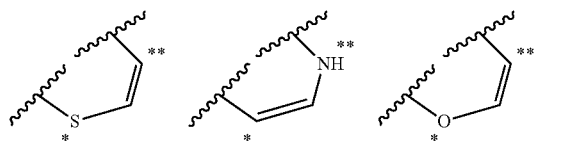

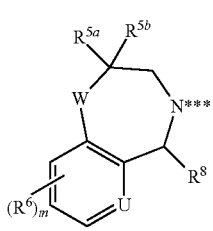

wherein * and ** are as defined above;

$R^7$ in the number of n are each independently a halogen atom, a cyano group, a $C_{1-6}$ alkyl group or a $C_{1-6}$ alkoxy group (preferably, each independently, a $C_{1-6}$ alkyl group);

n is an integer of 0 to 2 (preferably, 0 or 1); and

Z is a group represented by the following formula (A1) or (A2):

(A1)

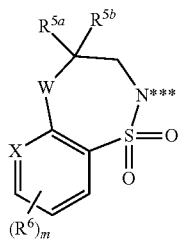

(A2)

wherein

*** is the bonding position to the carbon atom to which Z is bonded, $R^8$ is a methyl group or an ethyl group, $R^{5a}$ and $R^{5b}$ are each independently a hydrogen atom, a methyl group, an ethyl group or a cyclopropyl group, or $R^{5a}$ and $R^{5b}$ are bonded together to form cyclopropane, cyclobutane, oxetane or tetrahydropyran, $R^6$ in the number of m are each independently a hydroxy group, a fluorine atom, a chlorine atom, a methyl group, an ethoxy group or a trifluoromethyl group, and m is an integer of 0 to 2, W is —$CH_2$— or an oxygen atom, X is —CH—, —$CR^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —$CR^{11}$— or a nitrogen atom, and $R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1L)]

Compound (1) wherein $R^{1a}$ and $R^{1b}$ are each independently a hydrogen atom or a methyl group;

$R^2$ is a $C_{1-6}$ alkyl group, a 2-dimethylaminoethyl group, a 2,2,2-trifluoroethyl group, a 2-hydroxy-2-methylpropyl group or a 3-(methylsulfonyl)propyl group;

$R^3$ is a halogen atom or a $C_{1-6}$ alkyl group;

Y is —CH—, —$CR^4$— or a nitrogen atom;

$R^4$ is a hydroxy group, a chlorine atom, a cyano group, a methyl group, a methoxy group, a cyclopropyl group, a trifluoromethyl group, a difluoromethoxy group or a trifluoromethoxy group;

—V— is a group represented by any of the following formulas:

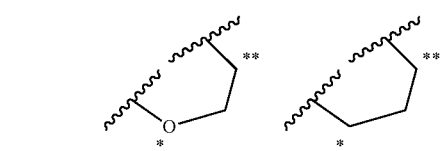

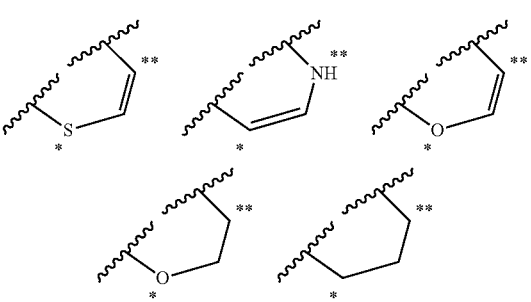

wherein * and ** are as defined above;

$R^7$ in the number of n are each independently a $C_{1-6}$ alkyl group;

n is 0 or 1; and

Z is a group represented by the following formula (A1) or (A2):

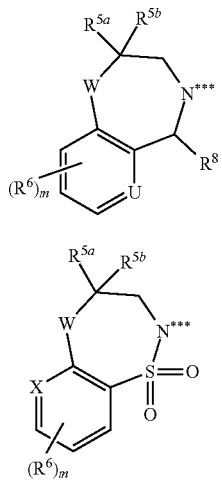

wherein
*** is the bonding position to the carbon atom to which Z is bonded,
$R^8$ is a $C_{1-6}$ alkyl group optionally substituted by 1 to 3 substituents selected from the aforementioned substituent group a,
$R^{5a}$ and $R^{5b}$ are each a hydrogen atom, a $C_{1-6}$ alkyl group optionally substituted by 1 to 3 substituents selected from the aforementioned substituent group a, or a $C_{3-6}$ cycloalkyl group, or
$R^{5a}$ and $R^{5b}$ are bonded together to form, together with the carbon atom to which $R^{5a}$ and $R^{5b}$ are bonded, a $C_{3-8}$ cycloalkane which is optionally substituted by 1 to 3 substituents selected from substituent group b, or a 3- to 8-membered saturated oxygen-containing heterocycle,
$R^6$ in the number of m are each independently a hydroxy group, a halogen atom, a cyano group, a $C_{1-6}$ alkyl group, a $C_{1-6}$ alkoxy group, a $C_{3-6}$ cycloalkyl group, a $C_{1-6}$ haloalkyl group, a $C_{1-6}$ haloalkoxy group, or an amino group optionally substituted by 1 or 2 $C_{1-6}$ alkyl groups,
m is an integer of 0 to 3,
W is —$CH_2$—, —$CHR^9$— or an oxygen atom,
$R^9$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
X is —CH—, —$CR^{10}$— or a nitrogen atom,
$R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
U is —CH—, —$CR^{11}$— or a nitrogen atom, and
$R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group,
or a pharmaceutically acceptable salt thereof.

[Compound (1M)]

Compound (1) wherein $R^{1a}$ and $R^{1b}$ are each independently a hydrogen atom or a methyl group;
$R^2$ is a $C_{1-6}$ alkyl group, a 2-dimethylaminoethyl group, a 2,2,2-trifluoroethyl group, a 2-hydroxy-2-methylpropyl group or a 3-(methylsulfonyl)propyl group;
$R^3$ is a halogen atom or a $C_{1-6}$ alkyl group;
Y is —CH—, —$CR^4$— or a nitrogen atom;
$R^4$ is a hydroxy group, a chlorine atom, a cyano group, a methyl group, a methoxy group, a cyclopropyl group, a trifluoromethyl group, a difluoromethoxy group or a trifluoromethoxy group;
—V— is a group represented by any of the following formulas:

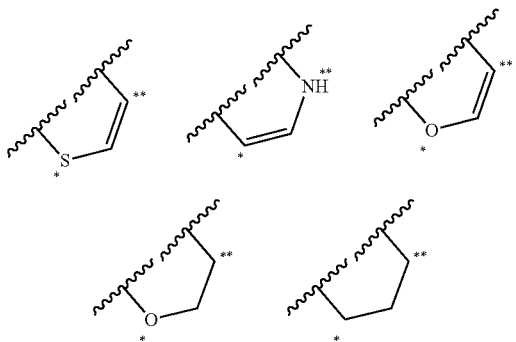

wherein * and ** are as defined above;
$R^7$ in the number of n are each independently a $C_{1-6}$ alkyl group;
n is 0 or 1; and
Z is a group represented by the following formula (A1) or (A2):

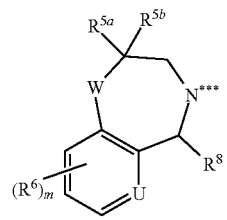

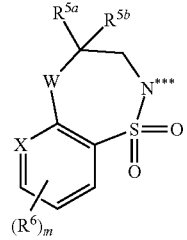

wherein
*** is the bonding position to the carbon atom to which Z is bonded,
$R^8$ is a methyl group or an ethyl group,
$R^{5a}$ and $R^{5b}$ are each independently a hydrogen atom, a methyl group, an ethyl group or a cyclopropyl group, or
$R^{5a}$ and $R^{5b}$ are bonded together to form cyclopropane, cyclobutane, oxetane or tetrahydropyran,
$R^6$ in the number of m are each independently a hydroxy group, a fluorine atom, a chlorine atom, a methyl group, an ethoxy group or a trifluoromethyl group, and
m is an integer of 0 to 2,
W is —$CH_2$— or an oxygen atom,
X is —CH—, —$CR^{10}$— or a nitrogen atom, $R^{10}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, U is —CH—, —$CR^{11}$— or a nitrogen atom, and $R^{11}$ is a halogen atom, a cyano group, a $C_{1-6}$ alkyl group, a $C_{1-6}$ alkoxy group, a $C_{3-6}$ cycloalkyl group, a $C_{1-6}$ haloalkyl group or a $C_{1-6}$ haloalkoxy group, or a pharmaceutically acceptable salt thereof.

[Compound (1N)]

Compound (1) wherein $R^{1a}$ and $R^{1b}$ are each independently a hydrogen atom or a methyl group;

$R^2$ is a methyl group;

$R^3$ is a chlorine atom or a methyl group;

Y is —CH—, —$CR^4$— or a nitrogen atom;

$R^4$ is a chlorine atom, a methyl group, a cyclopropyl group, a difluoromethoxy group or a trifluoromethoxy group;

—V— is a group represented by any of the following formulas:

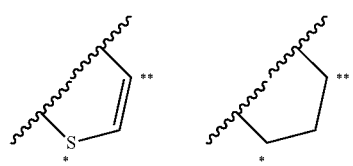 [SMILES: */C=C\S* ; *CCC*]

wherein * and ** are as defined above;

n is 0; and

Z is a group represented by the following formula:

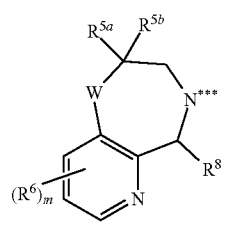

wherein *** is the bonding position to the carbon atom to which Z is bonded, $R^8$ is a methyl group or an ethyl group, $R^{5a}$ and $R^{5b}$ are each independently a hydrogen atom, a methyl group, an ethyl group or a cyclopropyl group, or $R^{5a}$ and $R^{5b}$ are bonded together to form cyclopropane, cyclobutane, oxetane or tetrahydropyran, $R^6$ in the number of m are each independently a hydroxy group, a fluorine atom, a chlorine atom, a methyl group, an ethoxy group or a trifluoromethyl group, m is an integer of 0 to 2, and W is —$CH_2$— or an oxygen atom, or a group represented by the following formula:

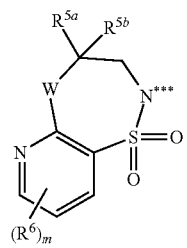

wherein *** is the bonding position to the carbon atom to which Z is bonded, $R^{5a}$ and $R^{5b}$ are each independently a hydrogen atom, a methyl group, an ethyl group or a cyclopropyl group, or $R^{5a}$ and $R^{5b}$ are bonded together to form cyclopropane, cyclobutane, oxetane or tetrahydropyran, $R^6$ in the number of m are each independently a hydroxy group, a fluorine atom, a chlorine atom, a methyl group, an ethoxy group or a trifluoromethyl group, m is an integer of 0 to 2, and W is —$CH_2$— or an oxygen atom, or a pharmaceutically acceptable salt thereof.

[Compound (1P)]

Compound (1) wherein $R^{1a}$ and $R^{1b}$ are each independently a hydrogen atom or a methyl group;

$R^2$ is a methyl group;

$R^3$ is a chlorine atom or a methyl group;

Y is —CH—, —$CR^4$— or a nitrogen atom;

$R^4$ is a chlorine atom, a methyl group, a cyclopropyl group, a difluoromethoxy group or a trifluoromethoxy group;

—V— is a group represented by any of the following formulas:

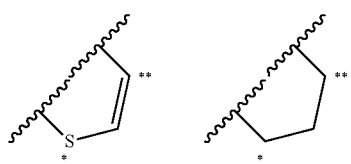 [SMILES: */C=C\S* ; *CCC*]

wherein * and ** are as defined above;

n is 0; and

Z is a group represented by the following formula:

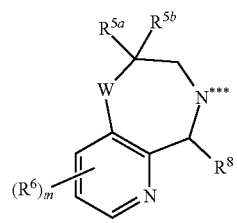

wherein *** is the bonding position to the carbon atom to which Z is bonded, $R^8$ is a methyl group or an ethyl group, $R^{5a}$ and $R^{5b}$ are each independently a hydrogen atom or an ethyl group, or $R^{5a}$ and $R^{5b}$ are bonded together to form cyclopropane, $R^6$ in the number of m are each independently a chlorine atom or a hydroxy group, m is 0 or 1, and W is an oxygen atom, or a group represented by the following formula:

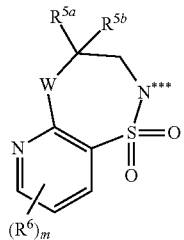

wherein *** is the bonding position to the carbon atom to which Z is bonded, $R^{5a}$ and $R^{5b}$ are each independently a hydrogen atom, a methyl group, an ethyl group or a cyclopropyl group, or $R^{5a}$ and $R^{5b}$ are bonded together to form cyclopropane, cyclobutane, oxetane or tetrahydropyran, $R^6$ in the number of m are each independently a hydroxy group, a fluorine atom, a chlorine atom, a methyl group, an ethoxy group or a trifluoromethyl group, m is an integer of 0 to 2, and W is an oxygen atom, or a pharmaceutically acceptable salt thereof.

Another preferred embodiment of the compound (1) of the present invention or a pharmaceutically acceptable salt thereof is a compound (1) represented by the following formula (1'):

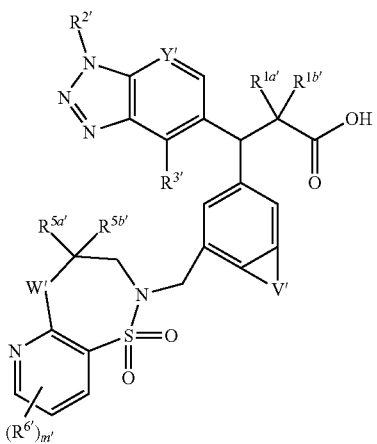

(1')

wherein $R^{1a'}$ and $R^{1b'}$ are each independently a hydrogen atom or a methyl group, $R^{2'}$ is a methyl group, $R^{3'}$ is a chlorine atom or a methyl group, Y' is —CH—, —CR$^{4'}$— or a nitrogen atom, $R^{4'}$ is a chlorine atom, a methyl group, a cyclopropyl group, a difluoromethoxy group or a trifluoromethoxy group, —V'— is any group selected from the following formulas:

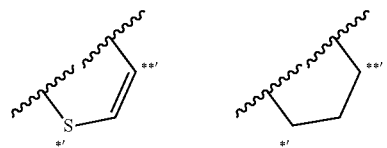 [SMILES: */C=C\S* ; *CCC*]

wherein *' and **' are each a bonding position to a benzene ring, $R^{5a'}$ and $R^{5b'}$ are each independently a hydrogen atom or an ethyl group, or $R^{5a'}$ and $R^{5b'}$ are bonded together to form cyclopropane, $R^{6'}$ in the number of m' are each independently a fluorine atom or a chlorine atom, m' is an integer of 0 to 2, and W' is an oxygen atom, or a pharmaceutically acceptable salt thereof, or a compound (1) represented by the following formula (1"):

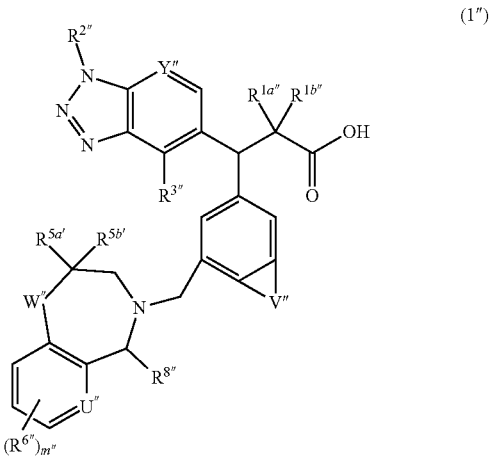

(1")

wherein $R^{1a''}$ and $R^{1b''}$ are each independently a hydrogen atom or a methyl group, $R^{2''}$ is a methyl group, $R^{3''}$ is a chlorine atom or a methyl group, Y" is —CH—, —CR$^{4''}$— or a nitrogen atom, $R^{4''}$ is a chlorine atom, a methyl group, a cyclopropyl group, a difluoromethoxy group or a trifluoromethoxy group, —V"— is any group selected from the following formulas:

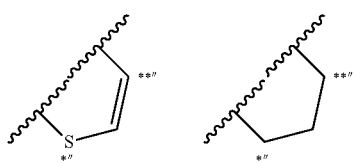 [SMILES: */C=C\S* ; *CCC*]

wherein *" and **" are each a bonding position to a benzene ring, $R^{5a''}$ and $R^{5b''}$ are each independently a hydrogen atom or an ethyl group, or $R^{5a''}$ and $R^{5b''}$ are bonded together to form cyclopropane, R⁸" is a methyl group or an ethyl group,
R⁶" in the number of m" are each a chlorine atom or a hydroxy group,
m" is 0 or 1,
U" is a nitrogen atom, and
W" is an oxygen atom,
or a pharmaceutically acceptable salt thereof.

Specific examples of preferred compound (1) are compounds of the below-mentioned Examples 1 to 112 or pharmaceutically acceptable salts thereof, more preferably any compound (1) selected from the following group or a pharmaceutically acceptable salt thereof:

(3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)-2,2-dimethylpropanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoic acid, (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid, (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoic acid, and (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoic acid, or any compound (1) selected from the following group or a pharmaceutically acceptable salt thereof:

(3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, (3S)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, (3R)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, (3R)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid, (3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid, (3R)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoic acid, (3S)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoic acid, (3S)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)-3-(1,4,7-trimethyl-1H-benzotriazol-5-yl)propanoic acid, (3R)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid, (3S)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid, (3S)-3-(4-chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, (3R)-3-(4-chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid, and (3S)-3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid.

Particularly preferred are
(3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid,
(3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid,
(3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid, and
(3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid.

Since the compound (1) of the present invention has a basic group such as a nitrogen-containing heterocyclic group in the molecule, it can generally form a pharmaceutically acceptable acid addition salt. Examples of such acid addition salts include hydrohalides such as hydrofluoride, hydrochloride, hydrobromide, hydroiodide and the like; inorganic acid salts such as nitrate, perchlorate, sulfate, phosphate and the like; lower alkane sulfonates such as methanesulfonate, trifluoromethanesulfonate, ethanesulfonate and the like; arylsulfonates such as benzenesulfonate, p-toluenesulfonate and the like; organic acid salts such as acetate, malate, fumarate, succinate, citrate, tartrate, oxalate, maleate, mucicate, adipate and the like; amino acid salts such as ornithinate, glutamate, aspartate and the like; and the like. Among them, hydrohalides, arylsulfonates, and organic acid salts are preferred.

The acid addition salt of the compound (1) of the present invention includes an acid addition salt that can be formed by combining an acid added to the compound of the present invention with the compound (1) of the present invention in any ratio. For example, the hydrochloride includes salts that can be formed such as monohydrochloride, dihydrochloride, trihydrochloride, and the like, the fumarate includes salts that can be formed such as monofumarate, ½ fumarate, and the like, and the succinate includes salts that can be formed such as monosuccinate, ⅔ succinate, ⅓ succinate, and the like.

Since the compound (1) of the present invention has a carboxy group in the molecule, it can generally form a pharmaceutically acceptable base addition salt. Examples of such base addition salt include alkali metal salts such as sodium salt, potassium salt, lithium salt and the like; alkaline earth metal salts such as calcium salt, magnesium salt and the like; inorganic salts such as ammonium salt and the like; and organic amine salts such as dibenzylamine salt, morpholine salt, alkyl phenylglycinate salt, ethylenediamine salt, N-methylglucamine salt, diethylamine salt, triethylamine salt, cyclohexylamine salt, dicyclohexylamine salt, N,N'-dibenzylethylenediamine salt, diethanolamine salt, N-benzyl-N-(2-phenylethoxy)amine salt, piperazine salt, tetramethylammonium salt, tris(hydroxymethyl)aminomethane salt and the like.

When the compound (1) of the present invention has an asymmetric carbon atom in the molecule, it may exist as a plurality of stereoisomers (i.e., diastereoisomers, optical isomers) based on the asymmetric carbon atom. The present invention encompasses any one of these stereoisomers and a mixture containing the plurality of stereoisomers in any ratio. In addition, isomers due to conformation or tautomerism may be generated. Such isomers and mixtures thereof are also encompassed in the compound (1) of the present invention.

In the names of the compounds of the present invention, when the compound has a carbon atom that serves as an asymmetric center in the compound structure, the absolute configuration thereof is indicated by R and S (along with the position number).

Even when optical isomers have been separated, if the configuration of the carbon atom that serves as an asymmetric center in the compound structure has not been determined, it is indicated by R* or S*.

Furthermore, by using R* and S* simultaneously, the relative configuration may be indicated even when the absolute configuration has not been determined.

The compound (1) of the present invention may be labeled or substituted by isotopes (e.g., $^2$H, $^3$H, $^{13}$C, $^{14}$C, $^{15}$N, $^{18}$F, $^{32}$P, $^{35}$S, $^{125}$I, etc.), and compounds (1) labeled or substituted by isotopes are useful as therapeutic or prophylactic agents, research reagents (e.g., assay reagents), and diagnostic agents (e.g., in vivo imaging agents). The compound of the present invention containing all proportions of radioactive or non-radioactive isotopes are within the scope of the present invention.

The compound (1) of the present invention or a pharmaceutically acceptable salt thereof may be crystal, in a single crystal form or in a mixture of several crystal forms.

The compound (1) of the present invention may also exist as a non-solvate or solvate. The solvate is not particularly limited as long as it is pharmaceutically acceptable, and hydrate, ethanol solvate and the like are specifically preferred.

The compound (1) of the present invention may be a prodrug.

Prodrugs of compound (1) of the present invention are compounds that are converted to compound (1) in vivo by reactions with enzymes, gastric acid and the like. Prodrugs of compound (1) may have a structure that are easily hydrolyzed or metabolized after administration to a patient.

As prodrugs of compound (1), for example, when compound (1) has an amino group, compounds in which the amino group is acylated, alkylated, or phosphorylated (e.g., eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, and the like); when compound (1) has an hydroxy group, compounds in which the hydroxy group of compound (1) is acylated, alkylated, phosphorylated, or borylated (e.g., compounds in which the hydroxy group of compound (1) is acetylated, palmitoylated, propanoylated, pivaloylated, succinylated, fumarylated, alanylated, dimethylaminomethylcarbonylated, etc.); compounds in which the carboxy group of compound (1) is esterified, amidated (e.g., compounds in which the carboxy group of compound (1) is ethyl esterified, phenyl esterified, carboxymethyl esterified, dimethylaminomethyl esterified, pivaloyloxymethyl esterified, 1-{(ethoxycarbonyl)oxy}ethyl esterified, phthalidyl esterified, (5-methyl-2-oxo-1,3-dioxolen-4-yl)methyl esterified, 1-{[(cyclohexyloxy)carbonyl]oxy}ethyl esterified, methylamidated compounds, etc.).

Prodrugs of compound (1) can be made from compound (1) by known methods. Prodrugs of compound (1) also include those that change to compound (1) under physiological conditions, as described in "Development of Pharmaceuticals", Vol. 7, Molecular Design, pp. 163-198, published by Hirokawa Shoten 1990. Furthermore, prodrugs of compound (1) may be both hydrate and non-hydrate.

(Production Methods of the Compound (1) of the Present Invention)

Representative methods for producing compound (1) of the present invention or a pharmaceutically acceptable salt thereof are described below. Compound (1') and compound (1") of the present invention are also included in compound (1), and therefore, the methods for producing compound (1') and compound (1") are hereinafter also referred to as the production method of compound (1).

The compound (1) of the present invention can be produced by various production methods, and the production methods shown below and Reference Examples and Examples described below are only examples, and the present invention should not be interpreted as being limited to these.

Each raw material compound may form a salt as long as it does not inhibit the reaction, and examples of such salts include the same as the pharmaceutically acceptable salts of compound (1) described above.

When no specific production method is described, the raw material compounds can be easily obtained from commercial sources and used, or can be produced according to a method known per se or a method equivalent thereto. In addition, the production intermediates generated in the following production methods may be isolated and purified by a method such as column chromatography (including normal phase and reverse phase) using silica gel or alumina, recrystallization, reprecipitation, distillation, and the like, or may be used directly in the next reaction without isolation and purification.

In the present specification, all patent literature, non-patent literature, or references expressly cited herein may all be cited herein as a part of the present specification.

The compound (1), a pharmaceutically acceptable salt thereof, and a production intermediate therefor can be produced utilizing the characteristics based on the kind of the basic skeleton or substituent, and applying various known production methods. Examples of the known method include the methods described in "ORGANIC FUNCTIONAL GROUP PREPARATIONS", 2nd edition, ACADEMIC PRESS, INC., 1989, "Comprehensive Organic Transformations", 2nd edition, VCH Publishers Inc., 1999, and the like.

In such cases, depending on the type of functional group present in the compound, it may be effective in terms of manufacturing technology to protect the functional group with an appropriate protecting group at the starting material or intermediate stage, or to replace the functional group with a group that can be easily converted to the functional group concerned.

Examples of the functional group include amino group, hydroxy group, formyl group, carbonyl group, carboxy group, and the like, and examples of the protecting group thereof include the protecting groups described in P.G. Wuts, "Protective Groups in Organic Synthesis (3rd ed., 1999)", and examples of the protecting group thereof include P. G. Wuts, "Protective Groups in Organic Synthesis", 5th edition, Wiley, 2014.

The protecting group or the group that can be easily converted into the functional group may be appropriately selected depending on the reaction conditions of the production method for producing the compound.

According to such a method, a desired compound can be obtained by introducing the group and performing a reaction, and then removing the protecting group as necessary or converting same into a desired group.

A prodrug of the compound can be produced by, similar to the above-mentioned protecting groups, introducing a particular group in the stage of a starting material or intermediate, or by a reaction using the obtained compound. The reaction for producing a prodrug can be performed by those of ordinary skill in the art, by applying a known method such as general esterification, amidation, dehydration, hydrogenation and the like.

The compound (1) of the present invention can be produced, for example, by the following Method A to Method C. The production intermediates used in Method A to Method C can be produced, for example, by the following Method D to Method J.

In the reactions in each step of the following Method A to Method J, the reaction temperature varies depending on the solvent, starting material, reagents, and the like, and the reaction time varies depending on the solvent, starting material, reagents, reaction temperature, and the like. Furthermore, the amounts of the solvent, starting material, reagents, and the like used can be appropriately determined depending on the progress of the reaction.

The conversion of functional groups on heterocycles in the production intermediates used in each step of the following Method A to Method J can be performed by a method known per se (specifically, the reaction conditions for converting a halogen atom to a $C_{1-6}$ alkyl group or a $C_{3-6}$ cycloalkyl group are described in, for example, Zou, G.; Reddy, Y. K.; Falck, J. R. Tetrahedron Lett. 2001, 42, 7213, Molander, G. A.; Yun, C. —S. Tetrahedron 2002, 58, 1465, Tsuji, J. Palladium Reagents and Catalysts; John Wiley & Sons, Inc.: England 2004, Metal-Catalyzed Cross-Coupling Reactions; de Meijere, A.; Diederich, F.; Wiley-VCH: Weinheim, 2004 and the like) or a method analogous thereto, or the method described in Examples below or a method analogous thereto.

(Method A)

In this production method, compound (IIA) and compound (III) are condensed to obtain compound (IV), and then the protecting group of compound (IV) is removed to produce compound (1).

(Method A)

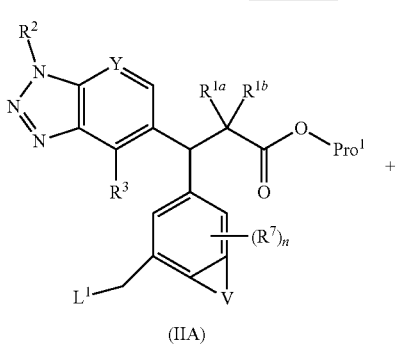

(IIA)

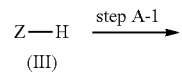

(III)

[Structure IV: triazole-fused ring with R², Y, R¹ᵃ, R¹ᵇ substituents and ester group -O-Pro¹, R³, Z, and phenyl with (R⁷)ₙ and V] step A-2 →

[Structure (1): same as IV but with -OH instead of -O-Pro¹]

wherein L¹ is a leaving group, Pro¹ is a protecting group (preferably a $C_{1-6}$ alkyl group such as methyl group, ethyl group, tert-butyl group and the like, or 2-(trimethylsilyl)ethyl group), and other symbols are as defined above.

(Step A-1)

In this step, compound (IIA) and compound (III) are condensed in the presence or absence of a base, in a solvent to produce compound (IV).

The solvent to be used is not particularly limited as long as it does not inhibit the reaction and dissolves the starting materials to some extent, and preferred examples include aromatic hydrocarbons such as benzene, toluene, xylene, and the like; halogenated hydrocarbons such as dichloromethane, chloroform, and the like; esters such as ethyl acetate, propyl acetate, and the like; ethers such as diethyl ether, tetrahydrofuran, 1,4-dioxane, 1,2-dimethoxyethane, and the like; alcohols such as methanol, ethanol, tert-butanol, and the like; nitriles such as acetonitrile, and the like; amides such as formamide, N,N-dimethylformamide, and the like; sulfoxides such as dimethyl sulfoxide, and the like; mixed solvents containing a plurality of the organic solvents mentioned above in any ratio; mixed solvents containing the organic solvents mentioned above and water in any ratio; and the like.

The base to be used is not particularly limited as long as it is one that is used as a base in a normal reaction. Preferred examples of the base include organic bases such as triethylamine, N,N-diisopropylethylamine, N-methylmorpholine, lutidine, pyridine, and the like; alkali metal carbonates such as sodium carbonate, potassium carbonate, and the like; alkaline earth metal carbonates such as magnesium carbonate, and the like; alkali metal hydrogen carbonates such as potassium hydrogen carbonate, and the like; alkaline earth metal hydrogen carbonates such as calcium hydrogen carbonate, and the like; alkali metal hydroxides such as sodium hydroxide, and the like; alkaline earth metal hydroxides such as magnesium hydroxide, and the like; alkali metal phosphates such as tripotassium phosphate, and the like.

While the reaction temperature varies depending on the raw material compounds, reagents, and the like, it is generally −10° C. to 150° C., preferably 0° C. to 100° C.

While the reaction time varies depending on the raw material compounds, reagents, and the like, it is generally 5 min to 48 hr, preferably 10 min to 24 hr.

(Step A-2)

In this step, the protecting group (Pro¹) of compound (IV) is removed to produce compound (1).

This step is performed according to a known method appropriately selected from, for example, P. G. Wuts, "Protective Groups in Organic Synthesis", 5th Edition, Wiley, 2014, and the like, depending on the type of Pro¹. Here, a method of converting Pro¹ to a hydrogen atom by using a base in a solvent (Step A-2-1), a method of converting Pro¹ to a hydrogen atom by using an acid in a solvent (Step A-2-2), or a method of converting Pro¹ to a hydrogen atom by using a fluoride salt in a solvent (Step A-2-3) is described; however, this step is not limited thereto.

(Step A-2-1)

The solvent to be used is not particularly limited as long as it does not inhibit the reaction and dissolves the starting materials to some extent, and preferred examples include aromatic hydrocarbons such as benzene, toluene, xylene, and the like; halogenated hydrocarbons such as dichloromethane, chloroform, and the like; ethers such as diethyl ether, tetrahydrofuran, 1,4-dioxane, 1,2-dimethoxyethane, and the like; alcohols such as methanol, ethanol, tert-butanol, and the like; esters such as ethyl acetate, propyl acetate, and the like; nitriles such as acetonitrile, and the like; amides such as formamide, N,N-dimethylformamide, and the like; sulfoxides such as dimethyl sulfoxide, and the like; mixed solvents containing a plurality of the organic solvents mentioned above in any ratio; mixed solvents containing the organic solvents mentioned above and water in any ratio; and the like.

The base to be used is not particularly limited as long as it is one that is used as a base in a normal reaction. Examples of the base include organic bases such as triethylamine, and the like; alkali metal carbonates such as sodium carbonate, potassium carbonate, and the like; alkaline earth metal carbonates such as magnesium carbonate, and the like; alkali metal hydrogen carbonates such as potassium hydrogen carbonate, and the like; alkaline earth metal hydrogen carbonates such as calcium hydrogen carbonate, and the like; alkali metal hydroxides such as lithium hydroxide, sodium hydroxide, potassium hydroxide and the like; alkaline earth metal hydroxides such as magnesium hydroxide, and the like; alkali metal phosphates such as tripotassium phosphate, and the like.

While the reaction temperature varies depending on the raw material compounds, reagents, and the like, it is generally −10° C. to 150° C., preferably 10° C. to 90° C.

While the reaction time varies depending on the raw material compounds, reagents, and the like, it is generally 1 min to 24 hr, preferably 10 min to 6 hr.

(Step A-2-2)

The solvent to be used is not particularly limited as long as it does not inhibit the reaction and dissolves the starting material to some extent, and preferred examples include aromatic hydrocarbons such as benzene, toluene, xylene, and the like; halogenated hydrocarbons such as dichloromethane, chloroform, and the like; ethers such as diethyl ether, tetrahydrofuran, 1,4-dioxane, 1,2-dimethoxyethane, and the like; alcohols such as methanol, ethanol, tert-butanol, and the like; esters such as ethyl acetate, propyl acetate, and the like; nitriles such as acetonitrile, and the like; amides such as formamide, N,N-dimethylformamide, and the like; sulfoxides such as dimethyl sulfoxide, and the like; mixed solvents containing a plurality of the organic solvents mentioned above in any ratio; mixed solvents containing the organic solvents mentioned above and water in any ratio; and the like.

The acid to be used is not particularly limited as long as it is an acid that is used in normal reactions. Examples thereof include inorganic acids such as hydrochloric acid, sulfuric acid and the like; Lewis acids such as boron trifluoride, boron trichloride, boron tribromide, iodotrimethylsilane and the like; and organic acids such as trifluoroacetic acid and the like.

While the reaction temperature varies depending on the raw material compounds, reagents, and the like, it is generally −100° C. to 150° C., preferably −78° C. to 100° C.

While the reaction time varies depending on the raw material compounds, reagents, and the like, it is generally 5 min to 24 hr, preferably 10 min to 6 hr.

(Step A-2-3)

The solvent to be used is not particularly limited as long as it does not inhibit the reaction and dissolves the starting material to some extent, and preferred examples include aromatic hydrocarbons such as benzene, toluene, xylene, and the like; halogenated hydrocarbons such as dichloromethane, chloroform, and the like; ethers such as diethyl ether, tetrahydrofuran, 1,4-dioxane, 1,2-dimethoxyethane, and the like; alcohols such as methanol, ethanol, tert-butanol, and the like; esters such as ethyl acetate, propyl acetate, and the like; nitriles such as acetonitrile, and the like; amides such as formamide, N,N-dimethylformamide, and the like; sulfoxides such as dimethyl sulfoxide, and the like; mixed solvents containing a plurality of the organic solvents mentioned above in any ratio; mixed solvents containing the organic solvents mentioned above and water in any ratio; and the like.

The fluoride salt to be used is not particularly limited and, for example, tetrabutylammonium fluoride, hydrogen fluoride pyridine and the like can be mentioned.

While the reaction temperature varies depending on the raw material compounds, reagents, and the like, it is generally −100° C. to 100° C., preferably −20° C. to 60° C.

While the reaction time varies depending on the raw material compounds, reagents, and the like, it is generally 5 min to 48 hr, preferably 10 min to 24 hr.

(Method B)

In the present production method, compound (IIB) and compound (III) are subjected to a reductive amination reaction to give compound (IV), and then the protecting group of compound (IV) is removed to produce compound (1).

(Method B)

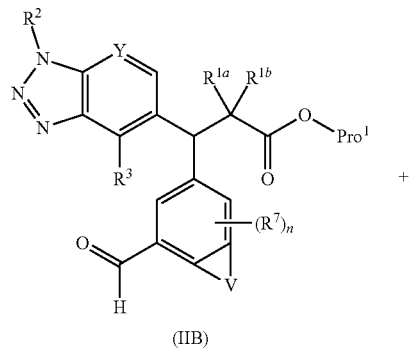

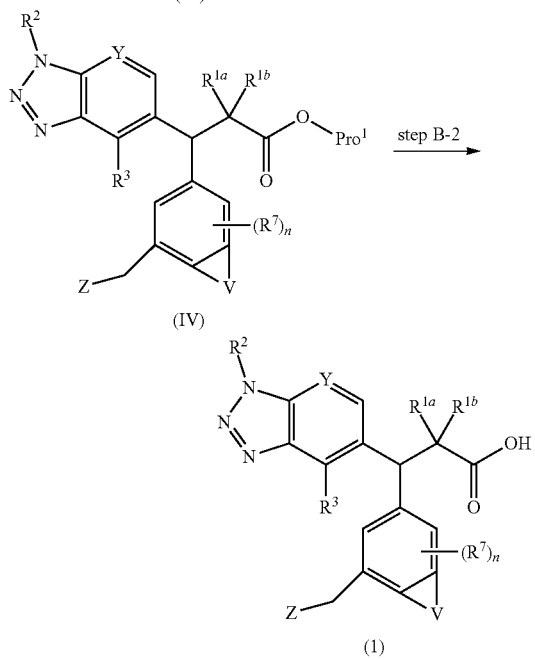

wherein $Pro^1$ is a protecting group (preferably a $C_{1-6}$ alkyl group such as methyl group, ethyl group, tert-butyl group and the like, or 2-(trimethylsilyl)ethyl group, and other symbols are as defined above.

(Step B-1)

In this step, compound (IIB) and compound (III) are subjected to a reductive amination reaction using a reducing agent in a solvent in the presence or absence of acid, and in the presence or absence of an additive to produce compound (IV).

The solvent to be used is not particularly limited as long as it does not inhibit the reaction and dissolves the starting materials to some extent, and preferred examples include aromatic hydrocarbons such as benzene, toluene, xylene, and the like; halogenated hydrocarbons such as dichloromethane, chloroform, and the like; esters such as ethyl acetate, propyl acetate, and the like; ethers such as diethyl ether, tetrahydrofuran, 1,4-dioxane, 1,2-dimethoxyethane, and the like; nitriles such as acetonitrile, and the like; amides such as formamide, N,N-dimethylformamide, and the like; sulfoxides such as dimethyl sulfoxide, and the like; mixed solvents containing a plurality of the organic solvents mentioned above in any ratio; and the like.

The reducing agent to be used is not particularly limited and, for example, reducing agents such as sodium cyanoborohydride, sodium triacetoxyborohydride, sodium borohydride, picoline borane, pyridineborane and the like can be mentioned.

The acid that can be used is not particularly limited as long as it is an acid that is used in normal reactions. Examples thereof include Lewis acids such as boron trifluoride, boron trichloride, boron tribromide, iodotrimethylsilane and the like; and organic acids such as acetic acid, trifluoroacetic acid and the like.

The additive that can be used is not particularly limited and, for example, inorganic salts such as sodium sulfate, magnesium sulfate and the like, and the like can be mentioned.

While the reaction temperature varies depending on the raw material compounds, reagents, and the like, it is generally −100° C. to 150° C., preferably 0° C. to 50° C.

While the reaction time varies depending on the raw material compounds, reagents, and the like, it is generally 5 min to 168 hr, preferably 10 min to 120 hr.
(Step B-2)

In this step, the protecting group (Pro$^1$) of compound (IV) is removed to produce compound (1).

In this step, the reaction can be performed under conditions similar to those in the aforementioned step A-2.
(Method C)

In the present production method, compound (IIC) and compound (III) are subjected to Mitsunobu reaction to obtain compound (IV), and then the protecting group of compound (IV) is removed to produce compound (1).

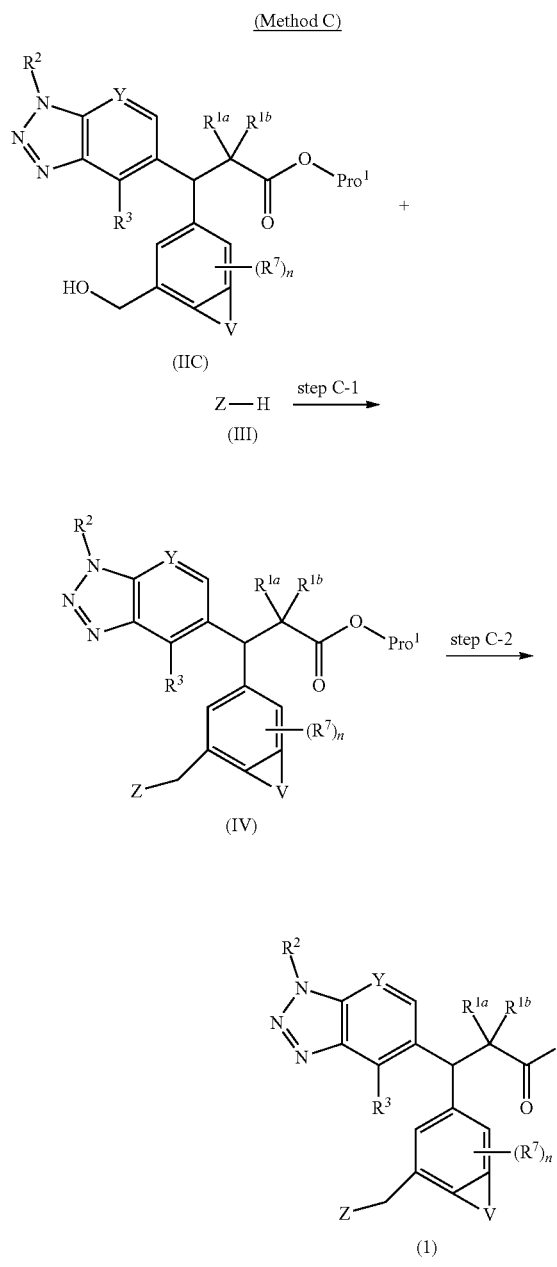

wherein Pro$^1$ is a protecting group (preferably a $C_{1-6}$ alkyl group such as methyl group, ethyl group, tert-butyl group and the like, or 2-(trimethylsilyl)ethyl group, and other symbols are as defined above.
(Step C-1)

In this step, compound (IIC) and compound (III) are subjected to Mitsunobu reaction in a solvent to produce compound (IV).

Examples of the solvent to be used include aromatic hydrocarbons such as benzene, toluene, xylene and the like; halogenated hydrocarbons such as dichloromethane, chloroform, carbon tetrachloride, dichloroethane, chlorobenzene, dichlorobenzene and the like; ethers such as diethyl ether, diisopropyl ether, tetrahydrofuran, dioxane, dimethoxyethane, diethylene glycol dimethylether and the like; and the like. Among these, halogenated hydrocarbons or ethers are preferred, dichloromethane or tetrahydrofuran is more preferred.

The reagent used in the Mitsunobu reaction is not particularly limited as long as it is a known reagent that can generally be used in the Mitsunobu reaction. Preferred examples include combinations of azo compounds such as di-lower alkyl azodicarboxylates, such as diethyl azodicarboxylate, diisopropyl azodicarboxylate, di-tert-butyl azodicarboxylate and the like; azodicarboxamides such as 1,1'-azobis(N,N-dimethylformamide), 1,1'-(azodicarbonyl) dipiperidine and the like, and phosphines such as triarylphosphines, such as triphenylphosphine and the like; and tri-lower alkyl phosphines, such as tri-n-butylphosphine and the like, and more preferred are combinations of di-tert-butyl azodicarboxylate or 1,1'-(azodicarbonyl)dipiperidine and tri-n-butylphosphine.

While the reaction temperature varies depending on the raw material compounds, reagents, and the like, it is generally −50° C. to 100° C., preferably −10° C. to 60° C.

While the reaction time varies depending on the reaction temperature, raw material compounds, reaction reagents or the kind of the solvent to be used, it is generally 10 min to 48 hr, preferably 30 min to 24 hr.
(Step C-2)

In this step, the protecting group (Pro$^1$) of compound (IV) is removed to produce compound (1).

In this step, the reaction can be performed under conditions similar to those in the aforementioned step A-2.
(Method D)

In this production method, compound (IIA-1), compound (IIB-1) and compound (IIC-1) (compounds in which $R^{1a}$ and $R^{1b}$ in the aforementioned formulas (IIA), (IIB) and (IIC) are both hydrogen atoms) which are intermediate compounds used in the aforementioned Method A to Method C are produced.

(Method D)

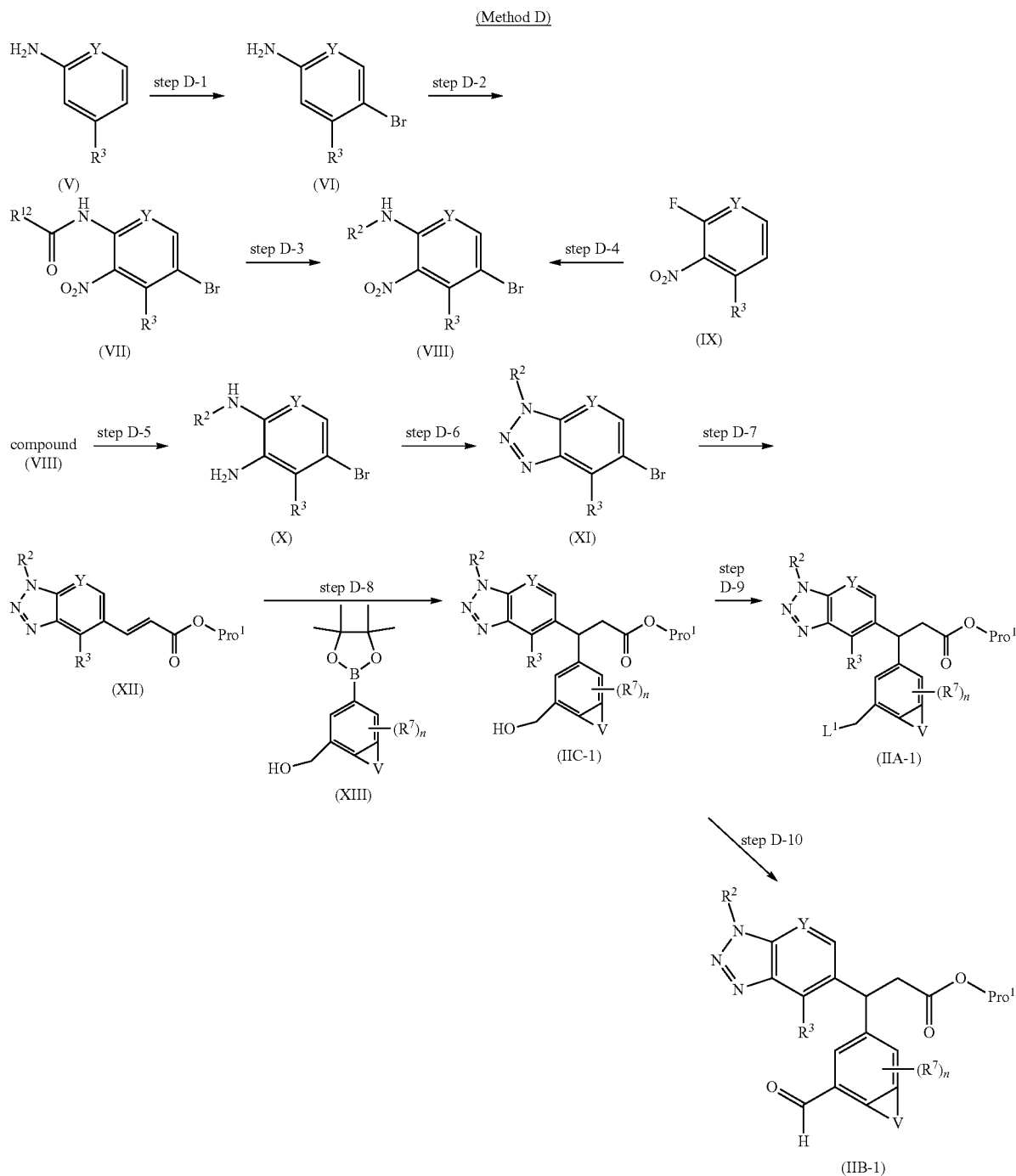

wherein $R^{12}$ is a hydrogen atom, an alkyl group or a haloalkyl group, $L^1$ is a leaving group, $Pro^1$ is a protecting group (preferably a $C_{1-6}$ alkyl group such as methyl group, ethyl group, tert-butyl group and the like, or 2-(trimethylsilyl)ethyl group, and other symbols are as defined above.

(Step D-1)

In this step, compound (V) is converted to compound (VI) in a solvent. Here, a method for bromination is described, but the method is not limited thereto.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; carboxylic acids such as acetic acid, trifluoroacetic acid and the like; sulfonic acids such as methanesulfonic acid and the like; mineral acids such as sulfuric acid and the like; mixed solvents containing a plurality of the organic solvents mentioned above in any ratio and the like.

The brominating agent to be used is not particularly limited and, for example, N-bromosuccinimide, bromine, and the like can be mentioned.

While the reaction temperature varies depending on the raw material compounds, reagents, and the like, it is generally −100° C. to 150° C., preferably −20° C. to 50° C.

While the reaction time varies depending on the raw material compounds, reagents, and the like, it is generally 5 min to 48 hr, preferably 10 min to 24 hr.

(Step D-2)

In this step, compound (VI) is converted to an amide compound in a solvent (Step D-2-1), and then a nitro group is introduced (Step D-2-2) (or converted to an amide compound after introduction of nitro group) to convert the compound to compound (VII).

(Step D-2-1) (Conversion Step to Amide Compound)

Here, a method of using formic acid ($R^{12}$ corresponds to a hydrogen atom) in a solvent in the presence or absence of a suitable acid anhydride to compound (VI) (Step D-2-1a), and a method of amidating compound (VI) and alkylcarboxylic acid ($R^{12}$ corresponds to an alkyl group or a haloalkyl group, $R^{12}CO_2H$) using a suitable condensing agent in the presence or absence of a base (Step D-2-1b) are described below, but the methods are not limited thereto.

(Step D-2-1a)

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

The acid anhydride that can be used is not particularly limited as long as it is used as an acid anhydride in a normal reaction, and examples thereof include carboxylic acid anhydrides such as acetic anhydride and the like.

While the reaction temperature varies depending on the raw material compounds, reagents, and the like, it is generally −100° C. to 150° C., preferably 0° C. to 50° C.

While the reaction time varies depending on the raw material compounds, reagents, and the like, it is generally 5 min to 48 hr, preferably 10 min to 24 hr.

(Step D-2-1b)

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

The base to be used is not particularly limited as long as it is used as a base in a normal reaction, and preferred examples include organic bases such as triethylamine, N,N-diisopropylethylamine, N-methylmorpholine, lutidine, pyridine and the like; alkali metal carbonates such as sodium carbonate, potassium carbonate and the like; alkaline earth metal carbonates such as magnesium carbonate and the like; alkali metal hydrogen carbonates such as potassium hydrogen carbonate and the like; alkaline earth metal hydrogen carbonates such as calcium hydrogen carbonate and the like; alkali metal hydroxides such as sodium hydroxide and the like; alkaline earth metal hydroxides such as magnesium hydroxide and the like; alkali metal phosphates such as tripotassium phosphate and the like, and the like.

The condensing agent to be used is not particularly limited to those used as condensing agents to form amide bonds (e.g., methods described in Shoichi Kusumoto et al. Experimental Science Course IV; Chemical Society of Japan; Maruzen, 1990, and Nobuo Izumiya et al. Fundamentals and Experiments of Peptide Synthesis; Maruzen, 1985. etc.). Preferably, for example, 1-[bis(dimethylamino)methylene]-1H-1,2,3-triazolo[4,5-b]pyridinium 3-oxide hexafluorophosphate (HATU), O-benzotriazole-N,N,N',N'-tetramethyluronium hexafluorophosphate (HBTU), 2-(1H-benzotriazol-1-yl)-1,1,3,3-tetramethyluronium tetrafluoroborate (TBTU), 1-(3-dimethylaminopropyl)-3-ethylcarbodiimide hydrochloride (EDCI), 4-(2-{[(cyclohexylimino)methylene]amino}ethyl-4-methylmorpholinium p-toluenesulfonate (CMC), dicyclohexylcarbodiimide (DCC), 1,1'-carbonyl bis(1H-imidazole) (CDI), (1H-benzotriazol-1-yloxy) (tripyrrolidin-1-yl)phosphonium hexafluorophosphate (PyBOP), bromo (tripyrrolidin-1-yl)phosphonium hexafluorophosphate (PyBrOP), 4-(4,6-dimethoxy-1,3,5-triazin-2-yl)-4-methylmorpholinium chloride (DMT-MM), 2-chloro-4,6-dimethoxy-1,3,5-triazine (DMT), and the like can be mentioned. Where necessary, additives such as 1-hydroxybenzotriazole (HOBT) and N,N-dimethylaminopyridine, and the like may be added.

While the reaction temperature varies depending on the raw material compounds, reagents, and the like, it is generally −10° C. to 150° C., preferably 0° C. to 100° C.

While the reaction time varies depending on the raw material compounds, reagents, and the like, it is generally 5 min to 48 hr, preferably 10 min to 24 hr.

(Step D-2-2) (Nitro Group Introducing Step)

In this step, a nitro group is introduced by using a nitrating agent. Here, a method of using a suitable nitrating agent in a solvent in the presence or absence of a suitable acid is described, but the method is not limited thereto.

The solvent to be used is not limited as long as it does not inhibit the reaction and dissolves the starting material to some extent, but it is preferable to use an acid that also serves as a solvent, for example, mineral acids such as sulfuric acid; mixed solvents containing plural solvents in any ratio.

The nitrating agent to be used is not limited as long as it is used as a nitrating agent in normal reactions. For example, mineral acids such as nitric acid and the like, and the like can be mentioned.

While the reaction temperature varies depending on the raw material compounds, reagents, and the like, it is generally −100° C. to 150° C., preferably −20° C. to 50° C.

While the reaction time varies depending on the raw material compounds, reagents, and the like, it is generally 5 min to 24 hr, preferably 10 min to 6 hr.
(Step D-3)

In this step, compound (VII) is reduced with an appropriate reducing agent in a solvent to convert to compound (VIII).

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio.

The reducing agents used are not limited to those used as reducing agents in normal reactions. For example, metal hydrides such as lithium aluminum hydride, diisobutylaluminum hydride, sodium bis(2-methoxyethoxy)aluminum dihydride; borone hydrides such as borane; silicon hydrides such as triethylsilane, and the like can be mentioned.

While the reaction temperature varies depending on the raw material compounds, reagents, and the like, it is generally −100° C. to 150° C., preferably 0° C. to 80° C.

While the reaction time varies depending on the raw material compounds, reagents, and the like, it is generally 5 min to 24 hr, preferably 10 min to 6 hr.
(Step D-4)

In this step, the fluorine atom of compound (IX) is converted to the $NHR^2$ group (Step D-4-1), and then the bromine atom is introduced (Step D-4-2) (or fluorine atom is converted to $NHR^2$ group after introduction of the bromine atom) to convert to compound (VIII). In Step D-4, either Step D-4-1 or Step D-4-2 may be performed first, and a person skilled in the art may select the order thereof as appropriate.
(Step D-4-1)

In this step, the fluorine atom is converted to an $NHR^2$ group by reacting with a primary amine ($R^2NH_2$ (wherein $R^2$ is as defined above)) in a solvent in the presence or absence of a base.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; alcohols such as methanol, ethanol and the like; sulfoxides such as dimethyl sulfoxide and the like; mixed solvents containing a plurality of the organic solvents mentioned above in any ratio; mixed solvents containing the aforementioned organic solvent and water in any ratio and the like.

The base to be used is not particularly limited as long as it is one that is used as a base in a normal reaction. Preferred examples include organic bases such as triethylamine, N,N-diisopropylethylamine, N-methylmorpholine, lutidine, pyridine and the like; alkali metal carbonates such as sodium carbonate, potassium carbonate and the like; alkaline earth metal carbonates such as magnesium carbonate and the like; alkali metal hydrogen carbonates such as potassium hydrogen carbonate and the like; alkaline earth metal hydrogen carbonates such as calcium hydrogen carbonate and the like; alkali metal hydroxides such as sodium hydroxide and the like; alkaline earth metal hydroxides such as magnesium hydroxide and the like; alkali metal phosphates such as tripotassium phosphate and the like; metal alkoxides such as sodium tert-butoxide, potassium tert-butoxide and the like, and the like.

While the reaction temperature varies depending on the raw material compounds, reagents, and the like, it is generally −10° C. to 150° C., preferably 0° C. to 100° C.

While the reaction time varies depending on the raw material compounds, reagents, and the like, it is generally 5 min to 48 hr, preferably 10 min to 12 hr.
(Step D-4-2)

This step involves the introduction of a bromine atom in a solvent. In this step, the reaction can be carried out under the same conditions as in the aforementioned step D-1.
(Step D-5)

This step is the step for producing compound (X) by converting a nitro group of compound (VIII) to an amino group in a solvent.

The methods for converting the nitro group of compound (VIII) to an amino group include the methods described below, but are not limited to, those using an appropriate metal and an appropriate acid (Step D-5-1), hydrogen in the presence of an appropriate metal catalyst (Step D-5-2), and a metal hydride (Step D-5-3).
(Step D-5-1)

This step is a step of converting a nitro group of compound (VIII) to an amino group using a metal in the presence of an acid in a solvent.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

The acid to be used is not particularly limited as long as it is an acid that is used in normal reactions. Preferred examples include inorganic acids such as hydrochloric acid, sulfuric acid, ammonium chloride and the like; Lewis acids such as boron trifluoride, boron trichloride, boron tribromide, iodotrimethylsilane and the like; organic acids such as acetic acid, trifluoroacetic acid and the like, and the like.

The metal to be used is not particularly limited and, for example, iron, zinc, tin and the like can be mentioned.

While the reaction temperature varies depending on the raw material compounds, reagents, and the like, it is generally −10° C. to 150° C., preferably 0° C. to 100° C.

While the reaction time varies depending on the raw material compounds, reagents, and the like, it is generally 5 min to 48 hr, preferably 10 min to 24 hr.

(Step D-5-2)

In this step, the nitro group of compound (VIII) is converted to an amino group using hydrogen in the presence of a suitable metal catalyst in a solvent.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

The metal catalysts used are not particularly limited, but preferably include, for example, palladium-activated carbon, platinum-activated carbon, nickel, osmium-activated carbon, and the like.

Examples of the hydrogen source to be used include hydrogen gas, ammonium formate, hydrazine and the like.

While the reaction temperature varies depending on the raw material compounds, reagents, and the like, it is generally −10° C. to 150° C., preferably 0° C. to 100° C.

While the reaction time varies depending on the raw material compounds, reagents, and the like, it is generally 5 min to 24 hr, preferably 10 min to 12 hr.

(Step D-5-3)

In this step, the nitro group of compound (VIII) is converted to an amino group by using an appropriate metal hydride in a solvent.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; ethers such as diethyl ether, tetrahydrofuran, 1,4-dioxane, 1,2-dimethoxyethane and the like; mixed solvents containing a plurality of the organic solvents mentioned above in any ratio and the like.

The metal hydride to be used is not particularly limited, and preferred examples include lithium aluminum hydride and the like.

While the reaction temperature varies depending on the raw material compounds, reagents, and the like, it is generally −10° C. to 150° C., preferably 0° C. to 100° C.

While the reaction time varies depending on the raw material compounds, reagents, and the like, it is generally 5 min to 24 hr, preferably 10 min to 12 hr.

(Step D-6)

This step is to produce compound (XI) by constructing a triazole ring from compound (X). In the following, the method using nitrites or nitrite esters in the presence of an acid in a solvent is described, but is not limited to this method.

That is, this step is the step of constructing a triazole ring by reacting compound (X) with nitrites or nitrite esters in the presence of an acid in a solvent.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

The acid to be used is not particularly limited as long as it is an acid that is used in normal reactions. Preferred examples include inorganic acids such as hydrochloric acid, sulfuric acid, tetrafluoroboric acid and the like; Lewis acids such as boron trifluoride, boron trichloride, boron tribromide, iodotrimethylsilane and the like; organic acids such as acetic acid, trifluoroacetic acid and the like, and the like.

The nitrites to be used are not particularly limited, but include, for example, alkali metal salts such as sodium nitrite, and the like.

The nitrite esters to be used are not particularly limited, but include, for example, isobutyl nitrite, tert-butyl nitrite, and the like.

While the reaction temperature varies depending on the raw material compounds, reagents, and the like, it is generally −20° C. to 100° C., preferably −10° C. to 60° C.

While the reaction time varies depending on the raw material compounds, reagents, and the like, it is generally 5 min to 24 hr, preferably 10 min to 6 hr.

(Step D-7)

This step is the step of producing compound (XII) by converting the bromo group of compound (XI) to an acrylic ester group (—CH=CH—CC$_2$Pro$^1$) by reacting an acrylic ester compound in a solvent, in the presence or absence of a base, in the presence or absence of an additive, and in the presence of a metal catalyst.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

The base that can be used is not particularly limited as long as it is one that is used as a base in a normal reaction. Preferred examples include organic bases such as triethylamine, N,N-diisopropylethylamine, N-methylmorpholine, lutidine, pyridine and the like; alkali metal carbonates such as sodium carbonate, potassium carbonate and the like; alkaline earth metal carbonates such as magnesium carbonate and the like; alkali metal hydrogen carbonates such as potassium hydrogen carbonate and the like; alkaline earth metal hydrogen carbonates such as calcium hydrogen carbonate and the like; alkali metal hydroxides such as sodium hydroxide and the like; alkaline earth metal hydroxides such as magnesium hydroxide and the like; alkali metal phosphates such as tripotassium phosphate and the like; metal alkoxides such as sodium tert-butoxide, potassium tert-butoxide and the like, and the like.

The additives that can be used are not particularly limited to those used as known methods. Preferred examples include metal oxides such as silver oxide and alumina; phosphines such as triphenylphosphine, tri-tert-butylphosphine, tricyclohexylphosphine, tri(o-toluyl)phosphine, diphenylphosphinoferrocene, 2-dicyclohexylphosphino-2',6'-dimethoxy-1,1'-biphenyl (S-PHOS), 2-dicyclohexylphosphino-2'-2',4',6'-triisopropyl-1,1'-biphenyl (X-PHOS), 2,2'-bis(diphenylphosphino)-1,1'-binaphthyl (BINAP) and the like; phosphine oxides such as triphenylphosphine oxide and the like; metal salts such as lithium chloride, potassium fluoride, cesium fluoride, and the like; ammonium salts such as tetrabutylammonium bromide, and the like. These may be used in any combination in any ratio.

The metal catalyst to be used is not particularly limited as long as it is used in a known method. Preferred examples include palladium catalysts such as tetrakis(triphenylphosphine)palladium, bis(tri-tert-butylphosphine)palladium, 2 palladium acetate, 2 palladium chloride diphenylphosphinoferrocene complex, 2 palladium chloride benzonitrile complex, 2 palladium chloride acetonitrile complex, bis(dibenzylideneacetone)palladium, tris(dibenzylideneacetone) dipalladium, bis[1,2-bis(diphenylphosphino)ethane] palladium, 3-chloropyridine[1,3-bis(2,6-diisopropylphenyl) imidazo-2-ylidene]palladium, palladium-activated carbon and the like.

The acrylic ester compounds to be used are not particularly limited, but include, for example, methyl acrylate, ethyl acrylate, tert-butyl acrylate and the like.

While the reaction temperature varies depending on the raw material compounds, reagents, and the like, it is generally 0° C. to 150° C., preferably 20° C. to 120° C.

While the reaction time varies depending on the raw material compounds, reagents, and the like, it is generally 5 min to 24 hr, preferably 10 min to 12 hr.

(Step D-8)

In this step, compound (XII) is reacted with compound (XIII) obtained by Method E described below in a solvent in the presence or absence of a base and in the presence or absence of an additive, by using a metal catalyst, to produce compound (IIC-1).

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

The base that can be used is not particularly limited as long as it is one that is used as a base in a normal reaction. Preferred examples include organic bases such as triethylamine, N,N-diisopropylethylamine, N-methylmorpholine, lutidine, pyridine and the like; alkali metal carbonates such as sodium carbonate, potassium carbonate and the like; alkaline earth metal carbonates such as magnesium carbonate and the like; alkali metal hydrogen carbonates such as potassium hydrogen carbonate and the like; alkaline earth metal hydrogen carbonates such as calcium hydrogen carbonate and the like; alkali metal hydroxides such as sodium hydroxide, potassium hydroxide and the like; alkaline earth metal hydroxides such as magnesium hydroxide and the like; alkali metal phosphates such as tripotassium phosphate and the like; metal alkoxides such as sodium tert-butoxide, potassium tert-butoxide and the like, and the like.

The additives that may be used are not particularly limited to those used as known methods. Preferred examples include phosphines such as 2,3-bis(diphenylphosphino)butane and the like, and different types of phosphines may be used in any combination in any ratio.

The metal catalysts used are not particularly limited to those used in known methods. Preferred examples include rhodium catalysts such as bis(norbornadiene)rhodium(I) tetrafluoroborate, chloro(1,5-cyclooctadiene)rhodium(I) dimer and the like, and the like.

While the reaction temperature varies depending on the raw material compounds, reagents, and the like, it is generally 0° C. to 150° C., preferably 20° C. to 100° C.

While the reaction time varies depending on the raw material compounds, reagents, and the like, it is generally 5 min to 24 hr, preferably 10 min to 12 hr.

(Step D-9)

In this step, the hydroxy group of compound (IIC-1) is converted to a leaving group (L) by reacting with an acid chloride or an acid anhydride in a solvent in the presence or absence of a base, to produce compound (IIA-1).

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as N,N-dimethylformamide and the like; sulfoxides such as dimethyl sulfoxide and the like; mixed solvents containing a plurality of the organic solvents mentioned above in any ratio and the like.

The acid chlorides or acid anhydrides used are not particularly limited, but preferably include, for example, sulfurous chlorides such as thionyl chloride, and the like, substituted or unsubstituted alkyl sulfonic anhydrides or arylsulfonic anhydrides such as trifluoromethanesulfonic anhydride, and the like; substituted or unsubstituted alkyl sulfonyl chlorides or aryl sulfonyl chloride such as methanesulfonyl chloride, p-toluenesulfonyl chloride, and the like; substituted or unsubstituted alkyl chlorophosphate or aryl chlorophosphate, and the like.

The base that can be used is not particularly limited as long as it is one that is used as a base in a normal reaction. Preferred examples include organic bases such as triethylamine, N,N-diisopropylethylamine, N-methylmorpholine, lutidine, pyridine and the like; alkali metal carbonates such as sodium carbonate, potassium carbonate and the like; alkaline earth metal carbonates such as magnesium carbonate and the like; alkali metal hydrogen carbonates such as potassium hydrogen carbonate and the like; alkaline earth metal hydrogen carbonates such as calcium hydrogen carbonate and the like; alkali metal hydroxides such as sodium hydroxide and the like; alkaline earth metal hydroxides such as magnesium hydroxide and the like; alkali metal phosphates such as tripotassium phosphate and the like, and the like.

While the reaction temperature varies depending on the raw material compounds, reagents, and the like, it is generally −100° C. to 150° C., preferably −80° C. to 40° C.

While the reaction time varies depending on the raw material compounds, reagents, and the like, it is generally 5 min to 24 hr, preferably 10 min to 6 hr.
(Step D-10)

In this step, the hydroxy group of compound (IIC-1) is converted to a formyl group by using an appropriate oxidizing agent in a solvent to produce compound (IIB-1).

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

The oxidizing agent to be used is not particularly limited. For example, a known method described in the fourth edition of Experimental Chemistry Course (21. Organic Synthesis III Aldehydes, Ketones, and Quinones), Kazuhiro Maruyama et al, Chemical Society of Japan, Maruzen Corporation, 1990, and the like can be appropriately selected. This step is performed according thereto. Representative examples of oxidation reactions include, for example, oxidation reaction using a chromic acid such as chromic anhydride, chromium(VI)-pyridine complex (Collins reagent), pyridinium chlorochromate (PCC), pyridinium dichromate (PDC); oxidation reaction using activated manganese dioxide; oxidation using dicyclohexylcarbodiimide (DCC), acetic anhydride, phosphorus pentoxide, sulfur trioxide-pyridine complexes, or oxalyl chloride in combination with dimethyl sulfoxide (DMSO); oxidation reaction using a hypervalent iodine compound (Dess-Martin reagent), and the like.

While the reaction temperature varies depending on the raw material compounds, reagents, and the like, it is generally −100° C. to 150° C., preferably 0° C. to 50° C.

While the reaction time varies depending on the raw material compounds, reagents, and the like, it is generally 5 min to 24 hr, preferably 10 min to 6 hr.
(Method E)

In this production method, compound (IIA-2), compound (IIB-2) and compound (IIC-2) (compounds in which $R^{1a}$ and $R^{1b}$ in the aforementioned formulas (IIA), (IIB) and (IIC) are each independently a $C_{1-6}$ alkyl group) which are intermediate compounds used in the aforementioned Method A to Method C are produced.

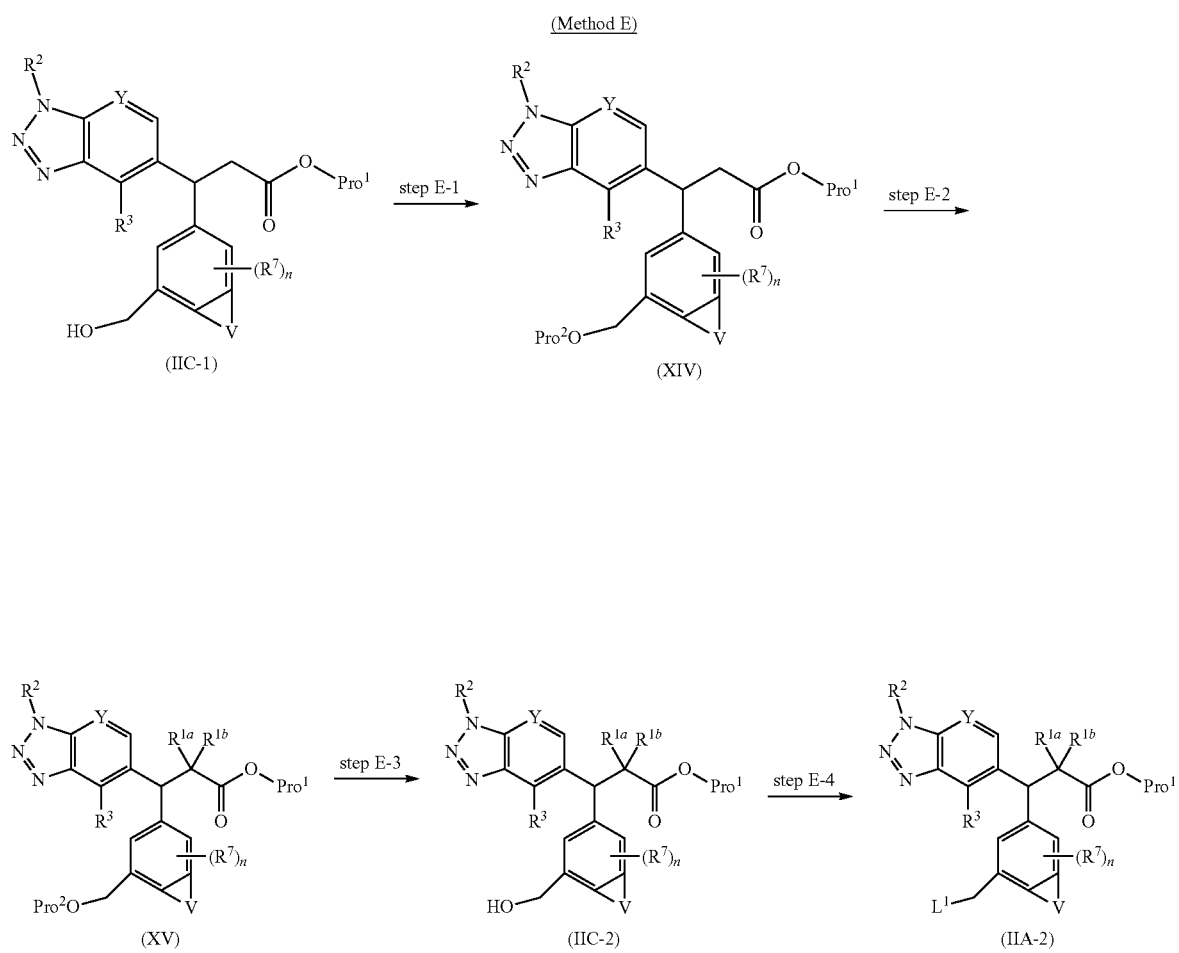

-continued

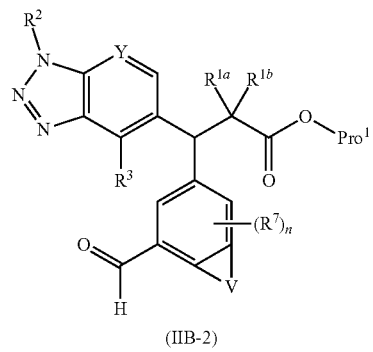

(IIB-2)

wherein Pro¹ is a protecting group (preferably a $C_{1-6}$ alkyl group such as methyl group, ethyl group and the like, or a 2-(trimethylsilyl)ethyl group), Pro² is a protecting group (preferably a p-methoxybenzyl group), and other symbols are as defined above.

(Step E-1)

In this step, the hydroxy group of compound (IIC-1) is protected with a protecting group (Pro²). Here, the protecting group is a p-methoxybenzyl group, and a method using an appropriate protecting reagent in the presence of an acid is described, but the method is not limited thereto.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform, 1,2-dichloroethane and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

The acid to be used is not particularly limited as long as it is an acid that is used in normal reactions. For example, inorganic acids such as hydrochloric acid, sulfuric acid, tetrafluoroboric acid and the like; Lewis acids such as boron trifluoride, boron trichloride, boron tribromide, iodotrimethylsilane and the like; organic acids such as acetic acid, trifluoroacetic acid and the like; sulfonic acids such as p-toluenesulfonic acid, methanesulfonic acid, (S)-(+)-camphor-10-sulfonic acid and the like, and the like can be mentioned.

Examples of the protecting reagent to be used include 4-methoxybenzyl-2,2,2-trichloroacetimidate, 2,4,6-tris(p-methoxybenzyloxy)-1,3,5-triazine and the like.

While the reaction temperature varies depending on the raw material compounds, reagents, and the like, it is generally −50° C. to 150° C., preferably −20° C. to 100° C.

While the reaction time varies depending on the raw material compounds, reagents, and the like, it is generally 5 min to 48 hr, preferably 10 min to 24 hr.

(Step E-2)

In this step, $C_{1-6}$ alkyl groups $R^{1a}$ and $R^{1b}$ are successively introduced into the α-position of the ester group of compound (XIV) by using an appropriate base and a $C_{1-6}$ alkyl halide or a $C_{1-6}$ alkyl pseudohalide in a solvent or without solvent to produce compound (XV)).

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; ethers such as diethyl ether, tetrahydrofuran, 1,4-dioxane, 1,2-dimethoxyethane and the like; N,N-dimethylformamide and the like amides; sulfoxides such as dimethyl sulfoxide and the like; mixed solvents containing a plurality of the organic solvents mentioned above in any ratio and the like.

The base to be used is not particularly limited and preferred examples include organic bases such as 1,8-diazabicyclo[5.4.0]-7-undecene and the like; alkali metal carbonates such as sodium carbonate, potassium carbonate and the like; alkaline earth metal carbonates such as magnesium carbonate and the like; alkali metal hydroxides such as sodium hydroxide and the like; alkaline earth metal hydroxides such as magnesium hydroxide and the like; metal alkoxides such as sodium tert-butoxide, potassium tert-butoxide and the like; metal amides such as lithium diisopropyl amide, sodium hexamethyl disilazide and the like; organic metal compounds such as tert-butyllithium and the like; metal hydrides such as potassium hydride, sodium hydride and the like, and the like.

Pseudohalide refers to a substituent that is known to undergo a substitution reaction in an alkylation reaction, similar to a halide. It is not particularly limited as long as it is a substituent known to undergo a substitution reaction. Examples thereof include sulfonyloxy groups such as trifluoromethanesulfonyloxy, methanesulfonyloxy, and p-toluenesulfonyloxy; and acyloxy groups such as acetoxy and the like. The alkyl halide or alkyl pseudohalide to be used is not particularly limited as long as it is a known compound or can be synthesized according to a known method.

While the reaction temperature varies depending on the raw material compounds, reagents, and the like, it is generally −80° C. to 150° C., preferably −20° C. to 60° C.

While the reaction time varies depending on the raw material compounds, reagents, and the like, it is generally 5 min to 48 hr, preferably 10 min to 24 hr.

(Step E-3)

In this step, the protecting group (Pro²) is removed. Here, when Pro² is a p-methoxybenzyl group, a method for removing using an appropriate oxidizing agent in a solvent (Step E-3a) and a method for removing using an appropriate acid in the presence or absence of anisole (Step E-3b) are described, but the method is not limited thereto.

(Step E-3a) (Deprotection Step Using Oxidizing Agent)

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

Examples of the oxidizing agent to be used include 2,3-dichloro-5,6-dicyano-p-benzoquinone and the like.

While the reaction temperature varies depending on the raw material compounds, reagents, and the like, it is generally −20° C. to 150° C., preferably 0° C. to 100° C.

While the reaction time varies depending on the raw material compounds, reagents, and the like, it is generally 5 min to 24 hr, preferably 10 min to 12 hr.

(Step E-3b) (Deprotection Step Using Acid)

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like can be mentioned.

The acid to be used is not particularly limited as long as it is an acid that is used in normal reactions for example, inorganic acids such as hydrochloric acid, sulfuric acid and the like; Lewis acids such as boron trifluoride, boron trichloride, boron tribromide, iodotrimethylsilane and the like; organic acids such as trifluoroacetic acid and the like, and the like can be mentioned.

While the reaction temperature varies depending on the raw material compounds, reagents, and the like, it is generally −100° C. to 150° C., preferably −78° C. to 100° C.

While the reaction time varies depending on the raw material compounds, reagents, and the like, it is generally 5 min to 24 hr, preferably 10 min to 6 hr.

(Step E-4)

In this step, compound (IIC-2) is converted to compound (IIA-2), which can be performed according to the aforementioned step D-9.

(Step E-5)

In this step, compound (IIC-2) is converted to compound (IIB-2), which can be performed according to the aforementioned step D-10.

(Method F)

In this production method, compound (XIII), which is an intermediate compound used in the above-mentioned method D, is produced from compound (XVI).

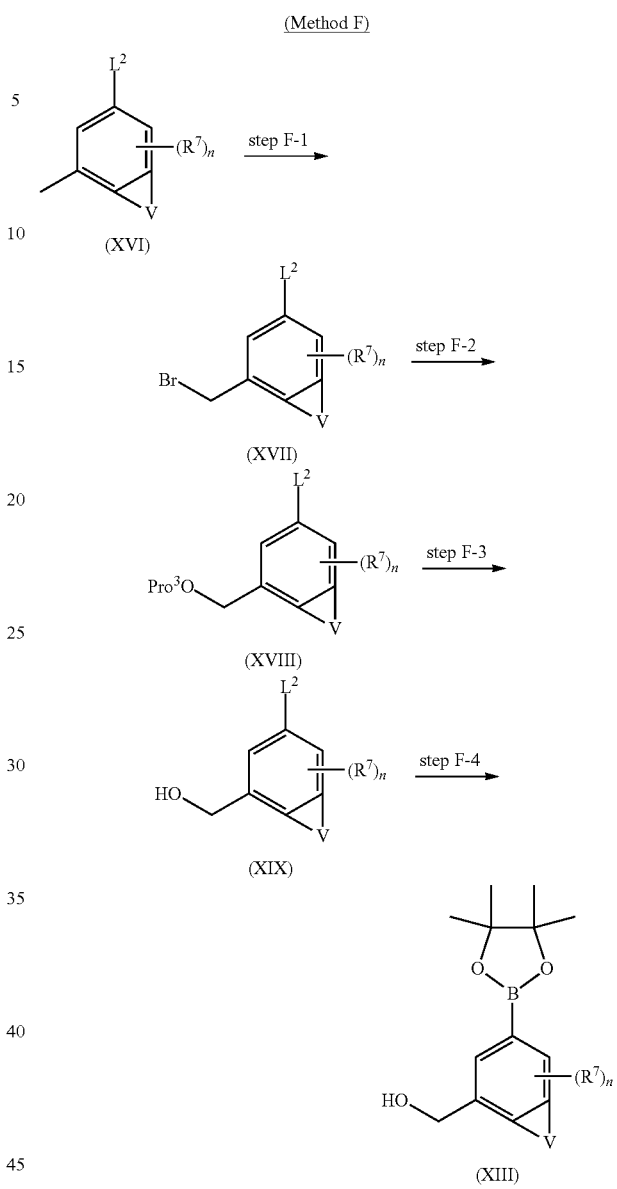

wherein $L^2$ is a leaving group, $Pro^3$ is a protecting group (preferably, an acetyl group), and other symbols are as defined above.

(Step F-1)

In this step, compound (XVII) is produced by introducing a bromo group into compound (XVI). Here, a method using a brominating agent in a solvent in the presence of a suitable catalyst is described, but the method is not limited thereto.

The solvent to be used is not particularly limited as long as it does not inhibit the reaction and dissolves the starting materials to some extent, and preferred examples include aromatic hydrocarbons such as benzene and the like; halogenated hydrocarbons such as dichloromethane, chloroform, carbon tetrachloride and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

Examples of the catalyst to be used include radical initiators such as azobisisobutyronitrile, benzoyl peroxide and the like.

Examples of the brominating agent to be used include N-bromosuccinimide, N-bromoacetamide and the like.

While the reaction temperature varies depending on the raw material compounds, reagents, and the like, it is generally 0° C. to 200° C., preferably 20° C. to 150° C.

While the reaction time varies depending on the raw material compounds, reagents, and the like, it is generally 5 min to 24 hr, preferably 10 min to 12 hr.

(Step F-2)

In this step, the bromo group of compound (XVII) is converted to a hydroxy group protected with a protecting group (Pro$^3$) to produce compound (XVIII). Here, a method using a metal carboxylate in a solvent is described, but the method is not limited thereto.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

Examples of the metal carboxylates to be used include potassium acetate, sodium acetate, potassium benzoate, sodium benzoate and the like.

While the reaction temperature varies depending on the raw material compounds, reagents, and the like, it is generally 0° C. to 150° C., preferably 20° C. to 100° C.

While the reaction time varies depending on the raw material compounds, reagents, and the like, it is generally 5 min to 48 hr, preferably 10 min to 24 hr.

(Step F-3)

In this step, the protecting group (Pro$^3$) of compound (XVIII) is removed to produce compound (XIX), which can be performed according to the aforementioned step A-2-1.

(Step F-4)

In this step, compound (XIII) is produced by converting the leaving group (L) of compound (XIX) to a boronic acid ester by using a suitable metal catalyst and a boron compound in an inert gas (nitrogen or argon) atmosphere in a solvent in the presence or absence of a base and in the presence or absence of an additive.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

The boron compound to be used is not particularly limited as long as it is generally used in boronic acid ester synthesis, and preferred examples include bis(pinacolato)diboron, pinacolborane and the like.

The base that can be used is not particularly limited as long as it is one that is used as a base in a normal reaction. Preferred examples include organic bases such as triethylamine, N,N-diisopropylethylamine and the like; alkali metal carbonates such as sodium carbonate, potassium carbonate and the like; alkaline earth metal carbonates such as magnesium carbonate and the like; alkali metal hydrogen carbonates such as sodium hydrogen carbonate and the like; alkaline earth metal hydrogen carbonates such as calcium hydrogen carbonate and the like; alkali metal hydroxides such as sodium hydroxide, cesium hydroxide and the like; alkaline earth metal hydroxides such as magnesium hydroxide and the like; alkali metal acetates such as sodium acetate, potassium acetate and the like; alkali metal phosphates such as tripotassium phosphate and the like; metal alkoxides such as sodium tert-butoxide, potassium tert-butoxide and the like, and the like.

The additives that may be used are not particularly limited to those used as known methods. Preferred examples include metal oxides such as silver oxide, alumina and the like; phosphines such as triphenylphosphine, tri-tert-butylphosphine, tricyclohexylphosphine, tri(o-toluyl)phosphine, diphenylphosphinoferrocene, 2-dicyclohexylphosphino-2',6'-dimethoxy-1,1'-biphenyl (S-PHOS), 2-dicyclohexylphosphino-2',4',6'-triisopropyl-1,1'-biphenyl (X-PHOS), 2,2'-bis(diphenylphosphino)-1,1'-binaphthyl (BINAP) and the like; phosphine oxides such as triphenylphosphine oxide and the like; metal salts such as lithium chloride, potassium fluoride, cesium fluoride and the like; ammonium salts such as tetrabutylammonium bromide and the like, and the like. These may be used in any combination in any ratio.

The metal catalyst to be used is not particularly limited as long as it is used in a known method. Preferred examples include palladium catalysts such as tetrakis(triphenylphosphine)palladium, bis(tri-tert-butylphosphine)palladium, 2 palladium acetate, 2 palladium chloride diphenylphosphinoferrocene complex, 2 palladium chloride benzonitrile complex, 2 palladium chloride acetonitrile complex, bis(dibenzylideneacetone)palladium, tris(dibenzylideneacetone)dipalladium, bis[1,2-bis(diphenylphosphino)ethane]palladium, [1,1'-bis(diphenylphosphino)ferrocene]dichloropalladium(II) dichloromethane adduct, 3-chloropyridine[1,3-bis(2,6-diisopropylphenyl)imidazo-2-ylidene]palladium, palladium-activated carbon and the like, and the like.

While the reaction temperature varies depending on the raw material compounds, reagents, and the like, it is generally −10° C. to 200° C., preferably 0° C. to 150° C.

While the reaction time varies depending on the raw material compounds, reagents, and the like, it is generally 5 min to 48 hr, preferably 10 min to 12 hr.

(Method G)

In this production method, compound (XIII), which is an intermediate compound used in the above-mentioned method D, is produced from compound (XX).

(Method G)

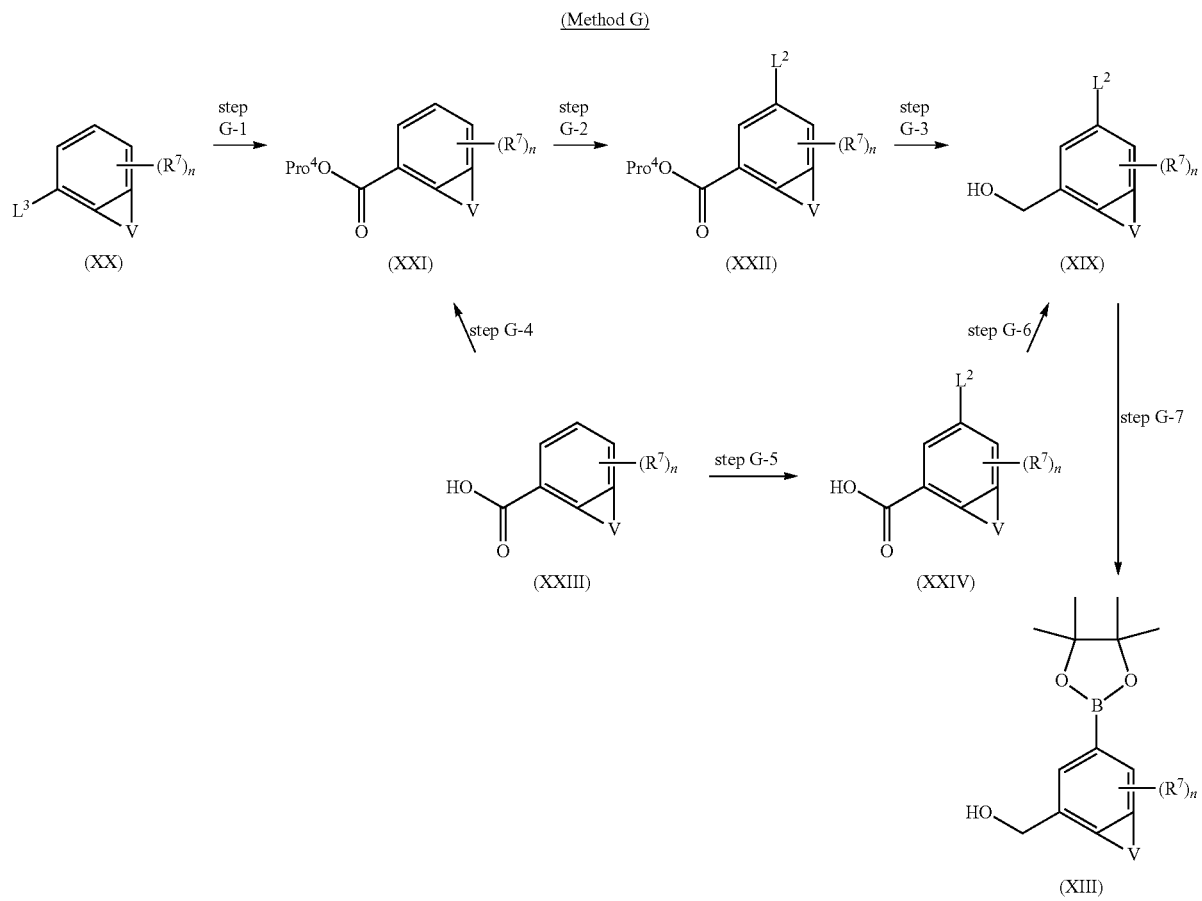

wherein $L^3$ is a leaving group, $Pro^4$ is a protecting group (preferably $C_{1-6}$ alkyl group such as methyl group, ethyl group and the like), and other symbols are as defined above.

(Step G-1)

In this step, compound (XX) is converted to compound (XXI) by inserting carbon monoxide by using a metal catalyst in a solvent in the presence or absence of a base, in the presence or absence of an additive, and in the presence of an alcohol.

The solvent to be used is not particularly limited as long as it does not inhibit the reaction and dissolves the starting is materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

The base that can be used is not particularly limited as long as it is one that is used as a base in a normal reaction. Preferred examples include organic bases such as triethylamine, N,N-diisopropylethylamine and the like; alkali metal carbonates such as sodium carbonate, potassium carbonate and the like; alkaline earth metal carbonates such as magnesium carbonate and the like; alkali metal hydrogen carbonates such as potassium hydrogen carbonate and the like; alkaline earth metal hydrogen carbonates such as calcium hydrogen carbonate and the like; alkali metal hydroxides such as sodium hydroxide and the like; alkaline earth metal hydroxides such as magnesium hydroxide and the like; alkali metal phosphates such as tripotassium phosphate and the like; metal alkoxides such as sodium tert-butoxide, potassium tert-butoxide and the like, and the like.

The additives that may be used are not particularly limited to those used as known methods. Preferred examples include metal oxides such as silver oxide, alumina and the like; phosphines such as triphenylphosphine, tri-tert-butylphosphine, tricyclohexylphosphine, tri(o-toluyl)phosphine, diphenylphosphinoferrocene, 2-dicyclohexylphosphino-2',6'-dimethoxy-1,1'-biphenyl (S-PHOS), 2-dicyclohexylphosphino-2',4',6'-triisopropyl-1,1'-biphenyl (X-PHOS), 2,2'-bis(diphenylphosphino)-1,1'-binaphthyl (BINAP), 4,5-bis(diphenylphosphino)-9,9-dimethylxanthene (Xantphos) and the like; phosphine oxides such as triphenylphosphine oxide and the like; metal salts such as lithium chloride, potassium fluoride, cesium fluoride and the like; ammonium salts such as tetrabutylammonium bromide and the like; acid anhydrides such as acetic anhydride and the like, and the like. These may be used in any combination in any ratio.

The metal catalyst to be used is not particularly limited as long as it is used in a known method. Preferred examples include palladium catalysts such as tetrakis(triphenylphosphine)palladium, bis(tri-tert-butylphosphine)palladium, 2 palladium acetate, 2 palladium chloride diphenylphosphinoferrocene complex, 2 palladium chloride benzonitrile complex, 2 palladium chloride acetonitrile complex, bis(dibenzylideneacetone)palladium, tris(dibenzylideneacetone) dipalladium, bis[1,2-bis(diphenylphosphino)ethane]palladium, 3-chloropyridine[1,3-bis(2,6-diisopropylphenyl)imidazo-2-ylidene]palladium, palladium-activated carbon and the like.

The alcohol (Pro$^4$H) to be used is not particularly limited and, for example, methanol, ethanol and the like can be mentioned.

The carbon monoxide source to be used is not particularly limited and, for example, carbon monoxide gas, lithium formate, 2,4,6-trichlorophenyl formate and the like can be mentioned.

While the reaction temperature varies depending on the raw material compounds, reagents, and the like, it is generally 0° C. to 150° C., preferably 20° C. to 120° C.

While the reaction time varies depending on the raw material compounds, reagents, and the like, it is generally 5 min to 24 hr, preferably 10 min to 12 hr.

(Step G-2)

In this step, compound (XXII) is produced by introducing a leaving group $L^2$ (preferably a halogen atom or a pseudohalogen atom group) into compound (XXI). For example, when $L^2$ is a bromo group, the reaction can be performed in accordance with the above-mentioned step D-1, but the method is not limited thereto.

(Step G-3)

In this step, compound (XXII) is reduced with a suitable reducing agent in a solvent to produce compound (XIX).

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; ethers such as diethyl ether, tetrahydrofuran, 1,4-dioxane, 1,2-dimethoxyethane and the like; amides such as N,N-dimethylformamide and the like; sulfoxides such as dimethyl sulfoxide and the like; mixed solvents containing a plurality of the organic solvents mentioned above in any ratio and the like.

The reducing agents to be used are not limited to those used as reducing agents in normal reactions. For example, lithium aluminum hydride, diisobutylaluminum hydride, sodium bis(2-methoxyethoxy)aluminum dihydride, lithium borohydride and the like can be mentioned.

While the reaction temperature varies depending on the raw material compounds, reagents, and the like, it is generally −100° C. to 150° C., preferably −78° C. to 80° C.

While the reaction time varies depending on the raw material compounds, reagents, and the like, it is generally 5 min to 24 hr, preferably 10 min to 6 hr.

(Step G-4)

In this step, compound (XXI) is produced by converting the carboxy group of compound (XXIII) to a $C_{1-6}$ alkyl ester group in a solvent. Here, a method of condensing with the corresponding alcohol in the presence of an acid is described, but the method is not limited thereto.

The solvent to be used is not particularly limited as long as it does not inhibit the reaction and dissolves the starting materials to some extent. Preferably, for example, alcohols such as methanol, ethanol, n-butanol and the like or a mixed solvent containing these alcohols and an organic solvent in any ratio can be used as both a solvent and a reactant.

The acid to be used is not particularly limited and, for example, inorganic acids such as sulfuric acid, hydrochloric acid, nitric acid and the like; organic acids such as p-toluenesulfonic acid and the like, and the like can be mentioned.

While the reaction temperature varies depending on the raw material compounds, reagents, and the like, it is generally 0° C. to 200° C., preferably 20° C. to 130° C.

While the reaction time varies depending on the raw material compounds, reagents, and the like, it is generally 5 min to 24 hr, preferably 10 min to 6 hr.

(Step G-5)

In this step, compound (XXIV) is produced by introducing a leaving group $L^2$ (preferably a halogen atom or a pseudohalogen atom group) into compound (XXIII) in a solvent. For example, when $L^2$ is a bromo group, the reaction can be performed in accordance with the above-mentioned step D-1, but is not limited thereto.

(Step G-6)

In this step, compound (XXIV) is reduced with a suitable reducing agent in a solvent to produce compound (XIX).

The solvent to be used is not particularly limited as long as it does not inhibit the reaction and dissolves the starting materials to some extent, and preferred examples include ethers such as diethyl ether, tetrahydrofuran and the like.

The reducing agents used are not limited to those used as reducing agents in normal reactions. For example, lithium aluminum hydride, borane-tetrahydrofuran complex and the like can be mentioned.

While the reaction temperature varies depending on the raw material compounds, reagents, and the like, it is generally −100° C. to 100° C., preferably −78° C. to 50° C.

While the reaction time varies depending on the raw material compounds, reagents, and the like, it is generally 5 min to 24 hr, preferably 10 min to 6 hr.

(Step G-7)

In this step, compound (XIII) is produced by converting the leaving group (L) of compound (XIX) into a boronic acid ester, and the reaction can be performed in accordance with the above-mentioned step F-4.

(Method H)

In this production method, compound (III), which is an intermediate compound used in Methods A and B, and in which Z is a group represented by the aforementioned formula A1, is produced. A method for producing a compound (IIIA1-1) wherein the group W in the aforementioned formula A1 is an oxygen atom is described below, but the method is not limited thereto.

(Method H)

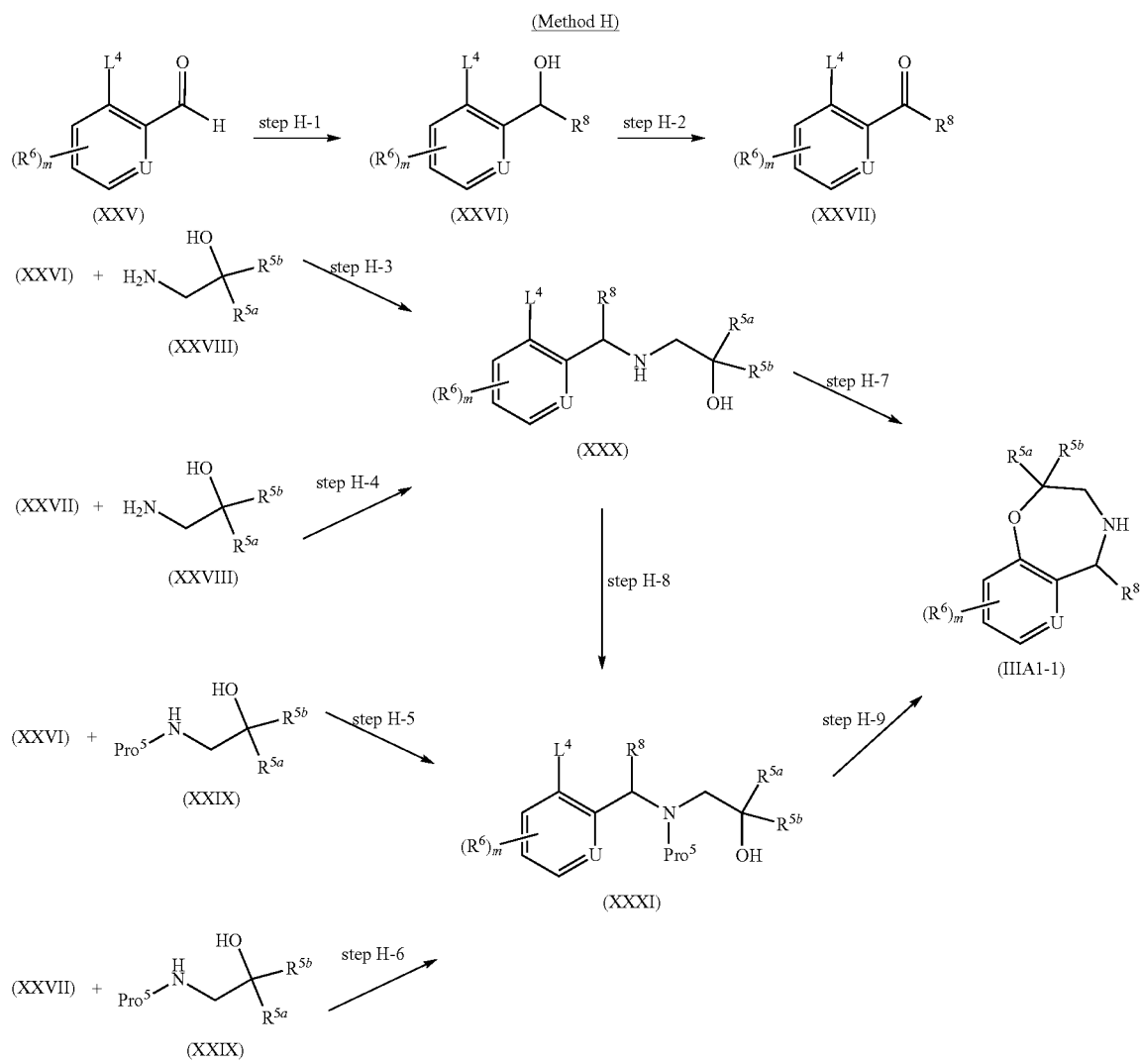

wherein L⁴ is a leaving group (preferably a halogen atom or a pseudohalogen atom group), Pro⁵ is a protecting group (preferably a p-methoxybenzyl group, an allyl group or a benzyl group), and other symbols are as defined above.

(Step H-1)

In this step, nucleophilic addition reaction is performed on the formyl group of compound (XXV) by using an appropriate organometallic compound in a solvent to introduce a substituent R⁸ to produce compound (XXVI).

The solvent to be used is not particularly limited as long as it does not inhibit the reaction and dissolves the starting materials to some extent, and preferred examples include aromatic hydrocarbons such as benzene, toluene, xylene and the like; ethers such as diethyl ether, tetrahydrofuran, 1,4-dioxane, 1,2-dimethoxyethane and the like; amides such as N,N-dimethylformamide and the like; sulfoxides such as dimethyl sulfoxide and the like; mixed solvents containing a plurality of the organic solvents mentioned above in any ratio and the like.

Examples of the organometallic reagent to be used include organic lithium compounds such as methyllithium, n-butyllithium and the like; Grignard reagents such as methylmagnesium bromide, ethylmagnesium bromide and the like; organic zinc compounds such as diethyl zinc and the like, and the like.

While the reaction temperature varies depending on the raw material compounds, reagents, and the like, it is generally −100° C. to 100° C., preferably −80° C. to 50° C.

While the reaction time varies depending on the raw material compounds, reagents, and the like, it is generally 5 min to 12 hr, preferably 10 min to 6 hr.

(Step H-2)

In this step, the hydroxy group of compound (XXVI) is oxidized to a carbonyl group, which can be performed according to the aforementioned step D-10.

(Step H-3)

In this step, compound (XXX) is produced from compound (XXVI) and compound (XXVIII). In the following, a method of converting the hydroxy group of compound (XXVI) to a leaving group (Step H-3-1) and then condensing with compound (XXVIII) (Step H-3-2) is described, but the present invention is not limited thereto.

(Step H-3-1)

This step can be performed according to the aforementioned step D-9.

(Step H-3-2)

This step can be performed according to the aforementioned step A-1.

(Step H-4)

In this step, compound (XXX) is produced by reductive amination of compound (XXVII) and compound (XXVIII). In the following, a method using a hydride reducing agent in a solvent (step H-4a) and a method using formic acid in the presence of an iridium catalyst (step H-4b) are described, but the method is not limited thereto.

(Step H-4a)

This step can be performed according to the aforementioned step B-1.

(Step H-4b)

This step can be performed using formic acid in a solvent in the presence of an iridium catalyst.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

The iridium catalyst to be used is not particularly limited as long as it is used in a known method. Preferred examples include chloro(pentamethylcyclopentadienyl) (8-quinolinolato)iridium(III), chloro(pentamethylcyclopentadienyl) (4-dimethylamino-8-quinolinolato)iridium (III) and the like.

While the reaction temperature varies depending on the raw material compounds, reagents, and the like, it is generally −20° C. to 150° C., preferably 0° C. to 100° C.

While the reaction time varies depending on the raw material compounds, reagents, and the like, it is generally 5 min to 24 hr, preferably 10 min to 6 hr.

(Step H-5)

In this step, compound (XXXI) is produced from compound (XXVI) and compound (XXIX), which can be performed according to the aforementioned step H-3.

(Step H-6)

In this step, Compound (XXVII) is subjected to a reductive amination reaction with compound (XXIX) to produce compound (XXXI), which can be performed according to the aforementioned step H-4.

(Step H-7)

In this step, compound (IIIA1-1) is produced from compound (XXX) by using an appropriate base in a solvent.

The solvent to-be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

The base to be used is not particularly limited as long as it is one that is used as a base in a normal reaction. Preferred examples of the base include organic bases such as triethylamine and the like; alkali metal alkoxides such as potassium tert-butoxide, sodium tert-butoxide and the like; alkali metal carbonates such as sodium carbonate, potassium carbonate and the like; alkaline earth metal carbonates such as magnesium carbonate and the like; alkali metal hydrogen carbonates such as potassium hydrogen carbonate and the like; alkaline earth metal hydrogen carbonates such as calcium hydrogen carbonate and the like; alkali metal hydroxides such as sodium hydroxide, potassium hydroxide and the like; alkaline earth metal hydroxides such as magnesium hydroxide and the like; alkali metal phosphates such as tripotassium phosphate and the like, and the like.

While the reaction temperature varies depending on the raw material compounds, reagents, and the like, it is generally −100° C. to 150° C., preferably 0° C. to 80° C.

While the reaction time varies depending on the raw material compounds, reagents, and the like, it is generally 5 min to 24 hr, preferably 10 min to 6 hr.

(Step H-8)

In this step, the secondary amino group of compound (XXX) is protected with a protecting group ($Pro^5$) to produce compound (XXXI). This step is performed according to a known method appropriately selected from, for example, P. G. Wuts, "Protective Groups in Organic Synthesis", 5th Edition, Wiley, 2014, and the like, depending on the type of $Pro^5$. In the following, a method using reductive amination (Step H-8a) and a method using p-methoxybenzyl halides (Step H-8b) are described for the case where $Pro^5$ is a p-methoxybenzyl group, but the method is not limited thereto.

(Step H-8a)

This step includes reductive amination using compound (XXX) and p-methoxybenzaldehyde, which can be performed according to the aforementioned step B-1.

(Step H-8b)

In this step, the secondary amino group of compound (XXX) is protected using p-methoxybenzyl chloride or p-methoxybenzyl bromide in a solvent in the presence of a suitable base.

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio and the like.

The base to be used is not particularly limited as long as it is one that is used as a base in a normal reaction. Preferred examples of the base include organic bases such as triethylamine and the like; alkali metal alkoxides such as potassium tert-butoxide, sodium tert-butoxide and the like; alkali metal carbonates such as sodium carbonate, potassium carbonate and the like; alkaline earth metal carbonates such as magnesium carbonate and the like; alkali metal hydrogen carbonates such as potassium hydrogen carbonate and the like; alkaline earth metal hydrogen carbonates such as calcium hydrogen carbonate and the like; alkali metal hydroxides such as sodium hydroxide, potassium hydroxide and the like; alkaline earth metal hydroxides such as magnesium hydroxide and the like; metal hydrides such as sodium hydride and the like; alkali metal phosphates such as tripotassium phosphate and the like, and the like.

While the reaction temperature varies depending on the raw material compounds, reagents, and the like, it is generally −100° C. to 200° C., preferably 0° C. to 150° C.

While the reaction time varies depending on the raw material compounds, reagents, and the like, it is generally 5 min to 48 hr, preferably 10 min to 24 hr.

(Step H-9)

In this step, compound (IIIA1-1) is produced from compound (XXXI). In a solvent, a suitable base is used to form a 7-membered ring from compound (XXXI) (step H-9-1), which is then converted to compound (IIIA1-1) by removing the protecting group (Pro$^5$) (step H-9-2).

(Step H-9-1)

This step can be performed according to the aforementioned step H-7.

(Step H-9-2)

In this step, a protecting group (Pro$^5$) is removed, which can be performed according to step E-3.

(Method I)

In this production method, compound (III), which is an intermediate compound used in the aforementioned Methods A and C, and in which Z is a group represented by the aforementioned formula A2, is produced. In the following, a method for producing a compound (IIIA2-1) wherein the group W in the aforementioned formula A2 is an oxygen atom is described below, but the method is not limited thereto.

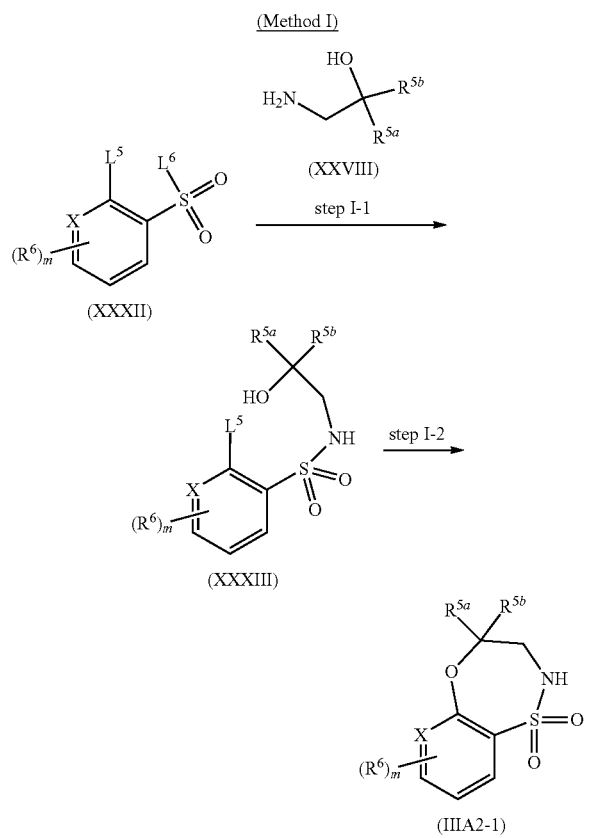

wherein L$^5$ and L$^6$ are each independently a leaving group (preferably a halogen atom or a pseudohalogen atom group), and other symbols are as defined above.

(Step I-1)

In this step, compound (XXXII) and compound (XXVIII) are condensed in a solvent in the presence or absence of a base to produce compound (XXXIII).

The solvent to be used is not particularly limited as long as it does not inhibit the reaction and dissolves the starting materials to some extent, and preferred examples include aromatic hydrocarbons such as benzene, toluene, xylene and the like; halogenated hydrocarbons such as dichloromethane, chloroform and the like; esters such as ethyl acetate, propyl acetate and the like; ethers such as diethyl ether, tetrahydrofuran, 1,4-dioxane, 1,2-dimethoxyethane and the like; alcohols such as methanol, ethanol, tert-butanol and the like; nitriles such as acetonitrile and the like; amides such as formamide, N,N-dimethylformamide and the like; sulfoxides such as dimethyl sulfoxide and the like; mixed solvents containing a plurality of the organic solvents mentioned above in any ratio; mixed solvents containing the aforementioned organic solvent and water in any ratio and the like.

The base to be used is not particularly limited as long as it is one that is used as a base in a normal reaction. Preferred examples of the base include organic bases such as triethylamine, N,N-diisopropylethylamine, N-methylmorpholine, lutidine, pyridine and the like; alkali metal carbonates such as sodium carbonate, potassium carbonate and the like; alkaline earth metal carbonates such as magnesium carbonate and the like; alkali metal hydrogen carbonates such as sodium hydrogen carbonate, potassium hydrogen carbonate and the like; alkaline earth metal hydrogen carbonates such as calcium hydrogen carbonate and the like; alkali metal hydroxides such as sodium hydroxide and the like; alkaline earth metal hydroxides such as magnesium hydroxide and the like; alkali metal phosphates such as tripotassium phosphate and the like, and the like.

While the reaction temperature varies depending on the raw material compounds, reagents, and the like, it is generally −80° C. to 100° C., preferably −20° C. to 50° C.

While the reaction time varies depending on the raw material compounds, reagents, and the like, it is generally 5 min to 24 hr, preferably 10 min to 6 hr.

(Step I-2)

In this step, compound (IIIA2-1) is produced from compound (XXXIII), which can be performed according to the aforementioned step H-7.

(Method J)

In this production method, compound (III), which is an intermediate compound used in the aforementioned Methods A and C, and in which Z is a group represented by the aforementioned formula A3, is produced. In the following, a method for producing a compound (IIIA3-1) wherein the group W in the aforementioned formula A3 is an oxygen atom is described below, but the method is not limited thereto.

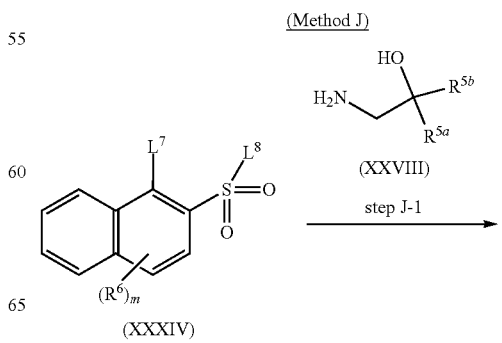

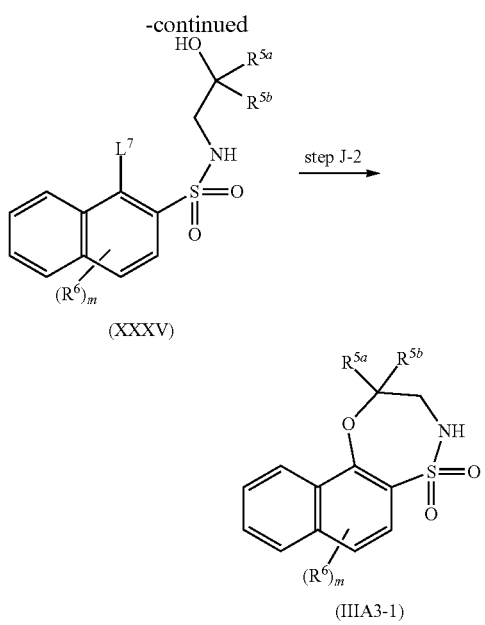

wherein $L^7$ and $L^8$ are each independently a leaving group (preferably a halogen atom or a pseudohalogen atom group), and other symbols are as defined above.
(Step J-1)

In this step, compound (XXXIV) and compound (XXVIII) are condensed to produce compound (XXXV), which can be performed according to the aforementioned step I-1.
(Step J-2)

In this step, compound (IIIA3-1) is produced from compound (XXXV), which can be performed according to the aforementioned step H-7.

The compound (1) or a pharmaceutically acceptable salt thereof obtained by the above-mentioned production method can be isolated and purified by a conventional separation means such as recrystallization, distillation, chromatography, and the like.

When the compound (1) or a pharmaceutically acceptable salt thereof exists as an optical isomer based on an asymmetric carbon, it can be separated into individual optical isomers by conventional optical resolution means (e.g., fractionated crystal method, resolution using a chiral column). Alternatively, the optical isomers can be synthesized using optically pure starting materials. Furthermore, optical isomers can also be synthesized by stereoselectively carrying out each reaction using chiral auxiliary groups or asymmetric catalysts.

(Medicament (or Pharmaceutical Composition) of the Present Invention)

The medicament of the present invention is a drug for preventing and/or treating oxidative stress-related diseases, which contains compound (1) or a pharmaceutically acceptable salt thereof as an active ingredient.

The medicament of the present invention may be either a medicament consisting of only compound (1) or a pharmaceutically acceptable salt thereof, or a pharmaceutical composition containing compound (1) or a pharmaceutically acceptable salt thereof and a pharmaceutically acceptable carrier, and the like. The medicament of the present invention can be administered in a pharmaceutical effective amount to a subject (e.g., a mammal such as human, mouse, rat, hamster, guinea pig, rabbit, cat, dog, pig, cow, horse, sheep, or monkey).

Examples of the pharmaceutically acceptable carrier include excipient (e.g., starch, lactose, sugar, calcium carbonate, calcium phosphate etc.), binder (e.g., starch, gum arabic, carboxymethylcellulose, hydroxypropylcellulose, crystalline cellulose etc.), lubricant (e.g., magnesium stearate, talc etc.), disintegrant (e.g., carboxymethylcellulose, talc etc.), solvent (e.g., water for injection, physiological brine, Ringer's solution, alcohol, propylene glycol, polyethylene glycol, sesame oil, corn oil, olive oil, cotton seed oil etc.), solubilizing agent (e.g., polyethylene glycol, propylene glycol, D-mannitol, trehalose, benzyl benzoate, ethanol, tris-aminomethane, cholesterol, triethanolamine, sodium carbonate, sodium citrate, sodium salicylate, sodium acetate etc.), suspending agent (e.g., surfactants such as stearyl triethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil etc.), isotonic agent (e.g., sodium chloride, glycerol, D-mannitol, D-sorbitol, glucose etc.), buffering agent (e.g., buffer such as phosphate, acetate, carbonate, citrate and the like), soothing agent (e.g., benzyl alcohol etc.), antiseptic (e.g., p-hydroxybenzoic acid esters, chlorobutanol, benzyl alcohol, phenethyl alcohol, dehydroacetic acid, sorbic acid etc.), antioxidizing agent (e.g., sulfite, ascorbate etc.), colorant (e.g., water-soluble food tar dyes (e.g., food colors such as Food Color Red Nos. 2 and 3, Food Color yellow Nos. 4 and 5, Food Color Blue Nos. 1 and 2 and the like), water insoluble lake pigment (e.g., aluminum salt of the aforementioned water-soluble food tar color), natural dye (e.g., p-carotene, chlorophyll, red iron oxide) etc.), sweetening agent (e.g., sodium saccharin, dipotassium glycyrrhizinate, stevia etc.), corrigent (e.g., fennel oil, cassia oil, ethyl vanillin, orange oil etc.), aromatic and the like.

The medicament (pharmaceutical composition) of the present invention can be formulated by mixing the above-mentioned components and then subjecting the mixture to a method known per se, into a preparation for oral administration such as tablets, pills, fine granules, granules, capsules, dry syrup, elixir, and the like; or a preparation for parenteral administration such as injections (e.g., subcutaneous injections, intravenous injections, intramuscular injections, intraperitoneal injections, drips, and the like), topical preparations (e.g., transdermal preparations, ointments, lotions, patches), suppositories (e.g., rectal suppositories, vaginal suppositories), pellets, nasal preparations, pulmonary preparations (inhalants), eye drops, implants, microcapsules, liposome preparations, and the like. Tablets or pills may be coated with sugar coating, or with a gastric or enteric coating agent as necessary. Preparations for parenteral administration can be sterilized, for example, by filtration through a bacteria-retaining filter, by blending with a bactericide, or by irradiation. Furthermore, a sterile solid composition may be dissolved or suspended in sterile water or a solvent for injection before use, and the resulting composition may be used as a preparation for parenteral administration.

The content of the compound (1) of the present invention or a pharmaceutically acceptable salt thereof in the medicament (pharmaceutical composition) of the present invention varies depending on the form of the preparation. It is generally in the range of about 0.001 to 100% by weight, preferably about 0.01 to 50% by weight, and more preferably about 0.01 to 20% by weight, based on the total weight of the preparation.

The dosage and frequency of administration of the compound (1) of the present invention or a pharmaceutically acceptable salt thereof are appropriately determined for each individual case, taking into consideration the symptoms, age or sex of the subject, and the like. The dosage is generally 0.001 mg/kg to 100 mg/kg per dose for adults when administered orally, and generally 0.0001 mg/kg to 10 mg/kg per dose for adults when administered intravenously. The frequency of administration is generally once to six times a day, or once a day to once every seven days.

The compound (1) of the present invention or a pharmaceutically acceptable salt thereof is effective for prophylactic and/or therapeutic use for a disease selected from the group consisting of a renal disease selected from the group consisting of chronic kidney disease, acute nephritis, chronic nephritis, acute renal failure, chronic renal failure, nephrotic syndrome, IgA nephropathy, diabetic nephropathy, gouty kidney, nephrosclerosis, hydronephrosis and tubulointerstitial nephritis; a liver disease selected from the group consisting of alcoholic fatty liver, non-alcoholic steatohepatitis, hepatic fibrosis and cirrhosis; a respiratory disease selected from the group consisting of bronchitis, pneumonia, pleurisy, chronic obstructive pulmonary diseases, acute lung disorder, diffuse panbronchiolitis, interstitial pneumonia and asthma; a dermatic disease selected from the group consisting of UV and radiation skin disorder, radiation mucosal disorder, epidermolysis blister syndrome, psoriasis, atopic dermatitis and scleroderma; a cardiovascular disease selected from the group consisting of cardiac failure, myocardial infarction, arteriosclerosis and pulmonary arterial hypertension; a central nervous system disease selected from the group consisting of Alzheimer's disease, Parkinson's disease, Huntington's disease, amyotrophic lateral sclerosis, cerebral infarction, polyglutamine disease and autism; a mitochondrial disease selected from the group consisting of Friedreich's ataxia and mitochondrial myopathy; an autoimmune disease selected from the group consisting of multiple sclerosis, rheumatoid arthritis, systemic lupus erythematosus, Sjogren syndrome, type 1 diabetes, ulcerative colitis and Crohn's disease; and an ophthalmic disease selected from the group consisting of allergic conjunctival diseases, viral conjunctivitis, pterygium, cornea infectious disease, dry eye, corneal disorders, uveitis, Behcet's disease, diabetic retinopathy, retinal detachment, retinal vein occlusion, central serous chorioretinopathy, age-related macular degeneration, diabetic macular edema, macular disease, retinitis pigmentosa, glaucoma and cataract, and among them, particularly effective for prophylactic and/or therapeutic use for an oxidative stress-related disease selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa and glaucoma.

The compound (1) of the present invention or a pharmaceutically acceptable salt thereof can be used in combination with other drugs (concomitant drugs) as long as the efficacy thereof is not impaired. The concomitant drug is not particularly limited and, for example, one or more known drugs that have been conventionally used for the treatment of oxidative stress-related diseases, which are exemplified above and selected from the group consisting of chronic kidney disease, non-alcoholic steatohepatitis, chronic obstructive pulmonary disease, radiation skin disorder, radiation mucosal disorder, cardiac failure, pulmonary arterial hypertension, Parkinson's disease, Friedreich's ataxia, multiple sclerosis, age-related macular degeneration, retinitis pigmentosa and glaucoma can be preferably used.

Other drugs (concomitant drugs) which are suitable for use in combination with the compound (1) of the present invention or a pharmaceutically acceptable salt thereof include, but are not limited to, for example, ACE inhibitor (e.g., enalapril etc.), angiotensin II receptor antagonists (e.g., olmesartan etc.), (3 blockers (e.g., carvedilol etc.), aldosteron antagonists (e.g., spironolactone etc.), bronchodilators (e.g., anticholinergics, theophylline etc.), steroids (e.g., predonisolone etc.), prostacyclins (e.g., veraprost etc.), endothelin receptor antagonist (e.g., bosentan etc.), phosphodiesterase-5 inhibitors (e.g., sildenafil etc.), soluble guanylate cyclase (sGC) stimulants (e.g., belisiguat etc.), L-dopa, dopamine agonists (e.g., pramipexole etc.), catechol-O-methyl transferase (COMT) inhibitors (e.g., entacapone etc.), monoamine oxidase B(MAO-B) inhibitors (e.g., selegiline etc.), interferon β, copaxone and the like.

When a concomitant drug is used, the administration period is not limited, and it may be administered to the administration subject simultaneously, or may be administered with a time lag. In the administration with a time lag, the medicament of the present invention may be administered first and the concomitant drug may be administered later, or the concomitant drug may be administered first and the medicament of the present invention may be administered later. The administration method of each may be the same or different. In addition, the compound (1) of the present invention or a pharmaceutically acceptable salt thereof and the concomitant drug may be administered in combination as a single preparation (combination drug). As a pharmaceutically acceptable carrier that may be used in the production of a combination drug, those similar to the ones used in the pharmaceutical composition of the present invention described above can be mentioned.

The dosage of the concomitant drug can be appropriately selected based on the dosage generally used in clinical practice. The mixing ratio of the compound of the present invention or a pharmaceutically acceptable salt thereof to the concomitant drug can be appropriately selected depending on the subject of administration (age, body weight, general health condition, sex, degree of disease, etc. of the subject), the administration route, the type of disease, the type of concomitant drug, and the like.

The mass ratio of compound (1) or a pharmaceutically acceptable salt thereof to a concomitant drug is not particularly limited.

Also, concomitant drugs that complement and/or enhance the therapeutic effect of compound (1) or pharmaceutically acceptable salts thereof include those that have not been found to date and will be found in the future based on the mechanism described above (i.e., the Nrf2 activation mechanism by inhibiting the protein-protein interaction between Keap1 and Nrf2).

The medicament or pharmaceutical composition of the present invention may be provided in the form of a kit together with instructions on how to administer the medicament or pharmaceutical composition. The medicament contained in the kit is supplied in a container manufactured from a material that will effectively sustain the activity of the components of the medicament or pharmaceutical composition for a long period of time, will not adsorb on the inner side of the container, and will not alter the components. For example, a sealed glass ampoule may contain buffer and the like sealed in the presence of a neutral, non-reactive gas such as nitrogen gas. The kit may also be accompanied by instructions for use. The instructions for use of the kit may be printed on paper or other media, or may be stored on an electromagnetically readable medium such as a CD-ROM, DVD-ROM, and the like, and supplied to the user.

Experimental Example 1: FP Assay (In Vitro)

The inhibitory activity of test compounds on the binding between Nrf2 and Keap1 was determined by fluorescence polarization. A solution of 50 mM Tris-HCl pH. 8.0 (NAC-ALAI, REF: 06938-15), and 5 mM DTT (SIGMA-ALDRICH, REF: 646563-10×0.5 mL) was used as a buffer solution. 8 μL of a buffer solution containing 40 nM GST-fused human Keap1 (amino acid residues: 325-642) protein (Protein tech, REF: Ag0779) was taken in a black 384-well plate (final concentration 20 nM), and 4 μL of the test compound solution prepared to each concentration in buffer solution was added thereto. A well containing a portion of the buffer solution without Keap1 was placed as a negative control. A well with no compound was used as a positive control. 40 nM of FITC-labeled Nrf2 peptide (FITC-X-LQLDEETGEFLPIQ (X=ε-Acp), Peptide Institute Inc.) was added thereto (10 nM final concentration). The wells were incubated at room temperature for 2 hr, and then fluorescence polarization was measured with a plate reader SPECTRAMAX Paradigm (Molecular devices) at excitation wavelength of 485 nm and fluorescence wavelength of 535 nm. The fluorescence polarization of the negative control was set to 100% inhibition and that of the positive control to 0% inhibition, and the inhibitory rate upon addition of the test compound was calculated using the following formula.

inhibitory rate (%)=(fluorescence polarization of negative control−fluorescence polarization when test compound is added)/(fluorescence polarization of positive control−fluorescence polarization of negative control)×100   [numerical formula 1]

The results of each test compound in this study are shown in Table 1 below in the range of two concentrations (μM) between 50% inhibitory rate (A: inhibitory rate 50% concentration $(IC_{50}) \leq 0.01$, B:$0.01<$inhibitory rate 50% concentration $(IC_{50}) \leq 0.03$, C:$0.03<$inhibitory rate 50% concentration $(IC_{50}) \leq 0.1$).

TABLE 1

| Example No. | $IC_{50}$ |
| --- | --- |
| 1 | C |
| 2 | B |
| 3 | A |
| 4 | A |
| 5 | B |
| 6 | A |
| 7 | A |
| 8 | A |
| 9 | B |
| 10 | B |
| 11 | B |
| 12 | A |
| 13 | A |
| 14 | B |
| 15 | C |
| 16 | A |
| 17 | A |
| 18 | C |
| 19 | B |
| 20 | B |
| 21 | A |

TABLE 1-continued

| Example No. | $IC_{50}$ |
| --- | --- |
| 22 | A |
| 23 | A |
| 24 | B |
| 25 | B |
| 26 | C |
| 27 | A |
| 28 | A |
| 29 | A |
| 30 | A |
| 31 | A |
| 32 | A |
| 33 | C |
| 34 | B |
| 35 | B |
| 36 | B |
| 37 | A |
| 38 | A |
| 39 | B |
| 40 | B |
| 41 | A |
| 42 | A |
| 43 | A |
| 44 | A |
| 45 | A |
| 46 | B |
| 47 | A |
| 48 | A |
| 49 | C |
| 50 | B |
| 51 | B |
| 52 | B |
| 53 | B |
| 54 | B |
| 55 | B |
| 56 | B |
| 57 | B |
| 58 | C |
| 59 | B |
| 60 | B |
| 61 | B |
| 62 | B |
| 63 | B |
| 64 | A |
| 65 | B |
| 66 | B |
| 67 | A |
| 68 | A |
| 69 | A |
| 70 | C |
| 71 | A |
| 72 | A |
| 73 | C |
| 74 | A |
| 75 | A |
| 76 | A |
| 77 | A |
| 78 | B |
| 79 | C |
| 80 | B |
| 81 | B |
| 82 | B |
| 83 | C |
| 84 | C |
| 85 | B |
| 86 | C |
| 87 | A |
| 88 | B |
| 89 | A |
| 90 | B |
| 91 | B |
| 92 | B |
| 93 | A |
| 94 | A |
| 95 | A |
| 96 | A |
| 97 | A |
| 98 | A |
| 99 | A |

TABLE 1-continued

| Example No. | IC$_{50}$ |
|---|---|
| 100 | A |
| 101 | A |
| 102 | A |
| 103 | A |
| 104 | B |
| 105 | B |
| 106 | A |
| 107 | B |
| 108 | C |
| 109 | C |
| 110 | C |
| 111 | A |
| 112 | A |

Experimental Example 2: NAD(P)H: Quinone Oxidoreductase-1 (NQO1) Enzyme Induction Assay (In Vitro)

The NQO1 assay was performed based on a previous report (Methods in Enzymology 2004; 382: 243-258). Hepa1c1c7 cells (mouse hepatocyte cell line, ATCC, cat. no. CRL-2026) were cultured in D-MEM medium containing 10% FBS and 1% penicillin/streptomycin (5% $CO_2$, 37° C.), and seeded into 96-well plates (Corning REF. 353072) at 1×104 cells/well. A portion of the wells were prepared with medium only for background measurement without seeding cells. The next day, 400 nM of the test compound (0.004% of the final concentration in DMSO) dissolved in DMSO was added thereto, and the wells were incubated for about 48 hr. A well without adding the test compound was prepared for base activity assay in part.

Cell lysate (solution containing 0.8% digitonin, 2 mM EDTA), reaction solution (solution containing 25 mM Tris-HCl, 0.07% albumin, 0.01% Tween-20, 2 U/mL glucose-6-phosphate dehydrogenase, 5 μM flavin adenine dinucleotide, 1 μM glucose-6-phosphate, 30 PM nicotinamide adenine dinucleotide phosphate, 0.03% 3-(4,5-dimethyl-2-thiazolyl)-2,5-diphenyltetrazolium bromide (MTT), and 50 μM menadione), stop solution (solution containing 0.3 mM dicoumarol and 5 mM potassium dihydrogen phosphate, pH 7.4) were prepared. After the medium was removed, 50 μL of the cell lysate was added and incubated at 37° C. for 10 minutes, followed by shaking at room temperature for 10 minutes. 200 μL of reaction solution was added thereto, and allowed to stand for 5 minutes at room temperature. 50 μL of the stop solution was added thereto, and absorbance was measured at 610 nm on a SpectraMax PLUS384 (Molecular devices) or POWERSCAN HT (DS Pharma Biomedical). The test results were analyzed in Excel, and the NQO1 activity upon addition of 400 nM of test compound was calculated as a ratio from the base without the compound.

NQO1 activity ratio when test compound is added= (absorbance when test compound is added− absorbance of medium only)/(absorbance without addition of compound−absorbance of medium only)     [numerical formula 2]

The results of each test compound in this test are shown in the following Table 2 (A:5<NQO1 activity ratio, B:3<NQO1 activity ratio≤5).

TABLE 2

| Example No. | activity ratio |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 16 | A |
| 16 | A |
| 17 | B |
| 18 | B |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | B |
| 31 | A |
| 32 | A |
| 33 | A |
| 34 | A |
| 35 | A |
| 36 | A |
| 37 | B |
| 38 | A |
| 39 | B |
| 40 | B |
| 41 | A |
| 42 | A |
| 43 | A |
| 44 | B |
| 45 | A |
| 46 | B |
| 47 | B |
| 48 | A |
| 49 | A |
| 50 | A |
| 51 | B |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | B |
| 65 | A |
| 66 | A |
| 67 | A |
| 68 | A |
| 69 | B |
| 70 | B |
| 71 | A |
| 72 | A |
| 73 | A |
| 74 | A |
| 75 | A |
| 76 | A |
| 77 | A |

TABLE 2-continued

| Example No. | activity ratio |
|---|---|
| 78 | A |
| 79 | A |
| 80 | A |
| 81 | B |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | B |
| 112 | B |

These results confirm that the compound (1) of the present invention or a pharmaceutically acceptable salt thereof has the action of activating Nrf2 by inhibiting the protein-protein interaction between Keap1 and Nrf2.

Experimental Example 3: Measurement Test of Plasma Drug Concentration after Oral Administration in Rats 10 mg/2 mL/kg of the test compound suspended in 0.5% methylcellulose solution were force-fed to Male SD rats (7 weeks old, Japan SLC). Blood was collected from the jugular vein using a syringe with heparin at 0.5, 1, 2, 4, 6, and 24 hr after administration. After blood collection, to 20 μL of centrifuged plasma was added an equal volume of acetonitrile followed by 200 μL of internal standard (IS) solution. After agitation, all the supernatant after centrifugation was filtered, and the collected filtrate was used as the assay sample. Equal volumes of the test compound solution prepared in acetonitrile were added to blank plasma, and the samples processed in the same manner as above were used as samples for the calibration curve. The prepared samples were measured using LC/MS/MS, and the area under the blood concentration-time curve (AUC) was calculated from the compound concentration in plasma.

TABLE 3

| Example | maximam plasma concentration (μM) | AUC0-24 (μM * hr) |
|---|---|---|
| Example 4 | 0.029 | 0.050 |
| Example 5 | 0.006 | 0.035 |

TABLE 3-continued

| Example | maximam plasma concentration (μM) | AUC0-24 (μM * hr) |
|---|---|---|
| Example 7 | 0.009 | 0.030 |
| Example 8 | 0.005 | 0.023 |

Among the example compounds, the four compounds listed in Table 3 above were confirmed to have excellent pharmacokinetics, especially as a drug for topical administration, with excellent kinetics with no systemic exposure.

EXAMPLE

The present invention is described in detail by the following examples, which are merely an implementation and do not limit the present invention, and may be varied to the extent not departing from the scope of the present invention.

In the following examples, "room temperature" usually indicates about 10° C. to about 35° C. % indicates mol/mol % for yield, volume % for solvents used in chromatography, and weight % for others.

Nuclear magnetic resonance spectra ($^1$H-NMR, resonance frequency 400 MHz or 500 MHz) are listed as δ values (ppm) with tetramethylsilane as the standard or with the chemical shift value of the deuterated solvent used as the reference value.

Other abbreviations used in the text have the following meanings.

s: singlet
d: doublet
dd: doublet of doublets
t: triplet
q: quartet
m: multiplet
br: broad
J: coupling constant
Hz: hertz
CDCl$_3$: deuterochloroform
DMSO-d$_6$: deuterodimethyl sulfoxide
CD$_3$OD: deuterated methanol
XPhos: 2-dicyclohexylphosphino-2',4',6'-triisopropyl-1,1'-biphenyl
$^1$H-NMR: proton nuclear magnetic resonance
HPLC: high performance liquid chromatography
APCI: atmospheric chemical ionization method
ESI: electrospray method.

The reagents, solvents, devices, and the like used in the following Examples and Experimental Examples are commercially available unless otherwise specified. Furthermore, the raw material compounds used are known compounds and commercially available, or compounds synthesized and identified according to a method known per se or a method analogous thereto, unless otherwise specified.

Example 1

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid 1a (2R)-1-Aminobutan-2-ol To a solution of (2R)-2-ethyloxirane (25 mL) in ethanol (100 mL) was added a 28% aqueous ammonia solution (100 mL), and the mixture was stirred at room temperature for 24 hr. The solvent was evaporated under reduced pressure, and toluene was added to perform azeotropic distillation. A mixture (21.6 g) containing the title compound was obtained as an oil.

1b 2,5-Dichloro-N-[(2R)-2-hydroxybutyl]pyridine-3-sulfonamide

To a mixture of (2R)-1-aminobutan-2-ol (5.10 g) of Example 1(1a), sodium hydrogen carbonate (2.00 g), and tetrahydrofuran (71 mL) was added water (13 mL), and the mixture was stirred at room temperature for 5 min. Then, 2,5-dichloropyridine-3-sulfonyl chloride (3.5 g) was added, and the mixture was stirred at room temperature for 12 hr. The reaction mixture was extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=100/0-75/25(V/V)] to give the title compound 4.38 g, yield: 100%) as an oil.

1c (4R)-8-Chloro-4-ethyl-3,4-dihydro-2H-pyrido[2,3-b][1,4,5]oxathiazepine 1,1-dioxide 2,5-Dichloro-N-[(2R)-2-hydroxybutyl]pyridine-3-sulfonamide (4.38 g) of Example 1(1b) and potassium tert-butoxide (4.93 g) were dissolved in N,N-dimethylformamide (100 mL), and the mixture was stirred at 80° C. for 1 hr. The reaction mixture was cooled to room temperature, poured into water (100 mL), 1M hydrochloric acid (1.35 mL) was added and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=70/30-40/60(V/V)] to give the title compound (3.18 g, yield: 83%) as a solid.

1d

5-Bromo-7-methyl-1-benzothiophene-2-carboxylic acid

Diisopropylamine (86.7 g) was dissolved in tetrahydrofuran (800 mL), n-butyllithium (1.6 M n-hexane solution) (500 mL) was added dropwise over 25 min at −78° C., and the mixture was stirred at 30 min. Then, a solution of 4-bromo-1-fluoro-2-methylbenzene (108 g) in tetrahydrofuran (300 mL) was added dropwise over 35 min, and the mixture was stirred at −78° C. for 30 min. To the reaction mixture was added N,N-dimethylformamide (53.3 mL) at −78° C. After stirring for 10 min, the mixture was stirred for 1 hr while raising the temperature to room temperature. To the reaction mixture was added 2M hydrochloric acid (800 mL), and the mixture was extracted with ethyl acetate. The organic layer was washed successively with water and saturated brine, and dried over anhydrous sodium sulfate, and the solvent was evaporated under reduced pressure. The obtained residue was dissolved in N,N-dimethylformamide (830 mL), potassium carbonate (86.5 g) and ethyl thioglycolate (54.7 mL) were added, and the mixture was stirred at 90° C. for 1 hr. The reaction mixture was allowed to cool to room temperature, water was added, and the mixture was extracted with ethyl acetate. The organic layer was washed successively with water and saturated brine and dried over anhydrous sodium sulfate, and the solvent was evaporated under reduced pressure. The obtained residue was dissolved in ethanol (820 mL), 5M aqueous sodium hydroxide solution (209 mL) was added, and the mixture was stirred at room temperature for 1 hr. Under 0° C., to the reaction mixture was added 6M hydrochloric acid (228 mL), and the mixture was stirred at 0° C. for 30 min. The solid was collected by filtration and washed with water. The obtained solid was dissolved in a mixed solvent of ethyl acetate (1 L) and tetrahydrofuran (1 L), washed with saturated brine and dried over anhydrous sodium sulfate, and the solvent was evaporated under reduced pressure to give a residue. The filtrate obtained by filtration was extracted with ethyl acetate. The organic layer was washed with saturated brine and dried over anhydrous sodium sulfate, and the solvent was evaporated under reduced pressure. The residue obtained above was combined, n-hexane was added, and the solid was collected by filtration to give the title compound (120.0 g, yield: 78%) as a solid.

1e

5-Bromo-7-methyl-1-benzothiophene

5-Bromo-7-methyl-1-benzothiophene-2-carboxylic acid (105 g) of Example 1(1d) was dissolved in 1-methyl-2-pyrrolidinone (390 mL), 1,8-diazabicyclo[5.4.0]-7-undecene (289 mL) was added, and the mixture was stirred at 190° C. for 20.5 hr. At 0° C., to the reaction mixture was added 3M hydrochloric acid (720 mL), and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=100/0-95/5(V/V)] to give the title compound (49.8 g, yield: 57%) as an oil.

1f (5-Bromo-1-benzothiophen-7-yl)methyl acetate

5-Bromo-7-methyl-1-benzothiophene (114.2 g) of Example 1(1e) was dissolved in carbon tetrachloride (1.0 L), N-bromosuccinimide (98.5 g) and 2,2'-azodiisobutyronitrile (8.26 g) were added thereto, and the mixture was heated under reflux for 12 hr. The reaction mixture was allowed to cool to room temperature, and insoluble matter was filtered off. The filtrate was washed with water, the organic layer was dried over anhydrous sodium sulfate, and the solvent was evaporated under reduced pressure. The obtained residue was dissolved in N,N-dimethylformamide (535 mL), potassium acetate (247 g) was added thereto, and the mixture was stirred at room temperature for 1 hr. To the reaction mixture was added water, and the mixture was extracted with ethyl acetate. The organic layer was washed with water and saturated brine and dried over anhydrous sodium sulfate, and the solvent was evaporated under reduced pressure. The obtained residue was purified by column chromatography [elution solvent:n-hexane/ethyl acetate=100/0-90/10(V/V)] to give the title compound (94.4 g, yield: 66%) as a solid.

1g (5-Bromo-1-benzothiophen-7-yl)methanol (5-Bromo-1-benzothiophen-7-yl)methyl acetate (50.2 g) of Example 1(1f) was dissolved in a mixed solvent of methanol (290 mL) and tetrahydrofuran (290 mL), 2M aqueous sodium hydroxide solution (264 mL) was added, and the mixture was stirred at room temperature for 1 hr. To the reaction mixture was added water, and the mixture was extracted with ethyl acetate. The organic layer was washed with saturated brine and dried over anhydrous sodium sulfate, and the solvent was evaporated under reduced pressure. To the obtained residue was added n-hexane, and the mixture was subjected to an ultrasonic treatment. The solid was collected by filtration to give the title compound (39.6 g, yield: 92%) as a solid.

1h

[5-(4,4,5,5-Tetramethyl-1,3,2-dioxaborolan-2-yl)-1-benzothiophen-7-yl]methanol (5-Bromo-1-benzothiophen-7-yl)methanol (2.00 g) of Example 1(1 g) was dissolved in 1,4-dioxane (25 mL), bis(pinacolato)diboron (2.51 g), [1,1'-bis(diphenylphosphino)ferrocene]dichloropalladium(II) dichloromethane adduct (672 mg) and potassium acetate (2.42 g) were added, and the mixture was stirred under a nitrogen atmosphere at 90° C. for 1 hr. The reaction mixture was allowed to cool to room temperature, water was added, and the mixture was extracted with ethyl acetate. The organic layer was washed with saturated brine and dried over anhydrous sodium sulfate, and the solvent was evaporated under reduced pressure. The obtained residue was purified by silica gel column chromatography [elution solvent:n-hexane/ethyl acetate=100/0-70/30(V/V)] to give the title compound (2.75 g, yield: quantitative) as an oil.

1i

Ethyl 3-(1,4-dimethyl-1H-benzotriazol-5-yl)-3-[7-(hydroxymethyl)-1-benzothiophen-5-yl]propanoate

[5-(4,4,5,5-Tetramethyl-1,3,2-dioxaborolan-2-yl)-1-benzothiophen-7-yl]methanol (500 mg) of Example 1(1h) was dissolved in a mixed solvent of 1,4-dioxane (11.2 mL) and water (5.6 mL), triethylamine (0.48 mL) and ethyl (2E)-3-(1,4-dimethyl-1H-benzotriazol-5-yl)prop-2-enoate (WO 2015/092713) (423 mg) were added, and the mixture was stirred at 90° C. for 5 min. Then, chloro(1,5-cyclooctadiene) rhodium(I) dimer (42 mg) was added, and the mixture was stirred at 90° C. for 15 min. The reaction mixture was allowed to cool to room temperature, water was added, and the mixture was extracted with ethyl acetate. The organic layer was washed with saturated brine and dried over anhydrous sodium sulfate, and the solvent was evaporated under reduced pressure. The obtained residue was purified by column chromatography [elution solvent:n-hexane/ethyl acetate=80/20-30/70(V/V)] to give the title compound (276 mg, yield: 39%) as a solid.

1j

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate Ethyl 3-(1,4-dimethyl-1H-benzotriazol-5-yl)-3-[7-(hydroxymethyl)-1-benzothiophen-5-yl]propanoate (127 mg) of Example 1(1i) and (4R)-8-chloro-4-ethyl-3,4-dihydro-2H-pyrido[2,3-b][1,4,5]oxathiazepine 1,1-dioxide (98 mg) of Example 1(1c) were dissolved in tetrahydrofuran (1 mL), tri-n-butylphosphine (0.12 mL) and 1,1'-(azodicarbonyl)dipiperidine (117 mg) were added, and the mixture was stirred at room temperature for 14 hr. The reaction mixture was concentrated under reduced pressure, and the obtained residue was purified by silica gel column chromatography [elution solvent:n-hexane/ethyl acetate=90/10-40/60(V/V)]. The obtained residue was purified by NH silica gel column chromatography [elution solvent:n-hexane/ethyl acetate=90/10-50/50(V/V)] to give the title compound (155 mg, yield: 76%) as a solid.

1k 3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate (155 mg) of Example 1(1j) was dissolved in a mixed solvent of tetrahydrofuran (2.1 mL) and methanol (0.71 mL), 1M aqueous lithium hydroxide solution (0.71 mL) was added, and the mixture was stirred at room temperature for 15 hr. To the reaction mixture was added saturated aqueous ammonium chloride solution, and the mixture was extracted with ethyl acetate. The organic layer was washed with saturated brine and dried over anhydrous sodium sulfate, and the solvent was evaporated under reduced pressure. The obtained residue was purified by silica gel column chromatography [elution solvent:chloroform/methanol=100/0-90/10(V/V)]. To the obtained residue were added ethyl acetate and n-hexane, and the mixture was subjected to an ultrasonic treatment. The solid was collected by filtration to give the title compound (75.3 mg, yield: 51%) as a solid.

Example 2

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(4-chloro-1-methyl-1H-benzotriazol-5-yl)propanoic acid 2a Ethyl 3-(4-chloro-1-methyl-1H-benzotriazol-5-yl)-3-[7-(hydroxymethyl)-1-benzothiophen-5-yl]propanoate Using [5-(4,4,5,5-tetramethyl-1,3,2-dioxaborolan-2-yl)-1-benzothiophen-7-yl]methanol (300 mg) of Example 1(1h), and ethyl (2E)-3-(4-chloro-1-methyl-1H-benzotriazol-5-yl)prop-2-enoate (WO 2015/092713) (275 mg), the title compound (167 mg, yield: 39%) was obtained as a solid in the same manner as in Example 1(1i).

2b

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(4-chloro-1-methyl-1H-benzotriazol-5-yl)propanoate Using ethyl 3-(4-chloro-1-methyl-1H-benzotriazol-5-yl)-3-[7-(hydroxymethyl)-1-benzothiophen-5-yl]propanoate (100 mg) of Example 2 (2a) and (4R)-8-chloro-4-ethyl-3,4-dihydro-2H-pyrido[2,3-b][1,4,5]oxathiazepine 1,1-dioxide (76 mg) of Example 1(1c), the title compound (141 mg, yield: 87%) was obtained as a solid in the same manner as in Example 1(1j).

2c 3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(4-chloro-1-methyl-1H-benzotriazol-5-yl)propanoic acid Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(4-chloro-1-methyl-1H-benzotriazol-5-yl)propanoate (141 mg) of Example 2(2b) was dissolved in a mixed solvent of tetrahydrofuran (1.8 mL) and methanol (0.63 mL), 1M aqueous lithium hydroxide solution (0.63 mL) was added, and the mixture was stirred at 40° C. for 1 hr. To the reaction mixture was added saturated aqueous ammonium chloride solution, and the mixture was extracted with ethyl acetate. The organic layer was washed with saturated brine and dried over anhydrous sodium sulfate, and the solvent was evaporated under reduced pressure. The obtained residue was purified by silica gel column chromatography [elution solvent:chloroform/methanol=100/0-90/10(V/V)]. To the obtained residue were added ethyl acetate and n-hexane, and the mixture was subjected to an ultrasonic treatment. The solid was collected by filtration to give the title compound (91.3 mg, yield: 68%) as a solid.

Example 3

3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid 3a Methyl 1-oxo-2,3-dihydro-1H-indene-4-carboxylate 4-Bromo-2,3-dihydro-1H-inden-1-one (31.7 g) was dissolved in N,N-dimethylformamide (750 mL), lithium formate monohydrate (52.5 g), 4,5-bis(diphenylphosphino)-9,9-dimethylxanthene (4.34 g), tris(dibenzylideneacetone)dipalladium(0) (6.87 g), lithium chloride (38.2 g), N,N-diisopropylethylamine (103 mL) and acetic anhydride (56.7 mL) were added, and the mixture was stirred under a nitrogen atmosphere at 80° C. for 17 hr. The reaction mixture was allowed to cool to room temperature, and 1M hydrochloric acid and ethyl acetate were added. The insoluble matter was removed by filtration through celite, and the filtrate was extracted with ethyl acetate. The organic layer was washed successively with water and saturated brine and dried over anhydrous sodium sulfate, and the solvent was evaporated under reduced pressure. The obtained residue (40.4 g) was dissolved in N,N-dimethylformamide (450 mL), potassium carbonate (31.1 g) and methyl iodide (11.2 mL) were added, and the mixture was stirred at room temperature for 1.5 hr. To the reaction mixture was added water was added, and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=90/10-65/35(V/V), chloroform] to give the title compound (24.9 g, yield: 87%) as a solid.

3b

Methyl 2,3-dihydro-1H-indene-4-carboxylate

Methyl 1-oxo-2,3-dihydro-1H-indene-4-carboxylate (21.4 g) of Example 3(3a) was dissolved in methanol (330 mL), sodium borohydride (8.51 g) was added in portions at 0° C., and the mixture was stirred at room temperature for 20 min. To the reaction mixture was added water, and the mixture was extracted with ethyl acetate. The organic layer was washed with saturated brine and dried over anhydrous sodium sulfate, and the solvent was evaporated under reduced pressure. The obtained residue was dissolved in trifluoroacetic acid (200 mL), triethylsilane (30 mL) was added, and the mixture was stirred at room temperature for 10 min. Triethylsilane (30 mL) was added thereto, and the mixture was stirred at room temperature for 70 min. The reaction mixture was added to a suspension of sodium hydrogen carbonate (200 g) in water (1 L), saturated aqueous sodium hydrogen carbonate solution was added to make the mixture basic, and the mixture was extracted with ethyl acetate. The organic layer was washed with saturated brine and dried over anhydrous sodium sulfate, and the solvent was evaporated under reduced pressure. The obtained residue was purified by silica gel column chromatography [elution solvent:n-hexane/ethyl acetate=100/0-90/10(V/V)] to give the title compound (10.0 g, yield: 53%) as an oil.

3c (6-Bromo-2,3-dihydro-1H-inden-4-yl)methanol methyl 2,3-dihydro-1H-indene-4-carboxylate (10.0 g) of Example 3(3b) was dissolved in methanesulfonic acid (100 mL), N-bromosuccinimide (10.6 g) was added, and the mixture was stirred at room temperature for 2 hr. The reaction mixture was added to a suspension of sodium hydrogen carbonate (200 g) in water (1 L), and the mixture was extracted with ethyl acetate. The organic layer was washed with saturated brine and dried over anhydrous sodium sulfate, and the solvent was evaporated under reduced pressure. The obtained residue was dissolved in tetrahydrofuran (210 mL), lithium aluminum hydride (2.15 g) was added in portions over 7 min at 0° C., and the mixture was stirred for 30 min at 0° C. Water (2.2 mL), 5M aqueous sodium hydroxide solution (2.2 mL), and water (6.6 mL) were added to the reaction mixture, and the mixture was stirred at room temperature for 25 min, and the precipitate was filtered off. The filtrate was dried over anhydrous sodium sulfate, and the solvent was evaporated under reduced pressure. The obtained residue was purified by silica gel column chromatography [elution solvent:n-hexane/ethyl acetate=90/10-60/40(V/V)] to give the title compound (8.13 g, yield: 63%) as an oil.

3d

[6-(4,4,5,5-Tetramethyl-1,3,2-dioxaborolan-2-yl)-2,3-dihydro-1H-inden-4-yl]methanol Using (6-bromo-2,3-dihydro-1H-inden-4-yl)methanol (8.13 g) of Example 3(3c), the title compound (7.85 g, yield: 80%) was obtained as a solid in the same manner as in Example 1(1h).

3e

Ethyl 3-(1,4-dimethyl-1H-benzotriazol-5-yl)-3-[7-(hydroxymethyl)-2,3-dihydro-1H-inden-5-yl]propanoate Ethyl (2E)-3-(1,4-dimethyl-1H-benzotriazol-5-yl)prop-2-enoate (WO 2015/092713) (3.979 g), [6-(4,4,5,5-tetramethyl-1,3,2-dioxaborolan-2-yl)-2,3-dihydro-1H-inden-4-yl]methanol (17.7 g), triethylamine (11.4 mL) and chloro(1,5-cyclooctadiene)rhodium(I) dimer (1.58 g) of Example 3(3d) were suspended in a mixed solvent of 1,4-dioxane (52 mL) and water (13.6 mL) and purged with nitrogen, and heated and stirred at 80° C. for 3 hr. The reaction mixture was allowed to cool to room temperature and concentrated under reduced pressure. To the obtained residue were added ethyl acetate and saturated aqueous sodium hydrogen carbonate solution, and the mixture was extracted with ethyl acetate. The organic layer was washed with saturated brine and dried over anhydrous magnesium sulfate. After filtration, the filtrate was concentrated under reduced pressure and the obtained residue was purified by silica gel column chromatography [elution solvent:n-hexane/ethyl acetate=80/20-0/100(V/V)] to give the title compound (4.651 g, yield: 73%) as a solid.

3f ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoate Ethyl 3-(1,4-dimethyl-1H-benzotriazol-5-yl)-3-[7-(hydroxymethyl)-2,3-dihydro-1H-inden-5-yl]propanoate (2.50 g) of Example 3(3e) and (4R)-8-chloro-4-ethyl-3,4-dihydro-2H-pyrido[2,3-b][1,4,5]oxathiazepine 1,1-dioxide (1.70 g) of Example 1(1c) were dissolved in toluene (32 mL), and di-tert-butyl azodicarboxylate (4.40 g) and then triphenylphosphine (5.00 g) were added under a nitrogen atmosphere and stirred at room temperature for 4 hr. The reaction mixture was poured into water, and the mixture was extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=70/30-50/50(V/V)] to give the title compound (4.16 g, yield: quantitative) as an oil.

3g 3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid To a mixture of ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoate (4.16 g) of Example 3(3f), ethanol (30 mL), and tetrahydrofuran (30 mL) was added 1M aqueous sodium hydroxide solution (32.6 mL), and the mixture was stirred at room temperature for 12 hr. To the reaction mixture was added 1M hydrochloric acid (32.6 mL), and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate/methanol=50/50/0-0/95/5(V/V/V)]. Ethyl acetate and n-hexane were added to the eluted compound, and the mixture was subjected to an ultrasonic treatment. The solid was collected by filtration and vacuum dried to give the title compound (2.00 g, yield: 50%).

Example 4

(3S)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid 4a Ethyl (3S)-3-(1,4-dimethyl-1H-benzotriazol-5-yl)-3-[7-(hydroxymethyl)-2,3-dihydro-1H-inden-5-yl]propanoate 4b Ethyl (3R)-3-(1,4-dimethyl-1H-benzotriazol-5-yl)-3-[7-(hydroxymethyl)-2,3-dihydro-1H-inden-5-yl]propanoate Ethyl 3-(1,4-dimethyl-1H-benzotriazol-5-yl)-3-[7-(hydroxymethyl)-2,3-dihydro-1H-inden-5-yl]propanoate (59 g) of Example 3(3e) was subjected to chiral HPLC [column: CHIRALPAK IG (50 mm I.D.×250 mm), mobile phase: acetonitrile, temperature: 40° C.] to give 27.5 g of ethyl (3S)-3-(1,4-dimethyl-1H-benzotriazol-5-yl)-3-[7-(hydroxymethyl)-2,3-dihydro-1H-inden-5-yl]propanoate as the first peak (yield: 47%).

Similarly, 27.3 g of ethyl (3R)-3-(1,4-dimethyl-1H-benzotriazol-5-yl)-3-[7-(hydroxymethyl)-2,3-dihydro-1H-inden-5-yl]propanoate was obtained as the second peak (yield: 46%).

Analysis HPLC conditions [column: CHIRALPAK IG (4.6 mm I.D.×250 mm), mobile phase: acetonitrile, flow rate: 1.0 mL/min, temperature: 40° C., wavelength: 260 nm]; retention time: 4.187 min (the first peak), 5.087 min (the second peak)

4c

Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoate To a mixture of ethyl (3S)-3-(1,4-dimethyl-1H-benzotriazol-5-yl)-3-[7-(hydroxymethyl)-2,3-dihydro-1H-inden-5-yl]propanoate (61.7 mg) of Example 4(4a) and (4R)-8-chloro-4-ethyl-3,4-dihydro-2H-pyrido[2,3-b][1,4,5]oxathiazepine 1,1-dioxide (49.4 mg) of Example 1(1c) were successively added, under a nitrogen atmosphere, di-tert-butyl azodicarboxylate (50.5 mg), tetrahydrofuran (2.24 mL), and tri-n-butylphosphine (0.0664 mL), and the mixture was stirred at room temperature for 8 hr. The reaction mixture was concentrated under reduced pressure and the obtained residue was purified by silica gel column chromatography [elution solvent:n-hexane/ethyl acetate=70/30-50/50(V/V)] to give the title compound (96.5 mg, yield: 96%) as an oil.

4d (3S)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoate (720 mg) of Example 4(4c) was dissolved in a mixed solvent of methanol (5 mL) and tetrahydrofuran (5 mL), 1M aqueous sodium hydroxide solution (2.2 mL) was added, and the mixture was stirred at room temperature for 24 hr. 1 M hydrochloric acid was added to the reaction mixture to adjust the pH to 5-6, and the reaction solvent was evaporated under reduced pressure. After azeotropic distillation with ethanol, the obtained residue was suspended in chloroform, anhydrous magnesium sulfate was added, and the mixture was stirred for 10 min. After filtration, the filtrate was concentrated under reduced pressure, and the obtained residue was purified by silica gel column chromatography [elution solvent:chloroform/methanol=90/1-20/1(V/V)]. Ethyl acetate and n-hexane were added to solidify the residue to give the title compound (446 mg, yield: 64%) as a solid.

Example 5

(3R)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid 5a Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoate Ethyl (3R)-3-(1,4-dimethyl-1H-benzotriazol-5-yl)-3-[7-(hydroxymethyl)-2,3-dihydro-1H-inden-5-yl]propanoate (3.15 g) of Example 4(4b) and (4R)-8-chloro-4-ethyl-3,4-dihydro-2H-pyrido[2,3-b][1,4,5]oxathiazepine 1,1-dioxide (2.31 g) of Example 1(1c) were dissolved in toluene (50 mL). 1,1'-(azodicarbonyl)dipiperidine (3.03 g) was added thereto under a nitrogen atmosphere, then tri-n-butylphosphine (2.99 mL) was added, and the mixture was stirred at room temperature for 3 hr. Tetrahydrofuran (10 mL) was added to the reaction mixture, and the mixture was stirred at room temperature for 30 min. The reaction mixture was diluted with dichloromethane, and the insoluble matter was filtered off. The filtrate was concentrated under reduced pressure to obtain a residue, which was purified by silica gel column chromatography [eluent: n-hexane/ethyl acetate=2/1-4/6 (V/V)], and the fraction containing impurities was purified again by silica gel column chromatography [eluent: n-hexane/ethyl acetate=6/4-4/6 (V/V)]. The product was further purified twice by NH silica gel column chromatography [eluent: n-hexane/ethyl acetate=2/1-1/1 (V/V)] to give the title compound (3.78 g, yield: 74%) as a solid.

5b (3R)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoic acid To a mixture of ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoate (3.75 g) of Example 5(5a), ethanol (30 mL), and tetrahydrofuran (60 mL) was added 1M aqueous sodium hydroxide solution (30 mL), and the mixture was stirred at 40° C. for 3 hr. The reaction mixture was cooled to room temperature, 1M hydrochloric acid (33 mL) was added, and the mixture was stirred and extracted with ethyl acetate. The organic layer was washed with saturated brine and dried over anhydrous sodium sulfate. After filtration, the filtrate was concentrated under reduced pressure and the obtained solid was dissolved in ethanol (100 mL), followed by recrystallization. The precipitated solid was collected by filtration, washed with a small amount of ethanol, and dried at 50° C. under reduced pressure to give the title compound (2.20 g, yield: 61%) as a solid.

Example 6

3-(4-Fluoro-1-methyl-1H-benzotriazol-5-yl)-3-(7-{[(4R)-4-methyl-1,1-dioxido-3,4-dihydro-2H-5,1,2-benzoxathiazepin-2-yl]methyl}-2,3-dihydro-1H-inden-5-yl)propanoic acid 6a 4-Bromo-3-fluoro-N'-methylbenzene-1,2-diamine 3-Fluoro-N-methyl-2-nitroaniline (WO 2011/021676) (5.27 g) was dissolved in N,N-dimethylformamide (60 mL), a solution of N-bromosuccinimide (4.88 g) in N,N-dimethylformamide (30 mL) was added at 0° C., and the mixture was stirred at 0° C. for 2 hr. To the reaction mixture was added water, and the mixture was extracted with ethyl acetate. The organic layer was washed with water and saturated brine and dried over anhydrous sodium sulfate, and the solvent was evaporated under reduced pressure. To the obtained residue was added n-hexane, and the solid was collected by filtration. The obtained solid was suspended in ethanol (50 mL), tin(II) chloride dihydrate (10.6 g) was added thereto, and the mixture was heated under reflux for 1 hr. The reaction mixture was cooled to room temperature and added to a suspension of sodium hydrogen carbonate (15 g) in water (100 mL) and ethyl acetate (100 mL), and stirred at room temperature for 0.5 hr. The mixture was filtered through celite to remove insoluble matter, and the filtrate was extracted with ethyl acetate. The organic layer was dried over anhydrous sodium sulfate, and the solvent was evaporated under reduced pressure. The obtained residue was purified by silica gel column chromatography [elution solvent:n-hexane/ethyl acetate=90/10-80/20(V/V)] to give the title compound (2.95 g, yield: 89%) as a solid.

6b

5-Bromo-4-fluoro-1-methyl-1H-benzotriazole

4-Bromo-3-fluoro-N$^1$-methylbenzene-1,2-diamine (2.95 g) of Example 6(6a) was dissolved in acetonitrile (27 mL), tert-butyl nitrite (2.4 mL) and 42% tetrafluoroboric acid (4.3 mL) were added dropwise at 0° C., and the mixture was stirred at room temperature for 30 min. To the reaction mixture was added saturated aqueous sodium hydrogen carbonate solution, and the mixture was extracted with ethyl acetate. The organic layer was washed with saturated brine and dried over anhydrous sodium sulfate, and the solvent was evaporated under reduced pressure. The obtained residue was purified by silica gel column chromatography [elution solvent:n-hexane/ethyl acetate=85/15-60/40(V/V)] to give the title compound (620 mg, yield: 17%) as a solid.

6c

Ethyl (2E)-3-(4-fluoro-1-methyl-1H-benzotriazol-5-yl)prop-2-enoate

5-Bromo-4-fluoro-1-methyl-1H-benzotriazole (620 mg) of Example 6(6b) was dissolved in N,N-dimethylformamide (8.0 mL), ethyl acrylate (2.46 mL), N,N-diisopropylethylamine (2.0 mL), tris(dibenzylideneacetone)dipalladium(0) (207 mg) and tri(o-tolyl)phosphine (275 mg) were added, and the mixture was stirred under a nitrogen atmosphere at 100° C. for 13.5 hr. The reaction mixture was allowed to cool to room temperature, water was added, and the mixture was extracted with ethyl acetate. The organic layer was washed with water and saturated brine and dried over anhydrous sodium sulfate, and the solvent was evaporated under reduced pressure. The obtained residue was purified by silica gel column chromatography [elution solvent:n-hexane/ethyl acetate=85/15-60/40(V/V)] to give the title compound (370 mg, yield: 43%) as a solid.

6d

Ethyl 3-(4-fluoro-1-methyl-1H-benzotriazol-5-yl)-3-[7-(hydroxymethyl)-2,3-dihydro-1H-inden-5-yl]propanoate Using [6-(4,4,5,5-tetramethyl-1,3,2-dioxaborolan-2-yl)-2,3-dihydro-1H-inden-4-yl]methanol (481 mg) of Example 3(3d) and ethyl (2E)-3-(4-fluoro-1-methyl-1H-benzotriazol-5-yl)prop-2-enoate (370 mg) of Example 6(6c), the title compound (390 mg, yield: 84%) was obtained as a solid in the same manner as in Example 95(95a).

6e

Ethyl 3-(4-fluoro-1-methyl-1H-benzotriazol-5-yl)-3-(7-{[(4R)-4-methyl-1,1-dioxido-3,4-dihydro-2H-5,1,2-benzoxathiazepin-2-yl]methyl}-2,3-dihydro-1H-inden-5-yl)propanoate Using ethyl 3-(4-fluoro-1-methyl-1H-benzotriazol-5-yl)-3-[7-(hydroxymethyl)-2,3-dihydro-1H-inden-5-yl]propanoate (190 mg) of Example 6(6d) and (4R)-4-methyl-3,4-dihydro-2H-5,1,2-benzoxathiazepine 1,1-dioxide (WO 2015/092713) (122 mg), the title compound (260 mg, yield: 92%) was obtained as a solid in the same manner as in Example 2(2b).

6f 3-(4-Fluoro-1-methyl-1H-benzotriazol-5-yl)-3-(7-{[(4R)-4-methyl-1,1-dioxido-3,4-dihydro-2H-5,1,2-benzoxathiazepin-2-yl]methyl}-2,3-dihydro-1H-inden-5-yl)propanoic acid Using ethyl 3-(4-fluoro-1-methyl-1H-benzotriazol-5-yl)-3-(7-{[(4R)-4-methyl-1,1-dioxido-3,4-dihydro-2H-5,1,2-benzoxathiazepin-2-yl]methyl}-2,3-dihydro-1H-inden-5-yl)propanoate (260 mg) of Example 6(6e), the title compound (186 mg, yield: 68%) was obtained as a solid in the same manner as in Example 2(2c).

Example 7

(3S)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid 7a Ethyl (3S)-3-(1,4-dimethyl-1H-benzotriazol-5-yl)-3-[7-(hydroxymethyl)-1-benzothiophen-5-yl]propanoate 7b Ethyl (3R)-3-(1,4-dimethyl-1H-benzotriazol-5-yl)-3-[7-(hydroxymethyl)-1-benzothiophen-5-yl]propanoate Ethyl 3-(1,4-dimethyl-1H-benzotriazol-5-yl) 3-[7-(hydroxymethyl)-1-benzothiophen-5-yl]propanoate (120 g) of Example 1(1i) was subjected to chiral SFC [column: CHIRALPAK AD (50 mm I.D.×250 mm), mobile phase: carbon dioxide/ethanol=60/40(V/V)] to obtain 51.0 g of ethyl (3S)-3-(1,4-dimethyl-1H-benzotriazol-5-yl)-3-[7-(hydroxymethyl)-1-benzothiophen-5-yl]propanoate was obtained as the first peak (yield: 43%).

Similarly, 52.5 g of ethyl (3R)-3-(1,4-dimethyl-1H-benzotriazol-5-yl)-3-[7-(hydroxymethyl)-1-benzothiophen-5-yl]propanoate was obtained as the second peak (yield: 44%).

Analysis SFC conditions [column: CHIRALPAK AD-3 (4.6 mm I.D.×50 mm), mobile phase: carbon dioxide/ethanol (0.05% diethylamine)=95/5-60/40(V/V), flow rate: 3.0 mL/min, temperature: 35° C., wavelength: 220 nm]; retention time: 2.078 min (the first peak), 2.455 min (the second peak)

7c

Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate Using ethyl (3S)-3-(1,4-dimethyl-1H-benzotriazol-5-yl)-3-[7-(hydroxymethyl)-1-benzothiophen-5-yl]propanoate (0.20 g) of Example 7(7a) and (4R)-8-chloro-4-ethyl-3,4-dihydro-2H-pyrido[2,3-b][1,4,5]oxathiazepine 1,1-dioxide (0.141 g) of Example 1(1c), the title compound (0.34 g, yield: quantitative) was obtained as an oil in the same manner as in Example 3(3f).

7d (3S)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoic acid Using ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate (0.35 g) of Example 7(7c), the title compound (0.24 g, yield: 72%) was obtained in the same manner as in Example 3(3g).

Example 8

(3R)-3-(7-{[(4R)-8-Chloro-4-ethyl-1,1-dioxido-3,4-dihydro-2H-pyrido[2,3-b][1,4,5]oxathiazepin-2-yl] methyl}-1-benzothiophen-5-yl)-3-(1,4-dimethyl-1H-benzotriazol-5-yl)propanoic acid 8a Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate Using ethyl (3R)-3-(1,4-dimethyl-1H-benzotriazol-5-yl)-3-[7-(hydroxymethyl)-1-benzothiophen-5-yl]propanoate (0.20 g) of Example 7(7b) and (4R)-8-chloro-4-ethyl-3,4-dihydro-2H-pyrido[2,3-b][1,4,5]oxathiazepine 1,1-dioxide (0.141 g) of Example 1(1c), the title compound (0.32 g, yield: quantitative) was obtained as an oil in the same manner as in Example 3(3f).

8b (3R)-3-(7-{[(4R)-8-Chloro-4-ethyl-1,1-dioxido-3,4-dihydro-2H-pyrido[2,3-b][1,4,5]oxathiazepin-2-yl] methyl}-1-benzothiophen-5-yl)-3-(1,4-dimethyl-1H-benzotriazol-5-yl)propanoic acid Using ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate (0.34 g) of Example 8(8a), the title compound (0.15 g, yield: 46%) was obtained in the same manner as in Example 3 (3g).

Example 9

3-(1,4-Dimethyl-1H-benzotriazol-5-yl)-3-(7-{[(4R)-7-ethoxy-4-ethyl-1,1-dioxido-3,4-dihydro-2H-pyrido [2,3-b][1,4,5]oxathiazepin-2-yl]methyl}-2,3-dihydro-1H-inden-5-yl)propanoic acid 9a 2,6-Dichloro-N-[(2R)-2-hydroxybutyl]pyridine-3-sulfonamide Using (2R)-1-aminobutan-2-ol (2.0 g) of Example 1(1a) and 2,6-dichloropyridine-3-sulfonyl chloride (1.4 g), the title compound (1.4 g, yield: 82%) was obtained as an oil in the same manner as in Example 1(1b).

9b (4R)-7-Chloro-4-ethyl-3,4-dihydro-2H-pyrido[2,3-b] [1,4,5]oxathiazepine 1,1-dioxide Using 2,6-dichloro-N-[(2R)-2-hydroxybutyl]pyridine-3-sulfonamide (1.25 g) of Example 9(9a), the title compound (1.04 g, yield: 95%) was obtained as a solid in the same manner as in Example 1(1c).

9c

Ethyl 3-(7-{[(4R)-7-chloro-4-ethyl-1,1-dioxido-3,4-dihydro-2H-pyrido[2,3-b][1,4,5]oxathiazepin-2-yl] methyl}-2,3-dihydro-1H-inden-5-yl)-3-(1,4-dimethyl-1H-benzotriazol-5-yl)propanoate Using ethyl 3-(1,4-dimethyl-1H-benzotriazol-5-yl)-3-[7-(hydroxymethyl)-2,3-dihydro-1H-inden-5-yl]propanoate (200 mg) of Example 3(3e) and (4R)-7-chloro-4-ethyl-3,4-dihydro-2H-pyrido[2,3-b][1,4,5]oxathiazepine 1,1-dioxide (133 mg) of Example 9(9b), the title compound (172 mg, yield: 53%) was obtained as a solid in the same manner as in Example 3(3f).

9d 3-(1,4-Dimethyl-1H-benzotriazol-5-yl)-3-(7-{[(4R)-7-ethoxy-4-ethyl-1,1-dioxido-3,4-dihydro-2H-pyrido [2,3-b][1,4,5]oxathiazepin-2-yl]methyl}-2,3-dihydro-1H-inden-5-yl)propanoic acid Using ethyl 3-(7-{[(4R)-7-chloro-4-ethyl-1,1-dioxido-3,4-dihydro-2H-pyrido[2,3-b][1,4,5]oxathiazepin-2-yl] methyl}-2,3-dihydro-1H-inden-5-yl)-3-(1,4-dimethyl-1H-benzotriazol-5-yl)propanoate (80 mg) of Example 9(9c), the title compound (14 mg, yield: 18%) was obtained in the same manner as in Example 3(3g).

Example 10

3-(1,4-Dimethyl-1H-benzotriazol-5-yl)-3-(7-{[(4R)-4-ethyl-8-methyl-1,1-dioxido-3,4-dihydro-2H-pyrido [2,3-b][1,4,5]oxathiazepin-2-yl]methyl}-2,3-dihydro-1H-inden-5-yl)propanoic acid 10a 2-Chloro-N-[(2R)-2-hydroxybutyl]-5-methylpyridine-3-sulfonamide Using (2R)-1-aminobutan-2-ol (1.41 g) of Example 1(1a) and 2-chloro-5-methylpyridine-3-sulfonyl chloride (0.90 g), the title compound (1.1 g, yield: quantitative) was obtained as an oil in the same manner as in Example 1(1b).

10b (4R)-4-Ethyl-8-methyl-3,4-dihydro-2H-pyrido[2,3-b][1,4,5]oxathiazepine 1,1-dioxide Using 2-chloro-N-[(2R)-2-hydroxybutyl]-5-methylpyridine-3-sulfonamide (1.2 g) of Example 10(10a), the title compound (0.68 g, yield: 65%) was obtained as a solid in the same manner as in Example 1(1c)

10c

Ethyl 3-(1,4-dimethyl-1H-benzotriazol-5-yl)-3-(7-{[(4R)-4-ethyl-8-methyl-1,1-dioxido-3,4-dihydro-2H-pyrido[2,3-b][1,4,5]oxathiazepin-2-yl]methyl}-2,3-dihydro-1H-inden-5-yl)propanoate Using ethyl 3-(1,4-dimethyl-1H-benzotriazol-5-yl)-3-[7-(hydroxymethyl)-2,3-dihydro-1H-inden-5-yl]propanoate (100 mg) of Example 3(3e) and (4R)-4-ethyl-8-methyl-3,4-dihydro-2H-pyrido[2,3-b][1,4,5]oxathiazepine 1,1-dioxide (120 mg) of Example 10(10b), the title compound (165 mg, yield: 53%) was obtained as a solid in the same manner as in Example 3(3f).

10d 3-(1,4-Dimethyl-1H-benzotriazol-5-yl)-3-(7-{[(4R)-4-ethyl-8-methyl-1,1-dioxido-3,4-dihydro-2H-pyrido[2,3-b][1,4,5]oxathiazepin-2-yl]methyl}-2,3-dihydro-1H-inden-5-yl)propanoic acid Using ethyl 3-(1,4-dimethyl-1H-benzotriazol-5-yl)-3-(7-{[(4R)-4-ethyl-8-methyl-1,1-dioxido-3,4-dihydro-2H-pyrido[2,3-b][1,4,5]oxathiazepin-2-yl]methyl}-2,3-dihydro-1H-inden-5-yl)propanoate (165 mg) of Example 10(10c), the title compound (90 mg, yield: 57%) was obtained as a solid in the same manner as in Example 3(3g).

Example 11

3-(1,4-Dimethyl-1H-benzotriazol-5-yl)-3-(7-{[(4R)-4-ethyl-7-methyl-1,1-dioxido-3,4-dihydro-2H-pyrido[2,3-b][1,4,5]oxathiazepin-2-yl]methyl}-2,3-dihydro-1H-inden-5-yl)propanoic acid 11a Ethyl 3-(1,4-dimethyl-1H-benzotriazol-5-yl)-3-(7-{[(4R)-4-ethyl-7-methyl-1,1-dioxido-3,4-dihydro-2H-pyrido[2,3-b][1,4,5]oxathiazepin-2-yl]methyl}-2,3-dihydro-1H-inden-5-yl)propanoate Ethyl 3-(7-{[(4R)-7-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)propanoate (79 mg) of Example 9(9c), trimethylboroxine 50% tetrahydrofuran solution (0.087 mL), palladium acetate (2.8 mg), cesium carbonate (120 mg), and 2-dicyclohexylphosphino-2',6'-dimethoxybiphenyl (5.1 mg) were dissolved in toluene (3.0 mL), and the mixture was stirred under heating under a nitrogen atmosphere at 100° C. for 4 hr. The reaction mixture was allowed to cool to room temperature, water was added, and the mixture was extracted with ethyl acetate. The organic layer was washed with saturated brine and dried over anhydrous sodium sulfate. After filtration, the filtrate was concentrated under reduced pressure, and the obtained residue was was purified by NH silica gel column chromatography [elution solvent: n-hexane/ethyl acetate=80/20-0/100(V/V)] to give the title compound (60 mg, yield: 78%) as an oil.

11b 3-(1,4-Dimethyl-1H-benzotriazol-5-yl)-3-(7-{[(4R)-4-ethyl-7-methyl-1,1-dioxido-3,4-dihydro-2H-pyrido[2,3-b][1,4,5]oxathiazepin-2-yl]methyl}-2,3-dihydro-1H-inden-5-yl)propanoic acid Using ethyl 3-(1,4-dimethyl-1H-benzotriazol-5-yl)-3-(7-{[(4R)-4-ethyl-7-methyl-1,1-dioxido-3,4-dihydro-2H-pyrido[2,3-b][1,4,5]oxathiazepin-2-yl]methyl}-2,3-dihydro-1H-inden-5-yl)propanoate (60 mg) of Example 11(11a), the title compound (35 mg, yield: 62%) was obtained as a solid in the same manner as in Example 3(3g).

Example 12

3-(1,4-Dimethyl-1H-benzotriazol-5-yl)-3-(7-{[(4R)-4-ethyl-1,1-dioxido-3,4-dihydro-2H-5,1,2-benzoxathiazepin-2-yl]methyl}-2,3-dihydro-1H-inden-5-yl)propanoic acid 12a Ethyl 3-(1,4-dimethyl-1H-benzotriazol-5-yl)-3-(7-{[(4R)-4-ethyl-1,1-dioxido-3,4-dihydro-2H-5,1,2-benzoxathiazepin-2-yl]methyl}-2,3-dihydro-1H-inden-5-yl)propanoate Using ethyl 3-(1,4-dimethyl-1H-benzotriazol-5-yl)-3-[7-(hydroxymethyl)-2,3-dihydro-1H-inden-5-yl]propanoate (140 mg) of Example 3(3e) and (4R)-4-ethyl-3,4-dihydro-2H-5,1,2-benzoxathiazepine 1,1-dioxide (WO 2015/092713) (80 mg), the title compound (140 mg, yield: 65%) was obtained as a solid in the same manner as in Example 3(3f).

12b 3-(1,4-Dimethyl-1H-benzotriazol-5-yl)-3-(7-{[(4R)-4-ethyl-1,1-dioxido-3,4-dihydro-2H-5,1,2-benzoxathiazepin-2-yl]methyl}-2,3-dihydro-1H-inden-5-yl)propanoic acid Using ethyl 3-(1,4-dimethyl-1-benzotriazol-5-yl)-3-(7-{[(4R)-4-ethyl-1,1-dioxido-3,4-dihydro-2H-5,1,2-benzoxathiazepin-2-yl]methyl}-2,3-dihydro-1H-inden-5-yl)propanoate (140 mg) of Example 12(12a), the title compound (120 mg, yield: 90%) was obtained as a solid in the same manner as in Example 3(3g).

Example 13

3-(7-{[(4R)-8-Chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid 13a 5-Chloro-2,4-difluoro-N-[(2R)-2-hydroxybutyl]benzenesulfonamide Using (2R)-1-aminobutan-2-ol (0.72 g) of Example 1(1a) and 5-chloro-2,4-difluorobenzenesulfonyl chloride (0.50 g), the title compound (0.70 g, yield: quantitative) was obtained as an oil in the same manner as in Example 1(1b).

13b (4R)-8-Chloro-4-ethyl-7-fluoro-3,4-dihydro-2H-5,1,2-benzoxathiazepine 1,1-dioxide Using 5-chloro-2,4-difluoro-N-[(2R)-2-hydroxybutyl]benzenesulfonamide (0.35 g) of Example 13(13a), the title compound (0.22 g, yield: 67%) was obtained as a solid in the same manner as in Example 1(1c).

13c

Ethyl 3-(7-{[(4R)-8-chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate Using ethyl 3-(1,4-dimethyl-1H-benzotriazol-5-yl)-3-[7-(hydroxymethyl)-2,3-dihydro-1H-inden-5-yl]propanoate (100 mg) of Example 3(3e) and (4R)-8-chloro-4-ethyl-7-fluoro-3,4-dihydro-2H-5,1,2-benzoxathiazepine 1,1-dioxide (80 mg) of Example 13(13b), the title compound (140 mg, yield: 84%) was obtained as a solid in the same manner as in Example 3(3f).

13d 3-(7-{[(4R)-8-Chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid Using ethyl 3-(7-{[(4R)-8-chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate (140 mg) of Example 13(13c), the title compound (90 mg, yield: 67%) was obtained as a solid in the same manner as in Example 3 (3g).

Example 14

3-(7-{[(4R)-8-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid

14a

5-Chloro-2-fluoro-N-[(2R)-2-hydroxybutyl]benzenesulfonamide

Using (2R)-1-aminobutan-2-ol (1.0 g) of Example 1(1a) and 5-chloro-2-fluorobenzenesulfonyl chloride (1.56 g), the title compound (1.3 g, yield: quantitative) was obtained as an oil in the same manner as in Example 1(1b).

14b (4R)-8-Chloro-4-ethyl-3,4-dihydro-2H-5,1,2-benzoxathiazepine 1,1-dioxide Using 5-chloro-2-fluoro-N-[(2R)-2-hydroxybutyl]benzenesulfonamide (1.3 g) of Example 14(14a), the title compound (1.0 g, yield: 83%) was obtained as a solid in the same manner as in Example 1(1c).

14c

Ethyl 3-(7-{[(4R)-8-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate Using ethyl 3-(1,4-dimethyl-1H-benzotriazol-5-yl)-3-[7-(hydroxymethyl)-2,3-dihydro-1H-inden-5-yl]propanoate (140 mg) of Example 3(3e) and (4R)-8-chloro-4-ethyl-3,4-dihydro-2H-5,1,2-benzoxathiazepine 1,1-dioxide (95 mg) of Example 14(14b), the title compound (160 mg, yield: 71%) was obtained as a solid in the same manner as in Example 3(3f).

14d 3-(7-{[(4R)-8-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid Using ethyl 3-(7-{[(4R)-8-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate (160 mg) of Example 14(14c), the title compound (140 mg, yield: 92%) was obtained as a solid in the same manner as in Example 3(3g).

Example 15

3-(7-{[(4R)-7-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid

15a

4-Chloro-2-fluoro-N-[(2R)-2-hydroxybutyl]benzenesulfonamide

Using (2R)-1-aminobutan-2-ol (1.55 g) of Example 1(1a) and 4-chloro-2-fluorobenzenesulfonyl chloride (1.0 g), the title compound (1.2 g, yield: 98%) was obtained as an oil in the same manner as in Example 1(1b).

15b (4R)-7-Chloro-4-ethyl-3,4-dihydro-2H-5,1,2-benzoxathiazepine 1,1-dioxide Using 4-chloro-2-fluoro-N-[(2R)-2-hydroxybutyl]benzenesulfonamide (1.2 g) of Example 15(15a), the title compound (0.92 g, yield: 83%) was obtained as a solid in the same manner as in Example 1(1c).

15c

Ethyl 3-(7-{[(4R)-7-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate Using ethyl 3-(1,4-dimethyl-1H-benzotriazol-5-yl)-3-[7-(hydroxymethyl)-2,3-dihydro-1H-inden-5-yl]propanoate (100 mg) of Example 3(3e) and (4R)-7-chloro-4-ethyl-3,4-dihydro-2H-5,1,2-benzoxathiazepine 1,1-dioxide (75 mg) of Example 15(15b), the title compound (160 mg, yield: 99%) was obtained as a solid in the same manner as in Example 3(3f).

15d 3-(7-{[(4R)-7-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid Using ethyl 3-(7-{[(4R)-7-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate (160 mg) of Example 15(15c), the title compound (110 mg, yield: 72%) was obtained as a solid in the same manner as in Example 3(3g).

Example 16

3-(7-{[(4R)-6-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid 16a 3-Chloro-2-fluoro-N-[(2R)-2-hydroxybutyl]benzenesulfonamide Using (2R)-1-aminobutan-2-ol (1.55 g) of Example 1(1a) and 5-chloro-2-fluorobenzenesulfonyl chloride (1.0 g), the title compound (1.2 g, yield: 98%) was obtained as an oil in the same manner as in Example 1(1b).

16b (4R)-6-Chloro-4-ethyl-3,4-dihydro-2H-5,1,2-benzoxathiazepine 1,1-dioxide

Using 3-chloro-2-fluoro-N-[(2R)-2-hydroxybutyl]benzenesulfonamide (1.2 g) of Example 16(16a), the title compound (0.90 g, yield: 81%) was obtained as a solid in the same manner as in Example 1(1c).

16c

Ethyl 3-(7-{[(4R)-6-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate Using ethyl 3-(1,4-dimethyl-1H-benzotriazol-5-yl)-3-[7-(hydroxymethyl)-2,3-dihydro-1H-inden-5-yl]propanoate (160 mg) of Example 3(3e) and (4R)-6-chloro-4-ethyl-3,4-dihydro-2H-5,1,2-benzoxathiazepine 1,1-dioxide (117 mg) of Example 16(16b), the title compound (250 mg, yield: 96%) was obtained as a solid in the same manner as in Example 3(3f).

16d 3-(7-{[(4R)-6-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid Using ethyl 3-(7-{[(4R)-6-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate (250 mg) of Example 16(16c), the title compound (160 mg, yield: 67%) was obtained as a solid in the same manner as in Example 3(3g).

Example 17

3-(7-{[(4R)-9-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid 17a 2-Chloro-6-fluoro-N-[(2R)-2-hydroxybutyl]benzenesulfonamide Using (2R)-1-aminobutan-2-ol (1.1 g) of Example 1(1a) and 2-chloro-6-fluorobenzenesulfonyl chloride (0.70 g), the title compound (0.90 g, yield: quantitative) was obtained as an oil in the same manner as in Example 1(1b).

17b (4R)-9-Chloro-4-ethyl-3,4-dihydro-2H-5,1,2-benzoxathiazepine 1,1-dioxide

Using 2-chloro-6-fluoro-N-[(2R)-2-hydroxybutyl]benzenesulfonamide (0.90 g) of Example 17(17a), the title compound (598 mg, yield: 72%) was obtained as a solid in the same manner as in Example 1(1c).

17c

Ethyl 3-(7-{[(4R)-9-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate Using ethyl 3-(1,4-dimethyl-1H-benzotriazol-5-yl)-3-[7-(hydroxymethyl)-2,3-dihydro-1H-inden-5-yl]propanoate (150 mg) of Example 3(3e) and (4R)-9-chloro-4-ethyl-3,4-dihydro-2H-5,1,2-benzoxathiazepine 1,1-dioxide (110 mg) of Example 17(17b), the title compound (100 mg, yield: 41%) was obtained as a solid in the same manner as in Example 3(3f).

17d 3-(7-{[(4R)-9-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid Using ethyl 3-(7-{[(4R)-9-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate (100 mg) of Example 17(17c), the title compound (65 mg, yield: 68%) was obtained as a solid in the same manner as in Example 3(3g).

Example 18

3-(7-{[(4R)-8-Chloro-7-ethoxy-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid 3-(7-{[(4R)-8-Chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid (400 mg) of Example 13(13d) was dissolved in ethanol (25 mL), 1M aqueous sodium hydroxide solution (3.2 mL) was added, and the mixture was stirred at room temperature for 48 hr. To the reaction mixture was added 1M hydrochloric acid (3.2 mL), and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent: n-hexane/ethyl acetate=60/40-40/60(V/V)] to give the title compound (250 mg, yield: 60%) as a solid.

Example 19

3-(1,4-Dimethyl-1H-benzotriazol-5-yl)-3-(7-{[(4R)-7-ethoxy-4-ethyl-1,1-dioxido-3,4-dihydro-2H-pyrido[2,3-b][1,4,5]oxathiazepin-2-yl]methyl}-1-benzothiophen-5-yl)propanoic acid 19a Ethyl 3-(7-{[(4R)-7-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate Using ethyl 3-(1,4-dimethyl-1H-benzotriazol-5-yl)-3-[7-(hydroxymethyl)-1-benzothiophen-5-yl]propanoate (130 mg) of Example 1(1i) and (4R)-7-chloro-4-ethyl-3,4-dihydro-2H-pyrido[2,3-b][1,4,5]oxathiazepine 1,1-dioxide (65 mg) of Example 9(9b), the title compound (150 mg, yield: 93%) was obtained as a solid in the same manner as in Example 3(3f).

19b 3-(1,4-Dimethyl-1H-benzotriazol-5-yl)-3-(7-{[(4R)-7-ethoxy-4-ethyl-1,1-dioxido-3,4-dihydro-2H-pyrido[2,3-b][1,4,5]oxathiazepin-2-yl]methyl}-1-benzothiophen-5-yl)propanoic acid Using ethyl 3-(7-{[(4R)-7-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate (150 mg) of Example 19(19a), the title compound (85 mg, yield: 58%) was obtained as a solid in the same manner as in Example 3(3g).

Example 20

(3R)-3-(7-{[(4R)-8-Chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid 20a Ethyl (3R)-3-(1,4-dimethyl-1H-benzotriazol-5-yl)-3-[7-({[tri(propan-2-yl)silyl]oxy}methyl)-2,3-dihydro-1H-inden-5-yl]propanoate Ethyl (3R)-3-(1,4-dimethyl-1H-benzotriazol-5-yl)-3-[7-(hydroxymethyl)-2,3-dihydro-1H-inden-5-yl]propanoate (520 mg) of Example 4(4b) was dissolved in N,N-dimethylformamide (5 mL), imidazole (110 mg) and triisopropylsilyl chloride (380 mg) were added, and the mixture was stirred at room temperature for 3 hr. To the reaction mixture was added water (2.5 mL), and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=90/10-50/50(V/V)] to give the title compound (720 mg, yield: 99%) as an oil.

20b tert-Butyl (3R)-3-(1,4-dimethyl-1H-benzotriazol-5-yl)-3-[7-({[tri(propan-2-yl)silyl]oxy}methyl)-2,3-dihydro-1H-inden-5-yl]propanoate Ethyl (3R)-3-(1,4-dimethyl-1H-benzotriazol-5-yl)-3-[7-({[tri(propan-2-yl)silyl]oxy}methyl)-2,3-dihydro-1H-inden-5-yl]propanoate (720 mg) of Example 20(20a) was dissolved in tetrahydrofuran (3 mL), ethanol (3 mL) and 1M aqueous sodium hydroxide solution (0.30 mL) were added, and the mixture was stirred at room temperature for 12 hr. To the reaction mixture was added 1M hydrochloric acid (0.30 mL), and the mixture was stirred and extracted with ethyl acetate. The organic layer was washed with saturated brine and dried over anhydrous sodium sulfate. After filtration, the filtrate was concentrated under reduced pressure and the obtained residue was dissolved in tert-butyl alcohol (5 mL), di-tert-butyl bicarbonate (600 mg) and 4-dimethylaminopyridine (48 mg) were added thereto, and the mixture was stirred at room temperature for 3 hr. The reaction mixture was poured into water, and the organic product was extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=90/10-60/40(V/V)] to give the title compound (540 mg, yield: 71%) as an oil.

20c tert-Butyl (3R)-3-(1,4-dimethyl-1H-benzotriazol-5-yl)-3-[7-(hydroxymethyl)-2,3-dihydro-1H-inden-5-yl]propanoate tert-Butyl (3R)-3-(1,4-dimethyl-1H-benzotriazol-5-yl)-3-[7-({[tri(propan-2-yl)silyl]oxy}methyl)-2,3-dihydro-1H-inden-5-yl]propanoate (540 mg) of Example 20(20b) was dissolved in tetrahydrofuran (5 mL), tetrabutylammonium fluoride (2.8 mL) was added, and the mixture was stirred at room temperature for 1 hr. To the reaction mixture was added water (3 mL), and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=70/30-20/80(V/V)] to give the title compound (283 mg, yield: 72%) as a solid.

20d tert-Butyl (3R)-3-(7-{[(4R)-8-chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate Using tert-butyl (3R)-3-(1,4-dimethyl-1H-benzotriazol-5-yl)-3-[7-(hydroxymethyl)-2,3-dihydro-1H-inden-5-yl]propanoate (283 mg) of Example 20(20c) and (4R)-8-chloro-4-ethyl-7-fluoro-3,4-dihydro-2H-5,1,2-benzoxathiazepine 1,1-dioxide (73 mg) of Example 13(13b), the title compound (140 mg, yield: 79%) was obtained as a solid in the same manner as in Example 3(3f).

20e (3R)-3-(7-{[(4R)-8-Chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid tert-Butyl (3R)-3-(7-{[(4R)-8-chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate (140 mg) of Example 20(20d) was dissolved in dichloromethane (2 mL), trifluoroacetic acid (1 mL) was added and the mixture was stirred at room temperature for 2 hr. To the reaction mixture was added aqueous sodium hydrogen carbonate solution, and the mixture was stirred and extracted with dichloromethane. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=50/50-20/80(V/V)] to give the title compound (73 mg, yield: 57%) as a solid.

Example 21

(3S)-3-(7-{[(4R)-8-Chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid 21a tert-Butyl (3S)-3-(1,4-dimethyl-1H-benzotriazol-5-yl)-3-[7-({[tri(propan-2-yl)silyl]oxy}methyl)-2,3-dihydro-1H-inden-5-yl]propanoate Using ethyl (3S)-3-(1,4-dimethyl-1H-benzotriazol-5-yl)-3-[7-(hydroxymethyl)-2,3-dihydro-1H-inden-5-yl]propanoate (520 mg) of Example 4(4a), the title compound (754 mg, yield: 98%) was obtained as an oil in the same manner as in Example 20(20a) and (20b).

21b tert-Butyl (3S)-3-(1,4-dimethyl-1H-benzotriazol-5-yl)-3-[7-(hydroxymethyl)-2,3-dihydro-1H-inden-5-yl]propanoate Using tert-butyl (3S)-3-(1,4-dimethyl-1H-benzotriazol-5-yl)-3-[7-({[tri(propan-2-yl)silyl]oxy}methyl)-2,3-dihydro-1H-inden-5-yl]propanoate (754 mg) of Example 21(21a), the title compound (484 mg, yield: 88%) was obtained as a solid in the same manner as in Example 20(20c).

21c tert-Butyl (3S)-3-(7-{[(4R)-8-chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate Using tert-butyl (3S)-3-(1,4-dimethyl-1H-benzotriazol-5-yl)-3-[7-(hydroxymethyl)-2,3-dihydro-1H-inden-5-yl]propanoate (110 mg) of Example 21(21b) and (4R)-8-chloro-4-ethyl-7-fluoro-3,4-dihydro-2H-5,1,2-benzoxathiazepine 1,1-dioxide (73 mg) of Example 13(13b), the title compound (145 mg, yield: 81%) was obtained as a solid in the same manner as in Example 3(3f).

21d (3S)-3-(7-{[(4R)-8-Chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid Using tert-butyl (3S)-3-(7-{[(4R)-8-chloro-4-ethyl-7-fluoro-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate (145 mg) of Example 21(21c), the title compound (77 mg, yield: 58%) was obtained as a solid in the same manner as in Example 20(20e).

Example 22

(3R)-3-(7-{[(4R)-8-Chloro-4-ethyl-7-fluoro-1,1-dioxido-3,4-dihydro-2H-5,1,2-benzoxathiazepin-2-yl]methyl}-1-benzothiophen-5-yl)-3-(1,4-dimethyl-1H-benzotriazol-5-yl)propanoic acid 22a Ethyl (3R)-3-(7-{[(4R)-8-chloro-4-ethyl-7-fluoro-1,1-dioxido-3,4-dihydro-2H-5,1,2-benzoxathiazepin-2-yl]methyl}-1-benzothiophen-5-yl)-3-(1,4-dimethyl-1H-benzotriazol-5-yl)propanoate Using ethyl (3R)-3-(1,4-dimethyl-1H-benzotriazol-5-yl)-3-[7-(hydroxymethyl)-1-benzothiophen-5-yl]propanoate (200 mg) of Example 7(7b) and (4R)-8-chloro-4-ethyl-7-fluoro-3,4-dihydro-2H-5,1,2-benzoxathiazepine 1,1-dioxide (136 mg) of Example 13(13b), the title compound (350 mg, yield: quantitative) was obtained as a solid in the same manner as in Example 3(3f).

22b (3R)-3-(7-{[(4R)-8-Chloro-4-ethyl-7-fluoro-1,1-dioxido-3,4-dihydro-2H-5,1,2-benzoxathiazepin-2-yl]methyl}-1-benzothiophen-5-yl)-3-(1,4-dimethyl-1H-benzotriazol-5-yl)propanoic acid To a mixture of ethyl (3R)-3-(7-{[(4R)-8-chloro-4-ethyl-7-fluoro-1,1-dioxido-3,4-dihydro-2H-5,1,2-benzoxathiazepin-2-yl]methyl}-1-benzothiophen-5-yl)-3-(1,4-dimethyl-1H-benzotriazol-5-yl)propanoate (350 mg) of Example 22(22a), tert-butanol (3.0 mL), and tetrahydrofuran (2.0 mL) was added 1M aqueous sodium hydroxide solution (1.5 mL), and the mixture was stirred at room temperature for 12 hr. To the reaction mixture was added 1M hydrochloric acid (1.5 mL), and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate/methanol=50/50/0-0/95/5(V/V/V)]. To the eluted compound were added ethyl acetate and n-hexane, and the mixture was subjected to an ultrasonic treatment. The solid was collected by filtration and vacuum dried to give the title compound (148 mg, yield: 44%).

Example 23

(3S)-3-(7-{[(4R)-8-Chloro-4-ethyl-7-fluoro-1,1-dioxido-3,4-dihydro-2H-5,1,2-benzoxathiazepin-2-yl]methyl}-1-benzothiophen-5-yl)-3-(1,4-dimethyl-1H-benzotriazol-5-yl)propanoic acid

23a

Ethyl (3S)-3-(7-{[(4R)-8-chloro-4-ethyl-7-fluoro-1,1-dioxido-3,4-dihydro-2H-5,1,2-benzoxathiazepin-2-yl]methyl}-1-benzothiophen-5-yl)-3-(1,4-dimethyl-1H-benzotriazol-5-yl)propanoate Using ethyl (3S)-3-(1,4-dimethyl-1H-benzotriazol-5-yl)-3-[7-(hydroxymethyl)-1-benzothiophen-5-yl]propanoate (200 mg) of Example 7(7a) and (4R)-8-chloro-4-ethyl-7-fluoro-3,4-dihydro-2H-5,1,2-benzoxathiazepine 1,1-dioxide (136 mg) of Example 13(13b), the title compound (330 mg, yield: quantitative) was obtained as a solid in the same manner as in Example 3(3f).

23b (3S)-3-(7-{[(4R)-8-Chloro-4-ethyl-7-fluoro-1,1-dioxido-3,4-dihydro-2H-5,1,2-benzoxathiazepin-2-yl]methyl}-1-benzothiophen-5-yl)-3-(1,4-dimethyl-1H-benzotriazol-5-yl)propanoic acid Using ethyl (3S)-3-(7-{[(4R)-8-chloro-4-ethyl-7-fluoro-1,1-dioxido-3,4-dihydro-2H-5,1,2-benzoxathiazepin-2-yl]methyl}-1-benzothiophen-5-yl)-3-(1,4-dimethyl-1H-benzotriazol-5-yl)propanoate (350 mg) of Example 23(23a), the title compound (70 mg, yield: 21%) was obtained as a solid in the same manner as in Example 22 (22b).

Example 24

3-(1,4-Dimethyl-1H-benzotriazol-5-yl)-3-(7-{[(4R)-4-ethyl-1,1-dioxido-3,4-dihydro-2H-pyrido[2,3-b][1,4,5]oxathiazepin-2-yl]methyl}-2,3-dihydro-1H-inden-5-yl)propanoic acid

24a

Ethyl 3-(1,4-dimethyl-1H-benzotriazol-5-yl)-3-(7-{[(4R)-4-ethyl-1,1-dioxido-3,4-dihydro-2H-pyrido[2,3-b][1,4,5]oxathiazepin-2-yl]methyl}-2,3-dihydro-1H-inden-5-yl)propanoate Using ethyl 3-(1,4-dimethyl-1H-benzotriazol-5-yl)-3-[7-(hydroxymethyl)-2,3-dihydro-1H-inden-5-yl]propanoate (90 mg) of Example 3(3e) and (4R)-4-ethyl-3,4-dihydro-2H-pyrido[2,3-b][1,4,5]oxathiazepine 1,1-dioxide (WO 2015/092713) (60 mg), the title compound (130 mg, yield: 94%) was obtained as a solid in the same manner as in Example 3 (3f).

24b 3-(1,4-Dimethyl-1H-benzotriazol-5-yl)-3-(7-{[(4R)-4-ethyl-1,1-dioxido-3,4-dihydro-2H-pyrido[2,3-b][1,4,5]oxathiazepin-2-yl]methyl}-2,3-dihydro-1H-inden-5-yl)propanoic acid Using ethyl 3-(1,4-dimethyl-1H-benzotriazol-5-yl)-3-(7-{[(4R)-4-ethyl-1,1-dioxido-3,4-dihydro-2H-pyrido[2,3-b][1,4,5]oxathiazepin-2-yl]methyl}-2,3-dihydro-1H-inden-5-yl)propanoate (130 mg) of Example 24(24a), the title compound (70 mg, yield: 56%) was obtained as a solid in the same manner as in Example 3(3g).

Example 25

3-(1,4-Dimethyl-1H-benzotriazol-5-yl)-3-(7-{[(4R)-4-ethyl-1,1-dioxido-8-(trifluoromethyl)-3,4-dihydro-2H-pyrido[2,3-b][1,4,5]oxathiazepin-2-yl]methyl}-2,3-dihydro-1H-inden-5-yl)propanoic acid

25a

2-Chloro-N-[(2R)-2-hydroxybutyl]-5-(trifluoromethyl)pyridine-3-sulfonamide

Using (2R)-1-aminobutan-2-ol (1.27 g) of Example 1(1a) and 2-chloro-5-(trifluoromethyl)pyridine-3-sulfonyl chloride (1.0 g), the title compound (417 mg, yield: 35%) was obtained as an oil in the same manner as in Example 1(1b).

25b (4R)-4-Ethyl-8-(trifluoromethyl)-3,4-dihydro-2H-pyrido[2,3-b][1,4,5]oxathiazepine 1,1-dioxide Using 2-chloro-N-[(2R)-2-hydroxybutyl]-5-(trifluoromethyl)pyridine-3-sulfonamide (417 mg) of Example 25(25a), the title compound (370 mg, yield: quantitative) was obtained as a solid in the same manner as in Example 1(1c).

25c

[(6-Bromo-2,3-dihydro-1H-inden-4-yl)methoxy](tert-butyl)dimethylsilane

To a mixture of (6-bromo-2,3-dihydro-1H-inden-4-yl)methanol (70 g) of Example 3(3c), imidazole (42 g), dichloromethane (800 mL) was added tert-butyldimethylchlorosilane (70 g), and the mixture was stirred at 15° C. for 1 hr. The reaction mixture was diluted with dichloromethane, the organic layer was washed twice with water and once with saturated brine and dried over anhydrous sodium sulfate. After filtration, the filtrate was concentrated under reduced pressure and the obtained residue was purified by silica gel column chromatography [elution solvent:petroleum ether] to give the title compound (98 g, yield: 93%) as a solid.

25d tert-Butyl(dimethyl){[6-(4,4,5,5-tetramethyl-1,3,2-dioxaborolan-2-yl)-2,3-dihydro-1H-inden-4-yl]methoxy}silane Using [(6-bromo-2,3-dihydro-1H-inden-4-yl)methoxy](tert-butyl)dimethylsilane (49 g) of Example 25(25c), the title compound (51 g, yield: 91%) was obtained as a solid in the same manner as in Example 1(1h).

25e tert-Butyl 3-[7-({[tert-butyl(dimethyl)silyl] oxy}methyl)-2,3-dihydro-1H-inden-5-yl]-3-(1,4-dimethyl-1H-benzotriazol-5-yl)propanoate Bis(norbornadiene)rhodium(I) tetrafluoroborate (152 mg), (2S,3S)-bis(diphenylphosphino)butane (87 mg), and (2R,3R)-bis(diphenylphosphino)butane (87 mg) were dissolved in a mixed solvent of 1,4-dioxane (27 mL) and water (7.2 mL) and the mixture was stirred at room temperature for 15 min. Then, tert-butyl (2E)-3-(1,4-dimethyl-1H-benzotriazol-5-yl)prop-2-enoate (WO 2018/109646) (2.22 g), tert-butyl(dimethyl){[6-(4,4,5,5-tetramethyl-1,3,2-dioxaborolan-2-yl)-2,3-dihydro-1H-inden-4-yl]methoxy}silane (4.73 g) of Example 25(25d), and 1M aqueous potassium hydroxide solution (8.12 mL) were added thereto, and the mixture was stirred under heating at 50° C. for 4 hr. The reaction mixture was allowed to cool to room temperature, saturated aqueous ammonium chloride solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent: n-hexane/ethyl acetate=90/10-60/40(V/V)] to give the title compound (4.0 g, yield: 92%) as an oil.

25f tert-Butyl 3-(1,4-dimethyl-1H-benzotriazol-5-yl)-3-[7-(hydroxymethyl)-2,3-dihydro-1H-inden-5-yl]propanoate Using tert-butyl 3-[7-({[tert-butyl(dimethyl)silyl] oxy}methyl)-2,3-dihydro-1H-inden-5-yl]-3-(1,4-dimethyl-1H-benzotriazol-5-yl)propanoate (4.0 g) of Example 25(25e), the title compound (3.0 g, yield: 95%) was obtained as a solid in the same manner as in Example 20(20c).

25g tert-Butyl 3-(1,4-dimethyl-1H-benzotriazol-5-yl)-3-(7-{[(4R)-4-ethyl-1,1-dioxido-8-(trifluoromethyl)-3,4-dihydro-2H-pyrido[2,3-b][1,4,5]oxathiazepin-2-yl] methyl}-2,3-dihydro-1H-inden-5-yl)propanoate Using tert-butyl 3-(1,4-dimethyl-1H-benzotriazol-5-yl)-3-[7-(hydroxymethyl)-2,3-dihydro-1H-inden-5-yl]propanoate (100 mg) of Example 25(25f) and (4R)-4-ethyl-8-(trifluoromethyl)-3,4-dihydro-2H-pyrido[2,3-b][1,4,5] oxathiazepine 1,1-dioxide (70 mg) of Example 25(25b), the title compound (116 mg, yield: 70%) was obtained as a solid in the same manner as in Example 3(3f).

25h 3-(1,4-Dimethyl-1H-benzotriazol-5-yl)-3-(7-{[(4R)-4-ethyl-1,1-dioxido-8-(trifluoromethyl)-3,4-dihydro-2H-pyrido[2,3-b][1,4,5]oxathiazepin-2-yl]methyl}-2,3-dihydro-1H-inden-5-yl)propanoic acid Using tert-butyl 3-(1,4-dimethyl-1H-benzotriazol-5-yl)-3-(7-{[(4R)-4-ethyl-1,1-dioxido-8-(trifluoromethyl)-3,4-dihydro-2H-pyrido[2,3-b][1,4,5]oxathiazepin-2-yl]methyl}-2,3-dihydro-1H-inden-5-yl)propanoate (116 mg) of Example 25(25g), the title compound (75 mg, yield: 70%) was obtained as a solid in the same manner as in Example 20(20e).

Example 26

3-(1,4-Dimethyl-1H-benzotriazol-5-yl)-3-(7-{[(2R)-2-ethyl-5,5-dioxido-2,3-dihydro-4H-naphtho[1,2-b][1,4,5]oxathiazepin-4-yl]methyl}-2,3-dihydro-1H-inden-5-yl)propanoic acid

26a

1-Fluoro-N-[(2R)-2-hydroxybutyl]naphthalene-2-sulfonamide

Using (2R)-1-aminobutan-2-ol (1.10 g) of Example 1(1a) and 1-fluoronaphthalene-2-sulfonyl chloride (0.75 g), the title compound (0.90 mg, yield: 99%) was obtained as a solid in the same manner as in Example 1(1b).

26b (2R)-2-Ethyl-3,4-dihydro-2H-naphtho[1,2-b][1,4,5] oxathiazepine 5,5-dioxide Using 1-fluoro-N-[(2R)-2-hydroxybutyl]naphthalene-2-sulfonamide (900 mg) of Example 26(26a), the title compound (700 mg, yield: 83%) was obtained as a solid in the same manner as in Example 1(1c).

26c tert-Butyl 3-(1,4-dimethyl-1H-benzotriazol-5-yl)-3-(7-{[(2R)-2-ethyl-5,5-dioxido-2,3-dihydro-4H-naphtho[1,2-b][1,4,5]oxathiazepin-4-yl]methyl}-2,3-dihydro-1H-inden-5-yl)propanoate Using tert-butyl 3-(1,4-dimethyl-1H-benzotriazol-5-yl)-3-[7-(hydroxymethyl)-2,3-dihydro-1H-inden-5-yl]propanoate (110 mg) of Example 25(25f) and (2R)-2-ethyl-3,4-dihydro-2H-naphtho[1,2-b][1,4,5]oxathiazepine 5,5-dioxide (72 mg) of Example 26(26b), the title compound (170 mg, yield: 96%) was obtained as a solid in the same manner as in Example 3(3f).

26d 3-(1,4-Dimethyl-1H-benzotriazol-5-yl)-3-(7-{[(2R)-2-ethyl-5,5-dioxido-2,3-dihydro-4H-naphtho[1,2-b][1,4,5]oxathiazepin-4-yl]methyl}-2,3-dihydro-1H-inden-5-yl)propanoic acid Using tert-butyl 3-(1,4-dimethyl-1H-benzotriazol-5-yl)-3-(7-{[(2R)-2-ethyl-5,5-dioxido-2,3-dihydro-4H-naphtho[1,2-b][1,4,5]oxathiazepin-4-yl]methyl}-2,3-dihydro-1H-inden-5-yl)propanoate (180 mg) of Example 26(26c), the title compound (100 mg, yield: 61%) was obtained as a solid in the same manner as in Example 20 (20e).

Example 27

(3R)-3-(1,4-Dimethyl-1H-benzotriazol-5-yl)-3-(7-{[(4S*)-4-ethyl-1,1-dioxido-4,5-dihydropyrido[2,3-f][1,2]thiazepin-2(3H)-yl]methyl}-2,3-dihydro-1H-inden-5-yl)propanoic acid

27a (4S*)-4-Ethyl-2,3,4,5-tetrahydropyrido[2,3-f][1,2]thiazepine 1,1-dioxide To a solution of 2-chloro-N-(2-methylidenebutyl)pyridine-3-sulfonamide (WO 2018/109643) (30 g) in toluene (500 mL) was added 2,2'-azo bis(isobutyronitrile) (10 g) at room temperature, and the reaction mixture was heated to 65° C. Tributyltin hydride (70 g) was added thereto, and the reaction mixture was stirred at 85° C. for 16 hr. A solution of potassium fluoride (50 g) in water (500 mL) was added to the reaction mixture, and the mixture was stirred at 15° C. for 10 hr. Insoluble matter was removed by filtration, and the filtrate was concentrated under reduced pressure. The obtained residue was purified by silica gel column chromatography [elution solvent:petroleum ether/ethyl acetate=20/1-5/1(V/V)] and then purified by preparative HPLC [column: Phenomenex Luna C18 (100 mm I.D.×250 mm), mobile phase: 0.225% aqueous formic acid solution/acetonitrile=75/25-55/45(V/V)] to give a racemate of the title compound. This was subjected to chiral SFC [column: CHIRALPAK IC (30 mm I.D.×250 mm), mobile phase: carbon dioxide/2-propanol (0.1% aqueous ammonia)=60/40(V/V)] to obtain 7.09 g of (4S*)-4-ethyl-2,3,4,5-tetrahydropyrido[2,3-f][1,2]thiazepine 1,1-dioxide as the first peak (yield: 26%).

Analysis SFC conditions [column: CHIRALPAK AS-3 (4.6 mm I.D.×50 mm), mobile phase: carbon dioxide/ethanol (0.05% diethylamine)=95/5-60/40(V/V), flow rate: 3 mL/min, temperature: 35° C., wavelength: 220 nm]; retention time: 1.081 min (the first peak)

27b

Ethyl (3R)-3-(1,4-dimethyl-1H-benzotriazol-5-yl)-3-(7-{[(4S*)-4-ethyl-1,1-dioxido-4,5-dihydropyrido[2,3-f][1,2]thiazepin-2(3H)-yl]methyl}-2,3-dihydro-1H-inden-5-yl)propanoate Using ethyl (3R)-3-(1,4-dimethyl-1H-benzotriazol-5-yl)-3-[7-(hydroxymethyl)-2,3-dihydro-1H-inden-5-yl]propanoate (158 mg) of Example 4(4b) and (4S*)-4-ethyl-2,3,4,5-tetrahydropyrido[2,3-f][1,2]thiazepine 1,1-dioxide (90 mg) of Example 27(27a), the title compound (230 mg, yield: 95%) was obtained as a solid in the same manner as in Example 3(3f).

27c (3R)-3-(1,4-Dimethyl-1H-benzotriazol-5-yl)-3-(7-{[(4S*)-4-ethyl-1,1-dioxido-4,5-dihydropyrido[2,3-f][1,2]thiazepin-2(3H)-yl]methyl}-2,3-dihydro-1H-inden-5-yl)propanoic acid Using ethyl (3R)-3-(1,4-dimethyl-1H-benzotriazol-5-yl)-3-(7-{[(4S*)-4-ethyl-1,1-dioxido-4,5-dihydropyrido[2,3-f][1,2]thiazepin-2(3H)-yl]methyl}-2,3-dihydro-1H-inden-5-yl)propanoate (120 mg) of Example 27(27b), the title compound (50 mg, yield: 44%) was obtained as a solid in the same manner as in Example 3(3g).

Example 28

(3R)-3-(1,4-Dimethyl-1H-benzotriazol-5-yl)-3-(7-{[(4S*)-4-ethyl-1,1-dioxido-4,5-dihydro-1,2-benzothiazepin-2(3H)-yl]methyl}-2,3-dihydro-1H-inden-5-yl)propanoic acid

28a (4S*)-4-Ethyl-2,3,4,5-tetrahydro-1,2-benzothiazepine 1,1-dioxide

4-Ethyl-2,3,4,5-tetrahydro-1,2-benzothiazepine 1,1-dioxide (WO 2017/060854) (16 g) was subjected to chiral SFC [column: CHIRALPAK AD (30 mm I.D.×250 mm), mobile phase: carbon dioxide/methanol (0.1% aqueous ammonia)=70/30(V/V)] to obtain 4.8 g of (4S*)-4-ethyl-2,3,4,5-tetrahydro-1,2-benzothiazepine 1,1-dioxide as the first peak.

Analysis SFC conditions [column: CHIRALPAK AY-3 (4.6 mm I.D.×50 mm), mobile phase: carbon dioxide/ethanol (0.05% diethylamine)=95/5-60/40(V/V), flow rate: 3 mL/min, temperature: 35° C., wavelength: 220 nm]; retention time: 1.513 min (the first peak)

28b

Ethyl (3R)-3-(1,4-dimethyl-1H-benzotriazol-5-yl)-3-(7-{[(4S*)-4-ethyl-1,1-dioxido-4,5-dihydro-1,2-benzothiazepin-2(3H)-yl]methyl}-2,3-dihydro-1H-inden-5-yl)propanoate Using ethyl (3R)-3-(1,4-dimethyl-1H-benzotriazol-5-yl)-3-[7-(hydroxymethyl)-2,3-dihydro-1H-inden-5-yl]propanoate (158 mg) of Example 4(4b) and (4S*)-4-ethyl-2,3,4,5-tetrahydro-1,2-benzothiazepine 1,1-dioxide (90 mg) of Example 28(28a), the title compound (100 mg, yield: 41%) was obtained as a solid in the same manner as in Example 3(3f).

28c (3R)-3-(1,4-Dimethyl-1H-benzotriazol-5-yl)-3-(7-{[(4S*)-4-ethyl-1,1-dioxido-4,5-dihydro-1,2-benzothiazepin-2(3H)-yl]methyl}-2,3-dihydro-1H-inden-5-yl)propanoic acid Using ethyl (3R)-3-(1,4-dimethyl-1H-benzotriazol-5-yl)-3-(7-{[(4S*)-4-ethyl-1,1-dioxido-4,5-dihydro-1,2-benzothiazepine-2 (3H)-yl]methyl}-2,3-dihydro-1H-inden-5-yl)propanoate (100 mg) of Example 28(28b), the title compound (85 mg, yield: 89%) was obtained as a solid in the same manner as in Example 3(3g).

Example 29

3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(4-chloro-1-methyl-1H-benzotriazol-5-yl)propanoic acid

29a

Ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(4-chloro-1-methyl-1H-benzotriazol-5-yl)propanoate Ethyl 3-(4-chloro-1-methyl-1H-benzotriazol-5-yl)-3-[7-(hydroxymethyl)-2,3-dihydro-1H-inden-5-yl]propanoate (181 mg) of Example 95(95a) and (4R)-8-chloro-4-ethyl-3,4-dihydro-2H-pyrido[2,3-b][1,4,5]oxathiazepine 1,1-dioxide (115 mg) of Example 1(1c) were dissolved in toluene (5 mL) and, under a nitrogen atmosphere, 1,1'-(azodicarbonyl)dipiperidine (221 mg), and then tri-n-butylphosphine (0.218 mL) were added, and the mixture was stirred at room temperature for 25 hr. The reaction mixture was diluted with dichloromethane and purified by silica gel column chromatography [elution solvent:n-hexane/ethyl acetate=2/1-1/2(V/V)] to give the title compound (270 mg, yield: 94%) as a solid.

29b 3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(4-chloro-1-methyl-1H-benzotriazol-5-yl)propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(4-chloro-1-methyl-1H-benzotriazol-5-yl)propanoate (270 mg) of Example 29(29a), the title compound (218 mg, yield: 84%) was obtained as a solid in the same manner as in Example 3(3g).

Example 30

(3S)-3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoic acid 30a 4-Bromo-6-chloro-N,3-dimethyl-2-nitroaniline 4-Bromo-N,3-dimethyl-2-nitroaniline (WO 2020/165776) (5.04 g) was dissolved in N,N-dimethylformamide, N-chlorosuccinimide (2.88 g) was added, and the mixture was stirred under a nitrogen atmosphere at 80° C. for 2 hr and cooled to room temperature. The reaction mixture was diluted with ethyl acetate, successively washed three times with water and once with saturated brine and dried over anhydrous sodium sulfate. After filtration, the filtrate was concentrated under reduced pressure to give an unpurified title compound (5.72 g, yield: quantitative) as a solid.

30b

4-Bromo-6-chloro-$N^1$,3-dimethylbenzene-1,2-diamine

Using 4-bromo-6-chloro-N,3-dimethyl-2-nitroaniline (5.84 g) of Example 30(30a), the title compound (2.69 g, yield: 52%) was obtained as an oil in the same manner as in Example 54(54d).

30c

5-Bromo-7-chloro-1,4-dimethyl-1H-benzotriazole

4-Bromo-6-chloro-$N^1$,3-dimethylbenzene-1,2-diamine (2.69 g) of Example 30(30b) was suspended in 5M hydrochloric acid (50 mL), and a solution of sodium nitrite (1.49 g) in water (6 mL) was added dropwise under a nitrogen atmosphere at 0° C. over 20 min. After stirring at room temperature for 1.5 hr, the reaction mixture was cooled to 0° C. and neutralized by adding 5 M aqueous sodium hydroxide solution (50 mL) dropwise. The reaction mixture was extracted with dichloromethane, and the organic layer was washed with saturated brine and dried over anhydrous sodium sulfate. After filtration, the filtrate was concentrated under reduced pressure to give an unpurified title compound (2.76 g, yield: 98%) as a solid.

30d

Ethyl (2E)-3-(7-chloro-1,4-dimethyl-1H-benzotriazol-5-yl)prop-2-enoate

A mixture of 5-bromo-7-chloro-1,4-dimethyl-1H-benzotriazole (2.76 g) of Example 30(30c), palladium acetate (II) (238 mg), tri(o-tolyl)phosphine (645 mg), and N,N-dimethylformamide (20 mL) was purged with nitrogen, and N,N-diisopropylethylamine (9.1 mL) and then ethyl acrylate (2.3 mL) were added, and the mixture was stirred under heating at 90° C. for 2 hr. To the reaction mixture were added tris(dibenzylideneacetone)dipalladium(0) (485 mg), tri(o-tolyl)phosphine (645 mg), and ethyl acrylate (2.3 mL), and the mixture was stirred under heating at 90° C. for 3 hr. The reaction mixture was allowed to cool to room temperature, ethyl acetate and saturated aqueous sodium hydrogen carbonate solution were added, and the mixture was stirred. The insoluble matter was filtered through a cotton plug. The organic layer of the filtrate was separated by a partitioning operation, washed twice with water and once with saturated brine, and dried over anhydrous sodium sulfate. After filtration, the filtrate was concentrated under reduced pressure, and the obtained residue was purified by silica gel column chromatography [eluent: n-hexane/dichloromethane/ethyl acetate=90/0/10-75/0/25-0/100/0-0/90/10 (V/V/V)]. The obtained solid was slurry washed with n-hexane/ethyl acetate to give the title compound (2.23 g, yield: 75%) as a solid.

30e

Ethyl 3-(7-chloro-1,4-dimethyl-1H-benzotriazol-5-yl)-3-[7-(hydroxymethyl)-1-benzothiophen-5-yl]propanoate Ethyl (2E)-3-(7-chloro-1,4-dimethyl-1H-benzotriazol-5-yl)prop-2-enoate (2.00 g) of Example 30(30d) and [5-(4,4,5,5-tetramethyl-1,3,2-dioxaborolan-2-yl)-1-benzothiophen-7-yl]methanol (2.41 g) of Example 1(1h) were suspended in a mixed solvent of 1,4-dioxane (48 mL) and water (8.4 mL), hydroxy(1,5-cyclooctadiene)rhodium(I) dimer (293 mg) and then 1M aqueous potassium hydroxide solution (3.57 mL) were added under a nitrogen atmosphere, and the mixture was stirred under heating at 50° C. for 2 hr. The reaction mixture was allowed to cool to room temperature, water was added, and the mixture was extracted three times with dichloromethane. The combined organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=4/1-1/1(V/V)] to give the title compound (1.61 g, yield: 51%) as a solid.

30f

Ethyl (3S)-3-(7-chloro-1,4-dimethyl-1H-benzotriazol-5-yl)-3-[7-(hydroxymethyl)-1-benzothiophen-5-yl]propanoate

30g

Ethyl (3R)-3-(7-chloro-1,4-dimethyl-1H-benzotriazol-5-yl)-3-[7-(hydroxymethyl)-1-benzothiophen-5-yl]propanoate Ethyl 3-(7-chloro-1,4-dimethyl-1H-benzotriazol-5-yl)-3-[7-(hydroxymethyl)-1-benzothiophen-5-yl]propanoate (1.61 g) of Example 30(30e) was subjected to chiral HPLC [column: CHIRALCEL OJ-H (20 mm I.D.×250 mm), mobile phase: n-hexane/2-propanol=50/50(V/V)] to obtain 593 mg of ethyl (3S)-3-(7-chloro-1,4-dimethyl-1H-benzotriazol-5-yl)-3-[7-(hydroxymethyl)-1-benzothiophen-5-yl]propanoate of Example 30(30f) as the first peak (yield: 37%).

In the same manner, 537 mg of ethyl (3R)-3-(7-chloro-1,4-dimethyl-1H-benzotriazol-5-yl)-3-[7-(hydroxymethyl)-1-benzothiophen-5-yl]propanoate of Example 30(30g) was obtained as the second peak (yield: 33%).

Analysis HPLC conditions [column: CHIRALCEL OJ-H (4.6 mm I.D.×250 mm), mobile phase: n-hexane/2-propanol=50/50(V/V), flow rate: 1.0 mL/min, temperature: 40° C., wavelength: 210 nm]; retention time: 7.797 min (the first peak), 14.150 min (the second peak)

30h

Ethyl (3S)-3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoate Using ethyl (3S)-3-(7-chloro-1,4-dimethyl-1H-benzotriazol-5-yl)-3-[7-(hydroxymethyl)-1-benzothiophen-5-yl]propanoate (116 mg) of Example 30(30f) and (4R)-8-chloro-4-ethyl-3,4-dihydro-2H-pyrido[2,3-b][1,4,5]oxathiazepine 1,1-dioxide (76 mg) of Example 1(1c), the title compound (186 mg, yield: quantitative) was obtained as a solid in the same manner as in Example 29(29a).

30i (3S)-3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoic acid To a mixture of ethyl (3S)-3-(7-chloro-1,4-dimethyl-H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoate (186 mg) of Example 30(30h), ethanol (2 mL), and tetrahydrofuran (4 mL) was added 1M aqueous sodium hydroxide solution (2 mL), and the mixture was stirred at 40° C. for 4 hr. To the reaction mixture were added ethanol (2 mL) and tetrahydrofuran (2 mL), and the mixture was stirred at 50° C. for 1 hr. The reaction mixture was cooled to room temperature, 1M hydrochloric acid (2 mL) and dichloromethane were added and the mixture was stirred. The organic layer was separated through a phase separator (Biotage) and the solvent was evaporated under reduced pressure. The obtained residue was purified by DIOL silica gel column chromatography [elution solvent:ethyl acetate/methanol=100/0-90/10 (V/V)] and the obtained residue was slurry washed with n-hexane/ethyl acetate to give the title compound (130 mg, yield: 75%) as a solid.

Example 31

(3R)-3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoic acid

31a

Ethyl (3R)-3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoate Using ethyl (3R)-3-(7-chloro-1,4-dimethyl-1H-benzotriazol-5-yl)-3-[7-(hydroxymethyl)-1-benzothiophen-5-yl]propanoate (116 mg) of Example 30(30g) and (4R)-8-chloro-4-ethyl-3,4-dihydro-2H-pyrido[2,3-b][1,4,5]oxathiazepine 1,1-dioxide (75 mg) of Example 1(1c), the title compound (166 mg, yield: 92%) was obtained as a solid in the same manner as in Example 29(29a).

31b (3R)-3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoic acid To a mixture of ethyl (3R)-3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoate (166 mg) of Example 31(31a), ethanol (2 mL), and tetrahydrofuran (4 mL) was added 1M aqueous sodium hydroxide solution (2 mL), and the mixture was stirred at 40° C. for 1.5 hr. The reaction mixture was cooled to room temperature, 1M hydrochloric acid (2 mL) and dichloromethane were added, and the mixture was stirred. The organic layer was separated through a phase separator (Biotage) and the solvent was evaporated under reduced pressure. The obtained residue was slurry washed with n-hexane/ethyl acetate to give the title compound (138 mg, yield: 87%) as a solid.

Example 32

(3R)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid

32a

Ethyl 3-[7-(difluoromethoxy)-1,4-dimethyl-1H-benzotriazol-5-yl]-3-[7-(hydroxymethyl)-1-benzothiophen-5-yl]propanoate Bis(norbornadiene)rhodium(I) tetrafluoroborate (53 mg) and (2S,3S)-bis(diphenylphosphino)butane (61 mg) were dissolved in a mixed solvent of 1,4-dioxane (5 mL) and water (2.8 mL), and the mixture was stirred at room temperature for 10 min. Then, a solution of ethyl (2E)-3-[7-(difluoromethoxy)-1,4-dimethyl-1H-benzotriazol-5-yl]prop-2-enoate (441 mg) of Example 55(55g) in 1,4-dioxane (7.5 mL), [5-(4,4,5,5-tetramethyl-1,3,2-dioxaborolan-2-yl)-1-benzothiophen-7-yl]methanol (617 mg) of Example 1(1h), and 1 M aqueous potassium hydroxide solution (1.45 mL) were added, and the mixture was heated and stirred at 50° C. for 3 hr. To the reaction mixture was added [5-(4,4,5,5-tetramethyl-1,3,2-dioxaborolan-2-yl)-1-benzothiophen-7-yl]methanol (283 mg) of Example 1(1h), and the mixture was heated and stirred at 50° C. for min. The reaction mixture was allowed to cool to room temperature, saturated aqueous ammonium chloride was added, and the mixture was extracted with ethyl acetate. The organic layer was washed with saturated brine and then dried over anhydrous sodium sulfate. After filtration, the filtrate was concentrated under reduced pressure, and the obtained residue was purified by silica gel column chromatography [eluent: n-hexane/ethyl acetate=2/1-1/1 (V/V)], and then purified by NH silica gel column chromatography [eluent: n-hexane/ethyl acetate=2/1-1/2 (V/V)] to give the title compound (668 mg, yield: 99%) (solid) as a mixture of both enantiomers.

32b

Ethyl (3R)-3-[7-(difluoromethoxy)-1,4-dimethyl-1H-benzotriazol-5-yl]-3-[7-(hydroxymethyl)-1-benzothiophen-5-yl]propanoate 32c Ethyl (3S)-3-[7-(difluoromethoxy)-1,4-dimethyl-1H-benzotriazol-5-yl]-3-[7-(hydroxymethyl)-1-benzothiophen-5-yl]propanoate Ethyl 3-[7-(difluoromethoxy)-1,4-dimethyl-1H-benzotriazol-5-yl]-3-[7-(hydroxymethyl)-1-benzothiophen-5-yl]propanoate (668 mg) of Example 32(32a) was subjected to chiral HPLC [column: CHIRALPAK IG (20 mm I.D.×250 mm), mobile phase: n-hexane/ethanol=80/20(V/V)] to obtain 515 mg of ethyl (3R)-3-[7-(difluoromethoxy)-1,4-dimethyl-1H-benzotriazol-5-yl]-3-[7-(hydroxymethyl)-1-benzothiophen-5-yl]propanoate as the first peak (yield: 77%).

Similarly, 126 mg of ethyl (3S)-3-[7-(difluoromethoxy)-1,4-dimethyl-1H-benzotriazol-5-yl]-3-[7-(hydroxymethyl)-1-benzothiophen-5-yl]propanoate was obtained as the second peak (yield: 19%).

Analysis HPLC conditions [column: CHIRALPAK IG (4.6 mm I.D. 10×250 mm), mobile phase: n-hexane/ethanol=80/20(V/V), flow rate: 1.0 mL/min, temperature: 40° C., wavelength: 210 nm]; retention time: 10.533 min (the first peak), 12.450 min (the second peak)

32d

Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoate Ethyl (3R)-3-[7-(difluoromethoxy)-1,4-dimethyl-1H-benzotriazol-5-yl]-3-[7-(hydroxymethyl)-1-benzothiophen-5-yl]propanoate (180 mg) of Example 32(32b) and (4R)-8-chloro-4-ethyl-3,4-dihydro-2H-pyrido[2,3-b][1,4,5]oxathiazepine 1,1-dioxide (119 mg) of Example 1(1c) were dissolved in toluene (4 mL), 1,1'-(azodicarbonyl)dipiperidine (143 mg), and then tri-n-butylphosphine (0.142 mL) were added under a nitrogen atmosphere and the mixture was stirred at room temperature for 5 hr. To the reaction mixture were added dichloromethane (2 mL), (4R)-8-chloro-4-ethyl-3,4-dihydro-2H-pyrido[2,3-b][1,4,5]oxathiazepine 1,1-dioxide (30 mg) of Example 1(1c), 1,1'-(azodicarbonyl)dipiperidine (30 mg), and then tri-n-butylphosphine (0.029 mL) and the mixture was stirred at room temperature for 14 hr. Dichloromethane was added to the reaction mixture and the mixture was dissolved by heating to 40° C., and this was purified by silica gel column chromatography [elution solvent:n-hexane/ethyl acetate=2/1-1/1(V/V)], and further by NH silica gel column chromatography [elution solvent:n-hexane/ethyl acetate=2/1-1/1(V/V)] to give the title compound (225 mg, yield: 83%) as a solid.

32e (3R)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid Using ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoate (223 mg) of Example 32(32d), the title compound (196 mg, yield: 91%) was obtained as a solid in the same manner as in Example 31(31b).

Example 33

3-(1,4-Dimethyl-1H-benzotriazol-5-yl)-3-{7-[(1,1'-dioxido-2,3,5,6-tetrahydrospiro[pyran-4,4'-pyrido[2,3-b][1,4,5]oxathiazepine]-2'(3'H)-yl)methyl]-2,3-dihydro-1H-inden-5-yl}propanoic acid 33a Ethyl 3-(1,4-dimethyl-1H-benzotriazol-5-yl)-3-{7-[(1',1'-dioxido-2,3,5,6-tetrahydrospiro[pyran-4,4'-pyrido[2,3-b][1,4,5]oxathiazepine]-2'(3'H)-yl)methyl]-2,3-dihydro-1H-inden-5-yl}propanoate Using ethyl 3-(1,4-dimethyl-1H-benzotriazol-5-yl)-3-[7-(hydroxymethyl)-2,3-dihydro-1H-inden-5-yl]propanoate (100 mg) of Example 3(3e) and 2,2',3,3',5,6-hexahydrospiro[pyran-4,4'-pyrido[2,3-b][1,4,5]oxathiazepine]1',1'-dioxide (US-A-2020/0055874) (70 mg), the title compound (71 mg, yield: 43%) was obtained as a solid in the same manner as in Example 29(29a).

33b 3-(1,4-Dimethyl-1H-benzotriazol-5-yl)-3-{7-[(1',1'-dioxido-2,3,5,6-tetrahydrospiro[pyran-4,4'-pyrido[2,3-b][1,4,5]oxathiazepine]-2'(3'H)-yl)methyl]-2,3-dihydro-1H-inden-5-yl}propanoic acid To a mixture of ethyl 3-(1,4-dimethyl-1H-benzotriazol-5-yl)-3-{7-[(1',1'-dioxido-2,3,5,6-tetrahydrospiro[pyran-4,4'-pyrido[2,3-b][1,4,5]oxathiazepine]-2' (3'H)-yl)methyl]-2,3- dihydro-1H-inden-5-yl}propanoate (70 mg) of Example 33(33a), ethanol (2 mL), and tetrahydrofuran (2 mL) was added 1M aqueous sodium hydroxide solution (2 mL), and the mixture was stirred at room temperature for 10 hr. To the reaction mixture were added 1M hydrochloric acid (2 mL) and dichloromethane, and the mixture was stirred. The organic layer was separated through a phase separator (Biotage) and the solvent was evaporated under reduced pressure. The obtained residue was purified by silica gel column chromatography [elution solvent:ethyl acetate/methanol=100/0-90/10(V/V)] and the obtained solid was slurry washed with diisopropyl ether to give the title compound (30.5 mg, yield: 46%) as a solid.

Example 34

3-(1,4-Dimethyl-1H-benzotriazol-5-yl)-3-{7-[(4,4-dimethyl-1,1-dioxido-3,4-dihydro-2H-pyrido[2,3-b][1,4,5]oxathiazepin-2-yl)methyl]-2,3-dihydro-1H-inden-5-yl}propanoic acid 34a Ethyl 3-(1,4-dimethyl-1H-benzotriazol-5-yl)-3-{7-[(4,4-dimethyl-1,1-dioxido-3,4-dihydro-2H-pyrido[2,3-b][1,4,5]oxathiazepin-2-yl)methyl]-2,3-dihydro-1H-inden-5-yl}propanoate Using ethyl 3-(1,4-dimethyl-1H-benzotriazol-5-yl)-3-[7-(hydroxymethyl)-2,3-dihydro-1H-inden-5-yl]propanoate (130 mg) of Example 3(3e) and 4,4-dimethyl-3,4-dihydro-2H-pyrido[2,3-b][1,4,5]oxathiazepine 1,1-dioxide (WO 2018/109643) (80 mg), the title compound (195 mg, yield: 98%) was obtained as a solid in the same manner as in Example 29(29a).

34b 3-(1,4-Dimethyl-1H-benzotriazol-5-yl)-3-{7-[(4,4-dimethyl-1,1-dioxido-3,4-dihydro-2H-pyrido[2,3-b][1,4,5]oxathiazepin-2-yl)methyl]-2,3-dihydro-1H-inden-5-yl}propanoic acid Using ethyl 3-(1,4-dimethyl-1H-benzotriazol-5-yl)-3-{7-[(4,4-dimethyl-1,1-dioxido-3,4-dihydro-2H-pyrido[2,3-b][1,4,5]oxathiazepin-2-yl)methyl]-2,3-dihydro-1H-inden-5-yl}propanoate (195 mg) of Example 34(34a), the title compound (68 mg, yield: 37%) was obtained as a solid in the same manner as in Example 33(33b)

Example 35

3-(1,4-Dimethyl-1H-benzotriazol-5-yl)-3-{7-[(1,1'-dioxido-spiro[cyclobutane-1,4'-pyrido[2,3-b][1,4,5]oxathiazepine]-2'(3'H)-yl)methyl]-2,3-dihydro-1H-inden-5-yl}propanoic acid 35a 2-Chloro-N-[(1-hydroxycyclobutyl)methyl]pyridine-3-sulfonamide 1-(Aminomethyl)cyclobutanol (477 mg) was dissolved in a mixed solvent of tetrahydrofuran (25 mL) and water (5 mL), potassium carbonate (652 mg) and then 2-chloropyridine-3-sulfonyl chloride (1.00 g) were added, and the mixture was stirred at room temperature for 4 hr. The solvent was evaporated under reduced pressure, dichloromethane was added to the obtained residue, and the mixture was stirred. The organic layer was separated through a phase separator (Biotage) and the solvent was evaporated under reduced pressure to give the title compound (1.26 g, yield: 97%) as a highly viscous oil.

35b

2',3'-Dihydrospiro[cyclobutane-1,4'-pyrido[2,3-b][1,4,5]oxathiazepine]1',1'-dioxide 2-Chloro-N-[(1-hydroxycyclobutyl)methyl]pyridine-3-sulfonamide (1.26 g) of Example 35(35a) and potassium tert-butoxide (1.53 g) were dissolved in N,N-dimethylformamide (5 mL), and the mixture was stirred at 80° C. for 1 hr. The reaction mixture was cooled to room temperature, 1M hydrochloric acid (14 mL) was added and the mixture was stirred and extracted with ethyl acetate. The organic layer was washed successively with water and saturated brine, and dried over anhydrous sodium sulfate. After filtration, the filtrate was concentrated under reduced pressure and the obtained residue was slurry washed with ethanol to give the title compound (716 mg, yield: 65%) as a solid.

35c

Ethyl 3-(1,4-dimethyl-1H-benzotriazol-5-yl)-3-{7-[(1,1'-dioxido-spiro[cyclobutane-1,4'-pyrido[2,3-b][1,4,5]oxathiazepine]-2'(3'H)-yl)methyl]-2,3-dihydro-1H-inden-5-yl}propanoate Using ethyl 3-(1,4-dimethyl-1H-benzotriazol-5-yl)-3-[7-(hydroxymethyl)-2,3-dihydro-1H-inden-5-yl]propanoate (130 mg) of Example 3(3e) and 2',3'-dihydrospiro[cyclobutane-1,4'-pyrido[2,3-b][1,4,5]oxathiazepine]1',1'-dioxide (80 mg) of Example 35(35b), the title compound (150 mg, yield: 74%) was obtained as a solid in the same manner as in Example 29(29a).

35d 3-(1,4-Dimethyl-1H-benzotriazol-5-yl)-3-{7-[(1,1'-dioxido-spiro[cyclobutane-1,4'-pyrido[2,3-b][1,4,5]oxathiazepine]-2'(3'H)-yl)methyl]-2,3-dihydro-1H-inden-5-yl}propanoic acid Using ethyl 3-(1,4-dimethyl-1H-benzotriazol-5-yl)-3-{7-[(1',1'-dioxido-spiro[cyclobutane-1,4'-pyrido[2,3-b][1,4,5]oxathiazepine]-2' (3'H)-yl)methyl]-2,3-dihydro-1H-inden-5-yl}propanoate (150 mg) of Example 35(35c), the title compound (70 mg, yield: 49%) was obtained as a solid in the same manner as in Example 33(33b).

Example 36

3-(1,4-Dimethyl-1H-benzotriazol-5-yl)-3-{7-[(1,1'-dioxido-spiro[oxetane-3,4'-pyrido[2,3-b][1,4,5]oxathiazepine]-2' (3'H)-yl)methyl]-2,3-dihydro-1H-inden-5-yl}propanoic acid 36a ethyl 3-(1,4-dimethyl-1H-benzotriazol-5-yl)-3-{7-[(1,1'-dioxido-spiro[oxetane-3,4'-pyrido[2,3-b][1,4,5]oxathiazepine]-2' (3'H)-yl)methyl]-2,3-dihydro-1H-inden-5-yl}propanoate Using ethyl 3-(1,4-dimethyl-1H-benzotriazol-5-yl)-3-[7-(hydroxymethyl)-2,3-dihydro-1H-inden-5-yl]propanoate (130 mg) of Example 3(3e) and 2',3'-dihydrospiro[oxetane-3,4'-pyrido[2,3-b][1,4,5]oxathiazepine]1',1'-dioxide (US-A-2020/0055874) (85 mg), the title compound (191 mg, yield: 94%) was obtained as a solid in the same manner as in Example 29(29a).

36b 3-(1,4-Dimethyl-1H-benzotriazol-5-yl)-3-{7-[(1',1'-dioxido-spiro[oxetane-3,4'-pyrido[2,3-b][1,4,5]oxathiazepine]-2' (3'H)-yl)methyl]-2,3-dihydro-1H-inden-5-yl}propanoic acid Using ethyl 3-(1,4-dimethyl-1H-benzotriazol-5-yl)-3-{7-[(1',1'-dioxido-spiro[oxetane-3,4'-pyrido[2,3-b][1,4,5]oxathiazepine]-2'(3'H)-yl)methyl]-2,3-dihydro-1H-inden-5-yl}propanoate (191 mg) of Example 36(36a), the title compound (92 mg, yield: 50%) was obtained as a solid in the same manner as in Example 33(33b).

Example 37

(3R)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid

37a

Ethyl 3-(7-cyclopropyl-1,4-dimethyl-1H-benzotriazol-5-yl)-3-[7-(hydroxymethyl)-1-benzothiophen-5-yl]propanoate Bis(norbornadiene)rhodium(I) tetrafluoroborate (50.1 mg) and (2S,3S)-bis(diphenylphosphino)butane (57.2 mg) were dissolved in a mixed solvent of 1,4-dioxane (22 mL) and water (5.5 mL) under a nitrogen atmosphere, and the mixture was stirred at room temperature for 15 min. Then, ethyl (2E)-3-(7-cyclopropyl-1,4-dimethyl-1H-benzotriazol-5-yl)prop-2-enoate (765 mg) of Example 49(49a) and [5-(4,4,5,5-tetramethyl-1,3,2-dioxaborolan-2-yl)-1-benzothiophen-7-yl]methanol (1.05 g) of Example 1(1h), and 1M aqueous potassium hydroxide solution (2.68 mL) were added thereto, and the mixture was stirred under heating at 50° C. for 4.5 hr. The reaction mixture was allowed to cool to room temperature, 2M hydrochloric acid (1 mL) and saturated brine were added, and the mixture was extracted with ethyl acetate. The organic layer was dried over anhydrous sodium sulfate. After filtration, the filtrate was concentrated under reduced pressure, and the obtained residue was purified by silica gel chromatography [elution solvent: n-hexane/ethyl acetate=70/30-40/60(V/V)] to give the title compound (807 mg, yield: 59%) (oil) as a mixture of both enantiomers.

37b

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate Using ethyl 3-(7-cyclopropyl-1,4-dimethyl-1H-benzotriazol-5-yl)-3-[7-(hydroxymethyl)-1-benzothiophen-5-yl]propanoate (538 mg) of Example 37(37a) and (4R)-8-chloro-4-ethyl-3,4-dihydro-2H-pyrido[2,3-b][1,4,5]oxathiazepine 1,1-dioxide (263 mg) of Example 1(1c), the title compound (725 mg, yield: 99%) containing diastereomer was obtained as an amorphous in the same manner as in Example 4(4c).

37c

Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate

37d

Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate (724 mg) of Example 37(37b) was subjected to chiral HPLC [column: CHIRALPAK IG (20 mm I.D.×250 mm), mobile phase: n-hexane/ethanol=20/80(V/V), temperature: 40° C.] to obtain 413 mg of ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate as the first peak (yield: 57%).

Similarly, 55.1 mg of ethyl(3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate was obtained as the second peak (yield: 7.6%).

Analysis HPLC conditions [column: CHIRALPAK IG (4.6 mm I.D.×250 mm), mobile phase: n-hexane/ethanol=20/80(V/V), flow rate: 1.0 mL/min, temperature: 40° C., wavelength: 210 nm]; retention time: 26.540 min (the first peak), 37.953 min (the second peak)

37e (3R)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid Using ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate (193 mg) of Example 37(37c), the title compound (141 mg, yield: 76%) was obtained as a solid in the same manner as in Example 3(3g).

Example 38

(3S)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)-2,2-dimethylpropanoic acid

38a

Ethyl (3S)-3-(1,4-dimethyl-1H-benzotriazol-5-yl)-3-(7-{[(4-methoxybenzyl)oxy]methyl}-2,3-dihydro-1H-inden-5-yl)propanoate To a mixture of ethyl (3S)-3-(1,4-dimethyl-1H-benzotriazol-5-yl)-3-[7-(hydroxymethyl)-2,3-dihydro-1H-inden-5-yl]propanoate (930 mg) of Example 4(4a), 2,4,6-tris(p-methoxybenzyloxy)-1,3,5-triazine (1.43 g) and (S)-(+)-camphor-10-sulfonic acid (88.6 mg) was added 1,2-dichloroethane (15.8 mL), and the mixture was stirred at 80° C. for 8 hr. To the reaction mixture were added saturated aqueous sodium hydrogen carbonate solution and water, and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=70/30-40/60(V/V)] to give the title compound (1.02 g, yield: 75%) as an oil.

38b 2-(Trimethylsilyl)ethyl (3S)-3-(1,4-dimethyl-1H-benzotriazol-5-yl)-3-(7-{[(4-methoxybenzyl)oxy]methyl}-2,3-dihydro-1H-inden-5-yl)propanoate To a mixture of ethyl (3S)-3-(1,4-dimethyl-1H-benzotriazol-5-yl)-3-(7-{[(4-methoxybenzyl)oxy]methyl}-2,3-dihydro-1H-inden-5-yl)propanoate (652 mg) of Example 38(38a), tetrahydrofuran (2.0 mL), and ethanol (2.0 mL) was added 1 M aqueous sodium hydroxide solution (2.00 mL) and the mixture was stirred at 60° C. for 3.5 hr. To the reaction mixture was added 5M hydrochloric acid (0.762 mL), and the mixture was stirred and extracted with ethyl acetate. The organic layer was washed with saturated brine and dried over anhydrous sodium sulfate. After filtration, the filtrate was concentrated under reduced pressure. To the obtained residue were successively added N,N-dimethylformamide (6.3 mL), 2-(trimethylsilyl) ethanol (0.364 mL), N,N-diisopropylethylamine (0.500 mL), and 1-[bis(dimethylamino)methylene]-1H-1,2,3-triazolo[4,5-b]pyridinium 3-oxide hexafluorophosphate (965 mg), and the mixture was stirred at room temperature for 2 hr. To the reaction mixture was added 4-dimethylaminopyridine (31.0 mg), and the mixture was stirred at room temperature for 2 hr. Subsequently, 4-dimethylaminopyridine (31.0 mg) was added to the reaction mixture, and the mixture was stirred at room temperature for 1 hr and left standing overnight. To the reaction mixture was added water, and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent: n-hexane/ethyl acetate=80/20-40/60(V/V)] to give the title compound (587 mg, yield: 79%) as an oil.

38c 2-(Trimethylsilyl)ethyl (3S)-3-(1,4-dimethyl-1H-benzotriazol-5-yl)-3-(7-{[(4-methoxybenzyl)oxy]methyl}-2,3-dihydro-1H-inden-5-yl)-2-methylpropanoate To a mixture of 2-(trimethylsilyl)ethyl (3S)-3-(1,4-dimethyl-1H-benzotriazol-5-yl)-3-(7-{[(4-methoxybenzyl)oxy]methyl}-2,3-dihydro-1H-inden-5-yl)propanoate (315 mg) of Example 38(38b) and tetrahydrofuran (3.0 mL) was added sodium bis(trimethylsilyl)amide (about 1.0 M tetrahydrofuran solution) (4.13 mL), and the mixture was stirred at 0° C. for 15 min. To the reaction mixture was added methyl iodide (0.100 mL), and the reaction mixture was stirred at room temperature for 1 hr. To the reaction mixture were successively added saturated aqueous ammonium chloride solution and saturated aqueous sodium hydrogen carbonate solution, and the mixture was stirred and extracted with ethyl acetate. The organic layer was dried over anhydrous sodium sulfate. After filtration, the filtrate was concentrated under reduced pressure and the obtained residue was purified by silica gel column chromatography [elution solvent: n-hexane/ethyl acetate=60/40-40/60(V/V)] to give the title compound (311 mg, yield: 96%) as an amorphous.

38d 2-(Trimethylsilyl)ethyl (3S)-3-(1,4-dimethyl-1H-benzotriazol-5-yl)-3-(7-{[(4-methoxybenzyl)oxy]methyl}-2,3-dihydro-1H-inden-5-yl)-2,2-dimethylpropanoate To 2-(trimethylsilyl)ethyl (3S)-3-(1,4-dimethyl-1H-benzotriazol-5-yl)-3-(7-{[(4-methoxybenzyl)oxy]methyl}-2,3-dihydro-1H-inden-5-yl)-2-methylpropanoate (310 mg) of Example 38(38c) was added sodium bis(trimethylsilyl)amide (about 1.0 M tetrahydrofuran solution) (4.13 mL) at 0° C., and the mixture was warmed to room temperature and stirred for 30 min. The reaction mixture was cooled to 0° C. and methyl iodide (0.321 mL) was added dropwise. The reaction mixture was warmed to room temperature and stirred for 50 min. The reaction mixture was cooled to 0° C., saturated aqueous ammonium chloride solution was added. After stirring, the mixture was warmed to room temperature and extracted with ethyl acetate. The solvent was evaporated under reduced pressure and the obtained residue was purified by silica gel column chromatography [elution solvent: n-hexane/ethyl acetate=80/20-50/50(V/V)] and further by NH silica gel column chromatography [elution solvent:n-hexane/ethyl acetate=70/30-20/80(V/V)] to give the title compound (172 mg, yield: 48%) as an oil.

38e 2-(Trimethylsilyl)ethyl (3S)-3-(1,4-dimethyl-1H-benzotriazol-5-yl)-3-[7-(hydroxymethyl)-2,3-dihydro-1H-inden-5-yl]-2,2-dimethylpropanoate To a mixture of 2-(trimethylsilyl)ethyl (3S)-3-(1,4-dimethyl-1H-benzotriazol-5-yl)-3-(7-{[(4-methoxybenzyl)oxy]methyl}-2,3-dihydro-1H-inden-5-yl)-2,2-dimethylpropanoate (172 mg) of Example 38(38d), dichloromethane (4.0 mL) and distilled water (0.40 mL) was added 2,3-dichloro- 5,6-dicyano-1,4-benzoquinone (40.0 mg), and the mixture was stirred at 0° C. for 1 hr. The reaction mixture was warmed to room temperature, saturated aqueous sodium hydrogen carbonate solution and water were added and the mixture was stirred and extracted with dichloromethane. The solvent was evaporated under reduced pressure and the obtained residue was purified by silica gel column chromatography [elution solvent:n-hexane/ethyl acetate=80/20-40/60(V/V)] to give the title compound (60.4 mg, yield: 49%) as an oil.

38f 2-(Trimethylsilyl)ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)-2,2-dimethylpropanoate To a mixture of 2-(trimethylsilyl)ethyl (3S)-3-(1,4-dimethyl-1H-benzotriazol-5-yl)-3-[7-(hydroxymethyl)-2,3-dihydro-1H-inden-5-yl]-2,2-dimethylpropanoate (60.4 mg) of Example 38 (38e) and (4R)-8-chloro-4-ethyl-3,4-dihydro-2H-pyrido[2,3-b][1,4,5]oxathiazepine 1,1-dioxide (35.4 mg) of Example 1(1c) were successively added, under a nitrogen atmosphere, di-tert-butyl azodicarboxylate (40.0 mg), tetrahydrofuran (2.45 mL), and tri-n-butylphosphine (0.0488 mL), and the mixture was stirred at room temperature for 3 hr. To the reaction mixture were successively added di-tert-butyl azodicarboxylate (12.9 mg) and tri-n-butylphosphine (0.0250 mL), and the mixture was stirred at room temperature for 1 hr, and left standing overnight. The reaction mixture was concentrated under reduced pressure and the obtained residue was purified by silica gel column chromatography [elution solvent:n-hexane/ethyl acetate=80/20-50/50(V/V)] and further by NH silica gel column chromatography [elution solvent:n-hexane/ethyl acetate=80/20-60/40(V/V)] to give the title compound (66.5 mg, yield: 74%) as an amorphous.

38g (3S)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)-2,2-dimethylpropanoic acid To a mixture of 2-(trimethylsilyl)ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4-dimethyl-1H-benzotriazol-5-yl)-2,2-dimethylpropanoate (66.5 mg) of Example 38(38f) and N,N-dimethylformamide (0.90 mL) was added tetrabutylammonium fluoride (1 M tetrahydrofuran solution) (0.0512 mL), and the mixture was stirred at room temperature for 1 hr, and at 40° C. for 1 hr. To the reaction mixture was added tetrabutylammonium fluoride (1 M tetrahydrofuran solution) (0.0512 mL) and the mixture was stirred at 40° C. for 1.5 hr. The reaction mixture was cooled to room temperature, 1M aqueous citric acid solution was added and stirred, and the mixture was extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent: chloroform/methanol=100/0-90/10(V/V)], and further slurry purified with ethyl acetate/n-hexane mixed solvent to give the title compound (48.7 mg, yield: 85%) as a solid.

Example 39

(3R)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoic acid 39a Ethyl 3-(7-cyclopropyl-1,4-dimethyl-1H-benzotriazol-5-yl)-3-[7-(hydroxymethyl)-2,3-dihydro-1H-inden-5-yl]propanoate To a mixture of bis(norbornadiene)rhodium(I) tetrafluoroborate (34.1 mg) and (2S,3S)-bis(diphenylphosphino)butane (38.9 mg) were added, under a nitrogen atmosphere, 1,4-dioxane (5.00 mL) and 1M aqueous potassium hydroxide solution (1.82 mL), and the mixture was stirred at room temperature for 15 min to prepare a catalyst solution. Then, a mixture of ethyl (2E)-3-(7-cyclopropyl-1,4-dimethyl-1H-benzotriazol-5-yl)prop-2-enoate (520 mg) of Example 49 (49a), [6-(4,4,5,5-tetramethyl-1,3,2-dioxaborolan-2-yl)-2,3-dihydro-1H-inden-4-yl]methanol (794 mg) of Example 3(3d), 1,4-dioxane (10.0 mL) and water (3.6 mL) was prepared in a separate container and stirred at 50° C. for 3 min under a nitrogen atmosphere, and the catalyst solution prepared above was added thereto. The reaction mixture was heated and stirred at 50° C. for 2 hr under a nitrogen atmosphere, [6-(4,4,5,5-tetramethyl-1,3,2-dioxaborolan-2-yl)-2,3-dihydro-1H-inden-4-yl]methanol (250 mg) of Example 3(3d) was added, and the mixture was heated and stirred at 50° C. for 2 hr. The reaction mixture was allowed to cool to room temperature, 2M hydrochloric acid (0.9 mL), saturated brine and water were added, and the mixture was extracted with ethyl acetate. The organic layer was washed with saturated brine and dried over anhydrous sodium sulfate. After filtration, the filtrate was concentrated under reduced pressure, and the obtained residue was purified by silica gel chromatography [eluent:n-hexane/ethyl acetate=70/30-30/70(V/V)] to give the title compound (653 mg, yield: 83%) (amorphous) as a mixture of both enantiomers.

39b

Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoate 39c Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoate Using ethyl 3-(7-cyclopropyl-1,4-dimethyl-1H-benzotriazol-5-yl)-3-[7-(hydroxymethyl)-2,3-dihydro-1H-inden-5-yl]propanoate (538 mg) of Example 39(39a) and (4R)-8-chloro-4-ethyl-3,4-dihydro-2H-pyrido[2,3-b][1,4,5]

oxathiazepine 1,1-dioxide (263 mg) of Example 1(1c), 725 mg of a diastereomer mixture was obtained in the same manner as in Example 4(4c). 714 mg of the obtained mixture was subjected to chiral HPLC [column: CHIRAL ART amylose SA (20 mm I.D.×250 mm), mobile phase: n-hexane/ethanol=75/25(V/V), temperature: 40° C.] to obtain 286 mg of ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-TH-benzotriazol-5-yl)propanoate as the second peak (yield: 43%).

Similarly, 100 mg of ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoate was obtained as the first peak (yield: 15%).

Analysis HPLC conditions [column: CHIRAL ART amylose-SA (4.6 mm I.D.×250 mm), mobile phase: n-hexane/ethanol=75/25(V/V), flow rate: 1.0 mL/min, temperature: 40° C., wavelength: 254 nm]; retention time: 6.703 min (the first peak), 7.563 min (the second peak)

39d (3R)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoic acid Using ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoate (286 mg) of Example 39(39b), the title compound (59.7 mg, yield: 22%) was obtained as a solid in the same manner as in Example 3(3g).

Example 40

(3S)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoic acid Using ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(7-cyclopropyl-1,4-dimethyl-1H-benzotriazol-5-yl)propanoate (100 mg) of Example 39(39c), the title compound (69.0 mg, yield: 72%) was obtained as a solid in the same manner as in Example 3(3g).

Example 41

(3S)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid To a mixture of ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate (55.1 mg) of Example 37(37d), ethanol (1.5 mL), and tetrahydrofuran (1.5 mL) was added 1M aqueous sodium hydroxide solution (1.5 mL), and the mixture was stirred at 50° C. for 1 hr. The reaction mixture was cooled to room temperature, 2M hydrochloric acid (1.05 mL) was added and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:chloroform/methanol=100/0-90/10(V/V)], and further slurry purified with an ethyl acetate/n-hexane mixed solvent to give the title compound (36.8 mg, yield: 70%) as a solid.

Example 42

(3R)-3-{7-[(8'-Chloro-1',1'-dioxido-spiro[cyclopropane-1,4'-pyrido[2,3-b][1,4,5]oxathiazepine]-2'(3'H)-yl)methyl]-2,3-dihydro-1H-inden-5-yl}-3-(1,4-dimethyl-1H-benzotriazol-5-yl)propanoic acid 42a Ethyl (3R)-3-{7-[(8'-chloro-1',1'-dioxido-spiro[cyclopropane-1,4'-pyrido[2,3-b][1,4,5]oxathiazepine]-2'(3'H)-yl)methyl]-2,3-dihydro-1H-inden-5-yl}-3-(1,4-dimethyl-1H-benzotriazol-5-yl)propanoate Using ethyl (3R)-3-(1,4-dimethyl-1H-benzotriazol-5-yl)-3-[7-(hydroxymethyl)-2,3-dihydro-1H-inden-5-yl]propanoate (147 mg) of Example 4(4b) and 8'-chloro-2',3'-dihydrospiro[cyclopropane-1,4'-pyrido[2,3-b][1,4,5]oxathiazepine]1',1'-dioxide (US-A-2020/0055874) (97.3 mg), the title compound (231 mg, yield: 97%) was obtained as an amorphous in the same manner as in Example 4(4c).

42b (3R)-3-{7-[(8'-Chloro-1',1'-dioxido-spiro[cyclopropane-1,4'-pyrido[2,3-b][1,4,5]oxathiazepine]-2'(3'H)-yl)methyl]-2,3-dihydro-1H-inden-5-yl}-3-(1,4-dimethyl-1H-benzotriazol-5-yl)propanoic acid Using ethyl (3R)-3-{7-[(8'-chloro-1',1'-dioxido-spiro[cyclopropane-1,4'-pyrido[2,3-b][1,4,5]oxathiazepine]-2'(3'H)-yl)methyl]-2,3-dihydro-1H-inden-5-yl}-3-(1,4-dimethyl-1H-benzotriazol-5-yl)propanoate (231 mg) of Example 42(42a), the title compound (184 mg, yield: 83%) was obtained as a solid in the same manner as in Example 41.

Example 43

(3S)-3-{7-[(8'-Chloro-1',1'-dioxido-spiro[cyclopropane-1,4'-pyrido[2,3-b][1,4,5]oxathiazepine]-2'(3'H)-yl)methyl]-2,3-dihydro-1H-inden-5-yl}-3-(1,4-dimethyl-1H-benzotriazol-5-yl)propanoic acid 43a Ethyl (3S)-3-{7-[(8'-chloro-1',1'-dioxido-spiro[cyclopropane-1,4'-pyrido[2,3-b][1,4,5]oxathiazepine]-2'(3'H)-yl)methyl]-2,3-dihydro-1H-inden-5-yl}-3-(1,4-dimethyl-1H-benzotriazol-5-yl)propanoate Using ethyl (3S)-3-(1,4-dimethyl-1H-benzotriazol-5-yl)-3-[7-(hydroxymethyl)-2,3-dihydro-1H-inden-5-yl]propanoate (136 mg) of Example 4(4a) and 8'-chloro-2',3'-dihydrospiro[cyclopropane-1,4'-pyrido[2,3-b][1,4,5]

oxathiazepine]1',1'-dioxide (US-A-2020/0055874) (86.5 mg), the title compound (226 mg, yield: quantitative) was obtained as an oil in the same manner as in Example 4(4c).

43b (3S)-3-{7-[(8'-Chloro-1',1'-dioxido-spiro[cyclopropane-1,4'-pyrido[2,3-b][1,4,5]oxathiazepine]-2'(3'H)-yl)methyl]-2,3-dihydro-1H-inden-5-yl}-3-(1,4-dimethyl-1H-benzotriazol-5-yl)propanoic acid Using ethyl (3S)-3-{7-[(8'-chloro-1',1'-dioxido-spiro[cyclopropane-1,4'-pyrido[2,3-b][1,4,5]oxathiazepine]-2'(3'H)-yl)methyl]-2,3-dihydro-1H-inden-5-yl}-3-(1,4-dimethyl-1H-benzotriazol-5-yl)propanoate (226 mg) of Example 43(43a), the title compound (182 mg, yield: 84%) was obtained as a solid in the same manner as in Example 41.

Example 44

(3R)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4,7-trimethyl-1H-benzotriazol-5-yl)propanoic acid 44a Ethyl 3-[7-(hydroxymethyl)-2,3-dihydro-1H-inden-5-yl]-3-(1,4,7-trimethyl-1H-benzotriazol-5-yl)propanoate Bis(norbornadiene)rhodium(I) tetrafluoroborate (35.8 mg), (2S,3S)-bis(diphenylphosphino)butane (41.1 mg) were dissolved under a nitrogen atmosphere in a mixed solvent of 1,4-dioxane (16 mL) and water (4.0 mL), and the mixture was stirred at room temperature for 15 min. Then, ethyl (2E)-3-(1,4,7-trimethyl-1H-benzotriazol-5-yl)prop-2-enoate (500 mg) of Example 67(67d), [6-(4,4,5,5-tetramethyl-1,3,2-dioxaborolan-2-yl)-2,3-dihydro-1H-inden-4-yl]methanol (792 mg) of Example 3(3d), and 1M aqueous potassium hydroxide solution (1.92 mL) were added thereto, and the mixture was stirred under heating at 40° C. for 2 hr and at 50° C. for 2.5 hr. The reaction mixture was allowed to cool to room temperature, 2M hydrochloric acid (1 mL) and saturated brine were added, and the mixture was extracted with ethyl acetate. The organic layer was dried over anhydrous sodium sulfate. After filtration, the filtrate was concentrated under reduced pressure, and the obtained residue was purified by silica gel chromatography [elution solvent: n-hexane/ethyl acetate=70/30-20/80(V/V)] to give the title compound (807 mg, yield: 90%) (oil) as a mixture of both enantiomers.

44b

Ethyl (3R)-3-[7-(hydroxymethyl)-2,3-dihydro-1H-inden-5-yl]-3-(1,4,7-trimethyl-1H-benzotriazol-5-yl)propanoate 44c Ethyl (3S)-3-[7-(hydroxymethyl)-2,3-dihydro-1H-inden-5-yl]-3-(1,4,7-trimethyl-1H-benzotriazol-5-yl)propanoate Ethyl 3-[7-(hydroxymethyl)-2,3-dihydro-1H-inden-5-yl]-3-(1,4,7-trimethyl-1H-benzotriazol-5-yl)propanoate (590 mg) of Example 44(44a) was subjected to chiral HPLC [column: CHIRALPAK IG (20 mm I.D.×250 mm), mobile phase: n-hexane/ethanol=65/35(V/V), temperature: 40° C.] to obtain 427 mg of ethyl (3R)-3-[7-(hydroxymethyl)-2,3-dihydro-1H-inden-5-yl]-3-(1,4,7-trimethyl-1H-benzotriazol-5-yl)propanoate was obtained as the second peak (yield: 72%).

Similarly, 128 mg of ethyl (3S)-3-[7-(hydroxymethyl)-2,3-dihydro-1H-inden-5-yl]-3-(1,4,7-trimethyl-1H-benzotriazol-5-yl)propanoate was obtained as the first peak (yield: 22%). Analysis HPLC conditions [column: CHIRALPAK IG (4.6 mm I.D.×250 mm), mobile phase: n-hexane/ethanol=60/40(V/V), flow rate: 1.0 mL/min, temperature: 40° C., wavelength: 254 nm]; retention time: 7.683 min (the first peak), 10.510 min (the second peak)

44d

Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4,7-trimethyl-1H-benzotriazol-5-yl)propanoate Using ethyl (3R)-3-[7-(hydroxymethyl)-2,3-dihydro-1H-inden-5-yl]-3-(1,4,7-trimethyl-1H-benzotriazol-5-yl)propanoate (136 mg) of Example 44(44b) and (4R)-8-chloro-4-ethyl-3,4-dihydro-2H-pyrido[2,3-b][1,4,5]oxathiazepine 1,1-dioxide (83.2 mg) of Example 1(1c), a mixture containing the title compound (277 mg, yield: 64%) was obtained as a solid in the same manner as in Example 4(4c).

44e (3R)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4,7-trimethyl-1H-benzotriazol-5-yl)propanoic acid Using ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-(1,4,7-trimethyl-1H-benzotriazol-5-yl)propanoate (277 mg) of Example 44(44d), the title compound (88.1 mg, yield: 51%) was obtained as a solid in the same manner as in Example 41.

Example 45

(3R)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoic acid 45a Ethyl 3-[1,4-dimethyl-7-(trifluoromethoxy)-1H-benzotriazol-5-yl]-3-[7-(hydroxymethyl)-1-benzothiophen-5-yl]propanoate Bis(norbornadiene)rhodium(I) tetrafluoroborate (20.0 mg), and (2S,3S)-bis(diphenylphosphino)butane (22.4 mg) were dissolved in a mixed solvent of 1,4-dioxane (8.7 mL) and water (2.1 mL) under a nitrogen atmosphere, and the mixture was stirred at room temperature for 15 min. Then, ethyl (2E)-3-[1,4-dimethyl-7-(trifluoromethoxy)-1H-benzotriazol-5-yl]prop-2-enoate (350 mg) of Example 54(54f), [5-(4,4,5,5-tetramethyl-1,3,2-dioxaborolan-2-yl)-1-benzothiophen-7-yl]methanol (462 mg) of Example 1(1h), and 1M aqueous potassium hydroxide solution (1.05 mL) were added thereto, and the mixture was stirred under heating at 50° C. for 2 hr, and at 60° C. for 1 hr. To the reaction mixture were added bis(norbornadiene)rhodium(I) tetrafluoroborate (44.0 mg), and (2S,3S)-bis(diphenylphosphino)butane (40.0 mg) and the mixture was stirred at 60° C. for 2 hr. The reaction mixture was allowed to cool to room temperature, 2M hydrochloric acid (1 mL) and saturated brine were added, and the mixture was extracted with ethyl acetate. The organic layer was dried over anhydrous sodium sulfate. After filtration, the filtrate was concentrated under reduced pressure, and the obtained residue was purified by silica gel chromatography [eluent:n-hexane/ethyl acetate=70/30-40/60(V/V)] to give the title compound (396 mg, yield: 66%) (amorphous) as a mixture of both enantiomers.

45b

Ethyl (3R)-3-[1,4-dimethyl-7-(trifluoromethoxy)-1H-benzotriazol-5-yl]-3-[7-(hydroxymethyl)-1-benzothiophen-5-yl]propanoate 45c Ethyl (3S)-3-[1,4-dimethyl-7-(trifluoromethoxy)-1H-benzotriazol-5-yl]-3-[7-(hydroxymethyl)-1-benzothiophen-5-yl]propanoate Ethyl 3-[1,4-dimethyl-7-(trifluoromethoxy)-1H-benzotriazol-5-yl]-3-[7-(hydroxymethyl)-1-benzothiophen-5-yl]propanoate (396 mg) of Example 45(45a) was repeatedly subjected to chiral HPLC [column: CHIRALCEL OZ—H (20 mm I.D.×250 mm), mobile phase: n-hexane/ethanol=80/20(V/V), temperature: 40° C.] to give 190 mg of ethyl (3R)-3-[1,4-dimethyl-7-(trifluoromethoxy)-1H-benzotriazol-5-yl]-3-[7-(hydroxymethyl)-1-benzothiophen-5-yl]propanoate as the second peak (yield: 48%).

Similarly, 46.3 mg of ethyl (3S)-3-[1,4-dimethyl-7-(trifluoromethoxy)-1H-benzotriazol-5-yl]-3-[7-(hydroxymethyl)-1-benzothiophen-5-yl]propanoate was obtained as the first peak (yield: 12%).

Analysis HPLC conditions [column: CHIRALCEL OZ—H (4.6 mm I.D.×250 mm), mobile phase: n-hexane/ethanol=80/20(V/V), flow rate: 1.0 mL/min, temperature: 40° C., wavelength: 254 nm]; retention time: 7.677 min (the first peak), 9.333 min (the second peak)

45d

Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoate Using ethyl (3R)-3-[1,4-dimethyl-7-(trifluoromethoxy)-1H-benzotriazol-5-yl]-3-[7-(hydroxymethyl)-1-benzothiophen-5-yl]propanoate (189 mg) of Example 45(45b) and (4R)-8-chloro-4-ethyl-3,4-dihydro-2H-pyrido[2,3-b][1,4,5]oxathiazepine 1,1-dioxide (95.6 mg) of Example 1(1c), a mixture containing the title compound (277 mg, yield: 73%) was obtained as an amorphous in the same manner as in Example 4(4c).

45e (3R)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoic acid Using ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoate (277 mg) of Example 45(45d), the title compound (143 mg, yield: 72%) was obtained as a solid in the same manner as in Example 41.

Example 46

(3S)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoic acid 46a Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoate Using ethyl (3S)-3-[1,4-dimethyl-7-(trifluoromethoxy)-1H-benzotriazol-5-yl]-3-[7-(hydroxymethyl)-1-benzothiophen-5-yl]propanoate (46.3 mg) of Example 45(45c) and (4R)-8-chloro-4-ethyl-3,4-dihydro-2H-pyrido[2,3-b][1,4,5]oxathiazepine 1,1-dioxide (27.1 mg) of Example 1(1c), a mixture containing the title compound (66.5 mg, yield: 65%) was obtained as an amorphous in the same manner as in Example 4(4c).

46b (3S)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoic acid Using ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoate (66.5 mg) of Example 46(46a), the title compound (22.0 mg, yield: 51%) was obtained as a solid in the same manner as in Example 41.

Example 47

(3R)-3-(1,4-Dimethyl-1H-benzotriazol-5-yl)-3-(7-{[(4R)-4-ethyl-8-methyl-1,1-dioxido-3,4-dihydro-2H-pyrido[2,3-b][1,4,5]oxathiazepin-2-yl]methyl}-2,3-dihydro-1H-inden-5-yl)propanoic acid

47a

Ethyl (3R)-3-(1,4-dimethyl-1H-benzotriazol-5-yl)-3-(7-{[(4R)-4-ethyl-8-methyl-1,1-dioxido-3,4-dihydro-2H-pyrido[2,3-b][1,4,5]oxathiazepin-2-yl]methyl}-2,3-dihydro-1H-inden-5-yl)propanoate Using ethyl (3R)-3-(1,4-dimethyl-1H-benzotriazol-5-yl)-3-[7-(hydroxymethyl)-2,3-dihydro-1H-inden-5-yl]propanoate (167 mg) of Example 4(4b) and (4R)-4-ethyl-8-methyl-3,4-dihydro-2H-pyrido[2,3-b][1,4,5]oxathiazepine 1,1-dioxide (102 mg) of Example 10(10b), the title compound (247 mg, yield: 94%) was obtained as an oil in the same manner as in Example 4(4c).

47b (3R)-3-(1,4-Dimethyl-1H-benzotriazol-5-yl)-3-(7-{[(4R)-4-ethyl-8-methyl-1,1-dioxido-3,4-dihydro-2H-pyrido[2,3-b][1,4,5]oxathiazepin-2-yl]methyl}-2,3-dihydro-1H-inden-5-yl)propanoic acid Using ethyl (3R)-3-(1,4-dimethyl-1H-benzotriazol-5-yl)-3-(7-{[(4R)-4-ethyl-8-methyl-1,1-dioxido-3,4-dihydro-2H-pyrido[2,3-b][1,4,5]oxathiazepin-2-yl]methyl}-2,3-dihydro-1H-inden-5-yl)propanoate (247 mg) of Example 47(47a), the title compound (177 mg, yield: 75%) was obtained as a solid in the same manner as in Example 41.

Example 48

(3R)-3-(7-{[(4R)-6-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid

48a

Ethyl (3R)-3-(7-{[(4R)-6-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate Using ethyl (3R)-3-(1,4-dimethyl-1H-benzotriazol-5-yl)-3-[7-(hydroxymethyl)-2,3-dihydro-1H-inden-5-yl]propanoate (146 mg) of Example 4(4b) and (4R)-6-chloro-4-ethyl-3,4-dihydro-2H-5,1,2-benzoxathiazepine 1,1-dioxide (92.0 mg) of Example 16(16b), the title compound (245 mg, yield: 95%) was obtained as an oil in the same manner as in Example 4(4c).

48b (3R)-3-(7-{[(4R)-6-Chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoic acid Using ethyl (3R)-3-(7-{[(4R)-6-chloro-4-ethyl-1,1-dioxido-3,4-dihydro-2H-5,1,2-benzoxathiazepin-2-yl]methyl}-2,3-dihydro-1H-inden-5-yl)-3-(1,4-dimethyl-1H-benzotriazol-5-yl)propanoate (245 mg) of Example 48(48a), the title compound (216 mg, yield: quantitative) was obtained as a solid in the same manner as in Example 41.

Example 49

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid

49a

Ethyl (2E)-3-(7-cyclopropyl-1,4-dimethyl-1H-benzotriazol-5-yl)prop-2-enoate

Ethyl (2E)-3-(7-chloro-1,4-dimethyl-1H-benzotriazol-5-yl)prop-2-enoate (27.9 mg) of Example 30(30d), potassium cyclopropyltrifluoroborate (17.7 mg), potassium carbonate (41.4 mg), and XPhos (9.8 mg) were dissolved in a mixed solvent of cyclopentylmethylether (30 mL) and water (0.20 mL), palladium acetate (II) (2.3 mg) was added, and the mixture was stirred under heating under a nitrogen atmosphere at 100° C. for 4 hr. The reaction mixture was allowed to cool to room temperature, saturated aqueous sodium hydrogen carbonate solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent: n-hexane/ethyl acetate=90/10-70/30(V/V)] to give the title compound (28.0 mg, yield: 98%) as a solid.

49b

Ethyl 3-(7-cyclopropyl-1,4-dimethyl-1H-benzotriazol-5-yl)-3-[7-(hydroxymethyl)-1-benzothiophen-5-yl]propanoate Using ethyl (2E)-3-(7-cyclopropyl-1,4-dimethyl-1H-benzotriazol-5-yl)prop-2-enoate (152 mg) of Example 49(49a) and [5-(4,4,5,5-tetramethyl-1,3,2-dioxaborolan-2-yl)-1-benzothiophen-7-yl]methanol (232 mg) of Example 1(1h), the title compound (182 mg, yield: 76%) was obtained as an oil in the same manner as in Example 54(54g).

49c

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate Using ethyl 3-(7-cyclopropyl-1,4-dimethyl-1H-benzotriazol-5-yl)-3-[7-(hydroxymethyl)-1-benzothiophen-5-yl]propanoate (40.0 mg) of Example 49(49b) and (4R)-8-chloro-4-ethyl-3,4-dihydro-2H-pyrido[2,3-b][1,4,5]oxathiazepine 1,1-dioxide (30.4 mg) of Example 1(1c), the title compound (61.0 mg, yield: 99%) was obtained as an oil in the same manner as in Example 54(54h).

49d 3-(7-{[(4R)-8-Chloro-4-ethyl-1,1-dioxido-3,4-di-hydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-cyclopropyl-1,4-dimethyl-1H-benzotriazol-5-yl)propanoate (61.0 mg) of Example 49(49c), the title compound (56.0 mg, yield: 96%) was obtained as a solid in the same manner as in Example 54(54i).

Example 50

3-(7-{[(4R)-8-Chloro-4-ethyl-1,1-dioxido-3,4-di-hydro-2H-pyrido[2,3-b][1,4,5]oxathiazepin-2-yl]methyl}-1-benzothiophen-5-yl)-3-(7-methoxy-1,4-dimethyl-1H-benzotriazol-5-yl)propanoic acid

50a

Ethyl 3-[7-(hydroxymethyl)-1-benzothiophen-5-yl]-3-(7-methoxy-1,4-dimethyl-1H-benzotriazol-5-yl)propanoate Ethyl (2E)-3-(7-methoxy-1,4-dimethyl-1H-benzotriazol-5-yl)prop-2-enoate (WO 2015/092713) (220 mg) was dissolved in a mixed solvent of 1,4-dioxane (4.0 mL) and water (1.3 mL), and the mixture was heated to 90° C. [5-(4,4,5,5-Tetramethyl-1,3,2-dioxaborolan-2-yl)-1-benzothiophen-7-yl]methanol (348 mg) of Example 1(1h), triethylamine (0.499 mL), and chloro(1,5-cyclooctadiene)rhodium(I) dimer (121 mg) were added in three portions every hour, and the mixture was heated and stirred for 2 hr. The reaction mixture was allowed to cool to room temperature, saturated aqueous sodium hydrogen carbonate solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent:n-hexane/ethyl acetate=70/30-40/60(V/V)] to give the title compound (164 mg, yield: 47%) as an oil.

50b

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-methoxy-1,4-dimethyl-1H-benzotriazol-5-yl)propanoate Using ethyl 3-[7-(hydroxymethyl)-1-benzothiophen-5-yl]-3-(7-methoxy-1,4-dimethyl-1H-benzotriazol-5-yl)propanoate (52.0 mg) of Example 50(50a) and (4R)-8-chloro-4-ethyl-3,4-dihydro-2H-pyrido[2,3-b][1,4,5]oxathiazepine 1,1-dioxide (37.3 mg) of Example so 1(1c), the title compound (68.0 mg, yield: 84%) was obtained as a solid in the same manner as in Example 54(54h).

50c 3-(7-{[(4R)-8-Chloro-4-ethyl-1,1-dioxido-3,4-di-hydro-2H-pyrido[2,3-b][1,4,5]oxathiazepin-2-yl]methyl}-1-benzothiophen-5-yl)-3-(7-methoxy-1,4-dimethyl-1H-benzotriazol-5-yl)propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(7-methoxy-1,4-dimethyl-1H-benzotriazol-5-yl)propanoate (68.0 mg) of Example 50(50b), the title compound (47.0 mg, yield: 72%) was obtained as a solid in the same manner as in Example 54(54i).

Example 51

3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoic acid

51a

Ethyl 3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoate Using ethyl 3-(7-chloro-1,4-dimethyl-1H-benzotriazol-5-yl)-3-[7-(hydroxymethyl)-1-benzothiophen-5-yl]propanoate (49.0 mg) of Example 30(30e) and (4R)-8-chloro-4-ethyl-3,4-dihydro-2H-pyrido[2,3-b][1,4,5]oxathiazepine 1,1-dioxide (34.8 mg) of Example 1(1c), the title compound (75.8 mg, yield: quantitative) was obtained as a solid in the same manner as in Example 54(54h).

51b 3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoic acid Using ethyl 3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)propanoate (75.8 mg) of Example 51(51a), the title compound (30.0 mg, yield: 45%) was obtained as a solid in the same manner as in Example 54(54i).

Example 52

3-(7-{[(4R)-8-Chloro-4-ethyl-1,1-dioxido-3,4-di-hydro-2H-pyrido[2,3-b][1,4,5]oxathiazepin-2-yl]methyl}-1-benzothiophen-5-yl)-3-(7-cyano-1,4-dimethyl-1H-benzotriazol-5-yl)propanoic acid

52a

Ethyl (2E)-3-(7-cyano-1,4-dimethyl-1H-benzotriazol-5-yl)prop-2-enoate

Ethyl (2E)-3-(7-chloro-1,4-dimethyl-1H-benzotriazol-5-yl)prop-2-enoate (226 mg) of Example 30(30d), potassium hexacyanoferrate(II) trihydrate (341 mg), potassium acetate (20.4 mg), and tBuXPhos (CAS Registry number: 564483-19-8) (35.4 mg) were dissolved in a mixed solvent of 1,4-dioxane (2.0 mL) and water (2.0 mL), tBuXPhos Pd G1 (CAS Registry number: 1142811-12-8) (2.3 mg) was added, and the mixture was stirred under heating under a nitrogen atmosphere at 90° C. for 8 hr. The reaction mixture was allowed to cool to room temperature, concentration under reduced pressure, saturated aqueous sodium hydrogen carbonate solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent:n-hexane/ethyl acetate=95/5-80/20(V/V)] to give the title compound (92.0 mg, yield: 42%) as a solid.

52b

Ethyl 3-(7-cyano-1,4-dimethyl-1H-benzotriazol-5-yl)-3-[7-(hydroxymethyl)-1-benzothiophen-5-yl] propanoate Using ethyl (2E)-3-(7-cyano-1,4-dimethyl-1H-benzotriazol-5-yl)prop-2-enoate (100 mg) of Example 52(52a) and [5-(4,4,5,5-tetramethyl-1,3,2-dioxaborolan-2-yl)-1-benzothiophen-7-yl]methanol (215 mg) of Example 1(1h), the title compound (109 mg, yield: 68%) was obtained as an oil in the same manner as in Example 50(50a).

52c

Ethyl 3-(7-{[(4R)-8-chloro-4-ethyl-1,1-dioxido-3,4-dihydro-2H-pyrido[2,3-b][1,4,5]oxathiazepin-2-yl] methyl}-1-benzothiophen-5-yl)-3-(7-cyano-1,4-dimethyl-1H-benzotriazol-5-yl)propanoate Using ethyl 3-(7-cyano-1,4-dimethyl-1H-benzotriazol-5-yl)-3-[7-(hydroxymethyl)-1-benzothiophen-5-yl]propanoate (50.0 mg) of Example 52(52b) and (4R)-8-chloro-4-ethyl-3,4-dihydro-2H-pyrido[2,3-b][1,4,5]oxathiazepine 1,1-dioxide (36.3 mg) of Example 1(1c), the title compound (78.0 mg, yield: quantitative) was obtained as a solid in the same manner as in Example 54(54h).

52d 3-(7-{[(4R)-8-Chloro-4-ethyl-1,1-dioxido-3,4-dihydro-2H-pyrido[2,3-b][1,4,5]oxathiazepin-2-yl] methyl}-1-benzothiophen-5-yl)-3-(7-cyano-1,4-dimethyl-1H-benzotriazol-5-yl)propanoic acid Using ethyl 3-(7-{[(4R)-8-chloro-4-ethyl-1,1-dioxido-3,4-dihydro-2H-pyrido[2,3-b][1,4,5]oxathiazepin-2-yl] methyl}-1-benzothiophen-5-yl)-3-(7-cyano-1,4-dimethyl-1H-benzotriazol-5-yl)propanoate (78.0 mg) of Example 52(52c), the title compound (41.0 mg, yield: 55%) was obtained as a solid in the same manner as in Example 54(54i).

Example 53

3-(7-{[(4R)-8-Chloro-4-ethyl-1,1-dioxido-3,4-dihydro-2H-pyrido[2,3-b][1,4,5]oxathiazepin-2-yl] methyl}-1-benzothiophen-5-yl)-3-[1,4-dimethyl-7-(trifluoromethyl)-1H-benzotriazol-5-yl]propanoic acid 53a N-[4-Bromo-5-methyl-2-(trifluoromethyl)phenyl] formamide Acetic anhydride (5.11 mL) and formic acid (5.10 mL) were mixed, stirred under heating at 60° C. for 2 hr, and cooled to room temperature. This mixture was cooled to 0° C., added to a solution of 4-bromo-5-methyl-2-(trifluoromethyl)aniline (WO 2015/180685) (2.29 g) in dichloromethane (45 mL), and the mixture was stirred at room temperature for 6 hr. To the reaction mixture was added saturated aqueous sodium hydrogen carbonate solution, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent: n-hexane/ethyl acetate=95/5-80/20(V/V)] to give the title compound (2.36 g, yield: 93%) as a solid.

53b

N-[4-Bromo-3-methyl-2-nitro-6-(trifluoromethyl) phenyl]formamide

To a mixture of N-[4-bromo-5-methyl-2-(trifluoromethyl) phenyl]formamide (2.79 g) of Example 53(53a) and concentrated sulfuric acid (9.9 mL) was added 69% nitric acid (1.19 mL) at 0° C. and the mixture was stirred at 0° C. for 3 hr. To the reaction mixture was added ice water, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent: n-hexane/ethyl acetate=95/5-80/20(V/V)] to give the title compound (2.70 g, yield: 84%) as a solid.

53c

4-Bromo-N,3-dimethyl-2-nitro-6-(trifluoromethyl) aniline

Using N-[4-bromo-3-methyl-2-nitro-6-(trifluoromethyl) phenyl]formamide (2.70 g) of Example 53(53b), the title compound (1.55 g, yield: 60%) was obtained as a solid in the same manner as in Example 54(54c).

53d

4-Bromo-N$^1$,3-dimethyl-6-(trifluoromethyl)benzene-1,2-diamine

Using 4-bromo-N,3-dimethyl-2-nitro-6-(trifluoromethyl) aniline (1.55 g) of Example 53(53c), the title compound (1.07 g, yield: 76%) was obtained as an oil in the same manner as in Example 54(54d).

53e

5-Bromo-1,4-dimethyl-7-(trifluoromethyl)-1H-benzotriazole

Using 4-bromo-N$^1$,3-dimethyl-6-(trifluoromethyl)benzene-1,2-diamine (1.07 g) of Example 53(53d), the title compound (933 mg, yield: 84%) was obtained as a solid in the same manner as in Example 54(54e).

53f

Ethyl (2E)-3-[1,4-dimethyl-7-(trifluoromethyl)-1H-benzotriazol-5-yl]prop-2-enoate Using 5-bromo-1,4-dimethyl-7-(trifluoromethyl)-1H-benzotriazole (933 mg) of Example 53(53e), the title compound (912 mg, yield: 92%) was obtained as a solid in the same manner as in Example 54(54f).

53g

Ethyl 3-[1,4-dimethyl-7-(trifluoromethyl)-1H-benzotriazol-5-yl]-3-[7-(hydroxymethyl)-1-benzothiophen-5-yl]propanoate Using ethyl (2E)-3-[1,4-dimethyl-7-(trifluoromethyl)-1H-benzotriazol-5-yl]prop-2-enoate (313 mg) of Example 53(53f) and [5-(4,4,5,5-tetramethyl-1,3,2-dioxaborolan-2-yl)-1-benzothiophen-7-yl]methanol (435 mg) of Example 1(1h), the title compound (408 mg, yield: 86%) was obtained as an oil in the same manner as in Example 54(54g).

53h

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethyl)-1H-benzotriazol-5-yl]propanoate Using ethyl 3-[1,4-dimethyl-7-(trifluoromethyl)-1H-benzotriazol-5-yl]-3-[7-(hydroxymethyl)-1-benzothiophen-5-yl]propanoate (47.8 mg) of Example 53(53g) and (4R)-8-chloro-4-ethyl-3,4-dihydro-2H-pyrido[2,3-b][1,4,5]oxathiazepine 1,1-dioxide (31.6 mg) of Example 1(1c), the title compound (67.0 mg, yield: 93%) was obtained as an oil in the same manner as in Example 54(54h).

53i 3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethyl)-1H-benzotriazol-5-yl]propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethyl)-1H-benzotriazol-5-yl]propanoate (67.0 mg) of Example 53(53h), the title compound (54.0 mg, yield: 84%) was obtained as a solid in the same manner as in Example 54(54i).

Example 54

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoic acid

54a

N-[4-Bromo-5-methyl-2-(trifluoromethoxy)phenyl]formamide

Acetic anhydride (2.74 mL) and formic acid (2.73 mL) were mixed, stirred under heating at 60° C. for 2 hr, and cooled to room temperature. This mixture was added to a cooled solution of 4-bromo-5-methyl-2-(trifluoromethoxy)aniline (WO 2015/180685) (2.61 g) in dichloromethane (48 mL) to 0° C., and the mixture was stirred at room temperature for 18 hr. To the reaction mixture was added saturated aqueous sodium hydrogen carbonate solution, and the mixture was extracted with ethyl acetate. The organic layer was washed with saturated brine and dried over anhydrous sodium sulfate. After filtration, the filtrate was concentrated under reduced pressure to give the title compound (crude product 2.73 g, yield: 95%) as a solid.

54b

N-[4-Bromo-3-methyl-2-nitro-6-(trifluoromethoxy)phenyl]formamide

To a mixture of N-[4-bromo-5-methyl-2-(trifluoromethoxy)phenyl]formamide (2.66 g) of Example 54(54a) and concentrated sulfuric acid (8.9 mL) was added 69% nitric acid (1.07 mL) at 0° C., and the mixture was stirred at 0° C. for 2 hr. To the reaction mixture was added ice water, and the mixture was extracted with ethyl acetate. The organic layer was washed with saturated brine and dried over anhydrous sodium sulfate. After filtration, the filtrate was concentrated under reduced pressure to give the title compound (crude product 2.97 g, yield: 97%) as a solid.

54c

4-Bromo-N,3-dimethyl-2-nitro-6-(trifluoromethoxy)aniline

To a solution of N-[4-bromo-3-methyl-2-nitro-6-(trifluoromethoxy)phenyl]formamide (2.48 g) of Example 54(54b) in tetrahydrofuran (36 mL) was added borane-tetrahydrofuran (0.9 M tetrahydrofuran solution) (23.8 mL) at 0° C., and the mixture was stirred at room temperature for 2 hr. The reaction mixture was cooled to 0° C., methanol was added, and the mixture was stirred under heating at 60° C. for 2 hr. The reaction mixture was allowed to cool to room temperature, saturated aqueous sodium hydrogen carbonate solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent:n-hexane/ethyl acetate=100/0-95/5(V/V)] to give the title compound (2.35 g, yield: 99%) as a solid.

54d

4-Bromo-$N^1$,3-dimethyl-6-(trifluoromethoxy)benzene-1,2-diamine

4-Bromo-N,3-dimethyl-2-nitro-6-(trifluoromethoxy)aniline (2.35 g) of Example 54(54c) and iron powder (1.99 g) were mixed with ethanol (14 mL) and water (7.1 mL), ammonium chloride (3.86 g) was added, and the mixture was stirred under heating at 80° C. for 4 hr. The reaction mixture was allowed to cool to room temperature, saturated aqueous sodium hydrogen carbonate solution and celite were added and the mixture was stirred for 4 hr. The mixture was filtered through celite, insoluble matter was removed, and the filtrate was extracted with ethyl acetate. The organic layer was washed with saturated brine and dried over anhydrous sodium sulfate. After filtration, the filtrate was concentrated under reduced pressure, and the obtained residue was purified by silica gel column chromatography

54e

5-Bromo-1,4-dimethyl-7-(trifluoromethoxy)-1H-benzotriazole

42% Tetrafluoroboric acid (1.27 mL) and tert-butyl nitrite (0.755 mL) were dissolved in acetonitrile (8.5 mL) and cooled to 0° C. A solution of 4-bromo-$N^1$,3-dimethyl-6-(trifluoromethoxy)benzene-1,2-diamine (1.27 g) of Example 54(54d) and 42% tetrafluoroboric acid (1.27 mL) in acetonitrile (8.5 mL) was added dropwise thereto over 20 min, and the mixture was stirred at 0° C. for 2 hr and at room temperature for 2 hr. The reaction mixture was neutralized by adding 5 M aqueous sodium hydroxide solution and extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent:n-hexane/ethyl acetate=95/5-10/90(V/V)] to give the title compound (10.9 g, yield: 83%) as a solid.

54f

Ethyl (2E)-3-[1,4-dimethyl-7-(trifluoromethoxy)-1H-benzotriazol-5-yl]prop-2-enoate 5-Bromo-1,4-dimethyl-7-(trifluoromethoxy)-1H-benzotriazole (310 mg) of Example 54(54e), ethyl acrylate (0.326 mL), and triethylamine (0.832 mL) were dissolved in N,N-dimethylformamide (2.0 mL), and bis(tri-tert-butylphosphine)palladium(0) (25.5 mg) was added, followed by heating and stirring at 90° C. for 4 hr under a nitrogen atmosphere. The reaction mixture was allowed to cool to room temperature, saturated aqueous sodium hydrogen carbonate solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent:n-hexane/ethyl acetate=100/0-90/10(V/V)] to give the title compound (313 mg, yield: 95%) as an oil.

54g

Ethyl 3-[1,4-dimethyl-7-(trifluoromethoxy)-1H-benzotriazol-5-yl]-3-[7-(hydroxymethyl)-1-benzothiophen-5-yl]propanoate Bis(norbornadiene)rhodium(I) tetrafluoroborate (35.2 mg), (2S,3S)-bis(diphenylphosphino)butane (20.1 mg), and (2R,3R)-bis(diphenylphosphino)butane (20.1 mg) were dissolved in a mixed solvent of 1,4-dioxane (7.5 mL) and water (1.9 mL), and the mixture was stirred at room temperature for 15 min. Then, ethyl (2E)-3-[1,4-dimethyl-7-(trifluoromethoxy)-1H-benzotriazol-5-yl]prop-2-enoate (310 mg) of Example 54(54f), [5-(4,4,5,5-tetramethyl-1,3,2-dioxaborolan-2-yl)-1-benzothiophen-7-yl]methanol (410 mg) of Example 1(1h), and 1 M aqueous potassium hydroxide solution (0.941 mL) were added thereto, and the mixture was heated and stirred at 50° C. for 4 hr. The reaction mixture was allowed to cool to room temperature, saturated aqueous ammonium chloride solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent: n-hexane/ethyl acetate=90/10-50/50(V/V)] to give the title compound (369 mg, yield: 79%) as an oil.

54h

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoate Ethyl 3-[1,4-dimethyl-7-(trifluoromethoxy)-1H-benzotriazol-5-yl]-3-[7-(hydroxymethyl)-1-benzothiophen-5-yl]propanoate (40.0 mg) of Example 54(54g) and (4R)-8-chloro-4-ethyl-3,4-dihydro-2H-pyrido[2,3-b][1,4,5]oxathiazepine 1,1-dioxide (25.6 mg) of Example 1(1c) were dissolved in toluene (2.0 mL), and triphenylphosphine (42.5 mg) and then di-tert-butyl azodicarboxylate (38.1 mg) were added under a nitrogen atmosphere, and the mixture was heated and stirred at 50° C. for 4 hr. The reaction mixture was allowed to cool to room temperature, and the solvent was evaporated under reduced pressure, and the obtained residue was purified by silica gel column chromatography [elution solvent:n-hexane/ethyl acetate=90/10-70/30(V/V)] to give the title compound (59.0 mg, yield: 99%) as an oil.

54i

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoic acid To a mixture of ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1,4-dimethyl-7-(trifluoromethoxy)-1H-benzotriazol-5-yl]propanoate (59.0 mg) of Example 54(54h), methanol (1.0 mL), and tetrahydrofuran (1.0 mL) was added 1M aqueous sodium hydroxide solution (0.400 mL), and the mixture was stirred at room temperature for 8 hr. To the reaction mixture was added 1M hydrochloric acid (0.400 mL), and the mixture was stirred and concentrated under reduced pressure. Saturated aqueous ammonium chloride solution and saturated brine were added thereto, and the mixture was extracted with chloroform/2-propanol=3/1(V/V). The organic layer was dried over anhydrous sodium sulfate. After filtration, the filtrate was concentrated under reduced pressure and the obtained residue was purified by silica gel column chromatography [elution solvent:n-hexane/ethyl acetate/methanol=30/70/0-0/100/0-0/90/10(V/V/V)]. To the solid were added ethyl acetate and n-hexane, and the mixture was subjected to an ultrasonic treatment. The solid was collected by filtration and vacuum dried to give the title compound (45.0 mg, yield: 79%) as a solid.

Example 55

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid

55a

4-Bromo-2-(difluoromethoxy)-5-methylaniline

N-bromosuccinimide (1.81 g) was added to a solution of 2-(difluoromethoxy)-5-methylaniline (1.73 g) in N,N-dimethylformamide (10 mL) at 0° C., and the mixture was stirred at room temperature for 24 hr. To the reaction mixture was added saturated aqueous sodium hydrogen carbonate solution, and the mixture was extracted with ethyl acetate. The organic layer was washed with 10% aqueous sodium chloride solution, and dried over anhydrous sodium sulfate. After filtration, the filtrate was concentrated under reduced pressure, and the filtrate was concentrated under reduced pressure, and the obtained residue was purified by silica gel column chromatography [elution solvent:n-hexane/ethyl acetate=95/5-80/20(V/V)] to give the title compound (2.30 g, yield: 91%) as an oil.

55b

N-[4-Bromo-2-(difluoromethoxy)-5-methylphenyl]formamide

Using 4-bromo-2-(difluoromethoxy)-5-methylaniline (2.30 g) of Example 55(55a), the title compound (crude product 2.37 g, yield: 93%) was obtained as a solid in the same manner as in Example 54(54a).

55c

N-[4-Bromo-6-(difluoromethoxy)-3-methyl-2-nitrophenyl]formamide

Using N-[4-bromo-2-(difluoromethoxy)-5-methylphenyl]formamide (2.31 g) of Example 55(55b), the title compound (crude product 2.42 g, yield: 97%) was obtained as a solid in the same manner as in Example 54(54b).

55d

4-Bromo-6-(difluoromethoxy)-N,3-dimethyl-2-nitroaniline

Using N-[4-bromo-6-(difluoromethoxy)-3-methyl-2-nitrophenyl]formamide (2.48 g) of Example 55(55c), the title compound (1.76 g, yield: 74%) was obtained as a solid in the same manner as in Example 54(54c).

55e

4-Bromo-6-(difluoromethoxy)-N$^1$,3-dimethylbenzene-1,2-diamine

Using 4-bromo-6-(difluoromethoxy)-N,3-dimethyl-2-nitroaniline (1.76 g) of Example 55(55d), the title compound (980 mg, yield: 62%) was obtained as an oil in the same manner as in Example 54(54d).

55f

5-Bromo-7-(difluoromethoxy)-1,4-dimethyl-1H-benzotriazole

Using 4-bromo-6-(difluoromethoxy)-N$^1$,3-dimethylbenzene-1,2-diamine (980 mg) of Example 55(55e), the title compound (845 mg, yield: 83%) was obtained as a solid in the same manner as in Example 54(54e).

55g

Ethyl (2E)-3-[7-(difluoromethoxy)-1,4-dimethyl-1H-benzotriazol-5-yl]prop-2-enoate Using 5-bromo-7-(difluoromethoxy)-1,4-dimethyl-1H-benzotriazole (292 mg) of Example 55(55f), the title compound (310 mg, yield: quantitative) was obtained as an oil in the same manner as in Example 54(54f).

55h

Ethyl 3-[7-(difluoromethoxy)-1,4-dimethyl-1H-benzotriazol-5-yl]-3-[7-(hydroxymethyl)-1-benzothiophen-5-yl]propanoate Using ethyl (2E)-3-[7-(difluoromethoxy)-1,4-dimethyl-1H-benzotriazol-5-yl]prop-2-enoate (310 mg) of Example 55(55g) and [5-(4,4,5,5-tetramethyl-1,3,2-dioxaborolan-2-yl)-1-benzothiophen-7-yl]methanol (432 mg) of Example 1(1h), the title compound (308 mg, yield: 65%) was obtained as an oil in the same manner as in Example 54(54g).

55i

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoate Using ethyl 3-[7-(difluoromethoxy)-1,4-dimethyl-1H-benzotriazol-5-yl]-3-[7-(hydroxymethyl)-1-benzothiophen-5-yl]propanoate (40.0 mg) of Example 55(55h) and (4R)-8-chloro-4-ethyl-3,4-dihydro-2H-pyrido[2,3-b][1,4,5]oxathiazepine 1,1-dioxide (26.5 mg) of Example 1(1c), the title compound (58.0 mg, yield: 96%) was obtained as an oil in the same manner as in Example 54(54h).

55j 3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoate (58.0 mg) of Example 55(55i), the title compound (49.0 mg, yield: 88%) was obtained as a solid in the same manner as in Example 54(54i).

Example 56

3-(7-{[(4R)-8-Chloro-4-ethyl-1,1-dioxido-3,4-di-hydro-2H-pyrido[2,3-b][1,4,5]oxathiazepin-2-yl]methyl}-1-benzothiophen-5-yl)-3-[1-(2-hydroxy-2-methylpropyl)-4-methyl-1H-benzotriazol-5-yl]propanoic acid

56a

2-Methyl-1-(3-methyl-2-nitroanilino)propan-2-ol

To a solution of 1-fluoro-3-methyl-2-nitrobenzene (1.00 g), potassium carbonate (1.35 g) in ethanol (13 mL) was added 1-amino-2-methyl-2-propanol (1.83 mL), and the mixture was stirred at 70° C. for 24 hr. The reaction mixture was allowed to cool to room temperature and concentrated under reduced pressure. To the residue was added saturated aqueous sodium hydrogen carbonate solution, and the mixture was extracted with ethyl acetate, and the organic layer was dried over anhydrous sodium sulfate. After filtration, the filtrate was concentrated under reduced pressure, and the obtained residue was purified by silica gel chromatography [elution solvent:n-hexane/ethyl acetate=95/5-80/20(V/V)] to give the title compound (750 mg, yield: 52%) as a solid.

56b 1-(4-Bromo-3-methyl-2-nitroanilino)-2-methylpropan-2-ol

To a solution of 2-methyl-1-(3-methyl-2-nitroanilino)propan-2-ol (750 mg) of Example 56(56a) in N,N-dimethylformamide (3.3 mL) was added N-bromosuccinimide (607 mg) at 0° C., and the mixture was stirred at room temperature for 24 hr. To the reaction mixture was added saturated aqueous sodium hydrogen carbonate solution, and the mixture was extracted with ethyl acetate. The organic layer was washed with 10% aqueous sodium chloride solution, and dried over anhydrous sodium sulfate. After filtration, the filtrate was concentrated under reduced pressure, and the obtained residue was purified by silica gel column chromatography [elution solvent:n-hexane/ethyl acetate=95/5-80/20(V/V)] to give the title compound (1.01 g, yield: 100%) as a solid.

56c 1-(2-Amino-4-bromo-3-methylanilino)-2-methylpropan-2-ol

Using 1-(4-bromo-3-methyl-2-nitroanilino)-2-methylpropan-2-(1.01 g) of Example 56(56b), the title compound (810 mg, yield: 89%) was obtained as a solid in the same manner as in Example 54(54d).

56d 1-(5-Bromo-4-methyl-1H-benzotriazol-1-yl)-2-methylpropan-2-ol

Using 1-(2-amino-4-bromo-3-methylanilino)-2-methylpropan-2-ol (810 mg) of Example 56(56c), the title compound (589 mg, yield: 70%) was obtained as a solid in the same manner as in Example 54(54e).

56e

Ethyl (2E)-3-[1-(2-hydroxy-2-methylpropyl)-4-methyl-1H-benzotriazol-5-yl]prop-2-enoate Using 1-(5-bromo-4-methyl-1H-benzotriazol-1-yl)-2-methylpropan-2-ol (284 mg) of Example 56(56d), the title compound (297 mg, yield: 98%) was obtained as a solid in the same manner as in Example 54(54f).

56f

Ethyl 3-[7-(hydroxymethyl)-1-benzothiophen-5-yl]–0.3-[1-(2-hydroxy-2-methylpropyl)-4-methyl-1H-benzotriazol-5-yl]propanoate Using ethyl (2E)-3-[1-(2-hydroxy-2-methylpropyl)-4-methyl-1H-benzotriazol-5-yl]prop-2-enoate (297 mg) of Example 56(56e) and 15 [5-(4,4,5,5-tetramethyl-1,3,2-dioxaborolan-2-yl)-1-benzothiophen-7-yl]methanol (426 mg) of Example 1h, the title compound (148 mg, yield: 32%) was obtained as an oil in the same manner as in Example 50(50a).

56g

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1-(2-hydroxy-2-methylpropyl)-4-methyl-1H-benzotriazol-5-yl]propanoate Using ethyl 3-[7-(hydroxymethyl)-1-benzothiophen-5-yl]-3-[1-(2-hydroxy-2-methylpropyl)-4-methyl-1H-benzotriazol-5-yl]propanoate (46.9 mg) of Example 56(56f) and (4R)-8-chloro-4-ethyl-3,4-dihydro-2H-pyrido[2,3-b][1,4,5]oxathiazepine 1,1-dioxide (28.9 mg) of Example 1c, the title compound (59.0 mg, yield: 83%) was obtained as a solid in the same manner as in Example 54(54h).

56h 3-(7-{[(4R)-8-Chloro-4-ethyl-1,1-dioxido-3,4-di-hydro-2H-pyrido[2,3-b][1,4,5]oxathiazepin-2-yl]methyl}-1-benzothiophen-5-yl)-3-[1-(2-hydroxy-2-methylpropyl)-4-methyl-1H-benzotriazol-5-yl]propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[1-(2-hydroxy-2-methylpropyl)-4-methyl-1H-benzotriazol-5-yl]propanoate (58.0 mg) of Example 56(56g), the title compound (30.2 mg, yield: 53%) was obtained as a solid in the same manner as in Example 54(54i).

Example 57

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-{4-methyl-1-[3-(methylsulfonyl)propyl]-1H-benzotriazol-5-yl}propanoic acid

57a

3-Methyl-N-[3-(methylsulfonyl)propyl]-2-nitroaniline

To a solution of 1-fluoro-3-methyl-2-nitrobenzene (1.00 g), potassium carbonate (2.70 g) in ethanol (13 mL) was added 3-methylsulfonylpropane-1-amine hydrochloride (1.41 g), and the mixture was stirred at 70° C. for 48 hr. The reaction mixture was allowed to cool to room temperature and concentrated under reduced pressure. To the residue was added saturated aqueous sodium hydrogen carbonate solution, and the mixture was extracted with ethyl acetate, and the organic layer was dried over anhydrous sodium sulfate. After filtration, the filtrate was concentrated under reduced pressure, and the obtained residue was purified by silica gel column chromatography [elution solvent:n-hexane/ethyl acetate=70/30-50/50(V/V)] to give the title compound (410 mg, yield: 23%) as a solid.

57b

4-Bromo-3-methyl-N-[3-(methylsulfonyl)propyl]-2-nitroaniline

N-Bromosuccinimide (273 mg) was added to a solution of 3-methyl-N-[3-(methylsulfonyl)propyl]-2-nitroaniline (410 mg) of Example 57(57a) in N,N-dimethylformamide (2.0 mL) at 0° C., and the mixture was stirred at room temperature for 18 hr. Saturated aqueous sodium hydrogen carbonate solution was added and the mixture was extracted with ethyl acetate. The organic layer was washed with 10% aqueous sodium chloride solution and dried over anhydrous sodium sulfate. After filtration, the filtrate was concentrated under reduced pressure, and the obtained residue was purified by silica gel column chromatography [elution solvent: n-hexane/ethyl acetate=70/30-20/80(V/V)] to give the title compound (528 mg, yield: quantitative) as a solid.

57c

4-Bromo-3-methyl-N$^1$-[3-(methylsulfonyl)propyl]benzene-1,2-diamine

Using 4-bromo-3-methyl-N-[3-(methylsulfonyl)propyl]-2-nitroaniline (528 mg) of Example 57(57b), the title compound (404 mg, yield: 84%) was obtained as a solid in the same manner as in Example 54(54d).

57d

5-Bromo-4-methyl-1-[3-(methylsulfonyl)propyl]-1H-benzotriazole

Using 4-bromo-3-methyl-N$^1$-[3-(methylsulfonyl)propyl]benzene-1,2-diamine (404 mg) of Example 57(57c), the title compound (210 mg, yield: 50%) was obtained as a solid in the same manner as in Example 54(54e).

57e

Ethyl (2E)-3-{4-methyl-1-[3-(methylsulfonyl)propyl]-1H-benzotriazol-5-yl}prop-2-enoate Using 5-bromo-4-methyl-1-[3-(methylsulfonyl)propyl]-1H-benzotriazole (210 mg) of Example 57(57d), the title compound (221 mg, yield: quantitative) was obtained as a solid in the same manner as in Example 54(54f).

57f

Ethyl 3-[7-(hydroxymethyl)-1-benzothiophen-5-yl]-3-{4-methyl-1-[3-(methylsulfonyl)propyl]-1H-benzotriazol-5-yl}propanoate Using ethyl (2E)-3-{4-methyl-1-[3-(methylsulfonyl)propyl]-1H-benzotriazol-5-yl}prop-2-enoate (221 mg) of Example 57(57e) and [5-(4,4,5,5-tetramethyl-1,3,2-dioxaborolan-2-yl)-1-benzothiophen-7-yl]methanol (274 mg) of Example 1h, the title compound (106 mg, yield: 33%) was obtained as an oil in the same manner as in Example 50(50a).

57g

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-{4-methyl-1-[3-(methylsulfonyl)propyl]-1H-benzotriazol-5-yl}propanoate Using ethyl 3-[7-(hydroxymethyl)-1-benzothiophen-5-yl]-3-{4-methyl-1-[3-(methylsulfonyl)propyl]-1H-benzotriazol-5-yl}propanoate (53.0 mg) of Example 57(57f) and (4R)-8-chloro-4-ethyl-3,4-dihydro-2H-pyrido[2,3-b][1,4,5]oxathiazepine 1,1-dioxide (32.4 mg) of Example 1(1c), the title compound (78.3 mg, yield: quantitative) was obtained as a solid in the same manner as in Example 54(54h).

57h

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-{4-methyl-1-[3-(methylsulfonyl)propyl]-1H-benzotriazol-5-yl}propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-{4-methyl-1-[3-(methylsulfonyl)propyl]-1H-benzotriazol-5-yl}propanoate (78.3 mg) of Example 57(57g), the title compound (49.0 mg, yield: 65%) was obtained as a solid in the same manner as in Example 54(54i).

Example 58

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-{1-[2-(dimethylamino)ethyl]-4-methyl-1H-benzotriazol-5-yl}propanoic acid

58a

N,N-Dimethyl-N'-(3-methyl-2-nitrophenyl)ethane-1,2-diamine

N,N-Dimethylethylenediamine (3.51 mL) was added to a solution of 1-fluoro-3-methyl-2-nitrobenzene (1.00 g) and potassium carbonate (2.70 g) in ethanol (13 mL), and the mixture was stirred at 70° C. for 24 hr. The reaction mixture was allowed to cool to room temperature and concentrated under reduced pressure. A saturated aqueous sodium hydrogen carbonate solution was added to the residue, and the mixture was extracted with ethyl acetate, and the organic layer was dried over anhydrous sodium sulfate. After filtration, the filtrate was concentrated under reduced pressure, and the obtained residue was purified by NH silica gel column chromatography [elution solvent:n-hexane/ethyl acetate=95/5-80/20(V/V)] to give the title compound (1.30 g, yield: 90%) as an oil.

58b

N'-(4-Bromo-3-methyl-2-nitrophenyl)-N,N-dimethylethane-1,2-diamine

N-Bromosuccinimide (1.04 g) was added to a solution of N,N-dimethyl-N'-(3-methyl-2-nitrophenyl)ethane-1,2-diamine (1.28 g) of Example 58(58a) in N,N-dimethylformamide (5.7 mL) at 0° C., and the mixture was stirred at room temperature for 24 hr. Saturated aqueous sodium hydrogen carbonate solution was added to the reaction mixture, and the mixture was extracted with ethyl acetate. The organic layer was washed with 10% aqueous sodium chloride solution and dried over anhydrous sodium sulfate. After filtration, the filtrate was concentrated under reduced pressure, and the obtained residue was purified by NH silica gel column chromatography [elution solvent:n-hexane/ethyl acetate=90/10-70/30(V/V)] to give the title compound (983 mg, yield: 57%) as a solid.

58c

4-Bromo-N$^1$-[2-(dimethylamino)ethyl]-3-methylbenzene-1,2-diamine

Using N'-(4-bromo-3-methyl-2-nitrophenyl)-N,N-dimethylethane-1,2-diamine (983 mg) of Example 58(58b), the title compound (509 mg, yield: 58%) was obtained as a solid in the same manner as in Example 54(54d).

58d 2-(5-Bromo-4-methyl-1H-benzotriazol-1-yl)-N,N-dimethylethanamine

Using 4-bromo-N$^1$-[2-(dimethylamino)ethyl]-3-methylbenzene-1,2-diamine (506 mg) of Example 58(58c), the title compound (416 mg, yield: 79%) was obtained as an oil in the same manner as in Example 54(54e).

58e

Ethyl (2E)-3-{1-[2-(dimethylamino)ethyl]-4-methyl-1H-benzotriazol-5-yl}prop-2-enoate Using 2-(5-bromo-4-methyl-1H-benzotriazol-1-yl)-N,N-dimethylethanamine (403 mg) of Example 58 (58d), the title compound (329 mg, yield: 77%) was obtained as a solid in the same manner as in Example 54(54f).

58f

Ethyl 3-{1-[2-(dimethylamino)ethyl]-4-methyl-1H-benzotriazol-5-yl}-3-[7-(hydroxymethyl)-1-benzothiophen-5-yl]propanoate Using ethyl (2E)-3-{1-[2-(dimethylamino)ethyl]-4-methyl-1H-benzotriazol-5-yl}prop-2-enoate (151 mg) of Example 58(58e) and [5-(4,4,5,5-tetramethyl-1,3,2-dioxaborolan-2-yl)-1-benzothiophen-7-yl]methanol (290 mg) of Example 1(1h), the title compound (96.0 mg, yield: 41%) was obtained as an oil in the same manner as in Example 50(50a).

58g

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-{1-[2-(dimethylamino)ethyl]-4-methyl-1H-benzotriazol-5-yl}propanoate Using ethyl 3-{1-[2-(dimethylamino)ethyl]-4-methyl-1H-benzotriazol-5-yl}-3-[7-(hydroxymethyl)-1-benzothiophen-5-yl]propanoate (37.0 mg) of Example 58(58f) and (4R)-8-chloro-4-ethyl-3,4-dihydro-2H-pyrido[2,3-b][1,4,5] oxathiazepine 1,1-dioxide (25.0 mg) of Example 1(1c), the title compound (56.4 mg, yield: quantitative) was obtained as a solid in the same manner as in Example 54(54h).

58h 3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-{1-[2-(dimethylamino)ethyl]-4-methyl-1H-benzotriazol-5-yl}propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-{1-[2-(dimethylamino)ethyl]-4-methyl-1H-benzotriazol-5-yl}propanoate (56.4 mg) of Example 58(58g), the title compound (36.0 mg, yield: 66%) was obtained as a solid in the same manner as in Example 54(54i).

Example 59

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(3,7-dimethyl-3H-[1,2,3]triazolo[4,5-b]pyridin-6-yl)propanoic acid 59a Ethyl 3-(3,7-dimethyl-3H-[1,2,3]triazolo[4,5-b]pyridin-6-yl)-3-[7-(hydroxymethyl)-1-benzothiophen-5-yl]propanoate Using ethyl (2E)-3-(3,7-dimethyl-3H-[1,2,3]triazolo[4,5-b]pyridin-6-yl)prop-2-enoate (WO 2015/092713) (2.5 g), and [5-(4,4,5,5-tetramethyl-1,3,2-dioxaborolan-2-yl)-1-benzothiophen-7-yl]methanol (4.4 g) of Example 1(1h), the title compound (2.4 g, yield: 58%) was obtained as a solid in the same manner as in Example 3(3e).

59b

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(3,7-dimethyl-3H-[1,2,3]triazolo[4,5-b]pyridin-6-yl)propanoate Using ethyl 3-(3,7-dimethyl-3H-[1,2,3]triazolo[4,5-b]pyridin-6-yl)-3-[7-(hydroxymethyl)-1-benzothiophen-5-yl]propanoate (41.0 mg) of Example 59(59a) and (4R)-8-chloro-4-ethyl-3,4-dihydro-2H-pyrido[2,3-b][1,4,5]oxathiazepine 1,1-dioxide (31.5 mg) of Example 1(1c), the title compound (64.0 mg, yield: 980%) was obtained as a solid in the same manner as in Example 54(54h).

59c 3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-(3,7-dimethyl-3H-[1,2,3]triazolo[4,5-b]pyridin-6-yl)propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-(3,7-dimethyl-3H-[1,2,3]triazolo[4,5-b]pyridin-6-yl)propanoate (64.0 mg) of Example 59(59b), the title compound (60.0 mg, yield: 98%) was obtained as a solid in the same manner as in Example 54(54i).

Example 60

3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[4-methyl-1-(2,2,2-trifluoroethyl)-1H-benzotriazol-5-yl]propanoic acid

60a

N-(4-Bromo-3-methyl-2-nitrophenyl)-2,2,2-trifluoroacetamide

Trifluoroacetic anhydride (0.662 mL) was added to a solution of 4-bromo-3-methyl-2-nitroaniline (1.00 g) and triethylamine (0.660 mL) in dichloromethane (22 mL), and the mixture was stirred at room temperature for 24 hr. Saturated aqueous sodium hydrogen carbonate solution was added to the reaction mixture, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent:n-hexane/ethyl acetate=95/5-90/10(V/V)] to give the title compound (1.02 g, yield: 72%) as a solid.

60b

4-Bromo-3-methyl-2-nitro-N-(2,2,2-trifluoroethyl)aniline

To a solution of N-(4-bromo-3-methyl-2-nitrophenyl)-2,2,2-trifluoroacetamide (960 mg) of Example 60(60a) in tetrahydrofuran (29 mL) was added borane-tetrahydrofuran (0.9 M tetrahydrofuran solution) (22.6 mL) at 0° C., and the mixture was stirred at room temperature for 24 hr. The reaction mixture was cooled to 0° C., methanol was added, and the mixture was heated and stirred at 60° C. for 2 hr. The reaction mixture was allowed to cool to room temperature, saturated aqueous sodium hydrogen carbonate solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent:n-hexane/ethyl acetate=95/5-80/20(V/V)] to give the title compound (89.0 mg, yield: 10%) as a solid, and 4-bromo-3-methyl-$N^1$-(2,2,2-trifluoroethyl)benzene-1,2-diamine (306 mg, yield: 37%) of Example 60(60c) as a solid.

60c

4-Bromo-3-methyl-$N^1$-(2,2,2-trifluoroethyl)benzene-1,2-diamine

Using 4-bromo-3-methyl-2-nitro-N-(2,2,2-trifluoroethyl)aniline (96.0 mg) of Example 60(60b), the title compound (64 mg, yield: 74%) was obtained as a solid in the same manner as in Example 54(54d).

60d

5-Bromo-4-methyl-1-(2,2,2-trifluoroethyl)-1H-benzotriazole

Using 4-bromo-3-methyl-$N^1$-(2,2,2-trifluoroethyl)benzene-1,2-diamine (392 mg) of Example 60(60c), the title compound (204 mg, yield: 50%) was obtained as a solid in the same manner as in Example 54(54e).

60e

Ethyl (2E)-3-[4-methyl-1-(2,2,2-trifluoroethyl)-1H-benzotriazol-5-yl]prop-2-enoate Using 5-bromo-4-methyl-1-(2,2,2-trifluoroethyl)-1H-benzotriazole (204 mg) of Example 60(60d), the title compound (199 mg, yield: 92%) was obtained as a solid in the same manner as in Example 54(54f).

60f

Ethyl 3-[7-(hydroxymethyl)-1-benzothiophen-5-yl]-3-[4-methyl-1-(2,2,2-trifluoroethyl)-1H-benzotriazol-5-yl]propanoate Using ethyl (2E)-3-[4-methyl-1-(2,2,2-trifluoroethyl)-1H-benzotriazol-5-yl]prop-2-enoate (195 mg) of Example 60(60e) and [5-(4,4,5,5-tetramethyl-1,3,2-dioxaborolan-2-yl)-1-benzothiophen-7-yl]methanol (271 mg) of Example 1h, the title compound (296 mg, yield: 85%) was obtained as an oil in the same manner as in Example 54(54g).

60g

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[4-methyl-1-(2,2,2-trifluoroethyl)-1H-benzotriazol-5-yl]propanoate Using ethyl 3-[7-(hydroxymethyl)-1-benzothiophen-5-yl]-3-[4-methyl-1-(2,2,2-trifluoroethyl)-1H-benzotriazol-5- yl]propanoate (48.0 mg) of Example 60(60f) and (4R)-8-chloro-4-ethyl-3,4-dihydro-2H-pyrido[2,3-b][1,4,5] oxathiazepine 1,1-dioxide (31.7 mg) of Example 1(1c), the title compound (72.9 mg, yield: quantitative) was obtained as an oil in the same manner as in Example 54(54h).

60h 3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[4-methyl-1-(2,2,2-trifluoroethyl)-1H-benzotriazol-5-yl]propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[4-methyl-1-(2,2,2-trifluoroethyl)-1H-benzotriazol-5-yl]propanoate (72.9 mg) of Example 60(60g), the title compound (63.0 mg, yield: 90%) was obtained as a solid in the same manner as in Example 54(54i).

Example 61

3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid 61a (2R,5S)-2-Ethyl-5-methyl-2,3,4,5-tetrahydropyrido[2,3-f][1,4]oxazepine 61b (2R,5R)-2-Ethyl-5-methyl-2,3,4,5-tetrahydropyrido[2,3-f][1,4]oxazepine Potassium tert-butoxide (401 mg) was added to a solution of (2R)-1-{[1-(3-fluoropyridin-2-yl)ethyl]amino}butan-2-ol (380 mg) of Example 62(62a) in dimethyl sulfoxide (9 mL), and the mixture was stirred at 80° C. for 15 min under a nitrogen atmosphere. After cooling the reaction mixture to room temperature, dichloromethane and saturated aqueous sodium hydrogen carbonate solution were added, and the mixture was extracted twice with dichloromethane. The combined organic layer was dried over anhydrous sodium sulfate, filtered, and the filtrate was concentrated under reduced pressure. The residue was purified twice by silica gel column chromatography [eluent: dichloromethane/methanol=100/0-80/20 (V/V)] to obtain 98 mg (yield: 28%) of (2R,5S)-2-ethyl-5-methyl-2,3,4,5-tetrahydropyrido[2,3-f][1,4]oxazepine of Example 61(61a) as a highly viscous oil as the first eluted compound. Also, 60 mg (yield: 17%) of (2R,5R)-2-ethyl-5-methyl-2,3,4,5-tetrahydropyrido[2,3-f][1,4]oxazepine of Example 61(61b) was obtained as a highly viscous oil as the second eluted compound.

61c

Ethyl 3-[7-(chloromethyl)-1-benzothiophen-5-yl]-3-(1,4-dimethyl-1H-benzotriazol-5-yl)propanoate To a solution of ethyl 3-(1,4-dimethyl-1H-benzotriazol-5-yl)-3-[7-(hydroxymethyl)-1-benzothiophen-5-yl]propanoate (380 mg) of Example 1(1i) in dichloromethane (5 mL) was added thionyl chloride (0.135 mL) and the mixture was stirred at room temperature for 40 min. The reaction mixture was concentrated under reduced pressure, and the residue was azeotropically distilled with toluene to obtain the title compound (397 mg, yield: quantitative) as a highly viscous oil.

61d

Ethyl 3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate A mixture of (2R,5S)-2-ethyl-5-methyl-2,3,4,5-tetrahydropyrido[2,3-f][1,4]oxazepine (40 mg) of Example 61(61a), ethyl 3-[7-(chloromethyl)-1-benzothiophen-5-yl]-3-(1,4-dimethyl-1H-benzotriazol-5-yl)propanoate (102 mg) of Example 61(61c), acetonitrile (2 mL), and N,N-diisopropylethylamine (0.178 mL) was stirred for 5 hr at 85° C. under a nitrogen atmosphere. Dichloromethane and water were added to the reaction mixture and the mixture was stirred, and the organic layer was separated through a phase separator (Biotage). The solvent was evaporated under reduced pressure, and the obtained residue was purified by silica gel column chromatography [elution solvent: n-hexane/ethyl acetate=3/1-1/2 (V/V)] to give the title compound (65 mg, yield: 54%) as a solid.

61e 3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid Using ethyl 3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (65 mg) of Example 61(61d), the title compound (31.7 mg, yield: 51%) was obtained as a solid in the same manner as in Example 62(62e).

Example 62

(3S)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid 62a (2R)-1-{[1-(3-Fluoropyridin-2-yl)ethyl]amino}butan-2-ol To a solution of 1-(3-fluoropyridin-2-yl)ethan-1-one (2.04 g) and (2R)-1-aminobutan-2-ol (3.39 g) of Example 1(1a) in tetrahydrofuran (50 mL) was added formic acid (2.77 mL) while cooling with water, chloro(pentamethylcyclopentadienyl) (4-dimethylamino-8-quinolinolato)iridium(III) (81 mg) was added and the mixture was stirred at 60° C. for 1.5 hr under a nitrogen atmosphere. After cooling the reaction mixture to room temperature, the reaction solvent was evaporated under reduced pressure, and the obtained residue was purified twice by NH silica gel column chromatography

62b tert-Butyl(2R,5S)-2-ethyl-5-methyl-2,3-dihydro-pyrido[2,3-f][1,4]oxazepine-4(5H)-carboxylate (2R)-1-{[1-(3-fluoropyridin-2-yl)ethyl]amino}butan-2-ol so (1.85 g) of Example 62(62a) was dissolved in dimethyl sulfoxide (30 mL), potassium tert-butoxide (1.97 g) was added, and the mixture was stirred at room temperature for 40 min. Saturated aqueous sodium hydrogen carbonate solution (25 mL), water (25 mL), and ethyl acetate (50 mL) were successively added, di-tert-butyl dicarbonate (3.8 g) was added thereto, and the mixture was stirred at room temperature for 30 min. The reaction solution was diluted with ethyl acetate/n-hexane, washed three times with water and once with saturated brine, and dried over anhydrous sodium sulfate. After filtration, the filtrate was concentrated under reduced pressure and the obtained residue was purified twice by silica gel column chromatography [elution solvent:n-hexane/ethyl acetate=4/1-1/1(V/V)]. The title compound, tert-butyl (2R,5S)-2-ethyl-5-methyl-2,3-dihydropyrido[2,3-f][1,4]oxazepine-4(5H)-carboxylate, was obtained as an oil (1.21 g, yield: 48%) as a later-eluted compound. In addition, the isomer, tert-butyl (2R,5R)-2-ethyl-5-methyl-2,3-dihydropyrido[2,3-f][1,4]oxazepine-4(5H)-carboxylate, was obtained as an oil (990 mg, yield: 39%) as an earlier-eluted compound.

62c (2R,5S)-2-Ethyl-5-methyl-2,3,4,5-tetrahydropyrido[2,3-f][1,4]oxazepine dihydrochloride 4 M Hydrogen chloride-1,4-dioxane solution (7 mL) was added to a solution of tert-butyl (2R,5S)-2-ethyl-5-methyl-2,3-dihydropyrido[2,3-f][1,4]oxazepine-4(5H)-carboxylate of Example 62(62b) in methanol (7 mL), and the mixture was stirred at room temperature for 90 min. The solvent was evaporated under reduced pressure and the obtained residue was slurry washed with diethyl ether, and dried under reduced pressure at 50° C. to give the title compound (1.07 g, yield: 98%) as a solid.

62d

Ethyl (3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate Thionyl chloride (0.354 mL) was added to a solution of ethyl (3S)-3-(1,4-dimethyl-1-benzotriazol-5-yl)-3-[7-(hydroxymethyl)-1-benzothiophen-5-yl]propanoate (1.00 g) of Example 7(7a) in dichloromethane (12 mL), and the mixture was stirred at room temperature for 1 hr. The solvent was evaporated under reduced pressure, and the residue was azeotropically distilled with toluene. The obtained residue was dissolved in acetonitrile (10 mL), and N,N-diisopropylethylamine (4 mL) and (2R,5S)-2-ethyl-5-methyl-2,3,4,5-tetrahydropyrido[2,3-f][1,4]oxazepine dihydrochloride (653 mg) of Example 62(62c) were added, and the mixture was stirred at 80° C. for 2 days and cooled to room temperature. Dichloromethane and water were added thereto, and the mixture was stirred, and the organic layer was separated through a phase separator (Biotage). The solvent was evaporated under reduced and the obtained residue was purified twice by silica gel column chromatography [elution solvent: n-hexane/ethyl acetate=3/1-1/1 (V/V)] to give the title compound (1.38 g, yield: 96%) as a solid.

62e (3S)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid To a mixture of ethyl (3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (1.38 g) of Example 62(62d), ethanol (10 mL), and tetrahydrofuran (10 mL) was added 1M aqueous sodium hydroxide solution (10 mL), and the mixture was stirred at room temperature for 4 hr. To the reaction mixture were added 1M hydrochloric acid (10 mL) and dichloromethane, and the mixture was stirred. The organic layer was separated through a phase separator (Biotage). The solvent was evaporated under reduced pressure, to the obtained residue was added n-hexane/ethyl acetate, and the mixture was subjected to an ultrasonic treatment. The solid was collected by filtration, and vacuum dried at 50° C. to give the title compound (1.25 g, yield: 95%) as a solid.

Example 63

(3R)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid

63a

Ethyl (3R)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate Using ethyl (3R)-3-(1,4-dimethyl-1H-benzotriazol-5-yl)-3-[7-(hydroxymethyl)-1-benzothiophen-5-yl]propanoate (65 mg) of Example 7 (7b) and (2R,5S)-2-ethyl-5-methyl-2,3,4,5-tetrahydropyrido[2,3-f][1,4]oxazepine (25 mg) of Example 61(61a), the title compound (52 mg, yield: 69%) was obtained as a solid in the same manner as in Example 62(62d).

63b (3R)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid Using ethyl (3R)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (52 mg) of Example 63(63a), the title compound (29.7 mg, yield: 60%) was obtained as a solid in the same manner as in Example 62(62e).

Example 64

(3S)-3-(7-Chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid

64a

Ethyl (3S)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate Thionyl chloride (0.0555 mL) was added to a solution of ethyl (3S)-3-(7-chloro-1,4-dimethyl-1H-benzotriazol-5-yl)-3-[7-(hydroxymethyl)-1-benzothiophen-5-yl]propanoate (170 mg) of Example 30(30f) in dichloromethane (2 mL), and the mixture was stirred at room temperature for 2 hr. The solvent was evaporated under reduced pressure, and dichloromethane was added thereto for azeotropic distillation. The obtained residue was dissolved in acetonitrile (4 mL), and N,N-diisopropylethylamine (0.525 mL) and (2R,5S)-2-ethyl-5-methyl-2,3,4,5-tetrahydropyrido[2,3-f][1,4]oxazepine dihydrochloride (122 mg) of Example 62(62c) were added, and the mixture was stirred at 90° C. for 7 hr and cooling to room temperature. Dichloromethane and saturated aqueous sodium hydrogen carbonate solution were added, and the mixture was stirred, and then the organic layer was separated through a phase separator (Biotage). The solvent was evaporated under reduced pressure and the obtained residue was purified by silica gel column chromatography [elution solvent:n-hexane/ethyl acetate=4/1-1/1(V/V)] to give the title compound (219 mg, yield: 93%) as a solid.

64b (3S)-3-(7-Chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid Using ethyl (3S)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (211 mg) of Example 64(64a), the title compound (188 mg, yield: 93%) was obtained as a solid in the same manner as in Example 62(62e).

Example 65

(3R)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid

65a

Ethyl (3R)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate Using ethyl (3R)-3-(1,4-dimethyl-1H-benzotriazol-5-yl)-3-[7-(hydroxymethyl)-2,3-dihydro-1H-inden-5-yl]propanoate (154 mg) of Example 4(4b) and (2R,5S)-2-ethyl-5-methyl-2,3,4,5-tetrahydropyrido[2,3-f][1,4]oxazepine dihydrochloride (104 mg) of Example 62(62c), the title compound (218 mg, yield: 80%) was obtained as an oil in the same manner as in Example 62(62d).

65b (3R)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid Using ethyl (3R)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate (218 mg) of Example 65(65a), the title compound (185 mg, yield: 89%) was obtained as a solid in the same manner as in Example 41.

Example 66

(3S)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid

66a

Ethyl (3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate Thionyl chloride (0.0531 mL) was added to a solution of ethyl (3S)-3-(1,4-dimethyl-1H-benzotriazol-5-yl)-3-[7-(hydroxymethyl)-2,3-dihydro-1H-inden-5-yl]propanoate (144 mg) of Example 4(4a) in dichloromethane (2.0 mL), and the mixture was stirred at room temperature for 30 min. The solvent was evaporated under reduced pressure, and toluene was added for azeotropic distillation. The mixture was dissolved in acetonitrile (3.9 mL), N,N-diisopropylethylamine (0.510 mL) and (2R,5S)-2-ethyl-5-methyl-2,3,4,5-tetrahydropyrido[2,3-f][1,4]oxazepine dihydrochloride (97.0 mg) of Example 62(62c) were added, and the mixture was stirred at 85° C. for 11 hr and cooled to room temperature. To the reaction mixture were added water and saturated brine, and the mixture was extracted with ethyl acetate. The organic layer was dried over anhydrous sodium sulfate and the solvent was evaporated under reduced pressure. The obtained residue was successively purified by NH silica gel column chromatography [elution solvent:n-hexane/ethyl acetate=90/10-50/50(V/V)] and silica gel column chromatography [elution solvent:n-hexane/ethyl acetate=70/30-20/80(V/V)] to give the title compound (192 mg, yield: 79%) as an oil.

66b (3S)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid To a mixture of ethyl (3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate (192 mg) of Example 66(66a), ethanol (2.0 mL), and tetrahydrofuran (2.0 mL) was added 1M aqueous sodium hydroxide solution (2.0 mL), and the mixture was stirred at 50° C. for 1.5 hr, and at room temperature for 2.5 hr. The reaction mixture was cooled to room temperature, 2M hydrochloric acid (1 mL) was added, and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:chloroform/methanol=100/0-85/15(V/V)], and further by slurry purification using an ethyl acetate/n-hexane mixed solvent to give the title compound (116 mg, yield: 74%) as a solid.

Example 67

(3R)-3-(7-{[(2R,5S)-2-Ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoic acid 67a 4-Bromo-N,3,6-trimethyl-2-nitroaniline 2,5-Dimethylaniline (25.1 g) was dissolved in N,N-dimethylformamide (207 mL), and N-bromosuccinimide (38.6 g) was added in portions over 17 min at 0° C., and the mixture was stirred at 0° C. for 15 min. Water was added to the reaction mixture, and the mixture was extracted with ethyl acetate. The organic layer was successively washed with water and saturated brine, dried over anhydrous sodium sulfate, and the solvent was evaporated under reduced pressure. The obtained residue was dissolved in dichloromethane (690 mL), and triethylamine (43.3 mL) was added thereto. Trifluoroacetic anhydride (35.0 mL) was added dropwise thereto at 0° C. over 11 min, and the mixture was stirred at room temperature for 25 min. Saturated aqueous sodium hydrogen carbonate solution was added to the reaction mixture, and the mixture was extracted with chloroform. The organic layer was successively washed with 1 M hydrochloric acid and saturated brine, dried over anhydrous sodium sulfate, and the solvent was evaporated under reduced pressure. The obtained residue was dissolved in concentrated sulfuric acid (150 mL), and then 69% concentrated nitric acid (13.6 mL) was added dropwise over 5 min while cooling in an ice-salt bath, and the mixture was stirred at room temperature for 45 min. The reaction mixture was added to ice water, and the precipitate was collected by filtration and washed with water. The obtained solid was dissolved in chloroform, and saturated aqueous sodium hydrogen carbonate solution was added, and the mixture was extracted with a mixed solvent of chloroform and methanol. The organic layer was dried over anhydrous sodium sulfate, and the solvent was evaporated under reduced pressure. tert-Butyl methyl ether and n-hexane were added to the obtained residue, and the mixture was subjected to an ultrasonic treatment, and then the solid was filtered. 60% Sodium hydride (7.40 g) was suspended in N,N-dimethylformamide (310 mL), and the solid obtained in the previous reaction was added thereto in portions over 10 min at 0° C., and the mixture was stirred at room temperature for 18 min. Methyl iodide (11.5 mL) was added dropwise thereto over 4 min at 0° C., and the mixture was stirred at room temperature for 50 min, at 50° C. for 5 min, and at room temperature for 80 min. The reaction mixture was added to a saturated aqueous ammonium chloride solution at 0° C., and extracted with ethyl acetate. The organic layer was washed with water and saturated brine, dried over anhydrous sodium sulfate, and the solvent was evaporated under reduced pressure. The obtained residue was dissolved in ethanol (510 mL), 5 M aqueous sodium hydroxide solution (154 mL) was added, and the mixture was heated under reflux for 20 min. The reaction mixture was allowed to cool to room temperature, concentrated under reduced pressure, water was added, and the mixture was extracted with a mixed solvent of chloroform and methanol. The organic layer was dried over anhydrous sodium sulfate, and the solvent was evaporated under reduced pressure. n-Hexane was added to the obtained residue, and the mixture was subjected to an ultrasonic treatment. The solid was collected by filtration to give the title compound (24.1 g, yield: 45%) as a solid.

67b

4-Bromo-$N^1$,3,6-trimethylbenzene-1,2-diamine

4-Bromo-N,3,6-trimethyl-2-nitroaniline (24.1 g) of Example 67(67a) was dissolved in acetic acid (280 mL), zinc powder (30.4 g) was added in portions over 9 min, and the mixture was stirred at room temperature for 14 min. Ethyl acetate was added to the reaction mixture, and the mixture was filtered through celite to remove insoluble matter. Saturated brine and water were added to the filtrate, and the mixture was extracted with ethyl acetate. The organic layer was washed successively with saturated aqueous sodium hydrogen carbonate solution and saturated brine, dried over anhydrous sodium sulfate, and the solvent was evaporated under reduced pressure. The obtained residue was purified by silica gel column chromatography [elution solvent:n-hexane/ethyl acetate/chloroform=90/10/5-50/50/5 (V/V/V)] to give the title compound (16.5 g, yield: 77%) as an oil.

67c

5-Bromo-1,4,7-trimethyl-1H-benzotriazole

4-Bromo-$N^1$,3,6-trimethylbenzene-1,2-diamine (16.5 g) of Example 67(67b) was dissolved in dichloromethane (144 mL) and cooled in an ice-salt bath. tert-Butyl nitrite (10.4 mL) was added dropwise thereto over 5 min, 42% tetrafluoroboric acid (23.0 mL) was added dropwise thereto over 7 min, and the mixture was stirred at room temperature for 28 min. The reaction mixture was added to saturated aqueous sodium hydrogen carbonate solution and extracted with chloroform. The organic layer was dried over anhydrous sodium sulfate, and the solvent was evaporated under reduced pressure. Ethyl acetate and n-hexane were added to the obtained residue, and the mixture was subjected to an ultrasonic treatment. The solid was collected by filtration to give the title compound (13.5 g, yield: 78%) as a solid.

67d

Ethyl (2E)-3-(1,4,7-trimethyl-1H-benzotriazol-5-yl)prop-2-enoate

5-Bromo-1,4,7-trimethyl-1H-benzotriazole (13.5 g) of Example 67(67c) was dissolved in N,N-dimethylformamide (187 mL), and ethyl acrylate (61.2 mL), N,N-diisopropylethylamine (48.9 mL), tris(dibenzylideneacetone)dipalladium(0) (5.15 g) and tri(o-tolyl)phosphine (6.85 g) were added, and the mixture was stirred under a nitrogen atmosphere at 100° C. for 11 hr. The reaction mixture was allowed to cool to room temperature, water was added, and the mixture was extracted with a mixed solvent of ethyl acetate, methanol and tetrahydrofuran. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate/chloroform=90/10/10-40/60/20 (V/V/V)] to give the title compound (6.10 g, yield: 84%) as a solid.

67e

Ethyl 3-[7-(hydroxymethyl)-1-benzothiophen-5-yl]-3-(1,4,7-trimethyl-1H-benzotriazol-5-yl)propanoate Using ethyl (2E)-3-(1,4,7-trimethyl-1H-benzotriazol-5-yl)prop-2-enoate (6.10 g) of Example 67(67d) and [5-(4,4,5,5-tetramethyl-1,3,2-dioxaborolan-2-yl)-1-benzothiophen-7-yl]methanol (11.6 g) of Example 1(1h), the title compound (6.89 g, yield: 69%) was obtained as a solid in the same manner as in Example 1(1i).

67f

Ethyl 3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoate Using ethyl 3-[7-(hydroxymethyl)-1-benzothiophen-5-yl]-3-(1,4,7-trimethyl-1H-benzotriazol-5-yl)propanoate (151 mg) of Example 67(67e) and (2R,5S)-2-ethyl-5-methyl-2,3,4,5-tetrahydropyrido[2,3-f][1,4]oxazepine dihydrochloride (93.9 mg) of Example 62(62c), the title compound (182 mg, yield: 85%) was obtained as an oil in the same manner as in Example 62(62d).

67g

Ethyl (3R)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoate 67h Ethyl (3S)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoate Ethyl 3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoate (182 mg) of Example 67(67f) was subjected to chiral HPLC [column: CHIRALPAK IG (20 mm I.D.×250 mm), mobile phase: n-hexane/2-propanol=50/50(V/V), temperature: 40° C.] to obtain 79.9 mg of ethyl (3R)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoate as the first peak (yield: 44%).

Similarly, 79.7 mg of ethyl (3S)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoate was obtained as the second peak (yield: 44%).

Analysis HPLC conditions [column: CHIRALPAK IG (4.6 mm I.D.×250 mm), mobile phase: n-hexane/2-propanol=50/50(V/V), flow rate: 1.0 mL/min, temperature: 40° C., wavelength: 254 nm]; retention time: 8.813 min (the first peak), 11.010 min (the second peak)

67i (3R)-3-(7-{[(2R,5S)-2-Ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoic acid Using ethyl (3R)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoate (79.9 mg) of Example 67(67g), the title compound (54.3 mg, yield: 71%) was obtained as a solid in the same manner as in Example 41.

Example 68

(3S)-3-(7-{[(2R,5S)-2-Ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoic acid Using ethyl (3S)-3-(7-{[(2R,5S)-2-ethyl-5-methyl-2,3-dihydropyrido[2,3-f][1,4]oxazepin-4(5H)-yl]methyl}-1-benzothiophen-5-yl)-3-(1,4,7-trimethyl-1H-benzotriazol-5-yl)propanoate (79.7 mg) of Example 67(67h), the title compound (59.8 mg, yield: 79%) was obtained as a solid in the same manner as in Example 41.

Example 69

(3S)-3-(7-{[(2R,5S)-2-Ethyl-5-methyl-2,3-dihydropyrido[2,3-f][1,4]oxazepin-4(5H)-yl]methyl}-2,3-dihydro-1H-inden-5-yl)-3-(1,4,7-trimethyl-1H-benzotriazol-5-yl)propanoic acid 69a Ethyl (3S)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)-3-(1,4,7-trimethyl-1H-benzotriazol-5-yl)propanoate Using ethyl (3S)-3-[7-(hydroxymethyl)-2,3-dihydro-1H-inden-5-yl]-3-(1,4,7-trimethyl-1H-benzotriazol-5-yl)propanoate (128 mg) of Example 44(44c) and (2R,5S)-2-ethyl-5-methyl-2,3,4,5-tetrahydropyrido[2,3-f][1,4]oxazepine dihydrochloride (83.6 mg) of Example 62(62c), the title compound (156 mg, yield: 71%) was obtained as an oil in the same manner as in Example 62(62d).

69b (3S)-3-(7-{[(2R,5S)-2-Ethyl-5-methyl-2,3-dihydropyrido[2,3-f][1,4]oxazepin-4(5H)-yl]methyl}-2,3-dihydro-1H-inden-5-yl)-3-(1,4,7-trimethyl-1H-benzotriazol-5-yl)propanoic acid Using ethyl (3S)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)-3-(1,4,7-trimethyl-1H-benzotriazol-5-yl)propanoate (156 mg) of Example 69(69a), the title compound (121 mg, yield: 82%) was obtained as a solid in the same manner as in Example 41.

Example 70

(3R)-3-(7-Chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid 70a Ethyl (3R)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate Using ethyl (3R)-3-(7-chloro-1,4-dimethyl-1H-benzotriazol-5-yl)-3-[7-(hydroxymethyl)-1-benzothiophen-5-yl]propanoate (160 mg) of Example 30(30g) and (2R,5S)-2-ethyl-5-methyl-2,3,4,5-tetrahydropyrido[2,3-f][1,4]oxazepine dihydrochloride (115 mg) of Example 62(62c), the title compound (211 mg, yield: 95%) was obtained as a solid in the same manner as in Example 62(62d).

70b (3R)-3-(7-Chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid Using ethyl (3R)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (210 mg) of Example 70(70a), the title compound (185 mg, yield: 92%) was obtained as a solid in the same manner as in Example 62(62e).

Example 71

(3R*)-3-(7-Chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid 71a Ethyl 3-(7-chloro-1,4-dimethyl-1H-benzotriazol-5-yl)-3-[7-(hydroxymethyl)-2,3-dihydro-1H-inden-5-yl]propanoate To a mixture of bis(norbornadiene)rhodium(I) tetrafluoroborate (33.4 mg), (2S,3S)-bis(diphenylphosphino)butane (20.0 mg), and (2R,3R)-bis(diphenylphosphino)butane (20.0 mg) were added, under a nitrogen atmosphere, 1,4-dioxane (5.00 mL) and 1M aqueous potassium hydroxide solution (1.78 mL), and the mixture was stirred at room temperature for 15 min to prepare a catalyst solution. Then, a mixture of ethyl (2E)-3-(7-chloro-1,4-dimethyl-1H-benzotriazol-5-yl)prop-2-enoate (500 mg) of Example 30(30d), [6-(4,4,5,5-tetramethyl-1,3,2-dioxaborolan-2-yl)-2,3-dihydro-1H-inden-4-yl]methanol (735 mg) of Example 3(3d) 1,4-dioxane (10.0 mL) and water (3.6 mL) was prepared in a separate container and stirred at 50° C. for 3 min under a nitrogen atmosphere, and the catalyst solution prepared above was added thereto. The reaction mixture was heated and stirred at 50° C. for 4.5 hr under a nitrogen atmosphere. The reaction mixture was allowed to cool to room temperature, 2M hydrochloric acid (0.9 mL), saturated brine and water were added, and the mixture was extracted with ethyl acetate. The organic layer was washed with saturated brine and dried over anhydrous sodium sulfate. After filtration, the filtrate was concentrated under reduced pressure, and the obtained residue was purified by silica gel chromatography [eluent: n-hexane/ethyl acetate=70/30-20/80(V/V)] to give a mixture containing the title compound (943 mg, yield: 90%) as an amorphous.

71b

Ethyl 3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate Using ethyl 3-(7-chloro-1,4-dimethyl-1H-benzotriazol-5-yl)-3-[7-(hydroxymethyl)-2,3-dihydro-1H-inden-5-yl]propanoate (475 mg) of Example 71(71a) and (2R,5S)-2-ethyl-5-methyl-2,3,4,5-tetrahydropyrido[2,3-f][1,4]oxazepine dihydrochloride (294 mg) of Example 62(62c), the title compound (446 mg, yield: 67%) was obtained as an oil in the same manner as in Example 62(62dd).

71c

Ethyl (3R*)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate 71d Ethyl (3S*)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate Ethyl 3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate (446 mg) of Example 71(71b) was subjected to chiral HPLC [column: CHIRALPAK IG (20 mm I.D.×250 mm), mobile phase: n-hexane/ethanol=90/10(V/V), temperature: 40° C.] to obtain 198 mg of ethyl (3R*)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate as the first peak (yield: 44%).

Similarly, 196 mg of ethyl (3S*)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate was obtained as the second peak (yield: 44%).

Analysis HPLC conditions [column: CHIRALPAK IG (4.6 mm I.D.×250 mm), mobile phase: n-hexane/ethanol=85/15(V/V), flow rate: 1.0 mL/min, temperature: 40° C., wavelength: 254 nm]; retention time: 10.090 min (the first peak), 11.303 min (the second peak)

71e (3R*)-3-(7-Chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid Using ethyl (3R*)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4 (5H)-yl]methyl}-2,3-dihydro-1H-inden-5-yl)propanoate (198 mg) of Example 71(71c), the title compound (160 mg, yield: 85%) was obtained as a solid in the same manner as in Example 3(3g).

Example 72

(3S*)-3-(7-Chloro-1,4-dimethyl-1H-benzotriazol-5-yl)-3-(7-{[(2R,5S)-2-ethyl-5-methyl-2,3-dihydropyrido[2,3-f][1, 4]oxazepin-4(5H)-yl]methyl}-2,3-dihydro-1H-inden-5-yl)propanoic acid Using ethyl (3S)-3-(7-chloro-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate (196 mg) of Example 71(71d), the title compound (134 mg, yield: 72%) was obtained as a solid in the same manner as in Example 3 (3g).

Example 73

3-(1,4-Dimethyl-1H-benzotriazol-5-yl)-3-(7-{[(2R,5R)-2-ethyl-5-methyl-2,3-dihydropyrido[2,3-f][1,4]oxazepin-4(5H)-yl]methyl}-1-benzothiophen-5-yl)propanoic acid 73a Ethyl 3-(1,4-dimethyl-1H-benzotriazol-5-yl)-3-(7-{[(2R,5R)-2-ethyl-5-methyl-2,3-dihydropyrido[2,3-f][1,4]oxazepin-4(5H)-yl]methyl}-1-benzothiophen-5-yl)propanoate Using (2R,5R)-2-ethyl-5-methyl-2,3,4,5-tetrahydropyrido[2,3-f][1, 4]oxazepine (26 mg) of Example 61(61b) and ethyl 3-[7-(chloromethyl)-1-benzothiophen-5-yl]-3-(1,4-dimethyl-H-benzotriazol-5-yl)propanoate (68 mg) of Example 61(61c), the title compound (64 mg, yield: 81%) was obtained as a solid in the same manner as in Example 61(61d).

73b 3-(1,4-Dimethyl-1H-benzotriazol-5-yl)-3-(7-{[(2R,5R)-2-ethyl-5-methyl-2,3-dihydropyrido[2,3-f][1,4]oxazepin-4(5H)-yl]methyl}-1-benzothiophen-5-yl)propanoic acid Using ethyl 3-(1,4-dimethyl-1H-benzotriazol-5-yl)-3-(7-{[(2R,5R)-2-ethyl-5-methyl-2,3-dihydropyrido[2,3-f][1,4]oxazepin-4(5H)-yl]methyl}-1-benzothiophen-5-yl)propanoate (64 mg) of Example 73(73a), the title compound (36.1 mg, yield: 59%) was obtained as a solid in the same manner as in Example 62(62e).

Example 74

(3S)-3-(4-Chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid 74a Ethyl (3S)-3-(4-chloro-1-methyl-1H-benzotriazol-5-yl)-3-[7-(hydroxymethyl)-1-benzothiophen-5-yl]propanoate 74b Ethyl (3R)-3-(4-chloro-1-methyl-1H-benzotriazol-5-yl)-3-[7-(hydroxymethyl)-1-benzothiophen-5-yl]propanoate Ethyl (2E)-3-(4-chloro-1-methyl-1H-benzotriazol-5-yl)prop-2-enoate (WO 2015/092713) (11.0 g) and chloro(1,5-cyclooctadiene)rhodium(I) (3.1 g) were added to 1,4-dioxane (200 mL), purged with nitrogen, and dissolved at 60° C. Then, [5-(4,4,5,5-tetramethyl-1,3,2-dioxaborolan-2-yl)-1-benzothiophen-7-yl]methanol (16.0 g) of Example 1(1h) and then 1 M aqueous potassium hydroxide solution (41.4 mL) were added thereto, and the mixture was stirred under heating at 60° C. for 5 hr. The reaction mixture was cooled to room temperature and the solvent was evaporated under reduced pressure. The obtained residue was purified by silica gel column chromatography [elution solvent:petroleum ether/ethyl acetate=10/1-1/1(V/V)] to give a racemate of the title compound. This was subjected to chiral SFC [column: CHIRALPAK AD (30 mm I.D.×250 mm), mobile phase: carbon dioxide/methanol (0.1% aqueous ammonia)=60/40 (V/V)] to obtain 2.8 g of ethyl (3S)-3-(4-chloro-1-methyl-1H-benzotriazol-5-yl)-3-[7-(hydroxymethyl)-1-benzothiophen-5-yl]propanoate as the first peak (yield: 16%).

In the same manner, 2.96 g of ethyl (3R)-3-(4-chloro-1-methyl-1H-benzotriazol-5-yl)-3-[7-(hydroxymethyl)-1-benzothiophen-5-yl]propanoate was obtained as the second peak (yield: 16%).

Analysis SFC conditions [column: CHIRALPAK AD-3 (4.6 mm I.D.×50 mm), mobile phase: carbon dioxide/methanol (0.05% diethylamine)=95/5-60/40(V/V), flow rate: 3 mL/min, temperature: 35° C., wavelength: 220 nm]; retention time: 1.823 min (the first peak), 2.271 min (the second peak)

74c

Ethyl (3S)-3-(4-chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate Using ethyl (3S)-3-(4-chloro-1-methyl-1H-benzotriazol-5-yl)-3-[7-(hydroxymethyl)-1-benzothiophen-5-yl]propanoate (150 mg) of Example 74(74a) and (2R,5S)-2-ethyl-5-methyl-2,3,4,5-tetrahydropyrido[2,3-f][1,4]oxazepine dihydrochloride (97 mg) of Example 62(62c), the title compound (166 mg, yield: 79%) was obtained as a solid in the same manner as in Example 62(62d).

74d (3S)-3-(4-Chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid To a mixture of ethyl (3S)-3-(4-chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (166 mg) of Example 74(74c), ethanol (3 mL), and tetrahydrofuran (3 mL) was added 1M aqueous sodium hydroxide solution (3 mL), and the mixture was stirred at 40° C. for 1 hr. To the reaction mixture were added 1M hydrochloric acid (3 mL) and dichloromethane and the mixture was stirred. The organic layer was separated through a phase separator (Biotage), and the solvent was evaporated under reduced pressure. To the obtained residue was added ethyl acetate, and the mixture was subjected to an ultrasonic treatment. The solid was collected by filtration and vacuum dried at 50° C. to give the title compound (128 mg, yield: 81%) as a solid.

Example 75

(3R)-3-(4-Chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid

75a

Ethyl (3R)-3-(4-chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate Using ethyl (3R)-3-(4-chloro-1-methyl-1H-benzotriazol-5-yl)-3-[7-(hydroxymethyl)-1-benzothiophen-5-yl]propanoate (200 mg) of Example 74(74b) and (2R,5S)-2-ethyl-5-methyl-2,3,4,5-tetrahydropyrido[2,3-f][1,4]oxazepine dihydrochloride (123 mg) of Example 62(62c), the title compound (194 mg, yield: 69%) was obtained as a solid in the same manner as in Example 62(62d).

75b (3R)-3-(4-Chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoic acid Using ethyl (3R)-3-(4-chloro-1-methyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (194 mg) of Example 75(75a), the title compound (193 mg, yield: quantitative) was obtained as a solid in the same manner as in Example 62(62e).

Example 76

(3S)-3-(7-{[(2R,5R*)-2,5-Diethyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoic acid

76a 1-(3-Fluoropyridin-2-yl)propan-1-ol

To a solution of 3-fluoropyridine-2-carbaldehyde (7.4 g) in tetrahydrofuran (100 mL) was added dropwise 3 M ethylmagnesium bromide (40 mL) at −70° C. The reaction mixture was stirred at 15° C. for 12 hr, water was added, and the mixture was extracted three times with ethyl acetate. The combined organic layer was washed with saturated brine and dried over anhydrous sodium sulfate. After filtration, the filtrate was concentrated under reduced pressure and the obtained residue was purified by silica gel column chromatography [elution solvent:petroleum ether/ethyl acetate=30/1-20/1(V/V)] to give the title compound (3.5 g, yield: 38%) as an oil.

76b 1-(3-Fluoropyridin-2-yl)propan-1-one 1-(3-Fluoropyridin-2-yl)propan-1-ol (4 g) of Example 76(76a) was dissolved in dichloromethane (80 mL), and manganese dioxide (11.2 g) was added at 40° C., oxygen gas was passed through three times, and the mixture was stirred at 40° C. for 12 hr. The reaction mixture was filtered, and the obtained filtrate was concentrated under reduced pressure to give an unpurified title compound (3.8 g) as an oil.

76c (2R)-1-{[1-(3-Fluoropyridin-2-yl)propyl]amino}butan-2-ol

To a solution of 1-(3-fluoropyridin-2-yl)propan-1-one (3.8 g) of Example 76(76b) in dichloroethane (50 mL) were added (2R)-1-aminobutan-2-ol (3.8 g) and tetraisopropyl orthotitanate (7.60 mL) at 15° C., and the mixture was stirred for 2 hr. Sodium triacetoxyborohydride (8.6 g) was added to the reaction mixture, and the mixture was heated and stirred at 70° C. for 12 hr and cooled to room temperature. A solution of sodium hydroxide (1 g) in water (50 mL) was added to the reaction mixture, and the mixture was further diluted with water (500 mL) and extracted three times with dichloromethane. The combined organic layer was dried over anhydrous sodium sulfate, filtered, and the residue obtained by concentrating the filtrate under reduced pressure was purified by silica gel column chromatography [elution solvent:dichloromethane/methanol=50/1-30/1(V/V)] to give the title compound (1 g, yield: 18%) as an oil.

76d (2R,5R*)-2,5-Diethyl-2,3,4,5-tetrahydropyrido[2,3-f][1,4]oxazepine dihydrochloride

76e (2R,5S*)-2,5-Diethyl-2,3,4,5-tetrahydropyrido[2,3-f][1,4]oxazepine dihydrochloride To a solution of (2R)-1-{[1-(3-fluoropyridin-2-yl)propyl]amino}butan-2-ol (0.8 g) of Example 76 (76c) in dimethyl sulfoxide (8 mL) was added potassium tert-butoxide (800 mg), and the mixture was heated and stirred under heating at 90° C. for 12 hr, and cooled to room temperature. The reaction mixture was diluted with water (100 mL) and extracted twice with ethyl acetate. The combined organic layer was washed twice with saturated brine and dried over anhydrous sodium sulfate. After filtration, the filtrate was concentrated under reduced pressure and the obtained residue was purified by silica gel column chromatography [elution solvent:dichloromethane/methanol=50/1-30/1(V/

V)]. The compound eluted earlier was subjected to preparative HPLC [column: Phenomenex Luna C18 (30 mm I.D.× 75 mm), mobile phase: 0.05% hydrochloric acid/acetonitrile=94/6-74/26(V/V)] to give (2R,5R*)-2,5-diethyl-2,3,4,5-tetrahydropyrido[2,3-f][1,4]oxazepine dihydrochloride (131 mg, yield: 13%) of Example 76(76d) as a solid.

The compound eluted later was treated in the same manner to give (2R,5S*)-2,5-diethyl-2,3,4,5-tetrahydropyrido[2,3-f][1,4]oxazepine dihydrochloride (120 mg, yield: 12%) of Example 76(76e) as a solid.

76f

Ethyl (3S)-3-(7-{[(2R,5R*)-2,5-diethyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoate Using ethyl (3S)-3-(1,4-dimethyl-1H-benzotriazol-5-yl)-3-[7-(hydroxymethyl)-1-benzothiophen-5-yl]propanoate (100 mg) of Example 7(7a) and (2R,5R*)-2,5-diethyl-2,3,4,5-tetrahydropyrido[2,3-f][1,4]oxazepine dihydrochloride (68 mg) of Example 76(76d), the title compound (102 mg, yield: 70%) was obtained as a solid in the same manner as in Example 62(62d).

76g (3S)-3-(7-{[(2R,5R*)-2,5-Diethyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoic acid Using ethyl (3S)-3-(7-{[(2R,5R*)-2,5-diethyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoate (102 mg) of Example 76(76f), the title compound (72.9 mg, yield: 75%) was obtained as a solid in the same manner as in Example 62(62e).

Example 77

(3S)-3-(7-{[(2R,5S*)-2,5-Diethyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoic acid 77a Ethyl (3S)-3-(7-{[(2R,5S*)-2,5-diethyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoate Using ethyl (3S)-3-(1,4-dimethyl-1H-benzotriazol-5-yl)-3-[7-(hydroxymethyl)-1-benzothiophen-5-yl]propanoate (100 mg) of Example 7(7a) and (2R,5S*)-2,5-diethyl-2,3,4,5-tetrahydropyrido[2,3-f][1,4]oxazepine dihydrochloride (68 mg) of Example 76(76e), the title compound (104 mg, yield: 71%) was obtained as a solid in the same manner as in Example 62(62d).

77b (3S)-3-(7-{[(2R,5S*)-2,5-Diethyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoic acid Using ethyl (3S)-3-(7-{[(2R,5S*)-2,5-diethyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoate (104 mg) of Example 77(77a), the title compound (82.4 mg, yield: 83%) was obtained as a solid in the same manner as in Example 62(62e).

Example 78

(3R)-3-(1,4-Dimethyl-1H-benzotriazol-5-yl)-3-(7-{[(2R,5S*)-2-ethyl-7-hydroxy-5-methyl-2,3-dihydropyrido[2,3-f][1,4]oxazepin-4(5H)-yl]methyl}-1-benzothiophen-5-yl)propanoic acid 78a (2R)-1-{[1-(6-Chloro-3-fluoropyridin-2-yl)ethyl]amino}butan-2-ol To a solution of (2R)-1-aminobutan-2-ol (1.67 g) of Example 1(1a) in dichloromethane (30 mL) were added 1-(6-chloro-3-fluoro-2-pyridyl)ethanone (1.00 g), acetic acid (1.65 mL), and sodium sulfate (818 mg), and the mixture was stirred at room temperature for 2 hr. Sodium triacetoxyborohydride (4.88 g) was added thereto, and the mixture was stirred at room temperature for 5 days. To the reaction mixture was added saturated aqueous sodium hydrogen carbonate solution, and the reaction mixture was extracted with dichloromethane. The organic layer was washed with saturated brine and dried over anhydrous sodium sulfate. The solvent was evaporated under reduced pressure and the obtained residue was purified by NH silica gel column chromatography [elution solvent:n-hexane/ethyl acetate=80/20-40/60(V/V)] to give the title compound (572 mg, yield: 40%) as a solid.

78b (2R)-1-{[1-(6-Chloro-3-fluoropyridin-2-yl)ethyl](4-methoxybenzyl)amino}butan-2-ol To a solution of (2R)-1-{[1-(6-chloro-3-fluoropyridin-2-yl)ethyl]amino}butan-2-ol (572 mg) of Example 78(78a) in dichloromethane (25 mL) were added p-anialdehyde (0.423 mL) and acetic acid (0.199 mL), and the mixture was stirred at room temperature for 30 min. Sodium triacetoxyborohydride (737 mg) was added thereto, and the mixture was stirred at room temperature for 3 days. To the reaction mixture was added saturated aqueous sodium hydrogen carbonate solution, and the mixture was extracted with dichloromethane. The organic layer was washed with saturated brine and dried over anhydrous sodium sulfate. The solvent was evaporated under reduced pressure and the obtained residue was purified by silica gel column chromatography [elution solvent:n-hexane/ethyl acetate=90/10-40/60(V/V)] to give the title compound (436 mg, yield: 51%) as an oil.

78c (2R,5S*)-7-Chloro-2-ethyl-4-(4-methoxybenzyl)-5-methyl-2,3,4,5-tetrahydropyrido[2,3-f][1,4]oxazepine

78d (2R,5R*)-7-Chloro-2-ethyl-4-(4-methoxybenzyl)-5-methyl-2,3,4,5-tetrahydropyrido[2,3-f][1,4]oxazepine To a solution of potassium tert-butoxide (108 mg) in tetrahydrofuran (4 mL) and N,N-dimethylformamide (4 mL) was added at 0° C. a solution of (2R)-1-{[1-(6-chloro-3-fluoropyridin-2-yl)ethyl](4-methoxybenzyl)amino}butan-2-ol (322 mg) of Example 78(78b) in tetrahydrofuran (2 mL) and N,N-dimethylformamide (2 mL), and the mixture was stirred at 0° C. for 1 hr. To the reaction mixture was added saturated brine, and the mixture was extracted with ethyl acetate. The organic layer was washed with saturated brine and dried over anhydrous sodium sulfate. The solvent was evaporated under reduced pressure and the obtained residue was purified by silica gel column chromatography [elution solvent:n-hexane/ethyl acetate=100/0-90/10-85/15(V/V)]. As the compound eluted earlier, (2R,5S*)-7-chloro-2-ethyl-4-(4-methoxybenzyl)-5-methyl-2,3,4,5-tetrahydropyrido[2,3-f][1,4]oxazepine (159 mg, yield: 52%) of Example 78(78c) was obtained as an oil. As the compound eluted later, (2R,5R*)-7-chloro-2-ethyl-4-(4-methoxybenzyl)-5-methyl-2,3,4,5-tetrahydropyrido[2,3-f][1,4]oxazepine (60 mg, yield: 20%) of Example 78(78d) was obtained as an oil.

78e (2R,5S*)-2-Ethyl-4-(4-methoxybenzyl)-5-methyl-2,3,4,5-tetrahydropyrido[2,3-f][1,4]oxazepin-7-ol To a solution of (2R,5S*)-7-chloro-2-ethyl-4-(4-methoxybenzyl)-5-methyl-2,3,4,5-tetrahydropyrido[2,3-f][1,4]oxazepine (156 mg) of Example 78(78c) in 1,4-dioxane (5 mL) were added tris(dibenzylideneacetone)dipalladium (0) (21 mg), 5-(di-tert-butylphosphino)-1',3',5'-triphenyl-1'H-1,4'-bipyrazole (23 mg), and cesium hydroxide monohydrate (227 mg), and the mixture was stirred at 100° C. for 6 hr, and cooled to room temperature. Saturated brine and chloroform were added to the reaction mixture, and the mixture was subjected to an ultrasonic treatment and filtered through celite to remove insoluble matter. The filtrate was extracted with chloroform, and the organic layer was washed with saturated brine and dried over anhydrous sodium sulfate. The solvent was evaporated under reduced pressure and the obtained residue was purified by NH silica gel column chromatography [elution solvent:n-hexane/ethyl acetate=20/80-0/100(V/V), dichloromethane/methanol=100/0-95/5(V/V)] to give the title compound (125 mg, yield: 85%) as an amorphous.

78f

Ethyl (3R)-3-[7-(chloromethyl)-1-benzothiophen-5-yl]-3-(1,4-dimethyl-1H-benzotriazol-5-yl)propanoate To a solution of ethyl (3R)-3-(1,4-dimethyl-1H-benzotriazol-5-yl)-3-[7-(hydroxymethyl)-1-benzothiophen-5-yl]propanoate (100 mg) of Example 7(7b) in dichloromethane (3 mL) was added thionyl chloride (0.035 mL), and the mixture was stirred at room temperature for 2 hr. The solvent was evaporated under reduced pressure to give an unpurified title compound (111 mg, yield: quantitative) as an amorphous.

78g (2R,5S*)-2-Ethyl-5-methyl-2,3,4,5-tetrahydropyrido[2,3-f][1,4]oxazepin-7-ol hydrochloride Anisole (0.100 mL) was added to (2R,5S*)-2-ethyl-4-(4-methoxybenzyl)-5-methyl-2,3,4,5-tetrahydropyrido[2,3-f][1,4]oxazepin-7-ol (30.0 mg) of Example 78(78e), and dissolved by adding trifluoroacetic acid (1 ml). The mixture was stirred at 120° C. for 30 min under microwave irradiation. The mixture was allowed to cool to room temperature, and azeotropically distilled twice with toluene to evaporate the solvent. Ethyl acetate (0.8 mL) was added to dissolve the mixture, 4 M hydrogen chloride-ethyl acetate solution (0.3 ml) was added and the mixture was stirred at room temperature for 5 min. The precipitated colorless solid was collected by filtration and washed with diisopropyl ether to give the title compound (24 mg, yield: quantitative) as a solid.

78h

Ethyl (3R)-3-(1,4-dimethyl-1H-benzotriazol-5-yl)-3-(7-{[(2R,5S*)-2-ethyl-7-hydroxy-5-methyl-2,3-dihydropyrido[2,3-f][1,4]oxazepin-4(5H)-yl]methyl}-1-benzothiophen-5-yl)propanoate To a suspension of (2R,5S*)-2-ethyl-5-methyl-2,3,4,5-tetrahydropyrido[2,3-f][1,4]oxazepin-7-ol hydrochloride (24.0 mg) of Example 78(78g) and ethyl (3R)-3-[7-(chloromethyl)-1-benzothiophen-5-yl]-3-(1,4-dimethyl-1H-benzotriazol-5-yl)propanoate (61 mg) of Example 78(78f) in acetonitrile (3 mL) was added N,N-diisopropylethylamine (0.134 mL), and the mixture was stirred at 85° C. for 6 hr and cooled to room temperature. To the reaction mixture was added water, and the reaction mixture was extracted with ethyl acetate. The organic layer was washed with saturated brine and dried over anhydrous sodium sulfate. The solvent was evaporated under reduced pressure and the obtained residue was purified by silica gel column chromatography [elution solvent:n-hexane/ethyl acetate=60/40-0/100(V/V), dichloromethane/methanol=100/0-90/10(V/V)] to give the title compound (40 mg, yield: 68%) as an oil.

78i (3R)-3-(1,4-Dimethyl-1H-benzotriazol-5-yl)-3-(7-{[(2R,5S*)-2-ethyl-7-hydroxy-5-methyl-2,3-dihydropyrido[2,3-f][1,4]oxazepin-4(5H)-yl]methyl}-1-benzothiophen-5-yl)propanoic acid Using ethyl (3R)-3-(1,4-dimethyl-1H-benzotriazol-5-yl)-3-(7-{[(2R,5S*)-2-ethyl-7-hydroxy-5-methyl-2,3-dihydropyrido[2,3-f][1,4]oxazepin-4(5H)-yl]methyl}-1-benzothiophen-5-yl)propanoate (40.0 mg) of Example 78(78h), the title compound (16 mg, yield: 42%) was obtained as a solid in the same manner as in Example 54(54i).

Example 79

(3R)-3-(1,4-Dimethyl-1H-benzotriazol-5-yl)-3-(7-{[(2R,5R*)-2-ethyl-7-hydroxy-5-methyl-2,3-dihydropyrido[2,3-f][1,4]oxazepin-4(5H)-yl]methyl}-1-benzothiophen-5-yl)propanoic acid

79a (2R,5R*)-2-Ethyl-4-(4-methoxybenzyl)-5-methyl-2,3,4,5-tetrahydropyrido[2,3-f][1,4]oxazepin-7-ol Using (2R,5R*)-7-chloro-2-ethyl-4-(4-methoxybenzyl)-5-methyl-2,3,4,5-tetrahydropyrido[2,3-f][1,4]oxazepine (92.0 mg) of Example 78(78d), the title compound (19 mg, yield: 22%) was obtained as an oil in the same manner as in Example 78 (78e).

79b (2R,5R*)-2-Ethyl-5-methyl-2,3,4,5-tetrahydropyrido[2,3-f][1,4]oxazepin-7-ol hydrochloride To a solution of (2R,5R*)-2-ethyl-4-(4-methoxybenzyl)-5-methyl-2,3,4,5-tetrahydropyrido[2,3-f][1,4]oxazepin-7-ol (19.0 mg) of Example 79(79a) in trifluoroacetic acid (1 mL) was added anisole (0.063 mL), and the mixture was stirred at 120° C. for 30 min under microwave irradiation. The mixture was cooled to room temperature, and azeotropically distilled twice with toluene. The obtained residue was dissolved in ethyl acetate (0.8 mL), 4 M hydrogen chloride-ethyl acetate solution (0.3 mL) was added, and the mixture was stirred at room temperature for 5 min. The solvent was evaporated under reduced pressure to give the title compound (15 mg, yield: quantitative) as a solid.

79c

Ethyl (3R)-3-(1,4-dimethyl-1H-benzotriazol-5-yl)-3-(7-{[(2R,5R*)-2-ethyl-7-hydroxy-5-methyl-2,3-dihydropyrido[2,3-f][1,4]oxazepin-4(5H)-yl]methyl}-1-benzothiophen-5-yl)propanoate To a suspension of (2R,5R*)-2-ethyl-5-methyl-2,3,4,5-tetrahydropyrido[2,3-f][1,4]oxazepin-7-ol hydrochloride (15.0 mg) of Example 79(79b) and ethyl (3R)-3-[7-(chloromethyl)-1-benzothiophen-5-yl]-3-(1,4-dimethyl-1H-benzotriazol-5-yl)propanoate (50 mg) of Example 78(78f) in acetonitrile (3 mL) was added N,N-diisopropylethylamine (0.084 mL), and the mixture was stirred at 85° C. for 6 hr and cooled to room temperature. To the reaction mixture was added water, and the mixture was extracted with ethyl acetate. The organic layer was washed with saturated brine and dried over anhydrous sodium sulfate. The solvent was evaporated under reduced pressure and the obtained residue was purified by silica gel column chromatography [elution solvent:n-hexane/ethyl acetate=60/40-0/100(V/V), dichloromethane/methanol=100/0-90/10(V/V)] to give the title compound (40 mg, yield: 68%) as an oil.

79d (3R)-3-(1,4-Dimethyl-1H-benzotriazol-5-yl)-3-(7-{[(2R,5R*)-2-ethyl-7-hydroxy-5-methyl-2,3-dihydropyrido[2,3-f][1,4]oxazepin-4(5H)-yl]methyl}-1-benzothiophen-5-yl)propanoic acid Using ethyl (3R)-3-(1,4-dimethyl-1H-benzotriazol-5-yl)-3-(7-{[(2R,5R*)-2-ethyl-7-hydroxy-5-methyl-2,3-dihydropyrido[2,3-f][1,4]oxazepin-4(5H)-yl]methyl}-1-benzothiophen-5-yl)propanoate (24.0 mg) of Example 79(79c), the title compound (14 mg, yield: 61%) was obtained as a solid in the same manner as in Example 54(54i).

Example 80

(3S)-3-(1,4-Dimethyl-1H-benzotriazol-5-yl)-3-(7-{[(2R,5S)-7-hydroxy-2,5-dimethyl-2,3-dihydropyrido[2,3-f][1,4]oxazepin-4(5H)-yl]methyl}-1-benzothiophen-5-yl)propanoic acid

80a (2R)-1-{(E)-[1-(6-Chloro-3-fluoropyridin-2-yl)ethylidene]amino}propan-2-ol 1-(6-Chloro-3-fluoropyridin-2-yl)ethanone (WO 2014/166906) (12.5 g) and (2R)-1-aminopropan-2-ol (6.8 mL) were dissolved in chloroform (100 mL), and magnesium sulfate (86.0 g) was added. The reaction mixture was stirred under heating at 60° C. for 12 hr, and cooled to room temperature. To the reaction mixture was diluted with dichloromethane (100 mL), the insoluble matter was filtered off, and the filtrate was concentrated under reduced pressure to give an unpurified the title compound (16.61 g) as an oil.

80b (2R)-1-{[1-(6-Chloro-3-fluoropyridin-2-yl)ethyl]amino}propan-2-ol

Sodium borohydride (3.58 g) was slowly added to a solution of (2R)-1-{(E)-[1-(6-chloro-3-fluoropyridin-2-yl)ethylidene]amino}propan-2-ol (16.87 g) of Example 80(80a) in methanol (100 mL) at 20° C., and the mixture was stirred at 20° C. for 2 hr. The reaction mixture was concentrated under reduced pressure at 10° C., and ethyl acetate and water were added to the residue containing some remaining solvent, and the mixture was extracted three times with ethyl acetate. The combined organic layer was washed with saturated brine and then dried over anhydrous sodium sulfate. After filtration, the filtrate was concentrated under reduced pressure and the obtained residue was purified by preparative HPLC [column: Phenomenex Luna C18 (100 mm I.D.×250 mm), mobile phase: 0.225% aqueous formic acid solution/acetonitrile=99/1-79/21(V/V)] to give the title compound (5 g, yield: 29%) as an oil.

80c (2R)-7-Chloro-2,5-dimethyl-2,3,4,5-tetrahydropyrido[2,3-f][1,4]oxazepine To a solution of (2R)-1-{[1-(6-chloro-3-fluoropyridin-2-yl)ethyl]amino}propan-2-ol (5 g) of Example 80(80b) in dimethyl sulfoxide (180 mL) was added potassium tert-butoxide (1.0 M tetrahydrofuran solution) (29 mL), and the mixture was stirred under a nitrogen atmosphere at 20° C. for 12 hr. The reaction mixture was diluted with water (200 mL) and extracted three times with ethyl acetate. The combined organic layer was washed twice with saturated brine and dried over anhydrous sodium sulfate. After filtration, the solvent was evaporated under reduced pressure to give an unpurified title compound (4.57 g) as an oil.

80d tert-Butyl (2R,5S)-7-chloro-2,5-dimethyl-2,3-dihydropyrido[2,3-f][1,4]oxazepine-4(5H)-carboxylate To a solution of (2R)-7-chloro-2,5-dimethyl-2,3,4,5-tetrahydropyrido[2,3-f][1,4]oxazepine (4.07 g) of Example 80(80c) in dichloromethane (80 mL) were added di-tert-butyl bicarbonate (6.25 g) and triethylamine (6.91 g), and the mixture was stirred at 20° C. for 2 hr. The reaction mixture was concentrated under reduced pressure, and the obtained residue was purified by silica gel column chromatography [elution solvent:petroleum ether/ethyl acetate=100/0-5/1(V/V)]. As the compound eluted later, the title compound, tert-butyl (2R,5S)-7-chloro-2,5-dimethyl-2,3-dihydropyrido[2,3-f][1,4]oxazepine-4(5H)-carboxylate (3.2 g, yield: 53%) was obtained as an oil. As the compound eluted earlier, an isomer, tert-butyl (2R,5R)-7-chloro-2,5-dimethyl-2,3-dihydropyrido[2,3-f][1,4]oxazepine-4(5H)-carboxylate (2 g, yield: 33%) was obtained as an oil.

80e tert-Butyl (2R,5S)-7-hydroxy-2,5-dimethyl-2,3-dihydropyrido[2,3-f][1,4]oxazepine-4(5H)-carboxylate To a solution of tert-butyl (2R,5S)-7-chloro-2,5-dimethyl-2,3-dihydropyrido[2,3-f][1,4]oxazepine-4(5H)-carboxylate (3.6 g) of Example 80(80d) in 1,4-dioxane (50 mL) were added 5-(di-tert-butylphosphino)-1',3',5'-triphenyl-1'H-1,4'-bipyrazole (612 mg), tris(dibenzylideneacetone)dipalladium (0) (468 mg) and cesium hydroxide monohydrate (5.2 g), and the mixture was stirred under a nitrogen atmosphere at 100° C. for 12 hr. To the reaction mixture was added water, and the mixture was neutralized with 4M hydrochloric acid and extracted three times with ethyl acetate. The combined organic layer was washed with saturated brine and dried over anhydrous sodium sulfate. After filtration, the filtrate was concentrated under reduced pressure and the obtained residue was subjected to preparative HPLC [column: Phenomenex Luna C18 (70 mm I.D.×250 mm), mobile phase: 0.225% aqueous formic acid solution/acetonitrile=72/28-42/58(V/V)] to give the title compound (1.4 g, yield: 41%) as a solid.

80f (2R,5S)-2,5-Dimethyl-2,3,4,5-tetrahydropyrido[2,3-f][1,4]oxazepin-7-ol hydrochloride tert-Butyl (2R,5S)-7-hydroxy-2,5-dimethyl-2,3-dihydropyrido[2,3-f][1,4]oxazepine-4(5H)-carboxylate (1.4 g) of Example 80(80e) was dissolved in dichloromethane (30 mL), 4 M hydrogen chloride-1,4-dioxane solution (10 mL) was added and the mixture was stirred at 20° C. for 12 hr, and the solvent was evaporated under reduced pressure, followed by drying to give the title compound (1.09 g, yield: 99%) as a solid.

80g

Ethyl (3S)-3-(1,4-dimethyl-1H-benzotriazol-5-yl)-3-(7-{[(2R,5S)-7-hydroxy-2,5-dimethyl-2,3-dihydropyrido[2,3-f][1,4]oxazepin-4(5H)-yl]methyl}-1-benzothiophen-5-yl)propanoate Using ethyl (3S)-3-(1,4-dimethyl-1H-benzotriazol-5-yl)-3-[7-(hydroxymethyl)-1-benzothiophen-5-yl]propanoate (120 mg) of Example 7 (7a) and (2R,5S)-2,5-dimethyl-2,3,4,5-tetrahydropyrido[2,3-f][1,4]oxazepin-7-ol hydrochloride (80 mg) of Example 80(80f), the title compound (151 mg, yield: 88%) was obtained as a solid in the same manner as in Example 62(62d).

80h (3S)-3-(1,4-Dimethyl-1H-benzotriazol-5-yl)-3-(7-{[(2R,5S)-7-hydroxy-2,5-dimethyl-2,3-dihydropyrido[2,3-f][1,4]oxazepin-4(5H)-yl]methyl}-1-benzothiophen-5-yl)propanoic acid Using ethyl (3S)-3-(1,4-dimethyl-1H-benzotriazol-5-yl)-3-(7-{[(2R,5S)-7-hydroxy-2,5-dimethyl-2,3-dihydropyrido[2,3-f][1,4]oxazepin-4(5H)-yl]methyl}-1-benzothiophen-5-yl)propanoate (151 mg) of Example 80(80g), the title compound (118 mg, yield: 82%) was obtained as a solid in the same manner as in Example 62(62e).

Example 81

(3R)-3-(3,7-Dimethyl-3H-[1,2,3]triazolo[4,5-b]pyridin-6-yl)-3-(7-{[(2R,5S*)-2-ethyl-7-hydroxy-5-methyl-2,3-dihydropyrido[2,3-f][1,4]oxazepin-4(5H)-yl]methyl}-1-benzothiophen-5-yl)propanoic acid 81a Ethyl (3R)-3-(3,7-dimethyl-3H-[1,2,3]triazolo[4,5-b]pyridin-6-yl)-3-[7-(hydroxymethyl)-1-benzothiophen-5-yl]propanoate Bis(norbornadiene)rhodium(I) tetrafluoroborate (300 mg) and (2S,3S)-(−)-bis(diphenylphosphino)butane (346 mg) were dissolved in a mixed solvent of 1,4-dioxane (5 mL) and water (1 mL) and stirred for 5 min. This was added to a mixed solution of [5-(4,4,5,5-tetramethyl-1,3,2-dioxaborolan-2-yl)-1-benzothiophen-7-yl]methanol (7.1 g) of Example 1(1h) and ethyl (2E)-3-(3,7-dimethyl-3H-[1,2,3]triazolo[4,5-b]pyridin-6-yl)prop-2-enoate (WO 2015/092713) (4.0 g) in 1,4-dioxane (60 mL) and water (10 mL) at room temperature. 1 M aqueous potassium hydroxide solution (16 mL) was added thereto, and the mixture was heated to 50° C. and stirred under heating for 2 hr. The reaction mixture was allowed to cool to room temperature, and extracted with an aqueous ammonium chloride solution and ethyl acetate. The organic layer was washed with saturated brine and dried over anhydrous sodium sulfate. After filtration, the filtrate was concentrated under reduced pressure, and the residue was purified by silica gel column chromatography [eluent: hexane/ethyl acetate=1/1 (V/V)] to give 6.1 g (yield: 91%) of a mixture of both enantiomers of the title compound as a solid. This was subjected to chiral HPLC [column: CHIRALCEL OZ—H (20 mm I.D.×250 mm), mobile phase: n-hexane/ethanol=70/30 (V/V)] to give 4.0 g of ethyl (3R)-3-(3,7-dimethyl-3H-[1,2,3]triazolo[4,5- b]pyridin-6-yl)-3-[7-(hydroxymethyl)-1-benzothiophen-5-yl]propanoate as the first peak (yield: 66%).

Analysis HPLC conditions [column: CHIRALCEL OZ—H (4.6 mm I.D.×250 mm), mobile phase: n-hexane/ethanol=70/30(V/V), flow rate: 1.0 mL/min, temperature: 40° C., wavelength: 254 nm]; retention time: 10.10 min (the first peak)

81b

Ethyl (3R)-3-[7-(chloromethyl)-1-benzothiophen-5-yl]-3-(3,7-dimethyl-3H-[1,2,3]triazolo[4,5-b]pyridin-6-yl)propanoate To a solution of ethyl (3R)-3-(3,7-dimethyl-3H-5 [1,2,3]triazolo[4,5-b]pyridin-6-yl)-3-[7-(hydroxymethyl)-1-benzothiophen-5-yl]propanoate (80.0 mg) of Example 81(81a) in dichloromethane (2 mL) was added thionyl chloride (0.028 mL), and the mixture was stirred at room temperature for 2 hr. The solvent was evaporated under reduced pressure to give the title compound (111 mg, yield: quantitative) as an oil.

81c

Ethyl (3R)-3-(3,7-dimethyl-3H-[1,2,3]triazolo[4,5-b]pyridin-6-yl)-3-(7-{[(2R,5S*)-2-ethyl-7-hydroxy-5-methyl-2,3-dihydropyrido[2,3-f][1,4]oxazepin-4(5H)-yl]methyl}-1-benzothiophen-5-yl)propanoate To a suspension of (2R,5S*)-2-ethyl-5-methyl-2,3,4,5-tetrahydropyrido[2,3-f][1,4]oxazepin-7-ol hydrochloride (44.0 mg) of Example 78(78g) and ethyl (3R)-3-[7-(chloromethyl)-1-benzothiophen-5-yl]-3-(3,7-dimethyl-3H-[1,2,3]triazolo[4,5-b]pyridin-6-yl)propanoate (85 mg) of Example 81(81b) in acetonitrile (3 mL) was added N,N-diisopropylethylamine (0.246 mL) and the mixture was stirred at 85° C. for 6 hr and cooled to room temperature. Water was added to the reaction mixture, and the mixture was extracted with ethyl acetate. The organic layer was washed with saturated brine and dried over anhydrous sodium sulfate. The solvent was evaporated under reduced pressure and the obtained residue was purified by silica gel column chromatography [elution solvent:n-hexane/ethyl acetate=60/40-0/100(V/V), dichloromethane/methanol=100/0-90/10(V/V)] to give the title compound (89 mg, yield: 82%) as an oil.

81d (3R)-3-(3,7-Dimethyl-3H-[1,2,3]triazolo[4,5-b]pyridin-6-yl)-3-(7-{[(2R,5S*)-2-ethyl-7-hydroxy-5-methyl-2,3-dihydropyrido[2,3-f][1,4]oxazepin-4(5H)-yl]methyl}-1-benzothiophen-5-yl)propanoic acid Using ethyl (3R)-3-(3,7-dimethyl-3H-[1,2,3]triazolo[4,5-b]pyridin-6-yl)-3-(7-{[(2R,5S*)-2-ethyl-7-hydroxy-5-methyl-2,3-dihydropyrido[2,3-f][1,4]oxazepin-4(5H)-yl]methyl}-1-benzothiophen-5-yl)propanoate (89.0 mg) of Example 81(81c), the title compound (46 mg, yield: 54%) was obtained as a solid in the same manner as in Example 54(54i).

Example 82

(3R)-3-(1,4-Dimethyl-1H-benzotriazol-5-yl)-3-(7-{[(2R,5S)-7-hydroxy-2,5-dimethyl-2,3-dihydropyrido[2,3-f][1,4]oxazepin-4(5H)-yl]methyl}-1-benzothiophen-5-yl)propanoic acid 82a Ethyl (3R)-3-(1,4-dimethyl-1H-benzotriazol-5-yl)-3-(7-{[(2R,5S)-7-hydroxy-2,5-dimethyl-2,3-dihydropyrido[2,3-f][1,4]oxazepin-4(5H)-yl]methyl}-1-benzothiophen-5-yl)propanoate To a suspension of (2R,5S)-2,5-dimethyl-2,3,4,5-tetrahydropyrido[2,3-f][1,4]oxazepin-7-ol hydrochloride (50.0 mg) of Example 80(80f) and ethyl (3R)-3-[7-(chloromethyl)-1-benzothiophen-5-yl]-3-(1,4-dimethyl-1H-benzotriazol-5-yl)propanoate (101 mg) of Example 78(78f) in acetonitrile (3 mL) was added N,N-diisopropylethylamine (0.297 mL), and the mixture was stirred at 85° C. for 12 hr and cooled to room temperature. To the reaction mixture was added water, and the mixture was extracted with ethyl acetate. The organic layer was washed with saturated brine and dried over anhydrous sodium sulfate. The solvent was evaporated under reduced pressure and the obtained residue was purified by silica gel column chromatography [elution solvent: n-hexane/ethyl acetate=60/40-0/100(V/V), dichloromethane/methanol=100/0-90/10(V/V)] to give the title compound (96 mg, yield: 76%) as an oil.

82b (3R)-3-(1,4-Dimethyl-1H-benzotriazol-5-yl)-3-(7-{[(2R,5S)-7-hydroxy-2,5-dimethyl-2,3-dihydropyrido[2,3-f][1,4]oxazepin-4(5H)-yl]methyl}-1-benzothiophen-5-yl)propanoic acid Using ethyl (3R)-3-(1,4-dimethyl-1H-benzotriazol-5-yl)-3-(7-{[(2R,5S)-7-hydroxy-2,5-dimethyl-2,3-dihydropyrido[2,3-f][1,4]oxazepin-4(5H)-yl]methyl}-1-benzothiophen-5-yl)propanoate (96.0 mg) of Example 82(82a), the title compound (86 mg, yield: 94%) was obtained as a solid in the same manner as in Example 54(54i).

Example 83

(3R)-3-(7-{[(2R,5S*)-2-Cyclopropyl-7-hydroxy-5-methyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoic acid 83a 2-[(2R)-2-Cyclopropyl-2-hydroxyethyl]-1H-isoindole-1,3(2H)-dione 2-(2-Cyclopropyl-2-oxoethyl)-1H-isoindole-1,3(2H)-dione (Angew. Chem. Int. Ed. (2020), 59(34), 14265-14269) (10.0 g) was suspended in tetrahydrofuran (87 mL) and, under a nitrogen atmosphere at room temperature, (−)—B-chlorodiisopinocampheylborane (1.7 M n-hexane solution) (77 mL) was added dropwise over 14 min, and the mixture was stirred at room temperature for 37 hr. To the reaction mixture was added 2M hydrochloric acid, and the mixture was stirred at room temperature for 20 min and extracted with ethyl acetate. The organic layer was washed successively with saturated aqueous sodium hydrogen carbonate solution and saturated brine and dried over anhydrous sodium sulfate. The solvent was evaporated under reduced pressure and the obtained residue was purified by silica gel column chromatography [elution solvent:n-hexane/ethyl acetate=90/10-50/50(V/V)]. The obtained residue was recrystallized from a mixed solvent of ethyl acetate (3.6 V/W) and n-hexane (2.0 V/W) to give the title compound (4.79 g, yield: 48%) as a solid.

83b

2-[(2R)-2-{[tert-Butyl(dimethyl)silyl]oxy}-2-cyclopropylethyl]-1H-isoindole-1,3(2H)-dione 2-[(2R)-2-Cyclopropyl-2-hydroxyethyl]-1H-isoindole-1,3(2H)-dione (4.79 g) of Example 83(83a) was dissolved in N,N-dimethylformamide (69 mL), imidazole (2.82 g) and tert-butyldimethylchlorosilane (4.69 g) were added, and the mixture was stirred at room temperature for 30 min. To the reaction mixture were added imidazole (2.82 g) and tert-butyldimethylchlorosilane (4.69 g) and the mixture was stirred at room temperature for 30 min. Further, imidazole (705 mg) and tert-butyldimethylchlorosilane (1.56 g) were added thereto, and the mixture was stirred at room temperature for 30 min. To the reaction mixture was added water, and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=100/0-90/10(V/V)] to give the title compound (9.38 g, yield: quantitative) as an oil.

83c (2R)-2-{[tert-Butyl(dimethyl)silyl]oxy}-2-cyclopropylmethanamine

2-[(2R)-2-{[tert-Butyl(dimethyl)silyl]oxy}-2-cyclopropylethyl]-1H-isoindole-1,3(2H)-dione (9.38 g) of Example 83(83b) was dissolved in ethanol (130 mL), hydrazine monohydrate (6.0 mL) was added, and the mixture was stirred at 80° C. for 1.5 hr. The reaction mixture was allowed to cool to room temperature and insoluble matter was filtered off and washed with ethyl acetate. Water was added to the filtrate, and the mixture was extracted with ethyl acetate. The organic layer was washed with saturated brine and dried over anhydrous sodium sulfate, and the solvent was evaporated under reduced pressure. The obtained residue was subjected to DIOL silica gel column chromatography [elution solvent:n-hexane/ethyl acetate=50/50-0/100(V/V), chloroform/methanol=100/0-95/5(V/V)] to give the title compound (3.90 g, yield: 85%) as an oil.

83d (2R)-2-{[tert-Butyl(dimethyl)silyl]oxy}-2-cyclopropyl-N-(4-methoxybenzyl)ethanamine (2R)-2-{[tert-Butyl(dimethyl)silyl]oxy}-2-cyclopropylethanamine (3.55 g) of Example 83(83c) and 4-methoxybenzaldehyde (1.85 mL) were dissolved in dichloromethane (64 mL), anhydrous magnesium sulfate (3.86 g) and acetic acid (0.18 mL) were added, and the mixture was stirred at room temperature for 1 hr. Sodium triacetoxyborohydride (6.80 g) was added thereto, and the mixture was stirred at room temperature for hr. To the reaction mixture was added saturated aqueous sodium hydrogen carbonate solution, and the mixture was extracted with chloroform. The organic layer was dried over anhydrous sodium sulfate, and the solvent was evaporated under reduced pressure. The obtained residue was purified by silica gel column chromatography [elution solvent:chloroform/methanol=100/0-95/5(V/V)] to give the title compound (4.55 g, yield: 89%) as an oil.

83e 1-(6-Bromo-3-fluoropyridin-2-yl)ethyl methanesulfonate 1-(6-Bromo-3-fluoropyridin-2-yl)ethanol (WO 2012/139425) (3.08 g) was dissolved in dichloromethane (55 mL), triethylamine (3.90 mL) was added, then methanesulfonylchloride (1.63 mL) was added at 0° C., and the mixture was stirred at 0° C. for 30 min. To the reaction mixture was added water, and the mixture was extracted with chloroform. The organic layers were combined and dried over anhydrous sodium sulfate. The solvent was evaporated under reduced pressure to give the title compound (4.54 g, yield: quantitative) as an oil.

83f (2R)—N-[1-(6-Bromo-3-fluoropyridin-2-yl)ethyl]-2-{[tert-butyl(dimethyl)silyl]oxy}-2-cyclopropyl-N-(4-methoxybenzyl)ethanamine (2R)-2-{[tert-Butyl(dimethyl)silyl]oxy}-2-cyclopropyl-N-(4-methoxybenzyl)ethanamine (4.87 g) of Example 83(83d) and 1-(6-bromo-3-fluoropyridin-2-yl)ethyl methanesulfonate (4.75 g) of Example 83(83e) were dissolved in acetonitrile (48 mL), N,N-diisopropylethylamine (5.05 mL) was added, and the mixture was heated under reflux for 38 hr. The reaction mixture was allowed to cool to room temperature, water was added, and the mixture was extracted with ethyl acetate. The organic layer was washed successively with water and saturated brine, dried over anhydrous sodium sulfate, and the solvent was evaporated under reduced pressure. The obtained residue was purified by silica gel column chromatography [elution solvent:n-hexane/ethyl acetate=100/0-92/8(V/V)] to give the title compound (5.89 g, yield: 76%) as an oil.

83g (1R)-2-{[1-(6-Bromo-3-fluoropyridin-2-yl)ethyl](4-methoxybenzyl)amino}-1-cyclopropylethanol (2R)—N-[1-(6-Bromo-3-fluoropyridin-2-yl)ethyl]-2-{[tert-butyl(dimethyl)silyl]oxy}-2-cyclopropyl-N-(4-methoxybenzyl)ethanamine (5.89 g) of Example 83(83f) was dissolved in tetrahydrofuran (22 mL), tetrabutylammonium fluoride (1 M tetrahydrofuran solution) (22 mL) was added, and the mixture was stirred at 40° C. for 14 hr. The reaction mixture was allowed to cool to room temperature, saturated aqueous sodium hydrogen carbonate solution was added, and the mixture was extracted with ethyl acetate. The organic layer was washed with saturated brine and dried over anhydrous sodium sulfate, and the solvent was evaporated under reduced pressure. The obtained residue was purified by silica gel column chromatography [elution sol-

83h (2R,5S\*)-7-Bromo-2-cyclopropyl-4-(4-methoxybenzyl)-5-methyl-2,3,4,5-tetrahydropyrido[2,3-f][1,4]oxazepine

83i (2R,5R\*)-7-Bromo-2-cyclopropyl-4-(4-methoxybenzyl)-5-methyl-2,3,4,5-tetrahydropyrido[2,3-f][1,4]oxazepine 60% Sodium hydride (1.10 g) was suspended in N,N-dimethylformamide (65 mL), and a solution of (1R)-2-{[1-(6-bromo-3-fluoropyridin-2-yl)ethyl](4-methoxybenzyl)amino}-1-cyclopropylethanol (4.18 g) in tetrahydrofuran (65 mL) was added dropwise over 40 min under an argon atmosphere and the mixture was stirred at 60° C. for 2 hr. 60% Sodium hydride (733 mg) was added to the reaction mixture, and the mixture was stirred at 60° C. for 1 hr, and then 60% sodium hydride (183 mg) was added and the mixture was stirred at 60° C. for another 1 hr. The reaction mixture was allowed to cool to room temperature, water was added, and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=95/5-85/15 (V/V)] to give (2R,5R\*)-7-bromo-2-cyclopropyl-4-(4-methoxybenzyl)-5-methyl-2,3,4,5-tetrahydropyrido[2,3-f][1,4]oxazepine (1.36 g, yield: 37%) of Example 83(83i), which is a compound eluted earlier, as an oil. In addition, (2R,5S\*)-7-bromo-2-cyclopropyl-4-(4-methoxybenzyl)-5-methyl-2,3,4,5-tetrahydropyrido[2,3-f][1,4]oxazepine (792 mg, yield: 21%) of Example 83(83h), which is a compound eluted later, was obtained as an oil.

83j (2R,5S\*)-2-Cyclopropyl-4-(4-methoxybenzyl)-5-methyl-2,3,4,5-tetrahydropyrido[2,3-f][1,4]oxazepin-7-ol (2R,5S\*)-7-Bromo-2-cyclopropyl-4-(4-methoxybenzyl)-5-methyl-2,3,4,5-tetrahydropyrido[2,3-f][1,4]oxazepine (790 mg) of Example 83(83h) was dissolved in 1,4-dioxane (14 mL), and cesium hydroxide monohydrate (987 mg), 5-(di-tert-butylphosphino)-1',3',5'-triphenyl-1'H-1,4'-bipyrazole (99 mg) and bis(dibenzylideneacetone)palladium (0) (56 mg) were added, and the mixture was stirred at 100° C. for 4 hr under a nitrogen atmosphere. The reaction mixture was allowed to cool to room temperature, saturated aqueous ammonium chloride solution was added, and the mixture was extracted with ethyl acetate. The organic layer was washed with saturated brine and dried over anhydrous sodium sulfate, and the solvent was evaporated under reduced pressure. The obtained residue was purified by silica gel column chromatography [elution solvent:n-hexane/ethyl acetate=50/50-0/100(V/V), chloroform/methanol=100/0-95/5(V/V)] to give the title compound (493 mg, yield: 74%) as a solid.

83k (2R,5S\*)-2-Cyclopropyl-5-methyl-2,3,4,5-tetrahydropyrido[2,3-f][1,4]oxazepin-7-ol hydrochloride (2R,5S\*)-2-Cyclopropyl-4-(4-methoxybenzyl)-5-methyl-2,3,4,5-tetrahydropyrido[2,3-f][1,4]oxazepin-7-ol (490 mg) of Example 83(83j) was dissolved in trifluoroacetic acid (14 mL), anisole (1.6 mL) was added, and the mixture was heated under reflux for 18 hr. The reaction mixture was allowed to cool to room temperature, toluene was added to perform azeotropic distillation. The obtained residue was dissolved in ethyl acetate (14 mL), 1 M hydrogen chloride-ethyl acetate solution (4.3 mL) was added, and the mixture was stirred at room temperature for 30 min. The solid was collected by filtration to give a mixture (402 mg) containing the title compound as a solid.

83l

Ethyl (3R)-3-(7-{[(2R,5S\*)-2-cyclopropyl-7-hydroxy-5-methyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoate Ethyl (3R)-3-(1,4-dimethyl-1H-benzotriazol-5-yl)-3-[7-(hydroxymethyl)-1-benzothiophen-5-yl]propanoate (369 mg) of Example 7(7b) was dissolved in dichloromethane (3.6 mL), dimethyl sulfoxide (0.32 mL) and N,N-diisopropylethylamine (0.47 mL) were added, and then sulfur trioxide-pyridine complex (430 mg) was added at 0° C. and the mixture was stirred at room temperature for 1 hr. Water was added to the reaction mixture, and the mixture was extracted with chloroform. The organic layer was dried over anhydrous sodium sulfate, and the solvent was evaporated under reduced pressure to obtain 504 mg of residue. The obtained residue (252 mg) was dissolved in dichloromethane (1.8 mL), and (2R,5S\*)-2-cyclopropyl-5-methyl-2,3,4,5-tetrahydropyrido[2,3-f][1,4]oxazepin-7-ol hydrochloride (139 mg) of Example 83(83k), N,N-diisopropylethylamine (0.094 mL), 2 drops of acetic acid and anhydrous magnesium sulfate (108 mg) were added, and the mixture was stirred at room temperature for 20 min. Sodium triacetoxyborohydride (238 mg) was added thereto, and the mixture was stirred at room temperature for 64.5 hr. Saturated aqueous sodium hydrogen carbonate solution was added to the reaction mixture, and the mixture was extracted with ethyl acetate. The organic layer was washed with saturated brine, dried over anhydrous sodium sulfate, and the solvent was evaporated under reduced pressure. The obtained residue was purified by silica gel column chromatography [elution solvent:n-hexane/ethyl acetate=50/50-0/100(V/V), chloroform/methanol=100/0-95/5(V/V)] to give the title compound (223 mg, yield: 71%) as an oil.

83m (3R)-3-(7-{[(2R,5S\*)-2-Cyclopropyl-7-hydroxy-5-methyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoic acid Using ethyl (3R)-3-(7-{[(2R,5S\*)-2-cyclopropyl-7-hydroxy-5-methyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoate (220 mg) of Example

--- vent:n-hexane/ethyl acetate=95/5-70/30(V/V)] to give the title compound (4.18 g, yield: 83%) as an oil.

83(831), the title compound (108 mg, yield: 86%) was obtained as a solid in the same manner as in Example 2(2c).

Example 84

(3R)-3-(7-{[(2R,5R*)-2-Cyclopropyl-7-hydroxy-5-methyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoic acid

84a (2R,5R*)-2-Cyclopropyl-4-(4-methoxybenzyl)-5-methyl-2,3,4,5-tetrahydropyrido[2,3-f][1,4]oxazepin-7-ol Using (2R,5R*)-7-bromo-2-cyclopropyl-4-(4-methoxybenzyl)-5-methyl-2,3,4,5-tetrahydropyrido[2,3-f][1,4]oxazepine (1.30 g) of Example 83(83i), the title compound (922 mg, yield: 84%) was obtained as a solid in the same manner as in Example 83(83j).

84b (2R,5R*)-2-Cyclopropyl-5-methyl-2,3,4,5-tetrahydropyrido[2,3-f][1,4]oxazepin-7-ol hydrochloride Using (2R,5R*)-2-cyclopropyl-4-(4-methoxybenzyl)-5-methyl-2,3,4,5-tetrahydropyrido[2,3-f][1,4]oxazepin-7-ol (920 mg) of Example 84(84a), a mixture (801 mg) containing the title compound was obtained as a solid in the same manner as in Example 83(83k).

84c

Ethyl (3R)-3-(7-{[(2R,5R*)-2-cyclopropyl-7-hydroxy-5-methyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoate Using (2R,5R*)-2-cyclopropyl-5-methyl-2,3,4,5-tetrahydropyrido[2,3-f][1,4]oxazepin-7-ol hydrochloride (139 mg) of Example 84(84b), the title compound (202 mg, yield: 49%) was obtained as an oil in the same manner as in Example 83(831).

84d (3R)-3-(7-{[(2R,5R*)-2-Cyclopropyl-7-hydroxy-5-methyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoic acid Ethyl (3R)-3-(7-{[(2R,5R*)-2-Cyclopropyl-7-hydroxy-5-methyl-2,3-dihydropyrido[2,3-f][1,4]oxazepin-4(5H)-yl]methyl}-1-benzothiophen-5-yl)-3-(1,4-dimethyl-1H-benzotriazol-5-yl)propanoate (200 mg) of Example 84(84c) was dissolved in a mixed solvent of tetrahydrofuran (1.3 mL) and methanol (0.65 mL), and 1 M aqueous lithium hydroxide solution (0.65 mL) was added and the mixture was stirred at 40° C. for 4.5 hr. 1 M aqueous lithium hydroxide solution (0.65 mL) was added to the reaction mixture and the mixture was stirred at 40° C. for 1.5 hr, and at 60° C. for 1 hr. The reaction mixture was allowed to cool to room temperature, water was added, and washed with diethylether. 1M Hydrochloric acid was added to the aqueous layer and the mixture was extracted with ethyl acetate. The organic layer was washed with saturated brine and dried over anhydrous sodium sulfate, and the solvent was evaporated under reduced pressure. The obtained residue was purified by silica gel column chromatography [elution solvent:n-hexane/ethyl acetate=50/50-0/100(V/V), chloroform/methanol=100/0-95/5(V/V)]. To the obtained residue were added ethyl acetate and n-hexane, and the solid was collected by filtration to give the title compound (137 mg, yield: 73%) as a solid.

Example 85

(3R)-3-(7-{[(2R,5R*)-2-Cyclopropyl-7-hydroxy-5-methyl-2,3-dihydropyrido[2,3-f][1,4]oxazepin-4(5H)-yl]methyl}-1-benzothiophen-5-yl)-3-(3,7-dimethyl-3H-[1,2,3]triazolo[4,5-b]pyridin-6-yl)propanoic acid

85a

Ethyl (3R)-3-(7-{[(2R,5R*)-2-cyclopropyl-7-hydroxy-5-methyl-2,3-dihydropyrido[2,3-f][1,4]oxazepin-4(5H)-yl]methyl}-1-benzothiophen-5-yl)-3-(3,7-dimethyl-3H-[1,2,3]triazolo[4,5-b]pyridin-6-yl)propanoate Ethyl (3R)-3-(3,7-dimethyl-3H-[1,2,3]triazolo[4,5-b]pyridin-6-yl)-3-[7-(hydroxymethyl)-1-benzothiophen-5-yl]propanoate (369 mg) of Example 81(81a) was dissolved in dichloromethane (3.6 mL), dimethyl sulfoxide (0.32 mL), N,N-diisopropylethylamine (0.47 mL) and sulfur trioxide-pyridine complex (430 mg) were added, and the mixture was stirred at room temperature for 1.5 hr. Water was added to the reaction mixture, and the mixture was extracted with chloroform. The organic layer was washed with saturated brine and dried over anhydrous sodium sulfate, and the solvent was evaporated under reduced pressure to obtain 447 mg of residue. The obtained residue (211 mg) was dissolved in dichloromethane (1.8 mL), and (2R,5R*)-2-cyclopropyl-5-methyl-2,3,4,5-tetrahydropyrido[2,3-f][1,4]oxazepin-7-ol hydrochloride (131 mg) of Example 84(84b), N,N-diisopropylethylamine (0.089 mL), 2 drops of acetic acid and anhydrous magnesium sulfate (102 mg) were added, and the mixture was stirred at room temperature for 30 min. Sodium triacetoxyborohydride (225 mg) was added thereto, and the mixture was stirred at 35° C. for 2 hr. Saturated aqueous sodium hydrogen carbonate solution was added to the reaction mixture, and the mixture was extracted with ethyl acetate and washed with saturated brine. The organic layer was dried over anhydrous sodium sulfate, and the solvent was evaporated under reduced pressure. The obtained residue was purified by silica gel column chromatography [elution solvent:n-hexane/ethyl acetate=50/50-0/100(V/V), chloroform/methanol=100/0-90/10(V/V)] to give the title compound (145 mg, yield: 56%) as an oil.

85b (3R)-3-(7-{[(2R,5R*)-2-Cyclopropyl-7-hydroxy-5-methyl-2,3-dihydropyrido[2,3-f][1,4]oxazepin-4(5H)-yl]methyl}-1-benzothiophen-5-yl)-3-(3,7-dimethyl-3H-[1,2,3]triazolo[4,5-b]pyridin-6-yl)propanoic acid Using ethyl (3R)-3-(7-{[(2R,5R*)-2-cyclopropyl-7-hydroxy-5-methyl-2,3-dihydropyrido[2,3-f][1,4]oxazepin-4(5H)-yl]methyl}-1-benzothiophen-5-yl)-3-(3,7-dimethyl- 3H-[1,2,3]triazolo[4,5-b]pyridin-6-yl)propanoate (143 mg) of Example 85(85a), the title compound (122 mg, yield: 89%) was obtained as a solid in the same manner as in Example 1(1k).

Example 86

(3R)-3-(7-{[(2R,5S*)-2-Cyclopropyl-7-hydroxy-5-methyl-2,3-dihydropyrido[2,3-f][1,4]oxazepin-4(5H)-yl]methyl}-1-benzothiophen-5-yl)-3-(3,7-dimethyl-3H-[1,2,3]triazolo[4,5-b]pyridin-6-yl)propanoic acid 86a Ethyl (3R)-3-(7-{[(2R,5S*)-2-cyclopropyl-7-hydroxy-5-methyl-2,3-dihydropyrido[2,3-f][1,4]oxazepin-4(5H)-yl]methyl}-1-benzothiophen-5-yl)-3-(3,7-dimethyl-3H-[1,2,3]triazolo[4,5-b]pyridin-6-yl)propanoate Using (2R,5S*)-2-cyclopropyl-5-methyl-2,3,4,5-tetrahydropyrido[2,3-f][1,4]oxazepin-7-ol hydrochloride (131 mg) of Example 83(83k), the title compound (172 mg, yield: 66%) was obtained as an oil in the same manner as in Example 85(85a).

86b (3R)-3-(7-{[(2R,5S*)-2-Cyclopropyl-7-hydroxy-5-methyl-2,3-dihydropyrido[2,3-f][1,4]oxazepin-4(5H)-yl]methyl}-1-benzothiophen-5-yl)-3-(3,7-dimethyl-3H-[1,2,3]triazolo[4,5-b]pyridin-6-yl)propanoic acid Using ethyl (3R)-3-(7-{[(2R,5S*)-2-cyclopropyl-7-hydroxy-5-methyl-2,3-dihydropyrido[2,3-f][1,4]oxazepin-4(5H)-yl]methyl}-1-benzothiophen-5-yl)-3-(3,7-dimethyl-3H-[1,2,3]triazolo[4,5-b]pyridin-6-yl)propanoate (170 mg) of Example 86(86a), the title compound (111 mg, yield: 69%) was obtained as a solid in the same manner as in Example 1(1k).

Example 87

(3R)-3-(1,4-Dimethyl-1H-benzotriazol-5-yl)-3-(7-{[(5'S*)-7'-hydroxy-5'-methyl-3'H-spiro[cyclopropane-1,2'-pyrido[2,3-f][1,4]oxazepin]-4' (5' H)-yl]methyl}-1-benzothiophen-5-yl)propanoic acid 87a 1-{[Bis(4-methoxybenzyl)amino]methyl}cyclopropanol Ethyl glycinate hydrochloride (64.1 g) was suspended in acetonitrile (920 mL), potassium carbonate (191 g), 4-methoxybenzyl chloride (125 mL) and sodium iodide (6.88 g) were added, and the mixture was stirred at 50° C. for 4 hr. The reaction mixture was allowed to cool to room temperature, insoluble matter was filtered off, and the mixture was washed with ethyl acetate. The filtrate was concentrated under reduced pressure to obtain 158.8 g of residue. The obtained residue (91.7 g) was dissolved in tetrahydrofuran (370 mL), and tetraisopropyl orthotitanate (19.0 mL) was added under a nitrogen atmosphere. Ethyl magnesium bromide (1 M tetrahydrofuran solution) (800 mL) was added dropwise thereto over 50 min at 0° C., and the mixture was stirred at room temperature for 35 min. A saturated aqueous ammonium chloride solution was added to the reaction mixture, and the mixture was filtered through celite to remove insoluble matter, and successively washed with a saturated aqueous ammonium chloride solution, water and ethyl acetate. A saturated aqueous sodium hydrogen carbonate solution was added to the filtrate, and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=100/0-80/20(V/V)] to give the title compound (70.2 g, yield: 81%) as an oil.

87b

1-{[(4-Methoxybenzyl)amino]methyl}cyclopropanol

20% Palladium hydroxide-activated carbon (3.5 g) was suspended in a small amount of ethyl acetate, and a solution of 1-{[bis(4-methoxybenzyl)amino]methyl}cyclopropanol (69.5 g) of Example 87(87a) in methanol (1.9 L) and acetic acid (210 mL) were added, and catalytic hydrogenation was performed at room temperature under an atmospheric pressure for 40 min and at 50° C. under an atmospheric pressure for 105 min. The reaction mixture was allowed to cool to room temperature, celite was added, and the mixture was filtered to remove insoluble matter, and washed with ethyl acetate. The filtrate was concentrated under reduced pressure and azeotropically distilled with toluene. The obtained residue was purified by NH silica gel column chromatography [elution solvent:n-hexane/ethyl acetate=100/0-0/100 (V/V)] to give the title compound (42.0 g, yield: 76%) as a solid.

87c 1-({[1-(6-Bromo-3-fluoropyridin-2-yl)ethyl](4-methoxybenzyl)amino}methyl)cyclopropanol 1-(6-Bromo-3-fluoropyridin-2-yl)ethanol (WO 2012/139425) (1.35 g) was dissolved in dichloromethane (25 mL), triethylamine (1.71 mL) was added, methanesulfonyl chloride (0.71 mL) was added dropwise at 0° C., and the mixture was stirred at 0° C. for 15 min. Water was added to the reaction mixture, and the mixture was extracted with chloroform. The organic layer was dried over anhydrous sodium sulfate, and the solvent was evaporated under reduced pressure. The obtained residue was dissolved in acetonitrile (31 mL), 1-{[(4-methoxybenzyl)amino]methyl}cyclopropanol (1.59 g) of Example 87 (87b) and potassium carbonate (2.13 g) were added, and the mixture was stirred at 50° C. for 17 hr. The reaction mixture was allowed to cool to room temperature, ethyl acetate was added, and insoluble matter was filtered off. The filtrate was concentrated under reduced pressure, and the obtained residue was purified by silica gel column chromatography [elution solvent:n-hexane/ethyl acetate=95/5-70/30(V/V)] to give the title compound (338 mg, yield: 13%) as an oil.

87d

7'-Bromo-4'-(4-methoxybenzyl)-5'-methyl-4',5'-dihydro-3'H-spiro[cyclopropane-1,2'-pyrido[2,3-f][1,4]oxazepine]

60% Sodium hydride (900 mg) was suspended in N,N-dimethylformamide (53 mL), and a solution of 1-({[1-(6- bromo-3-fluoropyridin-2-yl)ethyl](4-methoxybenzyl) amino}methyl)cyclopropanol (3.24 g) of Example 87 (87c) in tetrahydrofuran (43 mL) was added dropwise over 15 min at 60° C. under an argon atmosphere, and the mixture was stirred at 60° C. for 30 min. The reaction mixture was allowed to cool to room temperature, water was added, and the mixture was extracted with ethyl acetate. The organic layer was successively washed with water and saturated brine, dried over anhydrous sodium sulfate, and the solvent was evaporated under reduced pressure. The obtained residue was purified by silica gel column chromatography [elution solvent:n-hexane/ethyl acetate=95/5-70/30(V/V)] to give the title compound (2.64 g, yield: 90%) as an oil.

87e

4'-(4-Methoxybenzyl)-5'-methyl-4',5'-dihydro-3'H-spiro[cyclopropane-1,2'-pyrido[2,3-f][1,4]oxazepin]-7'-ol Using 7'-bromo-4'-(4-methoxybenzyl)-5'-methyl-4',5'-dihydro-3'H-spiro[cyclopropane-1,2'-pyrido[2,3-f][1,4]oxazepine] (2.54 g) of Example 87(87d), the title compound (1.70 g, yield: 80%) was obtained as a solid in the same manner as in Example 83(83j).

87f (5'S*)-4'-(4-Methoxybenzyl)-5'-methyl-4',5'-dihydro-3'H-spiro[cyclopropane-1,2'-pyrido[2,3-f][1,4]oxazepin]-7'-ol (87g) (5'R*)-4'-(4-Methoxybenzyl)-5'-methyl-4',5'-dihydro-3'H-spiro[cyclopropane-1,2'-pyrido[2,3-f][1,4]oxazepin]-7'-ol 4'-(4-Methoxybenzyl)-5'-methyl-4',5'-dihydro-3'H-spiro[cyclopropane-1,2'-pyrido[2,3-f][1,4]oxazepin]-7'-ol (1.5 g) of Example 87(87e) was subjected to chiral HPLC [column: CHIRALPAK IF (20 mm I.D.×250 mm), mobile phase: n-hexane/ethanol=70/30(V/V)] to obtain 683 mg of (5'S*)-4'-(4-methoxybenzyl)-5'-methyl-4',5'-dihydro-3'H-spiro[cyclopropane-1,2'-pyrido[2,3-f][1,4]oxazepin]-7'-ol as the first peak (yield: 46%).
Similarly, 709 mg of (5'R*)-4'-(4-methoxybenzyl)-5'-methyl-4',5'-dihydro-3'H-spiro[cyclopropane-1,2'-pyrido[2,3-f][1,4]oxazepin]-7'-ol was obtained as the second peak (yield: 47%).
Analysis HPLC conditions [column: CHIRALPAK IF (4.6 mm I.D.×250 mm), mobile phase: n-hexane/ethanol=70/30(V/V), flow rate: 1.0 mL/min, temperature: 40° C., wavelength: 254 nm]; retention time: 5.910 min (the first peak), 8.600 min (the second peak)

87h (5'S*)-5'-Methyl-4',5'-dihydro-3'H-spiro[cyclopropane-1,2'-pyrido[2,3-f][1,4]oxazepin]-7'-ol A mixture of (5'S*)-4'-(4-methoxybenzyl)-5'-methyl-4',5'-dihydro-3'H-spiro[cyclopropane-1,2'-pyrido[2,3-f][1,4]oxazepin]-7'-ol (683 mg) of Example 87(87f), trifluoroacetic acid (10 mL) and anisole (2 mL) was stirred at 90° C. for 5.5 hr. The solvent was evaporated under reduced pressure, and azeotropic distillation with toluene was performed. The obtained residue was purified by silica gel column chromatography [elution solvent:ethyl acetate/methanol=100/0-90/10(V/V)] to give the title compound (316 mg, yield: 73%) as a solid.

87i

Ethyl (3R)-3-(1,4-dimethyl-1H-benzotriazol-5-yl)-3-(7-{[(5'S*)-7'-hydroxy-5'-methyl-3'H-spiro[cyclopropane-1,2'-pyrido[2,3-f][1,4]oxazepin]-4'(5'H)-yl] methyl}-1-benzothiophen-5-yl)propanoate Using ethyl (3R)-3-(1,4-dimethyl-1H-benzotriazol-5-yl)-3-[7-(hydroxymethyl)-1-benzothiophen-5-yl]propanoate (540 mg) of Example 7(7b) and (5'S*)-5'-methyl-4',5'-dihydro-3'H-spiro[cyclopropane-1,2'-pyrido[2,3-f][1,4]oxazepin]-7'-ol (226 mg) of Example 87(87h), the title compound (477 mg, yield: 73%) was obtained as an oil in the same manner as in Example 62(62d).

87j (3R)-3-(1,4-Dimethyl-1H-benzotriazol-5-yl)-3-(7-{[(5'S*)-7'-hydroxy-5'-methyl-3'H-spiro[cyclopropane-1,2'-pyrido[2,3-f][1,4]oxazepin]-4'(5'H)-yl] methyl}-1-benzothiophen-5-yl)propanoic acid To a solution of ethyl (3R)-3-(1,4-dimethyl-1H-benzotriazol-5-yl)-3-(7-{[(5'S*)-7'-hydroxy-5'-methyl-3'H-spiro[cyclopropane-1,2'-pyrido[2,3-f][1,4]oxazepin]-4'(5'H)-yl] methyl}-1-benzothiophen-5-yl)propanoate (477 mg) of Example 87(87i) in ethanol (10 mL) was added 1M aqueous sodium hydroxide solution (2.39 mL), and the mixture was stirred at 60° C. for 3 hr. To the reaction mixture were added 1M hydrochloric acid (2.39 mL) and water, the solvent was evaporated under reduced pressure, and the obtained residue was purified by silica gel column chromatography [elution solvent:ethyl acetate/methanol=100/0-90/10(V/V)]. To the eluted compound were added ethyl acetate and n-hexane, and the mixture was subjected to an ultrasonic treatment. The solid was collected by filtration and vacuum dried to give the title compound (344 mg, yield: 76%) as a solid.

Example 88

(3R)-3-(1,4-Dimethyl-1H-benzotriazol-5-yl)-3-(7-{[(5'R*)-7'-hydroxy-5'-methyl-3'H-spiro[cyclopropane-1,2'-pyrido[2,3-f][1,4]oxazepin]-4'(5'H)-yl] methyl}-1-benzothiophen-5-yl)propanoic acid 88a (5'R*)-5'-Methyl-4',5'-dihydro-3'H-spiro[cyclopropane-1,2'-pyrido[2,3-f][1,4]oxazepin]-7'-ol A mixture of (5'R*)-4'-(4-methoxybenzyl)-5'-methyl-4',5'-dihydro-3'H-spiro[cyclopropane-1,2'-pyrido[2,3-f][1,4]oxazepin]-7'-ol (709 mg) of Example 87(87g), trifluoroacetic acid (10 mL) and anisole (2 mL) was stirred at 90° C. for 10 hr. The solvent was evaporated under reduced pressure, azeotropic distillation with toluene was performed. The obtained residue was purified by silica gel column chromatography [elution solvent:ethyl acetate/methanol=100/0-90/10(V/V)] to give the title compound (424 mg, yield: 95%) as a solid.

88b

Ethyl (3R)-3-(1,4-dimethyl-1H-benzotriazol-5-yl)-3-(7-{[(5'R*)-7'-hydroxy-5'-methyl-3'H-spiro[cyclopropane-1,2'-pyrido[2,3-f][1,4]oxazepin]-4'(5'H)-yl] methyl}-1-benzothiophen-5-yl)propanoate Using ethyl (3R)-3-(1,4-dimethyl-1H-benzotriazol-5-yl)-3-[7-(hydroxymethyl)-1-benzothiophen-5-yl]propanoate (348 mg) of Example 7(7b) and (5'R*)-5'-methyl-4',5'-dihydro-3'H-spiro[cyclopropane-1,2'-pyrido[2,3-f][1,4]oxazepin]-7'-ol (146 mg) of Example 88(88a), the title compound (306 mg, yield: 72%) was obtained as an oil in the same manner as in Example 62(62d).

88c (3R)-3-(1,4-Dimethyl-1H-benzotriazol-5-yl)-3-(7-{[(5'R*)-7'-hydroxy-5'-methyl-3'H-spiro[cyclopropane-1,2'-pyrido[2,3-f][1,4]oxazepin]-4'(5'H)-yl]methyl}-1-benzothiophen-5-yl)propanoic acid Using ethyl (3R)-3-(1,4-dimethyl-1H-benzotriazol-5-yl)-3-(7-{[(5'R*)-7'-hydroxy-5'-methyl-3'H-spiro[cyclopropane-1,2'-pyrido[2,3-f][1,4]oxazepin]-4'(5'H)-yl]methyl}-1-benzothiophen-5-yl)propanoate (306 mg) of Example 88(88b), the title compound (169 mg, yield: 58%) was obtained as a solid in the same manner as in Example 87(87j).

Example 89

(3S)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)-2,2-dimethylpropanoic acid 89a 2-(Trimethylsilyl)ethyl (3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)-2,2-dimethylpropanoate Using 2-(trimethylsilyl)ethyl (3S)-3-(1,4-dimethyl-1H-benzotriazol-5-yl)-3-(7-(hydroxymethyl)-2,3-dihydro-1H-inden-5-yl)-2,2-dimethylpropanoate (48.4 mg) of Example 38(38e) and (2R,5S)-2-ethyl-5-methyl-2,3,4,5-tetrahydropyrido[2,3-f][1,4]oxazepine dihydrochloride (31.2 mg) of Example 62(62c), the title compound (50.9 mg, yield: 78%) was obtained as an oil in the same manner as in Example 62(62d).

89b (3S)-3-(1,4-Dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)-2,2-dimethylpropanoic acid To a mixture of 2-(trimethylsilyl)ethyl (3S)-3-(1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)-2,2-dimethylpropanoate (50.0 mg) of Example 89(89a) and N,N-dimethylformamide (1.50 mL) was added tetrabutylammonium fluoride (1 M tetrahydrofuran solution) (0.0770 mL), and the mixture was stirred at 40° C. for 8 hr. To the reaction mixture was added tetrabutylamnonium fluoride (1 M tetrahydrofuran solution) (0.0210 mL), and the mixture was stirred at 40° C. for 0.5 hr and left standing at room temperature overnight. To the reaction mixture were added 1M aqueous citric acid solution and saturated brine, and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:n-hexane/ethyl acetate=50/50-0/100(V/V)] to give the title compound (32.4 mg, yield: 76%) as an oil.

Example 90

3-(1,4-Dimethyl-1H-benzotriazol-5-yl)-3-(4-{[(4R)-4-methyl-1,1-dioxido-3,4-dihydro-2H-5,1,2-benzoxathiazepin-2-yl]methyl}-1H-indol-6-yl)propanoic acid 90a tert-Butyl 4-(hydroxymethyl)-6-(4,4,5,5-tetramethyl-1,3,2-dioxaborolan-2-yl)-1H-indole-1-carboxylate tert-Butyl 6-bromo-4-(hydroxymethyl)-1H-indole-1-carboxylate (Journal of Medicinal Chemistry (2013), 56(11), 4465-4481) (3.81 g) was dissolved in 1,4-dioxane (58 mL), bis(pinacolato)diboron (4.45 g), potassium acetate (2.29 g), and [1,1'-bis(diphenylphosphino)ferrocene]dichloropalladium(II) dichloromethane adduct (0.477 g) were added, and the mixture was stirred under a nitrogen atmosphere at 70° C. for 4 hr. The reaction mixture was diluted with dichloromethane, insoluble matter was filtered off, and the filtrate was concentrated under reduced pressure. The obtained residue was purified by silica gel column chromatography [elution solvent:n-hexane/ethyl acetate=97/3-82/18(V/V)] to give the title compound (1.64 g, yield: 38%) as a solid.

90b tert-Butyl 6-[1-(1,4-dimethyl-1H-benzotriazol-5-yl)-3-ethoxy-3-oxopropyl]-4-(hydroxymethyl)-1H-indole-1-carboxylate Ethyl (2E)-3-(1,4-dimethyl-1H-benzotriazol-5-yl)prop-2-enoate (WO 2015/092713) (0.400 g) and tert-butyl 4-(hydroxymethyl)-6-(4,4,5,5-tetramethyl-1,3,2-dioxaborolan-2-yl)-1H-indole-1-carboxylate (1.28 g) of Example 90(90a) were dissolved in a mixed solvent of 1,4-dioxane (2.96 mL) and water (0.785 mL). Triethylamine (0.369 mL) and chloro (1,5-cyclooctadiene)rhodium(I) dimer (80 mg) were added, and the mixture was stirred under heating at 80° C. for 4 hr. The reaction mixture was allowed to cool to room temperature, saturated aqueous ammonium chloride solution was added, and the mixture was extracted with ethyl acetate. The organic layer was washed with saturated brine and dried over anhydrous sodium sulfate. After filtration, the filtrate was concentrated under reduced pressure, and the obtained residue was purified by silica gel column chromatography [elution solvent:n-hexane/ethyl acetate=90/10-50/50(V/V)] to give the title compound (677 mg, yield: 84%) as an oil.

90c tert-Butyl 6-[1-(1,4-dimethyl-1H-benzotriazol-5-yl)-3-ethoxy-3-oxopropyl]-4-{[(4R)-4-methyl-1,1-dioxido-3,4-dihydro-2H-5,1,2-benzoxathiazepin-2-yl]methyl}-1H-indole-1-carboxylate tert-Butyl 6-[1-(1,4-dimethyl-1H-benzotriazol-5-yl)-3-ethoxy-3-oxopropyl]-4-(hydroxymethyl)-1H-indole-1-carboxylate (150 mg) of Example 90(90b) and (4R)-4-methyl-3,4-dihydro-2H-5,1,2-benzoxathiazepine 1,1-dioxide (WO 2015/092713) (100 mg) were dissolved in toluene (2.4 mL), 1,1'-azo bis(N,N-dimethylformamide) (160 mg), then tri-n-butylphosphine (0.29 mL), and tetrahydrofuran (2.4 mL) were added under a nitrogen atmosphere, and the mixture was stirred at room temperature for 12 hr. The reaction mixture was diluted with dichloromethane, insoluble matter was filtered off, and the filtrate was concentrated under reduced pressure. The obtained residue was purified by silica gel column chromatography [elution solvent:n-hexane/ethyl acetate=9/1-1/1(V/V)] to give the title compound (170 mg, yield: 53%) as a solid.

90d

Ethyl 3-(1,4-dimethyl-1H-benzotriazol-5-yl)-3-(4-{[(4R)-4-methyl-1,1-dioxido-3,4-dihydro-2H-5,1,2-benzoxathiazepin-2-yl]methyl}-1H-indol-6-yl)propanoate tert-Butyl 6-[1-(1,4-dimethyl-1H-benzotriazol-5-yl)-3-ethoxy-3-oxopropyl]-4-{[(4R)-4-methyl-1,1-dioxido-3,4-dihydro-2H-5,1,2-benzoxathiazepin-2-yl]methyl}-1H-indole-1-carboxylate (170 mg) of Example 90(90c) was dissolved in 1,4-dioxane (2 mL), 4 M hydrogen chloride-1,4-dioxane solution (2 mL) was added, and the mixture was stirred at room temperature for 16 hr. To the reaction mixture was added saturated aqueous sodium hydrogen carbonate solution, and the mixture was extracted with dichloromethane. The organic layer was washed with saturated brine and dried over anhydrous sodium sulfate. After filtration, the filtrate was concentrated under reduced pressure and the obtained residue was purified by NH silica gel column chromatography [elution solvent:ethyl acetate/methanol=10/0-9/1(V/V)] to give the title compound (103 mg, yield: 71%) as a solid.

90e 3-(1,4-Dimethyl-1H-benzotriazol-5-yl)-3-(4-{[(4R)-4-methyl-1,1-dioxido-3,4-dihydro-2H-5,1,2-benzoxathiazepin-2-yl]methyl}-1H-indol-6-yl)propanoic acid Using ethyl 3-(1,4-dimethyl-1H-benzotriazol-5-yl)-3-(4-{[(4R)-4-methyl-1,1-dioxido-3,4-dihydro-2H-5,1,2-benzoxathiazepin-2-yl]methyl}-1H-indol-6-yl)propanoate (103 mg) of Example 90(90d), the title compound (80 mg, yield: 82%) was obtained as a solid in the same manner as in Example 3(3g).

Example 91

3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1-benzofuran-5-yl)-3-(1,4-dimethyl-1H-benzotriazol-5-yl)propanoic acid 91a (5-Bromo-2,3-dihydro-1-benzofuran-7-yl)methanol To a solution of 5-bromo-2,3-dihydro-1-benzofuran-7-carboxylic acid (5.20 g) in tetrahydrofuran (50 mL) was added borane-tetrahydrofuran (0.9 M tetrahydrofuran solution) (28 mL) at 0° C., and the mixture was stirred at 0° C. for 3 hr. To the reaction mixture was added methanol at 0° C. and the mixture was warmed to room temperature. The solvent was evaporated under reduced pressure, water was added to the obtained residue, and the mixture was extracted with ethyl acetate. The organic layer was washed with saturated brine and dried over anhydrous sodium sulfate. After filtration, the filtrate was concentrated under reduced pressure to give the title compound (4.83 g, yield: 99%) as a solid.

91b

[5-(4,4,5,5-Tetramethyl-1,3,2-dioxaborolan-2-yl)-2,3-dihydro-1-benzofuran-7-yl]methanol Using (5-bromo-2,3-dihydro-1-benzofuran-7-yl)methanol (4.83 g) of Example 91(91a), the title compound (5.64 g, yield: 97%) was obtained as an oil in the same manner as in Example 1(1h).

91c

Ethyl 3-(1,4-dimethyl-1H-benzotriazol-5-yl)-3-[7-(hydroxymethyl)-2,3-dihydro-1-benzofuran-5-yl]propanoate Using [5-(4,4,5,5-tetramethyl-1,3,2-dioxaborolan-2-yl)-2,3-dihydro-1-benzofuran-7-yl]methanol (5.64 g) of Example 91(91b) and ethyl (2E)-3-(1,4-dimethyl-1H-benzotriazol-5-yl)prop-2-enoate (WO 2015/092713) (2.00 g), the title compound (1.51 g, yield: 47%) was obtained as a solid in the same manner as in Example 90(90b).

91d

Ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1-benzofuran-5-yl)-3-(1,4-dimethyl-1H-benzotriazol-5-yl)propanoate Ethyl 3-(1,4-dimethyl-1H-benzotriazol-5-yl)-3-[7-(hydroxymethyl)-2,3-dihydro-1-benzofuran-5-yl]propanoate (90 mg) of Example 91(91c) and (4R)-8-chloro-4-ethyl-3,4-dihydro-2H-pyrido[2,3-b][1,4,5]oxathiazepine 1,1-dioxide (60 mg) of Example 1(1c) were dissolved in toluene (1.1 mL), 1,1'-azo bis(N,N-dimethylformamide) (78 mg), then tri-n-butylphosphine (0.14 mL), and tetrahydrofuran (1.1 mL) were added under a nitrogen atmosphere, and the mixture was stirred at room temperature for 3 hr. The reaction mixture was diluted with dichloromethane, insoluble matter was filtered off, and the filtrate was concentrated under reduced pressure. The obtained residue was purified by silica gel column chromatography [elution solvent:n-hexane/ethyl acetate=1/1-2/8(V/V)] to give the title compound (150 mg, yield: quantitative) as a solid.

91e 3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1-benzofuran-5-yl)-3-(1,4-dimethyl-1H-benzotriazol-5-yl)propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1-benzofuran-5-yl)-3-(1,4-dimethyl-1H-benzotriazol-5-yl)propanoate (150 mg) of Example

Example 92

3-(7-{[(4R)-8-Chloro-4-ethyl-1,1-dioxido-3,4-dihydro-2H-pyrido[2,3-b][1,4,5]oxathiazepin-2-yl]methyl}-1-benzofuran-5-yl)-3-(4-chloro-1-methyl-1H-benzotriazol-5-yl)propanoic acid 91(91d), the title compound (70 mg, yield: 49%) was obtained as a solid in the same manner as in Example 3(3g).

92a

Methyl 5-bromo-2,3-dihydro-1-benzofuran-7-carboxylate

To a solution of 5-bromo-2,3-dihydro-1-benzofuran-7-carboxylic acid (5.28 g) in N,N-dimethylformamide (45.0 mL) were added potassium carbonate (4.51 g) and methyl iodide (1.6 mL), and the mixture was stirred at 100° C. for 1.5 hr. The reaction mixture was allowed to cool to room temperature, water was added, and the mixture was extracted with ethyl acetate. The organic layer was washed successively with water and saturated brine and dried over anhydrous sodium sulfate. The solvent was evaporated under reduced pressure to give the title compound (5.61 g, yield: quantitative) as a solid.

92b (5-Bromo-1-benzofuran-7-yl)methanol

Methyl 5-bromo-2,3-dihydro-1-benzofuran-7-carboxylate (5.08 g) of Example 92(92a) was dissolved in carbon tetrachloride (150 mL), N-bromosuccinimide (3.52 g) and 2,2'-azodiisobutyronitrile (325 mg) were added, and the mixture was heated under reflux for 90 min. The reaction mixture was allowed to cool to room temperature, water was added, and the mixture was extracted with chloroform. The organic layer was washed with saturated brine and dried over anhydrous sodium sulfate, and the solvent was evaporated under reduced pressure. The obtained residue was dissolved in dichloromethane (80 mL), 1,8-diazabicyclo[5.4.0]-7-undecene (5.9 mL) was added dropwise, and the mixture was stirred at room temperature for 14 hr. Water was added to the reaction mixture, and the aqueous layer was extracted with chloroform. The organic layer was washed successively with 1 M hydrochloric acid and saturated brine, dried over anhydrous sodium sulfate, and the solvent was evaporated under reduced pressure. The obtained residue was dissolved in tetrahydrofuran (80 mL), lithium aluminum hydride (750 mg) was added at 0° C., and the mixture was stirred at 0° C. for 30 min. Water (0.8 mL), 1 M aqueous sodium hydroxide solution (0.8 mL), and water (2.4 mL) were successively added to the reaction mixture, and the mixture was stirred at room temperature for 25 min. The reaction mixture was filtered through celite to remove insoluble matter, and the filtrate was dried over anhydrous sodium sulfate, and the solvent was evaporated under reduced pressure. The obtained residue was purified by silica gel column chromatography [elution solvent:n-hexane/ethyl acetate=90/10-50/50(V/V)] to give the title compound (4.12 g, yield: 92%) as a solid.

92c

[5-(4,4,5,5-Tetramethyl-1,3,2-dioxaborolan-2-yl)-1-benzofuran-7-yl]methanol

Using (5-bromo-1-benzofuran-7-yl)methanol (4.12 g) of Example 92(92b), the title compound (4.91 g, yield: 99%) was obtained as an oil in the same manner as in Example 1(1h).

92d

Ethyl 3-(4-chloro-1-methyl-1H-benzotriazol-5-yl)-3-[7-(hydroxymethyl)-1-benzofuran-5-yl]propanoate Using [5-(4,4,5,5-tetramethyl-1,3,2-dioxaborolan-2-yl)-1-benzofuran-7-yl]methanol (0.82 g) of Example 92(92c) and ethyl(2E)-3-(4-chloro-1-methyl-1H-benzotriazol-5-yl)prop-2-enoate (WO 2015/092713) (736 mg), the title compound (550 mg, yield: 44%) was obtained as a solid in the same manner as in Example 95(95a).

92e 3-(7-{[(4R)-8-Chloro-4-ethyl-1,1-dioxido-3,4-dihydro-2H-pyrido[2,3-b][1,4,5]oxathiazepin-2-yl]methyl}-1-benzofuran-5-yl)-3-(4-chloro-1-methyl-1H-benzotriazol-5-yl)propanoic acid Ethyl 3-(4-chloro-1-methyl-1H-benzotriazol-5-yl)-3-[7-(hydroxymethyl)-1-benzofuran-5-yl]propanoate (100 mg) of Example 92(92d) and (4R)-8-chloro-4-ethyl-3,4-dihydro-2H-pyrido[2,3-b][1,4,5]oxathiazepine 1,1-dioxide (76 mg) of Example 1(1c) were dissolved in tetrahydrofuran (1 mL), tri-n-butylphosphine (0.090 mL) and 1,1'-(azodicarbonyl)dipiperidine (92 mg) were added, and the mixture was stirred at room temperature for 18 hr. The reaction mixture was concentrated under reduced pressure, and the obtained residue was purified by silica gel column chromatography [elution solvent:n-hexane/ethyl acetate=80/20-30/70(V/V)]. The obtained residue was dissolved in a mixed solvent of tetrahydrofuran (1.9 mL) and methanol (0.62 mL), 1M aqueous lithium hydroxide solution (0.62 mL) was added, and the mixture was stirred at room temperature for 20 hr. To the reaction mixture was added 2M hydrochloric acid (6 mL), and the mixture was extracted with ethyl acetate. The organic layer was washed with saturated brine and dried over anhydrous sodium sulfate, and the solvent was evaporated under reduced pressure. The obtained residue was purified by silica gel column chromatography [elution solvent:chloroform/methanol=100/0-97/3(V/V)]. To the obtained residue were added ethyl acetate and n-hexane, and the mixture was subjected to an ultrasonic treatment. The solid was collected by filtration to give the title compound (81 mg, yield: 53%) as a solid.

Example 93

(3S*)-3-(7-{[(2R,5S)-2-Ethyl-5-methyl-2,3-dihydropyrido[2,3-f][1,4]oxazepin-4(5H)-yl]methyl}-1-benzothiophen-5-yl)-3-(7-hydroxy-1,4-dimethyl-1H-benzotriazol-5-yl)propanoic acid

93a

Ethyl 5-bromo-2-formamide-4-methylbenzoate

Acetic anhydride (13.8 mL) was added to formic acid (15.5 mL), and the mixture was stirred at room temperature for 15 min. A solution of ethyl 2-amino-5-bromo-4-methylbenzoate (WO 2015/060373) (30.2 g) in dichloromethane (235 mL) was added thereto, and the mixture was stirred at room temperature for 40 min. To the reaction mixture was added saturated aqueous sodium hydrogen carbonate solution, and the mixture was extracted with ethyl acetate. The organic layer was washed successively with saturated aqueous sodium hydrogen carbonate solution and saturated brine and dried over anhydrous sodium sulfate. The solvent was evaporated under reduced pressure to give the title compound (29.9 g, yield: 89%) as a solid.

93b

Ethyl 5-bromo-2-formamido-4-methyl-3-nitrobenzoate

Ethyl 5-bromo-2-formamido-4-methylbenzoate (29.9 g) of Example 93(93a) was added in portions to fuming nitric acid (104 mL) at 0° C., and the mixture was stirred at 0° C. for 20 min. The reaction mixture was added to ice water, and extracted with ethyl acetate. The organic layer was washed successively with saturated aqueous sodium hydrogen carbonate solution and saturated brine, dried over anhydrous sodium sulfate, and the solvent was evaporated under reduced pressure to give the title compound (35.1 g, yield: quantitative) as a solid.

93c

[5-Bromo-4-methyl-2-(methylamino)-3-nitrophenyl]methanol

Ethyl 5-bromo-2-formamido-4-methyl-3-nitrobenzoate (35.1 g) of Example 93(93b) was dissolved in tetrahydrofuran (260 mL), borane-dimethylsulfide complex (29.6 mL) was added dropwise at 0° C., and the mixture was stirred at 0° C. for 14 hr. The reaction mixture was added to ice water, and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=100/0-80/20(V/V)] to give the title compound (17.8 g, yield: 51%) as an oil.

93d

[3-Amino-5-bromo-4-methyl-2-(methylamino)phenyl]methanol

[5-Bromo-4-methyl-2-(methylamino)-3-nitrophenyl]methanol (17.8 g) of Example 93(93c) was dissolved in methanol (265 mL), a suspension of osmium-activated carbon (661 mg) in toluene was added, hydrazine monohydrate (66 mL) was added at 0° C., and the mixture was heated under reflux for 13.5 hr. The reaction mixture was allowed to cool to room temperature, a suspension of osmium-activated carbon (661 mg) in toluene and hydrazine monohydrate (66 mL) were added and the mixture was heated under reflux for 2 hr. celite was added to the reaction mixture, and the mixture was filtered through celite to remove insoluble matter, and washed with ethyl acetate. Water was added to the filtrate, and the mixture was extracted with ethyl acetate. The organic layer was washed successively with water and saturated brine and dried over anhydrous sodium sulfate, and the solvent was evaporated under reduced pressure to give the title compound (11.7 g, yield: 90%) as a solid.

93e

(5-Bromo-1,4-dimethyl-1H-benzotriazol-7-yl)methanol

[3-Amino-5-bromo-4-methyl-2-(methylamino)phenyl]methanol (11.7 g) of Example 93(93d) was dissolved in dichloromethane (240 mL), 42% tetrafluoroboric acid (11.4 mL) was added at 0° C., tert-butyl nitrite (6.29 mL) was added dropwise, and the mixture was stirred at 0° C. for 30 min. The reaction mixture was concentrated to about half under reduced pressure, and the insoluble matter was filtered off and washed with water to obtain a solid and a filtrate. The obtained solid was dissolved in ethyl acetate, dried over anhydrous sodium sulfate, and the solvent was evaporated under reduced pressure to give 9.4 g of the title compound as a solid. The filtrate was also extracted with chloroform. The organic layer was washed with water, dried over anhydrous sodium sulfate, and the solvent was evaporated under reduced pressure. Chloroform was added to the obtained residue, and the solid was collected by filtration, and combined with the title compound (9.4 g) obtained earlier to give the title compound 10.6 g, yield: 87%) as a solid.

93f

5-Bromo-1,4-dimethyl-1H-benzotriazole-7-carbaldehyde (5-Bromo-1,4-dimethyl-1H-benzotriazol-7-yl)methanol (5.0 g) of Example 93(93e) was dissolved in dimethyl sulfoxide (13.9 mL), dichloromethane (100 mL), N,N-diisopropylethylamine (17.3 mL) and sulfur trioxide-pyridine complex (17.3 g) were added, and the mixture was stirred at room temperature for 30 min. To the reaction mixture was added water, and the mixture was extracted with ethyl acetate. The organic layer was washed successively with water, 1M hydrochloric acid and saturated brine, and dried over anhydrous sodium sulfate, and the solvent was evaporated under reduced pressure to give the title compound (4.8 g, yield: 97%) as a solid.

93g

5-Bromo-1,4-dimethyl-1H-benzotriazol-7-ol

5-Bromo-1,4-dimethyl-1H-benzotriazole-7-carbaldehyde (4.8 g) of Example 93(93f) was dissolved in dichloromethane (189 mL), 3-chloroperbenzoic acid (10.0 g) was added, and the mixture was stirred at room temperature 15 hr. To the reaction mixture was added ethyl acetate, the mixture was washed successively with saturated aqueous sodium hydrogen carbonate solution and saturated brine and dried over anhydrous sodium sulfate, and the solvent was evaporated under reduced pressure. To the obtained residue was added chloroform, and the mixture was subjected to an ultrasonic treatment. The solid was collected by filtration to give the title compound (1.67 g, yield: 37%) as a solid.

93h

7-(Benzyloxy)-5-bromo-1,4-dimethyl-1H-benzotriazole

5-Bromo-1,4-dimethyl-1H-benzotriazol-7-ol (1.67 g) of Example 93(93g) was dissolved in N,N-dimethylformamide (20 mL), potassium carbonate (2.86 g) and benzyl bromide (1.24 mL) were added, and the mixture was stirred at room temperature for 1 hr. To the reaction mixture was added water, and the mixture was extracted with ethyl acetate, washed successively with water and saturated brine and dried over anhydrous sodium sulfate. The solvent was evaporated under reduced pressure. To the obtained residue was added n-hexane, and the mixture was subjected to an ultrasonic treatment. The solid was collected by filtration to give the title compound (2.11 g, yield: quantitative) as a solid.

93i tert-Butyl (2E)-3-[7-(benzyloxy)-1,4-dimethyl-1H-benzotriazol-5-yl]prop-2-enoate Using 7-(benzyloxy)-5-bromo-1,4-dimethyl-1H-benzotriazole (2.11 g) of Example 93(93h) and tert-butyl acrylate (10.0 mL), the title compound (2.56 g, yield: 98%) was obtained as a solid in the same manner as in Example 6(6c).

93j tert-Butyl 3-[7-(benzyloxy)-1,4-dimethyl-1H-benzotriazol-5-yl]-3-[7-(hydroxymethyl)-1-benzothiophen-5-yl]propanoate tert-Butyl (2E)-3-[7-(benzyloxy)-1,4-dimethyl-1H-benzotriazol-5-yl]prop-2-enoate (1.27 g) of Example 93(93i) was dissolved in 1,4-dioxane (22 mL), [5-(4,4,5,5-tetramethyl-1,3,2-dioxaborolan-2-yl)-1-benzothiophen-7-yl]methanol (1.10 g) of Example 1(1h), water (11 mL) and triethylamine (0.93 mL) were added, and the mixture was stirred at 90° C. for 5 min. Then, chloro(1,5-cyclooctadiene)rhodium(I) dimer (83 mg) was added thereto and, after stirring the mixture at 90° C. for 35 min, chloro(1,5-cyclooctadiene)rhodium(I) dimer (42 mg) was added, the mixture was stirred at 90° C. for 25 min. The reaction mixture was allowed to cool to room temperature, water was added, and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=100/0-70/30(V/V)] to give the title compound (1.14 g, yield: 52%) as a solid.

93k tert-Butyl 3-[7-(benzyloxy)-1,4-dimethyl-1H-benzotriazol-5-yl]-3-[7-(chloromethyl)-1-benzothiophen-5-yl]propanoate tert-Butyl 3-[7-(benzyloxy)-1,4-dimethyl-1H-benzotriazol-5-yl]-3-[7-(hydroxymethyl)-1-benzothiophen-5-yl]propanoate (1.44 g) of Example 93(93j) was dissolved in dichloromethane (6 mL), thionyl chloride (0.32 mL) was added, and the mixture was stirred at room temperature for 30 min. The solvent was evaporated under reduced pressure, and azeotropic distillation with chloroform was performed. The obtained residue was purified by silica gel column chromatography [elution solvent:n-hexane/ethyl acetate=100/0-0/100(V/V)] to give the title compound (720 mg, yield: 58%) as a solid.

93l tert-Butyl 3-[7-(benzyloxy)-1,4-dimethyl-1H-benzotriazol-5-yl]-3-(7-{[(2R,5S)-2-ethyl-5-methyl-2,3-dihydropyrido[2,3-f][1,4]oxazepin-4(5H)-yl]methyl}-1-benzothiophen-5-yl)propanoate tert-Butyl 3-[7-(benzyloxy)-1,4-dimethyl-1H-benzotriazol-5-yl]-3-[7-(chloromethyl)-1-benzothiophen-5-yl]propanoate (720 mg) of Example 93(93k) was dissolved in acetonitrile (6 mL), (2R,5S)-2-ethyl-5-methyl-2,3,4,5-tetrahydropyrido[2,3-f][1,4]oxazepine dihydrochloride (340 mg) of Example 62(62c) and N,N-diisopropylethylamine (1.13 mL) was added, and the mixture was stirred at 90° C. for 6 hr, (2R,5S)-2-ethyl-5-methyl-2,3,4,5-tetrahydropyrido[2,3-f][1,4]oxazepine dihydrochloride (34 mg) of Example 62(62c) was added, and the mixture was further stirred at 90° C. for 19 hr. The reaction mixture was allowed to cool to room temperature, ethyl acetate was added. The mixture was washed successively with water and saturated brine and dried over anhydrous sodium sulfate, and the solvent was evaporated under reduced pressure. The obtained residue was purified by silica gel column chromatography [elution solvent:n-hexane/ethyl acetate=100/0-75/25(V/V)] to give the title compound (884 mg, yield: 89%) as a solid.

93m tert-Butyl (3S*)-3-[7-(benzyloxy)-1,4-dimethyl-1H-benzotriazol-5-yl]-3-(7-{[(2R,5S)-2-ethyl-5-methyl-2,3-dihydropyrido[2,3-f][1,4]oxazepin-4(5H)-yl]methyl}-1-benzothiophen-5-yl)propanoate 93n tert-Butyl (3R*)-3-[7-(benzyloxy)-1,4-dimethyl-1H-benzotriazol-5-yl]-3-(7-{[(2R,5S)-2-ethyl-5-methyl-2,3-dihydropyrido[2,3-f][1,4]oxazepin-4(5H)-yl]methyl}-1-benzothiophen-5-yl)propanoate tert-Butyl 3-[7-(benzyloxy)-1,4-dimethyl-1H-benzotriazol-5-yl]-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (757 mg) of Example 93(93l) was subjected to chiral HPLC [column: CHIRALPAK IG (20 mm I.D.×250 mm), mobile phase: n-hexane/2-propanol=50/50(V/V), temperature: 40° C.] to obtain 366 mg of tert-butyl (3S*)-3-[7-(benzyloxy)-1,4-dimethyl-1H-benzotriazol-5-yl]-3-(7-{[(2R,5S)-2-ethyl-5-methyl-2,3-dihydropyrido[2,3-f][1,4]oxazepin-4(5H)-yl]methyl}-1-benzothiophen-5-yl)propanoate as the first peak (yield: 48%).

Similarly, 342 mg of tert-butyl (3R*)-3-[7-(benzyloxy)-1,4-dimethyl-1H-benzotriazol-5-yl]-3-(7-{[(2R,5S)-2-ethyl-5-methyl-2,3-dihydropyrido[2,3-f][1,4]oxazepin-4(5H)-yl]methyl}-1-benzothiophen-5-yl)propanoate was obtained as the second peak (yield: 45%).

Analysis HPLC conditions [column: CHIRALPAK IG (4.6 mm I.D.×250 mm), mobile phase: n-hexane/2-propanol=50/50(V/V), flow rate: 1.0 mL/min, temperature: 40° C., wavelength: 254 nm]; retention time: 7.063 min (the first peak), 11.193 min (the second peak)

93o (3S*)-3-(7-{[(2R,5S)-2-Ethyl-5-methyl-2,3-dihydropyrido[2,3-f][1,4]oxazepin-4(5H)-yl]methyl}-1-benzothiophen-5-yl)-3-(7-hydroxy-1,4-dimethyl-1H-benzotriazol-5-yl)propanoic acid To a mixture of tert-butyl (3S*)-3-[7-(benzyloxy)-1,4-dimethyl-1H-benzotriazol-5-yl]-3-(7-{[(2R,5S)-2-ethyl-5- methyl-2,3-dihydropyrido[2,3-f][1,4]oxazepin-4(5H)-yl]methyl}-1-benzothiophen-5-yl)propanoate (150 mg) of Example 93(93m) and dichloromethane (2.5 mL) was added boron tribromide (about 1 M dichloromethane solution) (1.00 mL), and the mixture was stirred at room temperature for 20 min. To the reaction mixture was added water, and the mixture was stirred and extracted with ethyl acetate/methanol=19/1(V/V). The organic layer was washed with saturated brine and dried over anhydrous sodium sulfate. After filtration, the filtrate was concentrated under reduced pressure and the obtained residue was purified by silica gel column chromatography [elution solvent:chloroform/methanol=100/0-95/5(V/V)]. Further, slurry purification with ethyl acetate was performed to give the title compound (59.1 mg, yield: 50%) as a solid.

Example 94

(3R*)-3-(7-{[(2R,5S)-2-Ethyl-5-methyl-2,3-dihydropyrido[2,3-f][1,4]oxazepin-4(5H)-yl]methyl}-1-benzothiophen-5-yl)-3-(7-hydroxy-1,4-dimethyl-1H-benzotriazol-5-yl)propanoic acid Using tert-butyl (3R*)-3-[7-(benzyloxy)-1,4-dimethyl-1H-benzotriazol-5-yl]-3-(7-{[(2R,5S)-2-ethyl-5-methyl-2,3-dihydropyrido[2,3-f][1,4]oxazepin-4(5H)-yl]methyl}-1-benzothiophen-5-yl)propanoate (150 mg) of Example 93(93n), the title compound (73.6 mg, yield: 61%) was obtained as a solid in the same manner as in Example 93(93o).

Example 95

3-(4-Chloro-1-methyl-1H-benzotriazol-5-yl)-3-(7-{[(4R)-4-methyl-1,1-dioxido-3,4-dihydro-2H-5,1,2-benzoxathiazepin-2-yl]methyl}-2,3-dihydro-1H-inden-5-yl)propanoic acid 95a Ethyl 3-(4-chloro-1-methyl-1H-benzotriazol-5-yl)-3-[7-(hydroxymethyl)-2,3-dihydro-1H-inden-5-yl]propanoate

[6-(4,4,5,5-Tetramethyl-1,3,2-dioxaborolan-2-yl)-2,3-dihydro-1H-inden-4-yl]methanol (302 mg) of Example 3(3d) and ethyl (2E)-3-(4-chloro-1-methyl-1H-benzotriazol-5-yl)prop-2-enoate (WO 2015/092713) (295 mg) were dissolved in 1,4-dioxane (5.0 mL), triethylamine (0.31 mL) and water (2.5 mL) were added, and the mixture was stirred at 90° C. for 10 min. Then, chloro(1,5-cyclooctadiene)rhodium(I) dimer (27 mg) was added, and the mixture was stirred at 90° C. for 20 min. The reaction mixture was allowed to cool to room temperature, water was added, and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=50/50-20/80(V/V)] to give the title compound (0.32 g, yield: 58%) as an oil.

95b

Ethyl 3-(4-chloro-1-methyl-1H-benzotriazol-5-yl)-3-(7-{[(4R)-4-methyl-1,1-dioxido-3,4-dihydro-2H-5,1,2-benzoxathiazepin-2-yl]methyl}-2,3-dihydro-1H-inden-5-yl)propanoate Using ethyl 3-(4-chloro-1-methyl-1H-benzotriazol-5-yl)-3-[7-(hydroxymethyl)-2,3-dihydro-1H-inden-5-yl]propanoate (149 mg) of Example 95(95a) and (4R)-4-methyl-3,4-dihydro-2H-5,1,2-benzoxathiazepine 1,1-dioxide (WO 2015/092713) (75.7 mg), the title compound (191 mg, yield: quantitative) was obtained as an oil in the same manner as in Example 2(2b).

95c 3-(4-Chloro-1-methyl-1H-benzotriazol-5-yl)-3-(7-{[(4R)-4-methyl-1,1-dioxido-3,4-dihydro-2H-5,1,2-benzoxathiazepin-2-yl]methyl}-2,3-dihydro-1H-inden-5-yl)propanoic acid Using ethyl 3-(4-chloro-1-methyl-1H-benzotriazol-5-yl)-3-(7-{[(4R)-4-methyl-1,1-dioxido-3,4-dihydro-2H-5,1,2-benzoxathiazepin-2-yl]methyl}-2,3-dihydro-1H-inden-5-yl)propanoate (191 mg) of Example 95(95b), the title compound (99 mg, yield: 58%) was obtained as a solid in the same manner as in Example 1(1k).

Example 96

(3S)-3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)propanoic acid 96a Ethyl (3S)-3-(7-chloro-1,4-dimethyl-1H-benzotriazol-5-yl)-3-[7-(hydroxymethyl)-2,3-dihydro-1H-inden-5-yl]propanoate 96b ethyl (3R)-3-(7-chloro-1,4-dimethyl-1H-benzotriazol-5-yl)-3-[7-(hydroxymethyl)-2,3-dihydro-1H-inden-5-yl]propanoate Ethyl 3-(7-chloro-1,4-dimethyl-1H-benzotriazol-5-yl)-3-[7-(hydroxymethyl)-2,3-dihydro-1H-inden-5-yl]propanoate (426 mg) of Example 71(71a) was subjected to chiral HPLC [column: CHIRALPAK IG (20 mm I.D.×250 mm), mobile phase: n-hexane/2-propanol=70/30(V/V), temperature: 40° C.] to obtain 157 mg of ethyl (3S)-3-(7-chloro-1,4-dimethyl-1H-benzotriazol-5-yl)-3-[7-(hydroxymethyl)-2,3-dihydro-1H-inden-5-yl]propanoate as the first peak (yield: 37%).
Similarly, 167 mg of ethyl (3R)-3-(7-chloro-1,4-dimethyl-1H-benzotriazol-5-yl)-3-[7-(hydroxymethyl)-2,3-dihydro-1H-inden-5-yl]propanoate was obtained as the second peak (yield: 39%).
Analysis HPLC conditions [column: CHIRALPAK IG (4.6 mm I.D.×250 mm), mobile phase: n-hexane/2-propanol=70/30(V/V), flow rate: 1.0 mL/min, temperature: 40° C., wavelength: 254 nm]; retention time: 10.233 min (the first peak), 12.433 min (the second peak)

96c

Ethyl (3S)-3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)propanoate Using ethyl (3S)-3-(7-chloro-1,4-dimethyl-1H-benzotriazol-5-yl)-3-[7-(hydroxymethyl)-2,3-dihydro-1H-inden-5-yl]propanoate (157 mg) of Example 96(96a) and (4R)-8- chloro-4-ethyl-3,4-dihydro-2H-pyrido[2,3-b][1,4,5] oxathiazepine 1,1-dioxide (116 mg) of Example 1(1c), the title compound (235 mg, yield: 95%) was obtained as an oil in the same manner as in Example 4(4c).

96d (3S)-3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl] methyl}-2,3-dihydro-1H-inden-5-yl)propanoic acid To a mixture of ethyl (3S)-3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)propanoate (235 mg) of Example 96(96c), ethanol (3.0 mL), and tetrahydrofuran (2.0 mL) was added 1M aqueous sodium hydroxide solution (2.00 mL), and the mixture was stirred at room temperature for 6 hr. To the reaction mixture was added 2M hydrochloric acid (1.00 mL), and the mixture was stirred and extracted with ethyl acetate. The organic layer was dried over anhydrous sodium sulfate. After filtration, the filtrate was concentrated under reduced pressure and to the obtained residue were added again ethanol (3.0 mL), tetrahydrofuran (2.0 mL) and 2M aqueous sodium hydroxide solution (2.00 mL), and the mixture was stirred at room temperature for 3 hr. To the reaction mixture were added 2M hydrochloric acid (2.00 mL) and saturated brine and the mixture was stirred and extracted with ethyl acetate. The organic layer was dried over anhydrous sodium sulfate. After filtration, the filtrate was concentrated under reduced pressure and the obtained residue was purified by silica gel column chromatography [elution solvent:n-hexane/ethyl acetate=50/50-0/100(V/V)]. Furthermore, slurry purification with an ethyl acetate/n-hexane mixed solvent was performed to give the title compound (141 mg, yield: 62%) as a solid.

Example 97

(3R)-3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl] methyl}-2,3-dihydro-1H-inden-5-yl)propanoic acid 97a Ethyl (3R)-3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)propanoate Using ethyl (3R)-3-(7-chloro-1,4-dimethyl-1H-benzotriazol-5-yl)-3-[7-(hydroxymethyl)-2,3-dihydro-1H-inden-5-yl]propanoate (147 mg) of Example 96(96b) and (4R)-8-chloro-4-ethyl-3,4-dihydro-2H-pyrido[2,3-b][1,4,5] oxathiazepine 1,1-dioxide (108 mg) of Example 1(1c), the title compound (234 mg, yield: quantitative) was obtained as a solid in the same manner as in Example 4(4c).

97b (3R)-3-(7-Chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl] methyl}-2,3-dihydro-1H-inden-5-yl)propanoic acid Using ethyl (3R)-3-(7-chloro-1,4-dimethyl-1H-benzotriazol-5-yl)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)propanoate (234 mg) of Example 97(97a), the title compound (121 mg, yield: 54%) was obtained as a solid in the same manner as in Example 41.

Example 98

(3R)-3-(7-{[(4R)-8-Chloro-4-ethyl-1,1-dioxido-3,4-dihydro-2H-pyrido[2,3-b][1,4,5]oxathiazepin-2-yl] methyl}-2,3-dihydro-1H-inden-5-yl)-3-[7-(difluoromethoxy)-1,4-dimethyl-1H-benzotriazol-5-yl] propanoic acid 98a Ethyl 3-[7-(difluoromethoxy)-1,4-dimethyl-1H-benzotriazol-5-yl]-3-[7-(hydroxymethyl)-2,3-dihydro-1H-inden-5-yl]propanoate Using ethyl (2E)-3-[7-(difluoromethoxy)-1,4-dimethyl-1H-benzotriazol-5-yl]prop-2-enoate (600 mg) of Example 55(55g) and [6-(4,4,5,5-tetramethyl-1,3,2-dioxaborolan-2-yl)-2,3-dihydro-1H-inden-4-yl]methanol (793 mg) of Example 3(3d), the title compound (769 mg, yield: 87%) was obtained as an oil in the same manner as in Example 95(95a).

98b

Ethyl 3-(7-{[(4R)-8-chloro-4-ethyl-1,1-dioxido-3,4-dihydro-2H-pyrido[2,3-b][1,4,5]oxathiazepin-2-yl] methyl}-2,3-dihydro-1H-inden-5-yl)-3-[7-(difluoromethoxy)-1,4-dimethyl-1H-benzotriazol-5-yl] propanoate Using ethyl 3-[7-(difluoromethoxy)-1,4-dimethyl-1H-benzotriazol-5-yl]-3-[7-(hydroxymethyl)-2,3-dihydro-1H-inden-5-yl]propanoate (711 mg) of Example 98(98a) and (4R)-8-chloro-4-ethyl-3,4-dihydro-2H-pyrido[2,3-b][1,4,5] oxathiazepine 1,1-dioxide (318 mg) of Example 1(1c), the title compound (783 mg, yield: 92%) was obtained as an amorphous in the same manner as in Example 4(4c).

98c

Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoate 98d Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoate Ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoate (782 mg) of Example 98(98b) was subjected to chiral HPLC [column: CHIRALPAK IE (20 mm I.D.×250 mm), mobile phase: n-hexane/2-propanol/ethyl acetate=60/30/10(V/V/V), temperature: 40° C.] to obtain 379 mg of ethyl (3R)-3-(7-{

[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoate as the first peak (yield: 49%).

Similarly, 361 mg of ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoate was obtained as the second peak (yield: 46%).

Analysis HPLC conditions [column: CHIRALART amylose-SA (4.6 mm I.D.×250 mm), mobile phase: n-hexane/2-propanol=85/15(V/V), flow rate: 1.0 mL/min, temperature: 40° C., wavelength: 254 nm]; retention time: 10.590 min (Example 98(98c)), 8.743 min (Example 98 (98d)).

98e (3R)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoic acid Using ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoate (210 mg) of Example 98(98c), the title compound (140 mg, yield: 69%) was obtained as a solid in the same manner as in Example 41.

Example 99

(3S)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoic acid Using ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[7-(difluoromethoxy)-1,4-dimethyl-1H-benzotriazol-5-yl]propanoate (187 mg) of Example 98(98d), the title compound (143 mg, yield: 80%) was obtained as a solid in the same manner as in Example 41.

Example 100

(3S)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoic acid 100a Ethyl 3-[1,4-dimethyl-7-(trifluoromethoxy)-1H-benzotriazol-5-yl]-3-[7-(hydroxymethyl)-2,3-dihydro-1H-inden-5-yl]propanoate Using ethyl (2E)-3-[1,4-dimethyl-7-(trifluoromethoxy)-1H-benzotriazol-5-yl]prop-2-enoate (570 mg) of Example 54(54f) and [6-(4,4,5,5-tetramethyl-1,3,2-dioxaborolan-2-yl)-2,3-dihydro-1H-inden-4-yl]methanol (712 mg) of Example 3(3d), the title compound (728 mg, yield: 83%) was obtained as an oil in the same manner as in Example 95(95a).

100b

Ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoate Using ethyl 3-[1,4-dimethyl-7-(trifluoromethoxy)-1H-benzotriazol-5-yl]-3-[7-(hydroxymethyl)-2,3-dihydro-1H-inden-5-yl]propanoate (333 mg) of Example 100(100a) and (4R)-8-chloro-4-ethyl-3,4-dihydro-2H-pyrido[2,3-b][1,4,5]oxathiazepine 1,1-dioxide (220 mg) of Example 1(1c), the title compound (533 mg, yield: quantitative) was obtained as an amorphous in the same manner as in Example 4(4c).

100c

Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoate 100d Ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoate Ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoate (533 mg) of Example 100(100b) was subjected to chiral HPLC [column: CHIRALPAK IG (20 mm I.D.×250 mm), mobile phase: n-hexane/2-propanol/ethyl acetate=60/30/10(V/V/V), temperature: 40° C.] to obtain 210 mg of ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoate as the first peak (yield: 40%).

Similarly, 234 mg of ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoate was obtained as the second peak (yield: 44%).

Analysis HPLC conditions [column: CHIRALART amylose-SA (4.6 mm I.D.×250 mm), mobile phase: n-hexane/2-propanol=90/10(V/V), flow rate: 1.0 mL/min, temperature: 40° C., wavelength: 254 nm]; retention time: 9.147 min (the first peak), 11.293 min (the second peak)

100e (3S)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoic acid Using ethyl (3S)-3-(7-{[(4R)-8-chloro-4-ethyl-1,1-dioxido-3,4-dihydro-2H-pyrido[2,3-b][1,4,5]oxathiazepin-2- yl]methyl}-2,3-dihydro-1H-inden-5-yl)-3-[1,4-dimethyl-7-(trifluoromethoxy)-1H-benzotriazol-5-yl]propanoate (212 mg) of Example 100(100c), the title compound (153 mg, yield: 75%) was obtained as a solid in the same manner as in Example 41.

Example 101

(3R)-3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoic acid Using ethyl (3R)-3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1H-inden-5-yl)-3-[1,4-dimethyl-7-(trifluoromethoxy)-1H-benzotriazol-5-yl]propanoate (234 mg) of Example 100(100d), a method similar to that in Example 41 was performed and slurry purification was further performed using a methanol solvent to give the title compound (163 mg, yield: 73%) as a solid.

Example 102

3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1-benzofuran-5-yl)-3-(7-cyclopropyl-1,4-dimethyl-1H-benzotriazol-5-yl)propanoic acid 102a ethyl 3-(7-cyclopropyl-1,4-dimethyl-1H-benzotriazol-5-yl)-3-[7-(hydroxymethyl)-2,3-dihydro-1-benzofuran-5-yl]propanoate To a mixture of bis(norbornadiene)rhodium(I) tetrafluoroborate (17.0 mg), (2S,3S)-bis(diphenylphosphino)butane (11.7 mg) and (2R,3R)-bis(diphenylphosphino)butane (11.7 mg) were added under a nitrogen atmosphere 1,4-dioxane (2.50 mL) and 1M aqueous potassium hydroxide solution (0.911 mL), and the mixture was stirred at room temperature for 15 min to prepare a catalyst solution. Then, a mixture of ethyl (2E)-3-(7-cyclopropyl-1,4-dimethyl-1H-benzotriazol-5-yl)prop-2-enoate (260 mg) of Example 49(49a), [5-(4,4,5,5-tetramethyl-1,3,2-dioxaborolan-2-yl)-2,3-dihydro-1-benzofuran-7-yl]methanol (377 mg) of Example 91(91b), 1,4-dioxane (5.00 mL) and water (1.80 mL) was prepared in a separate container and stirred at 60° C. for 3 min under a nitrogen atmosphere, and the catalyst solution prepared above was added. The reaction mixture was heated and stirred at 60° C. for 3 hr under a nitrogen atmosphere. To the reaction mixture was added [5-(4,4,5,5-tetramethyl-1,3,2-dioxaborolan-2-yl)-2,3-dihydro-1-benzofuran-7-yl]methanol (250 mg) of Example 91(91b), and the mixture was stirred at 60° C. for 0.5 hr. To the reaction mixture was added chloro(1,5-cyclooctadiene)rhodium(I) dimer (22.4 mg), and the mixture was stirred at 60° C. for 0.5 hr. To the reaction mixture was added [5-(4,4,5,5-tetramethyl-1,3,2-dioxaborolan-2-yl)-2,3-dihydro-1-benzofuran-7-yl]methanol (250 mg) of Example 91(91b) and chloro(1,5-cyclooctadiene)rhodium(I) dimer (90.0 mg), and the mixture was stirred at 60° C. for 1 hr. The reaction mixture was allowed to cool to room temperature, 2M hydrochloric acid (0.45 mL), saturated brine and water were added, and the mixture was extracted with ethyl acetate. The organic layer was washed with saturated brine and dried over anhydrous sodium sulfate. After filtration, the filtrate was concentrated under reduced pressure, and the obtained residue was purified by silica gel chromatography [elution solvent:n-hexane/ethyl acetate=70/30-30/70(V/V)] to give the title compound (330 mg, yield: 83%) as an oil.

102b

Ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1-benzofuran-5-yl)-3-(7-cyclopropyl-1,4-dimethyl-1H-benzotriazol-5-yl)propanoate Using ethyl 3-(7-cyclopropyl-1,4-dimethyl-1H-benzotriazol-5-yl)-3-[7-(hydroxymethyl)-2,3-dihydro-1-benzofuran-5-yl]propanoate (185 mg) of Example 102(102a) and (4R)-8-chloro-4-ethyl-3,4-dihydro-2H-pyrido[2,3-b][1,4,5]oxathiazepine 1,1-dioxide (134 mg) of Example 1(1c), the title compound (295 mg, yield: quantitative) was obtained as a solid in the same manner as in Example 4(4c).

102c 3-(7-{[(4R)-8-Chloro-4-ethyl-1,1-dioxido-3,4-dihydro-2H-pyrido[2,3-b][1,4,5]oxathiazepin-2-yl]methyl}-2,3-dihydro-1-benzofuran-5-yl)-3-(7-cyclopropyl-1,4-dimethyl-1H-benzotriazol-5-yl)propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-2,3-dihydro-1-benzofuran-5-yl)-3-(7-cyclopropyl-1,4-dimethyl-1H-benzotriazol-5-yl)propanoate (295 mg) of Example 102(102b), the title compound (201 mg, yield: 71%) was obtained as a solid in the same manner as in Example 41.

Example 103

3-(4-{[(4R)-8-Chloro-4-ethyl-1,1-dioxido-3,4-dihydro-2H-pyrido[2,3-b][1,4,5]oxathiazepin-2-yl]methyl}-1H-indol-6-yl)-3-(7-cyclopropyl-1,4-dimethyl-1H-benzotriazol-5-yl)propanoic acid 103a tert-Butyl 6-[1-(7-cyclopropyl-1,4-dimethyl-1H-benzotriazol-5-yl)-3-ethoxy-3-oxopropyl]-4-(hydroxymethyl)-1H-indole-1-carboxylate To a mixture of ethyl (2E)-3-(7-cyclopropyl-1,4-dimethyl-1H-benzotriazol-5-yl)prop-2-enoate (588 mg) of Example 49(49a), bis(norbornadiene)rhodium(I) tetrafluoroborate (38.5 mg), (2S,3S)-bis(diphenylphosphino)butane (26.3 mg) and (2R,3R)-bis(diphenylphosphino)butane (26.3 mg) were added under a nitrogen atmosphere 1,4-dioxane (11.5 mL), water (4.12 mL), and 1M aqueous potassium hydroxide solution (2.00 mL), and the mixture was stirred under a nitrogen atmosphere at 50° C. for 10 min. To the reaction mixture was added a mixture of tert-butyl 4-(hydroxymethyl)-6-(4,4,5,5-tetramethyl-1,3,2-dioxaborolan-2-yl)-1H-indole-1-carboxylate (1.46 g) of Example 90(90a) and 1,4-dioxane (5.70 mL), and the mixture was stirred under heating under a nitrogen atmosphere at 50° C. for 2 hr. The reaction mixture was allowed to cool to room temperature, 2M hydrochloric acid (1.00 mL), saturated brine and water were added, and the mixture was extracted with ethyl acetate. The organic layer was washed with saturated brine and dried over anhydrous sodium sulfate. After filtration, the filtrate was concentrated under reduced pressure, and the obtained residue was purified by silica gel chromatography [elution solvent:n-hexane/ethyl acetate=40/60-20/80(V/V)] to give the title compound (995 mg, yield: 91%) as an amorphous.

103b tert-Butyl 4-{[(4R)-8-chloro-4-ethyl-1,1-dioxido-3,4-dihydro-2H-pyrido[2,3-b][1,4,5]oxathiazepin-2-yl]methyl}-6-[1-(7-cyclopropyl-1,4-dimethyl-1H-benzotriazol-5-yl)-3-ethoxy-3-oxopropyl]-1H-indol-1-carboxylate Using tert-butyl 6-[1-(7-cyclopropyl-1,4-dimethyl-1H-benzotriazol-5-yl)-3-ethoxy-3-oxopropyl]-4-(hydroxymethyl)-1H-indole-1-carboxylate (300 mg) of Example 103 (103a) and (4R)-8-chloro-4-ethyl-3,4-dihydro-2H-pyrido[2,3-b][1,4,5]oxathiazepine 1,1-dioxide (178 mg) of Example 1(1c), the title compound (355 mg, yield: 81%) was obtained as a solid in the same manner as in Example 4(4c).

103c 3-(4-{[(4R)-8-Chloro-4-ethyl-1,1-dioxido-3,4-dihydro-2H-pyrido[2,3-b][1,4,5]oxathiazepin-2-yl]methyl}-1H-indol-6-yl)-3-(7-cyclopropyl-1,4-dimethyl-1H-benzotriazol-5-yl)propanoic acid 2 M Aqueous sodium hydroxide solution (1.50 mL) was added to a mixture of tert-butyl 4-{[(4R)-8-chloro-4-ethyl-1,1-dioxide-3,4-dihydro-2H-pyrido[2,3-b][1,4,5]oxathiazepin-2-yl]methyl}-6-[1-(7-cyclopropyl-1,4-dimethyl-1H-benzotriazol-5-yl)-3-ethoxy-3-oxopropyl]-1H-indole-1-carboxylate (314 mg) of Example 103(103b), 1,4-dioxane (1.0 mL), and tetrahydrofuran (4.0 mL), and the mixture was stirred at 60° C. for 2 hr. 2-Propanol (2.0 mL) was added to the reaction solution, and the mixture was stirred at 60° C. for 1 hr, and then 2 M aqueous sodium hydroxide solution (0.500 mL) was added and the mixture was stirred at 60° C. for 3 hr. After the reaction solution was cooled to room temperature, 2 M hydrochloric acid (2.00 mL), water, and saturated brine were added, and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:chloroform/methanol=93/7-92/8 (V/V)], and slurry purification was further performed using an ethyl acetate/n-hexane mixed solvent to give the title compound (144 mg, yield: 55%) as a solid.

Example 104

3-(7-Cyclopropyl-1,4-dimethyl-1H-benzotriazol-5-yl)-3-(4-{[(2R,5S)-2-ethyl-5-methyl-2,3-dihydropyrido[2,3-f][1,4]oxazepin-4(5H)-yl]methyl}-1H-indol-6-yl)propanoic acid 104a tert-Butyl 6-[1-(7-cyclopropyl-1,4-dimethyl-1H-benzotriazol-5-yl)-3-ethoxy-3-oxopropyl]-4-{[(2R,5S)-2-ethyl-5-methyl-2,3-dihydropyrido[2,3-f][1,4]oxazepin-4(5H)-yl]methyl}-1H-indole-1-carboxylate Using tert-butyl 6-[1-(7-cyclopropyl-1,4-dimethyl-1H-benzotriazol-5-yl)-3-ethoxy-3-oxopropyl]-4-(hydroxymethyl)-1H-indole-1-carboxylate (376 mg) of Example 103 (103a) and (2R,5S)-2-ethyl-5-methyl-2,3,4,5-tetrahydropyrido[2,3-f][1,4]oxazepine dihydrochloride (224 mg) of Example 62(62c), the title compound (371 mg, yield: 74%) was obtained as an oil in the same manner as in Example 62(62d).

104b 3-(7-Cyclopropyl-1,4-dimethyl-1H-benzotriazol-5-yl)-3-(4-{[(2R,5S)-2-ethyl-5-methyl-2,3-dihydropyrido[2,3-f][1,4]oxazepin-4(5H)-yl]methyl}-1H-indol-6-yl)propanoic acid To a mixture of tert-butyl 6-[1-(7-cyclopropyl-1,4-dimethyl-1H-benzotriazol-5-yl)-3-ethoxy-3-oxopropyl]-4-{[(2R,5S)-2-ethyl-5-methyl-2,3-dihydropyrido[2,3-f][1,4]oxazepin-4(5H)-yl]methyl}-1H-indole-1-carboxylate (371 mg) of Example 104(104a), ethanol (2.00 mL), and tetrahydrofuran (2.00 mL) were added 2M aqueous sodium hydroxide solution (2.00 mL), and the mixture was stirred at 60° C. for 5 hr. The reaction mixture was cooled to room temperature, 2M hydrochloric acid (2.00 mL), saturated brine, and water were added, and the mixture was stirred and extracted with ethyl acetate. The organic layer was washed with saturated brine and dried over anhydrous sodium sulfate. After filtration, the filtrate was concentrated under reduced pressure and the obtained residue was purified by silica gel column chromatography [elution solvent:chloroform/methanol=98/2-92/8 (V/V)], and slurry purification was further performed using an ethyl acetate/n-hexane mixed solvent to give the title compound (215 mg, yield: 71%) as a solid.

Example 105

(3R)-3-(7-Cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid 105a Ethyl 3-(7-cyclopropyl-1,4-dimethyl-1H-benzotriazol-5-yl)-3-[7-(hydroxymethyl)-2,3-dihydro-1H-inden-5-yl]propanoate To a mixture of bis(norbornadiene)rhodium(I) tetrafluoroborate (16.4 mg), (2S,3S)-bis(diphenylphosphino)butane (11.2 mg) and (2R,3R)-bis(diphenylphosphino)butane (11.2 mg) were added under a nitrogen atmosphere 1,4-dioxane (2.50 mL) and 1M aqueous potassium hydroxide solution (0.900 mL), and the mixture was stirred at room temperature for 15 min to prepare a catalyst solution. Then, a mixture of ethyl (2E)-3-(7-cyclopropyl-1,4-dimethyl-1H-benzotriazol-5-yl)prop-2-enoate (275 mg) of Example 49(49a), [6-(4,4,5,5-tetramethyl-1,3,2-dioxaborolan-2-yl)-2,3-dihydro-1H-inden-4-yl]methanol (375 mg) of Example 3(3d), 1,4-dioxane (5.00 mL) and water (1.80 mL) was prepared in a separate container and stirred at 50° C. for 10 min under a nitrogen atmosphere, and the catalyst solution prepared above was added. The reaction mixture was heated and stirred at 50° C. for 4 hr under a nitrogen atmosphere. To the reaction mixture was added [6-(4,4,5,5-tetramethyl-1,3,2-dioxaborolan-2-yl)-2,3-dihydro-1H-inden-4-yl]methanol (320 mg) of Example 3(3d), and the mixture was stirred at 50° C. for 3 hr. The reaction mixture was allowed to cool to room temperature, 2M hydrochloric acid (0.45 mL), saturated brine and water were added, and the mixture was extracted with ethyl acetate. The organic layer was washed with saturated brine and dried over anhydrous sodium sulfate. After filtration, the filtrate was concentrated under reduced pressure, and the obtained residue was purified by silica gel chromatography [elution solvent:n-hexane/ethyl acetate=70/30-30/70(V/V)] to give the title compound (302 mg, yield: 72%) as an amorphous.

105b

Ethyl 3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate Using ethyl 3-(7-cyclopropyl-1,4-dimethyl-1H-benzotriazol-5-yl)-3-[7-(hydroxymethyl)-2,3-dihydro-1H-inden-5-yl]propanoate (302 mg) of Example 105(105a) and (2R,5S)-2-ethyl-5-methyl-2,3,4,5-tetrahydropyrido[2,3-f][1,4]oxazepine dihydrochloride (222 mg) of Example 62(62c), the title compound (421 mg, yield: 99%) was obtained as an oil in the same manner as in Example 62(62d).

105c

Ethyl (3R)-3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate 105d Ethyl (3S)-3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate Ethyl 3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate (421 mg) of Example 105(105b) was subjected to chiral HPLC [column: CHIRALPAK IG (20 mm I.D.×250 mm), mobile phase: n-hexane/2-propanol=70/30(V/V), temperature: 40° C.] to obtain 180 mg of ethyl (3R)-3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate as the first peak (yield: 44%).

Similarly, 163 mg of ethyl (3S)-3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate was obtained as the second peak (yield: 39%).

Analysis HPLC conditions [column: CHIRALPAK IG (20 mm I.D.×250 mm), mobile phase: n-hexane/2-propanol=65/35(V/V), flow rate: 1.0 mL/min, temperature: 40° C., wavelength: 254 nm]; retention time: 7.513 min (the first peak), 9.403 min (the second peak)

105e (3R)-3-(7-Cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid Using ethyl (3R)-3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate (180 mg) of Example 105 (105c), the title compound (117 mg, yield: 68%) was obtained as a solid in the same manner as in Example 41.

Example 106

(3S)-3-(7-Cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoic acid Using ethyl (3S)-3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1H-inden-5-yl)propanoate (163 mg) of Example 105 (105d), the title compound (93.6 mg, yield: 60%) was obtained as a solid in the same manner as in Example 41.

Example 107

3-(7-Cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4 (5H)-yl]methyl}-2,3-dihydro-1-benzofuran-5-yl)propanoic acid 107a Ethyl 3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1-benzofuran-5-yl)propanoate Using ethyl 3-(7-cyclopropyl-1,4-dimethyl-1H-benzotriazol-5-yl)-3-[7-(hydroxymethyl)-2,3-dihydro-1-benzofuran-5-yl]propanoate (144 mg) of Example 102(102a) and (2R,5S)-2-ethyl-5-methyl-2,3,4,5-tetrahydropyrido[2,3-f][1,4]oxazepine dihydrochloride (111 mg) of Example 62(62c), the title compound (128 mg, yield: 64%) was obtained as an oil in the same manner as in Example 62(62d).

107b 3-(7-Cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-2,3-dihydro-1-benzofuran-5-yl)propanoic acid Using ethyl 3-(7-cyclopropyl-1,4-dimethyl-1H-benzotriazol-5-yl)-3-(7-{[(2R,5S)-2-ethyl-5-methyl-2,3-dihydro-

Example 108

(3S)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid

108a

Ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoate Ethyl (3S)-3-[7-(difluoromethoxy)-1,4-dimethyl-1H-benzotriazol-5-yl]-3-[7-(hydroxymethyl)-1-benzothiophen-5-yl]propanoate (96 mg) of Example 32(32c) was dissolved in tetrahydrofuran (0.67 mL), (4R)-8-chloro-4-ethyl-3,4-dihydro-2H-pyrido[2,3-b][1,4,5]oxathiazepine 1,1-dioxide (53 mg) of Example 1(1c), tri-n-butylphosphine (0.10 mL) and 1,1'-(azodicarbonyl)dipiperidine (102 mg) were added. While stirring the mixture at room temperature, tri-n-butylphosphine (0.10 mL) and 1,1'-(azodicarbonyl)dipiperidine (102 mg) were added after 60 min, 80 min, and 100 min, respectively, and the mixture was stirred for a total of 130 min. The reaction mixture was concentrated under reduced pressure, and the obtained residue was purified by silica gel column chromatography [elution solvent:n-hexane/ethyl acetate=95/5-70/30(V/V)] to give the title compound (96.9 mg, yield: 49%) as an oil.

108b (3S)-3-(7-{[(4R)-8-Chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoic acid Using ethyl (3S)-3-(7-{[(4R)-8-chloro-4-ethyl-1,1-dioxido-3,4-dihydro-2H-pyrido[2,3-b][1,4,5]oxathiazepin-2-yl]methyl}-1-benzothiophen-5-yl)-3-[7-(difluoromethoxy)-1,4-dimethyl-1H-benzotriazol-5-yl]propanoate (140.3 mg) of Example 108(108a), the title compound (53.7 mg, yield: 49%) was obtained as a solid in the same manner as in Example 1(1k).

Example 109

3-(7-Cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzofuran-5-yl)propanoic acid

109a

Ethyl 3-(7-cyclopropyl-1,4-dimethyl-1H-benzotriazol-5-yl)-3-[7-(hydroxymethyl)-1-benzofuran-5-yl]propanoate Using ethyl (2E)-3-(7-cyclopropyl-1,4-dimethyl-1H-benzotriazol-5-yl)prop-2-enoate (973 mg) of Example 49(49a) and [5-(4,4,5,5-tetramethyl-1,3,2-dioxaborolan-2-yl)-1-benzofuran-7-yl]methanol (784 mg) of Example 92(92c), the title compound (573 mg, yield: 44%) was obtained as a solid in the same manner as in Example 95(95a).

109b

Ethyl 3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzofuran-5-yl)propanoate Using ethyl 3-(7-cyclopropyl-1,4-dimethyl-1H-benzotriazol-5-yl)-3-[7-(hydroxymethyl)-1-benzofuran-5-yl]propanoate (284 mg) of Example 109(109a) and (2R,5S)-2-ethyl-5-methyl-2,3,4,5-tetrahydropyrido[2,3-f][1,4]oxazepine dihydrochloride (197 mg) of Example 62(62c), the title compound (344 mg, yield: 82%) was obtained as a solid in the same manner as in Example 62(62d).

109c 3-(7-Cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzofuran-5-yl)propanoic acid Using ethyl 3-(7-cyclopropyl-1,4-dimethyl-1H-benzotriazol-5-yl)-3-(7-{[(2R,5S)-2-ethyl-5-methyl-2,3-dihydropyrido[2,3-f][1,4]oxazepin-4(5H)-yl]methyl}-1-benzofuran-5-yl)propanoate (170 mg) of Example 109(109b), the title compound (122 mg, yield: 75%) was obtained as a solid in the same manner as in Example 2(2c).

Example 110

3-(7-{[(4R)-8-Chloro-4-ethyl-1,1-dioxido-3,4-dihydro-2H-pyrido[2,3-b][1,4,5]oxathiazepin-2-yl]methyl}-1-benzofuran-5-yl)-3-(7-cyclopropyl-1,4-dimethyl-1H-benzotriazol-5-yl)propanoic acid

110a

Ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzofuran-5-yl)-3-(7-cyclopropyl-1,4-dimethyl-1H-benzotriazol-5-yl)propanoate Ethyl 3-(7-cyclopropyl-1,4-dimethyl-1H-benzotriazol-5-yl)-3-[7-(hydroxymethyl)-1-benzofuran-5-yl]propanoate (289 mg) of Example 109(109a) was dissolved in dichloromethane (2.1 mL), thionyl chloride (0.092 mL) was added, and the mixture was stirred at room temperature for 20 min. The reaction mixture was azeotropically distilled with chloroform to give a residue. (4R)-8-Chloro-4-ethyl-3,4-dihydro-2H-pyrido[2,3-b][1,4,5]oxathiazepine 1,1-dioxide (166 mg) of Example 1(1c) was dissolved in N,N-dimethylformamide (2.1 mL), 60% sodium hydride (30 mg) was added, and the mixture was stirred at room temperature for 15 min. A solution of the earlier residue in N,N-dimethylformamide (1.4 mL) was added thereto, and the mixture was stirred at room temperature for 15 hr. To the reaction mixture was added water, and the mixture was extracted with ethyl acetate. The organic layer was washed successively with water and saturated brine and dried over anhydrous sodium sulfate, and the solvent was evaporated under reduced pressure. The obtained residue was purified by silica gel column chromatography [elution solvent:n-hexane/ethyl acetate=90/10-55/45(V/V)] to give the title compound (392 mg, yield: 82%) as an oil.

110b 3-(7-{[(4R)-8-Chloro-4-ethyl-1,1-dioxido-3,4-dihydro-2H-pyrido[2,3-b][1,4,5]oxathiazepin-2-yl]methyl}-1-benzofuran-5-yl)-3-(7-cyclopropyl-1,4-dimethyl-1H-benzotriazol-5-yl)propanoic acid Using ethyl 3-(7-{[(4R)-8-chloro-4-ethyl-1,1-dioxido-3,4-dihydro-2H-pyrido[2,3-b][1,4,5]oxathiazepin-2-yl]methyl}-1-benzofuran-5-yl)-3-(7-cyclopropyl-1,4-dimethyl-1H-benzotriazol-5-yl)propanoate (170 mg) of Example 110(110a), the title compound (119 mg, yield: 73%) was obtained as a solid in the same manner as in Example 1(1k).

Example 111

(3S)-3-(1,4-Dimethyl-1H-benzotriazol-5-yl)-3-(7-{[(4R)-7-ethoxy-4-ethyl-1,1-dioxido-3,4-dihydro-2H-pyrido[2,3-b][1,4,5]oxathiazepin-2-yl]methyl}-1-benzothiophen-5-yl)propanoic acid 111a Ethyl (3S)-3-(7-{[(4R)-7-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate Using ethyl (3S)-3-(1,4-dimethyl-1H-benzotriazol-5-yl)-3-[7-(hydroxymethyl)-1-benzothiophen-5-yl]propanoate (960 mg) of Example 7(7a) and (4R)-7-chloro-4-ethyl-3,4-dihydro-2H-pyrido[2,3-b][1,4,5]oxathiazepine 1,1-dioxide (664 mg) of Example 9(9b), the title compound (1.35 g, yield: 90%) was obtained as a solid in the same manner as in Example 3(3f).

111b (3S)-3-(1,4-Dimethyl-1H-benzotriazol-5-yl)-3-(7-{[(4R)-7-ethoxy-4-ethyl-1,1-dioxido-3,4-dihydro-2H-pyrido[2,3-b][1,4,5]oxathiazepin-2-yl]methyl}-1-benzothiophen-5-yl)propanoic acid Using ethyl (3S)-3-(7-{[(4R)-7-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate (2.0 g) of Example 111(111a), the title compound (1.19 g, yield: 63%) was obtained as a solid in the same manner as in Example 3(3g).

Example 112

(3R)-3-(1,4-Dimethyl-1H-benzotriazol-5-yl)-3-(7-{[(4R)-7-ethoxy-4-ethyl-1,1-dioxido-3,4-dihydro-2H-pyrido[2,3-b][1,4,5]oxathiazepin-2-yl]methyl}-1-benzothiophen-5-yl)propanoic acid 112a Ethyl (3R)-3-(7-{[(4R)-7-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate Using ethyl (3R)-3-(1,4-dimethyl-1H-benzotriazol-5-yl)-3-[7-(hydroxymethyl)-1-benzothiophen-5-yl]propanoate (1.5 g) of Example 7(7b) and (4R)-7-chloro-4-ethyl-3,4-dihydro-2H-pyrido[2,3-b][1,4,5]oxathiazepine 1,1-dioxide (1.1 g) of Example 9(9b), the title compound (2.5 g, yield: 90%) was obtained as a solid in the same manner as in Example 3(3f).

112b (3R)-3-(1,4-Dimethyl-1H-benzotriazol-5-yl)-3-(7-{[(4R)-7-ethoxy-4-ethyl-1,1-dioxido-3,4-dihydro-2H-pyrido[2,3-b][1,4,5]oxathiazepin-2-yl]methyl}-1-benzothiophen-5-yl)propanoic acid Using ethyl (3R)-3-(7-{[(4R)-7-chloro-4-ethyl-1,1-dioxido-3,4-dihydro-2H-pyrido[2,3-b][1,4,5]oxathiazepin-2-yl]methyl}-1-benzothiophen-5-yl)-3-(1,4-dimethyl-1H-benzotriazol-5-yl)propanoate (2.3 g) of Example 112(112a), the title compound (1.33 g, yield: 60%) was obtained as a solid in the same manner as in Example 3(3g).

The structural formulas of the compounds described in the examples and physicochemical data thereof are summarize in the following Table 4 to Table 77.

TABLE 4

| Example No. | structural formula | physicochemical data |
|---|---|---|
| 1(1b) | (structure) | $^1$H-NMR (CDCl$_3$) δ: 0.94 (3H, t, J = 7.4 Hz), 1.44-1.51 (2H, m), 1.85 (1H, d, J = 4.7 Hz), 2.83-2.90 (1H, m), 3.14-3.20 (1H, m), 3.63-3.70 (1H, m), 5.65 (1H, t, J = 5.7 Hz), 8.38 (1H, d, J = 2.7 Hz), 8.53 (1H, d, J = 2.3 Hz). MS(ESI/APCI) m/z: 297 [M − H]$^-$ |

TABLE 4-continued

| Example No. | structural formula | physicochemical data |
|---|---|---|
| 1(1c) | 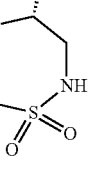 | $^1$H-NMR (CDCl$_3$) δ: 1.14 (3H, t, J = 7.4 Hz), 1.65-1.75 (1H, m), 1.78-1.88 (1H, m), 3.50-3.56 (1H, m), 3.62-3.71 (1H, m), 4.24-4.31 (1H, m), 5.02 (1H, brs), 8.14 (1H, d, J = 2.7 Hz), 8.36 (1H, d, J = 2.7 Hz).<br>MS(ESI/APCI) m/z: 263 [M + H]$^+$ |
| 1(1d) | 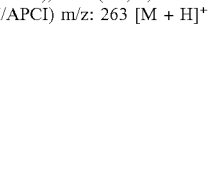 | $^1$H-NMR (DMSO-D$_6$) δ: 2.52 (3H, s), 7.54 (1H, s), 8.10 (2H, s), 13.65 (1H, br s). |
| 1(1e) | 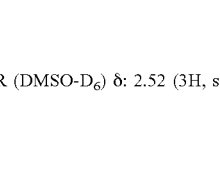 | $^1$H-NMR (CDCl$_3$) δ: 2.55 (3H, s), 7.24-7.30 (2H, m), 7.45 (1H, d, J = 5.4 Hz), 7.81 (1H, d, J = 1.5 Hz). |
| 1(1f) |  | $^1$H-NMR (CDCl$_3$) δ: 2.16 (3H, s), 5.33 (2H, s), 7.32 (1H, d, J = 5.4 Hz), 7.46-7.48 (1H, m), 7.50 (1H, d, J = 5.4 Hz), 7.94 (1H, d, J = 1.7 Hz). |

TABLE 5

| Example No. | structural formula | physicochemical data |
|---|---|---|
| 1(1g) | 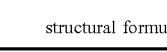 | $^1$H-NMR (CDCl$_3$) δ: 1.90 (1H, t, J = 6.1 Hz), 4.95 (2H, d, J = 6.1 Hz), 7.32 (1H, d, J = 5.4 Hz), 7.46-7.54 (2H, m), 7.91 (1H, d, J = 1.7 Hz). |

TABLE 5-continued

| Example No. | structural formula | physicochemical data |
| --- | --- | --- |
| 1(1h) | | ¹H-NMR (CDCl₃) δ: 1.38 (12H, s), 4.99 (2H, s), 7.40 (1H, d, J = 5.4 Hz), 7.45 (1H, d, J = 5.4 Hz), 7.75 (1H, s), 8.27 (1H, s). |
| 1(1i) | | ¹H-NMR (CDCl₃) δ: 1.10 (3H, t, J = 7.1 Hz), 1.86 (1H, t, J = 6.1 Hz), 2.87 (3H, s), 3.06-3.27 (2H, m), 4.02 (2H, q, J = 7.1 Hz), 4.24 (3H, s), 4.90 (2H, d, J = 6.1 Hz), 5.14 (1H, t, J = 8.0 Hz), 7.18-7.23 (1H, m), 7.28-7.34 (2H, m), 7.38-7.48 (2H, m), 7.60-7.66 (1H, m). |
| 1(1j) | | ¹H-NMR (CDCl₃) δ: 0.86-1.00 (3H, m), 1.12 (3H, t, J = 7.1 Hz), 1.36-1.54 (1H, m), 1.59-1.76 (1H, m), 2.81-2.88 (3H, m), 3.05-3.26 (3H, m), 3.54-3.70 (1H, m), 4.03 (2H, q, J = 7.1 Hz), 4.24-4.42 (5H, m), 4.61-4.73 (1H, m), 5.05-5.17 (1H, m), 7.06-7.14 (1H, m), 7.28-7.34 (2H, m), 7.36-7.42 (1H, m), 7.44-7.50 (1H, m), 7.65-7.71 (1H, m), 8.19-8.25 (1H, m), 8.37-8.43 (1H, m). |
| 1(1k) = 1 | | ¹H-NMR (DMSO-D₆) δ: 0.71 (1.5H, t, J = 7.3 Hz), 0.91 (1.5H, t, J = 7.3 Hz), 1.05-1.65 (2H, m), 2.71-2.95 (4H, m), 3.00-3.22 (2H, m), 3.62-3.78 (1H, m), 4.17-4.42 (5H, m), 4.62-4.73 (1H, m), 4.96 (1H, t, J = 7.8 Hz), 7.23-7.33 (1H, m), 7.40-7.60 (3H, m), 7.74-7.83 (1H, m), 7.83-7.91 (1H, m), 8.25-8.34 (1H, m), 8.58-8.68 (1H, m), 11.88-12.72 (1H, br s). MS(ESI) m/z: 624 [M − H]⁻; 626 [M + H]⁺, 648 [M + Na]⁺ |

TABLE 6

| Example No. | structural formula | physicochemical data |
|---|---|---|
| 2(2a) | | ¹H-NMR (CDCl₃) δ: 1.13 (3H, t, J = 7.1 Hz), 1.84 (1H, t, J = 5.9 Hz), 3.10-3.29 (2H, m), 4.04 (2H, q, J = 7.1 Hz), 4.27 (3H, s), 4.91 (2H, d, J = 5.9 Hz), 5.48 (1H, t, J = 8.1 Hz), 7.25-7.28 (1H, m), 7.31-7.37 (2H, m), 7.41 (1H, d, J = 8.8 Hz), 7.46 (1H, d, J = 5.4 Hz), 7.70-7.74 (1H, m). |
| 2(2b) | | ¹H-NMR (CDCl₃) δ: 0.90-1.06 (3H, m), 1.10-1.18 (3H, m), 1.38-1.78 (2H, m), 3.09-3.29 (3H, m), 3.55-3.75 (1H, m), 4.05 (2H, q, J = 7.1 Hz), 4.25-4.45 (5H, m), 4.63-4.74 (1H, m), 5.39-5.47 (1H, m), 7.16-7.21 (1H, m), 7.31-7.50 (4H, m), 7.72-7.76 (1H, m), 8.20-8.25 (1H, m) 8.38-8.43 (1H, m). |
| 2(2c) = 2 | | ¹H-NMR (DMSO-D₆) δ: 0.74-0.96 (3H, m), 1.21-1.63 (2H, m), 2.76-2.95 (1H, m), 3.05-3.25 (2H, m), 3.64-3.79 (1H, m), 4.25-4.42 (5H, m), 4.62-4.74 (1H, m), 5.22 (1H, t, J = 7.8 Hz), 7.30-7.40 (1H, m), 7.43-7.50 (1H, m), 7.62-7.84 (3H, m), 7.86-7.93 (1H, m), 8.26-8.30 (1H, m), 8.61-8.66 (1H, m), 11.26-13.16 (1H, br s).<br>MS(ESI) m/z: 644 [M − H]⁻, 668 [M + Na]⁺ |
| 3(3a) | | ¹H-NMR (CDCl₃) δ: 2.70-2.76 (2H, m), 3.47-3.54 (2H, m), 3.96 (3H, s), 7.48 (1H, t, J = 7.6 Hz), 7.93-7.98 (1H, m), 8.28 (1H, dd, J = 7.6, 1.2 Hz). |
| 3(3b) | | ¹H-NMR (CDCl₃) δ: 2.08 (2H, quintet, J = 7.6 Hz), 2.93 (2H, t, J = 7.6 Hz), 3.28 (2H, t, J = 7.6 Hz), 3.89 (3H, s), 7.20 (1H, t, J = 7.6 Hz), 7.36-7.42 (1H, m), 7.78-7.83 (1H, m). |

TABLE 6-continued

| Example No. | structural formula | physicochemical data |
|---|---|---|
| 3(3c) | (structure: 6-bromo-2,3-dihydro-1H-indene with CH2OH at 4-position) | ¹H-NMR (CDCl₃) δ: 1.55-1.62 (1H, m), 2.09 (2H, quintet, J = 7.3 Hz), 2.83 (2H, t, J = 7.3 Hz), 2.90 (2H, t, J = 7.3 Hz), 4.63 (1H, d, J = 4.2 Hz), 7.28-7.31 (1H, m), 7.31-7.35 (1H, m). |

TABLE 7

| Example No. | structural formula | physicochemical data |
|---|---|---|
| 3(3d) | (structure: pinacol boronate ester of indane with CH2OH) | ¹H-NMR (CDCl₃) δ: 1.34 (12H, s), 1.46 (1H, t, J = 5.8 Hz), 2.09 (2H, quintet, J = 7.3 Hz), 2.89-2.99 (4H, m), 4.68 (2H, d, J = 5.8 Hz), 7.61 (1H, s), 7.65 (1H, s).<br>MS(ESI/APCI) m/z: 257 [M + H − H₂O]⁺ |
| 3(3e) | (structure: benzotriazole-indane ethyl ester) | MS(ESI/APCI) m/z: 394 [M + H]⁺ |
| 3(3f) | (structure: benzotriazole-indane-pyridooxathiazepine with Cl) | ¹H-NMR (CDCl₃) δ: 0.93-0.95 (3H, m), 1.08 (3H, t, J = 7.1 Hz), 1.40-1.46 (1H, m), 1.58-1.69 (1H, m), 2.00-2.06 (2H, m), 2.79-2.86 (7H, m), 3.02 (1H, dd, J = 8.3, 3.9 Hz), 3.06-3.08 (2H, m), 3.48-3.58 (1H, m), 3.99-4.00 (3H, m), 4.22 (3H, s), 4.29 (1H, br s), 4.36 (1H, d, J = 13.7 Hz), 4.91-4.92 (1H, m), 6.83 (1H, s), 7.03 (1H, s), 7.28 (2H, d, J = 8.8 Hz), 7.34 (1H, d, J = 3.4 Hz), 7.36 (1H, d, J = 3.9 Hz), 8.16 (1H, d, J = 2.4 Hz), 8.36 (1H, t, J = 2.9 Hz).<br>MS(ESI/APCI) m/z: 638 [M + H]⁺ |

TABLE 7-continued

| Example No. | structural formula | physicochemical data |
|---|---|---|
| 3(3g) = 3 | | ¹H-NMR (CDCl₃) δ: 0.90-0.93 (3H, m), 1.42-1.43 (1H, m), 1.57-1.65 (1H, m), 1.99-2.03 (2H, m), 2.77 (1.5H, s), 2.78 (1.5H, s), 2.81-2.86 (4H, m), 3.00-3.13 (3H, m), 3.47-3.57 (1H, m), 3.98 (1H, d, J = 13.7 Hz), 4.22 (3H, s), 4.29 (1H, br s), 4.36 (1H, dd, J = 13.9, 5.6 Hz), 4.89-4.92 (1H, m), 6.84 (1H, s), 7.03 (1H, s), 7.28 (1H, d, J = 8.8 Hz), 7.32 (1H, dd, J = 8.5, 4.6 Hz), 8.16 (1H, d, J = 2.4 Hz), 8.35 (1H, d, J = 2.4 Hz). MS(ESI/APCI) m/z: 610 [M + H]⁺ |
| 4(4c) | | ¹H-NMR (CDCl₃) δ: 0.97 (3H, t, J = 7.3 Hz), 1.11 (3H, t, J = 7.0 Hz), 1.40-1.55 (1H, m), 1.61-1.75 (1H, m), 1.98-2.11 (2H, m), 2.76-2.95 (4H, m), 2.82 (3H, s), 3.00-3.15 (3H, m), 3.59 (1H, dd, J = 15.3, 11.0 Hz), 3.96-4.07 (3H, m), 4.25 (3H, s), 4.27-4.35 (1H, m), 4.39 (1H, d, J = 14.0 Hz), 4.94 (1H, t, J = 7.9 Hz), 6.86 (1H, s), 7.06 (1H, s), 7.31 (1H, d, J = 8.5 Hz), 7.38 (1H, d, J = 8.5 Hz), 8.19 (1H, d, J = 2.4 Hz), 8.39 (1H, d, J = 2.4 Hz). MS(APCI) m/z: 638 [M + H]⁺ |

TABLE 8

| Example No. | structural formula | physicochemical data |
|---|---|---|
| 4(4d) = 4 | | ¹H-NMR (CDCl₃) δ: 0.97 (3H, t, J = 7.3 Hz), 1.44-1.52 (1H, m), 1.63-1.72 (1H, m), 2.00-2.09 (2H, m), 2.77-2.91 (7H, m), 3.01-3.18 (3H, m), 3.56 (1H, dd, J = 14.9, 10.6 Hz), 4.05 (1H, d, J = 14.0 Hz), 4.22 (3H, s), 4.28-4.33 (1H, m), 4.37 (1H, d, J = 14.6 Hz), 4.94 (1H, t, J = 7.9 Hz), 6.89 (1H, s), 7.05 (1H, s), 7.28 (1H, d, J = 9,1 Hz), 7.35 (1H, d. J = 9.1 Hz), 8.17 (1H, d, J = 2.4 Hz), 8.36 (1H, d, J = 2.4 Hz): MS(APCI) m/z: 610 [M + H]⁺ |

TABLE 8-continued

| Example No. | structural formula | physicochemical data |
|---|---|---|
| 5(5a) | | ¹H-NMR (CDCl₃) δ: 0.96 (3H, t, J = 7.4 Hz), 1,11 (3H, t, J = 7.1 Hz), 1.40-1.51 (1H, m). 1.59-1.73 (1H, m), 2.00-2.10 (2H, m), 2.78-2.94 (7H, m), 3.03 (1H, dd, J = 15.3, 8.0 Hz), 3.07-3.13 (2H, m), 3.54 (1H, dd, J = 15.3, 11.0 Hz), 3.99-4.05 (3H, m), 4.25 (3H, s), 4.29-4.36 (1H, m), 4,39 (1H, d, J = 13.5 Hz), 4.95 (1H, t, J = 8.0 Hz), 6.85 (1H, s), 7.06 (1H, s), 7.31 (1H, d, J = 8.6 Hz), 7.37 (1H, d, J = 8.6 Hz), 8.19 (1H, d, J = 2.5 Hz), 8.39 (1H, d, J = 2.5 Hz).<br>MS(ESI/APCI) m/z: 638 [M + H]⁺ |
| 5(5b) = 5 | | ¹H-NMR (CDCl₃) δ: 0.95 (3H, t, J = 7.4 Hz), 1.39-1.49 (1H, m), 1.58-1.70 (1H, m), 2.01-2.10 (2H, m), 2.77-2.93 (7H, m), 3.02-3.18 (3H, m), 3.53 (1H, dd, J = 14.7, 1.1.0 Hz), 4,01 (1H, d. J = 14.1 Hz), 4.25 (3H, s), 4.30-4.36 (1H, m), 4.39 (1H, d, J = 14.1 Hz), 4.94 (1H, t, J = 8.0 Hz), 6.87 (1H, s), 7.05 (1H, s), 7.31 (1H, d, J = 8.6 Hz), 7.35 (1H, d, J = 8.6 Hz), 8.19 (1H, d, J = 2.5 Hz), 8.38 (1H, d, J = 2.5 Hz).<br>MS(ESI/APCI) m/z: 610 [M + H]⁺ |
| 6(6a) | | ¹H-NMR (CDCl₃) δ: 2.85 (3H, s), 3.15-3.60 (3H, br m). 6.31 (1H, d, J = 8.0 Hz), 6.94 (1H, t, J = 8.0 Hz). |
| 6(6b) | | ¹H-NMR (CDCl₃) δ: 4.32 (3H, s), 7.23 (1H, d, J = 8.8 Hz), 7.61 (1H, dd, J = 8.8, 5.6 Hz). |
| 6(6c) | | ¹H-NMR (CDCl₃) δ: 1.36 (3H, t, J = 7.1 Hz), 4.26-4.35 (5H, m), 6.57 (1H, d, J = 16.1 Hz), 7.28-7.34 (1H, m), 7.63-7.69 (1H, m), 8.00 (1H, d, J = 16.1 Hz). |

TABLE 9

| Example No. | structural formula | physicochemical data |
|---|---|---|
| 6(6d) | | ¹H-NMR (CDCl₃) δ: 1.13 (3H, t, J = 7.1 Hz), 1.58 (1H, t, J = 5.8 Hz), 2.01-2.10 (2H, m), 2.81-2.89 (4H, m), 3.14-3.20 (2H, m), 3.99-4.08 (2H, m), 4.26 (3H, s), 4.62 (2H, d, J = 5.8 Hz), 5.04 (1H, t, J = 8.3 Hz), 7.12 (2H, s), 7.22 (1H, d, J = 8.6 Hz), 7.40 (1H, dde, J = 8.6, 5.9 Hz). |
| 6(6e) | | ¹H-NMR (CDCl₃) δ: 1.10-1.16 (3H, m), 1.25-1.35 (3H, m), 1.98-2.10 (2H, m), 2.80-2.99 (5H, m), 3.10-3.17 (2H, m), 3.64-3.79 (2H, m), 3.99-4.07 (2H,m), 4.22-4.31 (4H, m), 4.47-4.55 (1H, m), 4.94-5.02 (1H, m), 6.94-7.00 (1H, m), 7.09-7.13 (1H, m), 7.16-7.25 (3H, m), 7.35-7.42 (1H, m), 7.48-7.54 (1H, m), 7.84-7.88 (1H, m). |
| 6(6f) = 6 | | ¹H-NMR (DMSO-D₆) δ: 1.20-1.24 (3H, m), 1.89-2.00 (2H, m), 2.66-2.89 (5H, m), 3.04-3.18 (2H, m), 3.57-3.66 (1H, m), 3.78-3.86 (1H, m), 4.26-4.42 (5H, m), 4.81-4.89 (1H, m), 71.2-7.18 (2H, m), 7.29 (1H, d, J = 7.8 Hz), 7.35 (1H, t, J = 7.6 Hz), 7.59-7.68 (3H, m), 7.76 (1H, d, J = 7.6 Hz). MS(APCI) m/z: 565 [M + H]⁺ |
| 7(7c) | | ¹H-NMR (CDCl₃) δ: 0.94 (3H, t, J = 7.2 Hz), 1.10 (3H, t, J = 7.2 Hz), 1.44-1.47 (1H, m), 1.63-1.67 (1H, m), 2.83 (3H, s), 3.05-3.21 (3H, m), 3.62 (1H, dd, J = 15.1, 10.8 Hz), 4.01 (2H, q, J = 7.0 Hz), 4.24 (3H, s), 4.28-4.32 (2H, m), 4.65 (1H, d, J = 14.1 Hz), 5.09 (1H, t, J = 7.8 Hz), 7.09 (1H, s), 7.28 (1H, s), 7.30 (1H, d, J = 3.9 Hz), 7.37 (1H, d, J = 8.6 Hz), 7.45 (1H, d, J = 5.5 Hz), 7.65 (1H, s), 8.20 (1H, d, J = 2.3 Hz), 8.39 (1H, d, J = 2.7 Hz). MS(ESI/APCI) m/z: 654 [M + H]⁺ |

TABLE 9-continued

| Example No. | structural formula | physicochemical data |
|---|---|---|
| 7(7d) = 7 | 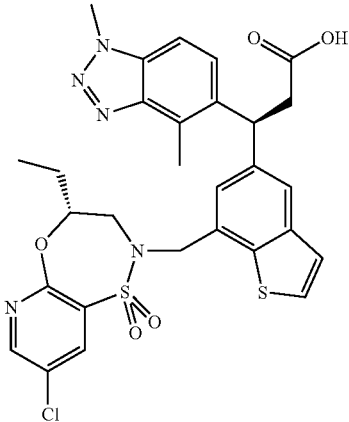 [SMILES: CC[C@@H]1CN(Cc2cc([C@H](CC(=O)O)c3ccc4c(nnn4C)c3C)cc3ccsc23)S(=O)(=O)c2cc(Cl)cnc2O1] | ¹H-NMR (CDCl₃) δ: 0.92 (3H, t, J = 7.3 Hz), 1.43-1.45 (1H, m), 1.62-1.65 (1H, m), 2.81 (3H, s), 3.12 (2H, dd, J = 15.6, 7.8 Hz), 3.22 (1H, dd, J = 15.9, 8.1 Hz), 3.61 (1H, dd, J = 14.6, 10.7 Hz), 4.22 (3H, s), 4.30-4.32 (2H, m), 4.64 (1H, d, J = 14.6 Hz), 5.07 (1H, t, J = 7.6 Hz), 7.09 (1H, s), 7.28 (1H, d, J = 5.4 Hz), 7.30 (1H, s), 7.35 (1H, d, J = 8.3 Hz), 7.45 (1H, d, J = 5.4 Hz), 7.65 (1H, s), 8.19 (1H, d, J = 2.4 Hz), 8.38 (1H, d, J = 2.4 Hz). MS(ESI/APCI) m/z: 626 [M + H]⁺ |

TABLE 10

| Example No. | structural formula | physicochemical data |
|---|---|---|
| 8(8a) | 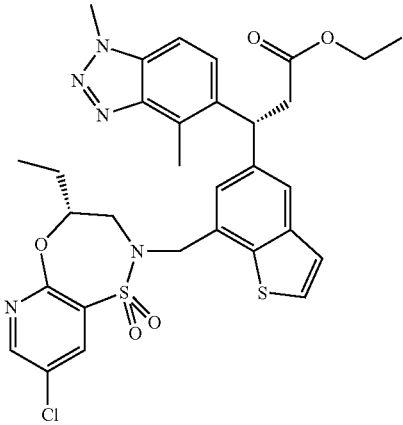 [SMILES: CCOC(=O)C[C@H](c1cc(CN2C[C@@H](CC)Oc3ncc(Cl)cc3S2(=O)=O)c2sccc2c1)c1ccc2c(nnn2C)c1C] | ¹H-NMR (CDCl₃) δ: 0.90 (3H, t, J = 7.3 Hz), 1.09 (3H, t, J = 7.1 Hz), 1.39-1.43 (1H, m), 1.59-1.65 (1H, m), 2.83 (3H, s), 3.09-3.15 (3H, m), 3.57 (1H, dd, J = 14.4, 11.5 Hz), 4.01 (2H, q, J = 7.1 Hz), 4.23 (3H, s), 4.29-4.32 (2H, m), 4.64 (1H, d, J = 14.2 Hz), 5.09 (1H, t, J = 8.1 Hz), 7.08 (1H, s), 7.29 (2H, d, J = 6.8 Hz), 7.36 (1H, d, J = 8.3 Hz), 7.45 (1H, d, J = 5.4 Hz), 7.65 (1H, s), 8.20 (1H, s), 8.38 (1H, s). MS(ESI/APC) m/z: 654 [M + H]⁺ |
| 8(8b) = 8 | 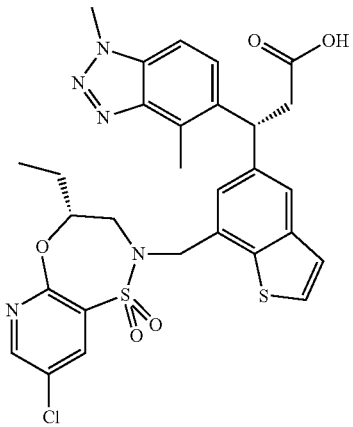 [SMILES: CC[C@@H]1CN(Cc2cc([C@@H](CC(=O)O)c3ccc4c(nnn4C)c3C)cc3ccsc23)S(=O)(=O)c2cc(Cl)cnc2O1] | ¹H-NMR (CDCl₃) δ: 0.89 (3H, t, J = 7.3 Hz), 1.36-1.43 (1H, m), 1.59-1.62 (1H, m), 2.82 (3H, s), 3.12 (2H, dd, J = 15.6, 7.8 Hz), 3.22 (1H, dd, J = 15.6, 7.8 Hz), 3.58 (1H, dd, J = 14.6, 10.7 Hz), 4.23 (3H, s), 4.31-4.35 (2H, m), 4.65 (1H, d, J = 14.2 Hz), 5.08 (1H, t, J = 7.8 Hz), 7.09 (1H, s), 7.29 (2H, d, J = 7.8 Hz), 7.34 (1H, d, J = 8.8 Hz), 7.45 (1H, d, J = 5.4 Hz), 7.65 (1H, s), 8.20 (1H, s), 8.37 (1H, s). MS(ESI/APCI) m/z: 626 [M + H]⁺ |

TABLE 10-continued

| Example No. | structural formula | physicochemical data |
| --- | --- | --- |
| 9(9a) | | MS(ESI/APCI) m/z: 299 [M + H]⁺ |
| 9(9b) | | MS(ESI/APCI) m/z: 263 [M + H]⁺ |
| 9(9c) | | MS(ESI/APCI) m/z: 638 [M + H]⁺ |
| 9(9d) = 9 | | $^1$H-NMR (CDCl$_3$) δ: 0.90-0.96 (3H, m), 1.35-1.42 (4H, m), 1.56-1.65 (1H, m), 1.98-2.01 (2H, m), 2.77-2.86 (7H, m), 3.02-3.05 (1H, m), 3.08-3.14 (2H, m), 3.35-3.41 (1H, m), 4.04 (1H, dd, J = 13.7, 10.3 Hz), 4.22-4.28 (4H, m), 4.32-4.41 (3H, m), 4.89-4.91 (1H, m), 6.55 (1H, d, J = 8.8 Hz), 6.88 (1H, s), 7.00 (1H, s), 7.27 (1H, d, J = 8.8 Hz), 7.33 (1H, dd, J = 8.5, 4.6 Hz), 8.01 (1H, d, J = 8.8 Hz). MS(ESI/APCI) m/z: 620 [M + H]⁺ |

TABLE 11

| Example No. | structural formula | physicochemical data |
| --- | --- | --- |
| 10(10a) | | MS(ESI/APCI) m/z: 279 [M + H]⁺ |

TABLE 11-continued

| Example No. | structural formula | physicochemical data |
|---|---|---|
| 10(10b) | | MS(ESI/APCI) m/z: 243 [M + H]+ |
| 10(10c) | | MS(ESI/APCI) m/z: 618 [M + H]+ |
| 10(10d) = 10 | | ¹H-NMR (CDCl₃) δ: 0.88-0.90 (3H, m), 1.36-1.40 (1H, m), 1.57-1.62 (1H, m), 2.01-2.02 (2H, m), 2.35 (3H, s), 2.80-2.86 (7H, m), 3.01-3.05 (2H, m), 3.11 (1H, dd, J = 15.9, 7.6 Hz), 3.48-3.58 (1H, m), 3.92 (1H, dd, J = 13.7, 10.3 Hz), 4.21 (4H, m), 4.36 (1H, dd, J = 13.7, 7.8 Hz), 4.91 (1H, dd, J = 13.9, 7.6 Hz), 6.85 (1H, s), 7.01 (1H, s), 7.25 (1H, d, J = 13.2 Hz), 7.33 (1H, d, J = 8.8 Hz), 8.01 (1H, s), 8.23 (1H, d, J = 2.4 Hz). MS(ESI/APCI) m/z: 590 [M + H]+ |
| 11(11a) | | MS(ESI/APCI) m/z: 618 [M + H]+ |

TABLE 11-continued

| Example No. | structural formula | physicochemical data |
|---|---|---|
| 11(11b) = 11 | | ¹H-NMR (CDCl₃) δ: 0.84-0.90 (3H, m), 1.44-1.48 (1H, m), 1.60-1.65 (1H, m), 1.98-2.04 (2H, m), 2.52 (3H, s), 2.77-2.87 (7H, m), 3.02 (1H, dd, J = 16.1, 8.3 Hz), 3.09-3.11 (2H, m), 3.38-3.48 (1H, m), 4.02 (1H, dd, J = 13.7, 9.3 Hz), 4.21 (3H, s), 4.28 (1H, dd, J = 13.7, 7.3 Hz), 4.42 (1H, br s), 4,89-4.91 (1H, m), 6.86 (1H, s), 7.00 (1H, s), 7.05 (1H, d. J = 7.8 Hz), 7.27 (1H, d, J = 8.3 Hz), 7.33 (1H, d, J = 8.8 Hz), 8.07 (1H, d, J = 7.8 Hz). MS(ESI/APCI) m/z: 590 [M + H]⁺ |

TABLE 12

| Example No. | structural formula | physicochemical data |
|---|---|---|
| 12(12a) | | MS(ESI/APCI) m/z: 603 [M + H]⁺ |
| 12(12b) = 12 | | ¹H-NMR (CDCl₃) δ: 0.90 (1.5H, t, J = 7.3 Hz), 0.94 (1.5H, t, J = 7.3 Hz), 1.22-1.32 (1H, m), 1.51-1.56 (1H, m), 1.99-2.01 (2H, m), 2.78-2.81 (6H, m), 2.87-2.90 (2H, m), 2.98-3.05 (1H, m), 3.10 (1H, dd, J = 15.6, 7.3 Hz), 3.58-3.66 (1H, m), 3.70 (1H, dd, J = 13.9, 7.6 Hz), 3.88 (1H, br s), 4.20 (1.5H, s), 4.21 (1.5H, s), 4.46 (1H, t, J = 12.7 Hz), 4.88-4.90 (1H, m), 6.83 (1H, d, J = 4.9 Hz), 6.99 (1H, s), 7.14 (1H, t, J = 6.6 Hz), 7.21 (1H, t. J = 7.6 Hz), 7.26-7.33 (2H, m), 7.47 (1H, t. J = 7.8 Hz), 7.83 (1H, dd, J = 6.3, 3.9 Hz). MS(ESI/APCI) m/z: 575 [M + H]⁺ |
| 13(13a) | | MS(ESI/APCI) m/z: 298 [M − H]⁻ |

TABLE 12-continued

| Example No. | structural formula | physicochemical data |
|---|---|---|
| 13(13b) | | MS(ESI/APCI) m/z: 278 [M − H]⁻ |
| 13(13c) | | MS(ESI/APCI) m/z: 655 [M + H]⁺ |
| 13(13d) = 13 | | ¹H-NMR (CDCl₃) δ: 0.88 (1.5H, t, J = 7.3 Hz), 0.92 (1.5H, t, J = 7.3 Hz), 1.27-1.30 (1H, m), 1.50-1.55 (1H, m), 2.01-2.03 (2H, m), 2.79-2.82 (6H, m), 2.88-2.91 (2H, m), 2.99-3.06 (1H, m), 3.09 (0.5H, dd, J = 7.6, 2.7 Hz), 3.12 (0.5H, dd, J = 7.6, 2.7 Hz), 3.54-3.63 (1H, m), 3.75 (1H, dd, J = 13.7, 2.9 Hz), 3,93 (1H, br s), 4.22 (3H, s), 4.44 (1H, t. J = 12.4 Hz), 4.89 (1H, dd, J = 12.2, 7.8 Hz), 6.82 (1H, s), 6.94 (1H, dd, J = 8.8, 3.4 Hz), 7.01 (1H, s), 7.26-7.33 (2H, m), 7.89 (1H, dd, J = 8.1, 3.7 Hz).<br>MS(ESI/APCI) m/z: 627 [M + H]⁺ |

TABLE 13

| Example No. | structural formula | physicochemical data |
|---|---|---|
| 14(14a) | | MS(ESI/APCI) m/z: 280 [M − H]⁻ |

TABLE 13-continued

| Example No. | structural formula | physicochemical data |
|---|---|---|
| 14(14b) | | MS(ESI/APCI) m/z: 260 [M − H]⁻ |
| 14(14c) | | MS(ESI/APCI) m/z: 637 [M + H]⁺ |
| 14(14d) = 14 | | ¹H-NMR (CDCl₃) δ: 0.91 (1.5H, t, J = 7.3 Hz), 0.96 (1.5H, t, J = 7.3 Hz), 1.24-1.34 (1H, m), 1.52-1.60 (1H, m), 2.02-2.09 (2H, m), 2.79-2.95 (8H, m), 3.04 (1H, dd, J = 15.8, 8.0 Hz), 3.11-3.14 (1H, m), 3.62-3.66 (1H, m), 3.76 (1H, d, J = 13.7 Hz), 3.86-3.91 (1H, m), 4.24 (1.5H, s), 4.24 (1.5H, s), 4.50 (1H, dd, J = 13.9, 8.4 Hz), 4.91-4.93 (1H, m), 6.85 (1H, d, J = 3.5 Hz), 7.03 (1H, s), 7.10 (0.5H, d, J = 4.7 Hz), 7.12 (0.5H, d, J = 4.7 Hz), 7.28-7.37 (2H, m), 7.43 (0.5H, d, J = 2.3 Hz), 7.45 (0.5H, d, J = 2.3 Hz), 7.83 (1H, t, J = 2.9 Hz). MS(ESI/APCI) m/z: 609 [M + H]⁺ |
| 15(15a) | | MS(ESI/APCI) m/z: 280 [M − H]⁻ |
| 15(15b) | | ¹H-NMR (CDCl₃) δ: 1.13 (3H, t, J = 7.4 Hz), 1.59-1.68 (1H, m), 1.71-1.83 (1H, m), 3.38-3.44 (1H, m), 3.61-3.71 (1H, m), 3.87-3.94 (1H, m), 4.65-4.70 (1H, m), 7.17-7.21 (2H, m), 7.76-7.79 (1H, m). |

TABLE 14
| Example No. | structural formula | physicochemical data |
|---|---|---|
| 15(15c) | 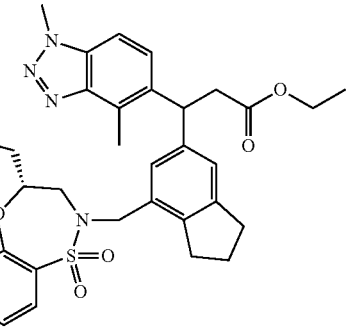 | MS(ESI/APCI) m/z: 637 [M + H]⁺ |
| 15(15d) = 15 | 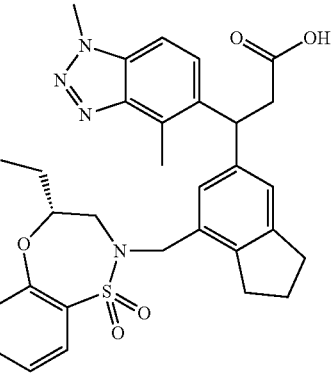 | $^1$H-NMR (CDCl$_3$) δ: 0.91-0.96 (3H, m), 1.26-1.29 (2H, m), 2.00-2.03 (2H, m), 2.80-2.82 (6H, m), 2.89-2.92 (2H, m), 3.01-3.07 (1H, m), 3.13 (1H, dd, J = 15.9, 7.6 Hz), 3.59-3.64 (1H, m), 3.74 (1H, dd, J = 14.2, 5.4 Hz), 3.93 (1H, br s), 4.22 (3H, s), 4.44 (1H, dd, J = 13.4, 10.0 Hz), 4.89-4.93 (1H, m), 6.86 (1H, s), 7.01 (1H, s), 7.17-7.19 (1H, m), 7.27-7.35 (3H, m), 7.77 (1H, dd, J = 8.3, 2.9 Hz).<br>MS(ESI/APCI) m/z: 609 [M + H]⁺ |
| 16(16a) | 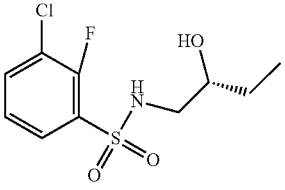 [SMILES: CC[C@@H](O)CNS(=O)(=O)c1cccc(Cl)c1F] | MS(ESI/APCI) m/z: 280 [M − H]⁻ |
| 16(16b) | 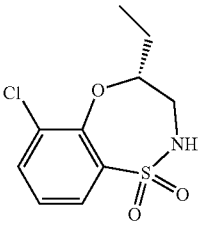 [SMILES: CC[C@@H]1CNS(=O)(=O)c2cccc(Cl)c2O1] | $^1$H-NMR (CDCl$_3$) δ: 1.15 (3H, t, J = 7.3 Hz), 1.72-1.82 (1H, m), 1.89-1.99 (1H, m), 3.43-3.50 (1H, m), 3.66-3.75 (1H, m), 3.95-4.02 (1H, m), 4.77 (1H, br s), 7.14 (1H, t, J = 7.8 Hz), 7.54-7.57 (1H, m), 7.74 (1H, d, J = 7.8 Hz). |
| 16(16c) | 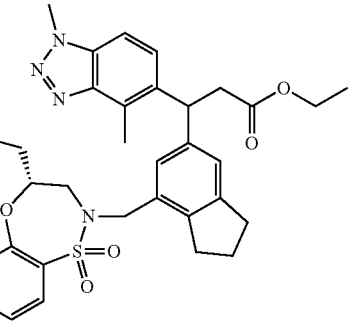 | MS(ESI/APCI) m/z: 637 [M + H]⁺ |

TABLE 14-continued
| Example No. | structural formula | physicochemical data |
|---|---|---|
| 16(16d) = 16 | 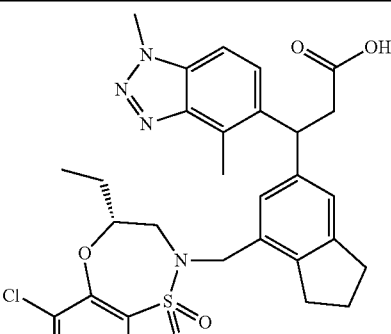 | ¹H-NMR (CDCl₃) δ: 0.89 (1.5H, t, J = 7.3 Hz), 0.95 (1.5H, t, J = 7.6 Hz), 1.44-1.50 (1H, m), 1.71-1.77 (1H, m), 2.00-2.05 (2H, m), 2.79-2.82 (6H, m), 2.88-2.95 (2H, m), 3.00-3.05 (1H, m), 3.09 (0.5H, d, J = 7.3 Hz), 3.13 (0.5H, d, J = 7.8 Hz), 3.67-3.72 (2H, m), 3.96 (1H, br s), 4.22 (3H, s), 4.44 (0.5H, d, J = 9.3 Hz), 4.47 (0.5H, d, J = 9.3 Hz), 4.90 (1H, t, J = 7.3 Hz), 6.84 (1H, d, J = 7.8 Hz), 7.01 (1H, s), 7.15 (1H, t, J = 7.8 Hz), 7.26-7.33 (2H, m), 7.55-7.57 (1H, m), 7.75 (1H, d, J = 7.8 Hz).<br>MS(ESI/APCI) m/z: 609 [M + H]⁺ |
| 17(17A) | | MS(ESI/APCI) m/z: 280 [M − H]⁻ |
TABLE 15
| Example No. | structural formula | physicochemical data |
|---|---|---|
| 17(17b) | | ¹H-NMR (CDCl₃) δ: 1.06 (3H, t, J = 7.3 Hz), 1.60-1.77 (2H, m), 3.09-3.17 (1H, m), 3.59-3.66 (1H, m), 4.26-4.32 (1H, m), 5.17-5.23 (1H, m), 7.04-7.07 (1H, m), 7.22-7.24 (1H, m), 7.28-7.32 (1H, m). |
| 17(17c) | 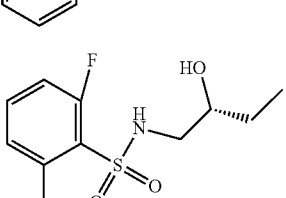 | MS(ESI/APCI) m/z: 637 [M + H]⁺ |

TABLE 15-continued

| Example No. | structural formula | physicochemical data |
|---|---|---|
| 17(17d) = 17 | | ¹H-NMR (CDCl₃) δ: 0.90-0.91 (3H, m), 1.36-1.53 (2H, m), 1.99-2.02 (3H, m), 2.79-2.80 (5H, m), 2.86-2.91 (3H, m), 3.04-3.07 (1H, m), 3.11-3.16 (1H, m), 3.29 (0.5H, dd, J = 14.2, 4.4 Hz), 3.37 (0.5H, dd, J = 14.2, 4.4 Hz), 4.21 (3H, s), 4.33-4.41 (1H, m), 4.64 (1H, t, J = 12.7 Hz), 4.92 (1H, t, J = 7.8 Hz), 6.98 (2H, s), 7.04 (1H, d, J = 8.3 Hz), 7.22-7.23 (1H, m), 7.27-7.30 (2H, m), 7.35 (1H, dd, J = 8.5, 5.1 Hz). MS(ESI/APCI) m/z: 609 [M + H]⁺ |
| 18 | | ¹H-NMR (CDCl₃) δ: 0.86 (1.5H, t, J = 7.3 Hz), 0.93 (1.5H, t, J = 7.3 Hz), 1.26-1.31 (1H, m), 1.48 (3H, t, J = 6.8 Hz), 1.53-1.58 (1H, m), 2.00-2.03 (2H, m), 2.76-2.81 (6H, m), 2.85-2.92 (2H, m), 3.00-3.07 (1H, m), 3.09-3.15 (1H, m), 3.56-3.61 (1H, m), 3.70 (0.5H, d, J = 2.9 Hz), 3.73 (0.5H, d, J = 3.4 Hz), 3.91-3.92 (1H, m), 4.08-4.14 (2H, m), 4.21 (1.5H, s), 4.22 (11.5H, s), 4.44 (1H, t, J = 12.9 Hz), 4.90 (1H, t, J = 6.6 Hz), 6.63 (1H, d, J = 3.4 Hz), 6.83 (1H, d, J = 7.3 Hz), 7.00 (1H, s), 7.26-7.33 (2H, m), 7.81 (1H, d, J = 4.4 Hz). MS(ESI/APCI) m/z: 653 [M + H]⁺ |
| 19(19a) | | MS(ESI/APCI) m/z: 654 [M + H]⁺ |

TABLE 16
| Example No. | structural formula | physicochemical data |
|---|---|---|
| 19(19b) = 19 | 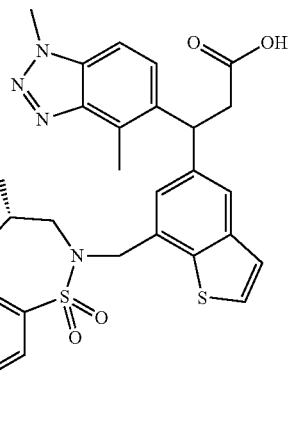 | ¹H-NMR (CDCl₃) δ: 0.88 (1.5H, t, J = 7.3 Hz), 0.93 (1.5H, t, J = 7.3 Hz), 1.36-1.38 (4H, m), 1.58-1.60 (1H, m), 2.78 (1.5H, s), 2.79 (1.5H, s), 3.06-3.15 (2H, m), 3.19 (0.5H, d, J = 7.6 Hz), 3.22 (0.5H, d, J = 7.6 Hz), 3.40-3.46 (1H, m), 4.20 (3H, s), 4.59 (5H, m), 5.07 (1H, t, J = 6.6 Hz), 6.56 (1H, d, J = 8.3 Hz), 7.08 (1H, d, J = 4.4 Hz), 7.25-7.26 (2H, m), 7.34 (1H, t, J = 9.8 Hz), 7.43 (1H, d, J = 4.9 Hz), 7.62 (1H, s), 8.03 (1H, d, J = 8.5 Hz).<br>MS(ESI/APCI) m/z: 636 [M + H]⁺ |
| 20(20a) | 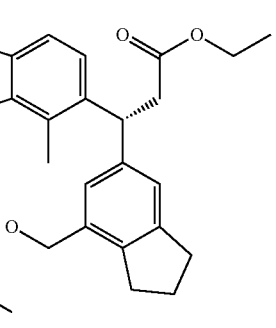 | MS(ESI/APCI) m/z: 550 [M + H]⁺ |
| 20(20c) | 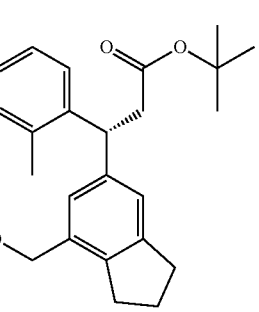 | MS(ESI/APCI) m/z: 422 [M + H]⁺ |
| 20(20d) | 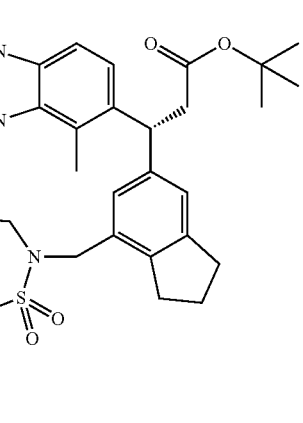 | MS(ESI/APCI) m/z: 683 [M + H]⁺ |

TABLE 16-continued

| Example No. | structural formula | physicochemical data |
| --- | --- | --- |
| 20(20e) = 20 | | ¹H-NMR (CDCl₃) δ: 0.89 (3H, t, J = 7.3 Hz), 1.26-1.29 (1H, m), 1.52-1.55 (1H, m), 2.01-2.06 (2H, m), 2.78-2.82 (6H, m), 2.86-2.89 (2H, m), 3.03 (1H, dd, J = 15.9, 8.1 Hz), 3.12 (1H, dd, J = 15.9, 7.6 Hz), 3.57 (1H, dd, J = 15.1, 10.7 Hz), 3.76 (1H, d, J = 13.7 Hz), 3.94 (1H, br s), 4.22 (3H, s), 4.45 (1H, d, J = 13.7 Hz), 4.91 (1H, t, J = 7.8 Hz), 6.83 (1H, s), 6.94 (1H, d, J = 9.3 Hz), 7.01 (1H, s), 7.27 (1H, d, J = 8.3 Hz), 7.31 (1H, d, J = 8.8 Hz), 7.89 (1H, d, J = 7.8 Hz). MS(ESI/APCI) m/z: 627 [M + H]⁺ |
| 21(21a) | | MS(ESI/APCI) m/z: 578 [M + H]⁺ |

TABLE 17

| Example No. | structural formula | physicochemical data |
| --- | --- | --- |
| 21(21c) | | MS(ESI/APCI) m/z: 683 [M + H]⁺ |

TABLE 17-continued

| Example No. | structural formula | physicochemical data |
|---|---|---|
| 21(21d) = 21 | | ¹H-NMR (CDCl₃) δ: 0.92 (3H, t, J = 7.3 Hz), 1.27-1.32 (1H, m), 1.53-1.59 (1H, m), 2.00-2.03 (2H, m), 2.79-2.84 (7H, m), 2.92 (1H, d, J = 14.9 Hz), 3.05 (1H, dd, J = 15.9, 8.1 Hz), 3.12 (1H, dd, J = 15.9, 7.6 Hz), 3.61 (1H, dd, J = 15.1, 10.7 Hz), 3.76 (1H, d, J = 13.7 Hz), 3.94 (1H, br s), 4.21 (3H, s), 4.43 (1H, d, J = 13.7 Hz), 4.90 (1H, t, J = 8.1 Hz), 6.83 (1H, s), 6.94 (1H, d, J = 9.3 Hz), 7.02 (1H, s), 7.27 (1H, d, J = 8.8 Hz), 7.33 (1H, d, J = 8.3 Hz), 7.89 (1H, d, J = 7.8 Hz). MS(ESI/APCI) m/z: 627 [M + H]⁺ |
| 22(22a) | | MS(ESI/APCI) m/z: 671 [M + H]⁺ |
| 22(22b) = 22 | | ¹H-NMR (CDCl₃) δ: 0.85 (3H, t, J = 7.3 Hz), 1.17-1.25 (1H, m), 1.49-1.52 (1H, m), 2.80 (3H, s), 2.91 (1H, d, J = 15.1 Hz), 3.09 (1H, dd, J = 15.9, 8.1 Hz), 3.20 (1H, dd, J = 15.6, 7.8 Hz), 3.63 (1H, dd, J = 14.9, 10.5 Hz), 3.97 (1H, br s), 4.06 (1H, d, J = 7.8 Hz), 4.21 (3H, s), 4.72 (1H, d, J = 14.2 Hz), 5.06 (1H, t, J = 7.6 Hz), 6.95 (1H, d, J = 8.8 Hz), 7.07 (1H, s), 7.26-7.27 (2H, m), 7.32 (1H, d, J = 8.8 Hz), 7.44 (1H, d, J = 5.4 Hz), 7.62 (1H, s), 7.92 (1H, d, J = 7.8 Hz). MS(ESI/APCI) m/z: 643 [M + H]⁺ |

TABLE 17-continued

| Example No. | structural formula | physicochemical data |
|---|---|---|
| 23(23a) | | MS(ESI/APCI) m/z: 671 [M + H]+ |

TABLE 18

| Example No. | structural formula | physicochemical data |
|---|---|---|
| 23(23b)=<br>23 | | 1H-NMR (CDCl3) δ: 0.91 (3H, t, J = 7.3 Hz), 1.31-1.32 (1H, m), 1.52-1.58 (1H, m), 2.78 (3H, s), 2.95 (1H, d, J = 15.1 Hz), 3.10 (1H, dd, J = 15.9, 8.1 Hz), 3.20 (1H, dd, J = 16.1, 7.8 Hz), 3.67 (1H, dd, J = 15.1. 10.7 Hz), 4.00 (1H, br s), 4.07 (1H, d, J = 5.9 Hz), 4.21 (3H, s), 4.71 (1H, d, J = 14.6 Hz), 5.05 (1H, t, J = 7.8 Hz), 6.96 (1H, d, J = 9.3 Hz), 7.08 (1H, s), 7.26 (1H, s), 7.28 (1H, s), 7.33 (1H, d, J = 8.8 Hz), 7.43 (1H, d, J = 5.4 Hz), 7.62 (1H, s), 7.91 (1H, d, J = 7.8 Hz).<br>MS(ESI/APCI) m/z: 643 [M + H]+ |
| 24(24a) | | MS(ESI/APCI) m/z: 604 (M + H]+ |

TABLE 18-continued

| Example No. | structural formula | physicochemical data |
|---|---|---|
| 24(24b)= 24 | (structure) | ¹H-NMR (CDCl₃) δ: 0.91-0.93 (3H, m), 1.42-1.43 (1H, m), 1.60-1.64 (1H, m), 2.01-2.04 (2H, m), 2.78 (1.5H, s), 2.78 (1.5H, s), 2.81-2.87 (4H, m), 3.00-3.15 (3H, m), 3.50-3.55 (1H, m), 3.95. (0.5H, d, J = 5.5 Hz), 3.98 (0.5H, d, J = 5.5 Hz), 4.22 (3H, s), 4.33-4.37 (2H, m), 4.88-4.93 (1H, m), 6.85 (1H, s), 7.02 (1H, s), 7.22-7.24 (1H, m), 7.28 (1H, d, J = 8.6 Hz), 7.33 (1H, dd, J = 8.8, 2.5 Hz), 8.21 (0.5H, d, J = 2.0 Hz), 8.22 (0.5H, d, J = 2.0 Hz), 8.43-8.45 (1H, m). MS(ESI/APCI) m/z: 576 [M + H]⁺ |
| 25(25a) | (structure) | MS(ESI/APCI) m/z: 331 [M − H]⁻ |
| 25(25b) | (structure) | MS(ESI/APCI) m/z: 297 [M + H]⁺ |
| 25(25c) | (structure) | ¹H-NMR (CDCl₃) δ: 0.11 (6H, s), 0.95 (9H, s), 2.02-2.14 (2H, m), 2.77 (2H, t, J = 7.6 Hz), 2.91 (2H, t, J = 7.6 Hz), 4.64 (2H, s), 7.27 (1H, s), 7.35 (1H, s). |

TABLE 19

| Example No. | structural formula | physicochemical data |
|---|---|---|
| 25(25d) | (structure) | ¹H-NMR (CDCl₃) δ: 0.11 (6H, s), 0.95 (9H, s), 1.35 (12H, s), 2.04-2.12 (2H, m), 2.90-2.95 (4H, m), 4.70 (2H, s), 7.61 (1H, s), 7.63 (1H, s). |

TABLE 19-continued
| Example No. | structural formula | physicochemical data |
|---|---|---|
| 25(25e) | 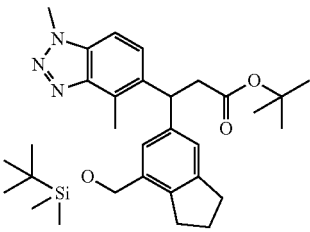 | MS(ESI/APCI) m/z: 536 [M + H]⁺ |
| 25(25f) | 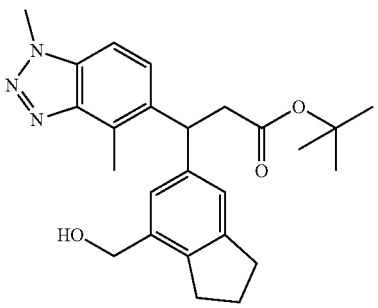 [SMILES: Cc1c(C(CC(=O)OC(C)(C)C)c2cc(CO)c3c(c2)CCC3)ccc2c1nnn2C] | MS(ESI/APCI) m/z: 422 [M + H]⁺ |
| 25(25g) | 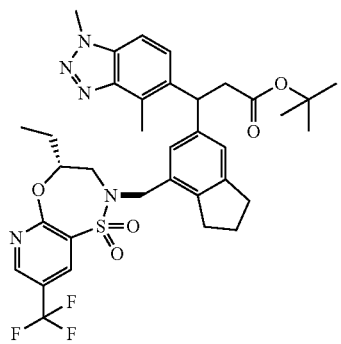 | MS(ESI/APCI) m/z: 700 [M + H]⁺ |
| 25(25h)= 25 | 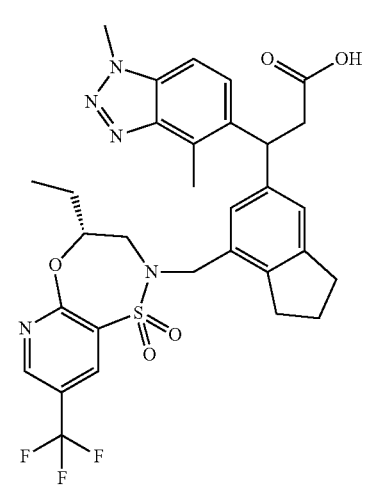 [SMILES: CC[C@@H]1CN(Cc2cc(C(CC(=O)O)c3ccc4c(nnn4C)c3C)cc3c2CCC3)S(=O)(=O)c2cc(C(F)(F)F)cnc2O1] | $^1$H-NMR (CDCl$_3$) δ: 0.92-0.94 (3H, m), 1.44-1.48 (1H, m), 1.61-1.67 (1H, m), 1.99-2.05 (2H, m), 2.76 (3H, s), 2.80-2.86 (4H, m), 3.01 (0.5H, dd, J = 8.3, 3.9 Hz), 3.05 (0.5H, dd, J = 8.3, 4.4 Hz), 3.09-3.10 (1H, m), 3.12-3.16 (1H, m), 3.42-3.52 (1H, m), 4.07-4.08 (1H, m), 4.21 (3H, s), 4.30 (0.5H, d, J = 5.4 Hz), 4.33-(0.5H, d, J = 5.9 Hz), 4.49 (1H, s), 4.89-4.92 (1H, m), 6.85 (1H, s), 7.03 (1H, s), 7.28 (1H, d, J = 8.8 Hz), 7.33 (1H, d, J = 8.8 Hz), 8.44 (1H, s), 8.67 (1H, s). MS(ESI/APCI) m/z: 644 [M + H]⁺ |

TABLE 20

| Example No. | structural formula | physicochemical data |
|---|---|---|
| 26(26a) | | MS(ESI/APCI) m/z: 298 [M + H]⁺ |
| 26(26b) | | ¹H-NMR (CDCl₃) δ: 1.15 (3H, t, J = 7.6 Hz), 1.82-1.91 (1H, m), 1.97-2.06 (1H, m), 3.57-3.69 (2H, m), 4.30-4.36 (1H, m), 4.85 (1H, t, J = 6.3 Hz), 7.57-7.65 (3H, m), 7.81 (1H, d, J = 8.8 Hz), 7.85 (1H, d, J = 7.8 Hz), 8.39 (1H, d, J = 7.8 Hz). |
| 26(26c) | | MS(ESI/APCI) m/z: 681 [M + H]⁺ |
| 26(26d)=26 | | ¹H-NMR (CDCl₃) δ: 0.91 (1.5H, t, J = 7.6 Hz), 0.95 (1.5H, t, J = 7.6 Hz), 1.63-1.66 (1H, m), 1.82-1.88 (1H, m), 2.00-2.02 (2H, m), 2.79 (1.5H, s), 2.80 (1.5H, s), 2.81-2.86 (3H, m), 2.89 (0.5H, d, J = 6.8 Hz), 2.92 (0.5H, d, J = 6.3 Hz), 3.02 (0.5H, d, J = 7.8 Hz), 3.05 (0.5H, d, J = 8.0 Hz), 3.09-3.16 (2H, m), 3.58-3.62 (1H, m), 3.91-3.94 (1H, m), 4.21 (1.5H, s), 4.22 (1.5H, s), 4.31 (1H, s), 4.38 (0.5H, d, J = 8.8 Hz), 4.41 (0.5H, d, J = 8.8 Hz), 4.90 (1H, t, J = 8.1 Hz), 6.88 (1H, d, J = 5.4 Hz), 7.00 (1H, s), 7.26-7.33 (2H, m), 7.56-7.66 (3H, m), 7.85 (2H, t, J = 8.8 Hz), 8.36 (1H, t, J = 7.8 Hz). MS(ESI/APCI) m/z: 625 [M + H]⁺ |
| 27(27a) | or enantiomer | ¹H-NMR (CDCl₃) δ: 0.96 (3H, t, J = 7.6 Hz), 1.17-1.39 (2H, m), 1.75 (1H, s), 3.30-3.56 (3H, m), 3.62 (1H, s), 5.04 (1H, t, J = 6.4 Hz), 7.21-7.27 (1H, m), 8.04-8.12 (1H, m), 8.57 (1H, dd, J = 4.8. 1.6 Hz). MS(ESI/APCI) m/z: 227 [M + H]⁺ |

TABLE 20-continued

| Example No. | structural formula | physicochemical data |
|---|---|---|
| 27(27b) | 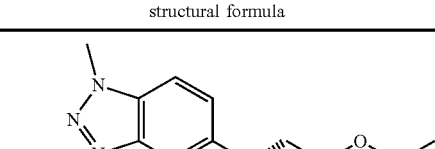<br>optically active isomer | MS(ESI/APCI) m/z: 602 [M + H]+ |

TABLE 21

| Example No. | structural formula | physicochemical data |
|---|---|---|
| 27(27c)=<br>27 | 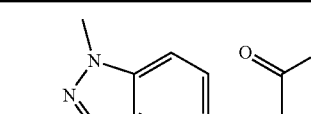<br>optically active isomer | 1H-NMR (CDCl3) δ: 0.71 (3H, t, J = 7.3 Hz), 1.05-1.11 (1H, m), 1.17-1.23 (1H, m), 1.73-1.75 (1H, m), 1.99-2.03 (2H, m), 2.74-2.82 (7H, m), 2.86-2.92 (1H, m), 3.03 (1H, dd, J = 16.1. 8.3 Hz), 3.11 (2H, dd, J = 15.9, 7.6 Hz), 3.45 (1H, br s), 3.58-3.63 (2H, m), 4.21 (3H, s), 4.35 (1H, d, J = 12.7 Hz), 4.90 (1H, t, J = 7.8 Hz), 6.80 (1H, s), 7.00 (1H, s), 7.26-7.32 (3H, m), 8.18 (1H, d, J = 7.3 Hz), 8.60 (1H, d, J = 4.4 Hz).<br>MS(ESI/APCI) m/z: 574 [M + H]+ |
| 28(28a) | 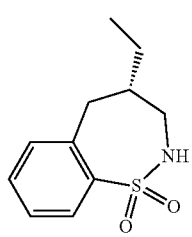<br>or enantiomer | 1H-NMR (CDCl3) δ: 0.97 (3H, t, J = 7.2 Hz), 1.22-1.30 (2H, m), 1.68 (1H, s), 3.26 (2H, br s), 3.48 (1H, br s), 3.60 (1H, br s), 4.67 (1H, br s), 7.22-7.32 (2H, m), 7.37-7.47 (1H, m), 7.87 (1H, d, J = 7.6 Hz).<br>MS(ESI/APCI) m/z: 226 [M + H]+ |

TABLE 21-continued

| Example No. | structural formula | physicochemical data |
|---|---|---|
| 28(28b) | optically active isomer | MS(ESI/APCI) m/z: 601 [M + H]⁺ |
| 28(28c)= 28 | optically active isomer | $^1$H-NMR (CDCl$_3$) δ: 0.68 (3H, t, J = 7.3 Hz), 1.02-1.08 (1H, m), 1.13-1.18 (1H, m), 1.62-1.63 (1H, m), 1.98-2.02 (2H, m), 2.78-2.80 (8H, m), 2.88-2.94 (1H, m), 3.03 (1H, dd, J = 16.1. 8.3 Hz), 3.11 (1H, dd, J = 15.6, 7.3 Hz), 3.45-3.47 (2H, m), 3.56-3.58 (1H, m), 4.21 (3H, s), 4.34 (1H, br s), 4.90 (1H, t, J = 8.1 Hz), 6.82 (1H, s), 6.98 (1H, s), 7.26 (2H, d, J = 8.3 Hz), 7.31-7.33 (2H, m), 7.43 (1H, t, J = 7.3 Hz), 7.93 (1H, d, J = 7.8 Hz).<br>MS(ESI/APCI) m/z: 573 [M + H]⁺ |
| 29(29a) |  | $^1$H-NMR (CDCl$_3$) δ: 0.96-1.05 (3H, m), 1.11-1.15 (3H, m), 1.45-1.53 (1H, m), 1.64-1.77 (1H, m), 2.02-2.09 (2H, m), 2.79-2.93 (4H, m), 3.04-3.16 (3H, m), 3.51-3.66 (1H, m), 4.02-4.06 (3H, m), 4.27-4.30 (3H, m), 4.33-4.44 (2H, m), 5.27 (1H, t, J = 8.1 Hz), 6.95 (1H, s), 7.12 (1H, s), 7.37-7.45 (2H, m), 8.19 (1H, t, J = 2.4 Hz), 8.38-8.40 (1H, m).<br>MS(ESI/APCI) m/z: 658 [M + H]⁺ |

TABLE 22

| Example No. | structural formula | physicochemical data |
|---|---|---|
| 29(29b)= 29 | 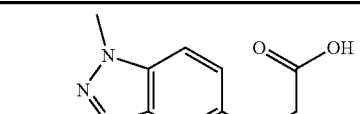 | $^1$H-NMR (CDCl$_3$) δ: 0.93-1.02 (3H, m), 1.41-1.77 (2H, m), 2.00-2.08 (2H, m), 2.76-2.89 (4H, m), 3.05-3.19 (3H, m), 3.48-3.63 (1H, m), 3.99-4.05 (1H, m), 4.24-4.26 (3H, m), 4.30-4.42 (2H, m), 5.23 (1H, t, J = 8. 1 Hz), 6.95 (1H, s), 7.09 (1H, s), 7.37 (2H, d, J = 5.9 Hz), 8.15-8.18 (1H, m), 8.35-8.37 (1H, m).<br>MS(ESI/APCI) m/z: 630 [M + H]⁺ |

TABLE 22-continued

| Example No. | structural formula | physicochemical data |
|---|---|---|
| 30(30a) | | $^1$H-NMR (CDCl$_3$) δ: 2.29 (3H, s), 2.84 (3H, d, J = 5.5 Hz), 4.46 (1H, br s), 7.55 (1H, s).<br>MS(ESI/APCI) m/z: 279, 281 [M + H]$^+$ |
| 30(30b) | | $^1$H-NMR (CDCl$_3$) δ: 2.24 (3H, s), 2.65 (3H, s), 3.19 (1H, br s), 4.17 (2H, br s), 7.03 (1H, s).<br>MS(ESI/APCI) m/z: 249, 251 [M + H]$^+$ |
| 30(30c) | | $^1$H-NMR (CDCl$_3$) δ: 2.78 (3H, s), 4.53 (3H, s), 7.59 (1H, s).<br>MS(ESI/APCI) m/z: 260, 262 [M + H]$^+$ |
| 30(30d) | | $^1$H-NMR (CDCl$_3$) δ: 1.33 (3H, t, J = 7.2 Hz), 2.83 (3H, s), 4.27 (2H, q, J = 7.2 Hz), 4.51 (3H, s), 6.37 (1H, d, J = 15.9 Hz), 7.61 (1H, s), 8.01 (1H, d, J = 15.9 Hz).<br>MS(ESI/APCI) m/z: 280 [M + H]$^+$ |
| 30(30e) | | MS(ESI/APCI) m/z: 444 [M + H]$^+$ |

TABLE 23

| Example No. | structural formula | physicochemical data |
|---|---|---|
| 30(30h) | | MS(ESI/APCI) m/z: 688 [M + H]+ |
| 30(30i)= 30 | | 1H-NMR (CDCl3) δ: 0.97 (3H, t, J = 7.4 Hz), 1.43-1.55 (1H, m), 1.62-1.74 (1H, m), 2.80 (3H, s), 3.11 (1H, dd, J = 15.9, 8.0 Hz), 3.16-3.28 (2H, m), 3.63 (1H, dd, J = 14.7, 11.0 Hz), 4.34-4.44 (2H, m), 4.50 (3H, s), 4.68 (1H, d, J = 14.7 Hz), 5.06 (1H, t. J = 7.7 Hz), 7.11 (1H, s), 7.24-7.27 (1H, m), 7.33 (1H, d, J = 5.5 Hz), 7.50 (1H, d, J = 5.5 Hz), 7.65 (1H, s), 8.23 (1H, d, J = 3.1 Hz), 8.41 (1H, d, J = 2.5 Hz). MS(ESI/APCI) m/z: 660 [M + H]+ |
| 31(31a) | | MS(ESI/APCI) m/z: 688 [M + H]+ |
| 31(31b)= 31 | | 1H-NMR (CDCl3) δ: 0.95 (3H, t. J = 7.4 Hz), 1.42-1.53 (1H, m), 1.63-1.74 (1H, m), 2.82 (3H, s), 3.11 (1H, dd, J = 15.9, 8.0 Hz), 3.16-3.20 (1H, m), 3.23 (1H, dd, J = 15.9, 8.0 Hz), 3.63 (1H, dd, J = 15.0, 10.7 Hz), 4.32-4.46 (2H, m), 4.51 (3H, s), 4.69 (1H, d, J = 14.7 Hz), 5.07 (1H, t. J = 8.0 Hz), 7.11 (1H. s), 7.24-7.27 (1H, m), 7.34 (1H, d, J = 5.5 Hz), 7.50 (1H, d, J = 5.5 Hz), 7.66 (1H, s), 8.23 (1H, d, J = 3.1 Hz), 8.40 (1H, d, J = 2.5 Hz). MS(ESI/APCI) m/z: 660 [M + H]+ |

TABLE 23-continued
| Example No. | structural formula | physicochemical data |
|---|---|---|
| 32(32a) | 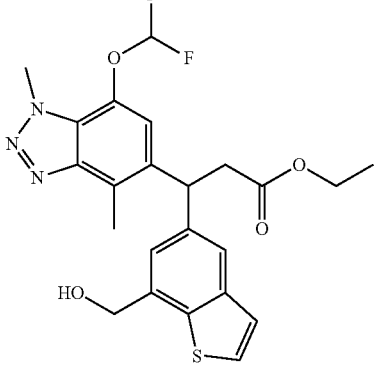 | MS(ESI/APCI) m/z: 476 [M + H]+ |
TABLE 24
| Example No. | structural formula | physicochemical data |
|---|---|---|
| 32(32d) | 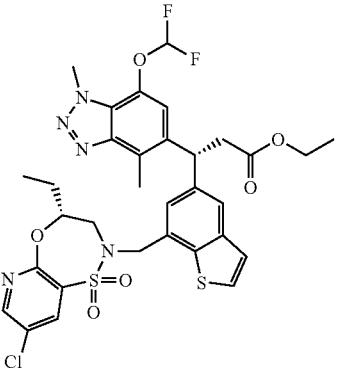 [SMILES: CCOC(=O)C[C@H](c1cc(CN2C[C@@H](CC)Oc3ncc(Cl)cc3S2(=O)=O)c2sccc2c1)c1cc(OC(F)F)c2c(nnn2C)c1C] | MS(ESI/APCI) m/z: 720 [M + H]+ |
| 32(32e)= 32 | 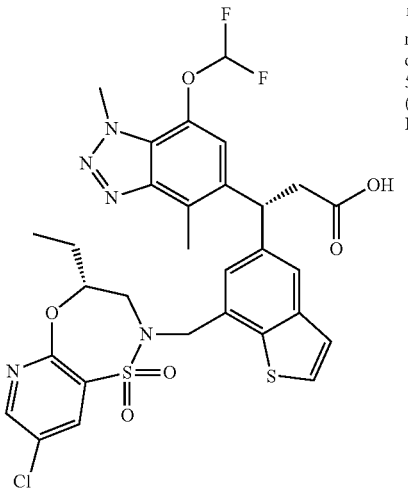 | ¹H-NMR (CDCl₃) δ: 0.97 (3H, t, J = 7.4 Hz), 1.43-1.54 (1H, m), 1.62-1.73 (1H, m), 2.80 (3H, s), 3.11 (1H, dd, J = 15.9, 8.0 Hz), 3.18-3.26 (2H, m), 3.62 (1H, dd, J = 15.0, 10.7 Hz), 4.32-4.43, (2H, m), 4.41 (3H, s), 4.68 (1H, d, J = 14.7 Hz), 5.09 (1H, t, J = 7.7 Hz), 6.66 (1H, t, J = 72.7 Hz), 7.07 (1H, s), 7.15 (1H, s), 7.33 (1H, d, J = 5.5 Hz), 7.49 (1H, d, J = 5.5 Hz), 7.66 (1H, s), 8.22 (1H, d, J = 2.5 Hz), 8.40 (1H, d, J = 3.1 Hz). |

TABLE 24-continued
| Example No. | structural formula | physicochemical data |
|---|---|---|
| 33(33a) | 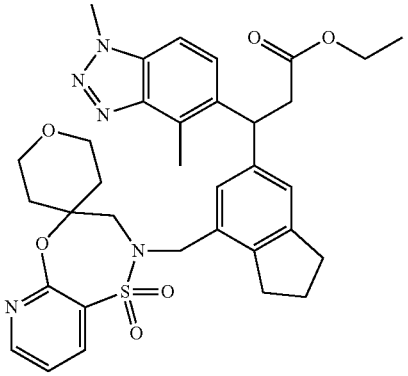 [SMILES: CCOC(=O)CC(c1cc2c(c(CN3CC4(CCOCC4)Oc4ncccc4S3(=O)=O)c1)CCC2)c1ccc2c(nnn2C)c1C] | MS(ESI/APCI) m/z: 646 [M + H]+ |
| 33(33b)=33 | 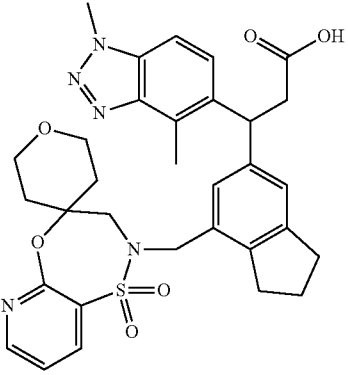 [SMILES: Cc1c(C(CC(=O)O)c2cc3c(c(CN4CC5(CCOCC5)Oc5ncccc5S4(=O)=O)c2)CCC3)ccc2c1nnn2C] | $^1$H-NMR (CDCl$_3$) δ: 1.31-1.84 (4H, m), 1.94-2.02 (2H, m), 2.65-2.86 (7H, m), 2.96-3.03 (1H, m), 3.13-3.21 (1H, m), 3.37-3.68 (3H, m), 3.74-3.84 (1H, m), 3.88-4.04 (2H, m), 4.24-4.31 (1H, m), 4.26 (3H, s), 4.68 (1H, d, J = 13.7 Hz), 4.90-4.95 (1H, m), 6.99 (2H, s), 7.25-7.28 (1H, m), 7.34 (1H, d, J = 8.8 Hz), 7.42 (1H, d, J = 8.8 Hz), 8.24 (1H, d, J = 7.3 Hz), 8.48 (1H, d, J = 3.9 Hz). MS(ESI/APCI) m/z: 618 [M + H]+ |
| 34(34a) | 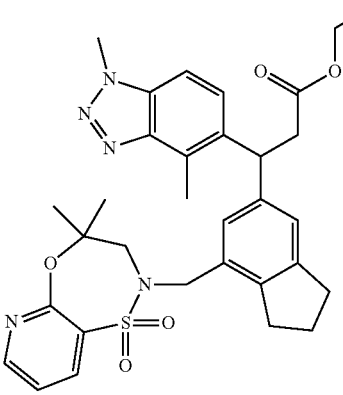 | MS(ESI/APCI) m/z: 604 [M + H]+ |

TABLE 25

| Example No. | structural formula | physicochemical data |
|---|---|---|
| 34(34b)=34 | 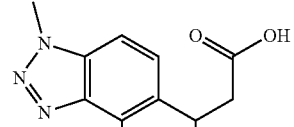 | ¹H-NMR (CDCl₃) δ: 1.16 (3H, s), 1.17 (3H, s), 1.99-2.05 (2H, m), 2.77-2.82 (4H, m), 2.83 (3H, s), 3.09 (1H, dd, J = 15.6, 7.8 Hz), 3.18 (1H, dd, J = 15.9, 8.1 Hz), 3.45 (2H, br s), 4.25 (3H, s), 4.44 (2H, br s), 4.97 (1H, t, J = 7.6 Hz), 6.98 (1H, s), 7.01 (1H, s), 7.22-7.25 (1H, m), 7.32 (1H, d, J = 8.8 Hz), 7.39 (1H, d, J = 8.8 Hz), 8.19 (1H, d, J = 7.3 Hz), 8.45 (1H, d, J = 4.9 Hz).<br>MS(ESI/APCI) m/z: 576 [M + H]⁺ |
| 35(35a) | 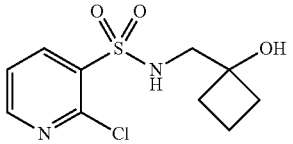 [SMILES: O=S(=O)(NCC1(O)CCC1)c1cccnc1Cl] | MS(ESI/APCI) m/z: 277 [M + H]⁺ |
| 35(35b) | 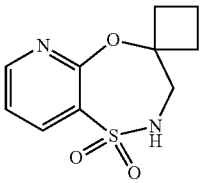 [SMILES: O=S1(=O)NCC2(CCC2)Oc2ncccc21] | ¹H-NMR (CDCl₃) δ: 1.62-1.71 (1H, m), 1.90-2.08 (3H, m), 2.32-2.42 (2H, m), 3.77 (2H, d, J = 6.7 Hz), 4.81-4.86 (1H, m), 7.23-7.26 (1H, m), 8.18 (1H, dd, J = 7.4, 1.8 Hz), 8.50 (1H, dd, J = 4.9, 1.8 Hz). |
| 35(35c) | 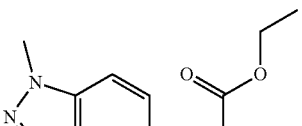 | ¹H-NMR (CDCl₃) δ: 1.11 (2H, t. J = 7.1 Hz), 1.30-1.39 (1H, m), 1.77-1.96 (3H, m), 2.01-2.08 (2H, m), 2.20-2.29 (2H, m), 2.82-2.87 (7H, m), 3.05 (1H, dd, J = 14.7. 8.6 Hz), 3.12 (1H, dd, J = 15.6, 7.7 Hz), 3.54 (2H, s), 4.24 (3H, s), 4.35 (2H, s). 4.96 (1H, t, J = 8.0 Hz), 6.91 (1H, s), 7.07 (1H, s), 7.25-7.27 (1H, m), 7.29 (1H, d, J = 8.6 Hz), 7.38 (1H, d, J = 9:2 Hz), 8.20 (1H, d, J = 7.4 Hz), 8.50 (1H, d, J = 4.9 Hz).<br>MS(ESI/APCI) m/z: 6.16 [M + H]⁺ |
| 35(35d)=35 | 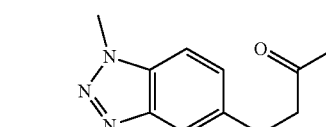 | ¹H-NMR (CDCl₃) δ: 1.25-1.36 (1H, m), 1.75-1.93 (3H, m), 2.00-2.08 (2H, m), 2.17-2.26 (2H, m), 2.80-2.87 (7H, m), 3.07 (1H, dd, J = 15.9, 8.0 Hz), 3.16 (1H, dd, J = 15.9, 8.0 Hz), 3.54 (2H, s), 4.24 (3H, s), 4.35 (2H, s), 4.95 (1H, t, J = 8.0 Hz), 6.93 (1H, s), 7.05 (1H, s), 7.24-7.28 (1H, m), 7.30 (1H, d, J = 9.2 Hz), 7.36 (1H, d, J = 8.6 Hz), 8.20 (1H, d, J = 7.4 Hz), 8.50 (1H, d, J = 4.3 Hz).<br>MS(ESI/APCI) m/z: 588 [M + H]⁺ |

TABLE 25-continued

| Example No. | structural formula | physicochemical data |
|---|---|---|
| 36(36a) | | MS(ESI/APCI) m/z: 618 [M + H]+ |

TABLE 26

| Example No. | structural formula | physicochemical data |
|---|---|---|
| 36(36b)=36 | | $^1$H-NMR (CDCl$_3$) δ: 1.92-2.06 (2H, m), 2.71 (3H, s), 2.73-2.91 (4H, m), 2.99-3.10 (2H, m), 3.78 (1H, d, J = 15.3 Hz), 3.95 (1H, d, J = 15.3 Hz), 4.07 (1H, d, J = 13.5 Hz), 4.28 (3H, s), 4.42-4.50 (2H, m), 4.65 (1H, d, J = 13.5 Hz), 4.84-4.89 (1H, m), 4.92 (2H, t, J = 8.3 Hz), 6.85 (1H, s), 7.07 (1H, s), 7.35-7.40 (2H, m), 7.47 (1H, d, J = 8.6 Hz), 8.27 (1H, dd, J = 8.0, 1.8 Hz), 8.57 (1H, dd, J = 4.9, 1.8 Hz).<br>MS(ESI/APCI) m/z: 590 [M + H]+ |
| 37(37a) | | $^1$H-NMR (CDCl$_3$) δ: 0.68-0.76 (1H, m), 0.82-0.88 (1H, m), 1.00-1.06 (2H, m), 1.10 (3H, t, J = 7.1 Hz), 1.99 (1H, t. J = 6.1 Hz), 2.24-2.35 (1H, m), 2.78 (3H, s), 3.08 (1H, dd, J = 15.3. 8.5 Hz), 3.19 (1H, dd, J = 15.3, 7.3 Hz), 4.01 (2H, q, J = 7.1 Hz), 4.57 (3H, s), 4.90 (2H, d, J = 6.1 Hz), 5.03-5.10 (1H, m), 7.12 (1H, s), 7.20 (1H, s), 7.31 (1H, d, J = 5.5 Hz), 7.44 (1H, d, J = 5.5 Hz), 7.60 (1H, s).<br>MS(ESI/APCI) m/z: 450 [M + H]+ |

| Example No. | structural formula | physicochemical data |
| --- | --- | --- |
| 37(37c) | | ¹H-NMR (CDCl₃) δ: 0.70-0.79 (1H, m), 0.82-0.90 (1H, m), 0.95 (3H, t, J = 7.3 Hz), 1.01-1.07 (2H, m), 1.11 (3H, t. J = 7.3 Hz), 1.40-1.52 (1H, m), 1.60-1.74 (1H, m), 2.24-2.35 (1H, m), 2.77 (3H, s), 3.03-3.22 (3H, m), 3.61 (1H, dd, J = 15.3, 11.0 Hz), 4.03 (2H, q, J = 7.3 Hz), 4.29-4.42 (2H, m), 4.58 (3H, s), 4.67 (1H, d, J = 14.6 Hz), 5.05 (1H, t, J = 7.9 Hz), 7.08 (1H, s), 7.12 (1H, s), 7.32 (1H, d, J = 5.5 Hz), 7.47 (1H, d, J = 5.5 Hz), 7.64 (1H, s), 8.23 (1H, d, J = 2.7 Hz), 8.41 (1H, d, J = 2.7 Hz).<br>MS(ESI/APCI) m/z: 694 [M + H]⁺ |
| 37(37d) | | ¹H-NMR (CDCl₃) δ: 0.68-0.78 (1H, m), 0.82-0.92 (1H, m), 0.98 (3H, t. J = 7.3 Hz), 1.02-1.07 (2H, m), 1.11 (3H. t. J = 7.3 Hz), 1.43-1.56 (1H, m), 1.65-1.77 (1H, m), 2.26-2.36 (1H, m), 2.75 (3H, s), 3.02-3.21 (3H, m), 3.58-3.69 (1H, m), 4.03 (2H, q, J = 7.3 Hz), 4.26-4.42 (2H, m), 4.58 (3H, s), 4.66 (1H, d, J = 14.0 Hz), 5.04 (1H, t, J = 7.9 Hz), 7.10 (1H, s), 7.11 (1H, s), 7.31 (1H, d, J = 5.5 Hz), 7.47 (1H, d, J = 5.5 Hz), 7.64 (1H, s), 8.23 (1H, d, J = 2.7 Hz), 8.41 (1H, d, J = 2.7 Hz).<br>MS(ESI/APCI) m/z: 694 [M + H]⁺ |
| 37(37e)=37 | | ¹H-NMR (CDCl₃) δ: 0.69-0.78 (1H, m), 0.79-0.89 (1H, m), 0.95 (3H, t, J = 7.3 Hz), 1.01-1.08 (2H, m), 1.38-1.51 (1H, m), 1.62-1.75 (1H, m), 2.24-2.33 (1H, m), 2.77 (3H, s), 3.06-3.28 (3H, m), 3.61 (1H, dd, J = 15.0, 10.7 Hz), 4.30-4.44 (2H, m), 4.58 (3H, s), 4.68 (1H, d, J = 14.6 Hz), 5.05 (1H, t, J = 7.9 Hz), 7.07 (1H, s), 7.14 (1H, s), 7.32 (1H, d, J = 5.5 Hz), 7.47 (1H, d, J = 5.5 Hz), 7.64 (1H, s), 8.23 (1H, d, J = 3.1 Hz), 8.40 (1H, d, J = 3.1 Hz).<br>MS(ESI/APCI) m/z: 666 [M + H]⁺ |

TABLE 27

| Example No. | structural formula | physicochemical data |
|---|---|---|
| 38(38a) | | ¹H-NMR (CDCl₃) δ: 1.09 (3H, t, J = 7.1 Hz), 1.98-2.08 (2H, m), 2.76-2.88 (4H, m), 2.86 (3H, s), 3.05 (1H, dd, J = 15.5, 9.2 Hz), 3.14 (1H, dd, J = 15.5, 7.0 Hz), 3.81 (3H, s), 4.00 (2H, q, J = 7.1 Hz), 4.24 (3H, s), 4.42 (4H, s), 4.95-5.01 (1H, m), 6.85 (2H, d, J = 8.5 Hz), 7.00 (1H, s), 7.02 (1H, s), 7.21 (2H, d, J = 8.5 Hz), 7.28 (1H, d, J = 8.5 Hz), 7.40 (1H, d, J = 8.5 Hz).<br>MS(ESI/APCI) m/z: 514 [M + H]⁺ |
| 38(38b) | | ¹H-NMR (CDCl₃) δ: -0.03 (9H, s), 0.77-0.86 (2H, m), 1.97-2.08 (2H, m), 2.76-2.87 (4H, m), 2.86 (3H, s), 3.03 (1H, dd, J = 15.5, 8.5 Hz), 3.12 (1H, dd, J = 15.5, 7.0 Hz), 3.81 (3H, s), 3.99-4.07 (2H, m), 4.24 (3H, s), 4.42 (4H, s), 4.93-5.02 (1H, m), 6.85 (2H, d, J = 8.9 Hz), 7.01 (2H, s), 7.21 (2H, d, J = 8.9 Hz), 7.28 (1H, d, J = 8.5 Hz), 7.39 (1H, d, J = 8.5 Hz).<br>MS(ESI/APCI) m/z: 586 [M + H]⁺ |
| 38(38c) | | MS(ESI/APCI) m/z: 600 [M + H]⁺ |
| 38(38d) | | ¹H-NMR (CDCl₃) δ: -0.08 (9H, s), 0.52-0.70 (2H, m), 1.31 (3H, s), 1.40 (3H, s), 1.98-2.07 (2H, m), 2.76-2.92 (4H, m), 2.81 (3H, s), 3.81 (3H, s), 3.84-4.00 (2H, m), 4.24 (3H, s), 4.39 (2H, s), 4.42 (2H, s), 4.86 (1H, s), 6.84 (2H, d, J = 8.5 Hz), 7.02 (1H, s), 7.04 (1H, s), 7.19 (2H, d, J = 8.5 Hz), 7.26 (1H, d, J = 8.5 Hz), 7.66 (1H, d, J = 8.5 Hz).<br>MS(ESI/APCI) m/z: 614 [M + H]⁺ |
| 38(38e) | | ¹H-NMR (CDCl₃) δ: -0.07 (9H, s), 0.53-0.71 (2H, m), 1.31 (3H, s), 1.40 (3H, s), 1.56-1.68 (1H, m), 1.99-2.09 (2H, m), 2.77-2.88 (4H, m), 2.81 (3H, s), 3.85-4.02 (2H, m), 4.24 (3H, s), 4.59 (2H, d, J = 5.5 Hz), 4.86 (1H, s), 7.05 (2H, s), 7.28 (1H, d, J = 8.5 Hz), 7.68 (1H, d, J = 8.5 Hz).<br>MS(ESI/APCI) m/z: 494 [M + H]⁺ |
| 38(38f) | | ¹H-NMR (CDCl₃) δ: -0.07 (9H, s), 0.54-0.69 (2H, m), 0.93 (3H, t; J = 7.3 Hz), 1.30 (3H, s), 1.32-1.41 (1H, m), 1.37 (3H, s), 1.60-1.71 (1H, m), 1.99-2.12 (2H, m), 2.76 (3H, s), 2.79-2.95 (4H, m), 3.04 (1H, dd, J = 15.0, 2.1 Hz), 3.56 (1H, dd, J = 15.0, 10.7 Hz), 3.85-4.04 (3H, m), 4.20-4.40 (1H, m), 4.25 (3H, s), 4.36 (1H, d, J = 14.0 Hz), 4.81 (1H, s), 6.86 (1H, s), 7.09 (1H, s), 7.29 (1H, d, J = 8.9 Hz), 7.67 (1H, d, J = 8.9 Hz), 8.19 (1H, d, J = 3.1 Hz), 8.39 (1H, d, J = 3.1 Hz).<br>MS(ESI/APCI) m/z: 738.[M + H]⁺ |

TABLE 28

| Example No. | structural formula | physicochemical data |
|---|---|---|
| 38(38g)=38 | 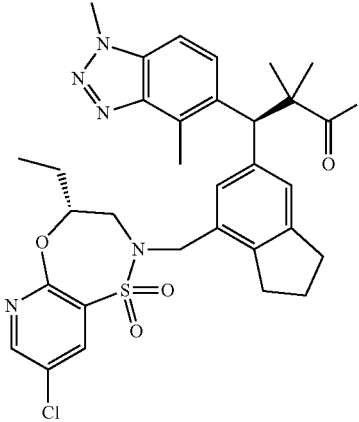 | ¹H-NMR (DMSO-D₅) δ: 0.89 (3H, t, J = 7.3 Hz), 1.13-1.33 (1H, m), 1.21 (3H, s), 1.27 (3H, s), 1.38-1.55 (1H, m), 1.87-2.06 (2H, m), 2.66 (3H, s), 2.72-2.90 (5H, m), 3.68 (1H, dd, J = 15.3, 10.4 Hz), 4.01 (1H, d, J = 14.3 Hz), 4.25 (3H, s), 4.27-4.35 (1H, m), 4.39 (1H, d, J = 14.3 Hz), 4.76 (1H, s), 7.05 (1H, s), 7.16 (1H, s), 7.57 (1H, d, J = 9.2 Hz), 7.68 (1H, d, J = 9.2 Hz), 8.24 (1H, d, J = 2.4 Hz), 8.63 (1H, d, J = 2.4 Hz), 12.20 (1H, br s). MS(ESI/APCI) m/z: 637 [M + H]⁺ |
| 39(39a) | 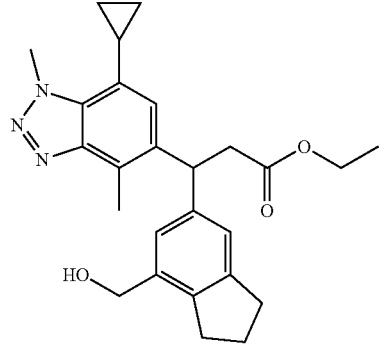 [SMILES: CCOC(=O)CC(c1cc(CO)c2c(c1)CCC2)c1cc(C2CC2)c2c(nnn2C)c1C] | ¹H-NMR (CDCl₃) δ: 0.70-0.78 (1H, m), 0.84-0.91 (1H, m), 0.99-1.06 (2H, m), 1.09 (3H, t, J = 7.2 Hz), 1.52-1.58 (1H, m), 2.00-2.10 (2H, m), 2.25-2.34 (1H, m), 2.76 (3H, s), 2.81-2.88 (4H, m), 3.03 (1H, dd, J = 15.3, 8.5 Hz), 3.10 (1H, dd, J = 15.3, 7.3 Hz), 4.00 (2H, q, J = 7.2 Hz), 4.57 (3H, s), 4.61 (2H, d, J = 6.1 Hz), 4.87-4.95 (1H, m), 6.99 (1H, s), 7.03 (1H, s), 7.12 (1H, s). MS(ESI/APCI) m/z: 434 [M + H]⁺ |
| 39(39b) | 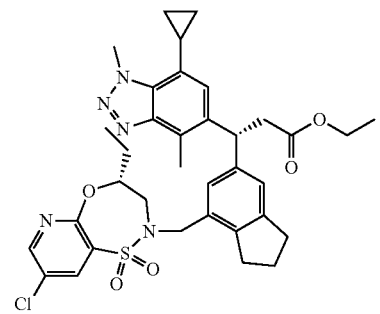 [SMILES: CCOC(=O)C[C@H](c1cc2c(c(CN3C[C@@H](CC)Oc4ncc(Cl)cc4S3(=O)=O)c1)CCC2)c1cc(C2CC2)c2c(nnn2C)c1C] | ¹H-NMR (CDCl₃) δ: 0.71-0.79 (1H, m), 0.83-0.91 (1H, m), 0.98 (3H, t, J = 7.3 Hz), 1.02-1.07 (2H, m), 1.11 (3H, t, J = 7.3 Hz), 1.41-1.52 (1H, m), 1.63-1.75 (1H, m), 1.99-2.11 (2H, m), 2.25-2.36 (1H, m), 2.73 (3H, s), 2.76-2.95 (4H, m), 2.96-3.14 (3H, m), 3.56 (1H, dd, J = 15.0, 10.7 Hz), 3.92-4.07 (3H, m), 4.29-4.42 (1H, m), 4.39 (1H, d, J = 14.0 Hz), 4.58 (3H, s), 4.84-4.92 (1H, m), 6.87 (1H, s), 7.03 (1H, s), 7.07 (1H, s), 8.20 (1H, d, J = 2.4 Hz), 8.39 (1H, d, J = 2.4 Hz). MS(ESI/APCI) m/z: 678 [M + H]⁺ |
| 39(39c) | 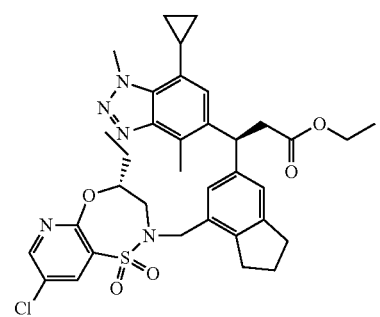 [SMILES: CCOC(=O)C[C@@H](c1cc2c(c(CN3C[C@@H](CC)Oc4ncc(Cl)cc4S3(=O)=O)c1)CCC2)c1cc(C2CC2)c2c(nnn2C)c1C] | ¹H-NMR (CDCl₃) δ: 0.70-0.79 (1H, m), 0.84-0.91 (1H, m), 0.99 (3H, t, J = 7.6 Hz), 1.02-1.08 (2H, m), 1.11 (3H, t, J = 7.0 Hz), 1.42-1.55 (1H, m), 1.63-1.77 (1H, m), 1.99-2.11 (2H, m), 2.26-2.35 (1H, m), 2.72 (3H, s), 2.76-2.94 (4H, m), 2.97-3.14 (3H, m), 3.58 (1H, dd, J = 15.3, 11.0 Hz), 3.96-4.05 (3H, m), 4.28-4.40 (1H, m), 4.37 (1H, d, J = 14.0 Hz), 4.57 (3H, s), 4.82-4.91 (1H, m), 6.86 (1H, s), 7.03 (1H, s), 7.09 (1H, s), 8.19 (1H, d, J = 2.4 Hz), 8.39 (1H, d, J = 2.4 Hz). MS(ESI/APCI) m/z: 678 [M + H]⁺ |

TABLE 28-continued

| Example No. | structural formula | physicochemical data |
|---|---|---|
| 39(39d)= 39 | 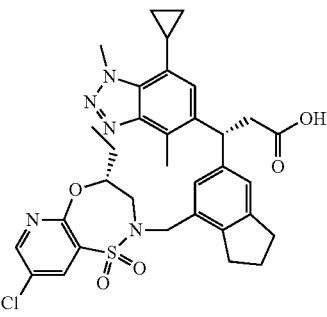 [SMILES: CC[C@@H]1CN(Cc2cc([C@@H](CC(=O)O)c3cc(C4CC4)c4c(nnn4C)c3C)cc3c2CCC3)S(=O)(=O)c2cc(Cl)cnc2O1] | ¹H-NMR (DMSO-D$_6$) δ: 0.66-0.74 (1H, m), 0.77-0.84 (1H, m), 0.88 (3H, t, J = 7.3 Hz), 0.93-1.06 (2H, m), 1.22-1.38 (1H, m), 1.44-1.61 (1H, m), 1.89-2.06 (2H, m), 2.38-2.47 (1H, m), 2.67 (3H, s), 2.71-2.85 (4H, m), 2.90 (1H, d, J = 14.6 Hz), 2.97 (1H, dd, J = 15.9, 8.5 Hz), 3.04 (1H, dd, J = 15.9, 7.3 Hz), 3.64-3.74 (1H, m), 4.00 (1H, d, J = 14.6 Hz), 4.27-4.35 (1H, m), 4.39 (1H, d, J = 14.6 Hz), 4.51 (3H, s), 4.70-4.78 (1H, m), 7.02 (1H, s), 7.05 (1H, s), 7.13 (1H, s), 8.25 (1H, d, J = 2.7 Hz), 8.62 (1H, d, J = 2.7 Hz), 12.13 (1H, s). MS(ESI/APCI) m/z: 650 [M + H]⁺ |
| 40 | 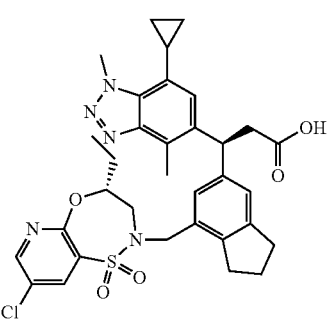 [SMILES: CC[C@@H]1CN(Cc2cc([C@H](CC(=O)O)c3cc(C4CC4)c4c(nnn4C)c3C)cc3c2CCC3)S(=O)(=O)c2cc(Cl)cnc2O1] | ¹H-NMR (DMSO-D6) δ: 0.67-0.77 (1H, m), 0.79-0.89 (1H, m), 0.93 (3H, t, J = 7.3 Hz), 0.96-1.06 (2H, m), 1.34-1.46 (1H, m), 1.49-1.63 (1H, m), 1.88-2.05 (2H, m), 2.38-2.47 (1H, m), 2.64 (3H, s), 2.71-2.86 (4H, m), 2.91-3.11 (3H, m), 3.66-3.78 (1H, m), 4.00 (1H, d, J = 14.6 Hz), 4.28-4.37 (1H, m), 4.37 (1H, d, J = 14.6 Hz), 4.52 (3H, s), 4.68-4.77 (1H, m), 6.99 (1H, s), 7.10 (1H, s), 7.13 (1H, s), 8.24 (1H, d, J = 2.4 Hz), 8.62 (1H, d, J = 2.4 Hz), 12.13 (1H, s). MS(ESI/APCI) m/z: 650 [M + H]⁺ |

TABLE 29

| Example No. | structural formula | physicochemical data |
|---|---|---|
| 41 | 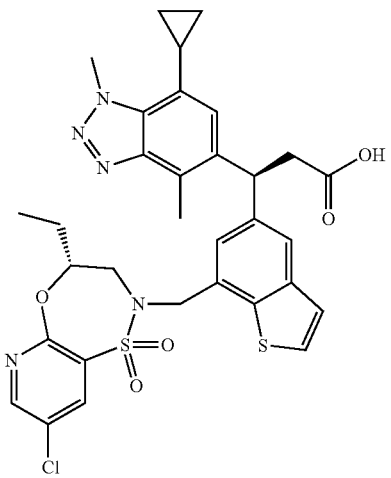 [SMILES: CC[C@@H]1CN(Cc2cc([C@H](CC(=O)O)c3cc(C4CC4)c4c(nnn4C)c3C)cc3ccsc23)S(=O)(=O)c2cc(Cl)cnc2O1] | ¹H-NMR (CDCl$_3$) δ: 0.70-0.78 (1H, m), 0.80-0.87 (1H, m), 0.98 (3H, t, J = 7.3 Hz), 1.01-1.07 (2H, m), 1.42-1.55 (1H, m), 1.63-1.75 (1H, m), 2.23-2.37 (1H, m), 2.76 (3H, s), 3.06-3.28 (3H, m), 3.65 (1H, dd, J = 15.3, 11.0 Hz), 4.29-4.44 (2H, m), 4.58 (3H, s), 4.66 (1H, d, J = 14.6 Hz), 5.04 (1H, t, J = 7.6 Hz), 7.08 (1H, s), 7.13 (1H, s), 7.32 (1H, d, J = 5.5 Hz), 7.47 (1H, d, J = 5.5 Hz), 7.64 (1H, s), 8.22 (1H, d, J = 2.4 Hz), 8.41 (1H, d, J = 2.4 Hz). MS(ESI/APCI) m/z: 666 [M + H]⁺ |

TABLE 29-continued

| Example No. | structural formula | physicochemical data |
|---|---|---|
| 42(42a) | | MS(ESI/APCI) m/z: 636 [M + H]+ |
| 42(42b)= 42 | | ¹H-NMR (CDCl₃) δ: 0.41-0.53 (2H, m), 1.07-1.19 (2H, m), 1.98-2.10 (2H, m), 2.76-2.90 (4H, m), 2.81 (3H, s), 3.06 (1H, dd, J = 15.9, 7.9 Hz), 3.15 (1H, dd, J = 15.9, 7.9 Hz), 3.49 (2H, br s), 4.20-4.33 (2H, m), 4.25 (3H, s), 4.93 (1H, t, J = 7.9 Hz), 6.82 (1H, s), 7.03 (1H, s), 7.28-7.35 (2H, m), 8.24 (1H, d, J = 2.4 Hz), 8.37 (1H, d, J = 2.4 Hz). MS(ESI/APCI) m/z: 608 [M + H]+ |
| 43(43a) | | MS(ESI/APCI) m/z: 636 [M + H]+ |
| 43(43b)= 43 | | ¹H-NMR (CDCl₃) δ: 0.41-0.53 (2H, m), 1.05-1.19 (2H, m), 1.98-2.10 (2H, m), 2.76-2.90 (4H, m), 2.80 (3H, s), 3.06 (1H, dd, J = 15.9, 7.9 Hz), 3.15 (1H, dd, J = 15.9, 7.9 Hz), 3.48 (2H, br s), 4.20-4.33 (2H, m), 4.25 (3H, s), 4.93 (1H, t, J =7.9 Hz), 6.81 (1H, s), 7.03 (1H, s), 7.28-7.35 (2H, m), 8.24, (1H, d, J = 2.4 Hz), 8.37 (1H, d, J = 2.4 Hz). MS(ESVAPCI) m/z: 608 [M + H]+ |

TABLE 30

| Example No. | structural formula | physicochemical data |
|---|---|---|
| 44(44a) | | ¹H-NMR (CDCl₃) δ: 1.11 (3H, t, J = 7.2 Hz), 1.55 (1H, t, J = 6.1 Hz), 2.00-2.11 (2H, m), 2.68 (3H, s), 2.79 (3H, s), 2.81-2.88 (4H, m), 3.03 (1H, dd, J = 15.7, 8.9 Hz), 3.12 (1H, dd, J = 15.7, 7.3 Hz), 4.02 (2H, q, J = 7.2 Hz), 4.43 (3H, s), 4.61 (2H, d, J = 6.1 Hz), 4.90-4.97 (1H, m), 7.02 (1H, s), 7.04 (1H, s), 7.06 (1H, s).<br>MS(ESI/APCI) m/z: 408 [M + H]⁺ |
| 44(44d) | | MS(ESI/APCI) m/z: 652 [M + H]⁺ |
| 44(44e)=44 | | ¹H-NMR (CDCl₃) δ: 0.96 (3H, t, J = 7.3 Hz), 1.37-1.75 (2H, m), 2.01-2.12 (2H, m), 2.69 (3H, s), 2.76 (3H, s), 2.81-2.96 (4H, m), 3.01-3.18, (3H, m), 3.54 (1H, dd, J = 14.6. 11.0 Hz), 4.02 (1H, d, J = 14.0 Hz), 4.32-4.42 (1H, m), 4.41 (1H, d, J = 14.0 Hz), 4.44 (3H, s), 4.89 (1H, t, J = 7.9 Hz), 6.89 (1H, s), 7.00 (1H, s), 7.05 (1H, s), 8.20 (1H, d, J = 2.8 Hz), 8.38 (1H, d, J = 2.8 Hz).<br>MS(ESI/APCI) m/z: 624 [M + H]⁺ |
| 45(45a) | | MS(ESI/APCI) m/z: 494 [M + H]⁺ |

TABLE 30-continued
| Example No. | structural formula | physicochemical data |
|---|---|---|
| 45(45d) | 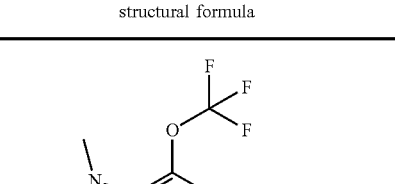 | MS(ESI/APCI) m/z: 738 [M + H]⁺ |
TABLE 31
| Example No. | structural formula | physicochemical data |
|---|---|---|
| 45(45e)= 45 | 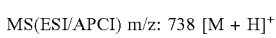 | ¹H-NMR (CDCl₃) δ: 0.96 (3H, t. J = 7.3 Hz), 1.42-1.53 (1H, m), 1.64-1.75 (1H, m), 2.82 (3H, s), 3.07-3.27 (3H, m), 3.63 (1H, dd, J = 15.0, 11.3 Hz), 4.32-4.47 (5H, m), 4.69 (1H, d, J = 15.3 Hz), 5.10 (1H, t, J = 7.9 Hz), 7.14 (1H, s), 7.22 (1H, s), 7.32 (1H, d, J = 5.5 Hz), 7.50 (1H, d, J = 5.5 Hz), 7.62 (1H, s), 8.23 (1H, d, J = 2.4 Hz), 8.41 (1H, d, J = 2.4 Hz). MS(ESI/APCI) m/z: 710 [M + H]⁺ |
| 46(46a) | 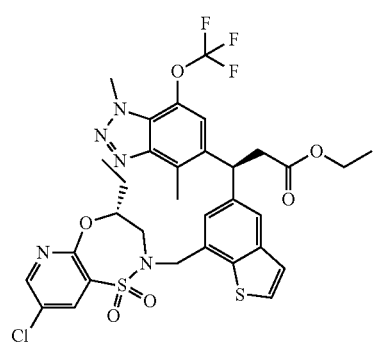 [SMILES: CCOC(=O)C[C@@H](c1cc(CN2C[C@@H](CC)Oc3ncc(Cl)cc3S2(=O)=O)c2sccc2c1)c1cc(OC(F)(F)F)c2c(nnn2C)c1C] | MS(ESI/APCI) m/z: 738 [M + H]⁺ |

TABLE 31-continued

| Example No. | structural formula | physicochemical data |
| --- | --- | --- |
| 46(46b)= 46 | 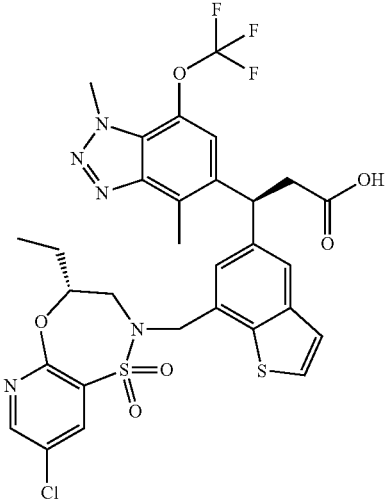 [SMILES: CC[C@@H]1CN(Cc2cc([C@H](CC(=O)O)c3cc(OC(F)(F)F)c4c(nnn4C)c3C)cc3ccsc23)S(=O)(=O)c2cc(Cl)cnc2O1] | ¹H-NMR (CDCl₃) δ: 0.97 (3H, t, J = 7.3 Hz), 1.44-1.55 (1H, m), 1.64-1.73 (1H, m), 2.82 (3H, s), 3.06-3.27 (3H, m), 3.62 (1H, dd, J = 15.0, 10.7 Hz), 4.33-4.45 (2H, m), 4.40 (3H, s), 4.67 (1H, d, J = 14.6 Hz), 5.04-5.13 (1H, m), 7.14 (1H, s), 7.23 (1H, s), 7.32 (1H, d, J = 5.5 Hz), 7.49 (1H, d, J = 5.5 Hz), 7.63 (1H, s), 8.23 (1H, d, J = 2.4 Hz), 8.41 (1H, d, J = 2.4 Hz). MS(ESI/APCI) m/z: 710 [M + H]⁺ |
| 47(47a) | 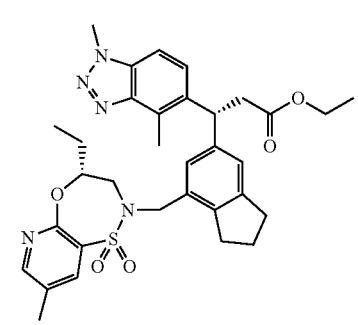 [SMILES: CCOC(=O)C[C@H](c1cc2c(c(CN3C[C@@H](CC)Oc4ncc(C)cc4S3(=O)=O)c1)CCC2)c1ccc2c(nnn2C)c1C] | MS(ESI/APCI) m/z: 618 [M + H]⁺ |
| 47(47b)= 47 | 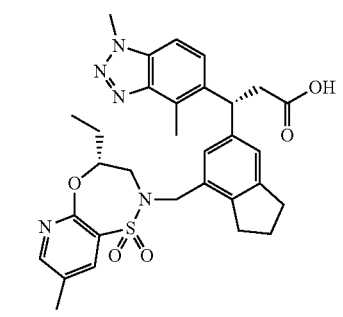 [SMILES: CC[C@@H]1CN(Cc2cc([C@@H](CC(=O)O)c3ccc4c(nnn4C)c3C)cc3c2CCC3)S(=O)(=O)c2cc(C)cnc2O1] | ¹H-NMR (CDCl₃) δ: 0.93 (3H, t, J = 7.3 Hz), 1.35-1.49 (1H, m), 1.56-1.70 (1H, m), 2.00-2.10 (2H, m), 2.38 (3H, s), 2.76-2.96 (4H, m), 2.82 (3H, s), 3:00-3.10 (2H, m), 3.15 (1H, dd, J = 15.9, 7.9 Hz), 3.53 (1H, dd, J = 14.6. 11.0 Hz), 3.96 (1H, d, J = 14.0 Hz). 4.20-4.34 (1H, m), 4.25 (3H, s), 4.40 (1H, d, J = 14.0 Hz), 4.94 (1H, t, J = 7.6 Hz), 6.88 (1H, s), 7.04 (1H, s), 7.31 (1H, d, J = 8.8 Hz), 7.36 (1H, d, J = 8.8 Hz), 8.03 (1H, d, J = 1.8 Hz), 8.26 (1H, d, J = 1.8 Hz). MS(ESI/APCI) m/z: 590 [M + H]⁺ |

TABLE 32

| Example No. | structural formula | physicochemical data |
| --- | --- | --- |
| 48(48a) | 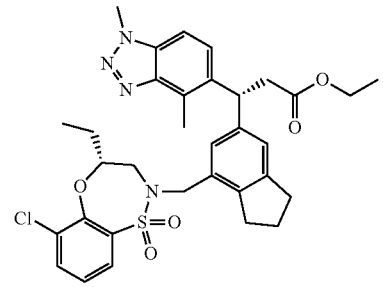 [SMILES: CCOC(=O)C[C@H](c1cc2c(c(CN3C[C@@H](CC)Oc4c(Cl)cccc4S3(=O)=O)c1)CCC2)c1ccc2c(nnn2C)c1C] | MS(ESI/APCI) m/z: 637 [M + H]⁺ |

TABLE 32-continued

| Example No. | structural formula | physicochemical data |
|---|---|---|
| 48(48b)=48 | 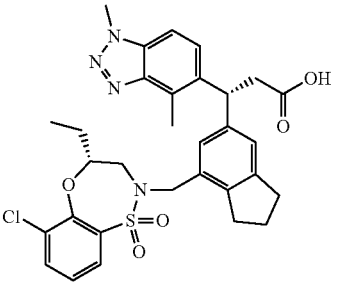 [SMILES: CC[C@@H]1CN(Cc2cc([C@@H](CC(=O)O)c3ccc4c(nnn4C)c3C)cc3c2CCC3)S(=O)(=O)c2cccc(Cl)c2O1] | ¹H-NMR (CDCl₃) δ: 0.92 (3H, t, J = 7.6 Hz), 1.43-1.55 (1H, m), 1.69-1.84 (1H, m), 1.98-2.13 (2H, m), 2.76-2.88 (3H, m), 2.82 (3H, s), 2.89-2.99 (2H, m), 3.05 (1H, dd, J = 15.9, 8.5 Hz), 3.14 (1H, dd, J = 15.9, 7.3 Hz), 3.65-3.79 (2H, m), 3.94-4.04 (1H, m), 4.25 (3H, s), 4.50 (1H, d, J = 13.4 Hz), 4.90-4.97 (1H, m), 6.86 (1H, s), 7.04 (1H, s), 7.18 (1H, t, J = 7.9 Hz), 7.30 (1H, d, J = 8.9 Hz), 7.34 (1H, d, J = 8.9 Hz), 7.56-7.61 (1H, m), 7.75-7.80 (1H, m).<br>MS(ESI/APCI) m/z: 609 [M + H]⁺ |
| 49(49a) | 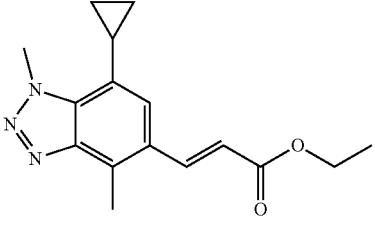 [SMILES: CCOC(=O)/C=C/c1cc(C2CC2)c2c(nnn2C)c1C] | ¹H-NMR (CDCl₃) δ: 0.84-0.92 (2H, m), 1.03-1.13 (2H, m), 1.36 (3H, t, J = 7.1 Hz), 2.27-2.32 (1H, m), 2.85 (3H, s), 4.29 (2H, q, J = 7.0 Hz), 4.60 (3H, s), 6.39 (1H, d, J = 16.1 Hz), 7.38 (1H, s), 8.09 (1H, d, J = 16.1 Hz).<br>MS(ESI/APCI) m/z: 286 [M + H]⁺ |
| 49(49b) | 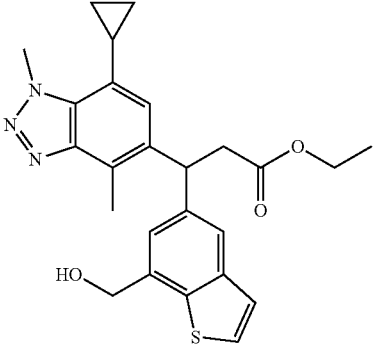 [SMILES: CCOC(=O)CC(c1cc(CO)c2sccc2c1)c1cc(C2CC2)c2c(nnn2C)c1C] | ¹H-NMR (CDCl₃) δ: 0.70-0.76 (1H, m), 0.83-0.90 (1H, m), 1.00-1.05 (2H, m), 1.10 (3H, t, J = 7.1 Hz), 2.24-2.33 (1H, m), 2.77 (3H, s), 3.08 (1H, dd, J = 15.6, 8.3 Hz), 3.18 (1H, dd, J = 15.4, 7.6 Hz), 4.01 (2H, q, J = 7.0 Hz), 4.56 (3H, s), 4.90 (2H, d, J = 5.4 Hz), 5.07 (1H, t, J = 8.1 Hz), 7.12 (1H, s), 7.20 (1H, s), 7.30 (1H, d, J = 5.4 Hz), 7.44 (1H, d, J = 5.4 Hz), 7.59 (1H, s).<br>MS(ESI/APCI) m/z: 450 [M + H]⁺ |
| 49(49c) | 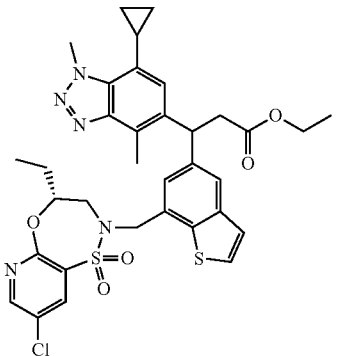 [SMILES: CCOC(=O)CC(c1cc(CN2C[C@@H](CC)Oc3ncc(Cl)cc3S2(=O)=O)c2sccc2c1)c1cc(C2CC2)c2c(nnn2C)c1C] | ¹H-NMR (CDCl₃) δ: 0.72-0.78 (1H, m), 0.82-0.90 (1H, m), 0.94-1.00 (3H, m), 1.05 (2H, d, J = 8.3 Hz), 1.11 (3H, t, J = 7.1 Hz), 1.41-1.52 (1H, m), 1.63-1.73 (1H, m), 2.26-2.34 (1H, m), 2.75-2.76 (3H, m), 3.04-3.20 (3H, m), 3.58-3.68 (1H, m), 4.03 (2H, q, J = 7.0 Hz), 4.30-4.41 (2H, m), 4.58 (3H, s), 4.64-4.70 (1H, m), 5.02-5.08 (1H, m), 7.06-7.14 (2H, m), 7.31 (1H, d, J = 5.4 Hz), 7.47 (1H, d, J = 5.4 Hz), 7.64 (1H, s), 8.23 (1H, s), 8.41 (1H, s).<br>MS(ESI/APCI) m/z: 694 [M + H]⁺ |

TABLE 32-continued

| Example No. | structural formula | physicochemical data |
|---|---|---|
| 49(49d)= 49 | 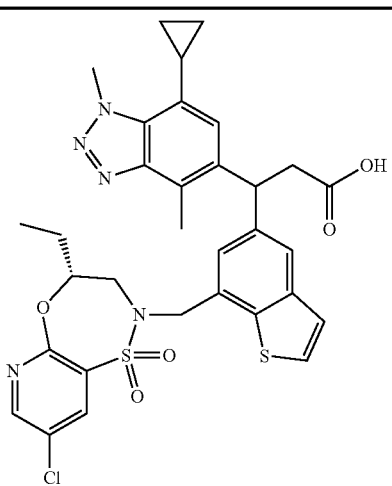 | ¹H-NMR (CDCl₃) δ: 0.70-0.77 (1H, m), 0.79-0.87 (1H, m), 0.91-0.99 (3H, m), 1.01-1.07 (2H, m), 1.40-1.55 (1H, m), 1.58-1.75 (1H, m), 2.25-2.37 (1H, m), 2.75-2.75 (3H, m), 3.08-3.24 (3H, m), 3.58-3.67 (1H, m), 4.29-4.44 (2H, m), 4.57 (3H, s), 4.62-4.73 (1H, m), 5.02-5.06 (1H, m), 7.07 (1H, d, J = 7.8 Hz), 7.13 (1H, d, J = 3.9 Hz), 7.31 (1H, d, J = 5.4 Hz), 7.47 (1H, d, J = 5.4 Hz), 7.64 (1H, s), 8.22 (1H, dd, J = 3.9, 2.4 Hz), 8.40 (1H, t. J = 2.9 Hz). MS(ESI/APCI) m/z: 666 [M + H]⁺ |

TABLE 33

| Example No. | structural formula | physicochemical data |
|---|---|---|
| 50(50a) | 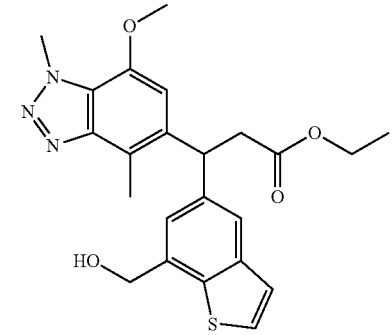 [SMILES: CCOC(=O)CC(c1cc(CO)c2sccc2c1)c1cc(OC)c2c(nnn2C)c1C] | ¹H-NMR (CDCl₃) δ: 1.12 (3H, t, J = 7.1 Hz), 1.85 (1H, t, J = 5.9 Hz), 2.75 (3H, s), 3.08 (1H, dd, J = 15.4. 8.5 Hz), 3.22 (1H, dd, J = 15.4. 7.6 Hz), 3.89 (3H, s), 4.04 (2H, q, J = 7.2.Hz), 4.41 (3H, s), 4.91 (2H, d, J = 5.9 Hz), 5.12 (1H, t, J = 8.1 Hz), 6.65 (1H, s), 7.22 (1H, s), 7.31 (1H, d, J = 5.4 Hz), 7.45 (1H, d, J = 5.4 Hz), 7.63 (1H, s). MS(ESI/APCI) m/z: 440 [M + H]⁺ |
| 50(50b) | 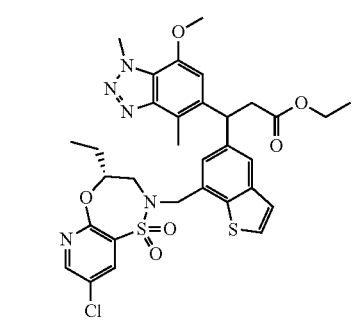 [SMILES: CCOC(=O)CC(c1cc(CN2C[C@@H](CC)Oc3ncc(Cl)cc3S2(=O)=O)c2sccc2c1)c1cc(OC)c2c(nnn2C)c1C] | ¹H-NMR (CDCl₃) δ: 0.95 (1.5H, t, J = 7.6 Hz), 0.99 (1.5H, t, J = 7.3 Hz), 1.13 (3H, t, J = 7.1 Hz), 1.41-1.54 (1H, m), 1.62-1.76 (1H, m), 2.71-2.74 (3H, m), 3.06-3.13 (1H, m), 3.15-3.23 (2H, m), 3.56-3.71 (1H, m), 3.91-3.93 (3H, m), 4.05 (2H, q, J = 7.0 Hz), 4.31-4.39 (2H, m), 4.42 (3H, s), 4.64-4.70 (1H, m), 5.07-5.12 (1H, m), 6.64-6.68 (1H, m), 7.18 (1H, s), 7.32 (1H, d, J = 5.4 Hz), 7.47 (1H, d, J = 5.4 Hz), 7.67 (1H, s), 8.21-8.23 (1H, m), 8.41 (1H, t, J = 2.4 Hz). |

TABLE 33-continued

| Example No. | structural formula | physicochemical data |
|---|---|---|
| 50(50c)= 50 | | $^1$H-NMR (CDCl$_3$) δ: 0.92 (1.5H, t, J = 7.3 Hz), 0.97 (1.5H, t, J = 7.3 Hz), 1.39-1.53 (1H, m), 1.58-1.73 (1H, m), 2.69-2.73 (3H, m), 3.07-3.33 (3H, m), 3.56-3.71 (1H, m), 3.88-3.92 (3H, m), 4.32-4.42 (2H, m), 4.41 (3H, s), 4.63-4.70 (1H, m), 5.04-5.11 (1H, m), 6.60-6.65 (1H, m), 7.18 (1H, s), 7.32 (1H, d, J = 5.4 Hz), 7.47 (1H, d, J = 5.4 Hz), 7.67 (1H, s), 8.20-8.23 (1H, m), 8.39-8.42 (1H, m). |
| 51(51a) | | $^1$H-NMR (CDCl$_3$) δ: 0.93-1.00 (3H, m), 1.10-1.17 (3H, m), 1.43-1.54 (1H, m), 1.65-1.75 (1H, m), 2.78-2.83 (3H, m), 3.03-3.10 (1H, m), 3.15-3.22 (2H, m), 3.50-3.70 (1H, m), 4.01-4.08 (2H, m), 4.25-4.41 (2H, m), 4.51 (3H, s), 4.69 (1H, d, J = 14.2 Hz), 5.05-5.10 (1H, m), 7.08-7.12 (1H, m), 7.27-7.30 (1H, m), 7.32-7.34 (1H, m), 7.49 (1H, d, J = 5.4 Hz), 7.65 (1H, s), 8.22-8.23 (1H, m), 8.39-8.42 (1H, m). |
| 51(51b)= 51 | | $^1$H-NMR (CDCl$_3$) δ: 0.89-0.97 (3H, m), 1.41-1.71 (2H, m), 2.78 (3H, s), 3.04-3.11 (1H, m), 3.13-3.23 (2H, m), 3.57-3.64 (1H, m), 4.30-4.40 (2H, m), 4.48 (3H, s), 4.63-4.68 (1H, m), 5.00-5.06 (1H, m), 7.08 (1H, d, J = 4.4 Hz), 7.21-7.23 (1H, m), 7.30 (1H, d, J = 5.4 Hz), 7.47 (1H, d, J = 5.4 Hz), 7.63 (1H, s), 8.19-8.20 (1H, m), 8.36-8.39 (1H, m). |

TABLE 34

| Example No. | structural formula | physicochemical data |
| --- | --- | --- |
| 52(52a) | | ¹H-NMR (CDCl₃) δ: 1.37 (3H, t, J = 7.3 Hz), 2.97 (3H, s), 4.31 (2H, q, J = 7.0 Hz), 4.55 (3H, s), 6.45 (1H, d, J = 16.1 Hz), 8.01-8.07 (2H, m). |
| 52(52b) | | ¹H-NMR (CDCl₃) δ: 1.15 (3H, t, J = 7.1 Hz), 1.93 (3H, s), 2.94 (3H, s), 3.11 (1H, dd, J = 15.9, 8.5 Hz), 3.22 (1H, dd, J = 15.6, 7.3 Hz), 4.51 (3H, s), 4.92 (2H, d, J = 5.9 Hz), 5.12 (1H, t, J = 7.8 Hz), 7.17 (1H, s), 7.33 (1H, d, J = 5.9 Hz), 7.49 (1H, d, J = 5.4 Hz), 7.59 (1H, s), 7.75 (1H, s). |
| 52(52c) | | ¹H-NMR (CDCl₃) δ: 0.98-1.03 (3H, m), 1.12-1.17 (3H, m), 1.48-1.58 (1H, m), 1.66-1.77 (1H, m), 2.93 (3H, s), 3.06-3.13 (1H, m), 3.16-3.25 (2H, m), 3.51-3.71 (1H, m), 4.06 (2H, q, J = 7.2 Hz), 4.24-4.47 (2H, m), 4.52 (3H, s), 4.67 (1H, d, J = 14.6 Hz), 5.07-5.13 (1H, m), 7.10-7.13 (1H, m), 7.33 (1H, d, J = 5.4 Hz), 7.51 (1H, d, J = 5.4 Hz), 7.61 (1H, s), 7.71 (1H, d, J = 4.4 Hz), 8.21-8.24 (1H, m), 8.40-8.42 (1H, m). |
| 52(52d)= 52 | | ¹H-NMR (CDCl₃) δ: 0.95-1.02 (3H, m), 1.46-1.76 (2H, m), 2.90-2.95 (3H, m), 3.09-3.29 (3H, m), 3.58-3.67 (1H, m), 4.35-4.47 (2H, m), 4.51 (3H, s), 4.65-4.69 (1H, m), 5.09 (1H, t, J = 7.6 Hz), 7.13 (1H, s), 7.33 (1H, d, J = 5.4 Hz), 7.51 (1H, d, J = 5.4 Hz), 7.60-7.62 (1H, m), 7.69 (1H, s), 8.21-8.23 (1H, m), 8.39-8.42 (1H, m). |

TABLE 34-continued

| Example No. | structural formula | physicochemical data |
|---|---|---|
| 53(53a) | | MS(ESI/APCI) m/z: 282, 284 [M + H]+ |
| 53(53b) | | ¹H-NMR (CDCl₃) δ: 2.47 (3H, s), 6.98 (1H, br s), 8.05-8.11 (1H, m), 8.34 (1H, s). |

TABLE 35

| Example No. | structural formula | physicochemical data |
|---|---|---|
| 53(53d) | | ¹H-NMR (CDCl₃) δ: 2.31 (3H, s), 2.69 (3H, d, J = 5.4 Hz), 3.17 (1H, br. s), 4.21 (2H, br s), 7.19 (1H, s). |
| 53(53e) | | ¹H-NMR (CDCl₃) δ: 2.90 (3H, s), 4.41 (3H, s), 7.95 (1H, s). |
| 53(53f) | | ¹H-NMR (CDCl₃) δ: 1.37 (3H, t, J = 7.1 Hz), 2.97 (3H, s), 4.31 (2H, q, J = 7.2 Hz), 4.42 (3H, s), 6.48 (1H, d, J = 16.1 Hz), 8.01 (1H, s), 8.10 (1H, d, J = 16.1 Hz).<br>MS(ESI/APCI) m/z: 314 [M + H]+ |

TABLE 35-continued
| Example No. | structural formula | physicochemical data |
|---|---|---|
| 53(53g) | 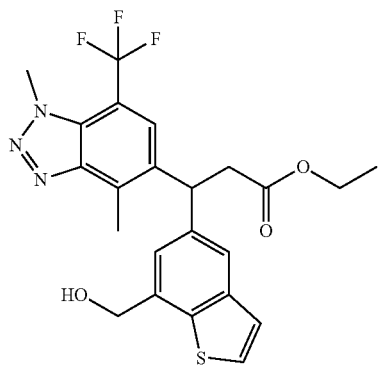 [SMILES: CCOC(=O)CC(c1cc(CO)c2sccc2c1)c1cc(C(F)(F)F)c2c(nnn2C)c1C] | ¹H-NMR (CDCl₃) δ: 1.11 (3H, t, J = 7.1 Hz), 2.91 (3H, s), 3.14 (1H, dd, J = 15.6, 8.3 Hz), 3.23 (1H, dd, J = 15:6, 7.3 Hz), 4.00-4.07 (2H, m), 4.39 (3H, s), 4.90-4.93 (2H, m), 5.15 (1H, t, J = 8.1 Hz), 7.20 (1H, s), 7.32 (1H, d, J = 5.4 Hz), 7.46 (1H, d, J = 5.4 Hz), 7.59 (1H, s), 7.73 (1H, s).<br>MS(ESI/APCI) m/z: 478 [M + H]⁺ |
| 53(53h) | 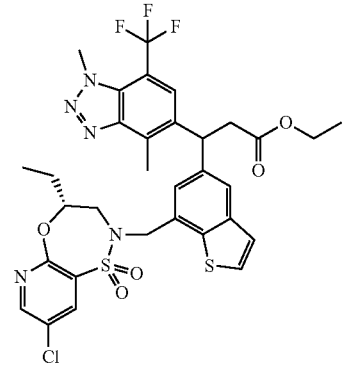 [SMILES: CCOC(=O)CC(c1cc(CN2C[C@@H](CC)Oc3ncc(Cl)cc3S2(=O)=O)c2sccc2c1)c1cc(C(F)(F)F)c2c(nnn2C)c1C] | ¹H-NMR (CDCl₃) δ: 0.95-1.00 (3H, m), 1.11-1.17 (3H, m), 1.45-1.59 (1H, m), 1.64-1.77 (1H, m), 2.91 (3H, s), 3.09-3.26 (3H, m), 3.51-3.71 (1H, m), 4.02-4.08 (2H, m), 4.24-4.45 (2H, m), 4.40 (3H, s), 4.64-4.72 (1H, m), 5.11-5.18 (1H, m), 7.14 (1H, s), 7.32 (1H, d, J = 5.4 Hz), 7.48-7.51 (1H, m), 7.63 (1H, s), 7.69 (1H, d. J = 7.3 Hz), 8.22-8.23 (1H, m), 8.40-8.42 (1H, m).<br>MS(ESI/APCI) m/z: 722 [M + H]⁺ |
| 53(53i)= 53 | 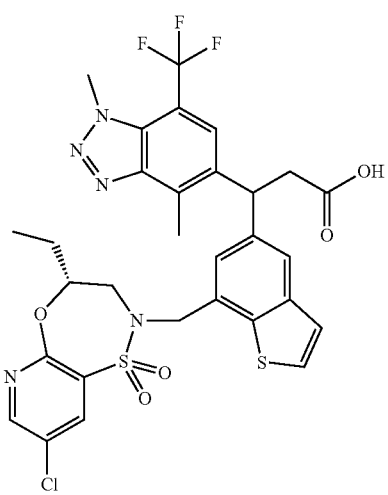 [SMILES: CC[C@@H]1CN(Cc2cc(C(CC(=O)O)c3cc(C(F)(F)F)c4c(nnn4C)c3C)cc3ccsc23)S(=O)(=O)c2cc(Cl)cnc2O1] | ¹H-NMR (CDCl₃) δ: 0.92-1.01 (3H, m), 1.44-1.75 (2H, m), 2.92 (3H, s), 3.11-3.33 (3H, m), 3.57-3.68 (1H, m), 4.34-4.44 (5H, m), 4.63-4.72 (1H, m), 5.11-5.16 (1H, m), 7.15 (1H, s), 7.33 (1H, d, J = 5.4 Hz), 7.50 (1H, d, J = 5.4 Hz), 7.62-7.67 (2H, m), 8.21-8.24 (1H, m), 8.39-8.42 (1H, m).<br>MS(ESI/APCI) m/z: 694 [M + H]⁺ |

TABLE 36

| Example No. | structural formula | physicochemical data |
|---|---|---|
| 54(54a) | | major rotamer: ¹H-NMR (CDCl₃) δ: 2.41 (3H, s), 7.38 (1H, s), 7.45 (1H, s), 8.39 (1H, s), 8.47 (1H, s). |
| 54(54b) | | ¹H-NMR (CDCl₃) δ: 2.42 (3H, s), 7.05 (1H, s), 7.74 (1H, s), 8.31 (1H, s). |
| 54(54c) | | ¹H-NMR (CDCl₃) δ: 2.32 (3H, s), 2.89 (3H, d, J = 5.9 Hz), 4.47 (1H, s), 7.43 (1H, s).<br>MS(ESI/APCI) m/z: 329 [M + H]⁺ |
| 54(54d) | | ¹H-NMR (CDCl₃) δ: 2.25 (3H, s), 2.67 (3H, s), 3.13 (1H, s), 4.12 (2H, s), 6.91 (1H, s).<br>MS(ESI/APCI) m/z: 299 [M + H]⁺ |
| 54(54e) | | ¹H-NMR (CDCl₃) δ: 2.81 (3H, s), 4.42 (3H, s), 7.50 (1H, s). |

TABLE 37

| Example No. | structural formula | physicochemical data |
|---|---|---|
| 54(54f) | | ¹H-NMR (CDCl₃) δ: 1.37 (3H, t, J = 6.8 Hz), 2.89 (3H, s), 4.30 (2H, q, J = 7.2 Hz), 4.43 (3H, s), 6.38 (1H, d, J = 16.1 Hz), 7.53 (1H, s), 8.07 (1H, d, J = 15.6 Hz), |
| 54(54g) | | ¹H-NMR (CDCl₃) δ: 1.11 (3H, t, J = 7.1 Hz), 1.82, (1H, t, J = 6.1 Hz), 2.83 (3H, s), 3.09 (1H, dd, J = 15.6, 8.3 Hz), 3.18 (1H, dd, J = 15.6, 7.8 Hz), 4.03 (2H, q, J = 7.0 Hz), 4.40 (3H, s), 4.91 (2H, d, J = 6.3 Hz), 5.11 (1H, t, J = 8.1 Hz), 7.19 (1H, s), 7.30 (1H, s), 7.31 (1H, d, J = 5.9 Hz), 7.45 (1H, t, J = 7.3 Hz). 7.60 (1H, s). |
| 54(54h) | | ¹H-NMR (CDCl₃) δ: 0.95-1.00 (3H, m), 1.13 (3H, t, J = 7.3 Hz), 1.44-1.74 (2H, m), 2.82 (3H, s), 3.04-3.11 (1H, m), 3.14-3.21 (2H, m), 3.51-3.70 (1H, m), 4.04 (2H, q, J = 7.0 Hz), 4.24-4.42 (2H, m), 4.40 (3H, s), 4.67 (1H, d, J = 14.6 Hz), 5.08-5.13 (1H, m), 7.12 (1H, s), 7.24-7.28 (1H, m), 7.32 (1H, d, J = 5.4 Hz), 7.49 (1H, d, J = 5.4 Hz), 7.63 (1H, s), 8.22-8.24 (1H, m), 8.40-8.43 (1H, m). |
| 54(54i)= 54 | | ¹H-NMR (CDCl₃) δ: 0.93-0.99 (3H, m), 1.42-1.75 (2H, m), 2.82 (3H, s), 3.08-3.25 (3H, m), 3.58-3.66 (1H, m), 4.35-4.44 (5H, m), 4.64-4.70 (1H, m), 5.05-5.11 (1H, m), 7.13 (1H, s), 7.21-7.24 (1H, m), 7.32 (1H, d, J = 5.4 Hz), 7.49 (1H, d, J = 5.4 Hz), 7.62-7.64 (1H, m), 8.22-8.24 (1H, m), 8.39-8.42 (1H, m). |

TABLE 37-continued

| Example No. | structural formula | physicochemical data |
|---|---|---|
| 55(55a) | (structure) | $^1$H-NMR (CDCl$_3$) δ: 2.28 (3H, s), 3.80 (2H, br s), 6.42 (1H, t, J = 74.0 Hz), 6.67 (1H, s), 7.19 (1H, s). |

TABLE 38

| Example No. | structural formula | physicochemical data |
|---|---|---|
| 55(55c) | (structure) | $^1$H-NMR (CDCl$_3$) δ: 2.40 (3H, s), 6.36-6.71 (1H, m), 7.05-7.20 (1H, m), 7.68 (1H, s), 8.26-8.37 (1H, m). |
| 55(55d) | (structure) | $^1$H-NMR (CDCl$_3$) δ: 2.30 (3H, s), 2.86 (3H, d, J = 5.4 Hz), 4.45 (1H, br s), 6.45 (1H, t, J = 73.0 Hz), 7.32 (1H, s). <br> MS(ESI/APCI) m/z: 311, 313.[M + H]$^+$ |
| 55(55e) | (structure) | $^1$H-NMR (CDCl$_3$) δ: 2.25 (3H, s), 2.65 (3H, s), 3.20 (1H, br s), 4.13 (2H, br s), 6.46 (1H, t, J = 74.0 Hz), 6.78 (1H, s). <br> MS(ESI/APCI) m/z: 281, 283 [M + H]$^+$ |
| 55(55f) | (structure) | $^1$H-NMR (CDCl$_3$) δ: 2.78 (3H, s), 4.43 (3H, s), 6.67 (1H, t, J = 72.5 Hz), 7.33 (1H, s). |

TABLE 38-continued

| Example No. | structural formula | physicochemical data |
|---|---|---|
| 55(55g) | 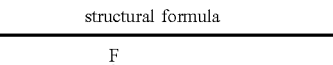 | $^1$H-NMR (CDCl$_3$) δ: 1.36 (3H, t, J = 7.1 Hz), 2.86 (3H, s), 4.30 (2H, q, J = 7.2 Hz), 4.44 (3H, s), 6.37 (1H, d, J = 16.1 Hz), 6.69 (1H, t, J = 72.5 Hz), 7.35 (1H, s), 8.08 (1H, d, J = 16.1 Hz). |

TABLE 39

| Example No. | structural formula | physicochemical data |
|---|---|---|
| 55(55h) | (structure shown) | $^1$H-NMR (CDCl$_3$) δ: 1.12 (3H, t, J = 7.1 Hz), 1.84 (1H, t, J = 5.9 Hz), 2.81 (3H, s), 3.08 (1H, dd, J = 15.4, 8.5 Hz), 3.19 (1H, dd, J = 15.4, 7.6 Hz), 4.03 (2H, q, J = 7.0 Hz), 4.40 (3H, s), 4.91 (2H, d, J = 5.9 Hz), 5.11 (1H, dd, J = 8.5, 7.6 Hz), 6.61 (1H, t, J = 73.0 Hz), 7.12 (1H, s), 7.20 (1H, s), 7.32 (1H, d, J = 5.9 Hz), 7.46 (1H, d, J = 5.4 Hz), 7.61 (1H, s). |
| 55(55i) | (structure shown) | $^1$H-NMR (CDCl$_3$) δ: 0.95-1.01 (3H, m), 1.13 (3H, t, J = 7.3 Hz), 1.44-1.74 (2H, m), 2.79-2.81 (3H, m), 3.04-3.11 (1H, m), 3.14-3.22 (2H, m), 3.58-3.67 (1H, m), 4.04 (2H, q, J = 7.2 Hz), 4.34-4.42 (5H, m), 4.64-4.70 (1H, m), 5.06-5.11 (1H, m), 6.51-6.83 (1H, m), 7.08-7.11 (1H, m), 7.14 (1H, s), 7.32 (1H, d, J = 5.4 Hz), 7.48 (1H, d, J = 5.4 Hz), 7.66 (1H, s), 8.21-8.23 (1H, m), 8.39-8.42 (1H, m). |

TABLE 39-continued
| Example No. | structural formula | physicochemical data |
|---|---|---|
| 55(55j)= 55 | 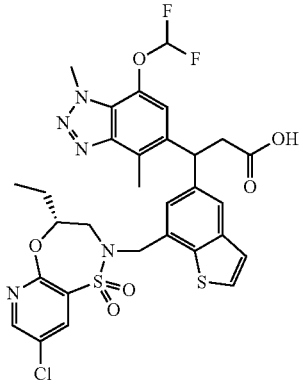 | ¹H-NMR (CDCl₃) δ: 0.94-1.00 (3H, m), 1.42-1.72 (2H, m), 2.78 (3H, s), 3.06-3.14 (1H, m), 3.16-3.25 (2H, m), 3.58-3.67 (1H, m), 4.32-4.43 (5H, m), 4.62-4.70 (1H, m), 5.05-5.11 (1H, m), 6.49-6.81 (1H, m), 7.05-7.08 (1H, m), 7.14 (1H, s), 7.32 (1H, d, J = 5.4 Hz), 7.48 (1H, d, J = 5.4 Hz), 7.66 (1H, s), 8.20-8.23 (1H, m), 8.39-8.41 (1H, m). |
| 56(56a) | 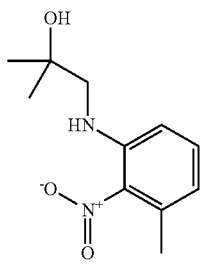 | MS(ESI/APCI) m/z: 225 [M + H]⁺ |
| 56(56b) | 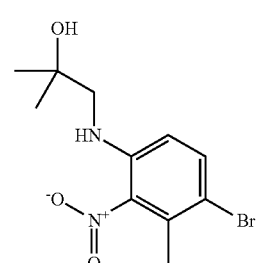 | MS(ESI/APCI) m/z: 303. 305 [M + H]⁺ |
TABLE 40
| Example No. | structural formula | physicochemical data |
|---|---|---|
| 56(56c) | 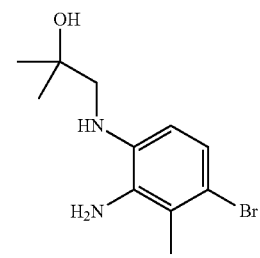 | ¹H-NMR (CDCl₃) δ: 1.35 (6H, s), 1.75 (1H, s), 2.32 (3H, s), 3.03 (2H, s), 3.56 (3H, br s), 6.49 (1H, d, J = 8.5 Hz), 6.99 (1H, d, J = 8.5 Hz). |

TABLE 40-continued

| Example No. | structural formula | physicochemical data |
|---|---|---|
| 56(56d) | 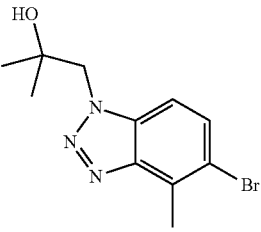 [SMILES: Cc1c(Br)ccc2c1nnn2CC(C)(C)O] | MS(ESI/APCI) m/z: 284, 286 [M + H]+ |
| 56(56e) | 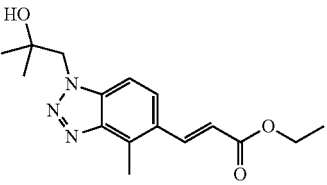 [SMILES: CCOC(=O)/C=C/c1ccc2c(nnn2CC(C)(C)O)c1C] | MS(ESI/APCI) m/z: 304 [M + H]+ |
| 56(56f) | 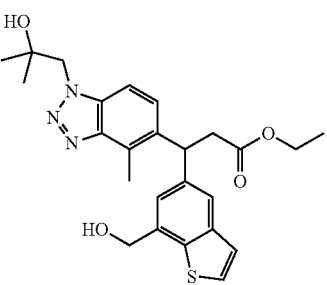 [SMILES: CCOC(=O)CC(c1cc(CO)c2sccc2c1)c1ccc2c(nnn2CC(C)(C)O)c1C] | $^1$H-NMR (CDCl$_3$) 1.10 (3H, t, J = 7.1 Hz), 1.26-1.31 (6H, m), 1.95 (1H, br s), 2.29 (1H, br s), 2.90 (3H, s), 3.10 (1H, dd, J = 15.4. 8.1 Hz), 3.22 (1H, dd, J = 15.6, 7.8 Hz), 4.03 (2H, q, J = 7.2 Hz), 4.53 (2H, s), 4.90 (2H, d, J = 5.9 Hz), 5.14 (1H, t, J = 7.8 Hz), 7.23 (1H, s), 7.32 (1H, d, J = 5.4 Hz), 7.37-7.41 (2H, m), 7.45 (1H, d, J = 5.4 Hz), 7.66 (1H, s). |
| 56(56g) | 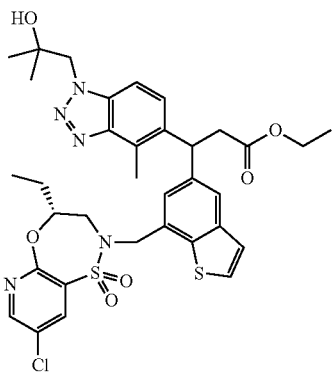 [SMILES: CCOC(=O)CC(c1cc(CN2C[C@@H](CC)Oc3ncc(Cl)cc3S2(=O)=O)c2sccc2c1)c1ccc2c(nnn2CC(C)(C)O)c1C] | $^1$H-NMR (CDCl$_3$) δ: 0.88 (1.5H, t, J = 7.3 Hz), 0.95 (1.5H, t, J = 7.3 Hz), 1.09 (3H, t, J = 7.1 Hz), 1.22-1.30 (6H, m), 1.38-1.70 (2H, m), 2.24-2.36 (1H, m), 2.84 (3H, s), 3.02-3.22 (3H, m), 3.53-3.64 (1H, m), 4.02 (2H, q, J = 7.2 Hz), 4.21-4.39 (2H, m), 4.52 (2H, s), 4.60-4.66 (1H, m), 5.06-5.12 (1H, m), 7.04-7.10 (1H, m), 7.29-7.41 (3H, m), 7.44-7.47 (1H, m), 7.68 (1H, d. J = 4.9 Hz), 8.18-8.19 (1H, m), 8.29-8.39 (1H, m).<br>MS(ESI/APCI) m/z: 712 [M + H]+ |
| 56(56h)=56 | 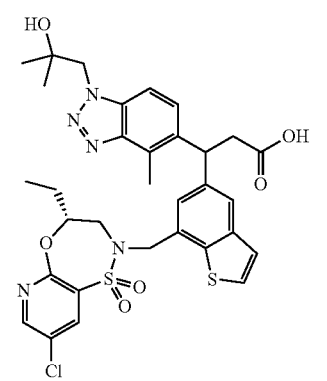 [SMILES: CC[C@@H]1CN(Cc2cc(C(CC(=O)O)c3ccc4c(nnn4CC(C)(C)O)c3C)cc3ccsc23)S(=O)(=O)c2cc(Cl)cnc2O1] | $^1$H-NMR (CDCl$_3$) δ: 0.86 (1.5H, t, J = 7.1 Hz), 0.92 (1.5H, t, J = 7.3 Hz), 1.26 (6H, s), 1.35-1.48 (1H, m), 1.55-1.67 (1H, m), 2.80 (3H, s), 3.05-3.23 (3H, m), 3.53-3.61 (1H, m), 4.21-4.38 (2H, m), 4.51 (2H, s), 4.59-4.66 (1H, m), 5.04-5.09 (1H, m), 7.05-7.09 (1H, m), 7.27-7.34 (2H, m), 7.38 (1H, d. J = 8.3 Hz), 7.44 (1H, d, J = 5.4 Hz), 7.66 (1H, s), 8.17-8.19 (1H, m), 8.29-8.38 (1H, m).<br>MS(ESI/APCI) m/z: 684 [M + H]+ |

TABLE 41

| Example No. | structural formula | physicochemical data |
|---|---|---|
| 57(57a) | | MS(ESI/APCI) m/z: 273 [M + H]+ |
| 57(57b) | | MS(ESI/APCI) m/z: 351. 353 [M + H]+ |
| 57(57c) | | 1H-NMR (CDCl3) δ: 2.18-2.25 (2H, m), 2.31 (3H, s), 2.93 (3H, s), 3.19 (2H, t, J = 7.6 Hz), 3.29 (2H, t, J = 6.3 Hz), 3.53 (1H, br s), 6.45 (1H, d, J = 8.3 Hz), 7.00 (1H, d, J = 8.3 Hz). |
| 57(57d) | | 1H-NMR (CDCl3) δ: 2.60-2.65 (2H, m), 2.85 (3H, s), 2.92 (3H, s), 3.05 (2H, t, J = 7.3 Hz), 4.83 (2H, t, J = 6.6 Hz), 7.30 (1H, d, J = 8.8 Hz), 7.65 (1H, d, J = 8.8 Hz). MS(ESI/APCI) m/z: 332, 334 [M + H]+ |
| 57(57e) | | MS(ESI/APCI) m/z: 352 [M + H]+ |

TABLE 41-continued

| Example No. | structural formula | physicochemical data |
|---|---|---|
| 57(57f) | 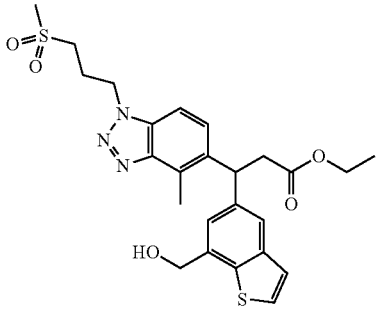 [SMILES: CCOC(=O)CC(c1cc(CO)c2sccc2c1)c1ccc2c(nnn2CCCS(C)(=O)=O)c1C] | $^1$H-NMR (CDCl$_3$) δ: 1.12 (3H, t, J = 7.1 Hz), 2.55-2.60 (2H, m), 2.89 (3H, s), 2.89 (3H, s), 3.04 (2H, t, J = 7.1 Hz), 3.12 (1H, dd, J = 15.1. 8.3 Hz), 3.23 (1H, dd, J = 15.6, 7.3 Hz), 4.04 (2H, q, J = 7.2 Hz), 4.77 (2H, t, J = 6.1 Hz), 4.91 (2H, d. J = 5.9 Hz), 5.15 (1H, t, J = 8.1 Hz), 7.23 (1H, s), 7.31-7.36 (2H, m), 7.42-7.47 (2H, m), 7.65 (1H, s). |

TABLE 42

| Example No. | structural formula | physicochemical data |
|---|---|---|
| 57(57g) | 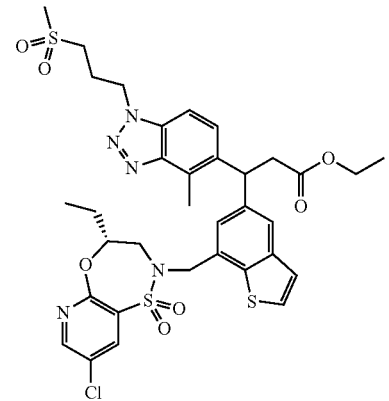 [SMILES: CCOC(=O)CC(c1cc(CN2C[C@@H](CC)Oc3ncc(Cl)cc3S2(=O)=O)c2sccc2c1)c1ccc2c(nnn2CCCS(C)(=O)=O)c1C] | MS(ESI/APCI) m/z: 760 [M + H]$^+$ |
| 57(57h)= 57 | 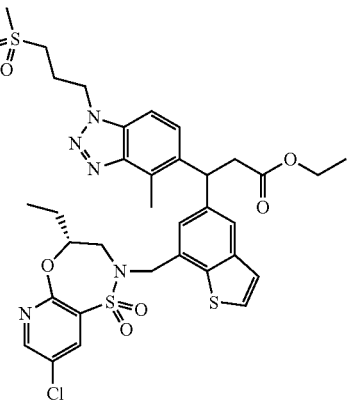 | $^1$H-NMR (CDCl$_3$) δ: 0.90-0.97 (3H, m), 1.40-1.72 (2H, m), 2.52-2.59 (2H, m), 2.82 (3H, s), 2.88 (3H, s), 3.03 (2H, t, J = 7.3 Hz), 3.08-3.26 (3H, m), 3.55-3.65 (1H, m), 4.29-4.39, (2H, m), 4.61-4.67 (1H, m), 4.76 (2H, t, J = 6.1 Hz), 5.08 (1H, t, J = 7.6 Hz), 7.11 (1H, s), 7.29 (1H, d, J = 5.4 Hz), 7.32-7.40 (2H, m), 7.45 (1H, d, J = 5.9 Hz), 7.64 (1H, s), 8.18-8.20 (1H, m), 8.35-8.38 (1H, m). |
| 58(58a) | 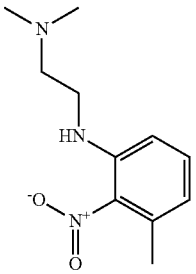 | $^1$H-NMR (CDCl$_3$) δ: 2.27 (6H, s), 2.46 (3H, s), 2.57 (2H, t, J = 6.1 Hz), 3.23 (2H, q, J = 5.7 Hz), 6.51 (1H, d, J = 7.3 Hz), 6.64 (1H, d, J = 8.3 Hz), 6.79 (1H, br s), 7.21 (1H, t, J = 7.8 Hz). |

TABLE 42-continued

| Example No. | structural formula | physicochemical data |
|---|---|---|
| 58(58b) | (structure) | MS(ESI/APCI) m/z: 302, 304 [M + H]+ |
| 58(58c) | (structure) | MS(ESI/APCI) m/z: 272, 274 [M + H]+ |

TABLE 43

| Example No. | structural formula | physicochemical data |
|---|---|---|
| 58(58d) | (structure) | MS(ESI/APCI) m/z: 283. 285 [M + H]+ |
| 58(58e) | (structure) | MS(ESI/APCI) m/z: 303. [M + H]+ |
| 58(58f) | (structure) | $^1$H-NMR (CDCl$_3$) δ: 1.10 (3H, t, J = 7.1 Hz), 2.27-2.30 (6H, m), 2.82-2.88 (2H, m), 2.87 (3H, s), 3.10 (1H, dd, J = 15.1. 8.3 Hz), 3.21 (1H, dd, J = 15.4. 7.6 Hz), 4.03 (2H, q, J = 7.0 Hz), 4.62-4.68 (2H, m), 4.89 (2H, s), 5.13 (1H, t, J = 7.8 Hz). 7.22 (1H, s), 7.28-7.33 (2H, m), 7.37 (1H, d, J = 8.3 Hz), 7.44 (1H, d, J = 5.4 Hz), 7.64 (1H, s). |

TABLE 43-continued

| Example No. | structural formula | physicochemical data |
|---|---|---|
| 58(58h)=58 | | ¹H-NMR (CDCl₃) δ: 0.94 (2H, t, J = 7.4 Hz), 0.97 (1H, t, J = 7.4 Hz), 1.45-1.52 (1H, m), 1.66-1.71 (1H, m), 2.38 (6H, s), 2.74 (1H, br s), 2.88 (3H, s), 2.93-2.95 (1H, br m), 3.10-3.22 (3H, m), 3.67 (1H, q, J = 13.3 Hz), 4.02 (1H, s), 4.31-4.37 (2H, m), 4.45-4.49 (1H, br m), 4.69 (1H, d, J = 14.6 Hz), 5.15 (1H, br s), 7.15 (1H, br s), 7.24 (1H, d, J = 8.3 Hz), 7.31 (1H, d, J = 4.4 Hz), 7.46-7.49 (2H, m), 7.68 (1H, s), 8.23 (1H, s), 8.40 (1H, d, J = 2.4 Hz). |
| 59(59a) | | MS(APCI) m/z: 411 [M + H]⁺ |
| 59(59b) | | MS(ESI/APCI) m/z: 655 [M + H]⁺ |

TABLE 44

| Example No. | structural formula | physicochemical data |
|---|---|---|
| 59(59c)= 59 | | ¹H-NMR (CDCl₃) δ: 0.94 (3H, t, J = 7.1 Hz), 1.43-1.51 (1H, m), 1.63-1.70 (1H, m), 2.73 (3H, s), 3.03-3.24 (3H, m), 3.66 (1H, q, J = 12.9 Hz), 4.24 (3H, s), 4.30-4.36 (2H, m), 4.61 (1H, d, J = 14.6 Hz), 5.00 (1H, t, J = 7.1 Hz), 7.20 (1H, d, J = 4.9 Hz), 7.24 (1H, d, J = 8.8 Hz), 7.39 (1H, d, J = 4.9 Hz), 7.50 (1H, s), 8.18 (1H, s), 8.35 (1H, s), 8:52 (1H, d, J = 8.8 Hz).<br>MS(ESI/APCI) m/z: 627 [M + H]⁺ |
| 60(60a) | | ¹H-NMR (CDCl₃) δ: 2.50 (3H, s), 7.81 (1H, d. J = 8.8 Hz), 8.01 (1H, d, J = 8.8 Hz), 8.97 (1H, br s). |
| 60(60c) | | ¹H-NMR (CDCl₃) δ: 2.32 (3H, s), 3.43-3.73 (5H, m), 6.52 (1H, d, J = 8.3 Hz), 7.01 (1H, d, J = 8.3 Hz). |
| 60(60d) | | MS(ESI/APCI) m/z: 294. 296 [M + H]⁺ |
| 60(60e) | | MS(ESI/APCI) m/z: 314 [M + H]⁺ |

TABLE 44-continued

| Example No. | structural formula | physicochemical data |
|---|---|---|
| 60(60f) | | $^1$H-NMR (CDCl$_3$) δ: 1.10 (3H, t, J = 7.1 Hz), 2.07 (1H, t, J = 5.6 Hz), 2.90 (3H, s), 3.11 (1H, dd, J = 15.6, 8.3 Hz), 3.22 (1H, dd, J = 15.6, 7.3 Hz), 4.03 (2H, q, J = 7.0 Hz), 4.90 (2H, d, J = 4.9 Hz), 5.12-5.20 (3H, m), 7.22 (1H, s), 7.32 (1H, d, J = 5.4 Hz), 7.34 (1H, d, J = 8.8 Hz), 7.45 (1H, d, J = 5.4 Hz), 7.48 (1H, d, J = 8.8 Hz), 7.63 (1H, s). |

TABLE 45

| Example No. | structural formula | physicochemical data |
|---|---|---|
| 60(60g) | | MS(ESI/APCI) m/z: 722 [M + H]$^+$ |
| 60(60h)= 60 | | $^1$H-NMR (CDCl$_3$) δ: 0.92 (1.5H, t, J = 6.6 Hz), 0.94 (1.5H, t, J = 6.6 Hz), 1.41-1.50 (1H, m), 1.60-1.69 (1H, m), 2.86 (3H, s), 3.09-3.25 (3H, m), 3.61 (1H, q, J = 13.0 Hz), 4.32-4.39 (2H, m), 4.66 (1H, t, J = 12.4 Hz), 5.10 (1H, t, J = 7.2 Hz), 5.15-5.22 (2H, m), 7.14 (1H, s), 7.31 (1H, d, J = 5.4 Hz), 7.35 (1H, d, J = 8.3 Hz), 7.43 (1H, d, J = 8.3 Hz), 7.47 (1H, d, J = 5.4 Hz), 7.66 (1H, s), 8.22 (1H, s), 8.40 (1H, s).<br>MS(ESI/APCI) m/z: 694 [M + H]$^+$ |
| 61(61a) | | $^1$H-NMR (CDCl$_3$) δ: 1.10 (3H, t, J = 7.6 Hz), 1.50-1.56 (1H, m), 1.60 (3H, d, J = 7.0 Hz), 1.65-1.74 (1H, m), 3.07 (1H, dd, J = 13.9, 10.0 Hz), 3.25 (1H, dd, J = 13.9, 1.5 Hz), 3.49-3.55 (1H, m), 4.19 (1H, q, J = 7.0 Hz), 7.11 (1H, dd, J = 7.8, 4.9 Hz). 7.31 (1H, d, J = 7.8 Hz), 8.26 (1H, d, J = 4.9 Hz).<br>MS(ESI/APCI) m/z: 193 [M + H]$^+$ |

TABLE 45-continued

| Example No. | structural formula | physicochemical data |
|---|---|---|
| 61(61b) | | $^1$H-NMR (CDCl$_3$) δ: 1.05 (3H, t, J = 7.3 Hz), 1.51-1.56 (4H, m), 1.62-1.71 (2H, m), 3.04 (1H, dd, J = 14.4, 1.7 Hz), 3.22 (1H, dd, J = 14.6, 9.3 Hz), 3.59-3.64 (1H, m), 4.31 (1H, q, J = 7.2 Hz), 7.07 (1H, dd, J = 7.8. 4.9. Hz), 7.27 (1H, d, J = 7.8 Hz), 8.18 (1H, d, J = 4.9 Hz).<br>MS(ESI/APCI) m/z: 193 [M + H]$^+$ |
| 61(61c) | | MS(ESI/APCI) m/z: 428 [M + H]$^+$ |

TABLE 46

| Example No. | structural formula | physicochemical data |
|---|---|---|
| 61(61d) | | $^1$H-NMR (CDCl$_3$) δ: 0.88 (1.5H, t, J = 7.3 Hz), 0.94 (1.5H, t, J = 7.3 Hz), 1.08 (3H, t, J = 7.1 Hz), 1.22-1.32 (1H, m), 1.49-1.58 (1H, m), 1.69-1.73 (3H, m), 2.84 (3H, s), 2.86-2.96 (2H, m), 3.06 (1H, dd, J = 15.0, 8.8 Hz), 3.17 (1H, dd, J = 15.0, 7.1 Hz), 3.45 (1H, d, J = 14.6 Hz), 3.81-3.89 (1H, m), 3.97-4.07 (3H, m), 4.24 (3H, s), 4.52-4.58 (1H, m), 5.05-5.09 (1H, m), 6.95 (1H, d, J = 13.7 Hz), 7.11-7.16 (1H, m), 7.23-7.27 (2H, m), 7.31-7.36 (2H, m), 7.41 (1H, d, J = 5.4 Hz), 7.55 (1H, d, J = 10.3 Hz), 8.29 (1H, d, J = 4.9 Hz).<br>MS(ESI/APCI) m/z: 584 [M + H]$^+$ |
| 61(61e)= 61 | | $^1$H-NMR (CDCl$_3$) δ: 0.91-0.96 (1.5H, m), 0.98-1.03 (1.5H, m), 1.37-1.71 (5H, m), 2.65 (1.5H, s), 2.73 (1.5H, s), 2.93-3.08 (2.5H, m), 3.10-3.22 (1H, m), 3.45-3.52 (0.5H, m), 3.62-3.69 (0.5H, m), 3.81-3.89 (0.5H, m), 3.92-4.02 (1H, m), 4.07-4.16 (1.5H, m), 4.23-4.27 (3H, m), 4.44-4.51 (0.5H, m), 4.87-5.02 (1H, m), 7.01-7.20 (3H, m), 7.29-7.51 (5H, m), 8.17-8.32 (1H, m).<br>MS(ESI/APCI) m/z: 556 [M + H]$^+$ |
| 62(62a) | | $^1$H-NMR (CDCl$_3$) δ: 0.87-0.92 (3H, m), 1.30-1.43 (5H, m), 1.46-1.70 (1H, m), 2.20-2.31 (1H, m), 2.49-2.62 (1H, m), 3.31-3.39 (1H, m), 3.46-3.57 (1H, m), 4.12-4.22 (1H, m), 7.15-7.19 (1H, m), 7.33 (1H, t; J = 9:0 Hz), 8.35-8.39 (1H, m).<br>MS(ESI/APCI) m/z: 213 [M + H]$^+$ |

TABLE 46-continued

| Example No. | structural formula | physicochemical data |
|---|---|---|
| 62(62b) | | ¹H-NMR (CDCl₃) δ: 1.04 (3H, t, J = 7.4 Hz), 1.34-1.48 (9H, m), 1.51-1.62 (2H, m), 1.64 (3H, d, J = 6.7 Hz), 3.47-3.58 (1H, m), 3.94-4.06 (2H, m), 5.31-5.73 (1H, m), 7.09 (1H, br s), 7.22-7.26 (1H, m), 8.24 (1H, d, J = 4.9 Hz). MS(ESI/APCI) m/z: 293 [M + H]⁺ |
| 62(62c) | | ¹H-NMR (CDCl₃) δ: 1.08 (3H, t, J = 7.4 Hz), 1.63-1.77 (5H, m), 3.35-3.44 (1H, m), 3.46-3.54 (1H, m), 3.73-3.84 (1H, m), 4.70-4.80 (1H, m), 7.45 (1H, dd, J = 8.0, 4.9 Hz), 7.58 (1H, d, J = 8.0 Hz), 8.42 (1H, d, J = 4.9 Hz), 9.48-9.58 (1H, m), 9.75-9.85 (1H, m). MS(ESI/APCI) m/z: 193 [M + H]⁺ |
| 62(62d) | | ¹H-NMR (CDCl₃) δ: 0.94 (3H, t, J = 7.4 Hz), 1.08 (3H, t, J = 7.1 Hz), 1.24-1.33 (1H, m), 1.50-1.57 (1H, m), 1.71 (3H, d, J = 6.7 Hz), 2.84-2.90 (1H, m), 2.85 (3H, s), 2.94 (1H, dd, J = 14.1, 9.8 Hz), 3.07 (1H, dd, J = 15.3, 8.6 Hz), 3.18 (1H, dd, J = 15.3, 7.4 Hz), 3.44 (1H, d, J = 14.1 Hz), 3.80-3.90 (1H, m), 3.97-4.06 (3H, m), 4.24 (3H, s), 4.56 (1H, q, J = 7.2 Hz), 5.03-5.10 (1H, m), 6.93 (1H, s), 7.14 (1H, dd, J = 8.0, 4.9 Hz), 7.24-7.28 (2H, m), 7.32-7.36 (2H, m), 7.42 (1H, d, J = 5.5 Hz), 7.56 (1H, s), 8.29 (1H, dd, J = 4.6, 1.5 Hz). MS(ESI/APCI) m/z: 584 [M + H]⁺ |

TABLE 47

| Example No. | structural formula | physicochemical data |
|---|---|---|
| 62(62e)=62 | | ¹H-NMR (CDCl₃) δ: 1.03 (3H, t, J = 7.4 Hz), 1.46 (3H, d, J = 7.4 Hz), 1.50-1.60 (1H, m), 1.62-1.75 (1H, m), 2.67 (3H, s), 2.98 (1H, dd, J = 12.6, 5.2 Hz), 3.02-3.10 (2H, m), 3.51-3.57 (1H, m), 3.89 (1H, d, J = 13.5 Hz), 4.09-4.19 (3H, m), 4.29 (3H, s), 4.93 (1H, dd, J = 10.4, 4.9 Hz), 7.08 (1H, s), 7.15 (1H, d, J = 5.5 Hz), 7.21-7.25 (2H, m), 7.37 (1H, d, J = 5.5 Hz), 7.41 (2H, t, J = 9.5 Hz), 7.52 (1H, d, J = 8.6 Hz), 8.34 (1H, d, J = 4.9 Hz). MS(ESI/APCI) m/z: 556 [M + H]⁺ |
| 63(63a) | | ¹H-NMR (CDCl₃) δ: 0.88 (3H, t, J = 7.4 Hz), 1.08 (3H, t, J = 7.1 Hz), 1.20-1.29 (1H, m), 1.45-1.53 (1H, m), 1.71 (3H, d, J = 6.7 Hz), 2.84 (3H, s), 2.86-2.96 (2H, m), 3.06 (1H, dd, J = 15.3, 8.6 Hz), 3.17 (1H, dd, J = 15.3, 7.4 Hz), 3.45 (1H, d, J = 14.7 Hz), 3.79-3.88 (1H, m), 4.00 (2H, q, J = 7.2 Hz), 4.06 (1H, d, J = 14.1 Hz), 4.24 (3H, s), 4.55 (1H, q, J = 7.0 Hz), 5.07 (1H, t, J = 8.0 Hz), 6.96 (1H, s), 7.14 (1H, dd, J = 8.0, 4.3 Hz), 7.23-7.26 (2H, m), 7.31-7.36 (2H, m), 7.41 (1H, d, J = 5.5 Hz), 7.54 (1H, s), 8.29 (1H, d, J = 4.3 Hz). MS(ESI/APCI) m/z: 584 [M + H]⁺ |

TABLE 47-continued

| Example No. | structural formula | physicochemical data |
|---|---|---|
| 63(63b)=63 | 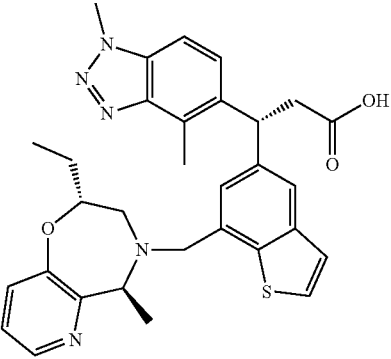 [SMILES: CC[C@@H]1CN(Cc2cc([C@@H](CC(=O)O)c3ccc4c(nnn4C)c3C)cc3ccsc23)[C@@H](C)c2ncccc2O1] | ¹H-NMR (CDCl₃) δ: 0.96 (3H, t, J = 7.1 Hz), 1.38-1.49 (1H, m), 1.53 (3H, d, J = 6.7 Hz), 1.57-1.69 (1H, m), 2.76 (3H, s), 2.98-3.07 (2H, m), 3.13-3.24 (2H, m), 3.68 (1H, d, J = 13.5 Hz), 3.95-4.04 (2H, m), 4.27 (3H, s), 4.47-4.55 (1H, m), 5.02 (1H, dd, J = 9.5, 6.4 Hz), 7.11 (1H, br s), 7.15-7.20 (2H, m), 7.32-7.42 (4H, m), 7.46-7.51 (1H, m), 8.20-8.24 (1H, m).<br>MS(ESI/APCI) m/z: 556 [M + H]⁺ |
| 64(64a) | 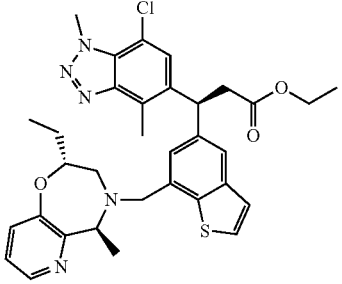 [SMILES: CCOC(=O)C[C@@H](c1cc(CN2C[C@@H](CC)Oc3cccnc3[C@@H]2C)c2sccc2c1)c1cc(Cl)c2c(nnn2C)c1C] | ¹H-NMR (CDCl₃) δ: 0.96 (3H, t, J = 7.4 Hz), 1.11 (3H, t, J = 6.7 Hz), 1.26-1.35 (1H, m), 1.49-1.58 (1H, m), 1.72 (3H, d, J = 6.7 Hz), 2.79 (3H, s), 2.85-2.91 (1H, m), 2.91-2.98 (1H, m), 3.03 (1H, dd, J = 15.6, 8.9 Hz), 3.15 (1H, dd, J = 15.3, 6.7 Hz), 3.46 (1H, d, J = 14.7 Hz), 3.83-3.91 (1H, m), 3.99-4.08 (3H, m), 4.49 (3H, s), 4.57 (1H, q, J = 7.2 Hz), 5.02 (1H, t, J = 8.0 Hz), 6.93 (1H, s), 7.14 (1H, dd, J = 8.0, 4.9 Hz), 7.24-7.28 (2H, m), 7.34 (1H, d, J = 8.0 Hz), 7.43 (1H, d, J = 5.5 Hz), 7.55 (1H, s), 8.30 (1H, d, J = 4.3 Hz).<br>MS(ESI/APCI) m/z: 618 [M + H]⁺ |
| 64(64b)=64 | 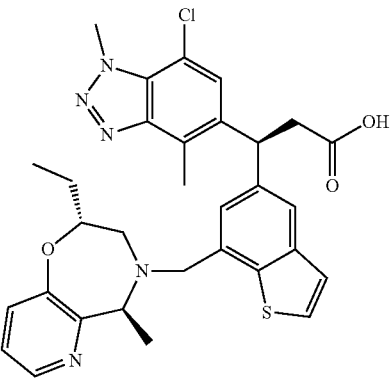 [SMILES: CC[C@@H]1CN(Cc2cc([C@H](CC(=O)O)c3cc(Cl)c4c(nnn4C)c3C)cc3ccsc23)[C@@H](C)c2ncccc2O1] | ¹H-NMR (CDCl₃) δ: 1.03 (3H, t, J = 7.4 Hz), 1.46 (3H, d, J = 6.7 Hz), 1.50-1.58 (1H, m), 1.63-1.73 (1H, m), 2.61 (3H, s), 2.94-3.09 (3H, m), 3.53 (1H, dd, J = 14.4. 2.8 Hz), 3.88 (1H, d, J = 14.1 Hz), 4.09-4.19 (3H, m), 4.55 (3H, s), 4.88 (1H, dd, J = 9.8. 5.5 Hz), 7.06 (1H, s), 7.18 (1H, d, J = 5.5 Hz), 7.21-7.26 (2H, m), 7.39 (1H, d, J = 5.5 Hz), 7.41-7.44 (2H, m), 8.33 (1H, dd, J = 4.9, 1.2 Hz).<br>MS(ESI/APCI) m/z: 590 [M + H]⁺ |
| 65(65a) | 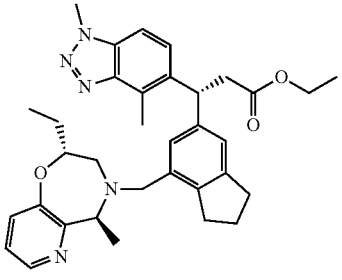 [SMILES: CCOC(=O)C[C@H](c1cc2c(c(CN3C[C@@H](CC)Oc4cccnc4[C@@H]3C)c1)CCC2)c1ccc2c(nnn2C)c1C] | ¹H-NMR (CDCl₃) δ: 0.92 (3H, t, J = 7.3 Hz), 1.08 (3H, t, J = 7.3 Hz), 1.19-1.31 (1H, m), 1.42-1.59 (1H, m), 1.60 (3H, d, J = 7.1 Hz), 1.91-2.07 (2H, m), 2,63-2.75 (1H, m), 2.77-2.90 (5H, m), 2.82 (3H, s), 3.02 (1H, dd, J = 15.3, 9.2 Hz), 3.09 (1H, dd, J = 15.3. 7.3 Hz), 3.14 (1H, d, J = 13.7 Hz), 3.69 (1H, d, J = 13.7 Hz), 3.78-3.87 (1H, m), 3.99 (2H, q, J = 7.3 Hz), 4.24 (3H, s), 4.45 (1H, q, J = 7.1 Hz), 4.89-4.96 (1H, m), 6.88 (1H, s), 6.92 (1H, s), 7.12 (1H, dd, J = 7.9, 4.9 Hz), 7.26 (1H, d, J = 8.5 Hz), 7.31 (1H, dd, J = 7.9, 1.2 Hz), 7.36 (1H, d, J = 8.5 Hz), 8.27 (1H, dd, J = 4.9, 1.2 Hz).<br>MS(ESI/APCI) m/z: 568 [M + H]⁺ |

TABLE 48

| Example No. | structural formula | physicochemical data |
|---|---|---|
| 65 (65b) = 65 | | ¹H-NMR (DMSO-D₆) δ: 0.82 (3H, t, J = 7.6 Hz), 1.07-1.20 (1H, m), 1.33-1.45 (1H, m), 1.49 (3H, d, J = 6.8 Hz), 1.82-1.98 (2H, m), 2.61-2.87 (6H, m), 2.69 (3H, s), 2.90-3.10 (3H, m), 3.57 (1H, d, J = 13.4 Hz), 3.82-3.93 (1H, m), 4.23 (3H, s), 4.33 (1H, q, J = 6.8 Hz), 4.71-4.78 (1H, m), 6.87 (1H, s), 7.03 (1H, s), 7.23 (1H, dd, J = 7.9, 4.3 Hz), 7.36-7.42 (2H, m), 7.52 (1H, d, J = 8.5 Hz), 8.22 (1H, dd, J = 4.6, 1.5 Hz), 12.08 (1H, s). MS (ESI/APCI) m/z: 540 [M + H]⁺ |
| 66 (66a) | | ¹H-NMR (CDCl₃) δ: 0.94 (3H, t, J = 7.3 Hz), 1.08 (3H, t, J = 7.3 Hz), 1.18-1.31 (1H, m), 1.47-1.59 (1H, m), 1.61 (3H, d, J = 7.1 Hz), 1.91-2.04 (2H, m), 2.62-2.73 (1H, m), 2.75-2.91 (5H, m), 2.82 (3H, s), 3.02 (1H, dd, J = 15.3, 9.2 Hz), 3.08 (1H, dd, J = 15.3, 7.3 Hz), 3.14 (1H, d, J = 13.7 Hz), 3.68 (1H, d, J = 13.7 Hz), 3.76-3.85 (1H, m), 3.99 (2H, q, J = 7.3 Hz), 4.24 (3H, s), 4.45 (1H, q, J = 7.1 Hz), 4.89-4.96 (1H, m), 6.88 (1H, s), 6.92 (1H, s), 7.12 (1H, dd, J = 7.9, 4.9 Hz), 7.27 (1H, d, J = 8.5 Hz), 7.31 (1H, d, J = 7.9 Hz), 7.38 (1H, d, J = 8.5 Hz), 8.28 (1H, d, J = 4.9 Hz). MS (ESI/APCI) m/z: 568 [M + H]⁺ |
| 66 (66b) = 66 | | ¹H-NMR (DMSO-D₆) δ: 0.88 (3H, t, J = 7.3 Hz), 1.11-1.20 (1H, m), 1.35-1.45 (1H, m), 1.49 (3H, d, J = 6.8 Hz), 1.85-1.97 (2H, m), 2.59-2.86 (6H, m), 2.69 (3H, s), 2.98 (2H, d, J = 7.9 Hz), 3.09 (1H, d, J = 13.4 Hz), 3.58 (1H, d, J = 13.4 Hz), 3.82-3.93 (1H, m), 4.24 (3H, s), 4.33 (1H, q, J = 6.8 Hz), 4.74 (1H, t, J = 7.9 Hz), 6.89 (1H, s), 7.02 (1H, s), 7.22 (1H, dd, J = 7.9, 4.9 Hz), 7.38 (1H, dd, J = 7.9, 1.5 Hz), 7.46 (1H, d, J = 8.5 Hz), 7.53 (1H, d, J = 8.5 Hz), 8.23 (1H, dd, J = 4.9, 1.5 Hz), 12.09 (1H, br s). MS (ESI/APCI) m/z: 540 [M + H]⁺ |
| 67 (67a) | | ¹H-NMR (CDCl₃) δ: 2.23 (3H, s), 2.29 (3H, s), 2.79 (3H, dd, J = 5.8, 0.7 Hz), 3.70 (1H, br s), 7.36 (1H, s). |
| 67 (67b) | | ¹H-NMR (CDCl₃) δ: 2.21 (3H, s), 2.25 (3H, s), 2.58-2.72 (4H, m), 4.08 (2H, br s), 6.83 (1H, s). |

TABLE 48-continued

| Example No. | structural formula | physicochemical data |
|---|---|---|
| 67 (67c) | (structure: 1,4,7-trimethyl-benzotriazole with Br) | ¹H-NMR (CDCl₃) δ: 2.69 (3H, s), 2.77 (3H, s), 4.46 (3H, s), 7.32 (1H, s). |
| 67 (67d) | (structure: 1,4,7-trimethyl-benzotriazole with ethyl acrylate) | ¹H-NMR (CDCl₃) δ: 1.36 (3H, t, J = 7.1 Hz), 2.72 (3H, s), 2.85 (3H, s), 4.29 (2H, q, J = 7.1 Hz), 4.47 (3H, s), 6.39 (1H, d, J = 15.9 Hz), 7.39 (1H, s), 8.09 (1H, d, J = 15.9 Hz). |

TABLE 49

| Example No. | structural formula | physicochemical data |
|---|---|---|
| 67 (67e) | (structure: benzotriazole-benzothiophene ethyl ester with hydroxymethyl) | ¹H-NMR (CDCl₃) δ: 1.12 (3H, t, J = 7.1 Hz), 1.79 (1H, t, J = 6.1 Hz), 2.67 (3H, s), 2.82 (3H, s), 3.04-3.12 (1H, m), 3.17-3.24 (1H, m), 4.03 (2H, q, J = 7.1 Hz), 4.43 (3H, s), 4.90 (2H, d, J = 6.1 Hz), 5.09 (1H, t, J = 8.0 Hz), 7.04 (1H, s), 7.19 (1H, s), 7.32 (1H, d, J = 5.6 Hz), 7.45 (1H, d, J = 5.6 Hz), 7.63 (1H, s). |
| 67 (67f) | (structure: full compound with pyrido-oxazepine, benzothiophene, benzotriazole, ethyl ester) | MS (ESI/APCI) m/z: 598 [M + H]⁺ |

TABLE 49-continued

| Example No. | structural formula | physicochemical data |
|---|---|---|
| 67 (67g) | | ¹H-NMR (CDCl₃) δ: 0.88 (3H, t, J = 7.3 Hz), 1.09 (3H, t, J = 7.0 Hz), 1.17-1.31 (1H, m), 1.45-1.57 (1H, m), 1.72 (3H, d, J = 7.2 Hz), 2.64 (3H, s), 2.78 (3H, s), 2.82-2.96 (2H, m), 3.03 (1H, dd, J = 15.5, 8.5 Hz), 3.16 (1H, dd, J = 15.5, 7.6 Hz), 3.45 (1H, d, J = 14.6 Hz), 3.78-3.89 (1H, m), 3.96-4.09 (3H, m), 4.43 (3H, s), 4.56 (1H, q, J = 7.2 Hz), 4.98-5.06 (1H, m), 6.96 (1H, s), 6.98 (1H, s), 7.15 (1H, dd, J = 8.2, 4.6 Hz), 7.25 (1H, d, J = 5.5 Hz), 7.33 (1H, dd, J = 8.2, 1.5 Hz), 7.41 (1H, d, J = 5.5 Hz), 7.54 (1H, s), 8.30 (1H, dd, J = 4.6, 1.5 Hz). MS (ESI/APCI) m/z: 598 [M + H]⁺ |
| 67 (67h) | | ¹H-NMR (CDCl₃) δ: 0.96 (3H, t, J = 7.3 Hz), 1.10 (3H, t, J = 7.0 Hz), 1.20-1.39 (1H, m), 1.47-1.63 (1H, m), 1.71 (3H, d, J = 7.2 Hz), 2.64 (3H, s), 2.79 (3H, s), 2.85-2.99 (2H, m), 3.03 (1H, dd, J = 15.3, 8.5 Hz), 3.17 (1H, dd, J = 15.3, 7.9 Hz), 3.44 (1H, d, J = 14.6 Hz), 3.82-3.91 (1H, m), 3.96-4.07 (3H, m), 4.43 (3H, s), 4.57 (1H, q, J = 7.2 Hz), 4.98-5.06 (1H, m), 6.93 (1H, s), 6.98 (1H, s), 7.14 (1H, dd, J = 7.9, 4.9 Hz), 7.26 (1H, d, J = 5.5 Hz), 7.34 (1H, dd, J = 7.9, 1.5 Hz), 7.42 (1H, d, J = 5.5 Hz), 7.56 (1H, s), 8.29 (1H, dd, J = 4.9, 1.5 Hz). MS (ESI/APCI) m/z: 598 [M + H]⁺ |
| 67 (67i) = 67 | | ¹H-NMR (CDCl₃) δ: 0.95 (3H, t, J = 7.6 Hz), 1.36-1.48 (1H, m), 1.54 (3H, d, J = 7.1 Hz), 1.56-1.67 (1H, m), 2.70 (3H, s), 2.71 (3H, s), 2.97-3.05 (2H, m), 3.10-3.23 (2H, m), 3.66 (1H, d, J = 14.0 Hz), 3.92-4.06 (1H, m), 4.01 (1H, d, J = 14.0 Hz), 4.45 (3H, s), 4.51 (1H, q, J = 7.1 Hz), 4.97 (1H, dd, J = 9.8, 6.1 Hz), 7.11 (2H, s), 7.13-7.22 (2H, m), 7.33-7.39 (2H, m), 7.42 (1H, s), 8.23 (1H, dd, J = 4.9, 1.2 Hz). MS (ESI/APCI) m/z: 570 [M + H]⁺ |
| 68 | | ¹H-NMR (CDCl₃) δ: 1.03 (3H, t, J = 7.3 Hz), 1.44-1.58 (1H, m), 1.48 (3H, d, J = 7.3 Hz), 1.61-1.76 (1H, m), 2.62 (3H, s), 2.76 (3H, s), 2.96 (1H, dd, J = 13.1, 5.2 Hz), 3.01-3.11 (2H, m), 3.43-3.53 (1H, m), 3.84 (1H, d, J = 13.4 Hz), 4.08-4.23 (3H, m), 4.47 (3H, s), 4.89 (1H, dd, J = 10.1, 5.2 Hz), 7.06 (1H, s), 7.14 (1H, s), 7.17 (1H, d, J = 5.5 Hz), 7.22 (1H, dd, J = 7.9, 4.9 Hz), 7.29 (1H, s), 7.38 (1H, d, J = 5.5 Hz), 7.41 (1H, dd, J = 7.9, 1.2 Hz), 8.32 (1H, dd, J = 4.9, 1.2 Hz). MS (ESI/APCI) m/z: 570 [M + H]⁺ |

TABLE 50

| Example No. | structural formula | physicochemical data |
|---|---|---|
| 69 (69a) | | ¹H-NMR (CDCl₃) δ: 0.96 (3H, t, J = 7.3 Hz), 1.09 (3H, t, J = 7.0 Hz), 1.22-1.34 (1H, m), 1.49-1.65 (1H, m), 1.61 (3H, d, J = 7.1 Hz), 1.93-2.03 (2H, m), 2.61-2.72 (1H, m), 2.67 (3H, s), 2.76 (3H, s), 2.78-2.93 (5H, m), 3.00 (1H, dd, J = 15.5, 8.9 Hz), 3.07 (1H, dd, J = 15.5, 6.7 Hz), 3.15 (1H, d, J = 14.0 Hz), 3.68 (1H, d, J = 14.0 Hz), 3.78-3.87 (1H, m), 3.95-4.05 (2H, m), 4.43 (3H, s), 4.47 (1H, q, J = 7.1 Hz), 4.84-4.92 (1H, m), 6.91 (1H, s), 6.92 (1H, s), 7.03 (1H, s), 7.12 (1H, dd, J = 8.2, 4.6 Hz), 7.31 (1H, dd, J = 8.2, 1.5 Hz), 8.28 (1H, dd, J = 4.6, 1.5 Hz).<br>MS (ESI/APCI) m/z: 582 [M + H]⁺ |
| 69 (69b) = 69 | | ¹H-NMR (CDCl₃) δ: 1.02 (3H, t, J = 7.3 Hz), 1.43 (3H, d, J = 7.3 Hz), 1.46-1.60 (1H, m), 1.62-1.73 (1H, m), 1.91-2.06 (2H, m), 2.61 (3H, s), 2.66-2.85 (3H, m), 2.75 (3H, s), 2.86-3.07 (4H, m), 3.34-3.45 (1H, m), 3.57 (1H, d, J = 13.4 Hz), 3.81 (1H, d, J = 13.4 Hz), 4.05-4.16 (1H, m), 4.19-4.30 (1H, m), 4.46 (3H, s), 4.75 (1H, dd, J = 10.7, 5.2 Hz), 6.68 (1H, s), 6.93 (1H, s), 7.14 (1H, s), 7.19 (1H, dd, J = 7.9, 4.9 Hz), 7.38 (1H, d, J = 7.9 Hz), 8.29 (1H, d, J = 4.9 Hz).<br>MS (ESI/APCI) m/z: 554 [M + H]⁺ |
| 70 (70a) | | ¹H-NMR (CDCl₃) δ: 0.89 (3H, t, J = 7.4 Hz), 1.11 (3H, t, J = 7.1 Hz), 1.25-1.33 (1H, m), 1.48-1.56 (1H, m), 1.72 (3H, d, J = 6.7 Hz), 2.79 (3H, s), 2.87 (1H, dd, J = 14.7, 3.1 Hz), 2.94 (1H, dd, J = 14.4, 10.1 Hz), 3.03 (1H, dd, J = 15.3, 8.6 Hz), 3.15 (1H, dd, J = 15.6, 7.7 Hz), 3.46 (1H, d, J = 14.1 Hz), 3.80-3.88 (1H, m), 3.98-4.09 (3H, m), 4.50 (3H, s), 4.56 (1H, q, J = 7.0 Hz), 5.02 (1H, t, J = 8.0 Hz), 6.94 (1H, br s), 7.15 (1H, dd, J = 8.0, 4.9 Hz), 7.24-7.28 (2H, m), 7.34 (1H, dd, J = 8.0, 1.2 Hz), 7.43 (1H, d, J = 5.5 Hz), 7.54 (1H, d, J = 1.2 Hz), 8.30 (1H, dd, J = 4.9, 1.2 Hz).<br>MS (ESI/APCI) m/z: 618 [M + H]⁺ |
| 70 (70b) = 70 | | ¹H-NMR (CDCl₃) δ: 0.96 (3H, t, J = 7.4 Hz), 1.39-1.48 (1H, m), 1.53 (3H, d, J = 6.7 Hz), 1.57-1.68 (1H, m), 2.71 (3H, s), 2.98-3.04 (2H, m), 3.13 (1H, dd, J = 14.1, 9.8 Hz), 3.21 (1H, dd, J = 14.1, 2.5 Hz), 3.67 (1H, d, J = 14.1 Hz), 3.96-4.05 (2H, m), 4.46-4.52 (1H, m), 4.51 (3H, s), 4.97 (1H, dd, J = 9.5, 6.4 Hz), 7.09 (1H, br s), 7.16 (1H, dd, J = 8.3, 4.6 Hz), 7.21 (1H, d, J = 5.5 Hz), 7.35-7.39 (3H, m), 7.42 (1H, d, J = 1.2 Hz), 8.22 (1H, dd, J = 4.9, 1.8 Hz).<br>MS (ESI/APCI) m/z: 590 [M + H]⁺ |

TABLE 50-continued

| Example No. | structural formula | physicochemical data |
|---|---|---|
| 71 (71a) | | $^1$H-NMR (CDCl$_3$) δ: 1.13 (3H, t, J = 7.1 Hz), 1.55 (1H, t, J = 5.7 Hz), 2.02-2.12 (2H, m), 2.80 (3H, s), 2.82-2.89 (4H, m), 3.02 (1H, dd, J = 15.6, 8.9 Hz), 3.11 (1H, dd, J = 15.6, 7.0 Hz), 4.03 (2H, q, J = 7.1 Hz), 4.50 (3H, s), 4.62 (2H, d, J = 5.7 Hz), 4.89-4.97 (1H, m), 7.00 (1H, s), 7.03 (1H, s), 7.31 (1H, s).<br>MS (ESI/APCI) m/z: 428 [M + H]$^+$ |

TABLE 51

| Example No. | structural formula | physicochemical data |
|---|---|---|
| 71 (71c) | optically active isomer | $^1$H-NMR (CDCl$_3$) δ: 0.95 (3H, t, J = 7.3 Hz), 1.11 (3H, t, J = 7.3 Hz), 1.20-1.62 (2H, m), 1.61 (3H, d, J = 6.7 Hz), 1.90-2.09 (2H, m), 2.62-2.73 (1H, m), 2.77 (3H, s), 2.78-2.91 (5H, m), 2.94-3.10 (2H, m), 3.16 (1H, d, J = 13.4 Hz), 3.69 (1H, d, J = 13.4 Hz), 3.78-3.90 (1H, m), 3.95-4.08 (2H, m), 4.42-4.53 (4H, m), 4.83-4.92 (1H, m), 6.89 (1H, s), 6.91 (1H, s), 7.12 (1H, dd, J = 7.9, 4.3 Hz), 7.29 (1H, s), 7.31 (1H, d, J = 7.9 Hz), 8.28 (1H, d, J = 4.3 Hz).<br>MS (ESI/APCI) m/z: 602 [M + H]$^+$ |
| 71 (71d) | optically active isomer | $^1$H-NMR (CDCl$_3$) δ: 0.93 (3H, t, J = 7.3 Hz), 1.11 (3H, t, J = 7.0 Hz), 1.21-1.57 (2H, m), 1.61 (3H, d, J = 7.3 Hz), 1.90-2.09 (2H, m), 2.62-2.73 (1H, m), 2.76 (3H, s), 2.79-2.92 (5H, m), 2.98 (1H, dd, J = 15.3, 9.2 Hz), 3.06 (1H, dd, J = 15.3, 7.3 Hz), 3.16 (1H, d, J = 14.0 Hz), 3.70 (1H, d, J = 14.0 Hz), 3.77-3.90 (1H, m), 3.96-4.07 (2H, m), 4.41-4.53 (1H, m), 4.49 (3H, s), 4.83-4.91 (1H, m), 6.90 (1H, s), 6.91 (1H, s), 7.13 (1H, dd, J = 7.9, 4.9 Hz), 7.23-7.29 (1H, m), 7.32 (1H, dd, J = 7.9, 1.2 Hz), 8.28 (1H, dd, J = 4.9, 1.2 Hz).<br>MS (ESI/APCI) m/z: 602 [M + H]$^+$ |

TABLE 51-continued

| Example No. | structural formula | physicochemical data |
|---|---|---|
| 71 (71e) = 71 | 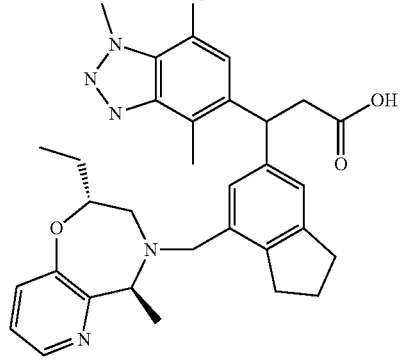optically active isomer | ¹H-NMR (DMSO-D₆) δ: 0.88 (3H, t, J = 7.0 Hz), 1.12-1.46 (2H, m), 1.50 (3H, d, J = 7.3 Hz), 1.84-2.00 (2H, m), 2.60-2.88 (6H, m), 2.67 (3H, s), 2.94-3.05 (2H, m), 3.10 (1H, d, J = 13.7 Hz), 3.59 (1H, d, J = 13.7 Hz), 3.86-3.96 (1H, m), 4.29-4.39 (1H, m), 4.44 (3H, s), 4.67-4.75 (1H, m), 6.91 (1H, s), 7.05 (1H, s), 7.22 (1H, dd, J = 7.9, 4.9 Hz), 7.38 (1H, d, J = 7.9 Hz), 7.47 (1H, s), 8.22 (1H, d, J = 4.9 Hz), 12.14 (1H, s). MS (ESI/APCI) m/z: 574 [M + H]⁺ |
| 72 | 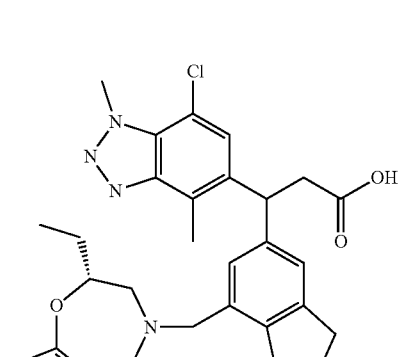optically active isomer | ¹H-NMR (DMSO-D₆) δ: 0.82 (3H, t, J = 7.3 Hz), 1.09-1.45 (2H, m), 1.49 (3H, d, J = 6.7 Hz), 1.82-2.02 (2H, m), 2.63-2.87 (6H, m), 2.69 (3H, s), 2.97-3.05 (2H, m), 3.09 (1H, d, J = 13.4 Hz), 3.58 (1H, d, J = 13.4 Hz), 3.81-3.94 (1H, m), 4.29-4.38 (1H, m), 4.43 (3H, s), 4.69-4.77 (1H, m), 6.90 (1H, s), 7.07 (1H, s), 7.23 (1H, dd, J = 7.9, 4.9 Hz), 7.38 (1H, d, J = 7.9 Hz), 7.41 (1H, s), 8.22 (1H, d, J = 4.9 Hz), 12.15 (1H, s). MS (ESI/APCI) m/z: 574 [M + H]⁺ |

TABLE 52

| Example No. | structural formula | physicochemical data |
|---|---|---|
| 73 (73a) | 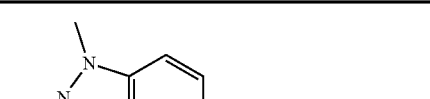 | MS (ESI/APCI) m/z: 584 [M + H]⁺ |

TABLE 52-continued

| Example No. | structural formula | physicochemical data |
|---|---|---|
| 73 (73b) = 73 | | ¹H-NMR (CDCl₃) δ: 1.08 (1.5H, t, J = 7.1 Hz), 1.15 (1.5H, t, J = 7.3 Hz), 1.32-1.46 (3H, m), 1.50-1.80 (2H, m), 2.56-2.78 (3H, m), 2.76-4.15 (8H, m), 4.21-4.34 (3H, m), 4.81-5.04 (1H, m), 7.02-7.15 (2H, m), 7.18-7.61 (6H, m), 8.13-8.45 (1H, m). MS (ESI/APCI) m/z: 556 [M + H]⁺ |
| 74 (74c) | | MS (ESI/APCI) m/z: 604 [M + H]⁺ |
| 74 (74d) = 74 | | ¹H-NMR (CDCl₃) δ: 1.02 (3H, t, J = 7.4 Hz), 1.46-1.55 (1H, m), 1.51 (3H, d, J = 6.7 Hz), 1.60-1.72 (1H, m), 3.00-3.06 (2H, m), 3.11 (1H, dd, J = 13.5, 10.4 Hz), 3.40 (1H, dd, J = 14.7, 3.1 Hz), 3.80 (1H, d, J = 13.5 Hz), 4.05-4.15 (2H, m), 4.20-4.27 (1H, m), 4.30 (3H, s), 5.28 (1H, dd, J = 10.1, 5.8 Hz), 7.11 (1H, s), 7.18-7.22 (2H, m), 7.37-7.42 (3H, m), 7.43 (1H, d, J = 8.6 Hz), 7.50 (1H, d, J = 8.6 Hz), 8.30 (1H, dd, J = 4.9, 1.2 Hz). MS (ESI/APCI) m/z: 576 [M + H]⁺ |
| 75 (75a) | | MS (ESI/APCI) m/z: 604 [M + H]⁺ |

TABLE 52-continued

| Example No. | structural formula | physicochemical data |
|---|---|---|
| 75 (75b) = 75 | | ¹H-NMR (CDCl₃) δ: 0.92 (3H, t, J = 7.4 Hz), 1.33-1.44 (1H, m), 1.51-1.62 (1H, m), 1.57 (3H, d, J = 7.4 Hz), 2.93-3.01 (1H, m), 3.05-3.13 (2H, m), 3.18 (1H, dd, J = 14.4, 9.5 Hz), 3.62 (1H, d, J = 14.1 Hz), 3.92-3.99 (1H, m), 4.03 (1H, d, J = 14.1 Hz), 4.27 (3H, s), 4.49 (1H, q, J = 7.0 Hz), 5.36 (1H, dd, J = 9.8, 6.7 Hz), 7.12-7.17 (2H, m), 7.22 (1H, d, J = 5.5 Hz), 7.34-7.40 (3H, m), 7.46 (1H, d, J = 8.6 Hz), 7.54 (1H, d, J = 1.2 Hz), 8.23 (1H, dd, J = 4.9, 1.2 Hz). MS (ESI/APCI) m/z: 576 [M + H]⁺ |
| 76 (76a) | | ¹H-NMR (CDCl₃) δ: 0.79-0.87 (3H, m), 1.53-1.64 (1H, m), 1.71-1.86 (1H, m), 4.10 (1H, d, J = 3.6 Hz), 4.78-4.90 (1H, m), 7.11-7.18 (1H, m), 7.28-7.36 (1H, m), 8.26 (1H, d, J = 2.4 Hz). |

TABLE 53

| Example No. | structural formula | physicochemical data |
|---|---|---|
| 76 (76b) | | ¹H-NMR (CDCl₃) δ: 1.10-1.32 (3H, m), 3.13-3.24 (2H, m), 7.43-7.60 (2H, m), 8.47 (1H, s). MS (ESI/APCI) m/z: 154 [M + H]⁺ |
| 76 (76c) | | ¹H-NMR (CDCl₃) δ: 0.83-0.96 (6H, m), 1.30-1.47 (2H, m), 1.57-1.88 (2H, m), 2.15-2.32 (1H, m), 2.42-2.62 (1H, m), 3.32-3.60 (1H, m), 3.90-4.06 (1H, m), 7.12-7.19 (1H, m), 7.32-7.39 (1H, m), 8.33-8.48 (1H, m). MS (ESI/APCI) m/z: 227 [M + H]⁺ |
| 76 (76d) | optically active isomer ·2HCl | ¹H-NMR (CD₃OD) δ: 1.10-1.27 (6H, m), 1.68-1.84 (2H, m), 2.19-2.32 (1H, m), 2.36-2.49 (1H, m), 3.51-3.59 (1H, m), 3.70-3.76 (1H, m), 4.31-4.44 (1H, m), 4.88-4.92 (1H, m), 7.82-7.88 (1H, m), 8.10 (1H, d, J = 4.2 Hz), 8.62 (1H, d, J = 2.6 Hz). MS (ESI/APCI) m/z: 207 [M + H]⁺ |

TABLE 53-continued

| Example No. | structural formula | physicochemical data |
|---|---|---|
| 76 (76e) | 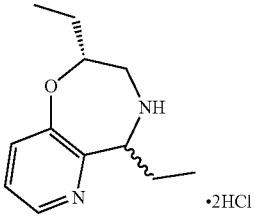<br>optically active isomer | ¹H-NMR (CD₃OD) δ: 0.93-1.00 (3H, m), 1.16-1.24 (3H, m), 1.73-1.99 (2H, m), 2.16-2.38 (2H, m), 3.62-3.73 (1H, m), 3.79-3.91 (1H, m), 4.15-4.33 (1H, m), 4.91-4.96 (1H, m), 8.02-8.16 (1H, m), 8.35 (1H, d, J = 4.2 Hz), 8.72 (1H, d, J = 2.8 Hz).<br>MS (ESI/APCI) m/z: 207 [M + H]⁺ |
| 76 (76f) | 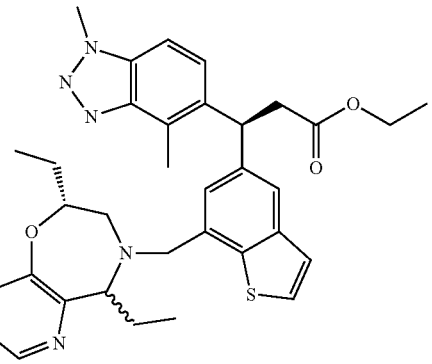<br>optically active isomer | MS (ESI/APCI) m/z: 598 [M + H]⁺ |
| 76 (76g) = 76 | 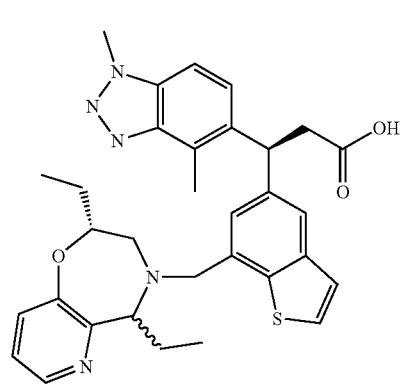<br>optically active isomer | ¹H-NMR (CDCl₃) δ: 0.64 (3H, t, J = 7.4 Hz), 1.06 (3H, t, J = 7.4 Hz), 1.52-1.62 (1H, m), 1.66-1.75 (1H, m), 1.81-1.91 (2H, m), 2.61 (3H, s), 2.96 (1H, dd, J = 11.7, 4.9 Hz), 3.02 (1H, d, J = 11.0 Hz), 3.09 (1H, dd, J = 15.0, 6.4 Hz), 3.61-3.74 (2H, m), 4.00 (1H, d, J = 13.5 Hz), 4.17-4.23 (2H, m), 4.31 (3H, s), 4.91 (1H, dd, J = 11.0, 4.3 Hz), 7.07 (1H, s), 7.11 (1H, d, J = 5.5 Hz), 7.13 (1H, s), 7.24-7.30 (1H, m), 7.37 (1H, d, J = 5.5 Hz), 7.42-7.47 (2H, m), 7.56 (1H, d, J = 8.6 Hz), 8.40 (1H, dd, J = 4.9, 1.2 Hz).<br>MS (ESI/APCI) m/z: 570 [M + H]⁺ |

TABLE 54

| Example No. | structural formula | physicochemical data |
|---|---|---|
| 77 (77a) | optically active isomer | MS (ESI/APCI) m/z: 598 [M + H]+ |
| 77 (77b) = 77 | optically active isomer | 1H-NMR (CDCl3) δ: 0.66 (3H, t, J = 7.4 Hz), 1.10 (3H, t, J = 7.4 Hz), 1.47-1.60 (1H, m), 1.66-1.77 (1H, m), 1.81-2.00 (2H, m), 2.82 (3H, s), 2.96 (1H, d, J = 14.1 Hz), 3.10 (1H, dd, J = 13.5, 6.1 Hz), 3.32 (1H, dd, J = 13.5, 9.2 Hz), 3.55 (1H, dd, J = 15.3, 10.4 Hz), 3.64 (1H, t, J = 8.0 Hz), 3.86-3.94 (1H, m), 3.86 (1H, d, J = 12.9 Hz), 3.97 (1H, d, J = 13.5 Hz), 4.23 (3H, s), 5.02 (1H, dd, J = 9.2, 6.1 Hz), 7.01 (1H, s), 7.22-7.31 (3H, m), 7.43 (1H, d, J = 5.5 Hz), 7.44-7.47 (1H, m), 7.56 (1H, d, J = 8.6 Hz), 7.69-7.70 (1H, m), 8.26 (1H, dd, J = 4.9, 1.8 Hz). MS (ESI/APCI) m/z: 570 [M + H]+ |
| 78 (78a) |  | 1H-NMR (CDCl3) δ: 0.93 (3H, t, J = 7.4 Hz), 1.48-1.59 (1H, m), 1.64-1.76 (1H, m), 2.30-2.39 (1H, m), 2.59-2.67 (1H, m), 3.47-3.56 (0.5H, m), 3.62-3.70 (0.5H, m), 4.20-4.32 (1H, m), 7.21-7.25 (1H, m), 7.37 (1H, td, J = 8.6, 3.1 Hz). MS (ESI/APCI) m/z: 247 [M + H]+ |
| 78 (78b) |  | 1H-NMR (CDCl3) δ: 0.92 (3H, t, J = 7.6 Hz), 1.30-1.49 (5H, m), 2.36-2.69 (2H, m), 3.34 (1H, d, J = 14.1 Hz), 3.37-3.45 (1H, m), 3.53 (1H, d, J = 13.7 Hz), 3.79 (3H, s), 4.34-4.39 (1H, m), 6.83 (2H, dd, J = 4.4, 2.2 Hz), 7.13-7.22 (3H, m), 7.30-7.36 (1H, m). MS (ESI/APCI) m/z: 367 [M + H]+ |
| 78 (78c) | optically active isomer | 1H-NMR (CDCl3) δ: 1.00 (3H, t, J = 7.4 Hz), 1.37-1.48 (1H, m), 1.56-1.68 (5H, m), 2.85-3.00 (2H, m), 3.26 (1H, d, J = 14.1 Hz), 3.74 (1H, d, J = 13.7 Hz), 3.79 (3H, s), 3.84-3.92 (1H, m), 4.40 (1H, q, J = 7.0 Hz), 6.83 (2H, dd, J = 6.7, 2.0 Hz), 7.11 (1H, d, J = 8.2 Hz), 7.17 (2H, d, J = 8.6 Hz), 7.27 (1H, d, J = 7.4 Hz). MS (ESI/APCI) m/z: 347 [M + H]+ |

TABLE 54-continued

| Example No. | structural formula | physicochemical data |
|---|---|---|
| 78 (78d) | optically active isomer | ¹H-NMR (CDCl₃) δ: 1.03 (3H, t, J = 7.2 Hz), 1.36-1.47 (1H, m), 1.50 (3H, d, J = 7.0 Hz), 1.54-1.71 (1H, m), 2.73 (1H, d, J = 14.9 Hz), 3.27 (1H, dd, J = 15.1, 10.4 Hz), 3.61 (1H, d, J = 13.3 Hz), 3.69 (1H, d, J = 13.3 Hz), 3.74-3.83 (4H, m), 4.16 (1H, d, J = 7.4 Hz), 6.84 (2H, dd, J = 6.7, 2.3 Hz), 7.13 (1H, d, J = 8.2 Hz), 7.19 (2H, d, J = 8.6 Hz), 7.28 (1H, d, J = 8.6 Hz). MS (ESI/APCI) m/z: 347 [M + H]⁺ |
| 78 (78e) | optically active isomer | ¹H-NMR (CDCl₃) δ: 0.97 (3H, t, J = 7.2 Hz), 1.32-1.44 (1H, m), 1.50-1.64 (4H, m), 2.76 (1H, dd, J = 14.1, 10.2 Hz), 2.97 (1H, dd, J = 14.5, 3.1 Hz), 3.52 (1H, d, J = 12.9 Hz), 3.76 (1H, br s), 3.79 (3H, s), 3.88 (1H, br s), 4.23 (1H, q, J = 7.2 Hz), 6.35 (1H, d, J = 9.4 Hz), 6.83 (2H, d, J = 8.6 Hz), 7.18 (2H, d, J = 8.6 Hz), 7.26 (1H, d, J = 9.8 Hz). MS (ESI/APCI) m/z: 329 [M + H]⁺ |

TABLE 55

| Example No. | structural formula | physicochemical data |
|---|---|---|
| 78 (78g) | ·HCl optically active isomer | ¹H-NMR (CD₃OD) δ: 1.15 (3H, t, J = 7.2 Hz), 1.60-1.73 (2H, m), 1.75 (3H, d, J = 7.0 Hz), 3.42 (1H, dd, J = 13.7, 10.6 Hz), 3.55 (1H, dd, J = 13.7, 2.3 Hz), 3.76-3.84 (1H, m), 4.69 (1H, q, J = 7.2 Hz), 6.64 (1H, d, J = 8.6 Hz), 7.43 (1H, d, J = 9.0 Hz). MS (ESI/APCI) m/z: 209 [M + H]⁺ |
| 78 (78h) | optically active isomer | ¹H-NMR (CDCl₃) δ: 0.86 (3H, t, J = 7.4 Hz), 1.09 (3H, t, J = 7.2 Hz), 1.21-1.30 (1H, m), 1.39-1.50 (1H, m), 1.67 (3H, d, J = 7.0 Hz), 2.70 (1H, dd, J = 14.5, 10.2 Hz), 2.86 (3H, s), 2.94 (1H, d, J = 11.3 Hz), 3.08 (1H, dd, J = 15.3, 8.6 Hz), 3.20 (1H, dd, J = 15.3, 7.4 Hz), 3.81 (1H, d, J = 14.1 Hz), 3.84-3.91 (1H, m), 4.01 (2H, q, J = 7.0 Hz), 4.12 (1H, d, J = 14.5 Hz), 4.20-4.30 (4H, m), 5.10 (1H, t, J = 8.0 Hz), 6.33 (1H, d, J = 9.4 Hz), 7.00 (1H, s), 7.22-7.30 (3H, m), 7.35-7.42 (2H, m), 7.57 (1H, s). MS (ESI/APCI) m/z: 600 [M + H]⁺ |

TABLE 55-continued

| Example No. | structural formula | physicochemical data |
|---|---|---|
| 78 (78i) = 78 | 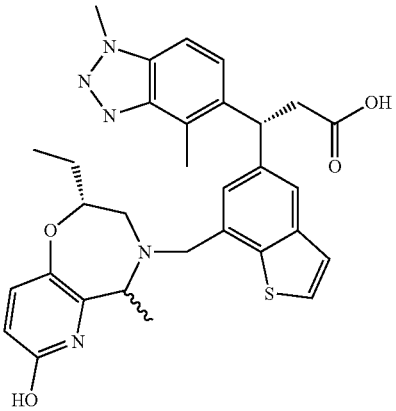<br>optically active isomer | $^1$H-NMR (CDCl$_3$) δ: 0.89 (3H, d, 6.7 Hz), 1.12 (3H, t, J = 7.4 Hz), 1.48-1.72 (2H, m), 2.57 (3H, s), 2.91 (1H, t, J = 11.7 Hz), 3.16 (1H, d, J = 9.4 Hz), 3.37 (2H, br s), 3.76-3.86 (2H, m), 3.95 (1H, d, J = 14.1 Hz), 4.31 (3H, s), 4.53 (1H, br s), 4.88 (1H, d, J = 12.1 Hz), 6.57 (1H, d, J = 9.8 Hz), 7.07 (2H, d, J = 4.7 Hz), 7.13 (1H, br s), 7.37 (1H, d, J = 5.5 Hz), 7.42-7.54 (2H, m), 7.57 (1H, br s).<br>MS (ESI/APCI) m/z: 572 [M + H]$^+$ |
| 79 (79a) | 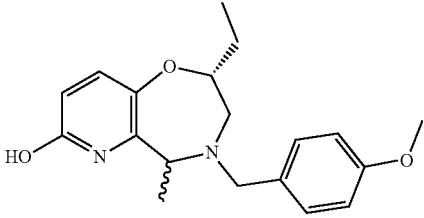<br>optically active isomer | $^1$H-NMR (CDCl$_3$) δ: 1.01 (3H, t, J = 7.4 Hz), 1.29-1.47 (1H, m), 1.51-1.63 (4H, m), 2.70 (1H, d, J = 15.3 Hz), 3.23 (1H, dd, J = 15.1, 10.0 Hz), 3.69 (2H, d, J = 3.1 Hz), 3.72-3.81 (4H, m), 3.88 (1H, d, J = 6.7 Hz), 6.33 (1H, d, J = 9.4 Hz), 6.82 (2H, d, J = 8.6 Hz), 7.19 (2H, d, J = 8.6 Hz), 7.28 (1H, d, J = 9.8 Hz).<br>MS (ESI/APCI) m/z: 329 [M + H]$^+$ |
| 79 (79b) | 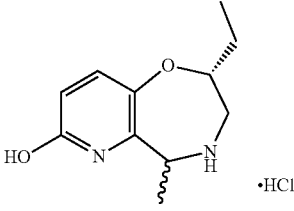<br>optically active isomer | $^1$H-NMR (CD$_3$OD) δ 1.14 (3H, t, J = 7.4 Hz), 1.65-1.86 (5H, m), 3.43-3.68 (2H, m), 3.82-3.93 (1H, m), 4.62 (1H, dd, J = 14.3, 7.2 Hz), 6.65 (1H, d, J = 9.0 Hz), 7.48 (1H, d, J = 9.0 Hz).<br>MS (ESI/APCI) m/z: 209 [M + H]$^+$ |

TABLE 56

| Example No. | structural formula | physicochemical data |
|---|---|---|
| 79 (79c) | | ¹H-NMR (CDCl₃) δ: 0.87 (3H, t, J = 7.2 Hz), 1.09 (3H, t, J = 7.2 Hz), 1.39-1.55 (2H, m), 1.57 (3H, d, J = 7.0 Hz), 2.58 (1H, d, J = 15.3 Hz), 2.86 (3H, s), 3.10 (1H, dd, J = 15.5, 8.4 Hz), 3.16-3.27 (2H, m), 3.69-3.77 (1H, m), 3.83-3.93 (1H, m), 3.94-4.05 (4H, m), 4.23 (3H, s), 5.10 (1H, t, J = 8.0 Hz), 6.32 (1H, d, J = 9.4 Hz), 7.05 (1H, s), 7.22-7.29 (2H, m), 7.31 (1H, d, J = 8.6 Hz), 7.40 (2H, t, J = 7.0 Hz), 7.58 (1H, s). MS (ESI/APCI) m/z: 600 [M + H]⁺ |
| | optically active isomer | |
| 79 (79d) = 79 | | ¹H-NMR (CDCl₃) δ: 1.15 (3H, t, J = 7.4 Hz), 1.45 (3H, d, J = 7.0 Hz), 1.51-1.64 (1H, m), 1.64-1.78 (1H, m), 2.57 (3H, s), 2.85 (1H, t, J = 11.3 Hz), 3.12 (1H, d, J = 14.9 Hz), 3.17 (1H, d, J = 10.2 Hz), 3.25 (1H, q, J = 6.9 Hz), 3.69 (1H, d, J = 10.6 Hz), 3.73 (1H, d, J = 10.6 Hz), 3.82-3.88 (1H, m), 3.90 (1H, d, J = 12.9 Hz), 4.05 (1H, d, J = 12.9 Hz), 4.33 (3H, s), 4.80 (1H, dd, J = 12.5, 2.3 Hz), 6.54 (1H, d, J = 9.4 Hz), 7.09 (2H, d, J = 5.5 Hz), 7.16 (1H, s), 7.36 (1H, d, J = 5.5 Hz), 7.49 (2H, t, J = 9.4 Hz), 7.63 (1H, d, J = 8.6 Hz). MS (ESI/APCI) m/z: 572 [M + H]⁺ |
| | optically active isomer | |
| 80 (80a) | | MS (ESI/APCI) m/z: 231 [M + H]⁺ |
| 80 (80b) | | ¹H-NMR (CDCl₃) δ: 1.08-1.13 (3H, m), 1.40 (3H, d, J = 6.8 Hz), 2.16-2.36 (1H, m), 2.47-2.66 (1H, m), 3.58-3.86 (1H, m), 4.07-4.24 (1H, m), 7.18-7.23 (1H, m), 7.32-7.38 (1H, m). MS (ESI/APCI) m/z: 233 [M + H]⁺ |
| 80 (80c) | | MS (ESI/APCI) m/z: 213 [M + H]⁺ |

TABLE 56-continued

| Example No. | structural formula | physicochemical data |
|---|---|---|
| 80 (80d) | | ¹H-NMR (CDCl₃) δ: 1.27 (3H, d, J = 6.4 Hz), 1.41 (9H, br s), 1.62 (3H, d, J = 7.2 Hz), 3.45-3.65 (1H, m), 3.89-4.04 (1H, m), 4.25-4.40 (1H, m), 5.32-5.68 (1H, m), 7.04-7.13 (1H, m), 7.19 (1H, br s). |

TABLE 57

| Example No. | structural formula | physicochemical data |
|---|---|---|
| 80 (80e) | | ¹H-NMR (CDCl₃) δ: 1.13-1.26 (3H, m), 1.37-1.49 (9H, m), 1.63 (3H, d, J = 7.2 Hz), 3.47-3.52 (1H, m), 3.91-4.17 (1H, m), 4.20-4.38 (1H, m), 5.27-5.24 (1H, m), 6.28-6.41 (1H, m), 7.10-7.22 (1H, m).<br>MS (ESI/APCI) m/z: 295 [M + H]⁺ |
| 80 (80f) | | ¹H-NMR (CDCl₃) δ: 1.43 (3H, d, J = 6.4 Hz), 1.79 (3H, d, J = 7.2 Hz), 3.42 (1H, dd, J = 13.6, 10.8 Hz), 3.58-3.68 (1H, m), 4.22-4.39 (1H, m), 4.72-4.81 (1H, m), 6.76-6.87 (1H, m), 7.57-7.69 (1H, m).<br>MS (ESI/APCI) m/z: 195 [M + H]⁺ |
| 80 (80g) | | MS (ESI/APCI) m/z: 586 [M + H]⁺ |

TABLE 57-continued

| Example No. | structural formula | physicochemical data |
|---|---|---|
| 80 (80h) = 80 | | ¹H-NMR (DMSO-D₆) δ: 1.07 (3H, d, J = 6.1 Hz), 1.50 (3H, d, J = 6.7 Hz), 2.68 (1H, dd, J = 14.1, 9.8 Hz), 2.77 (3H, s), 2.85-2.92 (1H, m), 3.09 (1H, dd, J = 15.6, 8.3 Hz), 3.16 (1H, dd, J = 15.9, 7.4 Hz), 3.73 (1H, d, J = 14.1 Hz), 3.99 (1H, d, J = 14.1 Hz), 4.05-4.13 (1H, m), 4.16-4.22 (1H, m), 4.23 (3H, s), 4.93 (1H, t, J = 7.7 Hz), 6.27 (1H, d, J = 9.2 Hz), 7.21 (1H, s), 7.24 (1H, d, J = 9.2 Hz), 7.36 (1H, d, J = 5.5 Hz), 7.51 (1H, d, J = 8.6 Hz), 7.56 (1H, d, J = 8.6 Hz), 7.67 (1H, d, J = 5.5 Hz), 7.71 (1H, s), 11.41 (1H, br s). MS (ESI/APCI) m/z: 558 [M + H]⁺ |
| 81 (81a) | | ¹H-NMR (CDCl₃) δ: 1.12 (3H, t, J = 7.0 Hz), 2.70 (1H, t, J = 6.1 Hz), 2.83 (3H, s), 3.14-3.29 (2H, m), 4.03 (2H, q, J = 7.1 Hz), 4.28 (3H, s), 4.90 (2H, d, J = 5.5 Hz), 5.07 (1H, t, J = 7.6 Hz), 7.22 (1H, s), 7.30 (1H, d, J = 5.5 Hz), 7.45 (1H, d, J = 5.5 Hz), 7.60 (1H, s), 8.56 (1H, s). MS (APCI) m/z: 411 [M + H]⁺ |
| 81 (81b) | | ¹H-NMR (CDCl₃) δ: 1.16 (3H, t, J = 7.0 Hz), 2.97 (3H, s), 3.22 (1H, dd, J = 16.0, 9.0 Hz), 3.29 (1H, dd, J = 16.0, 7.0 Hz), 4.07 (2H, ddd, J = 14.2, 7.1, 2.4 Hz), 4.47 (3H, d, J = 13.7 Hz), 4.77 (2H, d, J = 12.5 Hz), 5.10 (1H, dd, J = 14.3, 6.8 Hz), 5.30 (1H, s), 7.20 (1H, d, J = 1.6 Hz), 7.32 (1H, d, J = 5.5 Hz), 7.52 (1H, d, J = 5.5 Hz), 7.63 (1H, d, J = 1.6 Hz), 8.61 (1H, s). |

TABLE 58

| Example No. | structural formula | physicochemical data |
|---|---|---|
| 81 (81c) | 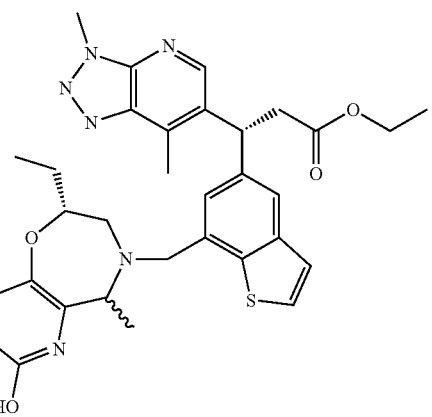 optically active isomer | ¹H-NMR (CDCl₃) δ: 0.88 (3H, t, J = 7.2 Hz), 1.11 (3H, t, J = 7.0 Hz), 1.23-1.34 (1H, m), 1.41-1.52 (1H, m), 1.66 (4H, d, J = 6.7 Hz), 2.70 (1H, t, J = 13.3 Hz), 2.83 (3H, s), 2.95 (1H, dd, J = 14.5, 3.1 Hz), 3.18 (1H, dd, J = 15.7, 8.6 Hz), 3.26 (1H, dd, J = 15.7, 7.4 Hz), 3.78-3.92 (2H, m), 4.03 (2H, q, J = 7.2 Hz), 4.13 (1H, d, J = 14.1 Hz), 4.27 (1H, dd, J = 17.0, 9.6 Hz), 4.31 (3H, s), 5.05 (1H, t, J = 8.0 Hz), 6.34 (1H, d, J = 9.4 Hz), 7.01 (1H, s), 7.23-7.28 (2H, m), 7.43 (1H, d, J = 5.5 Hz), 7.56 (1H, s), 8.59 (1H, s).<br>MS (ESI/APCI) m/z: 601 [M + H]⁺ |
| 81 (81d) = 81 | 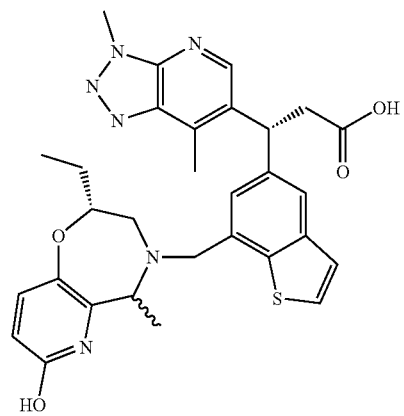 optically active isomer | ¹H-NMR (CDCl₃) δ: 0.99 (3H, br s), 1.09 (3H, t, J = 7.2 Hz), 1.46-1.57 (1H, m), 1.59-1.72 (1H, m), 2.61 (3H, s), 3.04 (1H, t, J = 11.9 Hz), 3.17-3.40 (3H, m), 3.78-3.87 (2H, m), 3.95 (1H, d, J = 14.1 Hz), 4.37 (3H, s), 4.47 (1H, br s), 4.88 (1H, d, J = 9.0 Hz), 6.54 (1H, br s), 7.08 (1H, s), 7.11 (1H, d, J = 5.5 Hz), 7.18 (1H, s), 7.40 (1H, d, J = 5.1 Hz), 7.49 (1H, d, J = 9.4 Hz), 8.71 (1H, s).<br>MS (ESI/APCI) m/z: 573 [M + H]⁺ |
| 82 (82a) | 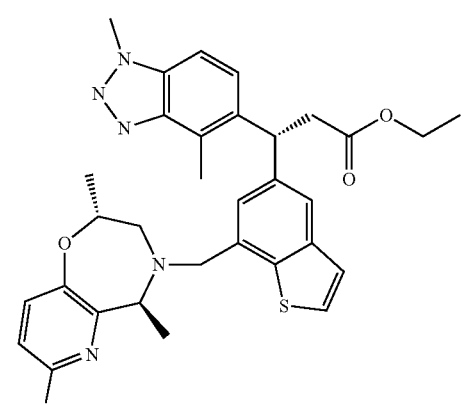 | ¹H-NMR (CDCl₃) δ: 1.06-1.12 (6H, m), 1.65 (4H, d, J = 7.0 Hz), 2.71 (1H, dd, J = 14.5, 10.2 Hz), 2.86 (3H, s), 2.94 (1H, dd, J = 14.7, 2.9 Hz), 3.09 (1H, dd, J = 15.3, 8.6 Hz), 3.20 (1H, dd, J = 15.5, 7.6 Hz), 3.79 (1H, d, J = 14.1 Hz), 4.01 (2H, q, J = 7.0 Hz), 4.07-4.20 (2H, m), 4.23 (3H, s), 4.26 (1H, q, J = 8.1 Hz), 5.09 (1H, t, J = 8.0 Hz), 6.33 (1H, d, J = 9.4 Hz), 7.02 (1H, s), 7.21-7.31 (3H, m), 7.35-7.42 (2H, m), 7.57 (1H, s).<br>MS (ESI/APCI) m/z: 586 [M + H]⁺ |

TABLE 58-continued

| Example No. | structural formula | physicochemical data |
|---|---|---|
| 82 (82b) = 82 | | ¹H-NMR (CDCl₃) δ: 1.00 (3H, br s), 1.31 (3H, d, J = 6.3 Hz), 2.60 (3H, s), 2.95 (1H, t, J = 11.9 Hz), 3.15 (1H, d, J = 11.7 Hz), 3.21-3.30 (1H, m), 3.36 (1H, d, J = 14.9 Hz), 3.84 (1H, d, J = 14.1 Hz), 3.94 (1H, d, J = 13.7 Hz), 4.08-4.18 (1H, m), 4.30 (3H, s), 4.47 (1H, br s), 4.90 (1H, d, J = 8.6 Hz), 6.54 (1H, d, J = 9.4 Hz), 7.04-7.11 (2H, m), 7.19 (1H, s), 7.37 (1H, d, J = 5.5 Hz), 7.44 (1H, d, J = 8.6 Hz), 7.48 (1H, d, J = 9.4 Hz), 7.56 (1H, d, J = 8.2 Hz).<br>MS (ESI/APCI) m/z: 558 [M + H]⁺ |
| 83 (83a) | | ¹H-NMR (CDCl₃) δ: 0.28-0.39 (2H, m), 0.49-0.58 (2H, m), 0.89-0.99 (1H, m), 2.16-2.25 (1H, m), 3.25-3.33 (1H, m), 3.90-3.93 (2H, m), 7.70-7.75 (2H, m), 7.83-7.89 (2H, m). |
| 83 (83b) | | ¹H-NMR (CDCl₃) δ: −0.13 (3H, s), 0.04 (3H, s), 0.16-0.24 (1H, m), 0.26-0.34 (1H, m), 0.40-0.53 (2H, m), 0.79 (9H, s), 0.85-0.98 (1H, m), 3.46 (1H, td, J = 7.6, 5.6 Hz), 3.74 (1H, dd, J = 13.7, 5.6 Hz), 3.85 (1H, dd, J = 13.7, 7.6 Hz), 7.67-7.75 (2H, m), 7.80-7.87 (2H, m). |

TABLE 59

| Example No. | structural formula | physicochemical data |
|---|---|---|
| 83 (83c) | | ¹H-NMR (CDCl₃) δ: 0.05 (3H, s), 0.09 (3H, s), 0.12-0.22 (1H, m), 0.25-0.35 (1H, m), 0.41-0.54 (2H, m), 0.80-0.94 (10H, m), 2.69-2.81 (2H, m), 2.96-3.04 (1H, m). |
| 83 (83d) | | ¹H-NMR (CDCl₃) δ: 0.03 (3H, s), 0.08 (3H, s), 0.13-0.20 (1H, m), 0.24-0.31 (1H, m), 0.41-0.53 (2H, m), 0.85-0.95 (10H, m), 2.71 (2H, d, J = 5.6 Hz), 3.15 (1H, dt, J = 7.8, 5.6 Hz), 3.69-3.78 (2H, m), 3.80 (3H, s), 6.83-6.88 (2H, m), 7.20-7.24 (2H, m). |

TABLE 59-continued

| Example No. | structural formula | physicochemical data |
|---|---|---|
| 83 (83e) | | $^1$H-NMR (CDCl$_3$) δ: 1.78 (3H, d, J = 6.6 Hz), 3.02 (3H, s), 6.01 (1H, q, J = 6.6 Hz), 7.34 (1H, t, J = 8.6 Hz), 7.49 (1H, dd, J = 8.6, 3.7 Hz). |
| 83 (83f) | | $^1$H-NMR (CDCl$_3$) δ: −0.06-0.30 (10H, m), 0.75-0.91 (10H, m), 1.39-1.44 (3H, m), 2.53-2.60 (1H, m), 2.66-2.76 (1H, m), 3.11-3.17 (0.5H, m), 3.24-3.30 (0.5H, m), 3.55-3.60 (0.5H, m), 3.64-3.74 (1H, m), 3.75-3.81 (3.5H, m), 4.28-4.38 (1H, m), 6.80-6.85 (2H, m), 7.15-7.21 (1H, m), 7.24-7.28 (2H, m), 7.29-7.33 (1H, m). |
| 83 (83g) | | $^1$H-NMR (CDCl$_3$) δ: 0.05-0.15 (1H, m), 0.26-0.34 (1H, m), 0.36-0.52 (2H, m), 0.57-0.73 (1H, m), 1.43 (1.5H, d, J = 6.8 Hz), 1.49 (1.5H, d, J = 6.8 Hz), 2.57-2.66 (1H, m), 2.68-2.83 (1.5H, m), 2.88-2.95 (0.5H, m), 3.31-3.48 (1.5H, m), 3.56 (0.5H, d, J = 13.4 Hz), 3.70-3.82 (4H, m), 4.28-4.40 (1H, m), 6.79-6.85 (2H, m), 7.12-7.24 (3H, m), 7.32-7.37 (1H, m). |
| 83 (83h) optically active isomer | | $^1$H-NMR (CDCl$_3$) δ: 0.12-0.20 (1H, m), 0.40-0.56 (2H, m), 0.59-0.68 (1H, m), 0.92-1.03 (1H, m), 1.52 (3H, d, J = 7.1 Hz), 2.91 (1H, d, J = 14.9 Hz), 3.23 (1H, t, J = 9.3 Hz), 3.43 (1H, dd, J = 14.9, 9.3 Hz), 3.54 (1H, d, J = 13.4 Hz), 3.68 (1H, d, J = 13.4 Hz), 3.80 (3H, s), 4.17 (1H, q, J = 7.1 Hz), 6.82-6.87 (2H, m), 7.14-7.21 (3H, m), 7.24-7.28 (1H, m). |
| 83 (83i) optically active isomer | | $^1$H-NMR (CDCl$_3$) δ: 0.11-0.19 (1H, m), 0.39-0.54 (2H, m), 0.55-0.63 (1H, m), 0.93-1.04 (1H, m), 1.57 (3H, d, J = 7.1 Hz), 3.03 (1H, dd, J = 14.4, 9.0 Hz), 3.12 (1H, dd, J = 14.4, 2.7 Hz), 3.20 (1H, d, J = 13.7 Hz), 3.28 (1H, td, J = 9.0, 2.7 Hz), 3.75 (1H, d, J = 13.7 Hz), 3.79 (3H, s), 4.40 (1H, q, J = 7.1 Hz), 6.80-6.85 (2H, m), 7.13-7.20 (3H, m), 7.24 (1H, d, J = 7.8 Hz). |

TABLE 60

| Example No. | structural formula | physicochemical data |
|---|---|---|
| 83 (83j) | 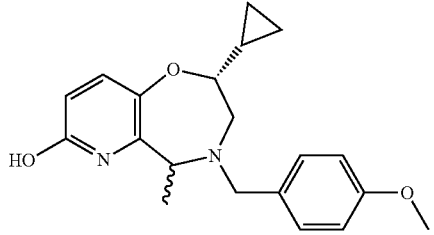<br>optically active isomer | ¹H-NMR (CDCl₃) δ: 0.11-0.19 (1H, m), 0.39-0.53 (2H, m), 0.57-0.66 (1H, m), 0.84-0.95 (1H, m), 1.51-1.70 (3H, m), 2.87 (1H, d, J = 15.1 Hz), 3.16-3.24 (1H, m), 3.38 (1H, dd, J = 15.1, 10.3 Hz), 3.60 (1H, d, J = 13.2 Hz), 3.69 (1H, d, J = 13.2 Hz), 3.77-3.90 (4H, m), 6.31 (1H, d, J = 9.5 Hz), 6.79-6.86 (2H, m), 7.14-7.21 (2H, m), 7.24-7.31 (1H, m). |
| 83 (83l) | 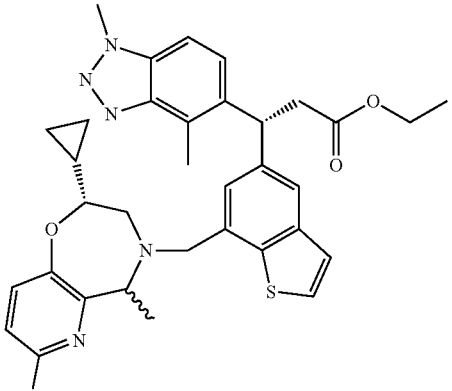<br>optically active isomer | ¹H-NMR (CDCl₃) δ: −0.14−−0.06 (1H, m), 0.28-0.40 (2H, m), 0.50-0.59 (1H, m), 0.75-0.87 (1H, m), 1.09 (3H, t, J = 7.1 Hz), 1.54-1.63 (3H, m), 2.79 (1H, d, J = 14.9 Hz), 2.86 (3H, s), 3.06-3.26 (3H, m), 3.41 (1H, dd, J = 14.9, 9.8 Hz), 3.75-3.84 (1H, m), 3.85-4.07 (4H, m), 4.23 (3H, s), 5.09 (1H, t, J = 8.0 Hz), 6.31 (1H, d, J = 9.5 Hz), 7.03 (1H, s), 7.23-7.28 (2H, m), 7.30-7.35 (1H, m), 7.37-7.43 (2H, m), 7.58 (1H, s). |
| 83 (83m) = 83 | 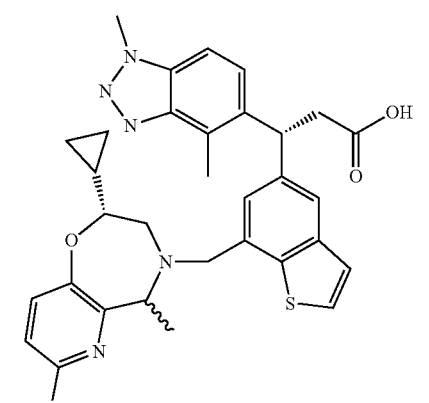<br>optically active isomer | ¹H-NMR (DMSO-D₆) δ: −0.18−−0.09 (1H, m), 0.09-0.20 (1H, m), 0.26-0.36 (1H, m), 0.37-0.46 (1H, m), 0.68-0.81 (1H, m), 1.46 (3H, d, J = 7.1 Hz), 2.57 (1H, d, J = 13.4 Hz), 2.78 (3H, s), 3.05-3.25 (3H, m), 3.27-3.45 (1H, m), 3.78 (1H, d, J = 13.9 Hz), 3.85-3.95 (2H, m), 4.22 (3H, s), 4.94 (1H, t, J = 7.3 Hz), 6.19 (1H, d, J = 9.3 Hz), 7.19 (1H, s), 7.24 (1H, d, J = 9.3 Hz), 7.38 (1H, d, J = 5.6 Hz), 7.51 (1H, d, J = 8.6 Hz), 7.56 (1H, d, J = 8.6 Hz), 7.67 (1H, d, J = 5.6 Hz), 7.73 (1H, s), 11.50-11.80 (1H, br s).<br>MS (ESI) m/z: 582 [M − H]⁻, 584 [M + H]⁺, 606 [M + Na]⁺ |
| 84 (84a) | 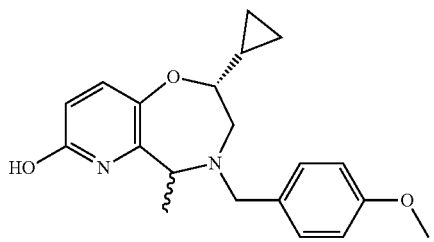<br>optically active isomer | ¹H-NMR (CDCl₃) δ: 0.10-0.18 (1H, m), 0.37-0.62 (3H, m), 0.90-1.02 (1H, m), 1.48-1.65 (3H, m), 2.94 (1H, dd, J = 14.6, 9.2 Hz), 3.12 (1H, dd, J = 14.6, 2.9 Hz), 3.25 (1H, td, J = 9.2, 2.9 Hz), 3.43 (1H, d, J = 13.2 Hz), 3.75 (1H, d, J = 13.2 Hz), 3.79 (3H, s), 4.22 (1H, q, J = 7.1 Hz), 6.34 (1H, d, J = 9.5 Hz), 6.79-6.86 (2H, m), 7.14-7.20 (2H, m), 7.23-7.30 (1H, m). |

TABLE 60-continued

| Example No. | structural formula | physicochemical data |
|---|---|---|
| 84 (84c) | optically active isomer | ¹H-NMR (CDCl₃) δ: −0.13−−0.05 (1H, m), 0.27-0.38 (2H, m), 0.44-0.54 (1H, m), 0.77-0.89 (1H, m), 1.09 (3H, t, J = 7.1 Hz), 1.50-1.65 (3H, m), 2.86 (3H, s), 2.91-3.00 (1H, m), 3.04-3.12 (2H, m), 3.15-3.24 (2H, m), 3.66 (1H, d, J = 14.2 Hz), 3.98-4.05 (3H, m), 4.22-4.09 (4H, m), 5.09 (1H, t, J = 8.1 Hz), 6.35 (1H, d, J = 9.5 Hz), 6.98 (1H, s), 7.25-7.31 (3H, m), 7.37 (1H, d, J = 8.8 Hz), 7.41 (1H, d, J = 5.4 Hz), 7.58 (1H, s). |
| 84 (84d) = 84 | optically active isomer | ¹H-NMR (DMSO-D₆) δ: −0.10−−0.03 (1H, m), 0.12-0.22 (1H, m), 0.25-0.33 (1H, m), 0.33-0.43 (1H, m), 0.74-0.88 (1H, m), 1.52 (3H, d, J = 6.8 Hz), 2.76 (3H, s), 2.81-2.95 (2H, m), 3.03-3.18 (2H, m), 3.23-3.42 (1H, m), 3.58 (1H, d, J = 13.9 Hz), 3.95 (1H, d, J = 13.9 Hz), 4.13-4.24 (4H, m), 4.92 (1H, t, J = 7.3 Hz), 6.27 (1H, d, J = 9.0 Hz), 7.17 (1H, s), 7.24 (1H, d, J = 9.0 Hz), 7.36 (1H, d, J = 5.4 Hz), 7.50 (1H, d, J = 8.6 Hz), 7.55 (1H, d, J = 8.6 Hz), 7.66 (1H, d, J = 5.4 Hz), 7.71 (1H, s).<br>MS (ESI) m/z: 582 [M − H]⁻, 584 [M + H]⁺, 606 [M + Na]⁺ |

TABLE 61

| Example No. | structural formula | physicochemical data |
|---|---|---|
| 85 (85a) | optically active isomer | ¹H-NMR (CDCl₃) δ: −0.10−−0.02 (1H, m), 0.30-0.40 (2H, m), 0.47-0.57 (1H, m), 0.79-0.91 (1H, m), 1.12 (3H, t, J = 7.1 Hz), 1.48-1.65 (3H, m), 2.84 (3H, s), 2.92-3.02 (1H, m), 3.05-3.12 (1H, m), 3.14-3.30 (3H, m), 3.67 (1H, d, J = 14.2 Hz), 3.99-4.08 (3H, m), 4.26-4.33 (4H, m), 5.04 (1H, t, J = 8.1 Hz), 6.37 (1H, d, J = 9.5 Hz), 6.96-7.01 (1H, m), 7.24-7.31 (2H, m), 7.43 (1H, d, J = 5.6 Hz), 7.56-7.60 (1H, m), 8.58 (1H, s). |

TABLE 61-continued

| Example No. | structural formula | physicochemical data |
|---|---|---|
| 85 (85b) = 85 | 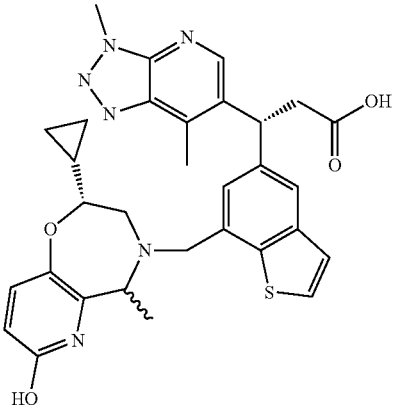<br>optically active isomer | ¹H-NMR (DMSO-D₆) δ: −0.16−−0.08 (1H, m), 0.09-0.19 (1H, m), 0.24-0.33 (1H, m), 0.34-0.43 (1H, m), 0.74-0.89 (1H, m), 1.53 (3H, d, J = 7.1 Hz), 2.79 (3H, s), 2.84-2.92 (2H, m), 3.20-3.45 (3H, m), 3.58 (1H, d, J = 13.9 Hz), 3.96 (1H, d, J = 13.9 Hz), 4.16-4.27 (4H, m), 4.91 (1H, t, J = 7.8 Hz), 6.28 (1H, d, J = 8.8 Hz), 7.21-7.27 (2H, m), 7.37 (1H, d, J = 5.6 Hz), 7.68 (1H, d, J = 5.6 Hz), 7.76-7.81 (1H, m), 8.73 (1H, s).<br>MS (ESI) m/z: 583 [M − H]⁻, 607 [M + Na]⁺ |
| 86 (86a) | 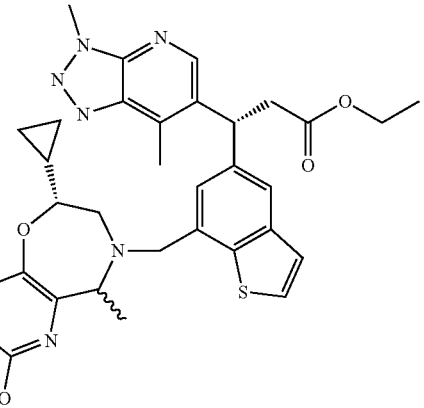<br>optically active isomer | ¹H-NMR (CDCl₃) δ: 0.02-0.10 (1H, m), 0.39-0.50 (2H, m), 0.57-0.66 (1H, m), 0.86-0.98 (1H, m), 1.11 (3H, t, J = 7.1 Hz), 1.49 (3H, d, J = 7.0 Hz), 2.87-2.98 (4H, m), 3.12-3.30 (3H, m), 3.50-3.62 (1H, m), 3.63-3.74 (1H, m), 3.90-4.08 (4H, m), 4.30 (3H, s), 5.06 (1H, t, J = 7.8 Hz), 6.38 (1H, d, J = 9.3 Hz), 7.12-7.17 (1H, m), 7.20-7.30 (2H, m), 7.43 (1H, d, J = 5.4 Hz), 7.57-7.62 (1H, m), 8.17 (1H, s). |
| 86 (86b) = 86 | 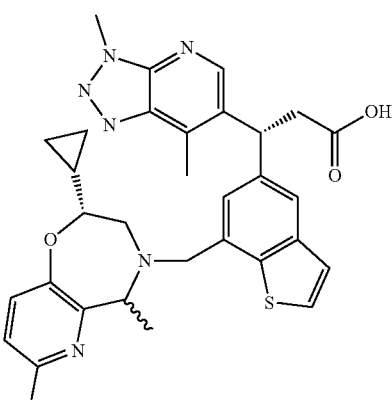<br>optically active isomer | ¹H-NMR (DMSO-D₆) δ: −0.26−−0.16 (1H, m), 0.04-0.14 (1H, m), 0.25-0.33 (1H, m), 0.36-0.45 (1H, m), 0.69-0.81 (1H, m), 1.46 (3H, d, J = 7.1 Hz), 2.55 (1H, d, J = 13.6 Hz), 2.81 (3H, s), 3.15-3.45 (5H, m), 3.79 (1H, d, J = 14.2 Hz), 3.85-3.95 (2H, m), 4.22 (3H, s), 4.93 (1H, t, J = 7.8 Hz), 6.18 (1H, d, J = 9.3 Hz), 7.21-7.26 (2H, m), 7.39 (1H, d, J = 5.6 Hz), 7.69 (1H, d, J = 5.6 Hz), 7.79-7.83 (1H, m), 8.72 (1H, s), 11.70 (1H br s).<br>MS (ESI) m/z: 583 [M − H]⁻, 585 [M + H]⁺, 607 [M + Na]⁺ |

TABLE 61-continued

| Example No. | structural formula | physicochemical data |
|---|---|---|
| 87 (87a) | | ¹H-NMR (CDCl₃) δ: 0.34-0.40 (2H, m), 0.75-0.80 (2H, m), 2.59 (2H, s), 3.43 (1H, br s), 3.63 (4H, s), 3.80 (6H, s), 6.84-6.89 (4H, m), 7.19-7.25 (4H, m). |
| 87 (87b) | | ¹H-NMR (CDCl₃) δ: 0.38-0.46 (2H, m), 0.75-0.83 (2H, m), 2.37-2.64 (2H, br m), 2.72 (2H, s), 3.78-3.84 (5H, m), 6.83-6.92 (2H, m), 7.20-7.30 (2H, m). |

TABLE 62

| Example No. | structural formula | physicochemical data |
|---|---|---|
| 87 (87c) | | ¹H-NMR (CDCl₃) δ: 0.26-0.35 (1H, m), 0.37-0.46 (1H, m), 0.68-0.83 (2H, m), 1.45 (3H, d, J = 6.8 Hz), 2.65 (1H, d, J = 13.2 Hz), 2.81 (1H, d, J = 13.2 Hz), 3.61 (1H, br s), 3.67-3.76 (2H, m), 3.79 (3H, s), 4.53-4.61 (1H, m), 6.80-6.86 (2H, m), 7.13-7.19 (2H, m), 7.23 (1H, t, J = 8.8 Hz), 7.34 (1H, dd, J = 8.8, 3.6 Hz). |
| 87 (87d) | | ¹H-NMR (CDCl₃) δ: 0.38-0.54 (2H, m), 0.78-0.95 (2H, m), 1.61 (3H, d, J = 7.3 Hz), 2.61 (1H, d, J = 15.1 Hz), 3.54-3.67 (2H, m), 3.71 (1H, d, J = 13.7 Hz), 3.79 (3H, s), 4.32 (1H, q, J = 7.3 Hz), 6.79-6.87 (2H, m), 7.00 (1H, d, J = 8.3 Hz), 7.15-7.22 (2H, m), 7.26 (1H, d, J = 8.3 Hz). |
| 87 (87f) | or enantiomer | ¹H-NMR (CDCl₃) δ: 0.34-0.40 (1H, m), 0.52-0.57 (1H, m), 0.83-0.93 (2H, m), 1.65 (3H, d, J = 7.3 Hz), 2.34 (1H, d, J = 15.3 Hz), 3.70-3.83 (5H, m), 3.89 (1H, d, J = 15.3 Hz), 3.99 (1H, q, J = 6.9 Hz), 6.28 (1H, d, J = 9.2 Hz), 6.81 (2H, d, J = 8.5 Hz), 7.09 (1H, d, J = 9.2 Hz), 7.20 (2H, d, J = 8.5 Hz), 12.09 (1H, br s). MS (APCI) m/z: 327 [M + H]⁺ |

TABLE 62-continued

| Example No. | structural formula | physicochemical data |
|---|---|---|
| 87 (87g) | or enantiomer | ¹H-NMR (CDCl₃) δ: 0.33-0.41 (1H, m), 0.50-0.59 (1H, m), 0.83-0.94 (2H, m), 1.65 (3H, d, J = 6.7 Hz), 2.34 (1H, d, J = 15.3 Hz), 3.71-3.83 (5H, m), 3.89 (1H, d, J = 14.6 Hz), 3.99 (1H, q, J = 7.1 Hz), 6.28 (1H, d, J = 9.2 Hz), 6.81 (2H, d, J = 8.5 Hz), 7.09 (1H, d, J = 9.8 Hz), 7.20 (2H, d, J = 8.5 Hz), 12.16 (1H, br s).<br>MS (APCI) m/z: 327 [M + H]⁺ |
| 87 (87h) |  | ¹H-NMR (CDCl₃) δ: 0.49 (1H, ddd, J = 11.2, 5.7, 4.4 Hz), 0.61-0.67 (1H, m), 0.79 (1H, ddd, J = 14.4, 8.3, 2.8 Hz), 1.00-1.06 (1H, m), 1.59 (3H, d, J = 6.7 Hz), 2.72 (1H, d, J = 14.7 Hz), 3.56 (1H, dd, J = 15.0, 1.5 Hz), 4.22 (1H, q, J = 7.2 Hz), 6.32 (1H, d, J = 9.8 Hz), 7.07 (1H, d, J = 9.2 Hz).<br>MS (ESI/APCI) m/z: 207 [M + H]⁺ |
| 87 (87i) | optically active isomer | ¹H-NMR (CDCl₃) δ: 0.26 (1H, dd, J = 10.4, 4.9 Hz), 0.45 (1H, dd, J = 10.1, 5.2 Hz), 0.83 (2H, t, J = 6.1 Hz), 1.09 (3H, t, J = 7.1 Hz), 1.68 (3H, d, J = 7.4 Hz), 2.32 (1H, d, J = 15.3 Hz), 2.84 (3H, s), 3.10 (1H, dd, J = 14.7, 8.0 Hz), 3.28 (1H, dd, J = 15.0, 8.3 Hz), 3.84 (1H, d, J = 15.3 Hz), 3.93-4.06 (5H, m), 4.23 (3H, s), 5.05 (1H, t, J = 8.3 Hz), 6.30 (1H, d, J = 9.8 Hz), 6.98 (1H, s), 7.07 (1H, d, J = 9.8 Hz), 7.25 (1H, d, J = 5.5 Hz), 7.32 (1H, d, J = 8.6 Hz), 7.43 (2H, dd, J = 8.9, 7.1 Hz), 7.60 (1H, s).<br>MS (ESI/APCI) m/z: 598 [M + H]⁺ |

TABLE 63

| Example No. | structural formula | physicochemical data |
|---|---|---|
| 87 (87j) = 87 | optically active isomer | ¹H-NMR (CDCl₃) δ: 0.61-0.66 (1H, m), 0.67-0.73 (1H, m), 0.90 (1H, dt, J = 15.5, 5.8 Hz), 0.98-1.04 (1H, m), 1.32 (3H, s), 2.74 (3H, s), 3.03 (1H, dd, J = 15.3, 4.3 Hz), 3.20 (1H, t, J = 12.6 Hz), 3.68 (1H, s), 4.01 (2H, s), 4.23 (3H, s), 5.02 (1H, dd, J = 9.8, 4.3 Hz), 6.46 (1H, d, J = 9.2 Hz), 7.01 (1H, s), 7.16 (1H, d, J = 5.5 Hz), 7.21 (1H, d, J = 9.8 Hz), 7.27 (1H, d, J = 8.6 Hz), 7.38 (1H, d, J = 5.5 Hz), 7.41 (1H, s), 7.47 (1H, d, J = 8.0 Hz).<br>MS (ESI/APCI) m/z: 570 [M + H]⁺ |

TABLE 63-continued

| Example No. | structural formula | physicochemical data |
| --- | --- | --- |
| 88 (88a) | *or enantiomer* | ¹H-NMR (CDCl₃) δ: 0.52 (1H, dt, J = 11.7, 4.9 Hz), 0.66 (1H, dt, J = 11.7, 4.9 Hz), 0.77-0.83 (1H, m), 1.01-1.07 (1H, m), 1.59 (3H, d, J = 7.4 Hz), 2.73 (1H, d, J = 14.7 Hz), 3.59 (1H, d, J = 15.3 Hz), 4.26 (1H, q, J = 7.2 Hz), 6.33 (1H, d, J = 9.2 Hz), 7.07 (1H, d, J = 9.2 Hz). MS (ESI/APCI) m/z: 207 [M + H]⁺ |
| 88 (88b) | *optically active isomer* | ¹H-NMR (CDCl₃) δ: 0.26 (1H, t, J = 11.7 Hz), 0.38 (1H, t, J = 11.7 Hz), 0.81 (2H, s), 1.10 (3H, t, J = 7.1 Hz), 1.67 (3H, d , J = 7.4 Hz), 2.28 (1H, d, J = 15.3 Hz), 2.86 (3H, s), 3.10 (1H, dd, J = 15.3, 8.0 Hz), 3.22 (1H, dd, J = 15.3, 8.0 Hz), 3.81 (1H, d, J = 15.9 Hz), 3.97-4.06 (4H, m), 4.24 (3H, s), 5.10 (1H, t, J = 8.0 Hz), 6.31 (1H, d, J = 9.2 Hz), 7.03 (1H, s), 7.07 (1H, d, J = 9.8 Hz), 7.24 (1H, d, J = 5.5 Hz), 7.32 (1H, d, J = 8.6 Hz), 7.38 (1H, d, J = 9.2 Hz), 7.42 (1H, d, J = 5.5 Hz), 7.57 (1H, s). MS (ESI/APCI) m/z: 598 [M + H]⁺ |
| 88 (88c) = 88 | *optically active isomer* | ¹H-NMR (CDCl₃) δ: 0.56-0.62 (1H, m), 0.72-0.78 (1H, m), 0.95 (1H, dd, J = 11.0, 4.9 Hz), 1.00-1.05 (1H, m), 1.52 (3H, d, J = 6.7 Hz), 2.56 (4H, d, J = 15.9 Hz), 2.84 (1H, t, J = 11.3 Hz), 3.15 (1H, d, J = 9.8 Hz), 3.35 (1H, q, J = 7.0 Hz), 4.05 (2H, dd, J = 17.2, 12.9 Hz), 4.30 (3H, s), 4.48 (1H, d, J = 15.9 Hz), 4.82 (1H, d, J = 12.9 Hz), 6.49 (1H, d, J = 9.2 Hz), 7.07 (1H, d, J = 5.5 Hz), 7.10 (1H, s), 7.16 (1H, s), 7.25 (4H, d, J = 9.2 Hz), 7.34 (1H, d, J = 5.5 Hz), 7.47 (1H, d, J = 8.6 Hz), 7.62 (1H, d, J = 8.6 Hz). MS (ESI/APCI) m/z: 570 [M + H]⁺ |
| 89 (89a) |  | ¹H-NMR (CDCl₃) δ: −0.08 (9H, s), 0.48-0.68 (2H, m), 0.93 (3H, t, J = 7.3 Hz), 1.10-1.23 (1H, m), 1.28 (3H, s), 1.32 (3H, s), 1.42-1.55 (1H, m), 1.58-1.64 (3H, m), 1.89-2.09 (2H, m), 2.61-2.93 (6H, m), 2.75 (3H, s), 3.12 (1H, d, J = 13.4 Hz), 3.68 (1H, d, J = 13.4 Hz), 3.74-3.98 (3H, m), 4.24 (3H, s), 4.39-4.50 (1H, m), 4.77 (1H, s), 6.87 (1H, s), 6.93 (1H, s), 7.12 (1H, dd, J = 7.9, 4.9 Hz), 7.22-7.27 (1H, m), 7.31 (1H, dd, J = 7.9, 1.2 Hz), 7.66 (1H, d, J = 9.2 Hz), 8.27 (1H, dd, J = 4.9, 1.2 Hz). MS (ESI/APCI) m/z: 668 [M + H]⁺ |

TABLE 64
| Example No. | structural formula | physicochemical data |
|---|---|---|
| 89 (89b) = 89 | 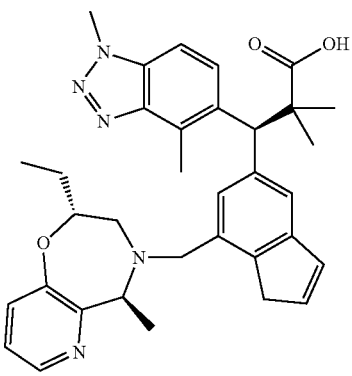 [SMILES: CC[C@@H]1CN(Cc2cc([C@@H](c3ccc4c(nnn4C)c3C)C(C)(C)C(=O)O)cc3c2CC=C3)[C@@H](C)c2ncccc2O1] | ¹H-NMR (DMSO-D₆) δ: 0.88 (3H, t, J = 6.8 Hz), 1.00-1.15 (1H, m), 1.18 (3H, s), 1.21 (3H, s), 1.32-1.45 (1H, m), 1.49 (3H, d, J = 6.8 Hz), 1.82-2.01 (2H, m), 2.62 (3H, s), 2.62-2.88 (6H, m), 3.09 (1H, d, J = 13.4 Hz), 3.58 (1H, d, J = 13.4 Hz), 3.80-3.88 (1H, m), 4.24 (3H, s), 4.33 (1H, q, J = 6.8 Hz), 4.72 (1H, s), 6.91 (1H, s), 6.98 (1H, s), 7.23 (1H, dd, J = 7.9, 4.9 Hz), 7.39 (1H, d, J = 7.9 Hz), 7.55 (1H, d, J = 8.5 Hz), 7.64 (1H, d, J = 8.5 Hz), 8.23 (1H, d, J = 4.9 Hz), 12.15 (1H, br s). MS (ESI/APCI) m/z: 568 [M + H]⁺ |
| 90 (90a) | 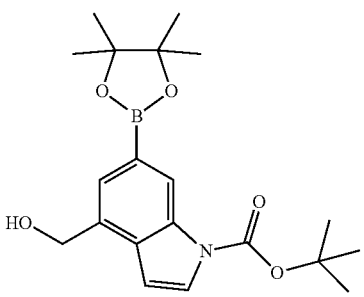 [SMILES: CC(C)(C)OC(=O)n1ccc2c(CO)cc(B3OC(C)(C)C(C)(C)O3)cc21] | MS (ESI/APCI) m/z: 356 [M + H − H₂O]⁺ |
| 90 (90b) | 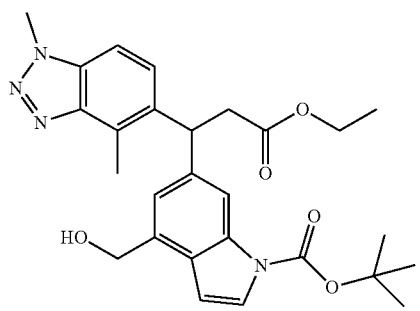 [SMILES: CCOC(=O)CC(c1cc(CO)c2ccn(C(=O)OC(C)(C)C)c2c1)c1ccc2c(nnn2C)c1C] | MS (ESI/APCI) m/z: 493 [M + H]⁺ |
| 90 (90c) | 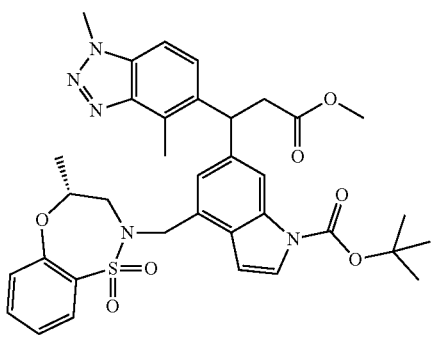 | MS (ESI/APCI) m/z: 688 [M + H]⁺ |

TABLE 64-continued

| Example No. | structural formula | physicochemical data |
|---|---|---|
| 90 (90d) | | MS (ESI/APCI) m/z: 588 [M + H]+ |
| 90 (90e) = 90 | | ¹H-NMR (CDCl₃) δ: 1.12 (1.5H, d, J = 6.7 Hz), 1.21 (1.5H, d, J = 6.3 Hz), 2.82 (3H, s), 2.89 (0.5H, dd, J = 15.3, 1.6 Hz), 2.96 (0.5H, dd, J = 15.1, 1.4 Hz), 3.05-3.13 (1H, m), 3.18-3.26 (1H, m), 3.64-3.71 (1H, m), 4.04 (1H, dd, J = 13.7, 9.0 Hz), 4.17-4.26 (4H, m), 4.85 (1H, t, J = 13.7 Hz), 5.07 (1H, t, J = 7.8 Hz), 6.75 (1H, s), 6.84 (1H, d, J = 5.9 Hz), 7.17-7.30 (4H, m), 7.36 (1H, t, J = 7.6 Hz), 7.52-7.54 (1H, m), 7.91-7.95 (1H, m), 8.43 (1H, d, J = 11.3 Hz). MS (ESI/APCI) m/z: 560 [M + H]+ |

TABLE 65

| Example No. | structural formula | physicochemical data |
|---|---|---|
| 91 (91a) | | ¹H-NMR (CDCl₃) δ: 3.21 (2H, t, J = 8.9 Hz), 4.62 (4H, dd, J = 9.5, 8.3 Hz), 7.24 (2H, s). MS (ESI/APCI) m/z: 211 [M + H − H₂O]+ |
| 91 (91b) | | ¹H-NMR (CDCl₃) δ: 1.33 (12H, s), 2.00 (1H, s), 3.21 (2H, t, J = 8.6 Hz), 4.64 (2H, t, J = 8.9 Hz), 4.68 (2H, d, J = 5.5 Hz), 7.57 (1H, s), 7.62 (1H, s). MS (ESI/APCI) m/z: 259 [M + H − H₂O]+ |

TABLE 65-continued

| Example No. | structural formula | physicochemical data |
|---|---|---|
| 91 (91c) | | ¹H-NMR (CDCl₃) δ: 1.11 (3H, t, J = 7.1 Hz), 2.05 (1H, t, J = 6.1 Hz), 2.84 (3H, s), 2.99-3.11 (2H, m), 3.14 (2H, dd, J = 10.7, 6.4 Hz), 4.02 (2H, q, J = 7.2 Hz), 4.25 (3H, s), 4.56 (2H, d, J = 8.6 Hz), 4.60 (2H, d, J = 6.1 Hz), 4.93 (1H, t, J = 8.0 Hz), 6.94 (1H, s), 6.96 (1H, s), 7.30 (1H, d, J = 9.2 Hz), 7.39 (1H, d, J = 8.6 Hz). MS (ESI/APCI) m/z: 396 [M + H]⁺ |
| 91 (91d) | | MS (ESI/APCI) m/z: 640 [M + H]⁺ |
| 91 (91e) = 91 | | ¹H-NMR (CDCl₃) δ: 1.00 (3H, t, J = 7.3 Hz), 1.51-1.53 (1H, m), 1.68-1.71 (1H, m), 2.77 (1.5H, s), 2.78 (1.5H, s), 2.98-3.09 (4H, m), 3.24 (1H, d, J = 15.6 Hz), 3.76-3.81 (1H, m), 4.06-4.12 (1H, m), 4.19 (1H, br s), 4.22 (3H, s), 4.31 (1H, dd, J = 14.4, 3.7 Hz), 4.41-4.43 (2H, m), 4.85 (1H, t, J = 8.1 Hz), 6.90 (1H, s), 6.96 (1H, d, J = 6.3 Hz), 7.31 (2H, dd, J = 11.7, 7.8 Hz), 8.14 (1H, dd, J = 6.1, 2.7 Hz), 8.32 (1H, t, J = 2.0 Hz). MS (ESI/APCI) m/z: 612 [M + H]⁺ |

TABLE 66

| Example No. | structural formula | physicochemical data |
|---|---|---|
| 92 (92a) | | ¹H-NMR (CDCl₃) δ: 3.23 (2H, t, J = 8.8 Hz), 3.90 (3H, s), 4.73 (2H, t, J = 8.8 Hz), 7.41-7.47 (1H, m), 7.82-7.88 (1H, m). |

TABLE 66-continued

| Example No. | structural formula | physicochemical data |
|---|---|---|
| 92 (92b) | 5-bromo-benzofuran-7-yl-methanol | ¹H-NMR (CDCl₃) δ: 1.94 (1H, t, J = 6.1 Hz), 4.98 (2H, d, J = 6.1 Hz), 6.74 (1H, d, J = 2.2 Hz), 7.45 (1H, d, J = 2.0 Hz), 7.63 (1H, d, J = 2.2 Hz), 7.67 (1H, d, J = 2.0 Hz). |
| 92 (92c) | (5-(4,4,5,5-tetramethyl-1,3,2-dioxaborolan-2-yl)benzofuran-7-yl)methanol | ¹H-NMR (CDCl₃) δ: 1.37 (12H, s), 1.86-1.98 (1H, br m), 4.97-5.06 (2H, m), 6.77-6.81 (1H, m), 7.63 (1H, d, J = 2.0 Hz), 7.74 (1H, s), 8.05 (1H, s). |
| 92 (92d) | ethyl ester intermediate with methylbenzotriazole, chloro, and hydroxymethyl benzofuran groups | ¹H-NMR (CDCl₃) δ: 1.12 (3H, t, J = 7.1 Hz), 1.87-1.95 (1H, m), 3.07-3.25 (2H, m), 4.04 (2H, q, J = 7.1 Hz), 4.27 (3H, s), 4.95 (2H, d, J = 6.4 Hz), 5.39-5.48 (1H, m), 6.73 (1H, d, J = 2.2 Hz), 7.18-7.22 (1H, m), 7.35 (1H, d, J = 8.6 Hz), 7.42 (1H, d, J = 8.6 Hz), 7.46-7.51 (1H, m), 7.61 (1H, d, J = 2.2 Hz). |
| 92 (92e) = 92 | final compound containing methylbenzotriazole, chloro, ethyl, sulfonyl-pyridyl-oxazepine, chloro, and benzofuran-carboxylic acid groups | ¹H-NMR (DMSO-D₆) δ: 0.80-0.93 (3H, m), 1.22-1.59 (2H, m), 3.09-3.26 (3H, m), 3.72-3.88 (1H, m), 4.00-4.16 (1H, m), 4.29 (3H, s), 4.39-4.50 (1H, m), 4.61-4.71 (1H, m), 5.19 (1H, t, J = 8.0 Hz), 6.90-6.96 (1H, m), 7.25-7.35 (1H, m), 7.59-7.64 (1H, m), 7.66-7.76 (1H, m), 7.77-7.85 (1H, m), 7.92-7.98 (1H, m), 8.23-8.30 (1H, m), 8.53-8.60 (1H, m), 11.70-12.90 (1H, br s). MS (ESI) m/z: 628 [M − H]⁻, 630 [M + H]⁺, 652 [M + Na]⁺ |
| 93 (93a) | ethyl 5-bromo-2-formamido-4-methylbenzoate | ¹H-NMR (CDCl₃) δ: 1.42 (3H, t, J = 7.1 Hz), 2.45 (3H, s), 4.38 (2H, q, J = 7.1 Hz), 8.18 (1H, s), 8.47-8.51 (1H, m), 8.66 (1H, s), 10.94 (1H, br s). |

TABLE 67
| Example No. | structural formula | physicochemical data |
|---|---|---|
| 93 (93b) | 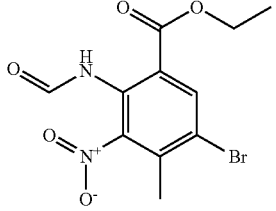 [SMILES: CCOC(=O)c1cc(Br)c(C)c([N+](=O)[O-])c1NC=O] | ¹H-NMR (CDCl₃) δ: 1.43 (3H, t, J = 7.1 Hz), 2.50 (3H, s), 4.42 (2H, q, J = 7.1 Hz), 8.25-8.40 (2H, m), 9.57 (1H, br s). |
| 93 (93c) | 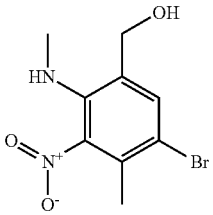 | ¹H-NMR (CDCl₃) δ: 2.31 (3H, s), 2.80 (3H, s), 4.65 (2H, s), 7.40 (1H, s). |
| 93 (93d) | 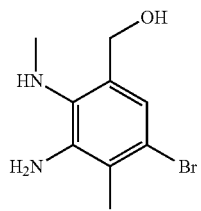 | ¹H-NMR (CDCl₃) δ: 2.28 (3H, s), 2.69 (3H, s), 3.30-4.20 (3H, br m), 4.57 (2H, s), 6.86 (1H, s). |
| 93 (93e) | 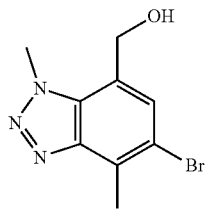 | ¹H-NMR (DMSO-D₆) δ: 2.69 (3H, s), 4.47 (3H, s), 4.89 (2H, s), 5.45-5.70 (1H, br m), 7.59 (1H, s). |
| 93 (93f) | 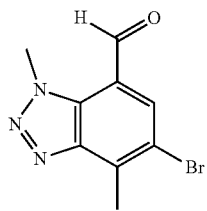 | ¹H-NMR (CDCl₃) δ: 2.92 (3H, s), 4.68 (3H, s), 8.05 (1H, s), 9.98 (1H, s). |
| 93 (93g) | 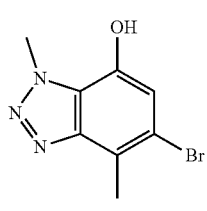 | ¹H-NMR (DMSO-D₆) δ: 2.55 (3H, s), 4.38 (3H, s), 6.90 (1H, s), 10.94 (1H, br s). |

TABLE 68

| Example No. | structural formula | physicochemical data |
|---|---|---|
| 93 (93h) | | ¹H-NMR (CDCl₃) δ: 2.72 (3H, s), 4.41 (3H, s), 5.17 (2H, s), 7.00 (1H, s), 7.36-7.50 (5H, m). |
| 93 (93i) | | ¹H-NMR (CDCl₃) δ: 1.56 (9H, s), 2.80 (3H, s), 4.42 (3H, s), 5.21 (2H, s), 6.27 (1H, d, J = 15.9 Hz), 7.03 (1H, s), 7.36-7.50 (5H, m), 8.03 (1H, d, J = 15.9 Hz). |
| 93 (93j) | | ¹H-NMR (CDCl₃) δ: 1.28 (9H, s), 1.81 (1H, t, J = 6.1 Hz), 2.74 (3H, s), 2.93 (1H, dd, J = 15.1, 8.3 Hz), 3.08 (1H, dd, J = 15.1, 8.0 Hz), 4.42 (3H, s), 4.87 (2H, d, J = 6.1 Hz), 5.00-5.07 (1H, m), 5.08-5.20 (2H, m), 6.70 (1H, s), 7.11-7.15 (1H, m), 7.26-7.39 (6H, m), 7.45 (1H, d, J = 5.4 Hz), 7.53-7.57 (1H, m). |

TABLE 68-continued

| Example No. | structural formula | physicochemical data |
| --- | --- | --- |
| 93 (93k) | | ¹H-NMR (CDCl₃) δ: 1.28 (9H, s), 2.74 (3H, s), 2.92 (1H, dd, J = 15.1, 8.1 Hz), 3.07 (1H, dd, J = 15.1, 8.1 Hz,), 4.42 (3H, s), 4.76 (2H, s), 5.02 (1H, t, J = 8.1), 5.08-5.21 (2H, m), 6.69 (1H, s), 7.14 (1H, d, J = 1.5 Hz), 7.29 (1H, d, J = 5.4 Hz), 7.30-7.39 (5H, m), 7.47 (1H, d, J = 5.4 Hz), 7.57 (1H, d, J = 1.5 Hz). |
| 93 (93l) | | ¹H-NMR (CDCl₃) δ: 0.85 (1.5H, t, J = 7.3 Hz), 0.93 (1.5H, t, J = 7.3 Hz), 1.25 (4.5H, s), 1.26 (4.5H, s), 1.44-1.65 (2H, m), 1.69-1.76 (3H, m), 2.706 (1.5H, s), 2.713 (1.5H, s), 2.79-2.98 (3H, m), 3.04 (1H, dd, J = 15.1, 7.6 Hz), 3.38-3.48 (1H, m), 3.78-3.88 (1H, m), 3.98-4.08 (1H, m), 4.41 (3H, s), 4.52-4.61 (1H, m), 4.96 (1H, t, J = 7.8 Hz), 5.04-5.16 (2H, m), 6.655 (0.5H, s), 6.663 (0.5H, s), 6.84 (0.5H, s), 6.92 (0.5H, s), 7.10-7.18 (1H, m), 7.20-7.39 (7H, m), 7.40-7.44 (1H, m), 7.46 (0.5H, s), 7.50 (0.5H, s), 8.26-8.32 (1H, m). MS (ESI) m/z: 718 [M + H]⁺, 740 [M + Na]⁺ |

TABLE 69

| Example No. | structural formula | physicochemical data |
| --- | --- | --- |
| 93 (93o) = 993 | | ¹H-NMR (DMSO-D₆) δ: 0.72 (3H, t, J = 7.4 Hz), 1.05-1.22 (1H, m), 1.33-1.46 (1H, m), 1.60 (3H, d, J = 7.4 Hz), 2.61 (3H, s), 2.65-2.71 (1H, m), 2.77-2.91 (2H, m), 3.02-3.11 (1H, m), 3.39 (1H, d, J = 14.1 Hz), 3.77-3.86 (1H, m), 3.90 (1H, d, J = 14.1 Hz), 4.32 (3H, s), 4.43 (1H, q, J = 7.4 Hz), 4.82-4.89 (1H, m), 6.52 (1H, s), 7.01 (1H, s), 7.23 (1H, dd, J = 8.0, 4.9 Hz), 7.39 (1H, dd, J = 8.0, 1.2 Hz), 7.40 (1H, d, J = 5.5 Hz), 7.65 (1H, s), 7.68 (1H, d, J = 5.5 Hz), 8.23 (1H, dd, J = 4.9, 1.2 Hz), 10.16 (1H, s), 12.19 (1H, s). MS (ESI/APCI) m/z: 572 [M + H]⁺ |

TABLE 69-continued

| Example No. | structural formula | physicochemical data |
|---|---|---|
| 94 | optically active isomer<br>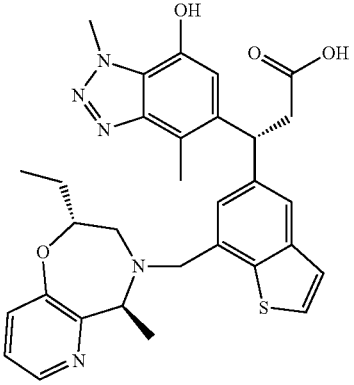 [SMILES: CC[C@@H]1CN(Cc2cc([C@@H](CC(=O)O)c3cc(O)c4c(nnn4C)c3C)cc3ccsc23)[C@@H](C)c2ncccc2O1] | ¹H-NMR (DMSO-D₆) δ: 0.87 (3H, t, J = 7.1 Hz), 1.19-1.29 (1H, m), 1.37-1.49 (1H, m), 1.57 (3H, d, J = 7.1 Hz), 2.58 (3H, s), 2.76-2.94 (3H, m), 3.06 (1H, dd, J = 15.6, 7.7 Hz), 3.47 (1H, d, J = 14.1 Hz), 3.85-3.96 (2H, m), 4.33 (3H, s), 4.41 (1H, q, J = 7.1 Hz), 4.81-4.89 (1H, m), 6.60 (1H, s), 7.02 (1H, s), 7.23 (1H, dd, J = 8.0, 4.3 Hz), 7.38-7.42 (2H, m), 7.64-7.70 (2H, m), 8.21-8.24 (1H, m), 10.20 (1H, s), 12.19 (1H, s).<br>MS (ESI/APCI) m/z: 572 [M + H]⁺ |
| 95 (95a) | optically active isomer<br>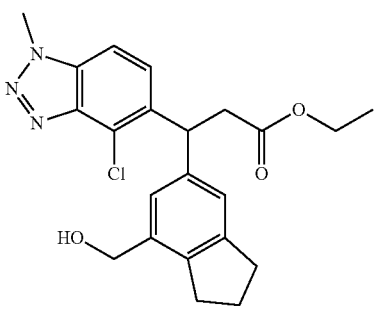 [SMILES: CCOC(=O)CC(c1cc(CO)c2c(c1)CCC2)c1ccc2c(nnn2C)c1Cl] | ¹H-NMR (CDCl₃) δ: 1.12 (3H, t, J = 7.1 Hz), 1.52-1.62 (1H, m), 2.00-2.12 (2H, m), 2.80-2.90 (4H, m), 3.03-3.20 (2H, m), 4.03 (2H, q, J = 7.1 Hz), 4.26 (3H, s), 4.62 (2H, d, J = 5.6 Hz), 5.32 (1H, t, J = 8.0 Hz), 7.08-7.13 (2H, m), 7.36 (1H, d, J = 8.6 Hz), 7.43 (1H, d, J = 8.6 Hz). |
| 95 (95b) | 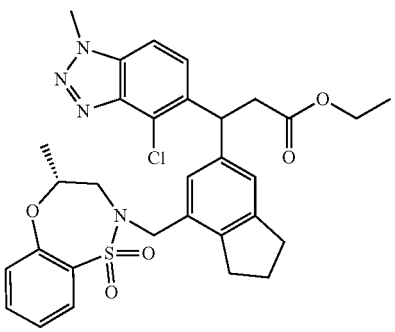 [SMILES: CCOC(=O)CC(c1cc2c(c(CN3C[C@@H](C)Oc4ccccc4S3(=O)=O)c1)CCC2)c1ccc2c(nnn2C)c1Cl] | ¹H-NMR (CDCl₃) δ: 1.09-1.16 (3H, m), 1.23-1.39 (1.5H, m), 1.33 (1.5H, d, J = 6.4 Hz), 1.99-2.07 (2H, m), 2.76-3.00 (5H, m), 3.02-3.18 (2H, m), 3.62-3.70 (1H, m), 3.71-3.79 (1H, m), 3.99-4.07 (2H, m), 4.22-4.30 (4H, m), 4.45-4.56 (1H, m), 5.21-5.30 (1H, m), 6.96-6.99 (1H, m), 7.05-7.09 (1H, m), 7.16-7.20 (1H, m), 7.21-7.26 (1H, m), 7.35-7.44 (2H, m), 7.47-7.53 (1H, m), 7.85-7.89 (1H, m). |
| 95 (95c) = 95 | 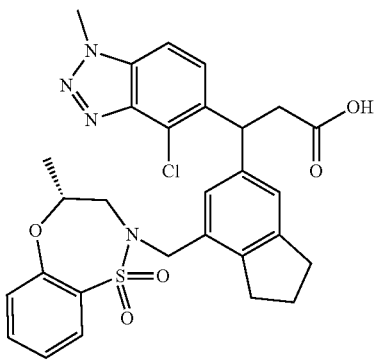 [SMILES: C[C@@H]1CN(Cc2cc(C(CC(=O)O)c3ccc4c(nnn4C)c3Cl)cc3c2CCC3)S(=O)(=O)c2ccccc2O1] | ¹H-NMR (DMSO-D₆) δ: 1.14-1.32 (3H, m), 1.87-2.02 (2H, m), 2.66-2.91 (5H, m), 3.02-3.18 (2H, m), 3.58-3.67 (1H, m), 3.77-3.86 (1H, m), 4.23-4.42 (5H, m), 5.02-5.09 (1H, m), 7.14-7.20 (2H, m), 7.29 (1H, d, J = 7.8 Hz), 7.35 (1H, t, J = 7.6 Hz), 7.61-7.72 (2H, m), 7.74-7.81 (2H, m).<br>MS (ESI) m/z: 579 [M − H]⁻, 581 [M + H]⁺ |

TABLE 70

| Example No. | structural formula | physicochemical data |
|---|---|---|
| 96 (96c) | | ¹H-NMR (CDCl₃) δ: 1.00 (3H, t, J = 7.3 Hz), 1.14 (3H, t, J = 7.0 Hz), 1.43-1.58 (1H, m), 1.65-1.78 (1H, m), 2.01-2.12 (2H, m), 2.78 (3H, s), 2.80-2.95 (4H, m), 3.00 (1H, dd, J = 15.6, 8.2 Hz), 3.05-3.18 (2H, m), 3.59 (1H, dd, J = 14.6, 11.0 Hz), 3.98-4.09 (3H, m), 4.29-4.46 (2H, m), 4.51 (3H, s), 4.86-4.94 (1H, m), 6.87 (1H, s), 7.03 (1H, s), 7.27 (1H, s), 8.20 (1H, d, J = 2.4 Hz), 8.40 (1H, d, J = 2.4 Hz).<br>MS (ESI/APCI) m/z: 672 [M + H]⁺ |
| 96 (96d) = 96 | | ¹H-NMR (DMSO-D₆) δ: 0.95 (3H, t, J = 7.3 Hz), 1.33-1.48 (1H, m), 1.48-1.64 (1H, m), 1.89-2.05 (2H, m), 2.72 (3H, s), 2.76-2.85 (4H, m), 2.94 (1H, d, J = 15.6 Hz), 3.01-3.10 (2H, m), 3.70 (1H, dd, J = 15.6, 10.1 Hz), 3.99 (1H, d, J = 15.3 Hz), 4.30-4.48 (2H, m), 4.44 (3H, s), 4.76 (1H, t, J = 7.9 Hz), 7.06 (1H, s), 7.20 (1H, s), 7.50 (1H, s), 8.25 (1H, d, J = 2.4 Hz), 8.62 (1H, d, J = 2.4 Hz), 12.19 (1H, br s).<br>MS (ESI/APCI) m/z: 644 [M + H]⁺ |
| 97 (97a) | | ¹H-NMR (CDCl₃) δ: 0.99 (3H, t, J = 7.3 Hz), 1.14 (3H, t, J = 7.0 Hz), 1.47-1.57 (1H, m), 1.65-1.78 (1H, m), 2.01-2.15 (2H, m), 2.78 (3H, s), 2.81-2.95 (4H, m), 2.96-3.17 (3H, m), 3.58 (1H, dd, J = 14.6, 11.0 Hz), 3.99-4.08 (3H, m), 4.30-4.44 (2H, m), 4.51 (3H, s), 4.91 (1H, t, J = 7.9 Hz), 6.86 (1H, s), 7.03 (1H, s), 7.26 (1H, s), 8.20 (1H, d, J = 2.7 Hz), 8.39 (1H, d, J = 2.7 Hz).<br>MS (ESI/APCI) m/z: 644 [M + H]⁺ |
| 97 (97b) = 97 | | ¹H-NMR (DMSO-D₆) δ: 0.85 (3H, t, J = 7.3 Hz), 1.22-1.38 (1H, m), 1.46-1.61 (1H, m), 1.89-2.06 (2H, m), 2.75 (3H, s), 2.78-2.94 (5H, m), 3.07 (2H, d, J = 7.9 Hz), 3.69 (1H, dd, J = 15.0, 10.1 Hz), 3.99 (1H, d, J = 13.4 Hz), 4.26-4.49 (2H, m), 4.44 (3H, s), 4.78 (1H, t, J = 7.9 Hz), 7.06 (1H, s), 7.21 (1H, s), 7.47 (1H, s), 8.25 (1H, d, J = 2.4 Hz), 8.62 (1H, d, J = 2.4 Hz), 12.20 (1H, br s).<br>MS (ESI/APCI) m/z: 644 [M + H]⁺ |

TABLE 70-continued

| Example No. | structural formula | physicochemical data |
| --- | --- | --- |
| 98 (98a) | | ¹H-NMR (CDCl₃) δ: 1.11 (3H, t, J = 7.1 Hz), 1.57-1.66 (1H, m), 2.01-2.12 (2H, m), 2.76-2.90 (7H, m), 3.02 (1H, dd, J = 15.4, 9.0 Hz), 3.11 (1H, dd, J = 15.4, 7.3 Hz), 4.01 (2H, q, J = 7.1 Hz), 4.39 (3H, s), 4.61 (2H, d, J = 5.8 Hz), 4.91-4.98 (1H, m), 6.62 (1H, t, J = 73.0 Hz), 6.97-7.06 (2H, m), 7.10 (1H, s). |
| 98 (98c) | | ¹H-NMR (CDCl₃) δ: 1.00 (3H, t, J = 7.3 Hz), 1.13 (3H, t, J = 7.0 Hz), 1.45-1.55 (1H, m), 1.64-1.76 (1H, m), 2.01-2.13 (2H, m), 2.77 (3H, s), 2.80-2.94 (4H, m), 2.95-3.11 (2H, m), 3.11-3.19 (1H, m), 3.56 (1H, dd, J = 15.0, 11.3 Hz), 3.97-4.08 (3H, m), 4.31-4.46 (2H, m), 4.41 (3H, s), 4.87-4.98 (1H, m), 6.68 (1H, t, J = 72.9 Hz), 6.89 (1H, s), 7.04 (1H, s), 7.06 (1H, s), 8.19 (1H, d, J = 2.4 Hz), 8.39 (1H, d, J = 2.4 Hz).<br>MS (ESI/APCI) m/z: 704 [M + H]⁺ |

TABLE 71

| Example No. | structural formula | physicochemical data |
| --- | --- | --- |
| 98 (98d) | 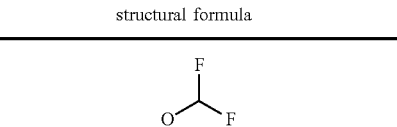 | ¹H-NMR (CDCl₃) δ: 1.00 (3H, t, J = 7.3 Hz), 1.13 (3H, t, J = 7.0 Hz), 1.44-1.54 (1H, m), 1.64-1.78 (1H, m), 2.00-2.14 (2H, m), 2.76 (3H, s), 2.80-2.93 (4H, m), 2.96-3.18 (3H, m), 3.50-3.64 (1H, m), 3.96-4.10 (3H, m), 4.29-4.45 (2H, m), 4.41 (3H, s), 4.86-4.97 (1H, m), 6.67 (1H, t, J = 72.9 Hz), 6.89 (1H, s), 7.04 (1H, s), 7.08 (1H, s), 8.19 (1H, d, J = 2.4 Hz), 8.39 (1H, d, J = 2.4 Hz).<br>MS (ESI/APCI) m/z: 704 [M + H]⁺ |

| Example No. | structural formula | physicochemical data |
|---|---|---|
| 98 (98e) = 98 | | ¹H-NMR (DMSO-D₆) δ: 0.86 (3H, t, J = 7.3 Hz), 1.21-1.38 (1H, m), 1.44-1.59 (1H, m), 1.88-2.06 (2H, m), 2.71 (3H, s), 2.75-2.85 (4H, m), 2.90 (1H, d, J = 15.3 Hz), 2.96-3.14 (2H, m), 3.70 (1H, dd, J = 15.3, 10.4 Hz), 4.00 (1H, d, J = 14.0 Hz), 4.26-4.35 (1H, m), 4.33 (3H, s), 4.39 (1H, d, J = 14.0 Hz), 4.79 (1H, t, J = 7.9 Hz), 7.04 (1H, s), 7.18 (1H, s), 7.23 (1H, s), 7.35 (1H, t, J = 73.2 Hz), 8.25 (1H, d, J = 2.7 Hz), 8.62 (1H, d, J = 2.7 Hz), 12.20 (1H, br s). MS (ESI/APCI) m/z: 676 [M + H]⁺ |
| 99 | | ¹H-NMR (DMSO-D₆) δ: 0.92 (3H, t, J = 7.3 Hz), 1.32-1.43 (1H, m), 1.47-1.62 (1H, m), 1.87-2.05 (2H, m), 2.68 (3H, s), 2.70-2.90 (4H, m), 2.95 (1H, d, J = 15.3 Hz), 2.98-3.11 (2H, m), 3.69 (1H, dd, J = 15.3, 10.4 Hz), 3.99 (1H, d, J = 14.0 Hz), 4.28-4.36 (1H, m), 4.33 (3H, s), 4.39 (1H, d, J = 14.0 Hz), 4.78 (1H, t, J = 7.9 Hz), 7.02 (1H, s), 7.18 (1H, s), 7.29 (1H, s), 7.37 (1H, t, J = 73.9 Hz), 8.25 (1H, d, J = 3.1 Hz), 8.62 (1H, d, J = 3.1 Hz), 12.19 (1H, br s). MS (ESI/APCI) m/z: 676 [M + H]⁺ |
| 100 (100a) | | ¹H-NMR (CDCl₃) δ: 1.11 (3H, t, J = 7.1 Hz), 1.55 (1H, t, J = 5.8 Hz), 2.00-2.12 (2H, m), 2.75-2.90 (7H, m), 2.98-3.15 (2H, m), 3.97-4.06 (2H, m), 4.39 (3H, s), 4.61 (2H, d, J = 5.8 Hz), 4.95 (1H, t, J = 8.6 Hz), 6.97-7.00 (1H, m), 7.01-7.06 (1H, m), 7.27-7.32 (1H, m). |

TABLE 71-continued

| Example No. | structural formula | physicochemical data |
|---|---|---|
| 100 (100c) | | $^1$H-NMR (CDCl$_3$) δ: 0.99 (3H, t, J = 7.3 Hz), 1.12 (3H, t, J = 7.3 Hz), 1.43-1.53 (1H, m), 1.64-1.77 (1H, m), 2.00-2.12 (2H, m), 2.79 (3H, s), 2.80-2.92 (4H, m), 2.98-3.14 (3H, m), 3.57 (1H, dd, J = 15.0, 10.7 Hz), 3.99-4.07 (3H, m), 4.30-4.43 (2H, m), 4.40 (3H, s), 4.93 (1H, t, J = 7.9 Hz), 6.87 (1H, s), 7.01 (1H, s), 7.23 (1H, s), 8.20 (1H, d, J = 2.4 Hz), 8.39 (1H, d, J = 2.4 Hz).<br>MS (ESI/APCI) m/z: 722 [M + H]$^+$ |
| 100 (100d) | | $^1$H-NMR (CDCl$_3$) δ: 1.00 (3H, t, J = 7.6 Hz), 1.12 (3H, t, J = 7.3 Hz), 1.42-1.54 (1H, m), 1.64-1.78 (1H, m), 2.01-2.11 (2H, m), 2.79 (3H, s), 2.82-2.96 (4H, m), 2.96-3.16 (3H, m), 3.57 (1H, dd, J = 14.6, 11.0 Hz), 3.98-4.07 (3H, m), 4.32-4.43 (2H, m), 4.40 (3H, s), 4.90-4.97 (1H, m), 6.87 (1H, s), 7.01 (1H, s), 7.21-7.22 (1H, m), 8.20 (1H, d, J = 2.7 Hz), 8.39 (1H, d, J = 2.7 Hz).<br>MS (ESI/APCI) m/z: 722 [M + H]$^+$ |

TABLE 72

| Example No. | structural formula | physicochemical data |
|---|---|---|
| 100 (100e) = 100 | 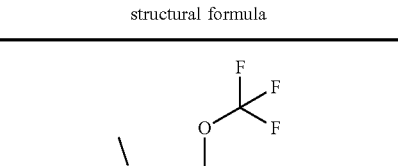 | $^1$H-NMR (DMSO-D$_6$) δ: 0.93 (3H, t, J = 7.3 Hz), 1.32-1.46 (1H, m), 1.48-1.63 (1H, m), 1.87-2.05 (2H, m), 2.73 (3H, s), 2.75-2.88 (4H, m), 2.94 (1H, d, J = 14.6 Hz), 3.02-3.13 (2H, m), 3.64-3.75 (1H, m), 3.99 (1H, d, J = 14.3 Hz), 4.29-4.40 (1H, m), 4.33 (3H, s), 4.39 (1H, d, J = 14.3 Hz), 4.80 (1H, t, J = 7.9 Hz), 7.06 (1H, s), 7.20 (1H, s), 7.51 (1H, s), 8.25 (1H, d, J = 3.1 Hz), 8.63 (1H, d, J = 3.1 Hz), 12.21 (1H, br s).<br>MS (ESI/APCI) m/z: 694 [M + H]$^+$ |

TABLE 72-continued

| Example No. | structural formula | physicochemical data |
|---|---|---|
| 101 | | $^1$H-NMR (DMSO-D$_6$) δ: 0.85 (3H, t, J = 7.3 Hz), 1.22-1.37 (1H, m), 1.43-1.59 (1H, m), 1.89-2.06 (2H, m), 2.76 (3H, s), 2.77-2.93 (5H, m), 3.07 (2H, d, J = 7.9 Hz), 3.68 (1H, dd, J = 15.0, 10.1 Hz), 3.99 (1H, d, J = 14.0 Hz), 4.27-4.35 (1H, m), 4.33 (3H, s), 4.40 (1H, d, J = 14.0 Hz), 4.81 (1H, t, J = 7.9 Hz), 7.05 (1H, s), 7.20 (1H, s), 7.45 (1H, s), 8.25 (1H, d, J = 3.1 Hz), 8.62 (1H, d, J = 3.1 Hz), 12.21 (1H, br s). MS (ESI/APCI) m/z 694 [M + H]$^+$ |
| 102 (102a) | | MS (ESI/APCI) m/z: 436 [M + H]$^+$ |
| 102 (102b) | | MS (ESI/APCI) m/z: 680 [M + H]$^+$ |
| 102 (102c) = 102 | | $^1$H-NMR (DMSO-D$_6$) δ: 0.70-0.78 (1H, m), 0.78-0.94 (4H, m), 0.95-1.06 (2H, m), 1.21-1.61 (2H, m), 2.40-2.55 (1H, m), 2.65 (1.5H, s), 2.66 (1.5H, s), 2.91-3.02 (2H, m), 3.04-3.13 (2H, m), 3.14-3.28 (1H, m), 3.71-3.84 (1H, m), 3.98-4.14 (2H, m), 4.21-4.30 (1H, m), 4.33-4.56 (2H, m), 4.52 (3H, s), 4.64-4.73 (1H, m), 6.93-7.03 (1H, m), 7.04-7.14 (2H, m), 8.18-8.25 (1H, m), 8.53-8.59 (1H, m), 12.11 (1H, br s). MS (ESI/APCI) m/z: 652 [M + H]$^+$ |

TABLE 72-continued
| Example No. | structural formula | physicochemical data |
|---|---|---|
| 103 (103a) | | MS (ESI/APCI) m/z: 533 [M + H]+ |
TABLE 73
| Example No. | structural formula | physicochemical data |
|---|---|---|
| 103 (103b) | | MS (ESI/APCI) m/z: 777 [M + H]+ |
| 103 (103c) = 103 | 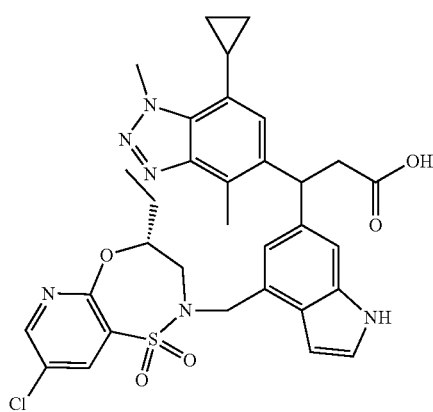 [SMILES: CC[C@@H]1CN(Cc2cc(C(CC(=O)O)c3cc(C4CC4)c4c(nnn4C)c3C)cc3[nH]ccc23)S(=O)(=O)c2cc(Cl)cnc2O1] | $^1$H-NMR (DMSO-D$_6$) δ: 0.62-0.89 (5H, m), 0.91-1.06 (2H, m), 1.09-1.60 (2H, m), 2.35-2.49 (1H, m), 2.65 (1.5H, s), 2.68 (1.5H, s), 2.81-3.16 (3H, m) 3.57-3.72 (1H, m), 4.18-4.33 (2H, m), 4.51 (1.5H, s), 4.52 (1.5H, s), 4.61-4.71 (1H, m), 4.79-4.90 (1H, m), 6.48-6.55 (1H, m), 6.87 (1H, s), 7.05 (0.5H, s), 7.12 (0.5H, s), 7.24 (0.5H, s), 7.25 (0.5H, s), 7.29-7.34 (1H, m), 8.25-8.32 (1H, m), 8.57-8.63 (1H, m), 11.08-11.16 (1H, m), 12.14 (1H, br s). MS (ESI/APCI) m/z: 649 [M + H]+ |

TABLE 73-continued

| Example No. | structural formula | physicochemical data |
|---|---|---|
| 104 (104a) | | MS (ESI/APCI) m/z: 707 [M + H]+ |
| 104 (104b) = 104 | | ¹H-NMR (DMSO-D₆) δ: 0.61-0.90 (5H, m), 0.91-1.47 (4H, m), 1.51-1.59 (3H, m), 2.38-2.46 (1H, m), 2.61 (1.5H, s), 2.63 (1.5H, s), 2.66-2.82 (2H, m), 2.91-3.11 (2H, m), 3.26-3.40 (1H, m), 3.79-3.92 (2H, m), 4.34-4.45 (1H, m), 4.51 (1.5H, s), 4.52 (1.5H, s), 4.76-4.85 (1H, m), 6.35-6.40 (1H, m), 6.70-6.78 (1H, m), 7.01-7.14 (2H, m), 7.18-7.26 (2H, m), 7.35-7.41 (1H, m), 8.18-8.25 (1H, m), 10.89-10.89 (1H, m), 12.09 (1H, br s). MS (ESI/APCI) m/z: 579 [M + H]+ |
| 105 (105a) | | MS (ESI/APCI) m/z: 434 [M + H]+ |
| 105 (105b) | | MS (ESI/APCI) m/z: 608 [M + H]+ |

TABLE 74

| Example No. | structural formula | physicochemical data |
|---|---|---|
| 105 (105e) = 105 | | ¹H-NMR (DMSO-D₆) δ: 0.63-0.72 (1H, m), 0.73-0.81 (1H, m), 0.84 (3H, t, J = 7.0 Hz), 0.91-1.05 (2H, m), 1.11-1.21 (1H, m), 1.34-1.46 (1H, m), 1.49 (3H, d, J = 7.1 Hz), 1.83-1.98 (2H, m), 2.37-2.46 (1H, m), 2.61 (3H, s), 2.64-2.84 (6H, m), 2.88-3.04 (2H, m), 3.09 (1H, d, J = 13.7 Hz), 3.57 (1H, d, J = 13.7 Hz), 3.82-3.90 (1H, m), 4.33 (1H, q, J = 7.1 Hz), 4.51 (3H, s), 4.65-4.73 (1H, m), 6.89 (1H, s), 6.99 (1H, s), 7.02 (1H, s), 7.23 (1H, dd, J = 7.9, 4.3 Hz), 7.35-7.41 (1H, m), 8.20-8.24 (1H, m), 12.07 (1H, s). MS (ESI/APCI) m/z: 580 [M + H]⁺ |
| 106 | | ¹H-NMR (DMSO-D₆) δ: 0.65-0.74 (1H, m), 0.75-0.91 (4H, m), 0.92-1.06 (2H, m), 1.14-1.33 (1H, m), 1.34-1.45 (1H, m), 1.48 (3H, d, J = 7.1 Hz), 1.84-1.97 (2H, m), 2.40-2.46 (1H, m), 2.60 (3H, s), 2.61-2.68 (1H, m), 2.71-2.84 (5H, m), 2.89-3.03 (2H, m), 3.11 (1H, d, J = 14.0 Hz), 3.56 (1H, d, J = 14.0 Hz), 3.78-3.89 (1H, m), 4.34 (1H, q, J = 7.1 Hz), 4.52 (3H, s), 4.64-4.72 (1H, m), 6.86 (1H, s), 6.98 (1H, s), 7.07 (1H, s), 7.22 (1H, dd, J = 7.9, 4.3 Hz), 7.37 (1H, dd, J = 7.9, 1.2 Hz), 8.21 (1H, dd, J = 4.3, 1.2 Hz), 12.07 (1H, s). MS (ESI/APCI) m/z: 580 [M + H]⁺ |
| 107 (107a) | | MS (ESI/APCI) m/z: 610 [M + H]⁺ |
| 107 (107b) = 107 | | ¹H-NMR (DMSO-D₆) δ: 0.67-0.82 (2H, m), 0.89-0.95 (3H, m), 0.96-1.03 (2H, m), 1.21-1.35 (1H, m), 1.39-1.52 (4H, m), 2.38-2.48 (1H, m), 2.62 (3H, s), 2.80-3.16 (7H, m), 3.38-3.46 (1H, m), 3.79-3.90 (1H, m), 4.31-4.46 (3H, m), 4.51 (1.5H, s), 4.52 (1.5H, s), 4.63-4.71 (1H, m), 6.93-6.99 (2H, m), 7.05 (0.5H, s), 7.06 (0.5H, s), 7.19-7.25 (1H, m), 7.35-7.40 (1H, m), 8.20-8.24 (1H, m), 12.07 (1H, s). MS (ESI/APCI) m/z: 582 [M + H]⁺ |

TABLE 74-continued

| Example No. | structural formula | physicochemical data |
|---|---|---|
| 108 (108a) | | ¹H-NMR (CDCl₃) δ: 0.99 (3H, t, J = 7.3 Hz), 1.13 (3H, t, J = 7.1 Hz), 1.44-1.63 (1H, m), 1.64-1.76 (1H, m), 2.79 (3H, s), 3.07 (1H, dd, J = 15.6, 8.3 Hz), 3.13-3.22 (2H, m), 3.64 (1H, dd, J = 15.1, 11.2 Hz), 4.04 (3H, t, J = 7.1 Hz), 4.32-4.43 (5H, m), 4.65 (1H, d, J = 14.6 Hz), 5.09 (1H, t, J = 8.0 Hz), 6.66 (1H, t, J = 73.0 Hz), 7.10 (1H, s), 7.13 (1H, s), 7.32 (1H, d, J = 5.4 Hz), 7.48 (1H, d, J = 5.4 Hz), 7.63-7.68 (1H, m), 8.21 (1H, d, J = 2.7 Hz), 8.40 (1H, d, J = 2.7 Hz). |

TABLE 75

| Example No. | structural formula | physicochemical data |
|---|---|---|
| 108 (108b) = 108 | | ¹H-NMR (DMSO-D₆) δ: 0.85-0.91 (3H, m), 1.29-1.40 (1H, m), 1.47-1.59 (1H, m), 2.72 (3H, s), 2.92 (1H, d, J = 15.1 Hz), 3.06-3.22 (2H, m), 3.73 (1H, dd, J = 15.1, 10.0 Hz), 4.30-4.40 (5H, m), 4.67 (1H, d, J = 14.4 Hz), 4.94 (1H, t, J = 7.8 Hz), 7.27 (1H, s), 7.30 (1H, s), 7.35 (1H, t, J = 73.7 Hz), 7.45 (1H, d, J = 5.4 Hz), 7.79 (1H, d, J = 5.4 Hz), 7.86 (1H, s), 8.28 (1H, d, J = 2.7 Hz), 8.64 (1H, d, J = 2.7 Hz), 12.00-12.50 (1H, br s). <br> MS (ESI) m/z: 690 [M − H]⁻ |
| 109 (109a) | | ¹H-NMR (CDCl₃) δ: 0.69-0.76 (1H, m), 0.82-0.91 (1H, m), 1.01-1.06 (2H, m), 1.10 (3H, t, J = 7.1 Hz), 1.89-1.93 (1H, m), 2.25-2.34 (1H, m), 2.77 (3H, s), 3.06 (1H, dd, J = 15.4, 8.6 Hz), 3.16 (1H, dd, J = 15.4, 7.6 Hz), 4.01 (2H, q, J = 7.1 Hz), 4.57 (3H, s), 4.93 (2H, d, J = 6.1 Hz), 5.00-5.06 (1H, m), 6.71 (1H, d, J = 2.2 Hz), 7.10-7.14 (2H, m), 7.34-7.37 (1H, m), 7.60 (1H, d, J = 2.2 Hz) |

TABLE 75-continued

| Example No. | structural formula | physicochemical data |
|---|---|---|
| 109 (109b) | | $^1$H-NMR (CDCl$_3$) δ: 0.70-0.90 (2H, m), 0.91-0.99 (3H, m), 1.00-1.05 (2H, m), 1.09 (3H, t, J = 7.1 Hz), 1.18-1.37 (1H, m), 1.50-1.63 (1H, m), 1.64-1.69 (3H, m), 2.23-2.33 (1H, m), 2.73-2.77 (3H, m), 2.87-3.17 (4H, m), 3.46-3.56 (1H, m), 3.86-3.95 (2H, m), 4.00 (2H, q, J = 7.1 Hz), 4.51-4.59 (4H, m), 5.00 (1H, t, J = 8.3 Hz), 6.63-6.66 (1H, m), 7.05-7.16 (3H, m), 7.22-7.27 (1H, m), 7.31-7.35 (1H, m), 7.50-7.53 (1H, m), 8.28-8.31 (1H, m). |
| 109 (109c) = 109 | | $^1$H-NMR (DMSO-D$_6$) δ: 0.67-0.90 (5H, m), 0.92-1.04 (2H, m), 1.15-1.31 (1H, m), 1.38-1.54 (4H, m), 2.29-2.57 (1H, m), 2.62-2.66 (3H, m), 2.75-2.88 (2H, m), 2.96-3.12 (2H, m), 3.41-3.52 (1H, m), 3.80-3.92 (2H, m), 4.34-4.42 (1H, m), 4.50-4.53 (3H, m), 4.84 (1H, t, J = 7.8 Hz), 6.85-6.87 (1H, m), 7.04-7.11 (1H, m), 7.11-7.14 (1H, m), 7.21-7.26 (1H, m), 7.36-7.44 (2H, m), 7.88-7.90 (1H, m), 8.21-8.25 (1H, m), 12.12 (1H, br s). MS (ESI) m/z: 578 [M − H]$^-$, 580 [M + H]$^+$, 602 [M + Na]$^+$ |
| 110 (110a) | | $^1$H-NMR (CDCl$_3$) δ: 0.73-0.81 (1H, m), 0.82-0.92 (1H, m), 0.94-1.02 (3H, m), 1.03-1.08 (2H, m), 1.12 (3H, t, J = 7.1 Hz), 1.42-1.64 (1H, m), 1.65-1.76 (1H, m), 2.26-2.36 (1H, m), 2.73-2.76 (3H, m), 3.02-3.15 (2H, m), 3.21-3.28 (1H, m), 3.72-3.82 (1H, m), 4.03 (2H, q, J = 7.1 Hz), 4.20-4.31 (1H, m), 4.46 (1H, d, J = 14.6 Hz), 4.58 (3H, s), 4.63-4.70 (1H, m), 4.97-5.03 (1H, m), 6.68-6.71 (1H, m), 7.09-7.12 (1H, m), 7.14-7.17 (1H, m), 7.33-7.36 (1H, m), 7.54 (1H, d, J = 2.2 Hz), 8.20-8.23 (1H, m), 8.35-8.38 (1H, m). |

TABLE 76

| Example No. | structural formula | physicochemical data |
| --- | --- | --- |
| 110 (110b) = 110 | | ¹H-NMR (DMSO-D₆) δ: 0.71-0.91 (5H, m), 0.93-1.04 (2H, m), 1.21-1.31 (0.5H, m), 1.34-1.57 (1.5H, m), 2.29-2.59 (1H, m), 2.66-2.70 (3H, m), 3.00-3.29 (3H, m), 3.74-3.85 (1H, m), 4.05-4.14 (1H, m), 4.40-4.48 (1H, m), 4.51 (3H, s), 4.60-4.69 (1H, m), 4.87 (1H, t, J = 8.3 Hz), 6.90-6.93 (1H, m), 7.07-7.15 (1H, m), 7.19-7.22 (1H, m), 7.54-7.56 (1H, m), 7.93-7.96 (1H, m), 8.24-8.27 (1H, m), 8.55-8.58 (1H, m), 12.16 (1H, br s). MS (ESI) m/z: 648 [M − H]⁻, 672 [M + Na]⁺ |

TABLE 77

| Example No. | structural formula | physicochemical data |
| --- | --- | --- |
| 111a | | ¹H-NMR (CDCl₃) δ: 0.94 (3H, t, J = 7.6 Hz), 1.11 (3H, t, J = 7.0 Hz), 1.47-1.54 (1H, m), 1.63-1.73 (1H, m), 2.84 (3H, s), 3.11 (1H, dd, J = 15.6, 8.2 Hz), 3.16-3.23 (2H, m), 3.55 (1H, dd, J = 14.6, 11.0 Hz), 4.03 (2H, q, J = 6.9 Hz), 4.26 (3H, s), 4.40 (1H, d, J = 14.0 Hz), 4.48-4.55 (1H, m), 4.59 (1H, d, J = 14.0 Hz), 5.11 (1H, t, J = 7.9 Hz), 7.11 (1H, s), 7.28-7.34 (3H, m), 7.41 (1H, d, J = 8.5 Hz), 7.47 (1H, d, J = 5.5 Hz), 7.67 (1H, d, J = 1.2 Hz), 8.19 (1H, d, J = 8.5 Hz). MS (ESI/APCI) m/z: 654 [M + H]⁺ |
| 111b = 111 | | ¹H-NMR (CDCl₃) δ: 0.97 (3H, t, J = 7.3 Hz), 1.40 (3H, t, J = 7.0 Hz), 1.42-1.47 (1H, m), 1.62-1.71 (1H, m), 2.83 (3H, s), 3.11-3.27 (3H, m), 3.47 (1H, dd, J = 15.0, 10.7 Hz), 4.24 (3H, s), 4.35-4.48 (4H, m), 4.56 (1H, d, J = 14.6 Hz), 5.09 (1H, t, J = 7.9 Hz), 6.60 (1H, d, J = 8.5 Hz), 7.13 (1H, d, J = 1.2 Hz), 7.28-7.32 (2H, m), 7.38 (1H, d, J = 8.5 Hz), 7.46 (1H, d, J = 4.9 Hz), 7.65 (1H, d, J = 1.2 Hz), 8.06 (1H, d, J = 8.5 Hz). MS (ESI/APCI) m/z: 636 [M + H]⁺ |

TABLE 77-continued

| Example No. | structural formula | physicochemical data |
|---|---|---|
| 112a | 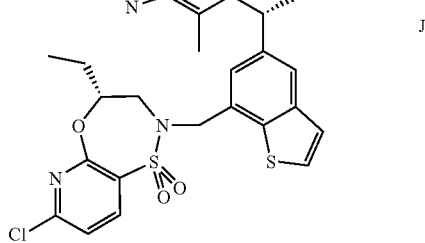 | $^{1}$H-NMR (CDCl$_3$) δ: 0.91 (3H, t, J = 7.3 Hz), 1.12 (3H, t, J = 7.0 Hz), 1.44-1.53 (1H, m), 1.61-1.70 (1H, m), 2.85 (3H, s), 3.10 (1H, dd, J = 15.6, 8.2 Hz), 3.16-3.23 (2H, m), 3.50 (1H, dd, J = 14.6, 11.0 Hz), 4.04 (2H, q, J = 7.1 Hz), 4.26 (3H, s), 4.40 (1H, d, J = 14.0 Hz), 4.49-4.56 (1H, m), 4.59 (1H, d, J = 14.6 Hz), 5.12 (1H, t, J = 7.9 Hz), 7.10 (1H, d, J = 1.2 Hz), 7.26-7.33 (3H, m), 7.39 (1H, d, J = 8.5 Hz), 7.47 (1H, d, J = 5.5 Hz), 7.68 (1H, d, J = 1.8 Hz), 8.19 (1H, d, J = 7.9 Hz). MS (ESI/APCI) m/z: 654 [M + H]$^+$ |
| 112b = 112 | 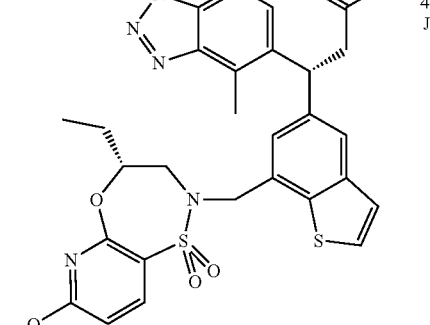 | $^{1}$H-NMR (CDCl$_3$) δ: 0.93 (3H, t, J = 7.6 Hz), 1.36-1.45 (4H, m), 1.58-1.69 (1H, m), 2.85 (3H, s), 3.10-3.27 (3H, m), 3.44 (1H, dd, J = 14.6, 11.0 Hz), 4.24 (3H, s), 4.33-4.51 (4H, m), 4.57 (1H, d, J = 14.6 Hz), 5.10 (1H, t, J = 7.9 Hz), 6.60 (1H, d, J = 8.5 Hz), 7.12 (1H, d, J = 1.2 Hz), 7.28-7.32 (2H, m), 7.36 (1H, d, J = 8.5 Hz), 7.47 (1H, d, J = 5.5 Hz), 7.65 (1H, d, J = 1.2 Hz), 8.06 (1H, d, J = 8.5 Hz). MS (ESI/APCI) m/z: 636 [M + H]$^+$ |

Although the present invention has been described in detail and with reference to specific embodiments, it is apparent to those skilled in the art that various changes and modifications can be made without departing from the spirit and scope of the present invention. This application is based on Japanese Patent Application No. 2022-075223 filed on Apr. 28, 2022 in Japan, the contents of which are incorporated in full herein.

The invention claimed is:

1. A compound represented by the following formula (1'):

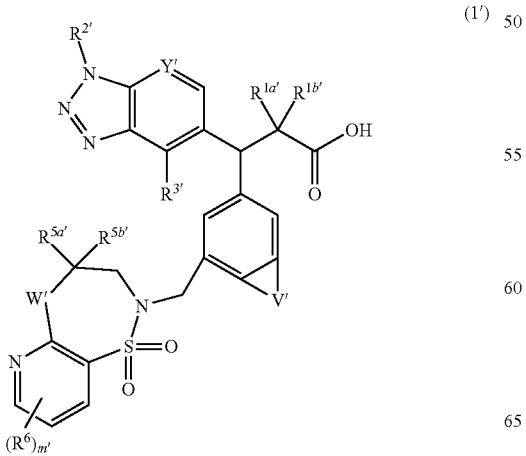

wherein
$R^{1a'}$ and $R^{1b'}$ are each independently a hydrogen atom or a methyl group,
$R^{2'}$ is a methyl group,
$R^{3'}$ is a chlorine atom or a methyl group,
Y' is —CH—, —CR$^{4'}$— or a nitrogen atom,
$R^{4'}$ is a chlorine atom, a methyl group, a cyclopropyl group, a difluoromethoxy group or a trifluoromethoxy group,
—V'— is a group represented by any of the following formulas:

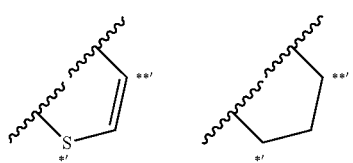 [SMILES: */C=C\S* ; *CCC*]

wherein *' and **' are each a bonding position to a benzene ring,
$R^{5a'}$ and $R^{5b'}$ are each independently a hydrogen atom or an ethyl group, or $R^{5a'}$ and $R^{5b'}$ are bonded together to form cyclopropane,
$R^{6'}$ in the number of m' are each independently a fluorine atom or a chlorine atom,
m' is an integer of 0 to 2, and
W' is an oxygen atom,
or a pharmaceutically acceptable salt thereof.

2. The compound according to claim 1, which is selected from the group consisting of:

(3R)-3-(7-{[(4R)-8-chloro-4-ethyl-1,1-dioxido-3,4-dihydro-2H-pyrido [2,3-b][1,4,5]oxathiazepin-2-yl]methyl}-1-benzothiophen-5-yl)-3-(1,4-dimethyl-1H-benzotriazol-5-yl) propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-1-benzothiophen-5-yl)-3-(1,4-dimethyl-1H-benzotriazol-5-yl) propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(1,4-dimethyl-1H-benzotriazol-5-yl) propanoic acid, (3R)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(1,4-dimethyl-1H-benzotriazol-5-yl) propanoic acid, (3R)-3-(7-{[(4R)-8-chloro-4-ethyl-1,1-dioxido-3,4-dihydro-2H-pyrido [2,3-b][1,4,5] oxathiazepin-2-yl]methyl}-1-benzothiophen-5-yl)-3-(7-cyclopropyl-1,4-dimethyl-1H-benzotriazol-5-yl) propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-1-benzothiophen-5-yl)-3-(7-cyclopropyl-1,4-dimethyl-1H-benzotriazol-5-yl) propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(1,4-dimethyl-1H-benzotriazol-5-yl)-2,2-dimethylpropanoic acid, (3R)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(7-cyclopropyl-1,4-dimethyl-1H-benzotriazol-5-yl) propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(7-cyclopropyl-1,4-dimethyl-1H-benzotriazol-5-yl) propanoic acid, (3R)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-[1,4-dimethyl-7-(trifluoromethoxy)-1H-benzotriazol-5-yl] propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-[1,4-dimethyl-7-(trifluoromethoxy)-1H-benzotriazol-5-yl]propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-1-benzothiophen-5-yl)-3-[1,4-dimethyl-7-(trifluoromethoxy)-1H-benzotriazol-5-yl] propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-1-benzothiophen-5-yl)-3-[7-(difluoromethoxy)-1,4-dimethyl-1H-benzotriazol-5-yl] propanoic acid, (3R)-3-(7-{[(4R)-8-chloro-4-ethyl-1,1-dioxido-3,4-dihydro-2H-pyrido [2,3-b][1,4,5] oxathiazepin-2-yl]methyl}-1-benzothiophen-5-yl)-3-[7-(difluoromethoxy)-1,4-dimethyl-1H-benzotriazol-5-yl] propanoic acid, (3R)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-[7-(difluoromethoxy)-1,4-dimethyl-1H-benzotriazol-5-yl] propanoic acid, and (3S)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-[7-(difluoromethoxy)-1,4-dimethyl-1H-benzotriazol-5-yl] propanoic acid, or a pharmaceutically acceptable salt thereof.

3. The compound according to claim 1, which is selected from the group consisting of:

(3R)-3-(7-{[(4R)-8-chloro-4-ethyl-1,1-dioxido-3,4-dihydro-2H-pyrido [2,3-b][1,4,5] oxathiazepin-2-yl]methyl}-1-benzothiophen-5-yl)-3-(1,4-dimethyl-1H-benzotriazol-5-yl) propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-1-benzothiophen-5-yl)-3-(1,4-dimethyl-1H-benzotriazol-5-yl) propanoic acid, (3S)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(1,4-dimethyl-1H-benzotriazol-5-yl) propanoic acid, and (3R)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(1,4-dimethyl-1H-benzotriazol-5-yl) propanoic acid, or a pharmaceutically acceptable salt thereof.

4. The compound according to claim 1, which is (3R)-3-(7-{[(4R)-8-chloro-4-ethyl-1,1-dioxido-3,4-dihydro-2H-pyrido [2,3-b][1,4,5] oxathiazepin-2-yl] methyl}-1-benzothiophen-5-yl)-3-(1,4-dimethyl-1H-benzotriazol-5-yl) propanoic acid or a pharmaceutically acceptable salt thereof.

5. The compound according to claim 1, which is (3S)-3-(7-{[(4R)-8-chloro-4-ethyl-1,1-dioxido-3,4-dihydro-2H-pyrido [2,3-b][1,4,5] oxathiazepin-2-yl] methyl}-1-benzothiophen-5-yl)-3-(1,4-dimethyl-1H-benzotriazol-5-yl) propanoic acid or a pharmaceutically acceptable salt thereof.

6. The compound according to claim 1, which is (3S)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(1,4-dimethyl-1H-benzotriazol-5-yl) propanoic acid or a pharmaceutically acceptable salt thereof.

7. The compound according to claim 1, which is (3R)-3-(7-{[(4R)-8-chloro-4-ethyl-1,1-dioxido-3,4-dihydro-2H-pyrido [2,3-b][1,4,5] oxathiazepin-2-yl]methyl}-2,3-dihydro-1H-inden-5-yl)-3-(1,4-dimethyl-1H-benzotriazol-5-yl) propanoic acid or a pharmaceutically acceptable salt thereof.

8. A pharmaceutical composition comprising the compound according to claim 1 or a pharmaceutically acceptable salt thereof as an active ingredient, and a pharmaceutically acceptable carrier.

* * * * *